US011081236B2

(12) United States Patent
Daemen et al.

(10) Patent No.: US 11,081,236 B2

(45) Date of Patent: Aug. 3, 2021

(54) DIAGNOSTIC AND THERAPEUTIC METHODS FOR THE TREATMENT OF BREAST CANCER

(71) Applicant: GENENTECH, INC., South San Francisco, CA (US)

(72) Inventors: Anneleen Daemen, South San Francisco, CA (US); Ciara Metcalfe, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 32 days.

(21) Appl. No.: 16/542,817

(22) Filed: Aug. 16, 2019

(65) Prior Publication Data

US 2020/0082944 A1 Mar. 12, 2020

Related U.S. Application Data

(60) Provisional application No. 62/719,545, filed on Aug. 17, 2018.

(51) Int. Cl.

*G16H 50/30* (2018.01)
*G16H 50/20* (2018.01)
(Continued)

(52) U.S. Cl.

CPC ....... *G16H 50/30* (2018.01); *G01N 33/57415* (2013.01); *G16H 50/20* (2018.01); *G16H 80/00* (2018.01)

(58) Field of Classification Search

USPC ............................................ 700/91; 600/604

See application file for complete search history.

(56) References Cited

U.S. PATENT DOCUMENTS 7,612,114 B2 11/2009 Hamaoka et al.
8,399,520 B2 3/2013 Hamaoka et al.
(Continued)

FOREIGN PATENT DOCUMENTS

WO WO-2009/108215 A1 9/2009
WO WO-2015/038682 A1 3/2015
(Continued)

OTHER PUBLICATIONS

Daemen, A. et al. (Jan. 30, 2018). "HER2 is not a cancer subtype but rather a pan-cancer event and is highly enriched in AR-driven breast tumors," *Breast Cancer Research* 20(1):8.
(Continued)

*Primary Examiner* — Pierre E Elisca

(74) *Attorney, Agent, or Firm* — Mintz, Levin, Cohn, Ferris, Glovsky and Popeo, P.C.

(57) ABSTRACT

Provided herein, inter alia, are predictive diagnostic, pharmacodynamic, and therapeutic methods for the treatment of breast cancer. In embodiments, the methods and compositions are based, at least in part, on the discovery that the estradiol (E2)-induced score or estrogen receptor (ER) pathway activity score determined from a sample (e.g., a tissue sample, e.g., a tumor tissue sample, e.g., a FFPE, a FF, an archival, a fresh, or a frozen tumor tissue sample) from an individual can be used in methods of determining whether the individual having breast cancer is likely to respond to a treatment including an endocrine therapy, selecting a therapy for an individual having breast cancer; treating an individual having breast cancer; and monitoring therapeutic efficacy of an endocrine therapy, as well as related kits.

42 Claims, 27 Drawing Sheets

Specification includes a Sequence Listing.

(51) Int. Cl.
*G16H 80/00* (2018.01)
*G01N 33/574* (2006.01)

(56) References Cited

U.S. PATENT DOCUMENTS

| | | | |
|---|---|---|---|
| 8,703,810 B2 | 4/2014 | Kahraman et al. | |
| 9,475,791 B2 | 10/2016 | Thatcher et al. | |
| 9,499,538 B2 | 11/2016 | Smith et al. | |
| 9,586,952 B2 | 3/2017 | Smith et al. | |
| 2004/0091423 A1* | 5/2004 | Hung | A61P 9/00 424/9.1 |
| 2015/0045406 A1* | 2/2015 | Gudkov | A61K 31/403 514/411 |
| 2015/0284357 A1 | 10/2015 | Thatcher et al. | |
| 2015/0347672 A1 | 12/2015 | Van Ooijen et al. | |
| 2017/0129855 A1 | 5/2017 | Liang et al. | |

FOREIGN PATENT DOCUMENTS

| | | |
|---|---|---|
| WO | WO-2017/136688 A1 | 8/2017 |
| WO | WO-2017/140669 A1 | 8/2017 |
| WO | WO-2017/162206 A1 | 9/2017 |
| WO | WO-2017/216279 A1 | 12/2017 |
| WO | WO-2017/216280 A1 | 12/2017 |
| WO | WO-2018/019793 A1 | 2/2018 |
| WO | WO-2018/077260 A1 | 5/2018 |
| WO | WO-2018/077630 A1 | 5/2018 |
| WO | WO-2018/081168 A2 | 5/2018 |
| WO | WO-2018/081168 A3 | 5/2018 |
| WO | WO-2018/091153 A1 | 5/2018 |
| WO | WO-2018/129387 A1 | 7/2018 |
| WO | WO-2020/037203 A2 | 2/2020 |
| WO | WO-2020/037203 A3 | 2/2020 |

OTHER PUBLICATIONS

Inda, M.A. et al. (Feb. 2020, e-published Nov. 14, 2019). "Estrogen Receptor Pathway Activity Score to Predict Clinical Response or Resistance to Neoadjuvant Endocrine Therapy in Primary Breast Cancer," MolCancer Ther19(2):680-689.

International Search Report dated Feb. 20, 2020, for PCT Application No. PCT/US2019/046814, filed on Aug. 16, 2019, 7 pages.

Huber, W. et al. (Feb. 2015). "Orchestrating high-throughput genomic analysis with Bioconductor," *Nature Methods* 12(2):115-121.

Klijn,C. et al. (Mar. 2015, e-published Dec. 8, 2014). "A comprehensive transcriptional portrait of human cancer cell lines," *Nat Biotech* 33(3):306-312.

Ma, X-J. et al. (Jun. 2004). "A two-gene expression ratio predicts clinical outcome in breast cancer patients treated with tamoxifen," *Cancer Cell* 5(6):607-616.

Wang, Z. et al. (Nov. 1, 2007). "The prognostic biomarkers HOXB13, IL17BR, and CHDH are regulated by estrogen in breast cancer," *Clin Cancer Res* 13(21):6327-6334.

Written Opinion dated Feb. 20, 2020, for PCT Application No. PCT/US2019/046814, filed on Aug. 16, 2019, 10 pages.

Wu, T.D. et al. (Apr. 1, 2010, e-published Feb. 10, 2010). "Fast and SNP-tolerant detection of complex variants and splicing in short reads," *Bioinforma Oxf Engl.* 26(7):873-881.

* cited by examiner

| E2-Induced | E2-repressed |
|---|---|
| AGR3 | BAMBI |
| AMZ1 | BCAS1 |
| AREG | CCNG2 |
| C5AR2 | DDIT4 |
| CELSR2 | EGLN3 |
| CT62 | FAM171B |
| FKBP4 | GRM4 |
| FMN1 | IL1R1 |
| GREB1 | LIPH |
| IGFBP4 | NBEA |
| NOS1AP | PNPLA7 |
| NXPH3 | PSCA |
| OLFM1 | SEMA3E |
| PGR | SSPO |
| PPM1J | STON1 |
| RAPGEFL1 | TGFB3 |
| RBM24 | TP53INP1 |
| RERG | TP53INP2 |
| RET | |
| SGK3 | |
| SLC9A3R1 | |
| TFF1 | |
| ZNF703 | |

FIG. 4J

| E2-Induced | E2-Repressed |
|---|---|
| AMZ1 | BCAS1 |
| AREG | CCNG2 |
| C5AR2 | IL1R1 |
| CELSR2 | NBEA |
| FKBP4 | PNPLA7 |
| FMN1 | SEMA3E |
| GREB1 | STON1 |
| OLFM1 | TP53INP1 |
| RBM24 | |
| SLC9A3R1 | |
| TFF1 | |

FIG. 4K

| E2-Induced | E2-Repressed |
|---|---|
| AMZ1 | BCAS1 |
| C5AR2 | CCNG2 |
| CELSR2 | IL1R1 |
| FKBP4 | PNPLA7 |
| GREB1 | SEMA3E |
| OLFM1 | STON1 |
| SLC9A3R1 | |
| TFF1 | |

FIG. 4L

DIAGNOSTIC AND THERAPEUTIC METHODS FOR THE TREATMENT OF BREAST CANCER

CROSS-REFERENCE TO RELATED APPLICATION

This application claims priority to U.S. Provisional Application No. 62/719,545, filed Aug. 17, 2018, the disclosure of which is incorporated herein in its entirety and for all purposes.

REFERENCES TO A "SEQUENCE LISTING"

The Sequence Listing written in file 048893-517001US_SEQUENCE_LISTING_ST25.txt, 560,154 bytes, created on Aug. 13, 2019, machine format IBM-PC, MS-Windows operating system, is hereby incorporated by reference in its entirety for all purposes.

FIELD

Provided herein, inter alia, are diagnostic and therapeutic methods for the treatment of breast cancer. For example, provided are methods of predicting therapeutic responsiveness, methods of monitoring responsiveness to treatment, methods of selecting a treatment, methods of treatment, and diagnostic kits.

BACKGROUND

Cancer remains one of the most deadly threats to human health. In the U.S., cancer affects nearly 1.3 million new patients each year and is the second leading cause of death after heart disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years.

The estrogen receptor ("ER") is a ligand-activated transcriptional regulatory protein that mediates induction of a variety of biological effects through its interaction with endogenous estrogens. Estrogens and estrogen receptors are implicated in cancers, such as breast cancer, lung cancer, ovarian cancer, colon cancer, prostate cancer, endometrial cancer, uterine cancer, as well as other diseases or conditions. Estrogen receptor degradation as measured by immunohistochemistry (IHC) however, is insufficient as a predictor of ER pathway activity or as a pharmacodynamics (PD) biomarker for endocrine therapy; levels of ER protein do not always correlate with ER pathway status. For example, activators of ER signaling, such as the ER ligand estradiol (E2), promote degradation of ER. Furthermore, the progesterone receptor (PR), a well-established ER target gene, is often measured as a read-out of ER pathway activity; however, PR is not always present in ER+ breast tumors, and, even if present, PR suppression may not fully capture ER pathway status.

Thus, there exists an unmet need for biomarkers (e.g., transcriptional signatures), which comprehensively reflect ER pathway activity and can be useful in both diagnostic and therapeutic methods.

SUMMARY

Provided herein, inter alia, are diagnostic methods, therapeutic methods, kits for informing the treating an individual having a breast cancer and kits for predicting of responsiveness of an individual to a treatment for breast cancer.

In an aspect is provided a method of identifying an individual having a breast cancer who may benefit from a treatment including an endocrine therapy, the method including determining an estrogen receptor (ER) pathway activity score from a sample from the individual, where an ER pathway activity score from the sample that is at or above a reference ER pathway activity score identifies the individual as one who may benefit from a treatment including an endocrine therapy.

In an aspect is provided a method for selecting a therapy for an individual having a breast cancer, the method including determining an ER pathway activity score from a sample from the individual, where an ER pathway activity score from the sample that is at or above a reference ER pathway activity score identifies the individual as one who may benefit from a treatment including an endocrine therapy.

In an aspect is provided a method of treating an individual having a breast cancer, the method including administering an effective amount of an endocrine therapy to the individual, where the individual has been identified as one who is more likely to benefit from a treatment including an endocrine therapy as described herein.

In an aspect is provided a method of treating an individual having a breast cancer, the individual being identified as having an ER pathway activity score that is at or above a reference ER pathway activity score, the method including administering to the individual an effective amount of an endocrine therapy.

In an aspect is provided a method of treating an individual having a breast cancer, the method including: (a) determining an ER pathway activity score from a sample from the individual, where the ER pathway activity score from the sample is determined to be at or above a reference ER pathway activity score; and (b) administering to the individual an effective amount of an endocrine therapy.

In an aspect is provided a method for monitoring the response of an individual having a breast cancer to treatment with an endocrine therapy, the method including: (a) determining a first ER pathway activity score from a sample from the individual at a first time point; (b) following step (a), determining a second ER pathway activity score from a sample from the individual at a second time point following administration of an endocrine therapy; and (c) comparing the first ER pathway activity score with the second ER pathway activity score, where a decrease in the second ER pathway activity score relative to the first ER pathway activity score is predictive of an individual who is likely to respond to treatment with an endocrine therapy.

In an aspect is provided a method of identifying an individual having a breast cancer who may benefit from a treatment including an endocrine therapy, the method including determining an estradiol (E2)-induced score from a sample from the individual, where an E2-induced score from the sample that is at or above a reference E2-induced score identifies the individual as one who may benefit from a treatment including an endocrine therapy.

In an aspect is provided a method for selecting a therapy for an individual having a breast cancer, the method including determining an E2-induced score from a sample from the individual, where an E2-induced score from the sample that is at or above a reference E2-induced score identifies the individual as one who may benefit from a treatment including an endocrine therapy.

In an aspect is provided a method of treating an individual having a breast cancer, the method including administering an effective amount of an endocrine therapy to the individual, where the individual has been identified as one who is more likely to benefit from a treatment including an endocrine therapy as described herein.

In an aspect is provided a method of treating an individual having a breast cancer, the individual being identified as having an E2-induced score that is at or above a reference E2-induced score, the method including administering to the individual an effective amount of an endocrine therapy.

In an aspect is provided a method of treating an individual having a breast cancer, the method including: (a) determining an E2-induced score from a sample from the individual, where the E2-induced score from the sample is determined to be at or above a reference E2-induced score; and (b) administering to the individual an effective amount of an endocrine therapy.

In an aspect is provided a method for monitoring the response of an individual having a breast cancer to treatment with an endocrine therapy, the method including: (a) determining a first E2-induced score from a sample from the individual at a first time point; (b) following step (a), determining a second E2-induced score from a sample from the individual at a second time point following administration of an endocrine therapy; and (c) comparing the first E2-induced score with the second E2-induced score, where a decrease in the second E2-induced score relative to the first E2-induced score is predictive of an individual who is likely to respond to treatment with an endocrine therapy.

In an aspect is provided a method of detecting estrogen receptor (ER) pathway activity in a subject that has breast cancer, the method including detecting an expression level of at least five genes set forth in Table 1 and at least five genes set forth in Table 4; at least five genes set forth in Table 2 and at least five genes set forth in Table 5; or at least five genes set forth in Table 3 and at least five genes set forth in Table 6.

In an aspect is provided a method, including: detecting, by one or more processors, a first expression level of at least five genes set forth in Table 1, at least five genes set forth in Table 2, or at least five genes set forth in Table 3; detecting, by the one or more processors, a second expression level of at least five genes set forth in Table 4, at least five genes set forth in Table 5 or at least five genes set forth in Table 6; and detecting, based at least on the first expression level and/or the second expression level, estrogen receptor (ER) pathway activity in a subject that has cancer.

In an aspect is provided a kit including a plurality of nucleic acids, where the plurality of nucleic acids are at least 5 nucleotides in length and are at least 95% identical to a 5 nucleotide continuous sequence within at least five genes set forth in Table 1 and at least five genes set forth in Table 4; at least five genes set forth in Table 2 and at least five genes set forth in Table 4; or at least five genes set forth in Table 3 and at least five genes set forth in Table 6, or 95% identical to a sequence complementary to the 5 nucleotide continuous sequence.

BRIEF DESCRIPTION OF THE DRAWINGS

The application file contains at least one drawing executed in color. Copies of this patent or patent application with color drawings will be provided by the Office upon request and payment of the necessary fee.

FIG. 4J is a table showing the 41-gene signature (23 E2-induced and 18 E2-repressed genes).

FIG. 4K is a table showing the 19-gene signature (11 E2-induced and 8 E2-repressed genes).

FIG. 4L is a table showing the 14-gene signature (8 E2-induced and 6 E2-repressed genes).

DETAILED DESCRIPTION

I. General Techniques

Figure 1A:
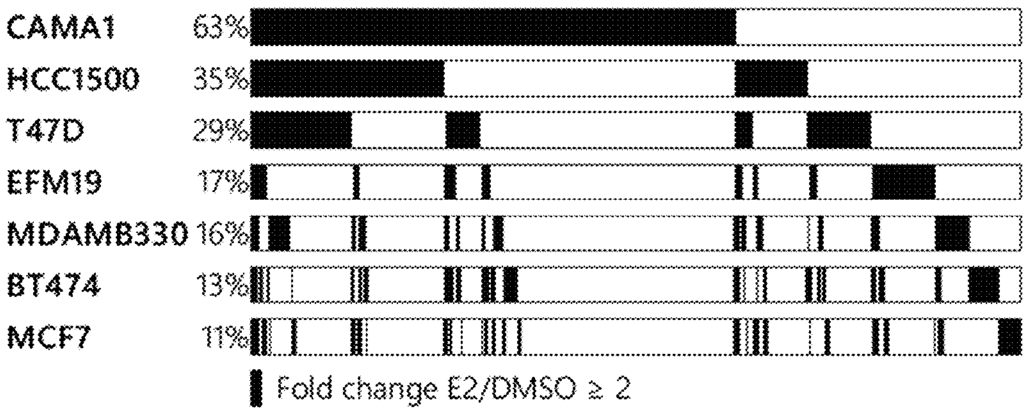
FIG. 1A is an overview of estradiol (E2)-induced genes shown in red (columns) in seven breast cancer cell lines (rows). E2 induction is defined as ≥2-fold change in expression following E2 treatment compared to treatment with DMSO (p-value ≤0.05).

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): PCR 2: A Practical Approach (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in*

*Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

II. Definitions

It is to be understood that aspects and embodiments described herein include "comprising," "consisting," and "consisting essentially of" aspects and embodiments. As used herein, the singular form "a," "an," and "the" includes plural references unless indicated otherwise.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X."

As used herein, "administering" is meant a method of giving a dosage of a compound (e.g., an endocrine therapy as described herein or a composition (e.g., a pharmaceutical composition, e.g., a pharmaceutical composition including an endocrine therapy (e.g., a selective estrogen receptor modulator (SERM) (e.g., a selective estrogen receptor degrader (SERD)), a gonadotropin-releasing hormone (GnRH) agonist, and/or an aromatase inhibitor (AI)) to a subject. The compounds and/or compositions utilized in the methods described herein can be administered, for example, orally, intramuscularly, intravenously (e.g., by intravenous infusion), subcutaneously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subconjunctivally, intravesicularlly, mucosally, intrapericardially, intraumbilically, intraocularly, topically, locally, by inhalation, by injection, by infusion, by continuous infusion, by localized perfusion bathing target cells directly, by catheter, by lavage, in creams, or in lipid compositions. The method of administration can vary depending on various factors (e.g., the compound or composition being administered and the severity of the condition, disease, or disorder being treated).

The term "anti-cancer therapy" refers to a therapy useful for treating a cancer (e.g., a breast cancer, e.g., an HR+ breast cancer (e.g., an ER+ breast cancer (e.g., a luminal A breast cancer or a luminal B breast cancer)) and/or a metastatic or a locally advanced breast cancer). Examples of anti-cancer therapeutic agents include, but are not limited to, endocrine therapies as described herein, growth inhibitory agents, cytotoxic agents, agents used in radiation therapy, anti-angiogenesis agents, apoptotic agents, anti-tubulin agents, and other agents to treat cancer, for example, anti-CD20 antibodies, platelet derived growth factor inhibitors (e.g., GLEEVEC™ (imatinib mesylate)), a COX-2 inhibitor (e.g., celecoxib), interferons, cytokines, antagonists (e.g., neutralizing antibodies), other bioactive and organic chemical agents, and the like. Combinations thereof are also included herein. An anti-cancer therapy as used herein can also be referred to a "non-endocrine therapy" which in turn refers to any anti-cancer therapy excluding endocrine therapies as defined herein.

The term "endocrine therapy" refers to a therapy or treatment useful for modulating (e.g. regulating, reducing, blocking, or inhibiting) the effects of the expression, a level, or an amount of one or more hormones found to cause or otherwise cause progression of a breast cancer as described herein. Endocrine therapy as described herein includes non-hormone and hormone therapies such as, for example, a selective estrogen receptor modulator (SERM) as described herein and understood in the art, a selective estrogen receptor degrader (SERD) as described herein and understood in the art, a gonadotropin-releasing hormone (GnRH) agonist as described herein and understood in the art, a Selective Estrogen Receptor Covalent Antagonist (SERCA) as described herein and understood in the art, a Selective Human Estrogen Receptor Partial Agonist (ShERPA) as described herein and understood in the art; an aromatase inhibitor (AI) as described herein, or a combination thereof. In one embodiment, an endocrine therapy comprises one or more compounds from Section IV-A herein.

Additional exemplary endocrine therapies for use in the methods described herein include, but are not limited to: anti-estrogens, for example, tamoxifen (including NOLVADEX® tamoxifen), raloxifene, droloxifene, 4-hydroxytamoxifen, trioxifene, keoxifene, LY117018, onapristone, FARESTON® (toremifene citrate), nafoxidine, clomifene, anordrin, bazedoxifene, broparestrol, cyclofenil, lasofoxifene, ormeloxifene, acolbifene, elacestrant (RAD1901), clomifenoxide, etacstil, ospemifene, fulvestrant (FASLODEX®), EM800, brilanestrant (GDC-0810), LX-039, AZ9496, GDC-0927 (SRN-0927); GDC-9545, G1T48 (G1 Therapeutics), H3B 6545 (H3 Biomedicine), SAR439859 (Sanofi), aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® (exemestane), formestanie, fadrozole, RIVISOR® (vorozole), FEMARA® (letrozole), and ARIMIDEX® (anastrozole); anti-androgens such as flutamide, nilutamide, bicalutamide, leuprolide, and goserelin; as well as troxacitabine (a 1,3-dioxolane nucleoside cytosine analog); and antisense oligonucleotides, particularly those which inhibit expression of genes in signaling pathways implicated in aberrant cell proliferation, as well as combinations of two or more of the above.

Examples of chemotherapeutic agents (and as applicable non-endrocrine therapies) include, but are not limited to, mammalian target of rapamycin (mTOR) inhibitors such as sirolimus (also known as rapamycin), temsirolimus (also known as CCI-779 or TORISEL®), everolimus (also known as RAD001 or AFINITOR®), ridaforolimus (also known as AP-23573, MK-8669, or deforolimus), 051-027, AZD8055, and INK128; phosphatidylinositol 3-kinase (PI3K) inhibitors such as idelalisib (also known as GS-1101 or CAL-101), BKM120, and perifosine (also known as KRX-0401); dual phosphatidylinositol 3-kinase (PI3K)/mTOR inhibitors such as XL765, GDC-0980, BEZ235 (also known as NVP-BEZ235), BGT226, GSK2126458, PF-04691502, and PF-05212384 (also known as PKI-587); and cyclin-dependent kinase (CDK)4/6 inhibitors such as abemaciclib (VERZENIO®), palbociclib (IBRANCE®), ribociclib (KISQALI®), trilaciclib (G1T28); anthracyclines such as daunorubicin, doxorubicin, epirubicin, idarubicin, mitoxantrone, valrubicin; taxanes, including paclitaxel and docetaxel; podophyllotoxin; gemcitabine (GEMZAR®); 5-fluorouracil (5-FU); cyclophosphamide (CYTOXAN®); platinum analogs such as cisplatin and carboplatin; vinorelbine (NAVELBINE®); capecitabine (XELODA®); ixabepilone (IXEMPRA®); and eribulin (HALAVEN®); ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), any of the compounds described in Section IV-A, below, and pharmaceutically acceptable salts, acids or derivatives of any of the above; as well as combinations of two or more of the above.

Further exemplary chemotherapeutic agents (and non-endocrine therapies) include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin $\gamma_1^1$ and calicheamicin omegaI1 (see, e.g., Nicolaou et al., *Angew. Chem Intl. Ed. Engl.,* 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); combretastatin; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®, Bristol-Myers Squibb Oncology, Princeton, N.J.), albumin-engineered nanoparticle formulation of paclitaxel (ABRAXANE™), and docetaxel (TAXOTERE®, Rhome-Poulene Rorer, Antony, France); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DNIFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R) (e.g., erlotinib (TARCEVA™)); and VEGF-A that reduce cell proliferation; vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors; tyrosine kinase inhibitors; serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin, and pharmaceutically acceptable salts, acids or derivatives of any of the above; as well as combinations of two or more of the above.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below. A cytotoxic agent can be a non-endocrine agent.

An "article of manufacture" is any manufacture (e.g., a package or container) or kit comprising at least one reagent, e.g., a medicament for treatment of a disease or disorder (e.g., a cancer, e.g., a breast cancer, e.g., an HR+ breast cancer (e.g., an ER+ breast cancer (e.g., luminal A breast cancer or luminal B breast cancer)), DCIS, and/or a metastatic or a locally advanced breast cancer), and/or a probe for specifically detecting a biomarker described herein. In certain embodiments, the manufacture or kit is promoted, distributed, or sold as a unit for performing the methods described herein.

The term "biomarker" as used herein refers to an indicator, e.g., a predictive, prognostic, and/or a pharmacodynamic indicator which can be detected in a sample (e.g., a tissue sample, e.g., a tumor tissue sample, e.g., a formalin-fixed and paraffin-embedded (FFPE), a fresh frozen (FF), an archival, a fresh, or a frozen tumor tissue sample). The biomarker may serve as an indicator of a particular subtype of a disease or disorder (e.g., a breast cancer, an HR+ breast cancer (e.g., an ER+ breast cancer (e.g., luminal A breast cancer or luminal B breast cancer)), DCIS, and/or a metastatic or a locally advanced breast cancer) characterized by certain molecular, pathological, histological, and/or clinical features. In some embodiments, a biomarker is a gene or a set of genes. Biomarkers include, but are not limited to, polynucleotides (e.g., DNA, and/or RNA), polynucleotide copy number alterations (e.g., DNA copy numbers), polypeptides, polypeptide and polynucleotide modifications (e.g., posttranslational modifications), carbohydrates, and/or glycolipid-based molecular markers. Exemplary sets of biomarkers are found in Tables 1-6.

The term "biomarker signature," "signature," "biomarker expression signature," or "expression signature" are used interchangeably herein and refer to a combination of biomarkers whose expression is an indicator, e.g., predictive, prognostic, and/or pharmacodynamic (e.g., the 41-gene signature (e.g., the combination of genes set forth in Tables 3 and 6), the 19-gene signature (e.g., the combination of genes set forth in Tables 2 and 5), or the 14-gene signature (e.g., the combination of genes set forth in Tables 1 and 4)). The biomarker signature may serve as an indicator of a particular subtype of a disease or disorder (e.g., cancer, e.g., breast cancer, e.g., an HR+ breast cancer (e.g., an ER+ breast cancer (e.g., luminal A breast cancer or luminal B breast cancer)), DCIS, and/or a metastatic or a locally advanced breast cancer) characterized by certain molecular, pathological, histological, and/or clinical features. In some embodiments, the biomarker signature is a "gene signature." The term "gene signature" is used interchangeably with "gene expression signature" and refers to a combination of polynucleotides whose expression is an indicator, e.g., predictive, diagnostic, and/or prognostic. In some embodiments, the biomarker signature is a "protein signature." The term "protein signature" is used interchangeably with "protein expression signature" and refers to a combination of polypeptides whose expression is an indicator, e.g., predictive, prognostic, and/or pharmacodynamic.

The term "AGR3" refers to any native Anterior Gradient 3, Protein Disulphide Isomerase Family Member from any vertebrate source, including mammals such as primates (e.g., humans) and rodents (e.g., mice and rats), unless otherwise indicated. The term encompasses "full-length," unprocessed AGR3 as well as any form of AGR3 that results from processing in the cell. The term also encompasses naturally occurring variants of AGR3, e.g., splice variants or allelic variants. AGR3 is also referred to in the art as Protein Disulfide Isomerase Family A Member 18, Breast Cancer Membrane Protein 11, BCMP11, PDIA18, HAG-3, HAG3, AG-3, AG3, and Anterior Gradient Protein 3 Homolog. The nucleic acid sequence of an exemplary human AGR3 is shown under *NCBI Reference Sequence*: NM_176813.4 or in SEQ ID NO: 1. The amino acid sequence of an exemplary protein encoded by human AGR3 is shown under UniProt Accession No. Q8TD06 or in SEQ ID NO: 2.

The term "AMZ1" refers to any native Archaelysin Family Metallopeptidase 1 from any vertebrate source, including mammals such as primates (e.g., humans) and rodents (e.g., mice and rats), unless otherwise indicated. The term encompasses "full-length," unprocessed AMZ1 as well as any form of AMZ1 that results from processing in the cell. The term also encompasses naturally occurring variants of AMZ1, e.g., splice variants or allelic variants. AMZ1 is also referred to in the art as Archeobacterial Metalloproteinase-Like Protein 1, Archaemetzincin-1, Metalloproteinase-Like Protein, and KIAA1950. The nucleic acid sequence of an exemplary human AMZ1 is shown under NCBI Reference Sequence: NM_133463.3 or in SEQ ID NO: 3. The amino acid sequence of an exemplary protein encoded by human AMZ1 is shown under UniProt Accession No. Q400G9 or in SEQ ID NO: 4.

The term "AREG" refers to any native Amphiregulin from any vertebrate source, including mammals such as primates (e.g., humans) and rodents (e.g., mice and rats), unless otherwise indicated. The term encompasses "full-length," unprocessed AREG as well as any form of AREG that results from processing in the cell. The term also encompasses naturally occurring variants of AREG, e.g., splice variants or allelic variants. AREG is also referred to in the art as Colorectum Cell-Derived Growth Factor, Schwannoma-Derived Growth Factor, Amphiregulin B, AREGB, CRDGF, and SDGF. The nucleic acid sequence of an exemplary human AREG is shown under NCBI Reference Sequence: NM_001657.3 or in SEQ ID NO: 5. The amino acid sequence of an exemplary protein encoded by human AREG is shown under UniProt Accession No. P15514 or in SEQ ID NO: 6.

The term "C5AR2" refers to any native Complement Component 5a Receptor 2 from any vertebrate source, including mammals such as primates (e.g., humans) and rodents (e.g., mice and rats), unless otherwise indicated. The term encompasses "full-length," unprocessed C5AR2 as well as any form of C5AR2 that results from processing in the cell. The term also encompasses naturally occurring variants of C5AR2, e.g., splice variants or allelic variants. C5AR2 is also referred to in the art as Complement Component 5a Receptor 2, G Protein-Coupled Receptor 77, GPR77, C5L2, C5a Anaphylatoxin Chemotactic Receptor C5L2, and GPF77. The nucleic acid sequence of an exemplary human C5AR2 is shown under NCBI Reference Sequence: NM 001271749.1 or in SEQ ID NO: 7. The amino acid sequence of an exemplary protein encoded by human C5AR2 is shown under UniProt Accession No. Q9P296 or in SEQ ID NO: 8.

The term "CELSR2" refers to any native Cadherin EGF LAG Seven-Pass G-Type Receptor 2 from any vertebrate source, including mammals such as primates (e.g., humans) and rodents (e.g., mice and rats), unless otherwise indicated. The term encompasses "full-length," unprocessed CELSR2 as well as any form of CELSR2 that results from processing in the cell. The term also encompasses naturally occurring variants of CELSR2, e.g., splice variants or allelic variants. CELSR2 is also referred to in the art as Multiple Epidermal Growth Factor-Like Domains Protein 3, Multiple Epidermal Growth Factor-Like Domains Protein 3, Adhesion G Protein-Coupled Receptor C2, Epidermal Growth Factor-Like Protein 2, Multiple EGF-Like Domains Protein 3, Cadherin Family Member 10, Flamingo Homolog 3, EGF-Like Protein 2, CDHF10, EGFL2, MEGF3, Flamingo1, KIAA0279, and ADGRC2. The nucleic acid sequence of an exemplary human CELSR2 is shown under NCBI Reference Sequence: NM_001408.2 or in SEQ ID NO: 9. The amino acid sequence of an exemplary protein encoded by human CELSR2 is shown under UniProt Accession No. Q9HCU4 or in SEQ ID NO: 10.

The term "CT62" refers to any native Cancer/Testis Antigen 62 from any vertebrate source, including mammals such as primates (e.g., humans) and rodents (e.g., mice and rats), unless otherwise indicated. The term encompasses "full-length," unprocessed CT62 as well as any form of CT62 that results from processing in the cell. The term also encompasses naturally occurring variants of CT62, e.g., splice variants or allelic variants. The nucleic acid sequence of an exemplary human CT62 is shown under NCBI Reference Sequence: XM_006720429 or in SEQ ID NO: 11. The amino acid sequence of an exemplary protein encoded by human CT62 is shown under UniProt Accession No. P005K7 or in SEQ ID NO: 12.

The term "FKBP4" refers to any native FK506 Binding Protein 4 from any vertebrate source, including mammals such as primates (e.g., humans) and rodents (e.g., mice and rats), unless otherwise indicated. The term encompasses "full-length," unprocessed FKBP4 as well as any form of FKBP4 that results from processing in the cell. The term also encompasses naturally occurring variants of FKBP4, e.g., splice variants or allelic variants. FKBP4 is also referred to in the art as Rotamase, FKBP51, FKBP52, FKBP59, HBI, Peptidyl-Prolyl Cis-Trans Isomerase FKBP4, T-Cell FK506-Binding Protein (59 kD), HSP Binding Immunophilin, Immunophilin FKBP52, PPlase FKBP4, PPIASE, Hsp56, P52, and P59. The nucleic acid sequence of an exemplary human FKBP4 is shown under NCBI Reference Sequence: NM_002014.3 or in SEQ ID NO: 13. The amino acid sequence of an exemplary protein encoded by human FKBP4 is shown under UniProt Accession No. Q02790 or in SEQ ID NO: 14.

The term "FMN1" refers to any native Formin 1 from any vertebrate source, including mammals such as primates (e.g., humans) and rodents (e.g., mice and rats), unless otherwise indicated. The term encompasses "full-length," unprocessed FMN1 as well as any form of FMN1 that results from processing in the cell. The term also encompasses naturally occurring variants of FMN1, e.g., splice variants or allelic variants. FMN1 is also referred to in the art as Limb Deformity Protein Homolog, FMN, and LD. The nucleic acid sequence of an exemplary human FMN1 is shown under NCBI Reference Sequence: NM_001277313.1 or in SEQ ID NO: 15. The amino acid sequence of an exemplary protein encoded by human FMN1 is shown under UniProt Accession No. Q68DA7 or in SEQ ID NO: 16.

The term "GREB1" refers to any native Growth Regulation By Estrogen in Breast Cancer 1 from any vertebrate source, including mammals such as primates (e.g., humans) and rodents (e.g., mice and rats), unless otherwise indicated. The term encompasses "full-length," unprocessed GREB1 as well as any form of GREB1 that results from processing in the cell. The term also encompasses naturally occurring variants of GREB1, e.g., splice variants or allelic variants. GREB1 is also referred to in the art as Gene Regulated in Breast Cancer 1 Protein and KIAA0575. The nucleic acid sequence of an exemplary human GREB1 is shown under NCBI Reference Sequence: NM_014668.3 or in SEQ ID NO: 17. The amino acid sequence of an exemplary protein encoded by human GREB1 is shown under UniProt Accession No. Q4ZG55 or in SEQ ID NO: 18.

The term "IGFBP4" refers to any native Insulin Like Growth Factor Binding Protein 4 from any vertebrate source, including mammals such as primates (e.g., humans) and rodents (e.g., mice and rats), unless otherwise indicated. The term encompasses "full-length," unprocessed IGFBP4 as well as any form of IGFBP4 that results from processing in the cell. The term also encompasses naturally occurring variants of IGFBP4, e.g., splice variants or allelic variants. IGFBP4 is also referred to in the art as IGF-Binding Protein 4, IBP-4, HT29-IGFBP, and BP-4. The nucleic acid sequence of an exemplary human IGFBP4 is shown under NCBI Reference Sequence: NM 001552.2 or in SEQ ID NO: 19. The amino acid sequence of an exemplary protein encoded by human IGFBP4 is shown under UniProt Accession No. P22692 or in SEQ ID NO: 20.

The term "NOS1AP" refers to any native Nitric Oxide Synthase 1 Adaptor Protein from any vertebrate source, including mammals such as primates (e.g., humans) and rodents (e.g., mice and rats), unless otherwise indicated. The term encompasses "full-length," unprocessed NOS1AP as well as any form of NOS1AP that results from processing in the cell. The term also encompasses naturally occurring variants of NOS1AP, e.g., splice variants or allelic variants. NOS1AP is also referred to in the art as C-Terminal PDZ Ligand of Neuronal Nitric Oxide Synthase Protein, Nitric Oxide Synthase 1 (Neuronal) Adaptor Protein, CAPON, Ligand of Neuronal Nitric Oxide Synthase with Carboxyl-Terminal PDZ Domain, 6330408P19Rik, and KIAA0464. The nucleic acid sequence of an exemplary human NOS1AP is shown under NCBI Reference Sequence: NM_014697.2 or in SEQ ID NO: 21. The amino acid sequence of an exemplary protein encoded by human NOS1AP is shown under UniProt Accession No. 075052 or in SEQ ID NO: 22.

The term "NXPH3" refers to any native Neurexophilin 3 from any vertebrate source, including mammals such as primates (e.g., humans) and rodents (e.g., mice and rats), unless otherwise indicated. The term encompasses "full-length," unprocessed NXPH3 as well as any form of NXPH3 that results from processing in the cell. The term also encompasses naturally occurring variants of NXPH3, e.g., splice variants or allelic variants. NXPH3 is also referred to in the art as NPH3 and KIAA1159. The nucleic acid sequence of an exemplary human NXPH3 is shown under NCBI Reference Sequence: NM_007225.2 or in SEQ ID NO: 23. The amino acid sequence of an exemplary protein encoded by human NXPH3 is shown under UniProt Accession No. 095157 or in SEQ ID NO: 24.

The term "OLFM1" refers to any native Olfactomedin 1 from any vertebrate source, including mammals such as primates (e.g., humans) and rodents (e.g., mice and rats), unless otherwise indicated. The term encompasses "full-length," unprocessed OLFM1 as well as any form of OLFM1 that results from processing in the cell. The term also encompasses naturally occurring variants of OLFM1, e.g., splice variants or allelic variants. OLFM1 is also referred to in the art as Neuronal Olfactomedin-Related ER Localized Protein, Noelin, NOE1, Olfactomedin Related ER Localized Protein, Neuroblastoma Protein, Pancortin 1, Pancortin, NOELIN1, NOEL1, OlfA, and AMY. The nucleic acid sequence of an exemplary human OLFM1 is shown under NCBI Reference Sequence: NM_014279.4 or in SEQ ID NO: 25. The amino acid sequence of an exemplary protein encoded by human OLFM1 is shown under UniProt Accession No. Q99784 or in SEQ ID NO: 26.

The term "PGR" refers to any native Progesterone Receptor from any vertebrate source, including mammals such as primates (e.g., humans) and rodents (e.g., mice and rats), unless otherwise indicated. The term encompasses "full-length," unprocessed PGR as well as any form of PGR that results from processing in the cell. The term also encompasses naturally occurring variants of PGR, e.g., splice variants or allelic variants. PGR is also referred to in the art as Nuclear Receptor Subfamily 3 Group C Member 3, NR3C3, and PR. The nucleic acid sequence of an exemplary human PGR is shown under NCBI Reference Sequence: NM_000926.4 or in SEQ ID NO: 27. The amino acid sequence of an exemplary protein encoded by human PGR is shown under UniProt Accession No. P06401 or in SEQ ID NO: 28.

The term "PPM1J" refers to any native Protein Phosphatase, Mg2+/Mn2+ Dependent 1J from any vertebrate source, including mammals such as primates (e.g., humans) and rodents (e.g., mice and rats), unless otherwise indicated. The term encompasses "full-length," unprocessed PPM1J as well as any form of PPM1J that results from processing in the cell. The term also encompasses naturally occurring variants of PPM1J, e.g., splice variants or allelic variants. PPM1J is also referred to in the art as Protein Phosphatase 1J (PP2C Domain Containing), Protein Phosphatase 2C Zeta, EC 3.1.3.16, PP2C-Zeta, Protein Phosphatase 2a, Catalytic Subunit, Zeta Isoform, Protein Phosphatase 1J, PP2Czeta, and PP2CZ. The nucleic acid sequence of an exemplary human PPM1J is shown under NCBI Reference Sequence: NM_005167.5 or in SEQ ID NO: 29. The amino acid sequence of an exemplary protein encoded by human PPM1J is shown under UniProt Accession No. Q5JR12 or in SEQ ID NO: 30.

The term "RAPGEFL1" refers to any native Rap Guanine Nucleotide Exchange Factor Like 1 from any vertebrate source, including mammals such as primates (e.g., humans) and rodents (e.g., mice and rats), unless otherwise indicated. The term encompasses "full-length," unprocessed RAPGEFL1 as well as any form of RAPGEFL1 that results from processing in the cell. The term also encompasses naturally occurring variants RAPGEFL1, e.g., splice variants or allelic variants. RAPGEFL1 is also referred to in the art as Link Guanine Nucleotide Exchange Factor II, Rap Guanine Nucleotide Exchange Factor (GEF)-Like 1, and Link GEFII. The nucleic acid sequence of an exemplary human RAPGEFL1 is shown under NCBI Reference Sequence: NM_001303533.1 or in SEQ ID NO: 31. The amino acid sequence of an exemplary protein encoded by human RAPGEFL1 is shown under UniProt Accession No. Q9UHV5 or in SEQ ID NO: 32.

The term "RBM24" refers to any native RNA Binding Motif Protein 24 from any vertebrate source, including mammals such as primates (e.g., humans) and rodents (e.g., mice and rats), unless otherwise indicated. The term encompasses "full-length," unprocessed RBM24 as well as any form of RBM24 that results from processing in the cell. The term also encompasses naturally occurring variants of RBM24, e.g., splice variants or allelic variants. RBM24 is also referred to in the art as RNA-Binding Region (RNP1, RRM) Containing 6, RNPC6, RNA-Binding Protein 24, and DJ259A10.1. The nucleic acid sequence of an exemplary human RBM24 is shown under NCBI Reference Sequence: NM 001143942.1 or in SEQ ID NO: 33. The amino acid sequence of an exemplary protein encoded by human RBM24 is shown under UniProt Accession No. Q9BX46 or in SEQ ID NO: 34.

The term "RERG" refers to any native RAS Like Estrogen Regulated Growth Inhibitor from any vertebrate source, including mammals such as primates (e.g., humans) and rodents (e.g., mice and rats), unless otherwise indicated. The term encompasses "full-length," unprocessed RERG as well as any form of RERG that results from processing in the cell. The term also encompasses naturally occurring variants of RERG, e.g., splice variants or allelic variants. The nucleic acid sequence of an exemplary human RERG is shown under NCBI Reference Sequence: NM_032918.2 or in SEQ ID NO: 35. The amino acid sequence of an exemplary protein encoded by human RERG is shown under UniProt Accession No. Q96A58 or in SEQ ID NO: 36.

The term "RET" refers to any native Ret Proto-Oncogene from any vertebrate source, including mammals such as primates (e.g., humans) and rodents (e.g., mice and rats), unless otherwise indicated. The term encompasses "full-length," unprocessed RET as well as any form of RET that results from processing in the cell. The term also encompasses naturally occurring variants of RET, e.g., splice variants or allelic variants. RET is also referred to in the art as Cadherin-Related Family Member 16, Rearranged During Transfection, RET Receptor Tyrosine Kinase, Cadherin Family Member 12, Proto-Oncogene C-Ret, EC 2.7.10.1, CDHF12, CDHR16, PTC, Multiple Endocrine Neoplasia And Medullary Thyroid Carcinoma 1, EC 2.7.10, RET-ELE1, HSCR1, MEN2A, MEN2B, RET51, and MTC1. The nucleic acid sequence of an exemplary human RET is shown under NCBI Reference Sequence: NM_020975.5 or in SEQ ID NO: 37. The amino acid sequence of an exemplary protein encoded by human RET is shown under UniProt Accession No. P07949 or in SEQ ID NO: 38.

The term "SGK3" refers to any native Serum/Glucocorticoid Regulated Kinase Family Member 3 from any vertebrate source, including mammals such as primates (e.g., humans) and rodents (e.g., mice and rats), unless otherwise indicated. The term encompasses "full-length," unprocessed SGK3 as well as any form of SGK3 that results from processing in the cell. The term also encompasses naturally occurring variants of SGK3, e.g., splice variants or allelic variants. SGK3 is also referred to in the art as Cytokine-Independent Survival Kinase, EC 2.7.11.1, SGKL, CISK, EC 2.7.11, Serine/Threonine-Protein Kinase Sgk3, and SGK2. The nucleic acid sequence of an exemplary human SGK3 is shown under NCBI Reference Sequence: NM 001033578.2 or in SEQ ID NO: 39. The amino acid sequence of an exemplary protein encoded by human SGK3 is shown under UniProt Accession No. Q96BR1 or in SEQ ID NO: 40.

The term "SLC9A3R1" refers to any native SLC9A3 Regulator 1 from any vertebrate source, including mammals such as primates (e.g., humans) and rodents (e.g., mice and rats), unless otherwise indicated. The term encompasses "full-length," unprocessed SLC9A3R1 as well as any form of SLC9A3R1 that results from processing in the cell. The term also encompasses naturally occurring variants of SLC9A3R1, e.g., splice variants or allelic variants. SLC9A3R1 is also referred to in the art as Solute Carrier Family 9, Subfamily A (NHE3, Cation Proton Antiporter 3), Member 3 Regulator 1, Regulatory Cofactor Of Na(+)/H(+) Exchanger, NHERF-1, EBP50, NHERF, Ezrin-Radixin-Moesin Binding Phosphoprotein-50, Sodium-Hydrogen Exchanger Regulatory Factor 1, and NPHLOP2. The nucleic acid sequence of an exemplary human SLC9A3R1 is shown under NCBI Reference Sequence: NM 004252.4 or in SEQ ID NO: 41. The amino acid sequence of an exemplary protein encoded by human SLC9A3R1 is shown under UniProt Accession No. 014745 or in SEQ ID NO: 42.

The term "TFF1" refers to any native Trefoil Factor 1 from any vertebrate source, including mammals such as primates (e.g., humans) and rodents (e.g., mice and rats), unless otherwise indicated. The term encompasses "full-length," unprocessed TFF1 as well as any form of TFF1 that results from processing in the cell. The term also encompasses naturally occurring variants of TFF1, e.g., splice variants or allelic variants. TFF1 is also referred to in the art as Breast Cancer Estrogen-Inducible Protein, Polypeptide P1.A, Protein PS2, HP1.A, PNR-2, BCEI, PS2, Gastrointestinal Trefoil Protein PS2, D21S21, and HPS2 The nucleic acid sequence of an exemplary human TFF1 is shown under NCBI Reference Sequence: NM_003225.2 or in SEQ ID NO: 43. The amino acid sequence of an exemplary protein encoded by human TFF1 is shown under UniProt Accession No. P04155 or in SEQ ID NO: 44.

The term "ZNF703" refers to any native Zinc Finger Protein 703 from any vertebrate source, including mammals such as primates (e.g., humans) and rodents (e.g., mice and rats), unless otherwise indicated. The term encompasses "full-length," unprocessed ZNF703 as well as any form of ZNF703 that results from processing in the cell. The term also encompasses naturally occurring variants of ZNF703, e.g., splice variants or allelic variants. ZNF703 is also referred to in the art as Zinc Finger Elbow-Related Proline Domain Protein 1, ZEPPO1, ZPO1, ZNF503L, and NLZ1. The nucleic acid sequence of an exemplary human ZNF703 is shown under NCBI Reference Sequence: NM_025069.2 or in SEQ ID NO: 45. The amino acid sequence of an exemplary protein encoded by human ZNF703 is shown under UniProt Accession No. Q9H7S9 or in SEQ ID NO: 46.

The term "BAMBI" refers to any native BMP and Activin Membrane Bound Inhibitor from any vertebrate source, including mammals such as primates (e.g., humans) and rodents (e.g., mice and rats), unless otherwise indicated. The term encompasses "full-length," unprocessed BAMBI as well as any form of BAMBI that results from processing in the cell. The term also encompasses naturally occurring variants of BAMBI, e.g., splice variants or allelic variants. BAMBI is also referred to in the art as Putative Transmembrane Protein NMA, Non-Metastatic Gene A Protein, NMA, and BMP And Activin Membrane-Bound Inhibitor Homolog. The nucleic acid sequence of an exemplary human BAMBI is shown under NCBI Reference Sequence: NM_012342.2 or in SEQ ID NO: 47. The amino acid sequence of an exemplary protein encoded by human MAIM is shown under UniProt Accession No. Q13145 or in SEQ ID NO: 48.

The term "BCAS1" refers to any native Breast Carcinoma Amplified Sequence 1 from any vertebrate source, including mammals such as primates (e.g., humans) and rodents (e.g., mice and rats), unless otherwise indicated. The term encompasses "full-length," unprocessed BCAS1 as well as any form of BCAS1 that results from processing in the cell. The term also encompasses naturally occurring variants of BCAS1, e.g., splice variants or allelic variants. BCAS1 is also referred to in the art as Amplified and Overexpressed in Breast Cancer, Novel Amplified in Breast Cancer 1, AIBC1, and NABC1. The nucleic acid sequence of an exemplary human BCAS1 is shown under NCBI Reference Sequence: NM_003657.3 or in SEQ ID NO: 49. The amino acid sequence of an exemplary protein encoded by human BCAS1 is shown under UniProt Accession No. 075363 or in SEQ ID NO: 50.

The term "CCNG2" refers to any native Cyclin G2 from any vertebrate source, including mammals such as primates (e.g., humans) and rodents (e.g., mice and rats), unless otherwise indicated. The term encompasses "full-length," unprocessed CCNG2 as well as any form of CCNG2 that results from processing in the cell. The term also encompasses naturally occurring variants of CCNG2, e.g., splice variants or allelic variants. The nucleic acid sequence of an exemplary human CCNG2 is shown under NCBI Reference Sequence: XM_011532399.2 or in SEQ ID NO: 51. The amino acid sequence of an exemplary protein encoded by human CCNG2 is shown under UniProt Accession No. Q16589 or in SEQ ID NO: 52.

The term "DDIT4" refers to any native DNA Damage Inducible Transcript 4 from any vertebrate source, including mammals such as primates (e.g., humans) and rodents (e.g., mice and rats), unless otherwise indicated. The term encompasses "full-length," unprocessed DDIT4 as well as any form of DDIT4 that results from processing in the cell. The term also encompasses naturally occurring variants of DDIT4, e.g., splice variants or allelic variants. DDIT4 is also referred to in the art as Protein Regulated in Development and DNA Damage Response 1, HIF-1 Responsive Protein RTP801, REDD1, RTP801, and Dig2. The nucleic acid sequence of an exemplary human DDIT4 is shown under NCBI Reference Sequence: NM_019058.3 or in SEQ ID NO: 53. The amino acid sequence of an exemplary protein encoded by human DDIT4 is shown under UniProt Accession No. Q9NX09 or in SEQ ID NO: 54.

The term "EGLN3" refers to any native Egl-9 Family Hypoxia Inducible Factor 3 from any vertebrate source, including mammals such as primates (e.g., humans) and rodents (e.g., mice and rats), unless otherwise indicated. The term encompasses "full-length," unprocessed EGLN3 as well as any form of EGLN3 that results from processing in the cell. The term also encompasses naturally occurring variants of EGLN3, e.g., splice variants or allelic variants. EGLN3 is also referred to in the art as Prolyl Hydroxylase Domain-Containing Protein 3, Hypoxia-Inducible Factor Prolyl Hydroxylase 3, HIF-Prolyl Hydroxylase 3, HPH-1, HPH-3, PHD3, Egl Nine-Like Protein 3 Isoform, Egl Nine Homolog 3, EC 1.14.11.29, EC 1.14.11, HIFP4H3, and HIFPH3. The nucleic acid sequence of an exemplary human EGLN3 is shown under NCBI Reference Sequence: NM_022073.3 or in SEQ ID NO: 55. The amino acid sequence of an exemplary protein encoded by human EGLN3 is shown under UniProt Accession No. Q9H6Z9 or in SEQ ID NO: 56.

The term "FAM171B" refers to any native Family With Sequence Similarity 171 Member B from any vertebrate source, including mammals such as primates (e.g., humans) and rodents (e.g., mice and rats), unless otherwise indicated. The term encompasses "full-length," unprocessed FAM171B as well as any form of FAM171B that results from processing in the cell. The term also encompasses naturally occurring variants of FAM171B, e.g., splice variants or allelic variants. FAM171B is also referred to in the art as KIAA1946 and Protein FAM171B. The nucleic acid sequence of an exemplary human FAM171B is shown under NCBI Reference Sequence: NM_177454.3 or in SEQ ID NO: 57. The amino acid sequence of an exemplary protein encoded by human FAM171B is shown under UniProt Accession No. Q6P995 or in SEQ ID NO: 58.

The term "GRM4" refers to any native Glutamate Metabotropic Receptor 4 from any vertebrate source, including mammals such as primates (e.g., humans) and rodents (e.g., mice and rats), unless otherwise indicated. The term encompasses "full-length," unprocessed GRM4 as well as any form of GRM4 that results from processing in the cell. The term also encompasses naturally occurring variants of GRM4, e.g., splice variants or allelic variants. GRM4 is also referred to in the art as GPRC1D, MGLUR4, and MGlu4. The nucleic acid sequence of an exemplary human GRM4 is shown under NCBI Reference Sequence: NM_000841.4 or in SEQ ID NO: 59. The amino acid sequence of an exemplary protein encoded by human GRM4 is shown under UniProt Accession No. Q14833 or in SEQ ID NO: 60.

The term "IL1R1" refers to any native Interleukin 1 Receptor Type 1 from any vertebrate source, including mammals such as primates (e.g., humans) and rodents (e.g., mice and rats), unless otherwise indicated. The term encompasses "full-length," unprocessed IL1R1 as well as any form of IL1R1 that results from processing in the cell. The term also encompasses naturally occurring variants of IL1R1, e.g., splice variants or allelic variants. IL1R1 is also referred to in the art as CD121 Antigen-Like Family Member A, Interleukin-1 Receptor Alpha, IL-1R-Alpha, IL1RA, IL1R, P80, CD121a Antigen, D2S1473, CD121A, and IL1RT1. The nucleic acid sequence of an exemplary human IL1R1 is shown under NCBI Reference Sequence: NM_001288706.1 or in SEQ ID NO: 61. The amino acid sequence of an exemplary protein encoded by human ILIR1 is shown under UniProt Accession No. P14778 or in SEQ ID NO: 62.

The term "LIPH" refers to any native Lipase H from any vertebrate source, including mammals such as primates (e.g., humans) and rodents (e.g., mice and rats), unless otherwise indicated. The term encompasses "full-length," unprocessed LIPH as well as any form of LIPH that results from processing in the cell. The term also encompasses naturally occurring variants of LIPH, e.g., splice variants or allelic variants. LIPH is also referred to in the art as Membrane-Associated Phosphatidic Acid-Selective Phospholipase A1-Alpha, PD Lipase-Related Protein, Phospholipase A1 Member B, MPA-PLA1 Alpha, LPDLR, Membrane-Bound Phosphatidic Acid-Selective Phospholipase A1, Lipase Member H, EC 3.1.1.3, C 3.1., ARWH2, HYPT7, LAH2, and AH. The nucleic acid sequence of an exemplary human LIPH is shown under NCBI Reference Sequence: XM_006713529.4 or in SEQ ID NO: 63. The amino acid sequence of an exemplary protein encoded by human LIPH is shown under UniProt Accession No. Q8WWY8 or in SEQ ID NO: 64.

The term "NBEA" refers to any native Neurobeachin from any vertebrate source, including mammals such as primates (e.g., humans) and rodents (e.g., mice and rats), unless otherwise indicated. The term encompasses "full-length," unprocessed NBEA as well as any form of NBEA that results from processing in the cell. The term also encompasses naturally occurring variants of NBEA, e.g., splice variants or allelic variants. NBEA is also referred to in the art as Lysosomal-Trafficking Regulator 2, BCL8B, LYST2, Protein BCL8B, EC 1.14.14.5, EC 6.1.1.11, and KIAA1544. The nucleic acid sequence of an exemplary human NBEA is shown under NCBI Reference Sequence: NM_015678.4 or in SEQ ID NO: 65. The amino acid sequence of an exemplary protein encoded by human NBEA is shown under UniProt Accession No. Q8NFP9 or in SEQ ID NO: 66.

The term "PNPLA7" refers to any native Patatin Like Phospholipase Domain Containing 7 from any vertebrate source, including mammals such as primates (e.g., humans) and rodents (e.g., mice and rats), unless otherwise indicated. The term encompasses "full-length," unprocessed PNPLA7 as well as any form of PNPLA7 that results from processing in the cell. The term also encompasses naturally occurring variants of PNPLA7, e.g., splice variants or allelic variants. PNPLA7 is also referred to in the art as C9orf111, Patatin-Like Phospholipase Domain-Containing Protein 7, Chromosome 9 Open Reading Frame 111, EC 3.1.1.5, NTE-R1, and NTEL1. The nucleic acid sequence of an exemplary human PNPLA7 is shown under NCBI Reference Sequence: NM_001098537.2 or in SEQ ID NO: 67. The amino acid sequence of an exemplary protein encoded by human PNPLA7 is shown under UniProt Accession No. Q6ZV29 or in SEQ ID NO: 68.

The term "PSCA" refers to any native Prostate Stem Cell Antigen from any vertebrate source, including mammals such as primates (e.g., humans) and rodents (e.g., mice and rats), unless otherwise indicated. The term encompasses "full-length," unprocessed PSCA as well as any form of PSCA that results from processing in the cell. The term also encompasses naturally occurring variants of PSCA, e.g., splice variants or allelic variants. PSCA is also referred to in the art as PRO232. The nucleic acid sequence of an exemplary human PSCA is shown under NCBI Reference Sequence: NM_005672.4 or in SEQ ID NO: 69. The amino acid sequence of an exemplary protein encoded by human PSCA is shown under UniProt Accession No. 043653 or in SEQ ID NO: 70.

The term "SEMA3E" refers to any native Semaphorin 3E from any vertebrate source, including mammals such as primates (e.g., humans) and rodents (e.g., mice and rats), unless otherwise indicated. The term encompasses "full-length," unprocessed SEMA3E as well as any form of SEMA3E that results from processing in the cell. The term also encompasses naturally occurring variants of SEMA3E, e.g., splice variants or allelic variants. SEMA3E is also referred to in the art as Sema Domain, Immunoglobulin Domain (Ig), Short Basic Domain, Secreted, (Semaphorin) 3E, SEMAH, Semaphorin-3E, M-Sema H, KIAA0331, M-SemaK, and Coll-5. The nucleic acid sequence of an exemplary human SEMA3E is shown under NCBI Reference Sequence: NM_012431.2 or in SEQ ID NO: 71. The amino acid sequence of an exemplary protein encoded by human SEMA3E is shown under UniProt Accession No. 015041 or in SEQ ID NO: 72.

The term "SSPO" refers to any native SCO-Spondin from any vertebrate source, including mammals such as primates (e.g., humans) and rodents (e.g., mice and rats), unless otherwise indicated. The term encompasses "full-length," unprocessed SSPO as well as any form of SSPO that results from processing in the cell. The term also encompasses naturally occurring variants of SSPO, e.g., splice variants or allelic variants. SSPO is also referred to in the art as SCO Protein, Thrombospondin Domain Containing, Subcommissural Organ Spondin, EC 3.4.24.82, EC 3.4.21.9, and KIAA2036. The nucleic acid sequence of an exemplary human SSPO is shown under NCBI Reference Sequence: BN000852.1 or in SEQ ID NO: 73. The amino acid sequence of an exemplary protein encoded by human SSPO is shown under UniProt Accession No. A2VEC9 or in SEQ ID NO: 74.

The term "STON1" refers to any native Stonin 1 from any vertebrate source, including mammals such as primates (e.g., humans) and rodents (e.g., mice and rats), unless otherwise indicated. The term encompasses "full-length," unprocessed STON1 as well as any form of STON1 that results from processing in the cell. The term also encompasses naturally occurring variants of STON1, e.g., splice variants or allelic variants. STON1 is also referred to in the art as Stoned B-Like Factor, SALF, SBLF, STN1, Stoned B Homolog 1, and STNB1. The nucleic acid sequence of an exemplary human STON1 is shown under NCBI Reference Sequence: NM_001198595.1 or in SEQ ID NO: 75. The amino acid sequence of an exemplary protein encoded by human STON1 is shown under UniProt Accession No. Q9Y6Q2 or in SEQ ID NO: 76.

The term "TGFB3" refers to any native Transforming Growth Factor Beta 3 from any vertebrate source, including mammals such as primates (e.g., humans) and rodents (e.g., mice and rats), unless otherwise indicated. The term encompasses "full-length," unprocessed TGFB3 as well as any form of TGFB3 that results from processing in the cell. The term also encompasses naturally occurring variants of TGFB3, e.g., splice variants or allelic variants. TGFB3 is also referred to in the art as Prepro-Transforming Growth Factor Beta-3, Arrhythmogenic Right Ventricular Dysplasia 1, TGF-Beta-3, ARVD1, LDSS, RNHF, and ARVD. The nucleic acid sequence of an exemplary human TGFB3 is shown under NCBI Reference Sequence: NM_003239.4 or in SEQ ID NO: 77. The amino acid sequence of an exemplary protein encoded by human TGFB3 is shown under UniProt Accession No. P10600 or in SEQ ID NO: 78.

The term "TP53INP1" refers to any native Tumor Protein P53 Inducible Nuclear Protein 1 from any vertebrate source, including mammals such as primates (e.g., humans) and rodents (e.g., mice and rats), unless otherwise indicated. The term encompasses "full-length," unprocessed TP53INP1 as well as any form of TP53INP1 that results from processing in the cell. The term also encompasses naturally occurring variants of TP53INP1, e.g., splice variants or allelic variants. TP53INP1 is also referred to in the art as P53-Dependent Damage-Inducible Nuclear Protein 1, Stress-Induced Protein, P53DINP1, SIP, P53-Inducible P53DINP1, TP53DINP1, TP53INP1A, TP53INP1B, and Teap. The nucleic acid sequence of an exemplary human TGFB3 is shown under NCBI Reference Sequence: NM_033285.3 or in SEQ ID NO: 79. The amino acid sequence of an exemplary protein encoded by human TP53INP1 is shown under UniProt Accession No. Q96A56 or in SEQ ID NO: 80.

The term "TP53INP2" refers to any native Tumor Protein P53 Inducible Nuclear Protein 2 from any vertebrate source, including mammals such as primates (e.g., humans) and rodents (e.g., mice and rats), unless otherwise indicated. The term encompasses "full-length," unprocessed TP53INP2 as well as any form of TP53INP2 that results from processing in the cell. The term also encompasses naturally occurring variants of TP53INP2, e.g., splice variants or allelic variants. TP53INP2 is also referred to in the art as P53-Inducible Protein U, C20orf110, PIG-U, PINH, DOR, Chromosome 20 Open Reading Frame 110, Diabetes And Obesity-Regulated Gene, and DJ1181N3.1. The nucleic acid sequence of an exemplary human TP53INP2 is shown under NCBI Reference Sequence: NM_021202.2 or in SEQ ID NO: 81. The amino acid sequence of an exemplary protein encoded by human TP53INP2 is shown under UniProt Accession No. Q8IXH6 or in SEQ ID NO: 82.

The term "GUSB" refers to any native Glucuronidase Beta from any vertebrate source, including mammals such as primates (e.g., humans) and rodents (e.g., mice and rats), unless otherwise indicated. The term encompasses "full-length," unprocessed GUSB as well as any form of GUSB that results from processing in the cell. The term also encompasses naturally occurring variants of GUSB, e.g., splice variants or allelic variants. GUSB is also referred to in the art as EC 3.2.1.31, Beta-G1, Beta-D-Glucuronidase, MPS7, and BG. The nucleic acid sequence of an exemplary human GUSB is shown under NCBI Reference Sequence: NM_000181.3 or in SEQ ID NO: 83. The amino acid sequence of an exemplary protein encoded by human GUSB is shown under UniProt Accession No. P08236 or in SEQ ID NO: 84.

The term "PPIA" refers to any native Peptidylprolyl Isomerase A from any vertebrate source, including mammals such as primates (e.g., humans) and rodents (e.g., mice and rats), unless otherwise indicated. The term encompasses "full-length," unprocessed PPIA as well as any form of PPIA that results from processing in the cell. The term also encompasses naturally occurring variants of PPIA, e.g., splice variants or allelic variants. PPIA is also referred to in the art as Cyclosporin A-Binding Protein, Cyclophilin A, Rotamase A, EC 5.2.1.8, PPlase A, CYPA, Epididymis Secretory Sperm Binding Protein Li 69p, Peptidyl-Prolyl Cis-Trans Isomerase A, T Cell Cyclophilin, HEL-S-69p, and CYPH. The nucleic acid sequence of an exemplary human PPIA is shown under NCBI Reference Sequence: NM_021130.4 or in SEQ ID NO: 85. The amino acid sequence of an exemplary protein encoded by human PPIA is shown under UniProt Accession No. P62937 or in SEQ ID NO: 86.

The term "UBC" refers to any native Ubiquitin C from any vertebrate source, including mammals such as primates (e.g., humans) and rodents (e.g., mice and rats), unless otherwise indicated. The term encompasses "full-length," unprocessed UBC as well as any form of UBC that results from processing in the cell. The term also encompasses naturally occurring variants of UBC, e.g., splice variants or allelic variants. UBC is also referred to in the art as Polyubiquitin-C and HMG20. The nucleic acid sequence of an exemplary human UBC is shown under NCBI Reference Sequence: NM_021009.6 or in SEQ ID NO: 87. The amino acid sequence of an exemplary protein encoded by human UBC is shown under UniProt Accession No. POCG48 or in SEQ ID NO: 88.

The term "SDHA" refers to Succinate Dehydrogenase Complex Flavoprotein Subunit A from any vertebrate source, including mammals such as primates (e.g., humans) and rodents (e.g., mice and rats), unless otherwise indicated. The term encompasses "full-length," unprocessed SDHA as well as any form of SDHA that results from processing in the cell. The term also encompasses naturally occurring variants of SDHA, e.g., splice variants or allelic variants. The nucleic acid sequence of an exemplary human SDHA is shown under NCBI Reference Sequence: NM_001330758 or in SEQ ID NO: 89. The amino acid sequence of an exemplary protein encoded by human SDHA is shown under UniProt Accession No. P31040 or in SEQ ID NO: 90.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but are not limited to, breast cancer (e.g., an HR+ breast cancer (e.g., an ER+ breast cancer (e.g., luminal A breast cancer or luminal B breast cancer)), DCIS, and/or a metastatic or a locally advanced breast cancer)); lung cancer, including small-cell lung cancer, non-small cell lung cancer, adenocarcinoma of the lung, and squamous carcinoma of the lung; bladder cancer (e.g., urothelial bladder cancer (UBC), muscle invasive bladder cancer (MIBC), and BCG-refractory non-muscle invasive bladder cancer (NMIBC)); kidney or renal cancer (e.g., renal cell carcinoma (RCC)); cancer of the urinary tract; prostate cancer, such as castration-resistant prostate cancer (CRPC); cancer of the peritoneum; hepatocellular cancer; gastric or stomach cancer, including gastrointestinal cancer and gastrointestinal stromal cancer; pancreatic cancer; glioblastoma; cervical cancer; ovarian cancer; liver cancer; hepatoma; colon cancer; rectal cancer; colorectal cancer; endometrial or uterine carcinoma; salivary gland carcinoma; prostate cancer; vulval cancer; thyroid cancer; hepatic carcinoma; anal carcinoma; penile carcinoma; melanoma, including superficial spreading melanoma, lentigo maligna melanoma, acral lentiginous melanomas, and nodular melanomas; multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); acute myologenous leukemia (AML); hairy cell leukemia; chronic myeloblastic leukemia (CML); post-transplant lymphoproliferative disorder (PTLD); and myelodysplastic syndromes (MDS), as well as abnormal vascular proliferation associated with phakomatoses, edema (such as that associated with brain tumors), Meigs' syndrome, brain cancer, head and neck cancer, and associated metastases.

The term "breast cancer" as used herein, refers to histologically or cytologically confirmed cancer of the breast. In some embodiments, the breast cancer is a carcinoma. In some embodiments, the breast cancer is an adenocarcinoma. In some embodiments, the breast cancer is a sarcoma. In some embodiments, the breast cancer is an HR+ breast cancer. In some embodiments, the HR+ breast cancer is an ER+ breast cancer. In some embodiments, the ER+ breast cancer is luminal A breast cancer. In some embodiments, the ER+ breast cancer is luminal B breast cancer. In some embodiments, the breast cancer is a metastatic or a locally advanced breast cancer.

The term "locally advanced breast cancer" refers to cancer that has spread from where it started in the breast to nearby tissue or lymph nodes, but not to other parts of the body.

The term "metastatic breast cancer" refers to cancer that has spread from the breast to other parts of the body, such as the bones, liver, lungs, or brain. Metastatic breast cancer may also be referred to as stage IV breast cancer.

The term "ductal carcinoma in situ breast cancer" or (DCIS cancer) refers breast cancers characterized as being intraductal, non-evasive, and pre-invasive primary tumors as understood in the art.

The terms "cell proliferative disorder" and "proliferative disorder" refer to disorders that are associated with some degree of abnormal cell proliferation. In one embodiment, the cell proliferative disorder is a breast cancer (e.g., an HR+ breast cancer (e.g., an ER+ breast cancer (e.g., luminal A breast cancer or luminal B breast cancer)), DCIS, and/or a metastatic or a locally advanced breast cancer). In another embodiment, the cell proliferative disorder is a tumor.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

As used herein, "delaying progression" of a disorder or disease means to defer, hinder, slow, retard, stabilize, and/or postpone development of the disease or disorder (e.g., a breast cancer, e.g., an HR+ breast cancer (e.g., an ER+ breast cancer (e.g., luminal A breast cancer or luminal B breast cancer)), DCIS, and/or a metastatic or a locally advanced breast cancer). This delay can be of varying lengths of time, depending on the history of the disease and/or subject being treated. As is evident to one skilled in the art, a sufficient or significant delay can, in effect, encompass prevention, in that the subject does not develop the disease.

The terms "determination," "determining," "detection," "detecting," and grammatical variations thereof include any means of determining or detecting, including direct and indirect determination or detection.

A "disorder" or "disease" is any condition that would benefit from treatment including, but not limited to, chronic and acute disorders or diseases including those pathological conditions which predispose the mammal to the disorder in question (e.g., a cancer, e.g., a breast cancer, e.g., an HR+ breast cancer (e.g., an ER+ breast cancer (e.g., luminal A breast cancer or luminal B breast cancer)), DCIS, and/or a metastatic or a locally advanced breast cancer).

The term "diagnosis" is used herein to refer to the identification or classification of a molecular or pathological state, disease, or condition (e.g., a cancer, e.g., a breast cancer, e.g., an HR+ breast cancer (e.g., an ER+ breast cancer (e.g., luminal A breast cancer or luminal B breast cancer)), DCIS, and/or a metastatic or a locally advanced breast cancer). For example, "diagnosis" may refer to identification of a particular type of breast cancer. "Diagnosis" may also refer to the classification of a particular subtype of breast cancer, e.g., by histopathological criteria, or by molecular features (e.g., a subtype characterized by expression of a combination of biomarkers (e.g., particular genes or proteins encoded by said genes)).

An "effective amount" of a compound, for example, an endocrine therapy as described herein, or a composition (e.g., pharmaceutical composition) thereof, is at least the minimum amount required to achieve the desired therapeutic or prophylactic result, such as a measurable increase in overall survival (OS) or progression-free survival (PFS) of a particular disease or disorder (e.g., a breast cancer, e.g., an HR+ breast cancer (e.g., an ER+ breast cancer (e.g., luminal A breast cancer or luminal B breast cancer)), DCIS, and/or a metastatic or a locally advanced breast cancer). An effective amount herein may vary according to factors such as the disease state, age, sex, and weight of the individual, and the ability of the antibody to elicit a desired response in the subject. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications, and intermediate pathological phenotypes presenting during development of the disease. An effective amount can be administered in one or more administrations. For purposes provided herein, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved. For example, an effective amount of an endocrine therapy as described herein as a cancer treatment may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The "expression level," "amount," or "level," or used herein interchangeably, of a biomarker is a detectable level in a biological sample. "Expression" generally refers to the process by which information (e.g., gene-encoded and/or epigenetic) is converted into the structures present and operating in the cell. Therefore, as used herein, "expression" may refer to transcription into a polynucleotide, translation into a polypeptide, or even polynucleotide and/or polypeptide modifications (e.g., posttranslational modification of a polypeptide). Fragments of the transcribed polynucleotide, the translated polypeptide, or polynucleotide and/or polypeptide modifications (e.g., posttranslational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs). Expression levels can be measured by methods known to one skilled in the art and also disclosed herein. The expression level or amount of a biomarker can be used to identify/characterize a subject having a breast cancer (e.g., an HR+ breast cancer (e.g., an ER+ breast cancer (e.g., luminal A breast cancer or luminal B breast cancer)), DCIS, and/or a metastatic or a locally advanced breast cancer) who may be likely to respond to, or benefit from, a particular therapy (e.g., a therapy comprising an endocrine therapy, e.g., a SERM (e.g., a SERD), a GnRH agonist, and/or an AI). The expression level or amount of a biomarker provided herein in a subject having a breast cancer described herein can also be used to determine and/or track the benefit of an administered endocrine therapy over time.

Expression levels can be measured using assays and techniques suitable for measuring RNA levels. For example, a RNA-Seq kit can be used to measure expression levels and is suitable for kits as described herein. Exemplary technologies useful in measuring expression levels herein include, but are not limited to, RNA ACCESS® protocol or TRUSEQ® RIBO-ZERO® protocol (ILLUMINA®)), RT-qPCR, qPCR, multiplex qPCR (e.g. fluidigm), nanostring technologies, RT-qPCR, microarray analysis, SAGE, or MassARRAY.

The term "E2-induced score" as used herein, refers to a numerical value that reflects an aggregated expression level of a predetermined set of genes whose induction is reflective of estrogen receptor (ER) pathway activity. For example, an E2-induced score may reflect an aggregated expression level of at least five, six, seven, or eight of the genes set forth in Table 1 (i.e., AMZ1, C5AR2, CELSR2, FKBP4, GREB1, OLFM1, SLC9A3R1, and TFF1), at least the 5, 6, 7, 8, 9, 10, or 11 of the genes set forth in Table 2 (i.e., AMZ1, AREG, C5AR2, CELSR2, FKBP4, FMN1, GREB1, OLFM1, RBM24, SLC9A3R1, and TFF1), or at least the 5, 6, 7, 8, 9, 10, 11, 12, 13, 14, 15, 16, 17, 18, 19, 20, 21, 22, or 23 of the genes set forth in Table 3 (i.e., AGR3, AMZ1, AREG, C5AR2, CELSR2, CT62, FKBP4, FMN1, GREB1, IGFBP4, NOS1AP, NXPH3, OLFM1, PGR, PPM1J, RAPGEFL1, RBM24, RERG, RET, SGK3, SLC9A3R1, TFF1, and ZNF703), whose induction is reflective of estrogen receptor (ER) pathway activity. The aggregated expression level of the predetermined set of genes may determine, for example as an average z-scored expression of the predetermined set of genes detected in a sample (e.g., a tissue sample, e.g., a tumor tissue sample, e.g., a FFPE, a FF, an archival, a fresh, or a frozen tumor tissue sample) obtained from an individual (e.g., an individual having a cancer, e.g., a breast cancer (e.g., an HR+ breast cancer (e.g., an ER+ breast cancer (e.g., luminal A breast cancer or luminal B breast cancer)), DCIS, and/or a metastatic or a locally advanced breast cancer). However, it should be understood that the aggregated expression levels can be determined using methods and known in the art such as, for example, an average expression of genes portrayed onto the space of a reference population or, for example, as an average expression of genes relative to an untreated or vehicle-treated tumor, optionally expressed as a fold change.

The "E2-repressed score" as used herein, refers to a numerical value that reflects an aggregated expression level of a predetermined set of genes whose repression is reflective of estrogen receptor (ER) pathway activity. For example, an E2-repressed score may reflect an aggregated expression level of at least the three, four, five, or six of the genes set forth in Table 4 (i.e., BCAS1, CCNG2, IL1R1, PNPLA7, SEMA3E, and STON1), at least the four, five, six, seven, or eight of the genes set forth in Table 5 (i.e., BCAS1, CCNG2, IL1R1, NBEA, PNPLA7, SEMA3E, STON1, and TP53INP1), or at least the 4, 5, 6, 7, 8, 9, 10, 11, 12, 13, 14, 15, 16, 17, or 18 of the genes set forth in Table 6 (i.e., BAMBI, BCAS1, CCNG2, DDIT4, EGLN3, FAM171B, GRM4, IL1R1, LIPH, NBEA, PNPLA7, PSCA, SEMA3E, SSPO, STON1, TGFB3, TP53INP1, and TP53INP2), whose repression is reflective of estrogen receptor (ER) pathway activity. The aggregated expression level of the predetermined set of genes can be calculated as described above for the E2-induced score an HR+ breast cancer (e.g., an ER+ breast cancer (e.g., luminal A breast cancer or luminal B breast cancer)), DCIS, and/or a metastatic or a locally advanced breast cancer.

The terms "estrogen receptor pathway activity score," "ER pathway activity score," and "composite score for ER pathway activity," as used herein, refer to a numerical value that reflects mathematical difference between the E2-induced score and the E2-repressed score. The ER pathway activity score can be used as a predictive, prognostic, and/or pharmacodynamic biomarker (e.g., to identify an individual having a breast cancer as one who is likely to benefit from a therapy comprising an endocrine therapy or to monitor responsiveness of an individual having a breast cancer to a treatment comprising an endocrine therapy).

The terms "reference estrogen receptor pathway activity score" and "reference ER pathway activity score" refer to an ER pathway activity score against which another ER pathway activity score is compared, e.g., to make a predictive, prognostic, and/or therapeutic determination. For example, the reference ER pathway activity score may be an ER pathway activity score in a reference sample, an ER pathway activity score in a reference population (e.g., a population of patients with HR+ breast cancer), and/or a pre-determined value. In some instances, the reference ER pathway activity score is a cut-off value that significantly separates individuals having a breast cancer with ER pathway activity from individuals having a breast cancer with low or no ER pathway activity (e.g., a reference ER pathway activity score that is at or above −1.0 (e.g., −1.0, −0.9, −0.8, −0.7, −0.6, −0.5, −0.4, −0.3, −0.2, or higher). In some instances, the reference ER pathway activity score is a cut-off value that significantly separates individuals having a breast cancer that are likely to respond to a therapy including an endocrine therapy as described herein from those who are not likely to respond to a therapy including an endocrine therapy (e.g., a reference ER pathway activity score that is at or above −1.0 (e.g., −1.0, −0.9, −0.8, −0.7, −0.6, −0.5, −0.4, −0.3, −0.2, or higher). It will be appreciated by one skilled in the art that the numerical value for the reference ER pathway activity score may vary depending on the type of breast cancer (e.g., an HR+ breast cancer (e.g., an ER+ breast cancer (e.g., luminal A breast cancer or luminal B breast cancer)), DCIS, and/or a metastatic or a locally advanced breast cancer), the methodology used to measure an ER pathway activity score, the specific gene signatures examined (e.g., the combination of genes set forth in Tables 1-6), and/or the statistical methods used to generate an ER pathway activity score. For example, the activity score described herein can be calculated by calculating a z-score for a reference population and using the formula below to re-scale the expression of each gene across the samples to a mean of 0 and a standard deviation of 1. The expression data for a given patient can then be overlayed onto the z-scored reference space as described herein.

The z score may described by the formula: $z=(x-\mu)/\sigma$, where z is the rescaled score, x is gene expression level measured, $\mu$ is the mean gene expression calculated from a reference population; and $\sigma$ is the standard deviation for gene expression calculated from a reference population.

In some embodiments, the reference estrogen receptor pathway activity score is calculated in reference to a standard control as defined herein.

The term "reference E2-induced activity score" refers to an E2-induced activity score against which another E2-induced activity score is compared, e.g., to make a predictive, prognostic, and/or therapeutic determination. For example, the reference E2-induced activity score may be a reference E2-induced activity score in a reference sample, a reference E2-induced activity score in a reference population (e.g., a population of patients with HR+ breast cancer), and/or a pre-determined value. In some instances, the reference E2-induced activity score is a cut-off value that significantly separates individuals having a breast cancer with E2-induced activity from individuals having a breast cancer with low or no E2-induced activity (e.g., a reference E2-induced activity score that is at or above −2.0 (e.g., −2.0, −1.9, −1.8, −1.7, −1.6, −1,5, −1.4, −1.3, −1.2, −1.1, 1.0, −0.9, −0.8, −0.7, −0.6, −0.5, −0.4, −0.3, −0.2, or higher). In some instances, the reference E2-induced activity score is a cut-off value that significantly separates individuals having a breast cancer that are likely to respond to a therapy including an endocrine therapy as described herein from those who are not likely to respond to a therapy including an endocrine therapy (e.g., a reference E2-induced activity score that is at or above −2.0 (e.g., −2.0 (e.g., −2.0, −1.9, −1.8, −1.7, −1.6, −1,5, −1.4, −1.3, −1.2, −1.1, 1.0, −0.9, −0.8, −0.7, −0.6, −0.5, −0.4, −0.3, −0.2, or higher). It will be appreciated by one skilled in the art that the numerical value for the reference E2-induced activity score may vary depending on the type of breast cancer (e.g., an HR+ breast cancer (e.g., an ER+ breast cancer (e.g., luminal A breast cancer or luminal B breast cancer)), DCIS, and/or a metastatic or a locally advanced breast cancer), the methodology used to measure an E2-induced activity score, the specific gene signatures examined (e.g., the combination of genes set forth herein and in, for example, in Tables 1-6), and/or the statistical methods used to generate an E2-induced activity score. A E2-induced activity score can be calculated as described herein for an estrogen receptor pathway activity score. In some embodiments, the E2-induced activity score is calculated in reference to a standard control as defined herein.

The ability to discriminate (e.g. calculate an activity score as defined herein) is relative to the identification/characterization/quantification of expression of the genes described herein and not by the form of the assay used to determine the level of expression of the genes.

A "reference gene" as used herein, refers to a gene or group of genes (e.g., one, two, three, or more genes) that is used for comparison purposes, such as a housekeeping gene. A "housekeeping gene" refers herein to a gene or group of genes (e.g., one, two, three, or more genes) which encode proteins whose activities are essential for the maintenance of cell function and which are typically similarly present in all cell types. Exemplary housekeeping genes include SDHA, GUSB, PPIA, and UBC.

As used herein, the terms "individual," "patient," and "subject" are used interchangeably and refer to any single animal, more preferably a mammal (including such non-human animals as, for example, dogs, cats, horses, rabbits, zoo animals, cows, pigs, sheep, and non-human primates)

for which treatment is desired. In certain embodiments, the individual, patient, or subject is a human.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The word "label" when used herein refers to a detectable compound or composition. The label is typically conjugated or fused directly or indirectly to a reagent, such as a polynucleotide probe or an antibody, and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which results in a detectable product.

The term "modulator" as used herein, refers to an agent that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

The term "degrader" as used herein, refers to an agent that binds to a nuclear hormone receptor and subsequently lowers the steady state protein levels of said receptor. In some embodiments, a degrader as described herein lowers steady state estrogen receptor levels by at least 10%, at least 20%, at least 30%, at least 40%, at least 50%, at least 60%, at least 65%, at least 70%, at least 75%, at least 80%, at least 85%, at least 90%, at least 95%, at least 96%, at least 97%, at least 98%, or at least 99%. In some embodiments, a degrader as described herein lowers steady state estrogen receptor levels by at least 65%. In some embodiments, a degrader as described herein lowers steady state estrogen receptor levels by at least 85%.

The term "nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothioates, phosphoramidates, methyl phosphonates, chiral-methyl phosphonates, 2-O-methyl ribonucleotides, and peptide-nucleic acids (PNAs). The term "oligonucleotide" refers to a relatively short polynucleotide (e.g., less than about 250 nucleotides in length), including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The term "package insert" is used to refer to instructions customarily included in commercial packages of therapeutic products, that contain information about the indications, usage, dosage, administration, combination therapy, contraindications and/or warnings concerning the use of such therapeutic products.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "protein," as used herein, refers to any native protein from any vertebrate source, including mammals such as primates (e.g., humans) and rodents (e.g., mice and rats), unless otherwise indicated. The term encompasses "full-length," unprocessed protein as well as any form of the protein that results from processing in the cell. The term also encompasses naturally occurring variants of the protein, e.g., splice variants or allelic variants.

"Percent (%) sequence identity" with respect to a reference polynucleotide or polypeptide sequence is defined as the percentage of nucleic acids or amino acid residues in a candidate sequence that are identical with the nucleic acids or amino acid residues in the reference polynucleotide or polypeptide sequence, after aligning the sequences and introducing gaps, if necessary, to achieve the maximum percent sequence identity, and not considering any conservative substitutions as part of the sequence identity. Alignment for purposes of determining percent nucleic acid or amino acid sequence identity can be achieved in various ways that are within the skill in the art, for instance, using publicly available computer software such as BLAST, BLAST-2, ALIGN, or Megalign (DNASTAR) software. Those skilled in the art can determine appropriate parameters for aligning sequences, including any algorithms needed to achieve maximal alignment over the full length of the sequences being compared. For purposes herein, however, % sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for nucleic acid or amino acid sequence comparisons, the % sequence identity of a given nucleic acid or amino acid sequence A to, with, or against a given nucleic acid or amino acid sequence B (which can alternatively be phrased as a given nucleic acid or amino acid sequence A that has or comprises a certain % sequence identity to, with, or against a given nucleic acid or amino acid sequence B) is calculated as follows:

100 times the fraction X/Y, where X is the number of nucleic acid or amino acid residues scored as identical matches by the sequence alignment program ALIGN-2 in that program's alignment of A and B, and where Y is the total number of nucleic acid or amino acid residues in B. It will be appreciated that where the length of nucleic acid or amino acid sequence A is not equal to the length of nucleic acid or amino acid sequence B, the % sequence identity of A to B will not equal the % sequence identity of B to A. Unless specifically stated otherwise, all % sequence identity values used herein are obtained as described in the immediately preceding paragraph using the ALIGN-2 computer program.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of polypeptide analysis or protocol, one may use the results of the polypeptide expression analysis or protocol to determine whether a specific therapeutic regimen should be performed. With respect to the embodiment of polynucleotide analysis or protocol, one may use the results of the polynucleotide expression analysis or protocol to determine whether a specific therapeutic regimen should be performed.

"Polynucleotide" or "nucleic acid," as used interchangeably herein, refers to polymers of nucleotides of any length, and includes DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction.

A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The technique of "polymerase chain reaction" or "PCR" as used herein generally refers to a procedure wherein minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor *Symp. Quant. Biol.,* 51: 263 (1987); Erlich, ed., PCR Technology, (Stockton Press, N Y, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

As used herein, the term "reverse transcriptase polymerase chain reaction" or "RT-PCR" refers to the replication and amplification of RNA sequences. In this method, reverse transcription is coupled to PCR, e.g., as described in U.S. Pat. No. 5,322,770, herein incorporated by reference in its entirety. In RT-PCR, the RNA template is converted to cDNA due to the reverse transcriptase activity of an enzyme, and then amplified using the polymerizing activity of the same or a different enzyme. Both thermostable and thermolabile reverse transcriptase and polymerase can be used. The "reverse transcriptase" (RT) may include reverse transcriptases from retroviruses, other viruses, as well as a DNA polymerase exhibiting reverse transcriptase activity.

As used herein, the term "reverse transcriptase quantitative polymerase chain reaction" or "RT-qPCR" is a form of PCR wherein the nucleic acid to be amplified is RNA that is first reverse transcribed into cDNA and the amount of PCR product is measured at each step in a PCR reaction.

"Quantitative real time polymerase chain reaction" or "qRT-PCR" refers to a form of PCR wherein the amount of PCR product is measured at each step in a PCR reaction. This technique has been described in various publications including Cronin et al., Am. J. Pathol. 164(1):35-42 (2004); and Ma et al., *Cancer Cell* 5:607-616 (2004).

The term "multiplex-PCR" refers to a single PCR reaction carried out on nucleic acid obtained from a single source (e.g., an individual) using more than one primer set for the purpose of amplifying two or more DNA sequences in a single reaction.

The term "RNA-seq," also called "Whole Transcriptome Shotgun Sequencing (WTSS)," refers to the use of high-throughput sequencing technologies to sequence and/or quantify cDNA to obtain information about a sample's RNA content. Publications describing RNA-seq include: Wang et al. "RNA-Seq: a revolutionary tool for transcriptomics" *Nature Reviews Genetics* 10 (1): 57-63 (January 2009); Ryan et al. *BioTechniques* 45 (1): 81-94 (2008); and Maher et al. "Transcriptome sequencing to detect gene fusions in cancer". *Nature* 458 (7234): 97-101 (January 2009). Exemplary RNA-seq protocols include the use of RNA ACCESS® protocol or TRUSEQ® RIBO-ZERO® protocol (ILLUMINA®).

"Response to a treatment," "responsiveness to treatment," or "benefit from a treatment" can be assessed using any endpoint indicating a benefit to the individual, including, without limitation, (1) inhibition, to some extent, of disease progression (e.g., breast cancer progression), including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e. reduction, slowing down or complete stopping) of metastasis; (5) relief, to some extent, of one or more symptoms associated with the disease or disorder (e.g., cancer); (6) increase or extend in the length of survival, including recurrence free survival (RFS), disease free survival (DFS), overall survival (OS HR<1) and progression free survival (PFS HR<1); and/or (9) decreased mortality at a given point of time following treatment (e.g., a treatment including an endocrine therapy, a SERM (e.g., a SERD), a GnRH agonist, and/or an AI). Response to a treatment can also refer to a pharmacodynamic response or the response of a pathway (e.g. the ER pathway) and can be assessed using methods known in the art.

As used herein, "progression-free survival" or "PFS" refers to the length of time during and after treatment during which the disease being treated (e.g., breast cancer, e.g., HR+ breast cancer, e.g., ER+ breast cancer, e.g., luminal A or luminal B breast cancer, e.g., advanced or metastatic breast cancer) does not progress or get worse. Progression-free survival may include the amount of time individuals have experienced a complete response or a partial response, as well as the amount of time individuals have experienced stable disease.

As used herein, "overall survival" or "OS" refers to the percentage of subjects in a group who are likely to be alive after a particular duration of time (e.g., 6 months, 1 year, 2 years, 3 years, 4 years, 5 years, 10 years, 15 years, 20 years, or more than 20 years from the time of diagnosis or treatment).

As used herein "recurrence free survival" or "RFS" refers to the length of time after primary treatment ends that the patient survives without any signs, symptoms, or relapses of the tumor in the same local or regional area.

As used herein "disease free survival" or "DFS" refers to the length of time after primary treatment ends that the patient survives without any signs, symptoms, or relapses of the tumor in any area, including development of distant metastases.

As used herein, "complete response" or "CR" refers to disappearance of all signs of cancer in response to treatment. This does not necessarily mean the cancer has been cured.

As used herein, "partial response" or "PR" refers to a decrease in the size of one or more tumors or lesions, or in the extent of cancer in the body, in response to treatment.

As used herein, "hazard ratio" or "HR" is a statistical definition for rates of events. For purposes provided herein, hazard ratio is defined as representing the probability of an event (e.g., PFS or OS) in the experimental (e.g., treatment) group/arm divided by the probability of an event in the control group/arm at any specific point in time. An HR with a value of 1 indicates that the relative risk of an endpoint (e.g., death) is equal in both the "treatment" and "control" groups; a value greater than 1 indicates that the risk is greater in the treatment group relative to the control group; and a value less than 1 indicates that the risk is greater in the control group relative to the treatment group. "Hazard ratio" in progression-free survival analysis (i.e., PFS RR) is a summary of the difference between two progression-free survival curves, representing the reduction in the risk of death on treatment compared to control, over a period of follow-up. "Hazard ratio" in overall survival analysis (i.e., OS HR) is a summary of the difference between two overall survival curves, representing the reduction in the risk of death on treatment compared to control, over a period of follow-up.

By "extending survival" is meant increasing overall survival or progression free survival in a treated individual relative to an untreated individual (i.e. relative to an individual not treated with the medicament), or relative to an individual who does not express a biomarker at the designated level, and/or relative to an individual treated with an approved anti-cancer therapy. An objective response refers to a measurable response, including complete response (CR) or partial response (PR).

By "reduce or inhibit" is meant the ability to cause an overall decrease of 20%, 30%, 40%, 50%, 60%, 70%, 75%, 80%, 85%, 90%, 95%, or greater. Reduce or inhibit can refer to the symptoms of the disorder being treated (e.g., a breast cancer, e.g., an HR+ breast cancer (e.g., an ER+ breast cancer (e.g., luminal A breast cancer or luminal B breast cancer)), DCIS, and/or a metastatic or a locally advanced breast cancer), the presence or size of metastases, or the size of the primary tumor. Reduce or inhibit, when referring to a tumor pathway, refers to the reduction of expression or activity of any component of the pathway (e.g. reduction of the expression ER, reduced activity of ER, or degradation of ER).

A "reference sample," "reference cell," "reference tissue," "control sample," "control cell," or "control tissue," as used herein, refers to a sample, cell, tissue, standard, or level that is used for comparison purposes. In one embodiment, a reference sample, reference cell, reference tissue, control sample, control cell, or control tissue is obtained from the same subject or individual. In another embodiment, a reference sample is obtained from one or more individuals who are not the subject or individual. In either of the preceding embodiments, the one or more individuals from which the reference sample, reference cell, reference tissue, control sample, control cell, or control tissue is obtained has a breast cancer (e.g., e.g., an HR+ breast cancer (e.g., an ER+ breast cancer (e.g., luminal A breast cancer or luminal B breast cancer)), DCIS, and/or a metastatic or a locally advanced breast cancer). In certain embodiments, the one or more individuals from which the reference sample, reference cell, reference tissue, control sample, control cell, or control tissue is obtained has a breast cancer and has been previously treated with an anti-cancer therapy (e.g., one or more doses of an endocrine therapy, e.g., a SERM (e.g., a SERD), a GnRH agonist, and/or an AI). In other embodiments, the one or more individuals from which the reference sample, reference cell, reference tissue, control sample, control cell, or control tissue is obtained has a breast cancer and is treatment naïve. In any of the preceding embodiments, the subject/individual and the one or more individuals who are not the subject or individual have the same breast cancer.

A "standard control" as used herein in reference to the expression level of one or more genes refers to the expression level measured in a control subject (e.g. in a sample form the control subject) or population of control subjects. In embodiments, the control subject is a healthy control subject relative to the subject being tested, wherein the healthy control subject does not have breast cancer. In embodiments, the control subject is the test subject prior to treatment of the test subject, wherein the test subject and control subject have breast cancer. For example, in embodiments, the test subject has been treated for breast cancer with an anticancer agent and the control subject is the test subject prior to treatment. In embodiments, the population of control subjects is a diverse collection of healthy subjects and diseased subjects, wherein the expression level of the test subject is compared to the expression levels of the population of control subjects (e.g. an average of expression levels of the population of control subjects). In embodiments, the population of control subjects is a collection of healthy subjects that do not have breast cancer, wherein the expression level of the test subject is compared to the expression levels of the population of control subjects (e.g. an average of expression levels of the population of control subjects). In embodiments, the population of control subjects is a collection of subjects that have been treated for breast cancer, wherein the expression level of the test subject is compared to the expression levels of the population of control subjects (e.g. an average of expression levels of the population of control subjects).

The term "sample," as used herein, refers to a composition that is obtained or derived from a subject and/or individual of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. Samples include, but are not limited to, tissue extracts such as homogenized tissue, tumor tissue, cellular extracts, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, and combinations thereof.

By "tissue sample" or "cell sample" is meant a collection of similar cells obtained from a tissue of a subject or individual. The source of the tissue or cell sample may be solid tissue as from a FFPE, FF, fresh, frozen, and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease (e.g., breast cancer, e.g., e.g., an HR+ breast cancer (e.g., an ER+ breast cancer (e.g., luminal A breast cancer or luminal B breast cancer)), DCIS, and/or a metastatic or a locally advanced breast cancer) tissue/organ. The tissue sample may contain compounds which are not naturally intermixed with the tissue in nature such as preservatives, anticoagulants, buffers, fixatives, nutrients, antibiotics, or the like.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis, provided that it is understood that the same section of tissue sample may be analyzed at both morphological and molecular levels, or analyzed with respect to both polypeptides and polynucleotides.

As used herein, "treatment" (and grammatical variations thereof, such as "treat" or "treating") refers to clinical intervention in an attempt to alter the natural course of the subject being treated, and can be performed either for prophylaxis or during the course of clinical pathology. Desirable effects of treatment include, but are not limited to, preventing occurrence or recurrence of a disease (e.g., a breast cancer, e.g., e.g., an HR+ breast cancer (e.g., an ER+ breast cancer (e.g., luminal A breast cancer or luminal B breast cancer)), DCIS, and/or a metastatic or a locally advanced breast cancer), alleviation of symptoms, diminishment of any direct or indirect pathological consequences of the disease, preventing metastasis, decreasing the rate of disease progression, amelioration or palliation of the disease state, and remission or improved prognosis. In some embodiments, the treatments described herein are used to delay development of a disease or to slow the progression of a disease (e.g., a breast cancer, e.g., e.g., an HR+ breast cancer (e.g., an ER+ breast cancer (e.g., luminal A breast cancer or luminal B breast cancer)), DCIS, and/or a metastatic or a locally advanced breast cancer). In some instances, the treatment may increase overall survival (OS) (e.g., by about 20% or greater, about 25% or greater, about 30% or greater, about 35% or greater, about 40% or greater, about 45% or greater, about 50% or greater, about 55% or greater, about 60% or greater, about 65% or greater, about 70% or greater, about 75% or greater, about 80% or greater, about 85% or greater, about 90% or greater, about 95% or greater, about 96% or greater, about 97% or greater, about 98% or greater, or about 99% or greater). In some instances, the treatment may increase OS, e.g., by about 5% to about 500%, e.g., from about 10% to about 450%, e.g., from about 20% to about 400%, e.g., from about 25% to about 350%, e.g., from about 30% to about 400%, e.g., from about 35% to about 350%, e.g., from about 40% to about 300%, e.g., from about 45% to about 250%, e.g., from about 50% to about 200%, e.g., from about 55% to about 150%, e.g., from about 60% to about 100%, e.g., from about 65% to about 100%, e.g., from about 70% to about 100%, e.g., from about 75% to about 100%, e.g., from about 80% to about 100%, e.g., from about 85% to about 100%, e.g., from about 90% to about 100%, e.g., from about 95% to about 100%, e.g., from about 98% to about 100%. In some instances, the treatment may increase the progression-free survival (PFS) (e.g., by about 20% or greater, about 25% or greater, about 30% or greater, about 35% or greater, about 40% or greater, about 45% or greater, about 50% or greater, about 55% or greater, about 60% or greater, about 65% or greater, about 70% or greater, about 75% or greater, about 80% or greater, about 85% or greater, about 90% or greater, about 95% or greater, about 96% or greater, about 97% or greater, about 98% or greater, or about 99% or greater). In some instances, the treatment may increase PFS, e.g., by about 5% to about 500%, e.g., from about 10% to about 450%, e.g., from about 20% to about 400%, e.g., from about 25% to about 350%, e.g., from about 30% to about 400%, e.g., from about 35% to about 350%, e.g., from about 40% to about 300%, e.g., from about 45% to about 250%, e.g., from about 50% to about 200%, e.g., from about 55% to about 150%, e.g., from about 60% to about 100%, e.g., from about 65% to about 100%, e.g., from about 70% to about 100%, e.g., from about 75% to about 100%, e.g., from about 80% to about 100%, e.g., from about 85% to about 100%, e.g., from about 90% to about 100%, e.g., from about 95% to about 100%, e.g., from about 98% to about 100%.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

III. Methods

Provided herein are methods and assays for identifying an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer, an ER+ breast cancer (e.g., luminal A breast cancer or luminal B breast cancer)), DCIS, and/or a metastatic or a locally advanced breast cancer who may benefit from a treatment including an endocrine therapy as described herein; selecting a therapy for an individual having breast cancer; treating an individual having breast cancer based on a diagnostic method provided herein; and monitoring therapeutic efficacy of an endocrine therapy. In one embodiment, the endocrine therapy is a compound as set forth herein. In another embodiment, the endocrine therapy is a SERM, a SERD, an AI, or a combination thereof.

The methods and assays described herein are based on the finding that the estradiol (E2)-induced score or estrogen receptor (ER) pathway activity score determined from a sample (e.g., a tissue sample, e.g., a tumor tissue sample, e.g., a FFPE, a FF, an archival, a fresh, or a frozen tumor tissue sample) from an individual may be used to predict the therapeutic efficacy of an endocrine therapy described herein. Any of the methods may further include administering an endocrine therapy (e.g., as described in Section IV-A, below) to the individual.

Accordingly, provided herein are also methods and assays of determining an E2-induced score and/or an ER pathway activity score from a sample from the individual. Any of the methods provided herein may include administering an anti-cancer therapy other than an endocrine therapy (e.g., as described in Section IV-A, below) to the individual. Any of the methods may further include administering an effective amount of an additional therapeutic agent, as described herein, to the individual.

A. Diagnostic Methods and Assays

Predictive Diagnostic Methods and Assays

In particular instances, the methods and assays provided herein may be used to identify an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) who may benefit from a treatment including an endocrine therapy as described herein, the method including determining an ER pathway activity score from a sample (e.g., a tissue sample, e.g., a tumor tissue sample, e.g., a formalin-fixed paraffin-embedded (FFPE), a fresh frozen (FF), an archival, a fresh, or a frozen tumor tissue sample) from the individual, wherein an ER pathway activity score that is at or above a reference ER pathway activity score identifies the individual as one who may benefit from a treatment including an endocrine therapy as described herein.

In particular instances, the methods and assays provided herein may be used to identify an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) who may benefit from a treatment including an endocrine therapy as described herein, the method including determining an E2-induced score from a sample (e.g., a tissue sample, e.g., a tumor tissue sample, e.g., a FFPE, a FF, an archival, a fresh, or a frozen tumor tissue sample) from the individual, wherein an E2-induced score that is at or above a reference E2-induced score identifies the individual as one who may benefit from a treatment including an endocrine therapy as described herein.

In particular instances, the methods and assays provided herein may be used to select a therapy for an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), the method including determining an ER pathway activity score from a sample (e.g., a tissue sample, e.g., a tumor tissue sample, e.g., a FFPE, a FF, an archival, a fresh, or a frozen tumor tissue sample) from the individual, wherein an ER pathway activity score that is at or above a reference ER pathway activity score identifies the individual as one who may benefit from a treatment including an endocrine therapy as described herein.

In particular instances, the methods and assays provided herein may be used to select a therapy for an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), the method including determining an E2-induced score from a sample (e.g., a tissue sample, e.g., a tumor tissue sample, e.g., a FFPE, a FF, an archival, a fresh, or a frozen tumor tissue sample) from the individual, wherein an E2-induced score that is at or above a reference E2-induced score identifies the individual as one who may benefit from a treatment including an endocrine therapy as described herein.

In particular instances, the methods and assays provided herein may be used to identify an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) who may benefit from a treatment including an endocrine therapy as described herein, the method including determining an ER pathway activity score from a sample (e.g., a tissue sample, e.g., a tumor tissue sample, e.g., a FFPE, a FF, an archival, a fresh, or a frozen tumor tissue sample) from the individual, wherein an ER pathway activity score that is below a reference ER pathway activity score identifies the individual as one who is less likely to benefit from a treatment including an endocrine therapy as described herein.

In particular instances, the methods and assays provided herein may be used to identify an individual having a breast cancer who may benefit from a treatment including an endocrine therapy as described herein, the method including determining an E2-induced score from a sample (e.g., a tissue sample, e.g., a tumor tissue sample, e.g., a FFPE, a FF, an archival, a fresh, or a frozen tumor tissue sample) from the individual, wherein an E2-induced score that is below a reference E2-induced score identifies the individual as one who is less likely to benefit from a treatment including an endocrine therapy as described herein.

In particular instances, the methods and assays provided herein may be used to select a therapy for an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), the method including determining an ER pathway activity score from a sample (e.g., a tissue sample, e.g., a tumor tissue sample, e.g., a FFPE, a FF, an archival, a fresh, or a frozen tumor tissue sample) from the individual, wherein an ER pathway activity score that is below a reference ER pathway activity score identifies the individual as one who is less likely to benefit from a treatment including an endocrine therapy as described herein. For example, the method involves selecting an anti-cancer therapy for the individual other than an endocrine therapy.

In particular instances, the methods and assays provided herein may be used to select a therapy for an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), the method including determining an E2-induced score from a sample (e.g., a tissue sample, e.g., a tumor tissue sample, e.g., a FFPE, a FF, an archival, a fresh, or a frozen tumor tissue sample) from the individual, wherein an E2-induced score that is below a reference E2-induced score identifies the individual as one who is less likely to benefit from a treatment including an endocrine therapy as described herein. For example, the method involves selecting an anti-cancer therapy for the individual other than an endocrine therapy.

In particular instances, the methods and assays provided herein may be used to identify an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) who may benefit from a treatment including an anti-cancer therapy other than an endocrine therapy, the method including determining an ER pathway activity score from a sample (e.g., a tissue sample, e.g., a tumor tissue sample, e.g., a FFPE, a FF, an archival, a fresh, or a frozen tumor tissue sample) from the individual, wherein an ER pathway activity score that is below a reference ER pathway activity score identifies the individual as one who may benefit from a treatment including an anti-cancer therapy other than an endocrine therapy.

In particular instances, the methods and assays provided herein may be used to identify an individual having a breast cancer who may benefit from a treatment including an anti-cancer therapy other than an endocrine therapy, the method including determining an E2-induced score from a sample (e.g., a tissue sample, e.g., a tumor tissue sample, e.g., a FFPE, a FF, an archival, a fresh, or a frozen tumor tissue sample) from the individual, wherein an E2-induced score that is below a reference E2-induced score identifies the individual as one who may benefit from a treatment including an anti-cancer therapy other than an endocrine therapy.

In particular instances, the methods and assays provided herein may be used to select a therapy for an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), the method including determining an ER pathway activity score from a sample (e.g., a tissue sample, e.g., a tumor tissue sample, e.g., a FFPE, a FF, an archival, a fresh, or a frozen tumor tissue sample) from the individual, wherein an ER pathway activity score that is below a reference ER pathway activity score identifies the individual as one who may benefit from a treatment including an anti-cancer therapy other than an endocrine therapy.

In particular instances, the methods and assays provided herein may be used to select a therapy for an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), the method including determining an E2-induced score from a sample (e.g., a tissue sample, e.g., a tumor tissue sample, e.g., a FFPE, a FF, an archival, a fresh, or a frozen tumor tissue sample) from the individual, wherein an E2-induced score that is below a reference E2-induced score identifies the individual as one who may benefit from a treatment including an anti-cancer therapy other than an endocrine therapy.

In any of the preceding instances, the reference ER pathway activity score may be an ER pathway activity score in a reference population of individuals having an HR+ breast cancer (e.g., an ER+ breast cancer (e.g., luminal A breast cancer or luminal B breast cancer)), DCIS, and/or a metastatic or a locally advanced breast cancer). In some instances, the reference population is a population of individuals who have not received a treatment including an endocrine therapy as described herein. In some instances, the reference population is a population of individuals who have not received a prior endocrine therapy as described herein. In some instances, the reference population is a population of individuals who are not currently receiving an anti-cancer treatment, including an endocrine therapy as described herein. In some instances, the reference ER pathway activity score may be a pre-assigned reference ER pathway activity score. In some instances, the reference ER pathway activity score may be at or above −1.0 (e.g., −1.0, −0.9, −0.8, −0.7, −0.6, −0.5, −0.4, −0.3, −0.2, or higher). For example, in some instances, the reference ER pathway activity score may be at or above −0.9. In some instances, the reference ER pathway activity score may be at or above −0.8. In some instances, the reference ER pathway activity score may be at or above −0.7. In some instances, the reference ER pathway activity score may be at or above −0.6. In some instances, the reference ER pathway activity score may be at or above −0.5. In some instances, the reference ER pathway activity score may be at or above −0.4. In some instances, the reference ER pathway activity score may be at or above −0.3. In some instances, the reference ER pathway activity score may be at or above −0.2. In some instances, the reference ER pathway activity score may be between about −1.0 to about −0.2 (e.g., between about −0.9 to about −0.2, e.g., between about −0.8 to about −0.2, e.g., between about −0.7 to about −0.2, e.g., between about −0.6 to about −0.2, e.g., between about −0.5 to about −0.2, e.g., between about −0.4 to about −0.2, or e.g., between about −0.3 to about −0.2).

In any of the preceding instances, the ER pathway activity score from the sample (e.g., a tissue sample, e.g., a tumor tissue sample, e.g., a FFPE, a FF, an archival, a fresh, or a frozen tumor tissue sample) from the individual may be at or above −1.0 (e.g., −1.0, −0.9, −0.8, −0.7, −0.6, −0.5, −0.4, −0.3, −0.2 or higher). For example, in some instances, the ER pathway activity score may be at or above −0.9. In some instances, the ER pathway activity score may be at or above −0.8. In some instances, the ER pathway activity score may be at or above −0.7. In some instances, the ER pathway activity score may be at or above −0.6. In some instances, the ER pathway activity score may be at or above −0.5. In some instances, the ER pathway activity score may be at or above −0.4. In some instances, the ER pathway activity score may be at or above −0.3. In some instances, the ER pathway activity score may be at or above −0.2. In some instances, the ER pathway activity score may be between about −1.0 to about −0.2 (e.g., between about −0.9 to about −0.2, e.g., between about −0.8 to about −0.2, e.g., between about −0.7 to about −0.2, e.g., between about −0.6 to about −0.2, e.g., between about −0.5 to about −0.2, e.g., between about −0.4 to about −0.2, or e.g., between about −0.3 to about −0.2). In some instances, the ER activity score from the sample may be less than −1.0.

In any of the preceding instances, the reference E2-induced score may be an E2-induced score in a reference population of individuals having a hormone receptor (HR)+ breast cancer (e.g., an ER+ breast cancer (e.g., luminal A breast cancer or luminal B breast cancer)) and/or a metastatic or a locally advanced breast cancer). In some instances, the reference population is a population of individuals who have not received a treatment including an endocrine therapy as described herein. In some instances, the reference E2-induced score may be a pre-assigned reference E2-induced score. In some instances, the reference E2-induced score may be at or above −2.0 (e.g., −2.0, −1.0, −0.9, −0.8, −0.7, −0.6, −0.5, −0.4, −0.3, −0.2, or higher). For example, in some instances, the reference E2-induced score may be at or above −1.0. In some instances, the reference E2-induced score may be at or above −0.9. In some instances, the reference E2-induced score may be at or above −0.8. In some instances, the reference E2-induced score may be at or above −0.7. In some instances, the reference E2-induced score may be at or above −0.6. In some instances, the reference E2-induced score may be at or above −0.5. In some instances, the reference E2-induced score may be at or above −0.4. In some instances, the reference E2-induced score may be at or above −0.3. In some instances, the reference E2-induced score may be at or above −0.2. In some instances, the reference E2-induced score may be at or above −0.1. In some instances, the reference E2-induced score may be between about −2.0 to about −0.1 (e.g., between about −1.0 to about −0.1, e.g., between about −0.7 to about −0.1, e.g., between about −0.6 to about −0.1, e.g., between about −0.5 to about −0.1, e.g., between about −0.4 to about −0.1, e.g., between about −0.3 to about −0.1, or e.g., between about −0.2 to about −0.1).

In any of the preceding instances, the E2-induced score from the sample (e.g., a tissue sample, e.g., a tumor tissue sample, e.g., a FFPE, a FF, an archival, a fresh, or a frozen tumor tissue sample) from the individual may be at or above −2.0 (e.g., −2.0, −1.0, −0.9, −0.8, −0.7, −0.6, −0.5, −0.4, −0.3, −0.2, −0.1 or higher). For example, in some instances, the E2-induced score may be at or above −1.0. In some instances, the E2-induced score may be at or above −0.9. In some instances, the E2-induced score may be at or above −0.8. In some instances, the E2-induced score may be at or above −0.7. In some instances, the E2-induced score may be at or above −0.6. In some instances, the E2-induced score may be at or above −0.5. In some instances, the E2-induced score may be at or above −0.4. In some instances, the E2-induced score may be at or above −0.3. In some instances, the E2-induced score may be at or above −0.2. In some instances, the E2-induced score may be at or above −0.1. In some instances, the E2-induced score may be between about −2.0 to about −0.1 (e.g., between about −1.0 to about −0.1, e.g., between about −0.7 to about −0.1, e.g., between about −0.6 to about −0.1, e.g., between about −0.5 to about −0.1, e.g., between about −0.4 to about −0.1, e.g., between about −0.3 to about −0.1, or e.g., between about −0.2 to about −0.1). In some instances, the E2-induced score from the sample may be less than −2.0.

In any of the predictive methods and assays described above, the methods and assays may further include administering to the individual an endocrine therapy (e.g., as described in Section IV-A, below). In particular instances, when the ER pathway activity score from a sample (e.g., a tissue sample, e.g., a tumor tissue sample, e.g., a FFPE, a FF, an archival, a fresh, or a frozen tumor tissue sample) from an individual is at or above a reference ER pathway activity score, the method further includes administering to the individual an endocrine therapy. In particular instances, when the E2-induced score from a sample (e.g., a tissue sample, e.g., a tumor tissue sample, e.g., a FFPE, a FF, an archival, a fresh, or a frozen tumor tissue sample) from an individual) is at or above a reference E2-induced score, the method further includes administering to the individual an endocrine therapy.

In any of the predictive methods and assays described above, the methods and assays may further include administering to the individual an anti-cancer therapy other than an endocrine therapy (e.g., as described in Section IV-A, below). In particular instances, when the ER pathway activity score from a sample (e.g., a tissue sample, e.g., a tumor tissue sample, e.g., a FFPE, a FF, an archival, a fresh, or a frozen tumor tissue sample) from an individual is below a reference ER pathway activity score, the method further includes administering to the individual an anti-cancer therapy other than an endocrine therapy. In particular instances, when the E2-induced score from a sample (e.g., a tissue sample, e.g., a tumor tissue sample, e.g., a FFPE, a FF, an archival, a fresh, or a frozen tumor tissue sample) from an individual is below a reference E2-induced score, the method further includes administering to the individual an anti-cancer therapy other than an endocrine therapy.

The methods provided herein may include determining an ER pathway activity score from a sample (e.g., a tissue sample, e.g., a tumor tissue sample, e.g., a FFPE, a FF, an archival, a fresh, or a frozen tumor tissue sample) from an individual. The methods provided herein may include determining an E2-induced score from a sample (e.g., a tissue sample, e.g., a tumor tissue sample, e.g., a FFPE, a FF, an archival, a fresh, or a frozen tumor tissue sample) from an individual. In some instances, the sample may be a FFPE tumor tissue sample. In some instances, the sample may be a FF tumor tissue sample.

In any of the preceding instances, the individual may have an HR+ breast cancer. In some instances, the HR+ cancer may be an ER+ breast cancer. In some instances, the individual may have an ER+ breast cancer selected from, for example, a luminal A breast cancer or a luminal B breast cancer. In some instances, the breast cancer may be an advanced or a metastatic breast cancer.

In some instances of any of the preceding methods or assays involving determining an ER pathway activity score and/or E2-induced score from a sample (e.g., a tissue sample, e.g., a tumor tissue sample, e.g., a FFPE, a FF, an archival, a fresh, or a frozen tumor tissue sample) from an individual, the individual has been previously treated with an endocrine therapy as described herein. In other instances, the individual has not been previously treated with an endocrine therapy. In another embodiment, the individual has received one or more prior therapies prior to performing the methods and assays described herein where such therapy may be an endocrine therapy or a non-endocrine therapy as described herein.

In some instances, the methods further comprise generating a report, e.g., an electronic, web-based, or paper report, to the individual or to another person or entity, a caregiver, a physician, an oncologist, a hospital, clinic, third-party payor, insurance company, a pharmaceutical or biotechnology company, or government office. In some embodiments, the report comprises output from the method which comprises evaluation of the ER pathway activity and/or E2-induced score.

Pharmacodynamic Diagnostic Methods

Also provided herein are pharmacodynamics methods. In some instances, the methods may involve monitoring a response of an individual to treatment with an endocrine therapy as described herein.

In some instances, the method includes: (a) determining an ER pathway activity score from a sample (e.g., a tissue sample, e.g., a tumor tissue sample, e.g., a FFPE, a FF, an archival, a fresh, or a frozen tumor tissue sample) from the individual at a first time point; (b) following step (a), determining a second ER pathway activity score from a sample from the individual at a second time point following administration of an endocrine therapy as described herein; and (c) comparing the first ER pathway activity score with the second ER pathway activity score, wherein a decrease (e.g., a decrease in the ER pathway activity score of about 0.1, 0.2, 0.3, or greater) in the second ER pathway activity score relative to the first ER pathway activity score is predictive of an individual who is likely to respond to treatment with an endocrine therapy e.g., a SERM (e.g., a SERD), a GnRH agonist, and/or an AI. In some instances, a decrease in the ER pathway activity score refers to an overall decrease of the ER pathway activity score of at least 0.1. In some instances, a decrease in the ER pathway activity score refers to an overall decrease of the ER pathway activity score of at least 0.2. In some instances, a decrease in the ER pathway activity score refers to an overall decrease of the ER pathway activity score of at least 0.3.

In some instances, the method further comprises administering one or more additional doses of the endocrine therapy if the second ER pathway activity score in the sample (e.g., a tissue sample, e.g., a tumor tissue sample, e.g., a formalin-fixed paraffin-embedded (FFPE), a fresh frozen (FF), an archival, a fresh, or a frozen tumor tissue sample) from the individual is decreased relative to the first ER pathway activity score. In some instances, a decreased ER pathway activity score refers to an overall decrease of the ER pathway activity score of at least 0.1 (e.g., a decrease of 0.1, 0.2, 0.3, or greater). In some instances, a decreased ER pathway activity score refers to an overall decrease of the ER pathway activity score of at least 0.2. In some instances, a decreased ER pathway activity refers to an overall decrease of ER pathway activity score of at least 0.3.

In some instances of any of the preceding methods, the first ER pathway activity score is an ER pathway activity score determined from a sample (e.g., a tissue sample, e.g., a tumor tissue sample, e.g., a FFPE, a FF, an archival, a fresh, or a frozen tumor tissue sample) from the individual obtained prior to administration of a first dose of an endocrine therapy as described herein. In other words, the sample may be a baseline sample. In other instances, the first ER pathway activity score is an ER pathway activity score determined from a sample from the individual obtained at a previous time point, wherein the previous time point is following administration of a first dose of an endocrine therapy as described herein. In other instances, the first ER pathway activity score is an ER pathway activity score determined from a sample from the individual obtained at a previous time point, wherein the previous time point is following administration of a first dose of a non-endocrine therapy as described herein. In other instances, the first ER pathway activity score is a pre-determined ER pathway activity score.

In some instances, the method includes: (a) determining an E2-induced score from a sample (e.g., a tissue sample, e.g., a tumor tissue sample, e.g., a FFPE, a FF, an archival, a fresh, or a frozen tumor tissue sample) from the individual at a first time point; (b) following step (a), determining a second E2-induced score from a sample from the individual at a second time point following administration of an endocrine therapy as described herein; and (c) comparing the first E2-induced score with the second E2-induced score, wherein a decrease (e.g., a decrease in the E2-induced score of at least 0.1, 0.2, 0.3, or greater) in the second E2-induced score relative to the first E2-induced score is predictive of an individual who is likely to respond to treatment with an endocrine therapy as described herein. In some instances, a decrease in the E2-induced score refers to an overall decrease of at least 0.1. In some instances, a decrease in the E2-induced score refers to an overall decrease of at least 0.2. In some instances, a decrease in the E2-induced score refers to an overall decrease of at least 0.3.

In some instances, the method further comprises administering one or more additional doses of the endocrine therapy as described herein if the second E2-induced in the sample (e.g., a tissue sample, e.g., a tumor tissue sample, e.g., a FFPE, a FF, an archival, a fresh, or a frozen tumor tissue sample) is decreased relative to the first E2-induced score. In some instances, a decreased E2-induced score refers to an overall decrease of the E2-induced score of at least 0.1 (e.g., a decrease of 0.1, 0.2, 0.3, or greater). In some instances, a decreased E2-induced score refers to an overall decrease of the E2-induced score of at least 0.2. In some instances, a decreased E2-induced score refers to an overall decrease of the E2-induced score of at least 0.3.

In some instances of any of the preceding methods, the first E2-induced score is E2-induced score determined from a sample (e.g., a tissue sample, e.g., a tumor tissue sample, e.g., a FFPE, a FF, an archival, a fresh, or a frozen tumor tissue sample) from the individual obtained prior to administration of a first dose of an anti-cancer therapy (e.g., an endocrine therapy as described herein. In other words, the sample may be a baseline sample. In other instances, the first E2-induced score is an E2-induced score determined from a sample from the individual obtained at a previous time point, wherein the previous time point is following administration of a first dose of an endocrine therapy as described herein. In other instances, the first E2-induced score is a pre-determined E2-induced score.

In some instances, the second ER pathway activity score from the sample (e.g., a tissue sample, e.g., a tumor tissue sample, e.g., a FFPE, a FF, an archival, a fresh, or a frozen tumor tissue sample) from the individual is decreased relative to the first ER pathway activity score, and the method or assay further involves administering an additional dose of an endocrine therapy as described herein to the individual. In some instances, the second E2-induced score from the sample (e.g., a tissue sample, e.g., a tumor tissue sample, e.g., a FFPE, a FF, an archival, a fresh, or a frozen tumor tissue sample) from the individual is decreased relative to the first E2-induced score, and the method or assay further involves administering an additional dose of an endocrine therapy as described herein to the individual.

The methods provided herein may include determining an ER pathway activity score from a sample (e.g., a tissue sample, e.g., a tumor tissue sample, e.g., a FFPE, a FF, an archival, a fresh, or a frozen tumor tissue sample) from an individual. The methods provided herein may include determining an E2-induced score from a sample (e.g., a tissue sample, e.g., a tumor tissue sample, e.g., a FFPE, a FF, an archival, a fresh, or a frozen tumor tissue sample) from an individual. In some instances, the sample may be a FFPE tumor tissue sample. In some instances, the sample may be a FF tumor tissue sample.

In any of the preceding instances, the individual may have an HR+ breast cancer. In some instances, the HR+ cancer may be an ER+ breast cancer. In some instances, the individual may have an ER+ breast cancer selected from, for example, a luminal A breast cancer or a luminal B breast cancer. In some instances, the breast cancer may be an advanced or a metastatic breast cancer.

In some instances of any of the preceding methods or assays involving determining an ER pathway activity score and/or E2-induced score from a sample (e.g., a tissue sample, e.g., a tumor tissue sample, e.g., a FFPE, a FF, an archival, a fresh, or a frozen tumor tissue sample) from the individual, the individual has been previously treated with an endocrine therapy as described herein. In other instances, the individual has not been previously treated with an endocrine therapy. In some instances of any of the methods and assays, the sample (e.g., a tissue sample, e.g., a tumor tissue sample, e.g., a FFPE, a FF, an archival, a fresh, or a frozen tumor tissue sample) is obtained from the individual prior to (e.g., minutes, hours, days, weeks, months, or years prior to) administration of an endocrine therapy as described herein. In other words, the sample may be a baseline sample. In some instances of any of the preceding methods, the sample is obtained from the individual following (e.g., minutes, hours, or days following) administration of an endocrine therapy. In some instances, the sample from the individual is obtained within thirty hours following administration of an endocrine therapy. In some instances, multiple samples are obtained from the same individual at different time points (e.g., prior to and following administration of an endocrine therapy).

In some instances, the methods further comprise generating a report, e.g., an electronic, web-based, or paper report, to the individual or to another person or entity, a caregiver, a physician, an oncologist, a hospital, clinic, third-party payor, insurance company, a pharmaceutical or biotechnology company, or government office. In some instances, the report comprises output from the method which comprises evaluation of the ER pathway activity and/or E2-induced score.

In one aspect, a method of detecting estrogen receptor (ER) pathway activity in a subject that has breast cancer is provided. The method includes detecting an expression level of at least five genes set forth in Table 1 and at least five genes set forth in Table 4; at least five genes set forth in Table 2 and at least five genes set forth in Table 5; or at least five genes set forth in Table 3 and at least five genes set forth in Table 6.

Controls used for the methods provided herein are valuable for determining the significance of data. For example, if values for a given parameter are widely variant in controls, variation in test samples will not be considered as significant. In some examples of the disclosed methods, when the expression level of any of the genes provided in Table 1-6 is assessed, the expression level is compared with a control expression level of the gene. By control expression level is meant the expression level of a gene from a sample or subject lacking breast cancer, a sample or subject at a selected stage of breast cancer or cancer state, or in the absence of a particular variable such as a therapeutic agent. Alternatively, the control level comprises a known amount of the gene. Such a known amount correlates with an average level of subjects lacking breast cancer, at a selected stage of breast cancer or cancer state, or in the absence of a particular variable such as a therapeutic agent. A control level also includes the expression level of the gene from one or more selected samples or subjects as described herein. For example, a control level includes an assessment of the expression level of the gene in a sample from a subject that does not have breast cancer, is at a selected stage of breast cancer or cancer state, or have breast cancer but have not yet received treatment for breast cancer. Another exemplary control level includes an assessment of the expression level of the gene in samples taken from multiple subjects that do not have breast cancer, are at a selected stage of cancer, or have cancer but have not yet received treatment for breast cancer. In embodiments, a threshold for elevated gene expression levels is above the median expression level of a group of control sample, where the control sample is optionally a group of subjects who have breast cancer.

In embodiments, the method includes detecting an expression level of at least five (e.g., 5, 6, 7, 8, etc.) genes set forth in Table 1 and at least five genes set forth in Table 4. In embodiments, the method includes detecting an expression level of at least five genes set forth in Table 2 and at least five genes set forth in Table 5. In embodiments, the method includes detecting an expression level of at least five genes set forth in Table 3 and at least five genes set forth in Table 6.

In embodiments, the expression level of the at least five genes set forth in Table 1, at least five genes set forth in Table 2 or at least five genes set forth in Table 3 are greater than a standard control. In embodiments, the expression level of all the genes set forth in Table 1, all of the genes set forth in Table 2 or all of the genes set forth in Table 3 are greater than a standard control. In embodiments, the expression level of the at least five genes set forth in Table 1 are greater than a standard control. In embodiments, the expression level of all genes set forth in Table 1 are greater than a standard control. In embodiments, the expression level of the at least five genes set forth in Table 2 are greater than a standard control. In embodiments, the expression level of all genes set forth in Table 2 are greater than a standard control. In embodiments, the expression level of the at least five genes set forth in Table 3 are greater than a standard control. In embodiments, the expression level of all genes set forth in Table 3 are greater than a standard control.

In embodiments, a threshold for elevated gene expression levels (e.g., expression of any one gene set forth in Table 1-6) is above the median expression level of a group of control samples, where the control sample is optionally a group of subjects who have breast cancer. In embodiments, it is above the first quartile of gene expression in a group of control samples, where the control sample is optionally a group of subjects who have breast cancer. In embodiments, it is above the third quartile of gene expression in a group of control samples, where the control sample is optionally a group of subjects who have breast cancer. In embodiments, it is above the 5th percentile of gene expression in a group of control samples, where the control sample is optionally a group of subjects who have breast cancer. In embodiments, it is above the 10th percentile of gene expression in a group of control samples, where the control sample is optionally a group of subjects who have breast cancer. In embodiments, it is above the 20th percentile of gene expression in a group of control samples, where the control sample is optionally a group of subjects who have breast cancer. In embodiments, it is above the 30th percentile of gene expression in a group of control samples, where the control sample is optionally a group of subjects who have breast cancer. In embodiments, it is above the 40th percentile of gene expression in a group of control samples, where the control sample is optionally a group of subjects who have breast cancer. In embodiments, it is above the 45th percentile of gene expression in a group of control samples, where the control sample is optionally a group of subjects who have breast cancer. In embodiments, it is above the 50th percentile of gene expression in a group of control samples, where the control sample is optionally a group of subjects who have breast cancer. In embodiments, it is above the 60th percentile of gene expression in a group of control samples, where the control sample is optionally a group of subjects who have breast cancer. In embodiments, it is above the 70th percentile of gene expression in a group of control samples, where the control sample is optionally a group of subjects who have breast cancer. In embodiments, it is above the 80th percentile of gene expression in a group of control samples, where the control sample is optionally a group of subjects who have breast cancer. In embodiments, it is above the 90th percentile of gene expression in a group of control samples, where the control sample is optionally a group of subjects who have breast cancer.

In embodiments, the expression level of the at least five genes set forth in Table 4, at least five genes set forth in Table 5 or at least five genes set forth in Table 6 are less than a standard control. In embodiments, the expression level of all genes set forth in Table 4, of all genes set forth in Table 5 or of all genes set forth in Table 6 are less than a standard control. In embodiments, the expression level of the at least five genes set forth in Table 4 are less than a standard control. In embodiments, the expression level of all genes set forth in Table 4 are less than a standard control. In embodiments, the expression level of the at least five genes set forth in Table 5 are less than a standard control. In embodiments, the expression level of all genes set forth in Table 5 are less than a standard control. In embodiments, the expression level of the at least five genes set forth in Table 6 are less than a standard control. In embodiments, the expression level of all genes set forth in Table 6 are less than a standard control.

In embodiments, a threshold for decreased gene expression levels (e.g., expression of any one gene set forth in Table 1-6) is below the median expression level of a group of control samples, where the control sample is optionally a group of subjects who have breast cancer. In embodiments, it is below the first quartile of gene expression in a group of control samples, where the control sample is optionally a group of subjects who have breast cancer. In embodiments, it is below the third quartile of gene expression in a group of control samples, where the control sample is optionally a group of subjects who have breast cancer. In embodiments, it is below the 5th percentile of gene expression in a group of control samples, where the control sample is optionally a group of subjects who have breast cancer. In embodiments, it is below the 10th percentile of gene expression in a group of control samples, where the control sample is optionally a group of subjects who have breast cancer. In embodiments, it is below the 20th percentile of gene expression in a group of control samples, where the control sample is optionally a group of subjects who have breast cancer. In embodiments, it is below the 30th percentile of gene expression in a group of control samples, where the control sample is optionally a group of subjects who have breast cancer. In embodiments, it is below the 40th percentile of gene expression in a group of control samples, where the control sample is optionally a group of subjects who have breast cancer. In embodiments, it is below the 45th percentile of gene expression in a group of control samples, where the control sample is optionally a group of subjects who have breast cancer. In embodiments, it is below the 50th percentile of gene expression in a group of control samples, where the control sample is optionally a group of subjects who have breast cancer. In embodiments, it is below the 60th percentile of gene expression in a group of control samples, where the control sample is optionally a group of subjects who have breast cancer. In embodiments, it is below the 70th percentile of gene expression in a group of control samples, where the control sample is optionally a group of subjects who have breast cancer. In embodiments, it is below the 80th percentile of gene expression in a group of control samples, where the control sample is optionally a group of subjects who have breast cancer. In embodiments, it is below the 90th percentile of gene expression in a group of control samples, where the control sample is optionally a group of subjects who have breast cancer.

In embodiments, the subject has been treated with an endocrine therapy prior to the detecting. In embodiments, the subject is treated with an endocrine therapy subsequent to the detecting.

In embodiments, the method includes detecting an expression level of all genes set forth in Table 1 and all genes set forth in Table 4. In embodiments, the method includes detecting an expression level of all genes set forth in Table 2 and all genes set forth in Table 5. In embodiments, the method includes detecting an expression level of all genes set forth in Table 3 and all genes set forth in Table 6. In embodiments, the method includes detecting an expression level of all genes set forth in Table 1 and all genes set forth in Table 4 and not detecting an expression level of any other genes in the subject. In embodiments, the method includes detecting an expression level of all genes set forth in Table 2 and all genes set forth in Table 5 and not detecting an expression level of any other genes in the subject. In embodiments, the method includes detecting an expression level of all genes set forth in Table 3 and all genes set forth in Table 6 and not detecting an expression level of any other genes in the subject.

In embodiments, the subject is treated with an endocrine therapy where the endocrine therapy is a selective estrogen receptor degrader.

In embodiments, the method includes determining an estrogen receptor (ER) pathway activity score from a sample from the subject. In embodiments, an ER pathway activity score from the sample that is at or above a reference ER pathway activity score identifies the individual as one who may benefit from a treatment including an endocrine therapy. In embodiments, the method includes comparing an ER pathway activity score from the sample that is at or above a reference ER pathway activity score identifies the individual as one who may benefit from a treatment including an endocrine therapy.

In one aspect a method is provided, the method includes detecting, by one or more processors, a first expression level of at least five genes set forth in Table 1, at least five genes set forth in Table 2, or at least five genes set forth in Table 3; detecting, by the one or more processors, a second expression level of at least five genes set forth in Table 4, at least five genes set forth in Table 5 or at least five genes set forth in Table 6; and detecting, based at least on the first expression level and/or the second expression level, estrogen receptor (ER) pathway activity in a subject that has cancer. In embodiments, the first expression is elevated relative to the second expression level. In embodiments, the first expression is decreased relative to the second expression level.

In embodiments, a threshold for an elevated first gene expression level (e.g., a first expression level of any one gene set forth in Table 1-6) is above the second expression level. In embodiments, it is above the first quartile of the second gene expression level. In embodiments, it is above the third quartile of the second gene expression level. In embodiments, it is above the 5th percentile of the second gene expression level. In embodiments, it is above the 10th percentile of the second gene expression level. In embodiments, it is above the 20th percentile of the second gene expression level. In embodiments, it is above the 30th percentile of the second gene expression level. In embodiments, it is above the 40th percentile of the second gene expression level. In embodiments, it is above the 45th percentile of the second gene expression level. In embodiments, it is above the 50th percentile of the second gene expression level. In embodiments, it is above the 60th percentile of the second gene expression level. In embodiments, it is above the 70th percentile of the second gene expression level. In embodiments, it is above the 80th percentile of the second gene expression level. In embodiments, it is above the 90th percentile of the second gene expression level.

In embodiments, a threshold for a decreased first gene expression level (e.g., a first expression level of any one gene set forth in Table 1-6) is below the second expression level. In embodiments, it is below the first quartile of the second gene expression level. In embodiments, it is below the third quartile of the second gene expression level. In embodiments, it is below the 5th percentile of the second gene expression level. In embodiments, it is below the 10th percentile of the second gene expression level. In embodiments, it is below the 20th percentile of the second gene expression level. In embodiments, it is below the 30th percentile of the second gene expression level. In embodiments, it is below the 40th percentile of the second gene expression level. In embodiments, it is below the 45th percentile of the second gene expression level. In embodiments, it is below the 50th percentile of the second gene expression level. In embodiments, it is below the 60th percentile of the second gene expression level. In embodiments, it is below the 70th percentile of the second gene expression level. In embodiments, it is below the 80th percentile of the second gene expression level. In embodiments, it is below the 90th percentile of the second gene expression level.

In embodiments, the expression level of the at least five genes set forth in Table 1, at least five genes set forth in Table 2 or at least five genes set forth in Table 3 are greater than a standard control. In embodiments, the expression level of the at least five genes set forth in Table 4, at least five genes set forth in Table 5 or at least five genes set forth in Table 6 are less than a standard control.

In embodiments, the method includes treating the subject with an endocrine therapy prior to the detecting. In embodiments, the method includes treating, based at least on the estrogen receptor (ER) pathway activity detected in the subject, the subject with an endocrine therapy.

B. Therapeutic Methods

Also provided herein are methods for treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer). Accordingly, in some instances, the methods provided herein include administering to the individual an endocrine therapy as described herein. In other instances, the methods provided herein include administering to the individual an anti-cancer agent other than an endocrine therapy. Any of the anti-cancer agents described herein (e.g., in Section IV, below), or known in the art may be used in connection with the methods.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) that includes (i) determining an ER pathway activity score from a sample (e.g., a tissue sample, e.g., a tumor tissue sample, e.g., a FFPE, a FF, an archival, a fresh, or a frozen tumor tissue sample) from the individual, wherein the ER pathway activity score is determined to be at or above a reference ER pathway activity score (e.g., a reference ER pathway activity score in a reference population, e.g., a reference ER pathway activity score at or above −1.0); and (ii) administering to the individual an effective amount of an endocrine therapy as described herein.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), that includes administering to the individual an endocrine therapy as described herein, wherein the individual has been identified to be more likely to benefit from a treatment comprising an endocrine therapy by one or more of the predictive diagnostic methods described in Section III-A, above.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), that includes administering to the individual an endocrine therapy as described herein, wherein the individual has been identified as having an ER pathway activity score that is at or above a reference ER pathway activity score by any of the predictive diagnostic methods described in Section III-A, above.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) that includes (i) determining an E2-induced score from a sample (e.g., a tissue sample, e.g., a tumor tissue sample, e.g., a FFPE, a FF, an archival, a fresh, or a frozen tumor tissue sample) from the individual, wherein the E2-induced score is determined to be at or above a reference E2-induced score (e.g., a reference E2-induced score in a reference population, e.g., a reference E2-induced score at or above −2.0); and (ii) administering to the individual an effective amount of an endocrine therapy as described herein.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), that includes administering to the individual an endocrine therapy as described herein, wherein the individual has been identified as having an E2-induced score that is at or above a reference E2-induced score by any of the predictive diagnostic methods described in Section III-A, above.

Also provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) that includes (i) determining an ER pathway activity score from a sample (e.g., a tissue sample, e.g., a tumor tissue sample, e.g., a FFPE, a FF, an archival, a fresh, or a frozen tumor tissue sample) from the individual, wherein the ER pathway activity score is determined to be below a reference ER pathway activity score (e.g., a reference ER pathway activity score in a reference population, e.g., a reference ER pathway activity score below −1.0); and (ii) administering to the individual an effective amount of an anti-cancer therapy other than endocrine therapy.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), that includes administering to the individual an effective amount of an anti-cancer therapy other than endocrine therapy, wherein the individual has been identified to be less likely to benefit from a treatment comprising an endocrine therapy by one or more of the predictive diagnostic methods described in Section III-A, above.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), that includes administering to the individual an anti-cancer therapy other than an endocrine therapy, wherein the individual has been identified to be more likely to benefit from a treatment comprising an anti-cancer therapy other than an endocrine therapy by one or more of the predictive diagnostic methods described in Section III-A, above.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), that includes administering to the individual an effective amount of an anti-cancer therapy other than endocrine therapy, wherein the individual has been identified as having an ER pathway activity score that is below a reference ER pathway activity score by any of the predictive diagnostic methods described in Section III-A, above.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) that includes (i) determining an E2-induced score from a sample (e.g., a tissue sample, e.g., a tumor tissue sample, e.g., a FFPE, a FF, an archival, a fresh, or a frozen tumor tissue sample) from the individual, wherein the E2-induced score is determined to be below a reference E2-induced score (e.g., a reference E2-induced score in a reference population, e.g., a reference E2-induced score below −2.0); and (ii) administering to the individual an effective amount of an effective amount of an anti-cancer therapy other than endocrine therapy.

Provided herein is a method of treating an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer), that includes administering to the individual an effective amount of an anti-cancer therapy other than endocrine therapy, wherein the individual has been identified as having an E2-induced score that is below a reference E2-induced score by any of the predictive diagnostic methods described in Section III-A, above.

In any of the preceding instances, the reference ER pathway activity score may be an ER pathway activity score in a reference population of individuals having an HR+ breast cancer (e.g., an ER+ breast cancer (e.g., luminal A breast cancer or luminal B breast cancer)), DCIS, and/or a metastatic or a locally advanced breast cancer). In some instances, the reference population is a population of individuals who have not received a treatment including an endocrine therapy, including those described herein. In some instances, the reference ER pathway activity score may be a pre-assigned reference ER pathway activity score. In some instances, the reference ER pathway activity score may at or above −1.0 (e.g., −1.0, −0.9, −0.8, −0.7, −0.6, −0.5, −0.4, −0.3, and −0.2, or higher). For example, in some instances, the reference ER pathway activity score may be at or above −0.9. In some instances, the reference ER pathway activity score may be at or above −0.8. In some instances, the reference ER pathway activity score may be at or above −0.7. In some instances, the reference ER pathway activity score may be at or above −0.6. In some instances, the reference ER pathway activity score may be at or above −0.5. In some instances, the reference ER pathway activity score may be at or above −0.4. In some instances, the reference ER pathway activity score may be at or above −0.3. In some instances, the reference ER pathway activity score may be at or above −0.2. In some instances, the reference ER pathway activity score may be between about −1.0 to about −0.2 (e.g., between about −0.9 to about −0.2, e.g., between about −0.8 to about −0.2, e.g., between about −0.7 to about −0.2, e.g., between about −0.6 to about −0.2, e.g., between about −0.5 to about −0.2, e.g., between about −0.4 to about −0.2, or e.g., between about −0.3 to about −0.2).

In any of the preceding instances, the ER pathway activity score from the sample (e.g., a tissue sample, e.g., a tumor tissue sample, e.g., a formalin-fixed paraffin-embedded (FFPE), a fresh frozen (FF), an archival, a fresh, or a frozen tumor tissue sample) from the individual may be at, or above −1.0 (e.g., −1.0, −0.9, −0.8, −0.7, −0.6, −0.5, −0.4, −0.3, −0.2 or higher). For example, in some instances, the ER pathway activity score may be at or above −0.9. In some instances, the ER pathway activity score may be at or above −0.8. In some instances, the ER pathway activity score may be at or above −0.7. In some instances, the ER pathway activity score may be at or above −0.6. In some instances, the ER pathway activity score may be at or above −0.5. In some instances, the ER pathway activity score may be at or above −0.4. In some instances, the ER pathway activity score may be at or above −0.3. In some instances, the ER pathway activity score may be at or above −0.2. In some instances, the ER pathway activity score may be between about −1.0 to about −0.2 (e.g., between about −0.9 to about −0.2, e.g., between about −0.8 to about −0.2, e.g., between about −0.7 to about −0.2, e.g., between about −0.6 to about −0.2, e.g., between about −0.5 to about −0.2, e.g., between about −0.4 to about −0.2, or e.g., between about −0.3 to about −0.2). In some instances, the ER activity score from the sample may be less than −1.0.

In any of the preceding instances, the reference E2-induced score may be an E2-induced score in a reference population of individuals having an HR+ breast cancer (e.g., an ER+ breast cancer (e.g., luminal A breast cancer or luminal B breast cancer)), DCIS, and/or a metastatic or a locally advanced breast cancer). In some instances, the reference population is a population of individuals who have not received a treatment including an endocrine therapy as described herein. In some instances, the reference E2-induced score may be a pre-assigned reference E2-induced score. In some instances, the reference E2-induced score may be at or above −2.0 (e.g., −2.0, −1.0, −0.9, −0.8, −0.7, −0.6, −0.5, −0.4, −0.3, −0.2, or higher). For example, in some instances, the reference E2-induced score may be at or above −1.0. In some instances, the reference E2-induced score may be at or above −0.9. In some instances, the reference E2-induced score may be at or above −0.8. In some instances, the reference E2-induced score may be at or above −0.7. In some instances, the reference E2-induced score may be at or above −0.6. In some instances, the reference E2-induced score may be at or above −0.5. In some instances, the reference E2-induced score may be at or above −0.4. In some instances, the reference E2-induced score may be at or above −0.3. In some instances, the reference E2-induced score may be at or above −0.2. In some instances, the reference E2-induced score may be at or above −0.1. In some instances, the reference E2-induced score may be between about −2.0 to about −0.1 (e.g., between about −1.0 to about −0.1, e.g., between about −0.7 to about −0.1, e.g., between about −0.6 to about −0.1, e.g., between about −0.5 to about −0.1, e.g., between about −0.4 to about −0.1, e.g., between about −0.3 to about −0.1, or e.g., between about −0.2 to about −0.1).

In any of the preceding instances, the E2-induced score from the sample (e.g., a tissue sample, e.g., a tumor tissue sample, e.g., a formalin-fixed paraffin-embedded (FFPE), a fresh frozen (FF), an archival, a fresh, or a frozen tumor tissue sample) from the individual may be at, or above −2.0 (e.g., −2.0, −1.0, −0.9, −0.8, −0.7, −0.6, −0.5, −0.4, −0.3, −0.2, −0.1 or higher). In some instances, the E2-induced score may be at or above −1.0. In some instances, the E2-induced score may be at or above −0.9. In some instances, the E2-induced score may be at or above −0.8. For example, in some instances, the E2-induced score may be at or above −0.7. In some instances, the E2-induced score may be at or above −0.6. In some instances, the E2-induced score may be at or above −0.5. In some instances, the E2-induced score may be at or above −0.4. In some instances, the E2-induced score may be at or above −0.3. In some instances, the E2-induced score may be at or above −0.2. In some instances, the E2-induced score may be at or above −0.1. In some instances, the E2-induced score may be between about −2.0 to about −0.1 (e.g., between about −1.0 to about −0.1, e.g., between about −0.7 to about −0.1, e.g., between about −0.6 to about −0.1, e.g., between about −0.5 to about −0.1, e.g., between about −0.4 to about −0.1, e.g., between about −0.3 to about −0.1, or e.g., between about −0.2 to about −0.1). In some instances, the E2-induced score from the sample may be less than −2.0.

The methods provided herein may include determining an ER pathway activity score from a sample (e.g., a tissue sample, e.g., a tumor tissue sample, e.g., a FFPE, a FF, an archival, a fresh, or a frozen tumor tissue sample) from an individual. The methods provided herein may include determining an E2-induced score from a sample (e.g., a tissue sample, e.g., a tumor tissue sample, e.g., a FFPE, a FF, an archival, a fresh, or a frozen tumor tissue sample) from an individual. In some instances, the sample may be a FFPE tumor tissue sample. In some instances, the sample may be a FF tumor tissue sample.

In any of the preceding instances, the individual may have an HR+ breast cancer. In some instances, the HR+ cancer may be an ER+ breast cancer. In some instances, the individual may have an ER+ breast cancer selected from, for example, a luminal A breast cancer or a luminal B breast cancer. In some instances, the breast cancer may be an advanced or a metastatic breast cancer.

In some instances of any of the preceding methods or assays involving determining an ER pathway activity score and/or E2-induced score in a sample (e.g., a tissue sample, e.g., a tumor tissue sample, e.g., a formalin-fixed paraffin-embedded (FFPE), a fresh frozen (FF), an archival, a fresh, or a frozen tumor tissue sample) from the individual, the individual has been previously treated with an endocrine therapy as described herein. In other instances, the individual has not been previously treated with an endocrine therapy.

In some instances, the methods further comprise generating a report, e.g., an electronic, web-based, or paper report, to the individual or to another person or entity, a caregiver, a physician, an oncologist, a hospital, clinic, third-party payor, insurance company, a pharmaceutical or biotechnology company, or government office. In some instances, the report comprises output from the method which comprises evaluation of the ER pathway activity and/or E2-induced score.

C. Exemplary Methods for Determination of an E2-Induced, E2-Repressed, and ER Pathway Activity Scores The methods and assays provided herein may include determining an E2-induced, an E2-repressed, and/or an ER pathway activity score based on an expression level of a predetermined set of genes (e.g., a biomarker) in a sample (e.g., a tissue sample, e.g., a tumor tissue sample, e.g., a FFPE, a FF, an archival, a fresh, or a frozen tumor tissue sample) from an individual (e.g., an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer)). In some instances, the predetermined set of genes is the set of genes listed in any one of Tables 1-3. In some instances, the pre-determined set of genes are the sets of genes listed in Table 1 and Table 4 (e.g., the 14-gene signature). In some instances, the pre-determined set of genes are the sets of genes listed in Table 2 and Table 5 (e.g., the 19-gene signature). In some instances, the pre-determined set of genes are the sets of genes listed in Table 3 and Table 6 (e.g., the 41-gene signature). In some instances, the pre-determined set of genes are the sets of genes listed in Table 1 and Table 4 (e.g., the 14-gene signature) and no other genes. In some instances, the pre-determined set of genes are the sets of genes listed in Table 2 and Table 5 (e.g., the 19-gene signature) and no other genes. In some instances, the pre-determined set of genes are the sets of genes listed in Table 3 and Table 6 (e.g., the 41-gene signature) and no other genes.

In some embodiments, the ER pathway activity score is calculated using an 8-gene signature by subtracting an E2-repressed score, determined from the average z-scored expression of three of the E2-repressed genes set forth in Table 6, from an E2-induced score, determined from the average z-scored expression of five of the E2-induced genes set forth in Table 3.

In some embodiments, the ER pathway activity score is calculated using a 9-gene signature by subtracting an E2-repressed score, determined from the average z-scored expression of four of the E2-repressed genes set forth in Table 6, from an E2-induced score, determined from the average z-scored expression of five of the E2-induced genes set forth in Table 3. In some embodiments, the ER pathway activity score is calculated using a 9-gene signature by subtracting an E2-repressed score, determined from the average z-scored expression of three of the E2-repressed genes set forth in Table 6, from an E2-induced score, determined from the average z-scored expression of six of the E2-induced genes set forth in Table 3.

In some embodiments, the ER pathway activity score is calculated using a 10-gene signature by subtracting an E2-repressed score, determined from the average z-scored expression of three of the E2-repressed genes set forth in Table 6, from an E2-induced score, determined from the average z-scored expression of seven of the E2-induced genes set forth in Table 3. In some embodiments, the ER pathway activity score is calculated using a 10-gene signature by subtracting an E2-repressed score, determined from the average z-scored expression of four of the E2-repressed genes set forth in Table 6, from an E2-induced score, determined from the average z-scored expression of six of the E2-induced genes set forth in Table 3. In some embodiments, the ER pathway activity score is calculated using a 10-gene signature by subtracting an E2-repressed score, determined from the average z-scored expression of five of the E2-repressed genes set forth in Table 6, from an E2-induced score, determined from the average z-scored expression of five of the E2-induced genes set forth in Table 3.

In some embodiments, the ER pathway activity score is calculated using an 11-gene signature by subtracting an E2-repressed score, determined from the average z-scored expression of three of the E2-repressed genes set forth in Table 6, from an E2-induced score, determined from the average z-scored expression of eight of the E2-induced genes set forth in Table 3. In some embodiments, the ER pathway activity score is calculated using an 11-gene signature by subtracting an E2-repressed score, determined from the average z-scored expression of four of the E2-repressed genes set forth in Table 6, from an E2-induced score, determined from the average z-scored expression of seven of the E2-induced genes set forth in Table 3. In some embodiments, the ER pathway activity score is calculated using an 11-gene signature by subtracting an E2-repressed score, determined from the average z-scored expression of five of the E2-repressed genes set forth in Table 6, from an E2-induced score, determined from the average z-scored expression of six of the E2-induced genes set forth in Table 3.

In some embodiments, the ER pathway activity score is calculated using a 12-gene signature by subtracting an E2-repressed score, determined from the average z-scored expression of three of the E2-repressed genes set forth in Table 6, from an E2-induced score, determined from the average z-scored expression of nine of the E2-induced genes set forth in Table 3. In some embodiments, the ER pathway activity score is calculated using a 12-gene signature by subtracting an E2-repressed score, determined from the average z-scored expression of four of the E2-repressed genes set forth in Table 6, from an E2-induced score, determined from the average z-scored expression of eight of the E2-induced genes set forth in Table 3. In some embodiments, the ER pathway activity score is calculated using a 12-gene signature by subtracting an E2-repressed score, determined from the average z-scored expression of five of the E2-repressed genes set forth in Table 6, from an E2-induced score, determined from the average z-scored expression of seven of the E2-induced genes set forth in Table 3. In some embodiments, the ER pathway activity score is calculated using a 12-gene signature by subtracting an E2-repressed score, determined from the average z-scored expression of six of the E2-repressed genes set forth in Table 6, from an E2-induced score, determined from the average z-scored expression of six of the E2-induced genes set forth in Table 3.

In some embodiments, the ER pathway activity score is calculated using a 13-gene signature by subtracting an E2-repressed score, determined from the average z-scored expression of three of the E2-repressed genes set forth in Table 6, from an E2-induced score, determined from the average z-scored expression of ten of the E2-induced genes set forth in Table 3. In some embodiments, the ER pathway activity score is calculated using a 13-gene signature by subtracting an E2-repressed score, determined from the average z-scored expression of four of the E2-repressed genes set forth in Table 6, from an E2-induced score, determined from the average z-scored expression of nine of the E2-induced genes set forth in Table 3. In some embodiments, the ER pathway activity score is calculated using a 13-gene signature by subtracting an E2-repressed score, determined from the average z-scored expression of five of the E2-repressed genes set forth in Table 6, from an E2-induced score, determined from the average z-scored expression of eight of the E2-induced genes set forth in Table 3. In some embodiments, the ER pathway activity score is calculated using a 13-gene signature by subtracting an E2-repressed score, determined from the average z-scored expression of six of the E2-repressed genes set forth in Table 6, from an E2-induced score, determined from the average z-scored expression of seven of the E2-induced genes set forth in Table 3.

In some embodiments, the ER pathway activity score is calculated using a 14-gene signature by subtracting an E2-repressed score, determined from the average z-scored expression of 3 E2-repressed genes set forth in Table 6, from an E2-induced score, determined from the average z-scored expression of 11 E2-induced genes set forth in Table 3. In some embodiments, the ER pathway activity score is calculated using a 14-gene signature by subtracting an E2-repressed score, determined from the average z-scored expression of 4 E2-repressed genes set forth in Table 6, from an E2-induced score, determined from the average z-scored expression of 10 E2-induced genes set forth in Table 3. In some embodiments, the ER pathway activity score is calculated using a 14-gene signature by subtracting an E2-repressed score, determined from the average z-scored expression of 5 E2-repressed genes set forth in Table 6, from an E2-induced score, determined from the average z-scored expression of 9 E2-induced genes set forth in Table 3. In some embodiments, the ER pathway activity score is calculated using a 14-gene signature by subtracting an E2-repressed score, determined from the average z-scored expression of 6 E2-repressed genes set forth in Table 6, from an E2-induced score, determined from the average z-scored expression of the 8 E2-induced genes set forth in Table 3. In some embodiments, the ER pathway activity score is calculated using a 14-gene signature by subtracting an E2-repressed score, determined from the average z-scored expression of the 6 E2-repressed genes set forth in Table 4, from an E2-induced score, determined from the average z-scored expression of the 8 E2-induced genes set forth in Table 1. In some embodiments, the ER pathway activity score is calculated using a 14-gene signature by subtracting an E2-repressed score, determined from the average z-scored expression of 7 E2-repressed genes set forth in Table 6, from an E2-induced score, determined from the average z-scored expression of 7 E2-induced genes set forth in Table 3.

In some embodiments, the ER pathway activity score is calculated using a 15-gene signature by subtracting an E2-repressed score, determined from the average z-scored expression of 3 of the E2-repressed genes set forth in Table 6, from an E2-induced score, determined from the average z-scored expression of 12 of the E2-induced genes set forth in Table 3. In some embodiments, the ER pathway activity score is calculated using a 15-gene signature by subtracting an E2-repressed score, determined from the average z-scored expression of 4 of the E2-repressed genes set forth in Table 6, from an E2-induced score, determined from the average z-scored expression of 11 of the E2-induced genes set forth in Table 3. In some embodiments, the ER pathway activity score is calculated using a 15-gene signature by subtracting an E2-repressed score, determined from the average z-scored expression of 5 of the E2-repressed genes set forth in Table 6, from an E2-induced score, determined from the average z-scored expression of 10 of the E2-induced genes set forth in Table 3. In some embodiments, the ER pathway activity score is calculated using a 15-gene signature by subtracting an E2-repressed score, determined from the average z-scored expression of 6 of the E2-repressed genes set forth in Table 6, from an E2-induced score, determined from the average z-scored expression of 9 of the E2-induced genes set forth in Table 3. In some embodiments, the ER pathway activity score is calculated using a 15-gene signature by subtracting an E2-repressed score, determined from the average z-scored expression of 7 of the E2-repressed genes set forth in Table 6, from an E2-induced score, determined from the average z-scored expression of 8 of the E2-induced genes set forth in Table 3.

In some embodiments, the ER pathway activity score is calculated using a 16-gene signature by subtracting an E2-repressed score, determined from the average z-scored expression of 3 of the E2-repressed genes set forth in Table 6, from an E2-induced score, determined from the average z-scored expression of 13 of the E2-induced genes set forth in Table 3. In some embodiments, the ER pathway activity score is calculated using a 16-gene signature by subtracting an E2-repressed score, determined from the average z-scored expression of 4 of the E2-repressed genes set forth in Table 6, from an E2-induced score, determined from the average z-scored expression of 12 of the E2-induced genes set forth in Table 3. In some embodiments, the ER pathway activity score is calculated using a 16-gene signature by subtracting an E2-repressed score, determined from the average z-scored expression of 5 of the E2-repressed genes set forth in Table 6, from an E2-induced score, determined from the average z-scored expression of 11 of the E2-induced genes set forth in Table 3. In some embodiments, the ER pathway activity score is calculated using a 16-gene signature by subtracting an E2-repressed score, determined from the average z-scored expression of 6 of the E2-repressed genes set forth in Table 6, from an E2-induced score, determined from the average z-scored expression of 10 of the E2-induced genes set forth in Table 3. In some embodiments, the ER pathway activity score is calculated using a 16-gene signature by subtracting an E2-repressed score, determined from the average z-scored expression of 7 of the E2-repressed genes set forth in Table 6, from an E2-induced score, determined from the average z-scored expression of 9 of the E2-induced genes set forth in Table 3. In some embodiments, the ER pathway activity score is calculated using a 16-gene signature by subtracting an E2-repressed score, determined from the average z-scored expression of 8 of the E2-repressed genes set forth in Table 6, from an E2-induced score, determined from the average z-scored expression of 8 of the E2-induced genes set forth in Table 3.

In some embodiments, the ER pathway activity score is calculated using a 17-gene signature by subtracting an E2-repressed score, determined from the average z-scored expression of 3 of the E2-repressed genes set forth in Table 6, from an E2-induced score, determined from the average z-scored expression of 14 of the E2-induced genes set forth in Table 3. In some embodiments, the ER pathway activity score is calculated using a 17-gene signature by subtracting an E2-repressed score, determined from the average z-scored expression of 4 of the E2-repressed genes set forth in Table 6, from an E2-induced score, determined from the average z-scored expression of 13 of the E2-induced genes set forth in Table 3. In some embodiments, the ER pathway activity score is calculated using a 17-gene signature by subtracting an E2-repressed score, determined from the average z-scored expression of 5 of the E2-repressed genes set forth in Table 6, from an E2-induced score, determined from the average z-scored expression of 12 of the E2-induced genes set forth in Table 3. In some embodiments, the ER pathway activity score is calculated using a 17-gene signature by subtracting an E2-repressed score, determined from the average z-scored expression of 6 of the E2-repressed genes set forth in Table 6, from an E2-induced score, determined from the average z-scored expression of 11 of the E2-induced genes set forth in Table 3. In some embodiments, the ER pathway activity score is calculated using a 17-gene signature by subtracting an E2-repressed score, determined from the average z-scored expression of 7 of the E2-repressed genes set forth in Table 6, from an E2-induced score, determined from the average z-scored expression of 10 of the E2-induced genes set forth in Table 3. In some embodiments, the ER pathway activity score is calculated using a 17-gene signature by subtracting an E2-repressed score, determined from the average z-scored expression of 8 of the E2-repressed genes set forth in Table 6, from an E2-induced score, determined from the average z-scored expression of 9 of the E2-induced genes set forth in Table 3.

In some embodiments, the ER pathway activity score is calculated using an 18-gene signature by subtracting an E2-repressed score, determined from the average z-scored expression of 3 of the E2-repressed genes set forth in Table 6, from an E2-induced score, determined from the average z-scored expression of 15 of the E2-induced genes set forth in Table 3. In some embodiments, the ER pathway activity score is calculated using an 18-gene signature by subtracting an E2-repressed score, determined from the average z-scored expression of 4 of the E2-repressed genes set forth in Table 6, from an E2-induced score, determined from the average z-scored expression of 14 of the E2-induced genes set forth in Table 3. In some embodiments, the ER pathway activity score is calculated using an 18-gene signature by subtracting an E2-repressed score, determined from the average z-scored expression of 5 of the E2-repressed genes set forth in Table 6, from an E2-induced score, determined from the average z-scored expression of 13 of the E2-induced genes set forth in Table 3. In some embodiments, the ER pathway activity score is calculated using an 18-gene signature by subtracting an E2-repressed score, determined from the average z-scored expression of 6 of the E2-repressed genes set forth in Table 6, from an E2-induced score, determined from the average z-scored expression of 12 of the E2-induced genes set forth in Table 3. In some embodiments, the ER pathway activity score is calculated using an 18-gene signature by subtracting an E2-repressed score, determined from the average z-scored expression of 7 of the E2-repressed genes set forth in Table 6, from an E2-induced score, determined from the average z-scored expression of 11 of the E2-induced genes set forth in Table 3. In some embodiments, the ER pathway activity score is calculated using an 18-gene signature by subtracting an E2-repressed score, determined from the average z-scored expression of 8 of the E2-repressed genes set forth in Table 6, from an E2-induced score, determined from the average z-scored expression of 10 of the E2-induced genes set forth in Table 3. In some embodiments, the ER pathway activity score is calculated using an 18-gene signature by subtracting an E2-repressed score, determined from the average z-scored expression of 9 of the E2-repressed genes set forth in Table 6, from an E2-induced score, determined from the average z-scored expression of 9 of the E2-induced genes set forth in Table 3.

In some embodiments, the ER pathway activity score is calculated using a 19-gene signature by subtracting an E2-repressed score, determined from the average z-scored expression of 3 of the E2-repressed genes set forth in Table 6, from an E2-induced score, determined from the average z-scored expression of 16 of the E2-induced genes set forth in Table 3. In some embodiments, the ER pathway activity score is calculated using a 19-gene signature by subtracting an E2-repressed score, determined from the average z-scored expression of 4 of the E2-repressed genes set forth in Table 6, from an E2-induced score, determined from the average z-scored expression of 15 of the E2-induced genes set forth in Table 3. In some embodiments, the ER pathway activity score is calculated using a 19-gene signature by subtracting an E2-repressed score, determined from the average z-scored expression of 5 of the E2-repressed genes set forth in Table 6, from an E2-induced score, determined from the average z-scored expression of 14 of the E2-induced genes set forth in Table 3. In some embodiments, the ER pathway activity score is calculated using a 19-gene signature by subtracting an E2-repressed score, determined from the average z-scored expression of 6 of the E2-repressed genes set forth in Table 6, from an E2-induced score, determined from the average z-scored expression of 13 of the E2-induced genes set forth in Table 3. In some embodiments, the ER pathway activity score is calculated using a 19-gene signature by subtracting an E2-repressed score, determined from the average z-scored expression of 7 of the E2-repressed genes set forth in Table 6, from an E2-induced score, determined from the average z-scored expression of 12 of the E2-induced genes set forth in Table 3. In some embodiments, the ER pathway activity score is calculated using a 19-gene signature by subtracting an E2-repressed score, determined from the average z-scored expression of 8 of the E2-repressed genes set forth in Table 6, from an E2-induced score, determined from the average z-scored expression of 11 of the E2-induced genes set forth in Table 3. In some embodiments, the ER pathway activity score is calculated using a 19-gene signature by subtracting an E2-repressed score, determined from the average z-scored expression of the 8 E2-repressed genes set forth in Table 5, from an E2-induced score, determined from the average z-scored expression of the 11 E2-induced genes set forth in Table 2. In some embodiments, the ER pathway activity score is calculated using a 19-gene signature by subtracting an E2-repressed score, determined from the average z-scored expression of 9 of the E2-repressed genes set forth in Table 6, from an E2-induced score, determined from the average z-scored expression of 10 of the E2-induced genes set forth in Table 3.

In some embodiments, the ER pathway activity score is calculated using a 20-gene signature by subtracting an E2-repressed score, determined from the average z-scored expression of 3 of the E2-repressed genes set forth in Table 6, from an E2-induced score, determined from the average z-scored expression of 17 of the E2-induced genes set forth in Table 3. In some embodiments, the ER pathway activity score is calculated using a 20-gene signature by subtracting an E2-repressed score, determined from the average z-scored expression of 4 of the E2-repressed genes set forth in Table 6, from an E2-induced score, determined from the average z-scored expression of 16 of the E2-induced genes set forth in Table 3. In some embodiments, the ER pathway activity score is calculated using a 20-gene signature by subtracting an E2-repressed score, determined from the average z-scored expression of 5 of the E2-repressed genes set forth in Table 6, from an E2-induced score, determined from the average z-scored expression of 15 of the E2-induced genes set forth in Table 3. In some embodiments, the ER pathway activity score is calculated using a 20-gene signature by subtracting an E2-repressed score, determined from the average z-scored expression of 6 of the E2-repressed genes set forth in Table 6, from an E2-induced score, determined from the average z-scored expression of 14 of the E2-induced genes set forth in Table 3. In some embodiments, the ER pathway activity score is calculated using a 20-gene signature by subtracting an E2-repressed score, determined from the average z-scored expression of 7 of the E2-repressed genes set forth in Table 6, from an E2-induced score, determined from the average z-scored expression of 13 of the E2-induced genes set forth in Table 3. In some embodiments, the ER pathway activity score is calculated using a 20-gene signature by subtracting an E2-repressed score, determined from the average z-scored expression of 8 of the E2-repressed genes set forth in Table 6, from an E2-induced score, determined from the average z-scored expression of 12 of the E2-induced genes set forth in Table 3. In some embodiments, the ER pathway activity score is calculated using a 20-gene signature by subtracting an E2-repressed score, determined from the average z-scored expression of 9 of the E2-repressed genes set forth in Table 6, from an E2-induced score, determined from the average z-scored expression of 11 of the E2-induced genes set forth in Table 3. In some embodiments, the ER pathway activity score is calculated using a 20-gene signature by subtracting an E2-repressed score, determined from the average z-scored expression of 10 of the E2-repressed genes set forth in Table 6, from an E2-induced score, determined from the average z-scored expression of 10 of the E2-induced genes set forth in Table 3.

In some embodiments, the ER pathway activity score is calculated using a 21-gene signature by subtracting an E2-repressed score, determined from the average z-scored expression of 3 of the E2-repressed genes set forth in Table 6, from an E2-induced score, determined from the average z-scored expression of 18 of the E2-induced genes set forth in Table 3. In some embodiments, the ER pathway activity score is calculated using a 21-gene signature by subtracting an E2-repressed score, determined from the average z-scored expression of 4 of the E2-repressed genes set forth in Table 6, from an E2-induced score, determined from the average z-scored expression of 17 of the E2-induced genes set forth in Table 3. In some embodiments, the ER pathway activity score is calculated using a 21-gene signature by subtracting an E2-repressed score, determined from the average z-scored expression of 5 of the E2-repressed genes set forth in Table 6, from an E2-induced score, determined from the average z-scored expression of 16 of the E2-induced genes set forth in Table 3. In some embodiments, the ER pathway activity score is calculated using a 21-gene signature by subtracting an E2-repressed score, determined from the average z-scored expression of 6 of the E2-repressed genes set forth in Table 6, from an E2-induced score, determined from the average z-scored expression of 15 of the E2-induced genes set forth in Table 3. In some embodiments, the ER pathway activity score is calculated using a 21-gene signature by subtracting an E2-repressed score, determined from the average z-scored expression of 7 of the E2-repressed genes set forth in Table 6, from an E2-induced score, determined from the average z-scored expression of 14 of the E2-induced genes set forth in Table 3. In some embodiments, the ER pathway activity score is calculated using a 21-gene signature by subtracting an E2-repressed score, determined from the average z-scored expression of 8 of the E2-repressed genes set forth in Table 6, from an E2-induced score, determined from the average z-scored expression of 13 of the E2-induced genes set forth in Table 3. In some embodiments, the ER pathway activity score is calculated using a 21-gene signature by subtracting an E2-repressed score, determined from the average z-scored expression of 9 of the E2-repressed genes set forth in Table 6, from an E2-induced score, determined from the average z-scored expression of 12 of the E2-induced genes set forth in Table 3. In some embodiments, the ER pathway activity score is calculated using a 21-gene signature by subtracting an E2-repressed score, determined from the average z-scored expression of 10 of the E2-repressed genes set forth in Table 6, from an E2-induced score, determined from the average z-scored expression of 11 of the E2-induced genes set forth in Table 3.

In some embodiments, the ER pathway activity score is calculated using a 22-gene signature by subtracting an E2-repressed score, determined from the average z-scored expression of 3 of the E2-repressed genes set forth in Table 6, from an E2-induced score, determined from the average z-scored expression of 19 of the E2-induced genes set forth in Table 3. In some embodiments, the ER pathway activity score is calculated using a 22-gene signature by subtracting an E2-repressed score, determined from the average z-scored expression of 4 of the E2-repressed genes set forth in Table 6, from an E2-induced score, determined from the average z-scored expression of 18 of the E2-induced genes set forth in Table 3. In some embodiments, the ER pathway activity score is calculated using a 22-gene signature by subtracting an E2-repressed score, determined from the average z-scored expression of 5 of the E2-repressed genes set forth in Table 6, from an E2-induced score, determined from the average z-scored expression of 17 of the E2-induced genes set forth in Table 3. In some embodiments, the ER pathway activity score is calculated using a 22-gene signature by subtracting an E2-repressed score, determined from the average z-scored expression of 6 of the E2-repressed genes set forth in Table 6, from an E2-induced score, determined from the average z-scored expression of 16 of the E2-induced genes set forth in Table 3. In some embodiments, the ER pathway activity score is calculated using a 22-gene signature by subtracting an E2-repressed score, determined from the average z-scored expression of 7 of the E2-repressed genes set forth in Table 6, from an E2-induced score, determined from the average z-scored expression of 15 of the E2-induced genes set forth in Table 3. In some embodiments, the ER pathway activity score is calculated using a 22-gene signature by subtracting an E2-repressed score, determined from the average z-scored expression of 8 of the E2-repressed genes set forth in Table 6, from an E2-induced score, determined from the average z-scored expression of 14 of the E2-induced genes set forth in Table 3. In some embodiments, the ER pathway activity score is calculated using a 22-gene signature by subtracting an E2-repressed score, determined from the average z-scored expression of 9 of the E2-repressed genes set forth in Table 6, from an E2-induced score, determined from the average z-scored expression of 13 of the E2-induced genes set forth in Table 3. In some embodiments, the ER pathway activity score is calculated using a 22-gene signature by subtracting an E2-repressed score, determined from the average z-scored expression of 10 of the E2-repressed genes set forth in Table 6, from an E2-induced score, determined from the average z-scored expression of 12 of the E2-induced genes set forth in Table 3. In some embodiments, the ER pathway activity score is calculated using a 22-gene signature by subtracting an E2-repressed score, determined from the average z-scored expression of 11 of the E2-repressed genes set forth in Table 6, from an E2-induced score, determined from the average z-scored expression of 11 of the E2-induced genes set forth in Table 3.

In some embodiments, the ER pathway activity score is calculated using a 23-gene signature by subtracting an E2-repressed score, determined from the average z-scored expression of 3 of the E2-repressed genes set forth in Table 6, from an E2-induced score, determined from the average z-scored expression of 20 of the E2-induced genes set forth in Table 3. In some embodiments, the ER pathway activity score is calculated using a 23-gene signature by subtracting an E2-repressed score, determined from the average z-scored expression of 4 of the E2-repressed genes set forth in Table 6, from an E2-induced score, determined from the average z-scored expression of 19 of the E2-induced genes set forth in Table 3. In some embodiments, the ER pathway activity score is calculated using a 23-gene signature by subtracting an E2-repressed score, determined from the average z-scored expression of 5 of the E2-repressed genes set forth in Table 6, from an E2-induced score, determined from the average z-scored expression of 18 of the E2-induced genes set forth in Table 3. In some embodiments, the ER pathway activity score is calculated using a 23-gene signature by subtracting an E2-repressed score, determined from the average z-scored expression of 6 of the E2-repressed genes set forth in Table 6, from an E2-induced score, determined from the average z-scored expression of 17 of the E2-induced genes set forth in Table 3. In some embodiments, the ER pathway activity score is calculated using a 23-gene signature by subtracting an E2-repressed score, determined from the average z-scored expression of 7 of the E2-repressed genes set forth in Table 6, from an E2-induced score, determined from the average z-scored expression of 16 of the E2-induced genes set forth in Table 3. In some embodiments, the ER pathway activity score is calculated using a 23-gene signature by subtracting an E2-repressed score, determined from the average z-scored expression of 8 of the E2-repressed genes set forth in Table 6, from an E2-induced score, determined from the average z-scored expression of 15 of the E2-induced genes set forth in Table 3. In some embodiments, the ER pathway activity score is calculated using a 23-gene signature by subtracting an E2-repressed score, determined from the average z-scored expression of 9 of the E2-repressed genes set forth in Table 6, from an E2-induced score, determined from the average z-scored expression of 14 of the E2-induced genes set forth in Table 3. In some embodiments, the ER pathway activity score is calculated using a 23-gene signature by subtracting an E2-repressed score, determined from the average z-scored expression of 10 of the E2-repressed genes set forth in Table 6, from an E2-induced score, determined from the average z-scored expression of 13 of the E2-induced genes set forth in Table 3. In some embodiments, the ER pathway activity score is calculated using a 23-gene signature by subtracting an E2-repressed score, determined from the average z-scored expression of 11 of the E2-repressed genes set forth in Table 6, from an E2-induced score, determined from the average z-scored expression of 12 of the E2-induced genes set forth in Table 3.

In some embodiments, the ER pathway activity score is calculated using a 24-gene signature by subtracting an E2-repressed score, determined from the average z-scored expression of 3 of the E2-repressed genes set forth in Table 6, from an E2-induced score, determined from the average z-scored expression of 21 of the E2-induced genes set forth in Table 3. In some embodiments, the ER pathway activity score is calculated using a 24-gene signature by subtracting an E2-repressed score, determined from the average z-scored expression of 4 of the E2-repressed genes set forth in Table 6, from an E2-induced score, determined from the average z-scored expression of 20 of the E2-induced genes set forth in Table 3. In some embodiments, the ER pathway activity score is calculated using a 24-gene signature by subtracting an E2-repressed score, determined from the average z-scored expression of 5 of the E2-repressed genes set forth in Table 6, from an E2-induced score, determined from the average z-scored expression of 19 of the E2-induced genes set forth in Table 3. In some embodiments, the ER pathway activity score is calculated using a 24-gene signature by subtracting an E2-repressed score, determined from the average z-scored expression of 6 of the E2-repressed genes set forth in Table 6, from an E2-induced score, determined from the average z-scored expression of 18 of the E2-induced genes set forth in Table 3. In some embodiments, the ER pathway activity score is calculated using a 24-gene signature by subtracting an E2-repressed score, determined from the average z-scored expression of 7 of the E2-repressed genes set forth in Table 6, from an E2-induced score, determined from the average z-scored expression of 17 of the E2-induced genes set forth in Table 3. In some embodiments, the ER pathway activity score is calculated using a 24-gene signature by subtracting an E2-repressed score, determined from the average z-scored expression of 8 of the E2-repressed genes set forth in Table 6, from an E2-induced score, determined from the average z-scored expression of 16 of the E2-induced genes set forth in Table 3. In some embodiments, the ER pathway activity score is calculated using a 24-gene signature by subtracting an E2-repressed score, determined from the average z-scored expression of 9 of the E2-repressed genes set forth in Table 6, from an E2-induced score, determined from the average z-scored expression of 15 of the E2-induced genes set forth in Table 3. In some embodiments, the ER pathway activity score is calculated using a 24-gene signature by subtracting an E2-repressed score, determined from the average z-scored expression of 10 of the E2-repressed genes set forth in Table 6, from an E2-induced score, determined from the average z-scored expression of 14 of the E2-induced genes set forth in Table 3. In some embodiments, the ER pathway activity score is calculated using a 24-gene signature by subtracting an E2-repressed score, determined from the average z-scored expression of 11 of the E2-repressed genes set forth in Table 6, from an E2-induced score, determined from the average z-scored expression of 13 of the E2-induced genes set forth in Table 3. In some embodiments, the ER pathway activity score is calculated using a 24-gene signature by subtracting an E2-repressed score, determined from the average z-scored expression of 12 of the E2-repressed genes set forth in Table 6, from an E2-induced score, determined from the average z-scored expression of 12 of the E2-induced genes set forth in Table 3.

In some embodiments, the ER pathway activity score is calculated using a 25-gene signature by subtracting an E2-repressed score, determined from the average z-scored expression of 3 of the E2-repressed genes set forth in Table 6, from an E2-induced score, determined from the average z-scored expression of 22 of the E2-induced genes set forth in Table 3. In some embodiments, the ER pathway activity score is calculated using a 25-gene signature by subtracting an E2-repressed score, determined from the average z-scored expression of 4 of the E2-repressed genes set forth in Table 6, from an E2-induced score, determined from the average z-scored expression of 21 of the E2-induced genes set forth in Table 3. In some embodiments, the ER pathway activity score is calculated using a 25-gene signature by subtracting an E2-repressed score, determined from the average z-scored expression of 5 of the E2-repressed genes set forth in Table 6, from an E2-induced score, determined from the average z-scored expression of 20 of the E2-induced genes set forth in Table 3. In some embodiments, the ER pathway activity score is calculated using a 25-gene signature by subtracting an E2-repressed score, determined from the average z-scored expression of 6 of the E2-repressed genes set forth in Table 6, from an E2-induced score, determined from the average z-scored expression of 19 of the E2-induced genes set forth in Table 3. In some embodiments, the ER pathway activity score is calculated using a 25-gene signature by subtracting an E2-repressed score, determined from the average z-scored expression of 7 of the E2-repressed genes set forth in Table 6, from an E2-induced score, determined from the average z-scored expression of 18 of the E2-induced genes set forth in Table 3. In some embodiments, the ER pathway activity score is calculated using a 25-gene signature by subtracting an E2-repressed score, determined from the average z-scored expression of 8 of the E2-repressed genes set forth in Table 6, from an E2-induced score, determined from the average z-scored expression of 17 of the E2-induced genes set forth in Table 3. In some embodiments, the ER pathway activity score is calculated using a 25-gene signature by subtracting an E2-repressed score, determined from the average z-scored expression of 9 of the E2-repressed genes set forth in Table 6, from an E2-induced score, determined from the average z-scored expression of 16 of the E2-induced genes set forth in Table 3. In some embodiments, the ER pathway activity score is calculated using a 25-gene signature by subtracting an E2-repressed score, determined from the average z-scored expression of 10 of the E2-repressed genes set forth in Table 6, from an E2-induced score, determined from the average z-scored expression of 15 of the E2-induced genes set forth in Table 3. In some embodiments, the ER pathway activity score is calculated using a 25-gene signature by subtracting an E2-repressed score, determined from the average z-scored expression of 11 of the E2-repressed genes set forth in Table 6, from an E2-induced score, determined from the average z-scored expression of 14 of the E2-induced genes set forth in Table 3. In some embodiments, the ER pathway activity score is calculated using a 25-gene signature by subtracting an E2-repressed score, determined from the average z-scored expression of 12 of the E2-repressed genes set forth in Table 6, from an E2-induced score, determined from the average z-scored expression of 13 of the E2-induced genes set forth in Table 3.

In some embodiments, the ER pathway activity score is calculated using a 26-gene signature by subtracting an E2-repressed score, determined from the average z-scored expression of 3 of the E2-repressed genes set forth in Table 6, from an E2-induced score, determined from the average z-scored expression of 23 of the E2-induced genes set forth in Table 3. In some embodiments, the ER pathway activity score is calculated using a 26-gene signature by subtracting an E2-repressed score, determined from the average z-scored expression of 4 of the E2-repressed genes set forth in Table 6, from an E2-induced score, determined from the average z-scored expression of 22 of the E2-induced genes set forth in Table 3. In some embodiments, the ER pathway activity score is calculated using a 26-gene signature by subtracting an E2-repressed score, determined from the average z-scored expression of 5 of the E2-repressed genes set forth in Table 6, from an E2-induced score, determined from the average z-scored expression of 21 of the E2-induced genes set forth in Table 3. In some embodiments, the ER pathway activity score is calculated using a 26-gene signature by subtracting an E2-repressed score, determined from the average z-scored expression of 6 of the E2-repressed genes set forth in Table 6, from an E2-induced score, determined from the average z-scored expression of 20 of the E2-induced genes set forth in Table 3. In some embodiments, the ER pathway activity score is calculated using a 26-gene signature by subtracting an E2-repressed score, determined from the average z-scored expression of 7 of the E2-repressed genes set forth in Table 6, from an E2-induced score, determined from the average z-scored expression of 19 of the E2-induced genes set forth in Table 3. In some embodiments, the ER pathway activity score is calculated using a 26-gene signature by subtracting an E2-repressed score, determined from the average z-scored expression of 8 of the E2-repressed genes set forth in Table 6, from an E2-induced score, determined from the average z-scored expression of 18 of the E2-induced genes set forth in Table 3. In some embodiments, the ER pathway activity score is calculated using a 26-gene signature by subtracting an E2-repressed score, determined from the average z-scored expression of 9 of the E2-repressed genes set forth in Table 6, from an E2-induced score, determined from the average z-scored expression of 17 of the E2-induced genes set forth in Table 3. In some embodiments, the ER pathway activity score is calculated using a 26-gene signature by subtracting an E2-repressed score, determined from the average z-scored expression of 10 of the E2-repressed genes set forth in Table 6, from an E2-induced score, determined from the average z-scored expression of 16 of the E2-induced genes set forth in Table 3. In some embodiments, the ER pathway activity score is calculated using a 26-gene signature by subtracting an E2-repressed score, determined from the average z-scored expression of 11 of the E2-repressed genes set forth in Table 6, from an E2-induced score, determined from the average z-scored expression of 15 of the E2-induced genes set forth in Table 3. In some embodiments, the ER pathway activity score is calculated using a 26-gene signature by subtracting an E2-repressed score, determined from the average z-scored expression of 12 of the E2-repressed genes set forth in Table 6, from an E2-induced score, determined from the average z-scored expression of 14 of the E2-induced genes set forth in Table 3. In some embodiments, the ER pathway activity score is calculated using a 26-gene signature by subtracting an E2-repressed score, determined from the average z-scored expression of 13 of the E2-repressed genes set forth in Table 6, from an E2-induced score, determined from the average z-scored expression of 13 of the E2-induced genes set forth in Table 3.

In some embodiments, the ER pathway activity score is calculated using a 27-gene signature by subtracting an E2-repressed score, determined from the average z-scored expression of 4 of the E2-repressed genes set forth in Table 6, from an E2-induced score, determined from the average z-scored expression of 23 of the E2-induced genes set forth in Table 3.

In some embodiments, the ER pathway activity score is calculated using a 28-gene signature by subtracting an E2-repressed score, determined from the average z-scored expression of 5 of the E2-repressed genes set forth in Table 6, from an E2-induced score, determined from the average z-scored expression of 23 of the E2-induced genes set forth in Table 3.

In some embodiments, the ER pathway activity score is calculated using a 29-gene signature by subtracting an E2-repressed score, determined from the average z-scored expression of 6 of the E2-repressed genes set forth in Table 6, from an E2-induced score, determined from the average z-scored expression of 23 of the E2-induced genes set forth in Table 3.

In some embodiments, the ER pathway activity score is calculated using a 30-gene signature by subtracting an E2-repressed score, determined from the average z-scored expression of 7 of the E2-repressed genes set forth in Table 6, from an E2-induced score, determined from the average z-scored expression of 23 of the E2-induced genes set forth in Table 3.

In some embodiments, the ER pathway activity score is calculated using a 31-gene signature by subtracting an E2-repressed score, determined from the average z-scored expression of 8 of the E2-repressed genes set forth in Table 6, from an E2-induced score, determined from the average z-scored expression of 23 of the E2-induced genes set forth in Table 3.

In some embodiments, the ER pathway activity score is calculated using a 32-gene signature by subtracting an E2-repressed score, determined from the average z-scored expression of 9 of the E2-repressed genes set forth in Table 6, from an E2-induced score, determined from the average z-scored expression of 23 of the E2-induced genes set forth in Table 3.

In some embodiments, the ER pathway activity score is calculated using a 33-gene signature by subtracting an E2-repressed score, determined from the average z-scored expression of 10 of the E2-repressed genes set forth in Table 6, from an E2-induced score, determined from the average z-scored expression of 23 of the E2-induced genes set forth in Table 3.

In some embodiments, the ER pathway activity score is calculated using a 34-gene signature by subtracting an E2-repressed score, determined from the average z-scored expression of 11 of the E2-repressed genes set forth in Table 6, from an E2-induced score, determined from the average z-scored expression of 23 of the E2-induced genes set forth in Table 3.

In some embodiments, the ER pathway activity score is calculated using a 35-gene signature by subtracting an E2-repressed score, determined from the average z-scored expression of 12 of the E2-repressed genes set forth in Table 6, from an E2-induced score, determined from the average z-scored expression of 23 of the E2-induced genes set forth in Table 3.

In some embodiments, the ER pathway activity score is calculated using a 36-gene signature by subtracting an E2-repressed score, determined from the average z-scored expression of 13 of the E2-repressed genes set forth in Table 6, from an E2-induced score, determined from the average z-scored expression of 23 of the E2-induced genes set forth in Table 3.

In some embodiments, the ER pathway activity score is calculated using a 37-gene signature by subtracting an E2-repressed score, determined from the average z-scored expression of 14 of the E2-repressed genes set forth in Table 6, from an E2-induced score, determined from the average z-scored expression of 23 of the E2-induced genes set forth in Table 3.

In some embodiments, the ER pathway activity score is calculated using a 38-gene signature by subtracting an E2-repressed score, determined from the average z-scored expression of 15 of the E2-repressed genes set forth in Table 6, from an E2-induced score, determined from the average z-scored expression of 23 of the E2-induced genes set forth in Table 3.

In some embodiments, the ER pathway activity score is calculated using a 39-gene signature by subtracting an E2-repressed score, determined from the average z-scored expression of 16 of the E2-repressed genes set forth in Table 6, from an E2-induced score, determined from the average z-scored expression of 23 of the E2-induced genes set forth in Table 3.

In some embodiments, the ER pathway activity score is calculated using a 40-gene signature by subtracting an E2-repressed score, determined from the average z-scored expression of 17 of the E2-repressed genes set forth in Table 6, from an E2-induced score, determined from the average z-scored expression of 23 of the E2-induced genes set forth in Table 3.

In some embodiments, the ER pathway activity score is calculated using a 41-gene signature by subtracting an E2-repressed score, determined from the average z-scored expression of the 18 E2-repressed genes set forth in Table 6, from an E2-induced score, determined from the average z-scored expression of the 23 E2-induced genes set forth in Table 3.

In some embodiments, the ER pathway activity score is calculated using a 14-gene signature by subtracting an E2-repressed score, determined from the average z-scored expression of the six E2-repressed genes set forth in Table 4, from an E2-induced score, determined from the average z-scored expression of the eight E2-induced genes set forth in Table 1. In some embodiments, the ER pathway activity score is calculated using a 19-gene signature by subtracting an E2-repressed score, determined from the average z-scored expression of the eight E2-repressed genes set forth in Table 5, from an E2-induced score, determined from the average z-scored expression of the 11 E2-induced genes set forth in Table 2. In some embodiments, the ER pathway activity score is calculated using a 41-gene signature by subtracting an E2-repressed score, determined from the average z-scored expression of the 18 E2-repressed genes set forth in Table 6, from an E2-induced score, determined from the average z-scored expression of the 23 E2-induced genes set forth in Table 3. The ER pathway activity score can serve as a surrogate biomarker of ER pathway activity in a tumor in an individual.

In any of the methods or assays provided herein in which the expression level of a predetermined set of genes is determined in a sample (e.g., a tissue sample, e.g., a tumor tissue sample, e.g., a formalin-fixed paraffin-embedded (FFPE), a fresh frozen (FF), an archival, a fresh, or a frozen tumor tissue sample) from an individual, it is to be understood that the expression level of the predetermined set of genes may be normalized, e.g., to a reference gene, e.g., a housekeeping gene. In some instances, the reference gene is SDHA, GUSB, PPIA, and/or UBC. In some instances, an expression level for more than one gene of interest (e.g., the predetermined set of genes listed in any one of Tables 1-6) may be determined by aggregation methods known to one skilled in the art and also disclosed herein, including, for example, by calculating the median or mean of all the expression levels of the genes of interest. Before aggregation, the expression level of each gene of interest may be normalized by using statistical methods known to one skilled in the art and also disclosed herein, including, for example, normalized to the expression level of one or more housekeeping genes, to the median or mean expression level value for each gene as measured across a reference population, normalized to a total library size, or normalized to the median or mean expression level value across all genes measured. In some instances, before aggregation across multiple genes of interest, the normalized expression level of each gene of interest may be standardized by using statistical methods known to one skilled in the art and also disclosed herein, including, for example, by calculating the Z-score of the normalized expression level of each gene of interest or by, for example, scaling the normalized expression level of each gene to the respective scaling of those expression levels in a reference population.

The sample from the individual may be a FFPE sample, a FF sample, a fresh sample, frozen sample, or an archival sample. In some instances, the sample is a FFPE sample. In some instances, the sample is a FF sample. The expression level of the predetermined set of genes can be determined quantitatively based on any suitable criterion known in the art, including, but not limited to, the measurement of mRNA, DNA, cDNA, and/or gene copy number levels in an individual.

TABLE 1

| Eight E2-induced genes of the 14-gene signature<br>E2-Induced |
|---|
| AMZ1 |
| C5AR2 |
| CELSR2 |
| FKBP4 |
| GREB1 |
| OLFM1 |
| SLC9A3R1 |
| TFF1 |

TABLE 2

| Eleven E2-induced genes of the 19-gene signature<br>E2-Induced |
|---|
| AMZ1 |
| AREG |
| C5AR2 |
| CELSR2 |
| FKBP4 |
| FMN1 |
| GREB1 |

TABLE 2-continued

| Eleven E2-induced genes of the 19-gene signature E2-Induced |
|---|
| OLFM1 |
| RBM24 |
| SLC9A3R1 |
| TFF1 |

TABLE 3

| Twenty-three E2-induced genes of the 41 gene signature E2-Induced |
|---|
| AGR3 |
| AMZ1 |
| AREG |
| C5AR2 |
| CELSR2 |
| CT62 |
| FKBP4 |
| FMN1 |
| GREB1 |
| IGFBP4 |
| NOS1AP |
| NXPH3 |
| OLFM1 |
| PGR |
| PPM1J |
| RAPGEFL1 |
| RBM24 |
| RERG |
| RET |
| SGK3 |
| SLC9A3R1 |
| TFF1 |
| ZNF703 |

TABLE 4

| Six E2-repressed genes of the 14-gene signature E2-repressed |
|---|
| BCAS1 |
| CCNG2 |
| IL1R1 |
| PNPLA7 |
| SEMA3E |
| STON1 |

TABLE 5

| Eight E2-repressed genes of the 19-gene signature E2-repressed |
|---|
| BCAS1 |
| CCNG2 |
| IL1R1 |
| NBEA |
| PNPLA7 |
| SEMA3E |
| STON1 |
| TP53INP1 |

TABLE 6

| Eighteen E2-repressed genes of the 41-gene signature E2-repressed |
|---|
| BAMBI |
| BCAS1 |
| CCNG2 |

TABLE 6-continued

| Eighteen E2-repressed genes of the 41-gene signature E2-repressed |
|---|
| DDIT4 |
| EGLN3 |
| FAM171B |
| GRM4 |
| IL1R1 |
| LIPH |
| NBEA |
| PNPLA7 |
| PSCA |
| SEMA3E |
| SSPO |
| STON1 |
| TGFB3 |
| TP53INP1 |
| TP53INP2 |

In some instances of any of the preceding methods and assays, the expression level of a gene may be a nucleic acid expression level (e.g., an RNA expression level (e.g., an mRNA expression level) or a DNA expression level). Any suitable method of determining a nucleic acid expression level may be used, for example, as described in Section VII, below. In some instances, the nucleic acid expression level is determined using RNA-seq (e.g., using an RNA ACCESS® protocol or TRUSEQ® RIBO-ZERO® protocol (ILLUMINA®)), RT-qPCR, qPCR, multiplex qPCR or RT-qPCR, microarray analysis, SAGE, MassARRAY techniques, or a combination thereof.

Methods for the evaluation of mRNAs in cells are well known and include, for example, RNA sequencing (RNA-seq), whole genome sequencing (WGS), serial analysis of gene expression (SAGE), and various nucleic acid amplification assays (such as RT-PCR (e.g., qRT-PCR) using complementary primers specific for the predetermined set of genes. In addition, such methods can include one or more steps that allow one to determine the levels of target mRNA in a biological sample (e.g., by simultaneously examining the levels of a comparative control mRNA sequence of a "housekeeping" gene such as an actin family member). Optionally, the sequence of the amplified target cDNA can be determined. Optional methods include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes whose expression correlates with increased or reduced clinical benefit of treatment comprising an immunotherapy and a suppressive stromal antagonist may be arrayed on a solid support. Hybridization of a labeled probe with a particular array member indicates that the sample from which the probe was derived expresses that gene.

In some instances of any of the methods and assays, the sample (e.g., a tissue sample, e.g., a tumor tissue sample, e.g., a FFPE, a FF, an archival, a fresh, or a frozen tumor tissue sample) is obtained from the individual prior to (e.g., minutes, hours, days, weeks, months, or years prior to) administration of an endocrine therapy as described herein. In other words, the sample may be a baseline sample. In some instances of any of the preceding methods, the sample is obtained from the individual following (e.g., minutes, hours, or days following) administration of an endocrine therapy. In some instances, the sample from the individual is obtained within thirty hours following administration of an endocrine therapy. In some instances, multiple samples are obtained from the same individual at different time points (e.g., prior to and following administration of an endocrine therapy.

In any of the preceding instances, the individual may have an HR+ breast cancer. In some instances, the HR+ cancer may be an ER+ breast cancer. In some instances, the individual may have an ER+ breast cancer selected from, for example, a luminal A breast cancer or a luminal B breast cancer. In some instances, the breast cancer may be an advanced or a metastatic breast cancer.

In some instances of any of the preceding methods or assays involving determining an ER pathway activity score and/or E2-induced score from a sample (e.g., a tissue sample, e.g., a tumor tissue sample, e.g., a formalin-fixed paraffin-embedded (FFPE), a fresh frozen (FF), an archival, a fresh, or a frozen tumor tissue sample) from an individual, the individual has been previously treated with an endocrine therapy as described herein. In other instances, the individual has not been previously treated with an endocrine therapy.

In some instances, the methods further comprise generating a report, e.g., an electronic, web-based, or paper report, to the individual or to another person or entity, a caregiver, a physician, an oncologist, a hospital, clinic, third-party payor, insurance company, a pharmaceutical or biotechnology company, or government office. In some instances, the report comprises output from the method which comprises evaluation of the ER pathway activity and/or E2-induced score.

IV. Anti-Cancer Agents

Provided herein are methods for treating an individual having a breast cancer (e.g., an HR+ breast cancer (e.g., an ER+ breast cancer (e.g., luminal A cancer breast or luminal B breast cancer)) and/or a metastatic or a locally advanced breast cancer). Any of the preceding methods may be based on the determination of an E2-induced score and/or an ER pathway activity score from a sample (e.g., a tissue sample, e.g., a tumor tissue sample, e.g., a FFPE, a FF, an archival, a fresh, or a frozen tumor tissue sample) from the individual.

In some instances of any of the preceding methods, the anti-cancer therapeutic agents utilized in the methods described herein can be administered, for example, orally, intramuscularly, subcutaneously, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subconjunctivally, intravesicularly, mucosally, intrapericardially, intraumbilically, intraocularly, intraorbitally, intravitreally (e.g., by intravitreal injection), by eye drop, topically, transdermally, parenterally, by inhalation, by injection, by implantation, by infusion, by continuous infusion, by localized perfusion bathing target cells directly, by catheter, by lavage, in creams, or in lipid compositions. In some instances of any of the preceding methods, the anti-cancer therapeutic agents utilized in the methods described herein can be administered orally. For example, in some instances, an endocrine therapy as described herein may be administered orally or intramuscularly. In some instances, a SERM may be administered orally or intramuscularly. In some instances, a SERD may be administered orally or intramuscularly. In some instances of any of the preceding methods, the anti-cancer therapeutic agents utilized in the methods described herein can be administered intramuscularly. For example, in some instances, an endocrine therapy as described herein may be administered orally. In some instances, a SERM may be administered orally. In some instances, a SERD may be administered orally. The anti-cancer therapeutic agents utilized in the methods described herein can also be administered systemically or locally. The method of administration can vary depending on various factors (e.g., the anti-cancer therapeutic agents being administered and the severity of the condition, disease, or disorder (e.g., breast cancer) being treated).

Anti-cancer agents, including endocrine agents as described herein (and any additional therapeutic agent) may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The anti-cancer agent need not be, but is optionally formulated with and/or administered concurrently with one or more agents currently used to prevent or treat the disorder in question. The effective amount of such other agents depends on the amount of the anti-cancer present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of a breast cancer e.g., an HR+ breast cancer (e.g., an ER+ breast cancer (e.g., luminal A breast cancer or luminal B breast cancer)), DCIS, and/or a metastatic or a locally advanced breast cancer), the appropriate dosage of an anti-cancer agent (e.g., an endocrine therapy) described herein (when used alone or in combination with one or more other additional therapeutic agents) will depend on the type of disease to be treated, the severity and course of the disease, whether the anti-cancer agent is administered for preventive or therapeutic purposes, previous therapy, the individual's clinical history and response to the anti-cancer agent, and the discretion of the attending physician. The anti-cancer agent is suitably administered to the individual at one time or over a series of treatments. For repeated administrations over several days or longer, depending on the condition, the treatment would generally be sustained until a desired suppression of disease symptoms occurs. An initial higher loading dose, followed by one or more lower doses may be administered. However, other dosage regimens may be useful. The progress of this therapy is easily monitored by conventional techniques and assays. In some instances, an endocrine therapy as provided herein is dosed at an amount of about 1 mg/kg to about 100 mg/kg. In another instance, an endocrine therapy provided herein is dosed at an amount of about 100 mg/kg to about 1000 mg/kg. In still another instance, an endocrine therapy described herein is dosed at an amount of about 1000 mg/kg to about 2000 mg/kg. Certain endocrine therapies described herein can be administered in cyclic administration routines as understood in the art—for example for 20, 21, 22, 23, 24, 25, 26, 27, or 28, or more continual days followed by a rest period of 1, 2, 3, 4, 5, 6, 7, or more days. In yet another instance, an endocrine therapy described herein is administered in accordance with a package insert.

A. Endocrine Therapies

In some instances of any of the preceding methods, an endocrine therapy may be administered to the individual.

Exemplary endocrine therapies for use in the methods described herein include compounds that modulate the activity of the estrogen receptor. In certain instances, the compounds herein include Selective Estrogen Receptor Modulators (SERMs), Selective Estrogen Receptor Degraders (SERDs), aromatase inhibitors (AIs), or combinations thereof.

In some instances, the endocrine therapy comprises an aromatase inhibitor. The aromatase inhibitor can be an agent known in the art. For example, in one instance, the aromatase inhibitor is letrozole, anastrozole, exemestane, or testolactone, or a pharmaceutically acceptable salt thereof, or a combination thereof.

In another instance, the endocrine therapy comprises a SERM.

The endocrine therapy can comprise a compound that can be a tetra-substituted olefin compound known to have antagonist activity against ER. For example, the endocrine therapy can be tamoxifen, including derivatives thereof such as hydroxytamoxifen. In one instance, the endocrine therapy comprises nafoxidine. In another instance, the endocrine therapy comprises clomifene, toremifene, raloxifene, anordrin, bazedoxifene, broparestrol, cyclofenil, lasofoxifene, ormeloxifene, acolbifene, elacestrant, brilanestrant, clomifenoxide, droloxifene, etacstil, or ospemifene, or a pharmaceutically acceptable salt thereof, or a combination thereof. In another instance, the endocrine therapy comprises G1T48, or a pharmaceutically acceptable salt thereof.

In still another instance, the endocrine therapy comprises a SERD.

In one instance, the endocrine therapy comprises fulvestrant.

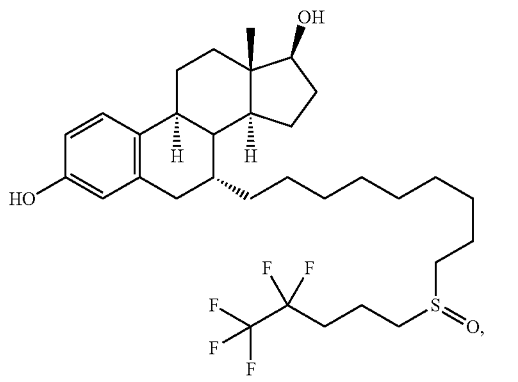

or a pharmaceutically acceptable salt thereof.

In one aspect, the endocrine therapy comprises a compound has formula (1):

(1)

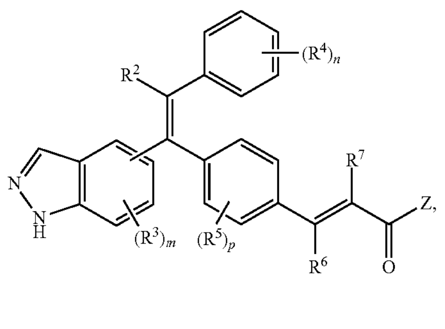

wherein;

Z is —OH or —$OR^{10}$;

$R^2$ is $C_{1-4}$ alkyl, $C_{1-4}$ fluoroalkyl, $C_{1-4}$ deuteroalkyl, $C_{3-6}$ cycloalkyl, or $C_{1-4}$ alkylene-W;

W is hydroxy, halogen, CN, $C_{1-4}$ alkyl, $C_{1-4}$ haloalkyl, $C_{1-4}$ alkoxy, $C_{1-4}$ haloalkoxy, or $C_{3-6}$ cycloalkyl;

each $R^3$ is independently halogen, $C_{1-4}$ alkyl, or $C_{1-4}$ fluoroalkyl;

each $R^4$ is independently halogen, —CN, —$OR^9$, —$S(O)_2R^{10}$, $C_{1-4}$ alkyl, $C_{1-4}$ fluoroalkyl, or $C_{1-4}$ heteroalkyl;

each $R^5$ is independently halogen, —CN, —$OR^9$, —$S(O)_2R^{10}$, $C_{1-4}$ alkyl, $C_{1-4}$ fluoroalkyl, or $C_{1-4}$ heteroalkyl;

$R^6$ is H, $C_{1-4}$ alkyl, or halogen;

$R^7$ is H, $C_{1-4}$ alkyl, or halogen;

$R^9$ is H, $C_{1-6}$ alkyl, $C_{1-6}$ fluoroalkyl, or $C_{3-6}$ cycloalkyl;

$R'''$ is $C_{1-6}$ alkyl;

m is 0, 1, or 2;

n is 0, 1, 2, 3, or 4; and p is 0, 1, or 2.

In another instance of the compound of formula (1), Z is —OH or —$OR'''$; $R^2$ is $C_{1-4}$ alkyl, $C_{1-4}$ fluoroalkyl, $C_{1-4}$ deuteroalkyl, $C_{3-6}$ cycloalkyl, or $C_{1-4}$ alkylene-W, where W is hydroxy, halogen, CN, or $C_{1-4}$ alkyl; each $R^3$ is independently halogen, $C_{1-4}$ alkyl, or $C_{1-4}$ fluoroalkyl; each $R^4$ is independently halogen, —CN, —$OR^9$, —$S(O)_2R^{10}$, $C_{1-4}$ alkyl, $C_{1-4}$ fluoroalkyl, or $C_{1-4}$ heteroalkyl; each $R^5$ is independently halogen, —CN, —$OR^9$, —$S(O)_2$R10, $C_{1-4}$ alkyl, $C_{1-4}$ fluoroalkyl, or $C_{1-4}$ heteroalkyl; $R^6$ is H, $C_{1-4}$ alkyl, or halogen; $R^7$ is H, $C_{1-4}$ alkyl, or halogen; $R^9$ is H, $C_{1-6}$ alkyl, $C_{1-6}$ fluoroalkyl, or $C_{3-6}$ cycloalkyl; $R^{10}$ is $C_{1-6}$ alkyl; m is 0, 1, or 2; n is 0, 1, 2, 3, or 4; and p is 0, 1, or 2.

In another instance of the compound of formula (1), Z is —OH. In another instance of the compound of formula (1), Z is —$OR^{10}$. In another instance of the compound of formula (1), Z is —OH, —$OCH_3$, or —$OCH_2CH_3$.

In another instance of the compound of formula (1), $R^6$ is H, —$CH_3$, F, or Cl. In another instance of the compound of formula (1), $R^6$ is H. In another instance of the compound of formula (1), $R^7$ is H, —$CH_3$, F, or Cl. In another instance of the compound of formula (1), $R^7$ is H.

In another instance of the compound of formula (1), $R^3$ is independently halogen, $C_{1-4}$ alkyl, or $C_{1-4}$ fluoroalkyl. In another instance of the compound of formula (1), each $R^3$ is independently F, Cl, or —$CH_3$. In another instance of the compound of formula (1), each $R^4$ is independently halogen, —CN, —OH, —$OR^9$, —$S(O)_2R^{10}$, $C_{1-4}$ alkyl, $C_{1-4}$ fluoroalkyl, or $C_{1-4}$ heteroalkyl. In another instance of the compound of formula (1), each $R^4$ is independently halogen, —CN, —OH, —$S(O)_2CH_3$, —$S(O)_2CH_2CH_3$, —$CH_3$, —$CH_2CH_3$, —$CF_3$, —$CH_2OH$, —$OCF_3$, —$OCH_3$, or —$OCH_2CH_3$. In another instance of the compound of formula (1), each $R^4$ is independently F, Cl, —CN, —OH, —$CH_3$, —$CH_2CH_3$, —$CF_3$, —$CH_2OH$, —$OCF_3$, —$OCH_3$, or —$OCH_2CH_3$. In another instance of the compound of formula (1), each $R^4$ is independently F or Cl. In another instance of the compound of formula (1), each $R^5$ is independently halogen, $C_{1-4}$ alkyl, or $C_{1-4}$ fluoroalkyl. In another instance of the compound of formula (1), each $R^5$ is independently F, Cl, or —$CH_3$.

In another instance of the compound of formula (1), m is 0 or 1. In another instance of the compound of formula (1), m is 0. In another instance of the compound of formula (1), m is 1. In another instance of the compound of formula (1), n is 0, 1, or 2. In another instance of the compound of formula (1), n is 0. In another instance of the compound of formula (1), n is 1. In another instance of the compound of formula (1), n is 2. In another instance of the compound of formula (1), p is 0 or 1. In another instance of the compound of formula (1), p is 0. In another instance of the compound of formula (1), p is 1.

In another instance of the compound of formula (1), Z is —OH; $R^6$ is H, —$CH_3$, F, or Cl; $R^7$ is H, —$CH_3$, F, or Cl; each $R^3$ is independently halogen, $C_{1-4}$ alkyl, or $C_{1-4}$ fluoroalkyl; each $R^4$ is independently halogen, —CN, —$OR^9$, —$S(O)_2R^{10}$, $C_{1-4}$ alkyl, $C_{1-4}$ fluoroalkyl, or $C_{1-4}$ heteroalkyl; each $R^5$ is independently halogen, $C_{1-4}$ alkyl, or $C_{1-4}$fluoroalkyl; m is 0 or 1; n is 0, 1, or 2; and p is 0 or 1.

In another instance of the compound of formula (1), $R^2$ is $C_{1-4}$ alkyl, $C_{1-4}$ fluoroalkyl, $C_{1-4}$ deuteroalkyl, $C_{3-6}$ cycloalkyl, or $C_{1-4}$ alkylene-W; W is hydroxy, halogen, CN, $C_{1-4}$ alkoxy, or $C_{3-6}$ cycloalkyl. In another instance of the compound of formula (1), $R^2$ is $C_{1-4}$ alkyl, $C_{1-4}$ fluoroalkyl, or $C_{1-4}$ deuteroalkyl. In another instance of the compound of formula (1), $R^2$ is $C_{1-4}$ alkyl. In another instance of the compound of formula (1), $R^2$ is —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH_2F$, —$CHF_2$, —$CF_3$, —$CH_2CF_3$, —$CD_3$, —$CH_2CD_3$, —$CD_2CD_3$, cyclopropyl, cyclobutyl, cyclopentyl, cyclohexyl, —$CH_2$—W, or —$CH_2CH_2$—W; W is hydroxy, F, Cl, —CN, —$OCH_3$, —$OCH_2CH_3$, —$OCH_2CH_2CH_3$, —$OCH(CH_3)_2$, cyclopropyl, cyclobutyl, cyclopentyl, or cyclohexyl. In another instance of the compound of formula (1), W is hydroxy, F, Cl, —CN, cyclopropyl, cyclobutyl, cyclopentyl, or cyclohexyl. In another instance of the compound of formula (1), $R^2$ is —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH_2F$, —$CHF_2$, —$CF_3$, —$CH_2CF_3$, —$CD_3$, —$CH_2CD_3$, —$CD_2CD_3$, —$CH_2$—W, or —$CH_2CH_2$—W. In another instance of the compound of formula (1), $R^2$ is —$CH_3$, —$CH_2CH_3$, —$CH_2F$, —$CHF_2$, —$CF_3$, —$CH_2CF_3$, —$CD_3$, —$CD_2CD_3$, —$CH_2CD_3$, or cyclopropyl.

In another instance of the compound of formula (1), Z is —OH; $R^6$ is H; $R^7$ is H; m is 0;

n is 0, 1, or 2; and p is 0.

In another instance of the compound of formula (1), the compound of Formula (1) has the structure of Formula (1a), or a pharmaceutically acceptable salt, or N-oxide thereof:

Formula (1a)

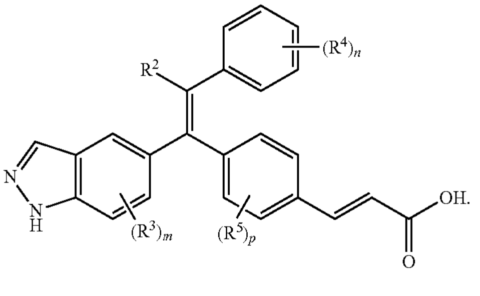

In another aspect, the endocrine therapy comprises a compound set forth in U.S. Pat. No. 8,299,112, for example in Table 1 therein, which is incorporated herein by reference in its entirety and for all purposes.

In another aspect, the endocrine therapy comprises a compound having the formula: (E)-Ethyl 3-(4-((E)-1-(1H-indazol-5-yl)-2-phenylbut-1-en-1-yl)phenyl)acrylate; (E)-3-(4-((E)-1-(1H-Indazol-5-yl)-2-phenylbut-1-en-1-yl)phenyl) acrylic acid; (E)-3-(4-((E)-1-(1H-Benzo[d][1,2,3]triazol-5-yl)-2-phenylbut-1-en-1-yl)phenyl) acrylic acid; (E)-3-(4-((E)-2-(4-Fluorophenyl)-1-(1H-indazol-5-yl)but-1-en-1-yl)phenyl)acrylic acid; (E)-3-(4-((E)-2-(4-Chlorophenyl)-1-(1H-indazol-5-yl)but-1-en-1-yl)phenyl)acrylic acid; (E)-3-(4-((E)-1-(1H-Indazol-5-yl)-2-(3-methoxyphenyl)but-1-en-1-yl)phenyl)acrylic acid; (E)-3-(4-((E)-2-(3-(Hydroxymethyl)phenyl)-1-(1H-indazol-5-yl)but-1-en-1-yl)phenyl)acrylic acid; (E)-3-(4-((E)-2-(4-(Hydroxymethyl)phenyl)-1-(1H-indazol-5-yl)but-1-en-1-yl)phenyl)acrylic acid; (E)-3-(4-((E)-2-(2-(Hydroxymethyl)phenyl)-1-(1H-indazol-5-yl)but-1-en-1-yl)phenyl)acrylic acid; (E)-3-(4-((E)-1-(1H-Indazol-5-yl)-2-(o-tolyl)but-1-en-1-yl)phenyl)acrylic acid; (E)-3-(4-((E)-1-(1H-Indazol-5-yl)-2-(m-tolyl)but-1-en-1-yl)phenyl)acrylic acid; (E)-3-(4-((E)-1-(1H-Indazol-5-yl)-2-(p-tolyl)but-1-en-1-yl)phenyl)acrylic acid; (E)-3-(4-((E)-1-(1H-Indazol-5-yl)-2-(2-methoxyphenyl)but-1-en-1-yl)phenyl)acrylic acid; (E)-3-(4-((E)-1-(1H-Indazol-5-yl)-2-(4-methoxyphenyl)but-1-en-1-yl)phenyl)acrylic acid; ((E)-3-(4-((E)-2-(2-Chlorophenyl)-1-(1H-indazol-5-yl)but-1-en-1-yl)phenyl)acrylic acid; (E)-3-(4-((E)-2-(3-Chlorophenyl)-1-(1H-indazol-5-yl)but-1-en-1-yl)phenyl)acrylic acid; (E)-3-(4-((E)-2-(2-Fluorophenyl)-1-(1H-indazol-5-yl)but-1-en-1-yl)phenyl)acrylic acid; (E)-3-(4-((E)-2-(3-Fluorophenyl)-1-(1H-indazol-5-yl)but-1-en-1-yl)phenyl)acrylic acid; (E)-3-(4-((E)-2-(2-Ethylphenyl)-1-(1H-indazol-5-yl)but-1-en-1-yl)phenyl)acrylic acid; (E)-3-(4-((E)-1-(1H-Indazol-5-yl)-2-(2-(trifluoromethyl)phenyl)but-1-en-1-yl)phenyl)acrylic acid; (E)-3-(4-((E)-4-Chloro-1-(1H-indazol-5-yl)-2-phenylbut-1-en-1-yl)phenyl)acrylic acid; (E)-3-(4-((E)-2-(2-Fluorophenyl)-1-(1H-indazol-4-yl)but-1-en-1-yl)phenyl)acrylic acid; (E)-3-(4-((E)-2-(2-Cyanophenyl)-1-(1H-indazol-5-yl)but-1-en-1-yl)phenyl)acrylic acid; (E)-3-(4-((E)-2-(2,4-Difluorophenyl)-1-(1H-indazol-5-yl)but-1-en-1-yl)phenyl)acrylic acid; (E)-3-(4-((E)-2-(2-Chloro-3-fluorophenyl)-1-(1H-indazol-5-yl)but-1-en-1-yl)phenyl)acrylic acid; (E)-3-(4-((E)-2-Cyclopropyl-1-(1H-indazol-5-yl)-2-phenylvinyl)phenyl)acrylic acid; (E)-3-(4-((E)-2-(4-Fluoro-2-methylphenyl)-1-(1H-indazol-5-yl)but-1-en-1-yl)phenyl)acrylic acid; (E)-3-(4-((E)-2-(2,6-Difluorophenyl)-1-(1H-indazol-5-yl)but-1-en-1-yl)phenyl)acrylic acid; (E)-3-(4-((E)-2-(2,6-Dichlorophenyl)-1-(1H-indazol-5-yl)but-1-en-1-yl)phenyl)acrylic acid; (E)-3-(4-((E)-4,4,4-Trideutero-1-(1H-indazol-5-yl)-2-phenylbut-1-en-1-yl)phenyl)acrylic acid; (E)-3-(4-((E)-2-(4-Fluoro-3-methyl phenyl)-1-(1H-indazol-5-yl)but-1-en-1-yl)phenyl)acrylic acid; (E)-3-(4-((E)-2-(5-Fluoro-2-methylphenyl)-1-(1H-indazol-5-yl)but-1-en-1-yl)phenyl)acrylic acid; (E)-3-(4-((E)-2-(2,3-Difluorophenyl)-1-(1H-indazol-5-yl)but-1-en-1-yl)phenyl)acrylic acid; (E)-3-(4-((E)-2-(2,5-Difluorophenyl)-1-(1H-indazol-5-yl)but-1-en-1-yl)phenyl)acrylic acid; (E)-3-(4-((E)-2-(2-Chloro-5-fluorophenyl)-1-(1H-indazol-5-yl)but-1-en-1-yl)phenyl)acrylic acid; (E)-3-(4-((E)-2-(2-Chloro-6-methylphenyl)-1-(1H-indazol-5-yl)but-1-en-1-yl)phenyl)acrylic acid; (E)-3-(4-((E)-1-(7-Chloro-1H-indazol-5-yl)-2-phenylbut-1-en-1-yl)phenyl)acrylic acid; (E)-3-(4-((E)-1-(4-Methyl-1H-indazol-5-yl)-2-phenylbut-1-en-1-yl)phenyl)acrylic acid; (E)-3-(4-((E)-1-(7-Methyl-1H-indazol-5-yl)-2-phenylbut-1-en-1-yl)phenyl)acrylic acid; (E)-3-(4-((E)-1-(6-Methyl-1H-indazol-5-yl)-2-phenylbut-1-en-1-yl)phenyl)acrylic acid; (E)-3-(4-((E)-1-(3-Methyl-1H-indazol-5-yl)-2-phenylbut-1-en-1-yl)phenyl)acrylic acid; (E)-3-(4-((E)-1-(3-Chloro-1H-indazol-5-yl)-2-phenylbut-1-en-1-yl)phenyl)acrylic acid; (E)-3-(4-((E)-2-(4-Chloro-2-methylphenyl)-1-(1H-indazol-5-yl)but-1-en-1-yl)phenyl)acrylic acid; (E)-3-(4-((E)-1-(1H-Indazol-5-yl)-2-phenylprop-1-en-1-yl)phenyl)acrylic acid; (E)-3-(4-((E)-1-(1H-Indazol-5-yl)-2-phenylpent-1-en-1-yl)phenyl)acrylic acid; (E)-3-(4-((E)-2-(3-Cyanophenyl)-1-(1H-indazol-5-yl)but-1-en-1-yl)phenyl)

acrylic acid; (E)-3-(4-((E)-2-(4-Cyanophenyl)-1-(1H-indazol-5-yl)but-1-en-1-yl)phenyl)acrylic acid; (E)-3-(4-((E)-4-Hydroxy-1-(1H-indazol-5-yl)-2-phenylbut-1-en-1-yl)phenyl)acrylic acid; (E)-3-(4-((E)-1-(1H-Indazol-5-yl)-4-methoxy-2-phenylbut-1-en-1-yl)phenyl)acrylic acid; (E)-3-(4-((Z)-1-(1H-Indazol-5-yl)-3-methoxy-2-phenylprop-1-en-1-yl)phenyl)acrylic acid; (E)-3-(4-((E)-1-(4-Fluoro-1H-indazol-5-yl)-2-phenylbut-1-en-1-yl)phenyl)acrylic acid; (E)-3-(4-((E)-1-(1H-Indol-5-yl)-2-phenylbut-1-en-1-yl)phenyl)acrylic acid; (E)-3-(4-((E)-1-(6-Chloro-1H-indazol-5-yl)-2-phenylbut-1-en-1-yl)phenyl)acrylic acid; (E)-3-(4-((E)-1-(1H-Indazol-5-yl)-4-methyl-2-phenylpent-1-en-1-yl)phenyl)acrylic acid; (E)-3-(4-((E)-1-(1H-Benzo[d][1,2,3]triazol-5-yl)-2-(2-chloro-4-fluorophenyl)but-1-en-1-yl)phenyl)acrylic acid; (E)-3-(4-((E)-1-(4-Chloro-1H-indazol-5-yl)-2-phenylbut-1-en-1-yl)phenyl)acrylic acid; (E)-3-(4-((E)-2-Cyclopentyl-1-(1H-indazol-5-yl)-2-phenylvinyl)phenyl)acrylic acid; (E)-3-(4-((E)-2-Cyclohexyl-1-(1H-indazol-5-yl)-2-phenylvinyl)phenyl)acrylic acid; (E)-3-(4-((E)-1-(1H-Indazol-5-yl)-3-methyl-2-phenylbut-1-en-1-yl)phenyl)acrylic acid; (E)-3-(4-((E)-3-Cyclopropyl-1-(1H-indazol-5-yl)-2-phenylprop-1-en-1-yl)phenyl)acrylic acid; (E)-3-(4-((E)-2-(2-Chlorophenyl)-2-cyclopropyl-1-(1H-indazol-5-yl)vinyl)phenyl)acrylic acid; (E)-3-(4-((E)-1-(6-Fluoro-1H-indazol-5-yl)-2-phenylbut-1-en-1-yl)phenyl)acrylic acid; (E)-3-(4-((E)-1-(1H-Benzo[d]imidazol-5-yl)-2-phenylbut-1-en-1-yl)phenyl)acrylic acid; (E)-3-(4-((E)-1-(1H-Indazol-5-yl)-2-phenylhex-1-en-1-yl)phenyl)acrylic acid; (E)-3-(4-((E)-3-Cyclopentyl-1-(1H-indazol-5-yl)-2-phenylprop-1-en-1-yl)phenyl)acrylic acid; (E)-3-(4-((E)-2-(2-Chloro-4-fluorophenyl)-1-(4-fluoro-1H-indazol-5-yl)but-1-en-1-yl)phenyl)acrylic acid; (E)-3-(4-((E)-1-(7-Fluoro-1H-indazol-5-yl)-2-phenylbut-1-en-1-yl)phenyl)acrylic acid; (E)-3-(4-((E)-1-(7-Fluoro-1H-indol-5-yl)-2-phenylbut-1-en-1-yl)phenyl)acrylic acid; (E)-3-(4-((E)-2-(2-Chloro-4-fluorophenyl)-1-(1H-indazol-5-yl)-4-methylpent-1-en-1-yl)phenyl)acrylic acid; (E)-3-(4-((Z)-3,3-Difluoro-1-(1H-indazol-5-yl)-2-phenylprop-1-en-1-yl)phenyl)acrylic acid; (E)-3-(4-((E)-2-(2-Chloro-4-fluorophenyl)-1-(7-fluoro-1H-indazol-5-yl)but-1-en-1-yl)phenyl)acrylic acid; (E)-3-(4-((E)-4-Fluoro-1-(1H-indazol-5-yl)-2-phenylbut-1-en-1-yl)phenyl)acrylic acid; (E)-3-(4-((E)-4-Chloro-2-(2-chloro-4-fluorophenyl)-1-(1H-indazol-5-yl)but-1-en-1-yl)phenyl)acrylic acid; (E)-3-(4-((Z)-3,3,3-Trifluoro-1-(1H-indazol-5-yl)-2-phenylprop-1-en-1-yl)phenyl)acrylic acid; (E)-3-(4-((E)-1-(4-Fluoro-1H-indazol-5-yl)-2-(4-fluoro-2-methylphenyl)but-1-en-1-yl)phenyl)acrylic acid; (E)-3-(4-((E)-2-(4-Chloro-2-methylphenyl)-1-(4-fluoro-1H-indazol-5-yl)but-1-en-1-yl)phenyl)acrylic acid; (E)-3-(4-((E)-2-Cyclopropyl-1-(4-fluoro-1H-indazol-5-yl)-2-(4-fluoro-2-methylphenyl)vinyl)phenyl)acrylic acid; (E)-3-(4-((E)-2-(4-Chloro-2-methylphenyl)-2-cyclopropyl-1-(4-fluoro-1H-indazol-5-yl)vinyl)phenyl)acrylic acid; (E)-3-(4-((E)-1-(4-Chloro-1H-indazol-5-yl)-2-(2-chloro-4-fluorophenyl)but-1-en-1-yl)phenyl)acrylic acid; (E)-3-(4-((Z)-2-(2-Chloro-4-fluorophenyl)-3,3-difluoro-1-(1H-indazol-5-yl)prop-1-en-1-yl)phenyl)acrylic acid; (E)-3-(4-((E)-2-Cyclopropyl-1-(4-fluoro-1H-indazol-5-yl)-2-phenylvinyl)phenyl)acrylic acid; (E)-3-(4-((E)-4-Chloro-1-(4-fluoro-1H-indazol-5-yl)-2-phenylbut-1-en-1-yl)phenyl)acrylic acid; (E)-3-(4-((E)-4-Chloro-2-(2-chloro-4-fluorophenyl)-1-(4-fluoro-1H-indazol-5-yl)but-1-en-1-yl)phenyl)acrylic acid; (E)-3-(4-((E)-4-Fluoro-2-(4-fluorophenyl)-1-(1H-indazol-5-yl)but-1-en-1-yl)phenyl)acrylic acid; (E)-3-(4-((E)-4-Fluoro-1-(4-fluoro-1H-indazol-5-yl)-2-phenylbut-1-en-1-yl)phenyl)acrylic acid; (E)-3-(4-((E)-1-(1H-Indazol-5-yl)-5-methoxy-2-phenylpent-1-en-1-yl)phenyl)acrylic acid; (E)-3-(4-((E)-1-(1H-Indazol-5-yl)-6-methoxy-2-phenylhex-1-en-1-yl)phenyl)acrylic acid; (E)-3-(4-((E)-2-(2-Chloro-4-fluorophenyl)-1-(1H-indazol-5-yl)-3-methylbut-1-en-1-yl)phenyl)acrylic acid; (E)-3-(4-((E)-1-(1H-Indazol-5-yl)-2-(3-(trifluoromethoxy)phenyl)but-1-en-1-yl)phenyl)acrylic acid; (E)-3-(4-((E)-2-Cyclobutyl-1-(1H-indazol-5-yl)-2-phenylvinyl)phenyl)acrylic acid; (E)-3-(4-((E)-2-(2-Chloro-4-fluorophenyl)-2-cyclobutyl-1-(1H-indazol-5-yl)vinyl)phenyl)acrylic acid; (E)-3-(4-((E)-1-(3-Fluoro-1H-indazol-5-yl)-2-phenylbut-1-en-1-yl)phenyl)acrylic acid; (E)-3-(4-((E)-2-Cyclobutyl-1-(3-fluoro-1H-indazol-5-yl)-2-phenylvinyl)phenyl)acrylic acid; (E)-3-(4-((E)-2-(2-Chloro-4-fluorophenyl)-1-(3-fluoro-1H-indazol-5-yl)but-1-en-1-yl)phenyl)acrylic acid; (E)-3-(4-((E)-2-(2-Chloro-4-fluorophenyl)-2-cyclobutyl-1-(3-fluoro-1H-indazol-5-yl)vinyl)phenyl)acrylic acid; (E)-Ethyl 3-(44E)-2-(4-fluorophenyl)-1-(1H-indazol-5-yl)but-1-en-1-yl)phenyl)acrylate; (E)-Ethyl 3-(4-((E)-1-(1H-Indazol-5-yl)-2-(2-methoxyphenyl)but-1-en-1-yl)phenyl)acrylate; (E)-Ethyl 3-(4-((E)-1-(1H-Indazol-5-yl)-2-(4-methoxyphenyl)but-1-en-1-yl)phenyl)acrylate; (E)-3-(4-((E)-1-(1H-Indazol-5-yl)-2-phenylbut-1-en-1-yl)phenyl)-2-methyl acrylic acid; (E)-3-(4-((Z)-1-(1H-Indazol-5-yl)-2-phenylbut-1-en-1-yl)-3-methylphenyl)acrylic acid; (E)-3-(4-((E)-1-(1H-Indazol-5-yl)-2-phenylbut-1-en-1-yl)-2-methylphenyl)acrylic acid; (E)-3-(4-((Z)-1-(1H-Indazol-5-yl)-2-phenylbut-1-en-1-yl)-2-chlorophenyl)acrylic acid; (Z)-3-(4-((E)-1-(1H-Indazol-5-yl)-2-phenylbut-1-en-1-yl)phenyl)-2-fluoroacrylic acid; (Z)-3-(4-((E)-1-(1H-Indazol-5-yl)-2-phenylbut-1-en-1-yl)phenyl)-2-chloroacrylic acid; (E)-3-(4-((Z)-1-(1H-Indazol-5-yl)-2-phenylbut-1-en-1-yl)-3-fluorophenyl)acrylic acid; (E)-3-(4-((Z)-1-(1H-Indazol-5-yl)-2-phenylbut-1-en-1-yl)-2-fluorophenyl)acrylic acid; (E)-3-(4-((Z)-1-(1H-Indazol-5-yl)-2-phenylbut-1-en-1-yl)-2-(trifluoromethyl)phenyl)acrylic acid; (E)-3-(4-((Z)-1-(1H-Indazol-5-yl)-2-phenylbut-1-en-1-yl)-3-methoxyphenyl)acrylic acid; (E)-3-(4-((Z)-1-(1H-Indazol-5-yl)-2-phenylbut-1-en-1-yl)-2-methoxyphenyl)acrylic acid; (E)-Ethyl 3-(4-((E)-2-(2-chloro-4-fluorophenyl)-1-(1H-indazol-5-yl)but-1-en-1-yl)phenyl)acrylate hydrochloride; (E)-3-(4-((E)-2-(2-Chloro-4-fluorophenyl)-1-(1H-indazol-5-yl)but-1-en-1-yl)phenyl)acrylic acid; (E)-Ethyl 3-(4-((E)-2-(2,4-di chlorophenyl)-1-(1H-indazol-5-yl)but-1-en-1-yl)phenyl)acrylate; (E)-3-(4-((E)-2-(2,4-Dichlorophenyl)-1-(1H-indazol-5-yl)but-1-en-1-yl)phenyl)acrylic acid; (E)-3-(4-((E)-2-(4-Chloro-2-(trifluoromethyl)phenyl)-1-(1H-indazol-5-yl)but-1-en-1-yl)phenyl)acrylic acid; (E)-3-(4-((E)-2-(2-Chloro-4-fluorophenyl)-2-cyclopropyl-1-(1H-indazol-5-yl)vinyl)phenyl)acrylic acid; (E)-3-(4-((E)-2-(4-Fluoro-2-(trifluoromethyl)phenyl)-1-(1H-indazol-5-yl)but-1-en-1-yl)phenyl)acrylic acid; (E)-3-(4-(1-(4-Fluoro-1H-indazol-5-yl)-2-(4-fluoro-2-(trifluoromethyl) phenyl)butyl)phenyl)acrylic acid; (E)-3-(4-((E)-2-(2,4-Dichlorophenyl)-1-(4-fluoro-1H-indazol-5-yl)but-1-en-1-yl)phenyl)acrylic acid; (E)-3-(4-((E)-2-(4-Chloro-2-(trifluoromethyl)phenyl)-1-(4-fluoro-1H-indazol-5-yl)but-1-en-1-yl)phenyl)acrylic acid; (E)-3-(4-((E)-2-(2-Chloro-4-fluorophenyl)-4-fluoro-1-(1H-indazol-5-yl)but-1-en-1-yl)phenyl)acrylic acid; (E)-3-(4-((E)-2-(2-Chloro-4-methoxyphenyl)-1-(1H-indazol-5-yl)but-1-en-1-yl)phenyl)acrylic acid; (E)-3-(4-((E)-2-(2,4-Dichlorophenyl)-4-fluoro-1-(4-fluoro-1H-indazol-5-yl)but-1-en-1-yl)phenyl)acrylic acid; (E)-3-(4-((E)-2-Cyclopropyl-2-(2,4-di chlorophenyl)-1-(4-fluoro-1H-indazol-5-yl)vinyl)phenyl)acrylic acid; (E)-3-(4-((E)-2-(2-Chloro-4-fluorophenyl)-2-cyclopropyl-1-(4-fluoro-1H-indazol-5-yl)vinyl)phenyl)acrylic acid; (E)-3-(4-((E)-2-Cyclopropyl-2-(2,4-di chlorophenyl)-1-(1H-indazol-5-yl)vinyl)phenyl)

acrylic acid; (E)-3-(4-((E)-2-(4-Chloro-2-methylphenyl)-2-cyclopropyl-1-(1H-indazol-5-yl)vinyl)phenyl)acrylic acid; (E)-3-(4-((E)-1-(1H-Indazol-5-yl)-2-(2-methyl-5-(methyl sulfonyl)phenyl)but-1-en-1-yl)phenyl)acrylic acid; (E)-3-(4-((E)-1-(1H-Indazol-5-yl)-2-(4-methoxy-2-methylphenyl) but-1-en-1-yl)phenyl)acrylic acid; (E)-3-(4-((E)-2-(2-Fluoro-4-methoxyphenyl)-1-(1H-indazol-5-yl)but-1-en-1-yl)phenyl)acrylic acid; (E)-3-(4-((E)-2-(2-Chloro-5-methoxyphenyl)-1-(1H-indazol-5-yl)but-1-en-1-yl)phenyl) acrylic acid; (E)-3-(4-((E)-2-(2-Fluoro-4-(methyl sulfonyl) phenyl)-1-(1H-indazol-5-yl)but-1-en-1-yl)phenyl)acrylic acid; (E)-3-(4-((E)-2-(2,4-Dichlorophenyl)-3,3,4,4,4-pentadeutero-1-(1H-indazol-5-yl)but-1-en-1-yl)phenyl)acrylic acid; (E)-3-(4-((E)-1-(1H-Indazol-5-yl)-2-(3-(methyl sulfonyl)phenyl)but-1-en-1-yl)phenyl)acrylic acid; (E)-3-(4-((E)-2-(2,4-Dichlorophenyl)-1-(7-fluoro-1H-indazol-5-yl)but-1-en-1-yl)phenyl)acrylic acid; (E)-3-(4-((E)-2-(2-Chloro-3-methoxyphenyl)-1-(1H-indazol-5-yl)but-1-en-1-yl)phenyl) acrylic acid; (E)-3-(4-((E)-2-(2,4-Dichlorophenyl)-1-(7-fluoro-1H-indol-5-yl)but-1-en-1-yl)phenyl)acrylic acid; (E)-3-(4-((E)-2-(2-Chloro-4-fluorophenyl)-1-(7-fluoro-1H-indol-5-yl)but-1-en-1-yl)phenyl)acrylic acid; (E)-3-(4-((E)-2-(2-Chloro-4-fluorophenyl)-3,3,4,4,4-pentadeutero-1-(1H-indazol-5-yl)but-1-en-1-yl)phenyl)acrylic acid; (E)-3-(4-((E)-2-(4-Chloro-2-cyanophenyl)-1-(1H-indazol-5-yl)but-1-en-1-yl)phenyl)acrylic acid; (E)-3-(4-((E)-2-(2-Cyano-4-fluorophenyl)-1-(1H-indazol-5-yl)but-1-en-1-yl)phenyl) acrylic acid; (E)-3-(4-((E)-2-(2-Cyano-4-(trifluoromethyl) phenyl)-1-(1H-indazol-5-yl)but-1-en-1-yl)phenyl)acrylic acid; (E)-3-(4-((E)-2-(2-Chloro-4-cyanophenyl)-1-(1H-indazol-5-yl)but-1-en-1-yl)phenyl)acrylic acid; (E)-3-(4-((E)-2-(3-Cyano-2-methylphenyl)-1-(1H-indazol-5-yl)but-1-en-1-yl)phenyl)acrylic acid; (E)-3-(4-((E)-2-(4-Cyano-2-methylphenyl)-1-(1H-indazol-5-yl)but-1-en-1-yl)phenyl) acrylic acid; (E)-3-(4-((E)-2-(5-Cyano-2-methylphenyl)-1-(1H-indazol-5-yl)but-1-en-1-yl)phenyl)acrylic acid; (E)-3-(4-((E)-2-(2-Cyano-4-methoxyphenyl)-1-(1H-indazol-5-yl) but-1-en-1-yl)phenyl)acrylic acid; (E)-3-(4-((E)-2-(3-Hydroxyphenyl)-1-(1H-indazol-5-yl)but-1-en-1-yl)phenyl) acrylic acid; (E)-3-(4-((E)-2-(2-Hydroxyphenyl)-1-(1H-indazol-5-yl)but-1-en-1-yl)phenyl)acrylic acid; (E)-3-(4-((E)-2-(4-Hydroxyphenyl)-1-(1H-indazol-5-yl)but-1-en-1-yl)phenyl)acrylic acid; (E)-3-(4-(1-(1H-Indazol-5-yl)-2-phenylbut-1-en-1-yl)phenyl)propanoic acid; (E)-3-(4-((E)-1-(1H-Indazol-5-yl)-2-(4-(2-methoxyethoxy)phenyl)but-1-en-1-yl)phenyl)acrylic acid; (E)-3-(4-((E)-1-(1H-Indazol-5-yl)-2-(4-(3-methoxypropoxy)phenyl)but-1-en-1-yl)phenyl) acrylic acid; (E)-3-(4-((E)-1-(1H-Indazol-5-yl)-2-(3-(2-methoxyethoxy)phenyl)but-1-en-1-yl)phenyl)acrylic acid; (E)-3-(4-((E)-1-(1H-Indazol-5-yl)-2-(3-(3-methoxypropoxy)phenyl)but-1-en-1-yl)phenyl)acrylic acid; (E)-3-(4-((E)-2-(3-(Cyclohexyloxy)phenyl)-1-(4-fluoro-1H-indazol-5-yl)but-1-en-1-yl)phenyl)acrylic acid; (E)-3-(4-((E)-2-(3-Butoxyphenyl)-1-(1H-indazol-5-yl)but-1-en-1-yl) phenyl)acrylic acid; (E)-3-(4-((E)-1-(1H-Indazol-5-yl)-2-(3-(pentyloxy)phenyl)but-1-en-1-yl)phenyl)acrylic acid; (E)-3-(4-((E)-2-(3-(Hexyloxy)phenyl)-1-(1H-indazol-5-yl)but-1-en-1-yl)phenyl)acrylic acid; (E)-3-(4-((E)-2-(4-Butoxyphenyl)-1-(1H-indazol-5-yl)but-1-en-1-yl)phenyl) acrylic acid; (E)-3-(4-((E)-1-(1H-Indazol-5-yl)-2-(4-(pentyloxy)phenyl)but-1-en-1-yl)phenyl)acrylic acid; (E)-3-(4-((E)-2-(4-(Hexyloxy)phenyl)-1-(1H-indazol-5-yl)but-1-en-1-yl)phenyl)acrylic acid; (E)-3-(4-((E)-2-(4-(2-Hydroxyethoxy)phenyl)-1-(1H-indazol-5-yl)but-1-en-1-yl) phenyl)acrylic acid; (E)-3-(4-((E)-1-(1H-Indazol-5-yl)-2-(2-(methyl sulfonyl)phenyl)but-1-en-1-yl)phenyl)acrylic acid; (E)-3-(4-((E)-2-(2-Chlorophenyl)-1-(1-methyl-1H-indazol-5-yl)but-1-en-1-yl)phenyl)acrylic acid; (E)-3-(4-((E)-2-Cyclobutyl-1-(1-methyl-1H-indazol-5-yl)-2-phenyl vinyl)phenyl)acrylic acid; (E)-3-(4-((E)-2-(2-Chloro-4-fluorophenyl)-1-(1-methyl-1H-indazol-5-yl)but-1-en-1-yl)phenyl)acrylic acid; (E)-3-(4-((E)-2-(2-Chloro-4-fluorophenyl)-1-(1-(difluoromethyl)-1H-indazol-5-yl)but-1-en-1-yl)phenyl)acrylic acid; or a pharmaceutically acceptable salt, or N-oxide thereof, or a combination thereof.

In one instance, the endocrine therapy comprises brilanestrant (GDC-0810) having the structure:

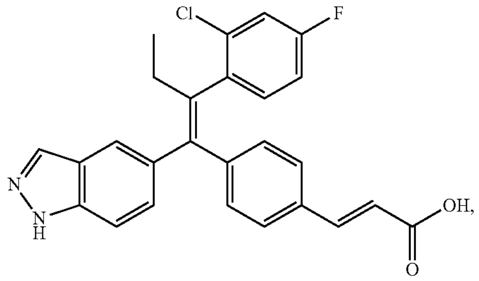 [SMILES: CC/C(=C(/c1ccc(/C=C/C(=O)O)cc1)c1ccc2[nH]ncc2c1)c1ccc(F)cc1Cl]

or a pharmaceutically acceptable salt thereof.

In another aspect, the endocrine therapy comprises a compound set forth in U.S. Pat. No. 9,499,538 or 9,586,952, each of which is incorporated herein by reference in its entirety and for all purposes.

In another aspect, the endocrine therapy comprises a compound set forth in U.S. Pat. No. 7,612,114 or 8,399,520, each of which is incorporated herein by reference in its entirety and for all purposes. In one instance, the endocrine therapy comprises elacestrant (RAD1901):

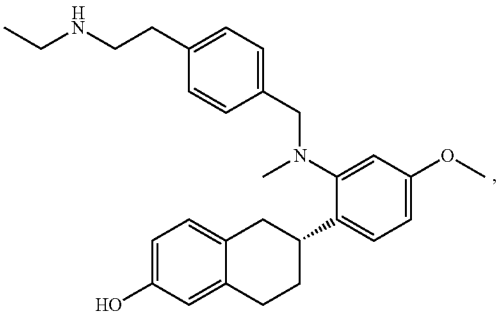 [SMILES: CCNCCc1ccc(CN(C)c2cc(OC)ccc2[C@@H]2CCc3cc(O)ccc3C2)cc1]

or a pharmaceutically acceptable salt thereof.

In another aspect, the endocrine therapy comprises a compound set forth in International Patent Application No. WO2018077260, for example in Table 2 therein, which is incorporated herein by reference in its entirety and for all purposes. In one instance, the endocrine therapy comprises a LX-039. In another instance, the endocrine therapy comprises a compound having the structure:

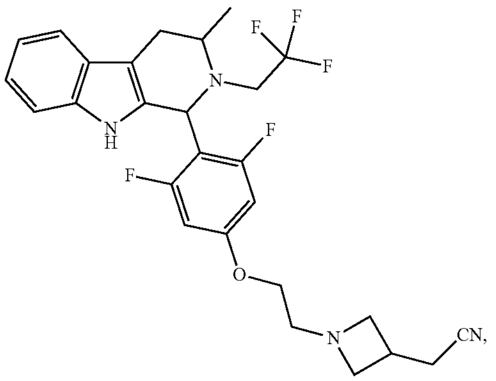 [SMILES: CC1Cc2c([nH]c3ccccc23)C(c2c(F)cc(OCCN3CC(CC#N)C3)cc2F)N1CC(F)(F)F]

or a pharmaceutically acceptable salt thereof.

In another aspect, the endocrine therapy comprises a compound set forth in International Patent Application No. WO2017136688, WO2017162206, WO2017140669, WO2017216280, WO2017216279, WO2018091153, WO2018019793, WO2018077630, each of which is incorporated herein by reference in its entirety and for all purposes.

In another instance, the endocrine therapy comprises AZ9496 having the structure:

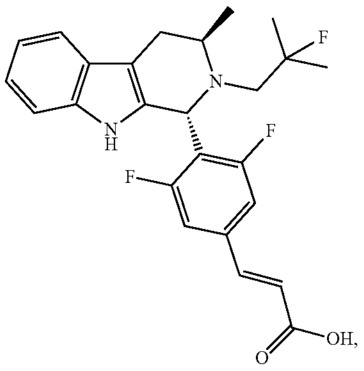 [SMILES: C[C@@H]1Cc2c([nH]c3ccccc23)[C@@H](c2c(F)cc(/C=C/C(=O)O)cc2F)N1CC(C)(C)F]

or a pharmaceutically acceptable salt thereof.

In another aspect, the endocrine therapy comprises a compound as set forth in U.S. Patent Application No. 20150284357, which is incorporated herein by reference in its entirety and for all purposes. In another aspect, the endocrine therapy comprises a compound as set forth in U.S. Pat. No. 9,475,791 which is incorporated herein by reference in its entirety and for all purposes. In still another aspect, the endocrine therapy comprises a compound as set forth in international patent application no WO2018081168 or WO2018129387, each of which is incorporated herein by reference in its entirety and for all purposes. In one aspect, the endocrine therapy comprises a compound having formula:

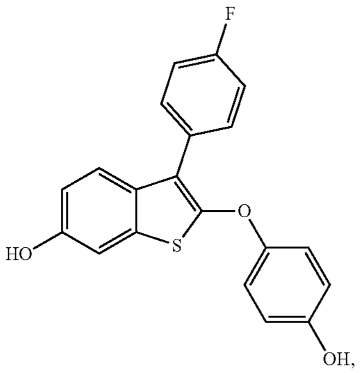

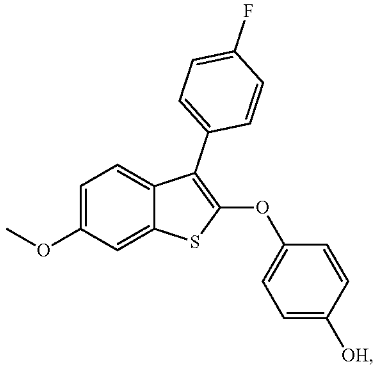

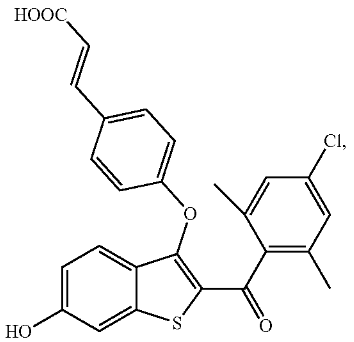

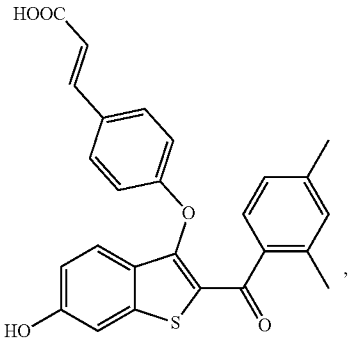

-continued

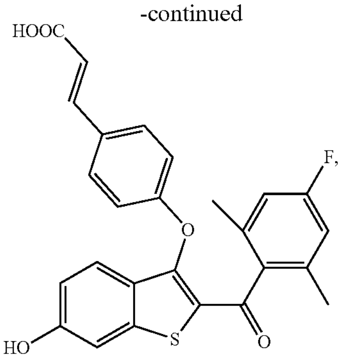

, or

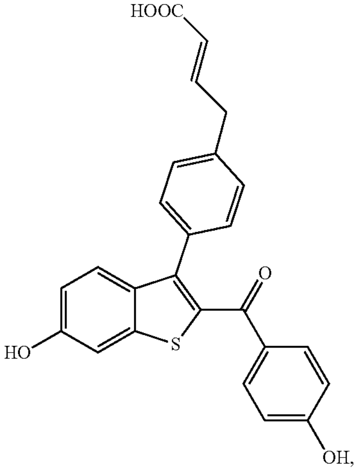

, or a stereoisomer or and pharmaceutically acceptable salt thereof.

In another aspect, the endocrine therapy comprises a compound set forth in U.S. Pat. No. 8,703,810, for example in table of compounds provided therein, which is incorporated herein by reference in its entirety and for all purposes.

In one aspect, the endocrine therapy comprises a compound having formula (2):

Formula (2)

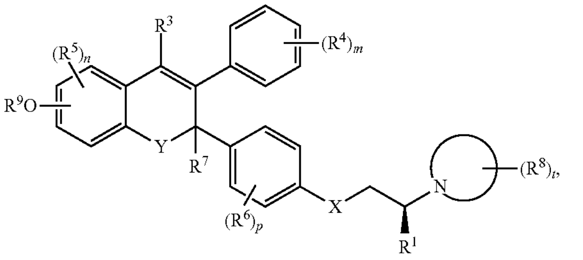

, or a pharmaceutically acceptable salt thereof, wherein:

$R^1$ is H, F, $C_1$-$C_4$alkyl, or $C_1$-$C_4$fluoroalkyl;

$R^3$ is H, halogen, $C_1$-$C_4$alkyl, $C_3$-$C_6$cycloalkyl, or $C_1$-$C_4$fluoroalkyl;

each $R^4$ is independently selected from H, halogen, —CN, —OH, —$OR^9$, —$SR^9$, —$S(O)R^{10}$, —$S(O)_2R^{10}$, —$C(O)R^{10}$, —C(O)OH, —$C(O)OR^{10}$, —$C(O)NHR^{10}$, —$C(O)N(R^{10})_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$ heteroalkyl;

each $R^5$ is independently selected from H, halogen, —CN, —OH, —$OR^9$, —$SR^9$, —$S(O)R^{10}$, —$S(O)_2R^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

each $R^6$ is independently selected from H, halogen, —CN, —OH, —$OR^9$, —$SR^9$, —$S(O)R^{10}$, —$S(O)_2R^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

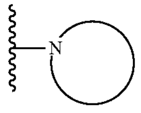

is pyrrolidinyl or azetidinyl;

$R^7$ is H or $C_1$-$C_4$alkyl;

each $R^8$ is independently selected from F, Cl, —CN, —OH, —$OR^9$, —$SR^9$, —$S(O)R^{10}$, —$S(O)_2R^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

or 1 $R^8$ is taken together with $R^1$ along with the intervening atoms joining $R^8$ to $R^1$ to form a 5-, 6-, or 7-membered ring;

each $R^9$ is independently selected from H, —$C(O)R^{10}$, —$C(O)OR^{10}$, —$C(O)NHR_{10}$, substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl); or each $R^{10}$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl);

Y is —O—, —S—, or —NR"—; R" is H, —$C(O)R^{10}$, substituted or unsubstituted $C_1$-$C_6$alkyl, substituted or unsubstituted $C_1$-$C_6$fluoroalkyl, or substituted or unsubstituted $C_1$-$C_6$heteroalkyl;

X is —O—, —S—, —$CH_2$—, —NH— or —N($C_1$-$C_6$alkyl)-;

m is 0, 1, 2, 3 or 4;

n is 0, 1, 2, or 3;

p is 0, 1, 2, 3 or 4; and t is 1, 2, 3 or 4.

In one instance, the compound of formula (2) is a compound wherein $R^1$ is H or $C_1$-$C_4$alkyl; $R^3$ is $C_1$-$C_4$alkyl or $C_1$-$C_4$fluoroalkyl; each $R^4$ is independently selected from H, halogen, —CN, —OH, —$OR^9$, —$SR^9$, —S(═O)$R^{10}$, —S(═O)$_2R^{10}$, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl; each $R^5$ is independently selected from H, F, Cl, —OH, —$CH_3$, —$CF_3$, —$OCF_3$, and —$OCH_3$; each $R^6$ is independently selected from H, F, Cl, —OH, —$CH_3$, —$CF_3$, —$OCF_3$, and —$OCH_3$; $R^7$ is H; each $R^8$ is independently selected from H, F, Cl, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl; Y is —O— or —S—; X is —O—, —S—, —$CH_2$—, —NH— or —N($CH_3$)—; and p is 0, 1, or 2.

In another aspect, the endocrine therapy comprises a compound having formula: 3-(3-Hydroxyphenyl)-4-methyl-2-(4-((S)-2-((R)-3-methylpyrrolidin-1-yl)propoxy)phenyl)-2H-chromen-6-ol; (S)-3-(3-Hydroxyphenyl)-4-methyl-2-(4-((S)-2-((R)-3-methylpyrrolidin-1-yl)propoxy)phenyl)-2H-chromen-6-ol; (R)-3-(3-Hydroxyphenyl)-4-methyl-2-(4-((S)-2-((R)-3-methylpyrrolidin-1-yl)propoxy)phenyl)-2H-chromen-6-ol; 3-(3-Hydroxyphenyl)-4-methyl-2-(4-(2-((R)-3-methylpyrrolidin-1-yl) ethoxy)phenyl)-2H-chromen-6-ol; 3-(3-Hydroxyphenyl)-4-methyl-2-(4-((R)-2-((R)-3-methylpyrrolidin-1-yl)propoxy)phenyl)-2H-chromen-6-ol; 3-(3-Hydroxyphenyl)-4-methyl-2-(4-(2-((S)-3-methylpyrrolidin-1-yl)ethoxy)phenyl)-2H-chromen-6-ol; 3-(3-hydroxyphenyl)-4-methyl-2-(4-((S)-2-((S)-3-methylpyrrolidin-1-yl)propoxy)phenyl)-2H-chromen-6-ol; 3-(3-hydroxyphenyl)-4-methyl-2-(4-((R)-2-((S)-3-methylpyrrolidin-1-yl)propoxy)phenyl)-2H-chromen-6-ol; 2-(4-((S)-2-(3,3-Dimethylpyrrolidin-1-yl)propoxy)phenyl)-3-(3-hydroxyphenyl)-4-methyl-2H-chromen-6-ol; 2-(4-(2-(3,3-Dimethylpyrrolidin-1-yl)ethoxy)phenyl)-3-(3-hydroxyphenyl)-4-methyl-2H-chromen-6-ol; 3-(3-Hydroxyphenyl)-4-methyl-2-(4-(2-((R)-2-methylpyrrolidin-1-yl)ethoxy)phenyl)-2H-chromen-6-ol; 3-(3-Hydroxyphenyl)-4-methyl-2-(4-((S)-2-((R)-2-methylpyrrolidin-1-yl)propoxy)phenyl)-2H-chromen-6-ol; 3-(3-Hydroxyphenyl)-4-methyl-2-(4-((S)-2-((S)-2-methylpyrrolidin-1-yl)propoxy)phenyl)-2H-chromen-6-ol; 3-(3-Hydroxyphenyl)-4-methyl-2-(4-((S)-2-((R)-3-methylpyrrolidin-1-yl)propoxy)phenyl)-2H-chromen-7-ol; 3-(4-Hydroxyphenyl)-4-methyl-2-(4-((S)-2-((R)-3-methylpyrrolidin-1-yl)propoxy)phenyl)-2H-chromen-7-ol; 4-Methyl-2-(4-((S)-2-((R)-3-methylpyrrolidin-1-yl)propoxy)phenyl)-3-phenyl-2H-chromen-6-ol; 3-(4-Fluorophenyl)-4-methyl-2-(4-((S)-2-((R)-3-methylpyrrolidin-1-yl)propoxy)phenyl)-2H-chromen-6-ol; (S)-3-(4-Fluorophenyl)-4-methyl-2-(4-((S)-2-((R)-3-methylpyrrolidin-1-yl)propoxy)phenyl)-2H-chromen-6-ol; (R)-3-(4-Fluorophenyl)-4-methyl-2-(4-((S)-2-((R)-3-methylpyrrolidin-1-yl)propoxy)phenyl)-2H-chromen-6-ol; 3-(4-Hydroxyphenyl)-4-methyl-2-(4-((S)-2-((R)-3-methylpyrrolidin-1-yl)propoxy)phenyl)-2H-chromen-6-ol; 3-(3-Fluorophenyl)-4-methyl-2-(4-((S)-2-((R)-3-methylpyrrolidin-1-yl)propoxy)phenyl)-2H-chromen-6-ol; 3-(3-Fluoro-4-hydroxyphenyl)-4-methyl-2-(4-((S)-2-((R)-3-methylpyrrolidin-1-yl)propoxy)phenyl)-2H-chromen-6-ol; 2-(2-Fluoro-4-((S)-2-((R)-3-methylpyrrolidin-1-yl)propoxy)phenyl)-3-(3-hydroxyphenyl)-4-methyl-2H-chromen-6-ol; 3-(3-Hydroxy-4-methylphenyl)-4-methyl-2-(4-((S)-2-((R)-3-methylpyrrolidin-1-yl)propoxy)phenyl)-2H-chromen-6-ol; 3-(3-Hydroxy-2-methylphenyl)-4-methyl-2-(4-((S)-2-((R)-3-methylpyrrolidin-1-yl)propoxy)phenyl)-2H-chromen-6-ol; 3-(4-Hydroxy-2-methylphenyl)-4-methyl-2-(4-((S)-2-((R)-3-methylpyrrolidin-1-yl)propoxy)phenyl)-2H-chromen-6-ol; 3-(4-Hydroxy-3-methylphenyl)-4-methyl-2-(4-((S)-2-((R)-3-methylpyrrolidin-1-yl)propoxy)phenyl)-2H-chromen-6-ol; 3-(3-Fluoro-5-hydroxyphenyl)-4-methyl-2-(4-((S)-2-((R)-3-methylpyrrolidin-1-yl)propoxy)phenyl)-2H-chromen-6-ol; 3-(4-Chlorophenyl)-4-methyl-2-(4-((S)-2-((R)-3-methylpyrrolidin-1-yl)propoxy)phenyl)-2H-chromen-6-ol; 3-(2-Fluoro-4-hydroxyphenyl)-4-methyl-2-(4-((S)-2-((R)-3-methylpyrrolidin-1-yl)propoxy)phenyl)-2H-chromen-6-ol; 3-(3,4-Difluorophenyl)-4-methyl-2-(4-((S)-2-((R)-3-methylpyrrolidin-1-yl)propoxy)phenyl)-2H-chromen-6-ol; 3-(3,5-Difluoro-4-hydroxyphenyl)-4-methyl-2-(4-((S)-2-((R)-3-methylpyrrolidin-1-yl)propoxy)phenyl)-2H-chromen-6-ol; 3-(2,4-Difluoro-3-hydroxyphenyl)-4-methyl-2-(4-((S)-2-((R)-3-methylpyrrolidin-1-yl)propoxy)phenyl)-2H-chromen-6-ol; 3-(3,4-Difluoro-5-hydroxyphenyl)-4-methyl-2-(4-((S)-2-((R)-3-methylpyrrolidin-1-yl)propoxy)phenyl)-2H-chromen-6-ol; 3-(2-Chloro-4-fluorophenyl)-4-methyl-2-(4-((S)-2-(R)-3-methylpyrrolidin-1-yl)propoxy)phenyl)-2H-chromen-6-ol; 3-(2,4-Difluorophenyl)-4-methyl-2-(4-((S)-2-((R)-3-methylpyrrolidin-1-yl)propoxy)phenyl)-2H-chromen-6-ol; 3-(4-Bromophenyl)-4-methyl-2-(4-((S)-2-((R)-3-methylpyrrolidin-1-yl)propoxy)phenyl)-2H-chromen-6-ol; 4-Methyl-2-(4-((S)-2-((R)-3-methylpyrrolidin-1-yl)propoxy)phenyl)-3-(o-tolyl)-2H-chromen-6-ol; 3-(4-Fluoro-3-hydroxyphenyl)-4-methyl-2-(4-((S)-2-((R)-3-methylpyrrolidin-1-yl)propoxy)phenyl)-2H-chromen-6-ol; 3-(4-Ethynylphenyl)-4-methyl-2-(4-((S)-2-((R)-3-methylpyrrolidin-1-yl)propoxy)phenyl)-2H-chromen-6-ol; 4-Methyl-2-(4-((S)-2-((R)-3-methylpyrrolidin-1-yl)propoxy)phenyl)-3-(4-(methyl sulfonyl)phenyl)-2H-chromen-6-ol; 3-(2-Fluoro-3-hydroxyphenyl)-4-methyl-2-(4-((S)-2-((R)-3-methylpyrrolidin-1-yl)propoxy)phenyl)-2H-chromen-6-ol; 5-Fluoro-3-(3-hydroxyphenyl)-4-methyl-2-(4-((S)-2-((R)-3-methylpyrrolidin-1-yl)propoxy)phenyl)-2H-chromen-6-ol; 3-(2-Fluoro-5-hydroxyphenyl)-4-methyl-2-(4-((S)-2-((R)-3-methylpyrrolidin-1-yl)propoxy)phenyl)-2H-chromen-6-ol; 3-(4-Fluorophenyl)-4-methyl-2-(4-((S)-2-((R)-2-methylpyrrolidin-1-yl)propoxy)phenyl)-2H-chromen-6-ol; 2-(4-((S)-2-((R)-3-Fluoropyrrolidin-1-yl)propoxy)phenyl)-3-(3-hydroxyphenyl)-4-methyl-2H-chromen-6-ol; 3-(4-Hydroxyphenyl)-2-(4-((S)-2-(R)-3-methylpyrrolidin-1-yl)propoxy)phenyl)-4-(trifluoromethyl)-2H-chromen-6-ol; 3-(3-Hydroxyphenyl)-2-(4-((S)-2-(R)-3-methylpyrrolidin-1-yl)propoxy)phenyl)-4-(trifluoromethyl)-2H-chromen-6-ol; 3-(3-Hydroxy-4-(trifluoromethyl)phenyl)-4-methyl-2-(4-((S)-2-((R)-3-methylpyrrolidin-1-yl)propoxy)phenyl)-2H-chromen-6-ol; 3-(4-Hydroxy-3-(trifluoromethyl)phenyl)-4-methyl-2-(4-((S)-2-(R)-3-methylpyrrolidin-1-yl)propoxy)phenyl)-2H-chromen-6-ol; or a pharmaceutically acceptable salt thereof, or a combination thereof.

In one instance, the endocrine therapy comprises a GDC-0927 (SRN-0927) having the structure:

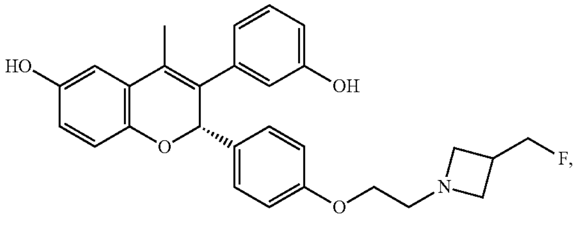 [SMILES: CC1=C(c2cccc(O)c2)[C@H](c2ccc(OCCN3CC(CF)C3)cc2)Oc2ccc(O)cc21]

or a pharmaceutically acceptable salt thereof.

In another aspect, the endocrine therapy comprises a compound set forth in U.S. Pat. No. 9,980,947, for example in Table 1 therein, which is incorporated herein by reference in its entirety and for all purposes.

In one aspect, the endocrine therapy comprises a compound of formula (3):

(3)

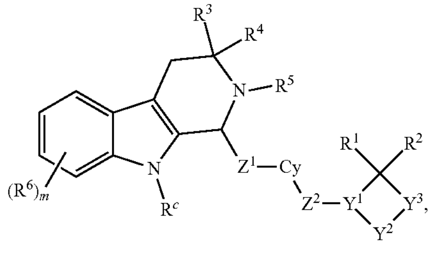

or a stereoisomer, tautomer, or pharmaceutically acceptable salt thereof, wherein:

$Y^1$ is $CR^b$ or N;

$Y^2$ is —($CH_2$)—, —($CH_2CH_2$)—, or $NR^a$;

$Y^3$ is $NR^a$ or $C(R^b)_2$;

where one of $Y^1$, $Y^2$ and $Y^3$ is N or $NR^a$; $R^a$ is H, $C_1$-$C_6$ alkyl, $C_2$-$C_8$ alkenyl, propargyl, $C_3$-$C_6$ cycloalkyl, or $C_3$-$C_6$ heterocyclyl, optionally substituted with one or more groups independently selected from the group consisting of F, Cl, Br, I, CN, OH, $OCH_3$, and $SO_2CH_3$;

$R^b$ is H, —O($C_1$-$C_3$ alkyl), $C_1$-$C_6$ alkyl, $C_2$-$C_8$ alkenyl, propargyl, —($C_1$-$C_6$ alkyldiyl)-($C_3$-$C_6$ cycloalkyl), $C_3$-$C_6$ cycloalkyl, or $C_3$-$C_6$ heterocyclyl, optionally substituted with one or more groups independently selected from the group consisting of F, Cl, Br, I, CN, —$CH_2F$, —$CHF_2$, —$CF_3$, —$CH_2CF_3$, —$CH_2CHF_2$, —$CH_2CH_2F$, OH, $OCH_3$, and $SO_2CH_3$, $R^c$ is H, $C_1$-$C_6$ alkyl, allyl, or propargyl, optionally substituted with one or more groups independently selected from the group consisting of F, Cl, Br, I, CN, OH, $OCH_3$, and $SO_2CH_3$;

$Z^1$ is $CR^aR^b$, C(O), or a bond;

Cy is $C_6$-$C_{20}$ aryldiyl, $C_3$-$C_{12}$ carbocyclyldiyl, $C_2$-$C_{20}$ heterocyclyldiyl, or $C_1$-$C_{20}$ heteroaryldiyl;

$Z^2$ is O, S, $NR^a$, $C_1$-$C_6$ alkyldiyl, $C_1$-$C_6$ fluoroalkyldiyl, O—($C_1$-$C_6$ alkyldiyl), O—($C_1$-$C_6$ fluoroalkyldiyl), C(O), or a bond;

$R^1$, $R^2$, $R^3$ and $R^4$ are independently H, F, Cl, Br, I, —CN, —$CH_3$, —$CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CH_2NH_2$, —$CH_2NHSO_2CH_3$, —$CH_2NHCH_3$, —$CH_2N(CH_3)_2$, —CF 3, —$CH_2$CF 3, —$CH_2CHF_2$, —CH($CH_3$)CN, —$C(CH_3)_2$CN, —$CH_2$CN, —$CO_2H$, —$COCH_3$, —$CO_2CH_3$, —$CO_2C(CH_3)_3$, —$COCH(OH)CH_3$, —$CONH_2$, —$CONHCH_3$, —$CONHCH_2CH_3$, —CONHCH$(CH_3)_2$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)$ $CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, —$S(O)_3H$, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, or morpholino;

$R^5$ is H, $C_1$-$C_9$ alkyl, $C_3$-$C_9$ cycloalkyl, $C_3$-$C_9$ heterocycle, $C_6$-$C_9$ aryl, $C_6$-$C_9$ heteroaryl, —($C_1$-$C_6$ alkyldiyl)-($C_3$-$C_9$ cycloalkyl), alkyldiyl)-($C_3$-$C_9$ heterocycle), C(O)$R^b$, C(O)$NR^a$, $SO_2R^a$, or $SO_2NR^a$, optionally substituted with one or more of halogen, CN, ORE, $N(R^a)_2$, $C_1$-$C_9$ alkyl, $C_3$-$C_9$ cycloalkyl, $C_3$-$C_9$ heterocycle, $C_6$-$C_9$ aryl, $C_6$-$C_9$ heteroaryl, C(O)$R^b$, C(O)$NR^a$, $SO_2R^a$, or $SO_2NR^a$;

$R^6$ is F, Cl, Br, I, —CN, —$CH_3$, —$CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CH_2NH_2$, —$CH_2NHSO_2CH_3$, —$CH_2NHCH_3$, —$CH_2N(CH_3)_2$, —$CF_3$, —$CH_2CF_3$, —$CH_2CHF_2$, —CH($CH_3$)CN, —$C(CH_3)_2$CN, —$CH_2$CN, —$CO_2H$, —$COCH_3$, —$CO_2CH_3$, —$CO_2C(CH_3)_3$, —$COCH(OH)CH_3$, —$CONH_2$, —$CONHCH_3$, —$CONHCH_2CH_3$, —$CONHCH(CH_3)_2$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, —$S(O)_3H$, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, or morpholino; and m is 0, 1, 2, 3, or 4;

where alkyldiyl, fluoroalkyldiyl, aryldiyl, carbocyclyldiyl, heterocyclyldiyl, and heteroaryldiyl are optionally substituted with one or more groups independently selected from the group consisting of F, Cl, Br, I, —CN, —$CH_3$, —$CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CF_3$, —$CH_2CF_3$, —$CH_2CHF_2$, —$CH_2CH_2F$, —CH($CH_3$)CN, —$C(CH_3)_2$CN, —$CH_2$CN, —$CH_2NH_2$, —$CH_2NHSO_2CH_3$, —$CH_2NHCH_3$, —$CH_2N(CH_3)_2$, —$CO_2H$, —$COCH_3$, —$CO_2CH_3$, —$CO_2C(CH_3)_3$, —$COCH(OH)CH_3$, —$CONH_2$, —$CONHCH_3$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, —$S(O)_3H$, cyclopropyl, cyclopropylamide, cyclobutyl, oxetanyl, azetidinyl, 1-methylazetidin-3-yl)oxy, N-methyl-N-oxetan-3-ylamino, azetidin-1 methyl, benzyloxyphenyl, pyrrolidin-1-yl, pyrrolidin-1-yl-methanone, piperazin-1-yl, morpholinomethyl, morpholino-methanone, and morpholino.

In one instance of the compounds of formula (3), $Y^1$ is $CR^b$ and $Y^3$ is $NR^a$. In another instance of the compounds of formula (3), $Y^1$ is N and $Y^3$ is $C(R^b)_2$. In another instance of the compounds of formula (3), $Y^2$ is —($CH_2$)—. In another instance of the compounds of formula (3), $Y^2$ is —($CH_2CH_2$)—.

In another instance of the compounds of formula (3), $R^c$ is H. In another instance of the compounds of formula (3), Cy is $C_6$-$C_{20}$ aryldiyl, $C_6$-$C_{20}$ aryldiyl is phenyldiyl, and phenyldiyl is substituted with one or more F. In another instance of the compounds of formula (3), $R^1$ and $R^2$ are H. In another instance of the compounds of formula (3), $R^3$ is H, and $R^4$ is —$CH_3$. In another instance of the compounds of formula (3), $R^5$ is $C_1$-$C_6$ fluoroalkyl. In another instance of the compounds of formula (3), m is 0.

In another instance, the endocrine therapy comprises a compound of formula (3) having formula (3a):

(3a)

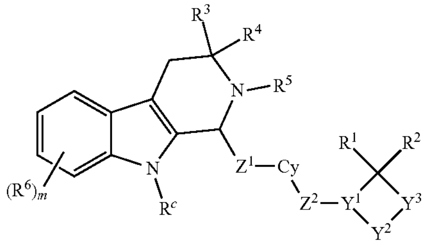

or a stereoisomer, tautomer, or pharmaceutically acceptable salt thereof, wherein:

$Y^1$ is $CR^b$ or N;

$Y^2$ is —($CH_2$)—, —($CH_2CH_2$)—, or $NR^a$;

$Y^3$ is $NR^a$ or $C(R^b)_2$;

where one of $Y^1$, $Y^2$ and $Y^3$ is N or $NR^a$;

$R^a$ is independently H, $C_1$-$C_6$ alkyl, $C_2$-$C_8$ alkenyl, propargyl, $C_3$-$C_6$ cycloalkyl, and $C_3$-$C_6$ heterocyclyl, optionally substituted with one or more groups independently selected from F, Cl, Br, I, CN, OH, $OCH_3$, or $SO_2CH_3$;

$R^b$ is independently H, —O($C_1$-$C_3$ alkyl), $C_1$-$C_6$ alkyl, $C_2$-$C_8$ alkenyl, propargyl, —($C_1$-$C_6$ alkyldiyl)-($C_3$-$C_6$ cycloalkyl), $C_3$-$C_6$ cycloalkyl, and $C_3$-$C_6$ heterocyclyl, optionally substituted with one or more groups independently selected from F, Cl, Br, I, CN, —$CH_2F$, —$CHF_2$, —$CF_3$, —$CH_2CF_3$, —$CH_2CHF_2$, —$CH_2CH_2F$, OH, $OCH_3$, or $SO_2CH_3$, $R^c$ is independently H, $C_1$-$C_6$ alkyl, allyl, propargyl, optionally substituted with one or more groups independently selected from F, Cl, Br, I, CN, OH, $OCH_3$, or $SO_2CH_3$;

$Z^1$ is $CR^aR^b$, C(O), or a bond;

Cy is $C_6$-$C_{20}$ aryldiyl, $C_3$-$C_{12}$ carbocyclyldiyl, $C_2$-$C_{20}$ heterocyclyldiyl, or $C_1$-$C_{20}$ heteroaryldiyl;

$Z^2$ is O;

$R^1$, $R^2$, $R^3$ and $R^4$ are each independently H, F, Cl, Br, I, —CN, —$CH_3$, —$CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CHF_2$, —$CHF_2$, —$CH_2NH_2$, —$CH_2NHSO_2CH_3$, —$CH_2NHCH_3$, —$CH_2N(CH_3)_2$, —$CF_3$, —$CH_2CF_3$, —$CH_2CHF_2$, —$CH(CH_3)CN$, —$C(CH_3)_2CN$, —$CH_2CN$, —$CO_2H$, —$COCH_3$, —$CO_2CH_3$, —$CO_2C(CH_3)_3$, —$COCH(OH)CH_3$, —$CONH_2$, —$CONHCH_3$, —$CONHCH_2CH_3$, —$CONHCH(CH_3)_2$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, —$S(O)_3H$, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, or morpholino;

$R^5$ is H, $C_1$-$C_9$ alkyl, $C_3$-$C_9$ cycloalkyl, $C_3$-$C_9$ heterocycle, $C_6$-$C_9$ aryl, $C_6$-$C_9$ heteroaryl, alkyldiyl)-($C_3$-$C_9$ cycloalkyl), alkyldiyl)-($C_3$-$C_9$ heterocycle), $C(O)R^b$, $C(O)NR^a$, $SO_2R^a$, and $SO_2NR^a$, optionally substituted with one or more of halogen, CN, $OR^a$, $N(R^a)_2$, $C_1$-$C_9$ alkyl, $C_3$-$C_9$ cycloalkyl, $C_3$-$C_9$ heterocycle, $C_6$-$C_9$ aryl, $C_6$-$C_9$ heteroaryl, $C(O)R^b$, $C(O)NR^a$, $SO_2R^a$, or $SO_2NR^a$;

$R^6$ is F, Cl, Br, I, —CN, —$CH_3$, —$CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CH_2NH_2$, —$CH_2NHSO_2CH_3$, —$CH_2NHCH_3$, —$CH_2N(CH_3)_2$, —$CF_3$, —$CH_2CF_3$, —$CH_2CHF_2$, —$CH_2CH_2F$, —$CH(CH_3)CN$, —$C(CH_3)_2CN$, —$CH_2CN$, —$CO_2H$, —$COCH_3$, —$CO_2CH_3$, —$CO_2C(CH_3)_3$, —$COCH(OH)CH_3$, —$CONH_2$, —$CONHCH_3$, —$CONHCH_2CH_3$, —$CONHCH(CH_3)_2$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, —$S(O)_3H$, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, or morpholino; and m is 0, 1, 2, 3, or 4;

where alkyldiyl, fluoroalkyldiyl, aryldiyl, carbocyclyldiyl, heterocyclyldiyl, and heteroaryldiyl are optionally substituted with one or more groups independently selected from the group consisting of F, Cl, Br, I, —CN, —$CH_3$, —$CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CF_3$, —$CH_2CF_3$, —$CH_2CHF_2$, —$CH_2CH_2F$, —$CH(CH_3)CN$, —$C(CH_3)_2CN$, —$CH_2CN$, —$CH_2NH_2$, —$CH_2NHSO_2CH_3$, —$CH_2NHCH_3$, —$CH_2N(CH_3)_2$, —$CO_2H$, —$COCH_3$, —$CO_2CH_3$, —$CO_2C(CH_3)_3$, —$COCH(OH)CH_3$, —$CONH_2$, —$CONHCH_3$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, —$S(O)_3H$, cyclopropyl, cyclopropylamide, cyclobutyl, oxetanyl, azetidinyl, 1-methylazetidin-3-yl)oxy, N-methyl-N-oxetan-3-ylamino, azetidin-1-yl methyl, benzyloxyphenyl, pyrrolidin-1-yl, pyrrolidin-1-yl-methanone, piperazin-1-yl, morpholinomethyl, morpholino-methanone, and morpholino.

In one instance, the compound of formula (3a) comprises formula (3b):

(3b)

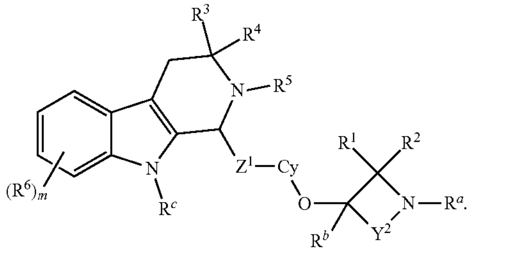

In another instance, the compound of formula (3a) comprises formula (3c):

(3c)

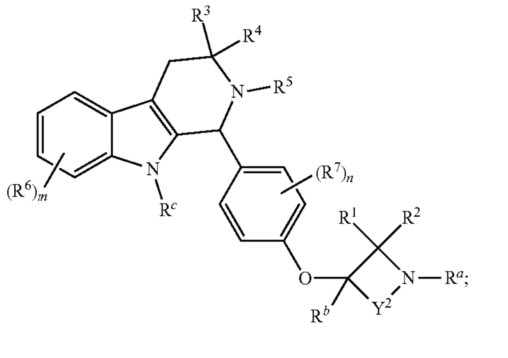

wherein $R^7$ is F, Cl, Br, I, $-CN$, $-CH_3$, $-CH_2CH_3$, $-CH(CH_3)_2$, $-CH_2CH(CH_3)_2$, $-CH_2OH$, $-CH_2OCH_3$, $-CH_2CH_2OH$, $-C(CH_3)_2OH$, $-CH(OH)CH(CH_3)_2$, $-C(CH_3)_2CH_2OH$, $-CH_2CH_2SO_2CH_3$, $-CH_2OP(O)(OH)_2$, $-CH_2F$, $-CHF_2$, $-CH_2NH_2$, $-CH_2NHSO_2CH_3$, $-CH_2NHCH_3$, $-CH_2N(CH_3)_2$, $-CF_3$, $-CH_2CF_3$, $-CH_2CHF_2$, $-CH(CH_3)CN$, $-C(CH_3)_2CN$, $-CH_2CN$, $-CO_2H$, $-COCH_3$, $-CO_2CH_3$, $-CO_2C(CH_3)_3$, $-COCH(OH)CH_3$, $-CONH_2$, $-CONHCH_3$, $-CONHCH_2CH_3$, $-CONHCH(CH_3)_2$, $-CON(CH_3)_2$, $-C(CH_3)_2CONH_2$, $-NH_2$, $-NHCH_3$, $-N(CH_3)_2$, $-NHCOCH_3$, $-N(CH_3)COCH_3$, $-NHS(O)_2CH_3$, $-N(CH_3)C(CH_3)_2CONH_2$, $-N(CH_3)CH_2CH_2S(O)_2CH_3$, $-NO_2$, $=O$, $-OH$, $-OCH_3$, $-OCH_2CH_3$, $-OCH_2CH_2OCH_3$, $-OCH_2CH_2OH$, $-OCH_2CH_2N(CH_3)_2$, $-OP(O)(OH)_2$, $-S(O)_2N(CH_3)_2$, $-SCH_3$, $-S(O)_2CH_3$, $-S(O)_3H$, cyclopropyl, cyclopropylamide, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, or morpholino; and n is 0, 1, 2, 3, or 4.

In another instance, the compound of formula (3a) comprises formula (3d):

(3d)

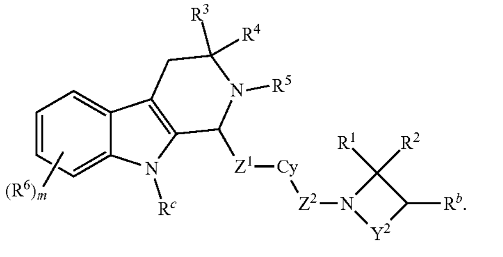

In still another instance, the compound of formula (3a) comprises formula (3e):

(3e)

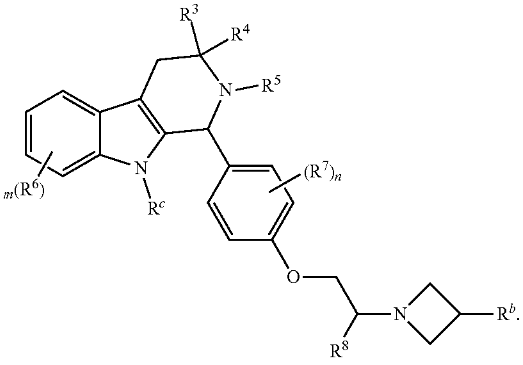

wherein $R^8$ is H or $CH_3$.

In another instance of the compounds of formula (3a)-(3e), $Y^1$ is $CR^b$ and $Y^3$ is NW. In another instance of the compounds of formula (3a)-(3e), $Y^1$ is N and $Y^3$ is $C(R^b)_2$. In another instance of the compounds of formula (3 a)-(3 e), $Y^2$ is $-(CH_2)-$ or $-(CH_2CH_2)-$. In another instance of the compounds of formula (3a)-(3e), $R^c$ is H. In another instance of the compounds of formula (3a)-(3e), Cy is phenyldiyl. In one instance of the compounds of formula (3a)-(3e), phenyldiyl is substituted with one or more F.

In another instance of the compounds of formula (3a)-(3e), $R^1$ and $R^2$ are H. In another instance of the compounds of formula (3 a)-(3 e), $R^3$ is H, and $R^4$ is $CH_3$. In another instance of the compounds of formula (3a)-(3e), $R^5$ is $C_1$-$C_6$ fluoroalkyl. In another instance of the compounds of formula (3a)-(3e), m is 0.

In another aspect, the endocrine therapy comprises a compound having formula: (1R,3R)-1-(2,6-difluoro-4-((1-(3-fluoropropyl)azetidin-3-yl)oxy)phenyl)-2-(2-fluoro-2-methylpropyl)-3-methyl-2,3,4,9-tetrahydro-1H-pyrido[3,4-b]indole; (1R,3R)-1-(2,6-difluoro-4-(2-(3-(fluoromethyl)azetidin-1-yl)ethoxy)phenyl)-2-(2-fluoro-2-methylpropyl)-3-methyl-2,3,4,9-tetrahydro-1H-pyrido[3,4-b]indole; 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-methylpropan-1-one; 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-fluoro-2-methylpropan-1-one; (1R,3R)-1-(4-(2-(3-(difluoromethyl)azetidin-1-yl)ethoxy)-2,6-difluorophenyl)-2-(2-fluoro-2-methylpropyl)-3-methyl-2,3,4,9-tetrahydro-1H-pyrido[3,4-b]indole; (1R,3R)-1-(4-((1-(3-chloropropyl)azetidin-3-yl)oxy)-2,6-difluorophenyl)-2-(2-fluoro-2-methylpropyl)-3-methyl-2,3,4,9-tetrahydro-1H- pyrido[3,4-b]indole; (1R,3R)-1-(2,6-difluoro-4-((1-propylazetidin-3-yl)oxy)phenyl)-2-(2-fluoro-2-methylpropyl)-3-methyl-2,3,4,9-tetrahydro-1H-pyrido[3,4-b]indole; (1R,3R)-1-(2,6-difluoro-4-((S)-2-((R)-3-(fluoromethyl)pyrrolidin-1-yl)propoxy)phenyl)-2-(2-fluoro-2-methylpropyl)-3-methyl-2,3,4,9-tetrahydro-1H-pyrido[3,4-b]indole; (1R,3R)-1-(2,6-difluoro-4-(2-((R)-3-(fluoromethyl)pyrrolidin-1-yl)ethoxy)phenyl)-2-(2-fluoro-2-methylpropyl)-3-methyl-2,3,4,9-tetrahydro-1H-pyrido[3,4-b]indole; (1R,3R)-2-(2-fluoro-2-methylpropyl)-1-(6-(2-(3-(fluoromethyl)azetidin-1-yl)ethoxy)pyridin-3-yl)-3-methyl-2,3,4,9-tetrahydro-1H-pyrido[3,4-b]indole; (1S,3R)-2-(2-fluoro-2-methylpropyl)-1-(3-fluoro-5-(2-(3-(fluoromethyl)azetidin-1-yl)ethoxy)pyridin-2-yl)-3-methyl-2,3,4,9-tetrahydro-1H-pyrido[3,4-b]indole; (1R,3R)-2-(cyclobutylmethyl)-1-(2,6-difluoro-4-(2-(3-(fluoromethyl)azetidin-1-yl)ethoxy)phenyl)-3-methyl-2,3,4,9-tetrahydro-1H-pyrido[3,4-b]indole; (1R,3R)-1-(2,6-difluoro-4-(2-(3-(fluoromethyl)azetidin-1-yl)ethoxy)phenyl)-3-methyl-2-((3-methyl oxetan-3-yl)methyl)-2,3,4,9-tetrahydro-1H-pyrido[3,4-b]indole; (1R,3R)-1-(2,6-difluoro-4-(2-(3-(fluoromethyl)azetidin-1-yl)ethoxy)phenyl)-3-methyl-2-(oxetan-3-ylmethyl)-2,3,4,9-tetrahydro-1H-pyrido[3,4-b]indole; (1R,3R)-1-(2,6-difluoro-4-(2-(3-(fluoromethyl)azetidin-1-yl)ethoxy)phenyl)-3-methyl-2-(oxetan-3-yl)-2,3,4,9-tetrahydro-1H-pyrido[3,4-b]indole; (1R,3R)-1-(2,6-difluoro-4-(2-(pyrrolidin-1-yl)ethoxy)phenyl)-2-(2-fluoro-2-methylpropyl)-3-methyl-2,3,4,9-tetrahydro-1H-pyrido[3,4-b]indole; (1R,3R)-1-(2,6-difluoro-4-(2-(piperidin-1-yl)ethoxy)phenyl)-2-(2-fluoro-2-methylpropyl)-3-methyl-2,3,4,9-tetrahydro-1H-pyrido[3,4-b]indole; (1-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)azetidin-3-yl)methanol; (1R,3R)-2-(2-fluoro-2-methylpropyl)-1-(2-fluoro-4-(2-(3-(fluoromethyl)azetidin-1-yl)ethoxy)phenyl)-3-methyl-2,3,4,9-tetrahydro-1H-pyrido[3,4-b]indole; 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)ethanone; 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-hydroxy-2-methylpropan-1-one; (R)-3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-methylpropan-1-ol; ((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)((1s,3S)-3-hydroxycyclobutyl)methanone; 1-(1-(2,6-difluoro-4-(2-(3-(fluoromethyl)azetidin-1-yl)ethoxy)phenyl)-3,3-dimethyl-3,4-dihydro-1H-pyrido[3,4-b]indol-2(9H)-yl)-2-methylpropan-1-one; (1R,3R)-1-(2,6-difluoro-4-(2-(3-(fluoromethyl)azetidin-1-yl)ethoxy)phenyl)-3-methyl-2-(methyl sulfonyl)-2,3,4,9-tetrahydro-1H-pyrido[3,4-b]indole; 1-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2-methyl-propan-2-ol; (1R,3R)-1-[4-[2-[3-(difluoromethyl)azetidin-1-yl]ethoxy]-2,6-difluoro-phenyl]-2-(2-fluoro-2-methyl-propyl)-3-methyl-1,3,4,9-tetrahydropyrido[3,4-b]indole; (1R,3R)-1-[4-[1-(3-chloropropyl)azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-[2,6-difluoro-4-(1-propyl azetidin-3-yl)oxy-phenyl]-2-(2-fluoro-2-methyl-propyl)-3-methyl-1,3,4,9-tetrahydropyrido[3,4-b]indole; ((1S,3R)-1-(2,6-difluoro-4-(2-(3-(fluoromethyl)azetidin-1-yl)ethoxy)phenyl)-2-(2-fluoro-2-methylpropyl)-2,3,4,9-tetrahydro-1H-pyrido[3,4-b]indol-3-yl)methanol; (1R,3R)-1-[4-(azetidin-3-yloxy)-2,6-difluoro-phenyl]-2-(2-fluoro-2-methyl-propyl)-3-methyl-1,3,4,9-tetrahydropyrido[3,4-b]indole; (1R,3R)-2-(2-fluoro-2-methylpropyl)-1-(2-fluoro-4-(2-(3-(fluoromethyl)azetidin-1-yl)ethoxy)phenyl)-3-methyl-2,3,4,9-tetrahydro-1H-pyrido[3,4-b]indole; (1R,3R)-2-cyclobutyl-1-[2,6-difluoro-4-[2-[3-(fluoromethyl)azetidin-1-yl]ethoxy]phenyl]-3-methyl-1,3,4,9-tetrahydropyrido[3,4-b]indole; (1R,3S)-1-[2,6-difluoro-4-[2-[3-(fluoromethyl)azetidin-1-yl]ethoxy]phenyl]-3-(fluoromethyl)-2-(2-fluoro-2-methyl-propyl)-1,3,4,9-tetrahydropyrido[3,4-b]indole; (1R,3R)-1-[2,6-difluoro-4-[2-[3-(fluoromethyl)azetidin-1-yl]ethoxy]phenyl]-2-[(3-fluorooxetan-3-yl)methyl]-3-methyl-1,3,4,9-tetrahydropyrido[3,4-b]indole; cyclohexyl((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)methanone; 1-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2,2-dimethyl-propan-1-one; cyclopropyl((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)methanone; (1R,3R)-1-[2,6-difluoro-4-[2-(3-methylazetidin-1-yl)ethoxy]phenyl]-2-(2-fluoro-2-methyl-propyl)-3-methyl-1,3,4,9-tetrahydropyrido[3,4-b]indole; (1R,3R)-1-(2,6-difluoro-4-(2-((R)-3-methylpyrrolidin-1-yl)ethoxy)phenyl)-2-(2-fluoro-2-methylpropyl)-3-methyl-2,3,4,9-tetrahydro-1H-pyrido[3,4-b]indole; (1R,3R)-1-[2,6-difluoro-4-[(2 S)-2-pyrrolidin-1-ylpropoxy]phenyl]-2-(2-fluoro-2-methyl-propyl)-3-methyl-1,3,4,9-tetrahydropyrido[3,4-b]indole; (1R,3R)-1-[2,6-difluoro-4-[2-[3-(fluoromethyl)azetidin-1-yl]propoxy]phenyl]-2-(2-fluoro-2-methyl-propyl)-3-methyl-1,3,4,9-tetrahydropyrido[3,4-b]indole; (1R,3R)-1-[2,6-difluoro-4-[(E)-3-[3-(fluoromethyl)azetidin-1-yl]prop-1-enyl]phenyl]-2-(2-fluoro-2-methyl-propyl)-3-methyl-1,3,4,9-tetrahydropyrido[3,4-b]indole; (1R,3R)-2-[(3,3-difluorocyclobutyl)methyl]-1-[2,6-difluoro-4-[2-[3-(fluoromethyl)azetidin-1-yl]ethoxy]phenyl]-3-methyl-1,3,4,9-tetrahydropyrido[3,4-b]indole; (1R,3R)-1-[2,6-difluoro-4-[2-[3-(fluoromethyl)azetidin-1-yl]ethoxy]phenyl]-2-(2,2-dimethylpropyl)-3-methyl-1,3,4,9-tetrahydropyrido[3,4-b]indole; cyclobutyl-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]methanone; cyclopentyl-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]methanone; (1R,3R)-1-[2,6-difluoro-4-[2-[(3 S)-3-methylpyrrolidin-1-yl]ethoxy]phenyl]-2-(2-fluoro-2-methyl-propyl)-3-methyl-1,3,4,9-tetrahydropyrido[3,4-b]indole; (1R,3R)-1-[2,6-difluoro-4-[(2R)-2-pyrrolidin-1-ylpropoxy]phenyl]-2-(2-fluoro-2-methyl-propyl)-3-methyl-1,3,4,9-tetrahydropyrido[3,4-b]indole; (1R,3R)-1-[2,6-difluoro-4-[(1-propylazetidin-3-yl)methoxy]phenyl]-2-(2-fluoro-2-methyl-propyl)-3-methyl-1,3,4,9-tetrahydropyrido[3,4-b]indole; (1R,3R)-1-[2,6-difluoro-4-[2-[3-(fluoromethyl)azetidin-1-yl]ethoxy]phenyl]-2-[(1-fluorocyclobutyl)methyl]-3-methyl-1,3,4,9-tetrahydropyrido[3,4-b]indole; (S)-3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-fluoro-2-methylpropan-1-ol; (2R)-3-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2-fluoro-2-methyl-propan-1-ol; (1R,3R)-1-[4-[2-[3-(fluoromethyl)azetidin-1-yl]ethoxy]phenyl]-2-(2-fluoro-2-methyl-propyl)-3-methyl-1,3,4,9-tetrahydropyrido[3,4-b]indole; 2-cyclopropyl-1-[(1R,3R)-1-[2,6-difluoro-4-[2-[3-

(fluoromethyl)azetidin-1-yl]ethoxy]phenyl]-3-methyl-1,3,4,9-tetrahydropyrido[3,4-b]indol-2-yl]ethanone; 2-cyclobutyl-1-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]ethanone; 1-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2,2-difluoro-propan-1-one; (1R,3R)-1-[2,6-difluoro-4-[2-[3-(fluoromethyl)-3-methyl-azetidin-1-yl]ethoxy]phenyl]-2-(2-fluoro-2-methyl-propyl)-3-methyl-1,3,4,9-tetrahydropyrido[3,4-b]indole; (1R,3R)-1-[2,6-difluoro-4-(1-methyl azetidin-3-yl)oxy-phenyl]-2-(2-fluoro-2-methyl-propyl)-3-methyl-1,3,4,9-tetrahydropyrido[3,4-b]indole; (1R,3R)-1-[4-(1-ethylazetidin-3-yl)oxy-2,6-difluoro-phenyl]-2-(2-fluoro-2-methyl-propyl)-3-methyl-1,3,4,9-tetrahydropyrido[3,4-b]indole; (1R,3R)-1-[2,6-difluoro-4-(1-pentylazetidin-3-yl)oxy-phenyl]-2-(2-fluoro-2-methyl-propyl)-3-methyl-1,3,4,9-tetrahydropyrido[3,4-b]indole; (1R,3R)-1-[4-[1-(cyclopropylmethyl)azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-[4-[1-(cyclopentylmethyl)azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-[2,6-difluoro-4-[1-(2-fluoroethyl)azetidin-3-yl]oxy-phenyl]-2-(2-fluoro-2-methyl-propyl)-3-methyl-1,3,4,9-tetrahydropyrido[3,4-b]indole; (1R,3R)-1-[2,6-difluoro-4-(1-prop-2-ynylazetidin-3-yl)oxy-phenyl]-2-(2-fluoro-2-methyl-propyl)-3-methyl-1,3,4,9-tetrahydropyrido[3,4-b]indole; (1R,3R)-1-[2,6-difluoro-4-(1-isopropylazetidin-3-yl)oxy-phenyl]-2-(2-fluoro-2-methyl-propyl)-3-methyl-1,3,4,9-tetrahydropyrido[3,4-b]indole; (1R,3R)-1-[2,6-difluoro-4-(1-isobutylazetidin-3-yl)oxy-phenyl]-2-(2-fluoro-2-methyl-propyl)-3-methyl-1,3,4,9-tetrahydropyrido[3,4-b]indole; tert-butyl 3-[3,5-difluoro-4-[(1R,3R)-2-(2-fluoro-2-methyl-propyl)-3-methyl-1,3,4,9-tetrahydropyrido[3,4-b]indol-1-yl]phenoxy]azetidine-1-carboxylate; (1R,3R)-1-(2,6-difluoro-4-(2-(3-(fluoromethyl)azetidin-1-yl)ethoxy)phenyl)-3-ethyl-2-(2-fluoro-2-methylpropyl)-2,3,4,9-tetrahydro-1H-pyrido[3,4-b]indole; (1R,3S)-1-(2,6-difluoro-4-(2-(3-(fluoromethyl)azetidin-1-yl)ethoxy)phenyl)-3-ethyl-2-(2-fluoro-2-methylpropyl)-2,3,4,9-tetrahydro-1H-pyrido[3,4-b]indole; (1R,3R)-1-[2,6-difluoro-4-[2-[3-(fluoromethyl)azetidin-1-yl]ethoxy]phenyl]-3-methyl-2-[(1-methylcyclobutyl)methyl]-1,3,4,9-tetrahydropyrido[3,4-b]indole; (1R,3R)-1-[2,6-difluoro-4-[2-[3-(fluoromethyl)azetidin-1-yl]ethoxy]phenyl]-3-methyl-2-(2,2,2-trifluoroethyl)-1,3,4,9-tetrahydropyrido[3,4-b]indole; (1S,3R)-1-[2,6-difluoro-4-[2-[3-(fluoromethyl)azetidin-1-yl]ethoxy]phenyl]-3-methyl-2-(2,2,2-trifluoroethyl)-1,3,4,9-tetrahydropyrido[3,4-b]indole; (1R,3R)-1-[4-[1-(3,3-dimethoxypropyl)azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-[2-fluoro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole; 1-[2,6-difluoro-4-[2-[3-(fluoromethyl)azetidin-1-yl]ethoxy]phenyl]-2-(2-fluoro-2-methyl-propyl)-1,3,4,9-tetrahydropyrido[3,4-b]indole; (1S,3R)-1-[4-[2-[3-(fluoromethyl)azetidin-1-yl]ethoxy]phenyl]-3-methyl-2-methyl sulfonyl-1,3,4,9-tetrahydropyrido[3,4-b]indole; (1R,3R)-1-(4-(2-(3-(fluoromethyl)azetidin-1-yl)ethoxy)phenyl)-3-methyl-2-(methylsulfonyl)-2,3,4,9-tetrahydro-1H-pyrido[3,4-b]indole; 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-3-hydroxy-2-methylpropan-1-one; azetidin-3-yl-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]methanone; ((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)(2-fluorocyclopropyl)methanone; (1R,3R)-1-[2,6-difluoro-4-[(2 S)-2-[(3R)-3-methylpyrrolidin-1-yl]propoxy]phenyl]-2-(2-fluoro-2-methyl-propyl)-3-methyl-1,3,4,9-tetrahydropyrido[3,4-b]indole; [(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-phenyl-methanone; (1R,3R)-2-(cyclopropylmethyl)-1-[2,6-difluoro-4-[2-[3-(fluoromethyl)azetidin-1-yl]ethoxy]phenyl]-3-methyl-1,3,4,9-tetrahydropyrido[3,4-b]indole; (1R,3R)-1-[4-[1-(2-cyclopropyl ethyl)azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-[4-(1-allylazetidin-3-yl)oxy-2,6-difluoro-phenyl]-2-(2-fluoro-2-methyl-propyl)-3-methyl-1,3,4,9-tetrahydropyrido[3,4-b]indole; (1R,3R)-1-[4-[1-(cyclobutylmethyl)azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-[2,6-difluoro-4-(isopentylazetidin-3-yl)oxy-phenyl]-2-(2-fluoro-2-methyl-propyl)-3-methyl-1,3,4,9-tetrahydropyrido[3,4-b]indole; (1R,3R)-1-(2,6-difluoro-4-((1-(2-methylbutyl)azetidin-3-yl)oxy)phenyl)-2-(2-fluoro-2-methylpropyl)-3-methyl-2,3,4,9-tetrahydro-1H-pyrido[3,4-b]indole; (1R,3R)-1-(2,6-difluoro-4-((1-(pentan-2-yl)azetidin-3-yl)oxy)phenyl)-2-(2-fluoro-2-methylpropyl)-3-methyl-2,3,4,9-tetrahydro-1H-pyrido[3,4-b]indole; (1R,3R)-1-[4-(1-cyclobutylazetidin-3-yl)oxy-2,6-difluoro-phenyl]-2-(2-fluoro-2-methyl-propyl)-3-methyl-1,3,4,9-tetrahydropyrido[3,4-b]indole; (1R,3R)-1-[2,6-difluoro-4-[1-(oxetan-3-yl)azetidin-3-yl]oxy-phenyl]-2-(2-fluoro-2-methyl-propyl)-3-methyl-1,3,4,9-tetrahydropyrido[3,4-b]indole; (1R,3R)-1-[4-(1-cyclopropyl azetidin-3-yl)oxy-2,6-difluoro-phenyl]-2-(2-fluoro-2-methyl-propyl)-3-methyl-1,3,4,9-tetrahydropyrido[3,4-b]indole; (1R,3R)-1-[2,6-difluoro-4-[1-(3-fluoropropyl)azetidin-3-yl]sulfanyl-phenyl]-2-(2-fluoro-2-methyl-propyl)-3-methyl-1,3,4,9-tetrahydropyrido[3,4-b]indole; (1R,3R)-1-[2,6-difluoro-4-[2-[3-(fluoromethyl)azetidin-1-yl]ethoxy]phenyl]-2-isobutyl-3-methyl-1,3,4,9-tetrahydropyrido[3,4-b]indole; (1R,3R)-1-(2,6-difluoro-4-(2-(3-(fluoromethyl)azetidin-1-yl)ethoxy)phenyl)-3-methyl-2-((R)-2-phenylpropyl)-2,3,4,9-tetrahydro-1H-pyrido[3,4-b]indole; (1R,3R)-1-(2,6-difluoro-4-(2-(3-(fluoromethyl)azetidin-1-yl)ethoxy)phenyl)-3-methyl-2-((S)-2-phenylpropyl)-2,3,4,9-tetrahydro-1H-pyrido[3,4-b]indole; (1R,3R)-1-[2,6-difluoro-4-(1-propyl azetidin-3-yl)oxy-phenyl]-2-isobutyl-3-methyl-1,3,4,9-tetrahydropyrido[3,4-b]indole; (1R,3R)-2-(2-fluoro-2-methyl-propyl)-1-[4-[1-(3-fluoropropyl)azetidin-3-yl]oxyphenyl]-3-methyl-1,3,4,9-tetrahydropyrido[3,4-b]indole; (1R,3R)-1-[2,6-difluoro-4-[1-(3-fluoropropyl)azetidin-3-yl]oxy-phenyl]-3-methyl-2-methylsulfonyl-1,3,4,9-tetrahydropyrido[3,4-b]indole; [1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-(3-fluorocyclobutyl)methanone; (1R,3R)-1-[4-[(2S)-2-[3-(difluoromethyl)azetidin-1-yl]propoxy]-2,6-difluoro-phenyl]-2-(2-fluoro-2-methyl-propyl)-3-methyl-1,3,4,9-tetrahydropyrido[3,4-b]indole; (1R,3R)-1-[2,6-difluoro-4-[2-[3-fluoro-3-(fluoromethyl)azetidin-1-yl]ethoxy]phenyl]-2-(2-fluoro-2-methyl-propyl)-3-methyl-1,3,4,9-tetrahydropyrido[3,4-b]indole; 4-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-4-oxo-butanenitrile; (1R,3R)-2-(cyclohexylmethyl)-1-[2,6-difluoro-4-[2-[3-

(fluoromethyl)azetidin-1-yl]ethoxy]phenyl]-3-methyl-1,3,4,9-tetrahydropyrido[3,4-b]indole; (1R,3R)-1-[2,6-difluoro-4-[1-[2-(oxetan-3-yl)ethyl]azetidin-3-yl]oxy-phenyl]-2-(2-fluoro-2-methyl-propyl)-3-methyl-1,3,4,9-tetrahydropyrido[3,4-b]indole; (1R,3R)-1-[4-[1-(cyclohexylmethyl)azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-[2-chloro-4-[2-[3-(fluoromethyl)azetidin-1-yl]ethoxy]phenyl]-2-(2-fluoro-2-methyl-propyl)-3-methyl-1,3,4,9-tetrahydropyrido[3,4-b]indole; (1R,3R)-1-[2-chloro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole; 1-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-3-hydroxybutan-1-one; [(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-(oxetan-3-yl)methanone; [(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-(thietan-3-yl)methanone; (R)-1-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-3-fluoro-2-methylpropan-1-one; (1R,3R)-2-(cyclopentylmethyl)-1-[2,6-difluoro-4-[2-[3-(fluoromethyl)azetidin-1-yl]ethoxy]phenyl]-3-methyl-1,3,4,9-tetrahydropyrido[3,4-b]indole; (1R,3R)-1-[4-[1-[(4,4-difluorocyclohexyl)methyl]azetidin-3-yl]oxy-2,6-difluoro-phenyl]-2-(2-fluoro-2-methyl-propyl)-3-methyl-1,3,4,9-tetrahydropyrido[3,4-b]indole; (S)-1-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-3-fluoro-2-methylpropan-1-one; ((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)(oxetan-2-yl)methanone; (1R,3R)-1-[2,6-difluoro-4-[2-[3-(fluoromethyl)azetidin-1-yl]ethoxy]phenyl]-3-methyl-2,3,4,9-tetrahydro-1H-pyrido[3,4-b]indole; 2-fluoro-1-[(1R,3R)-1-[4-[2-[3-(fluoromethyl)azetidin-1-yl]ethoxy]phenyl]-3-methyl-1,3,4,9-tetrahydropyrido[3,4-b]indol-2-yl]-2-methyl-propan-1-one; 1-[(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-2-fluoro-2-methyl-propan-1-one; 1-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2-(dimethylamino)ethanone; (1R,3R)-1-[2,6-difluoro-4-[1-[(1-fluorocyclopropyl)methyl]azetidin-3-yl]oxy-phenyl]-2-(2-fluoro-2-methyl-propyl)-3-methyl-1,3,4,9-tetrahydropyrido[3,4-b]indole; [(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-(1-fluorocyclobutyl)methanone; [(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-(1-methyl cyclopropyl)methanone; (1R,3R)-1-[2,6-difluoro-4-[1-(3-fluoropropyl)azetidin-3-yl]oxy-phenyl]-2-[[1-(fluoromethyl)cyclopropyl]methyl]-3-methyl-1,3,4,9-tetrahydropyrido[3,4-b]indole; [1-[[(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]methyl]cyclopropyl]methanol; 2-fluoro-1-[(1S,3R)-1-[2-fluoro-4-[2-[3-(fluoromethyl)azetidin-1-yl]ethoxy]phenyl]-3-methyl-1,3,4,9-tetrahydropyrido[3,4-b]indol-2-yl]-2-methyl-propan-1-one; 2-fluoro-1-[(1R,3R)-1-[2-fluoro-4-[2-[3-(fluoromethyl)azetidin-1-yl]ethoxy]phenyl]-3-methyl-1,3,4,9-tetrahydropyrido[3,4-b]indol-2-yl]-2-methyl-propan-1-one; (1S,3R)-1-[2-fluoro-4-[2-[3-(fluoromethyl)azetidin-1-yl]ethoxy]phenyl]-3-methyl-2-methyl sulfonyl-1,3,4,9-tetrahydropyrido[3,4-b]indole; (1R,3R)-1-[2-fluoro-4-[2-[3-(fluoromethyl)azetidin-1-yl]ethoxy]phenyl]-3-methyl-2-methyl sulfonyl-1,3,4,9-tetrahydropyrido[3,4-b]indole; 3-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)-2-fluoro-2-methylpropan-1-ol; 3-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)-2-fluoro-2-methylpropan-1-ol; 2-fluoro-1-[(1S,3R)-1-[4-[2-[3-(fluoromethyl)azetidin-1-yl]ethoxy]phenyl]-3-methyl-1,3,4,9-tetrahydropyrido[3,4-b]indol-2-yl]-2-methyl-propan-1-one; (1R)-1-[2,6-difluoro-4-[2-[3-(fluoromethyl)azetidin-1-yl]ethoxy]phenyl]-2-(2-fluoro-2-methyl-propyl)-1,3,4,9-tetrahydropyrido[3,4-b]indole; (1 S)-1-[2,6-difluoro-4-[2-[3-(fluoromethyl)azetidin-1-yl]ethoxy]phenyl]-2-(2-fluoro-2-methyl-propyl)-1,3,4,9-tetrahydropyrido[3,4-b]indole; [(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-(1-fluorocyclopropyl)methanone; (1R,3R)-6-chloro-1-(2,6-difluoro-4-((1-(3-fluoropropyl)azetidin-3-yl)oxy)phenyl)-2-(2-fluoro-2-methylpropyl)-3-methyl-2,3,4,9-tetrahydro-1H-pyrido[3,4-b]indole; (1R,3R)-1-(2,6-difluoro-4-(2-(3-(fluoromethyl)azetidin-1-yl)ethoxy)phenyl)-7-fluoro-2-(2-fluoro-2-methylpropyl)-3-methyl-2,3,4,9-tetrahydro-1H-pyrido[3,4-b]indole; (1R,3R)-1-(2,6-difluoro-4-(2-(3-(fluoromethyl)azetidin-1-yl)ethoxy)phenyl)-6-fluoro-2-(2-fluoro-2-methylpropyl)-3-methyl-2,3,4,9-tetrahydro-1H-pyrido[3,4-b]indole; (1R,3R)-1-(2,6-difluoro-4-((1-(3-fluoropropyl)azetidin-3-yl)oxy)phenyl)-6-fluoro-2-(2-fluoro-2-methylpropyl)-3-methyl-2,3,4,9-tetrahydro-1H-pyrido[3,4-b]indole; (1-(((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)methyl)cyclopropyl)methanol; (1S,3S)-6-chloro-1-(2,6-difluoro-4-((1-(3-fluoropropyl)azetidin-3-yl)oxy)phenyl)-2-(2-fluoro-2-methylpropyl)-3-methyl-2,3,4,9-tetrahydro-1H-pyrido[3,4-b]indole; (1S,3S)-1-(2,6-difluoro-4-(2-(3-(fluoromethyl)azetidin-1-yl)ethoxy)phenyl)-6-fluoro-2-(2-fluoro-2-methylpropyl)-3-methyl-2,3,4,9-tetrahydro-1H-pyrido[3,4-b]indole; (1R,3R)-1-[2,6-difluoro-4-[1-(3-fluoropropyl)azetidin-3-yl]oxy-phenyl]-3-methyl-2-[(3-methyloxetan-3-yl)methyl]-1,3,4,9-tetrahydropyrido[3,4-b]indole; (1R,3R)-1-(2,6-difluoro-4-(2-(3-(fluoromethyl)azetidin-1-yl)ethoxy)phenyl)-5-fluoro-2-(2-fluoro-2-methylpropyl)-3-methyl-2,3,4,9-tetrahydro-1H-pyrido[3,4-b]indole; (1R,3R)-1-(2,6-difluoro-4-((1-(3-fluoropropyl)azetidin-3-yl)oxy)phenyl)-7-fluoro-2-(2-fluoro-2-methylpropyl)-3-methyl-2,3,4,9-tetrahydro-1H-pyrido[3,4-b]indole; (1R,3R)-1-(2,6-difluoro-4-((1-(3-fluoropropyl)azetidin-3-yl)oxy)phenyl)-5-fluoro-2-(2-fluoro-2-methylpropyl)-3-methyl-2,3,4,9-tetrahydro-1H-pyrido[3,4-b]indole; (1R,3R)-2-(2-fluoro-2-methyl-propyl)-1-[4-[2-[(3R)-3-(fluoromethyl)pyrrolidin-1-yl]ethoxy]phenyl]-3-methyl-1,3,4,9-tetrahydropyrido[3,4-b]indole; (1S,3S)-1-(2,6-difluoro-4-(2-(3-(fluoromethyl)azetidin-1-yl)ethoxy)phenyl)-5-fluoro-2-(2-fluoro-2-methylpropyl)-3-methyl-2,3,4,9-tetrahydro-1H-pyrido[3,4-b]indole; (1S,3S)-1-(2,6-difluoro-4-((1-(3-fluoropropyl)azetidin-3-yl)oxy)phenyl)-7-fluoro-2-(2-fluoro-2-methylpropyl)-3-methyl-2,3,4,9-tetrahydro-1H-pyrido[3,4-b]indole; (1S,3S)-1-(2,6-difluoro-4-((1-(3-fluoropropyl)azetidin-3-yl)oxy)phenyl)-5-fluoro-2-(2-fluoro-2-methylpropyl)-3-methyl-2,3,4,9-tetrahydro-1H-pyrido[3,4-b]indole; 2-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2- yl]-N,N-dimethyl-acetamide; 3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2-fluoro-2-methylpropan-1-ol; (1R,3R)-2-(2-fluoro-2-methyl-propyl)-1-[4-[1-(3-fluoropropyl)azetidin-3-yl]oxy-2-methyl-phenyl]-3-methyl-1,3,4,9-tetrahydropyrido[3,4-b]indole; (1R)-1-[2,6-difluoro-4-[2-[3-(fluoromethyl)azetidin-1-yl]ethoxy]phenyl]-2-(2-fluoro-2-methyl-propyl)-3,3-dimethyl-4,9-dihydro-1H-pyrido[3,4-b]indole; (S)-1-(2,6-difluoro-4-(2-(3-(fluoromethyl)azetidin-1-yl)ethoxy)phenyl)-2-(2-fluoro-2-methylpropyl)-3,3-dimethyl-2,3,4,9-tetrahydro-1H-pyrido[3,4-b]indole; (1R,3R)-1-[4-[1-[(3,3-difluorocyclobutyl)methyl]azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-(2,6-difluoro-4-(2-(3-(fluoromethyl)azetidin-1-yl)ethoxy)phenyl)-8-fluoro-2-(2-fluoro-2-methylpropyl)-3-methyl-2,3,4,9-tetrahydro-1H-pyrido[3,4-b]indole; (1R,3R)-1-(2,6-difluoro-4-((1-(3-fluoropropyl)azetidin-3-yl)oxy)phenyl)-8-fluoro-2-(2-fluoro-2-methylpropyl)-3-methyl-2,3,4,9-tetrahydro-1H-pyrido[3,4-b]indole; (1S,3S)-1-(2,6-difluoro-4-(2-(3-(fluoromethyl)azetidin-1-yl)ethoxy)phenyl)-8-fluoro-2-(2-fluoro-2-methylpropyl)-3-methyl-2,3,4,9-tetrahydro-1H-pyrido[3,4-b]indole; (S)-1-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)propan-2-ol; (R)-1-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)propan-2-ol; (1R,3R)-1-[4-[2-[3-(chloromethyl)azetidin-1-yl]ethoxy]-2,6-difluoro-phenyl]-2-(2-fluoro-2-methyl-propyl)-3-methyl-1,3,4,9-tetrahydropyrido[3,4-b]indole; (1R,3R)-1-[3-chloro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole; (1R,3R)-1-[3-fluoro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole; (2R)-3-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]propane-1,2-diol; (1R,3R)-1-[2,6-difluoro-4-[1-[[(1S,2R)-2-fluorocyclopropyl]methyl]azetidin-3-yl]oxy-phenyl]-2-(2-fluoro-2-methyl-propyl)-3-methyl-1,3,4,9-tetrahydropyrido[3,4-b]indole; (1R,3R)-1-(2,6-difluoro-4-(2-(3-(fluoromethyl)azetidin-1-yl)ethoxy)phenyl)-2-((S)-3-fluoro-2-methylpropyl)-3-methyl-2,3,4,9-tetrahydro-1H-pyrido[3,4-b]indole; (S)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2-methylpropane-1,2-di ol; (1R,3R)-1-[2,6-difluoro-4-[1-(3-fluoropropyl)azetidin-3-yl]oxy-phenyl]-2-(3-fluoro-2,2-dimethyl-propyl)-3-methyl-1,3,4,9-tetrahydropyrido[3,4-b]indole; (R)-2-fluoro-3-((1R,3R)-1-(2-fluoro-4-(2-(3-(fluoromethyl)azetidin-1-yl)ethoxy)phenyl)-3-methyl-1,3,4,9-tetrahydro-2H-pyrido[3,4-b]indol-2-yl)-2-methylpropan-1-ol; (S)-2-fluoro-3-((1R,3R)-1-(2-fluoro-4-(2-(3-(fluoromethyl)azetidin-1-yl)ethoxy)phenyl)-3-methyl-1,3,4,9-tetrahydro-2H-pyrido[3,4-b]indol-2-yl)-2-methylpropan-1-ol; (R)-2-fluoro-3-((1R,3R)-1-(4-(2-(3-(fluoromethyl)azetidin-1-yl)ethoxy)phenyl)-3-methyl-1,3,4,9-tetrahydro-2H-pyrido[3,4-b]indol-2-yl)-2-methylpropan-1-ol; (S)-2-fluoro-3-((1R,3R)-1-(4-(2-(3-(fluoromethyl)azetidin-1-yl)ethoxy)phenyl)-3-methyl-1,3,4,9-tetrahydro-2H-pyrido[3,4-b]indol-2-yl)-2-methylpropan-1-ol; (1R,3R)-1-[2,6-difluoro-4-[1-(3-fluoropropyl)azetidin-3-yl]oxy-phenyl]-3-methyl-2-(2,2,2-trifluoroethyl)-1,3,4,9-tetrahydropyrido[3,4-b]indole; (2R)-3-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2-methyl-propane-1,2-di ol; (1R,3R)-2-(2-fluoro-2-methylpropyl)-1-(3-fluoro-4-(2-(3-(fluoromethyl)azetidin-1-yl)ethoxy)phenyl)-3-methyl-2,3,4,9-tetrahydro-1H-pyrido[3,4-b]indole; (1S,3R)-2-(2-fluoro-2-methylpropyl)-1-(3-fluoro-4-(2-(3-(fluoromethyl)azetidin-1-yl)ethoxy)phenyl)-3-methyl-2,3,4,9-tetrahydro-1H-pyrido[3,4-b]indole; (1R,3R)-1-(2,3-difluoro-4-(2-(3-(fluoromethyl)azetidin-1-yl)ethoxy)phenyl)-2-(2-fluoro-2-methylpropyl)-3-methyl-2,3,4,9-tetrahydro-1H-pyrido[3,4-b]indole; (1R,3R)-1-(2,6-difluoro-4-((1-(((1S,2S)-2-fluorocyclopropyl)methyl)azetidin-3-yl)oxy)phenyl)-2-(2-fluoro-2-methylpropyl)-3-methyl-2,3,4,9-tetrahydro-1H-pyrido[3,4-b]indole; 1-[(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]propan-2-one; 3-[(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-2,2-dimethyl-propan-1-ol; (1R,3R)-1-[2,6-difluoro-4-[1-(3-fluoropropyl)azetidin-3-yl]oxy-phenyl]-2-ethyl sulfonyl-3-methyl-1,3,4,9-tetrahydropyrido[3,4-b]indole; 3-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2,2-difluoro-propan-1-ol; 3-[(1R,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2,2-dimethyl-propan-1-ol; 3-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)-2-fluoro-2-methylpropan-1-ol; 1-((1S,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)propan-2-one; (S)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-N,N,2-trimethylpropanamide; (R)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-N,N,2-trimethylpropanamide; (S)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2-methylpropanoic acid; (R)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2-methylpropanoic acid; (1R,3S)-1-(2,6-difluoro-4-((1-(3-fluoropropyl)azetidin-3-yl)oxy)phenyl)-2-(2-fluoro-2-methylpropyl)-3-(fluoromethyl)-2,3,4,9-tetrahydro-1H-pyrido[3,4-b]indole; 3-((1R,3R)-1-(2,6-difluoro-4-((1-(3-fluoropropyl)azetidin-3-yl)oxy)phenyl)-3-methyl-3,4-dihydro-1H-pyrido[3,4-b]indol-2(9H)-yl)-2,2-difluoropropan-1-ol; (1R,3R)-2-(2,2-difluoroethyl)-1-[2,6-difluoro-4-[1-(3-fluoropropyl)azetidin-3-yl]oxy-phenyl]-3-methyl-1,3,4,9-tetrahydropyrido[3,4-b]indole; (1R,3R)-2-(2,2-difluoroethyl)-1-[2,6-difluoro-4-[2-[3-(fluoromethyl)azetidin-1-yl]ethoxy]phenyl]-3-methyl-1,3,4,9-tetrahydropyrido[3,4-b]indole; (1S,3R)-2-(2,2-difluoroethyl)-1-[2,6-difluoro-4-[2-[3-(fluoromethyl)azetidin-1-yl]ethoxy]phenyl]-3-methyl-1,3,4,9-tetrahydropyrido[3,4-b]indole; (1R,3R)-1-[4-[1-(3,3-difluorocyclobutyl)azetidin-3-yl]oxy-2,6-difluoro-phenyl]-2-(2-fluoro-2-methyl-propyl)-3-methyl-1,3,4,9-tetrahydropyrido[3,4-b]indole; (1R,3R)-1-[2,6-difluoro-4-[1-[(E)-3-fluoroallyl]azetidin-3-yl]oxy-phenyl]-2-(2-fluoro-2-methyl-propyl)-3-methyl-1,3,4,9-tetrahydropyrido[3,4-b]indole; (1R,3R)-1-(2,6-difluoro-4-((1-(3-fluoropropyl)azetidin-3-yl)oxy)phenyl)-3-methyl-2-(2-(methylsulfonyl)propyl)-2,3,4,9-tetrahydro-1H-pyrido[3,4-b]indole; (1R,3R)-1-[4-[2-[3-(fluoromethyl)azetidin-1-yl]ethoxy]phenyl]-

3-methyl-2-vinylsulfonyl-1,3,4,9-tetrahydropyrido[3,4-b]indole; (1R,3R)-1-[4-[2-[3-(fluoromethyl)azetidin-1-yl]ethoxy]phenyl]-N,3-dimethyl-1,3,4,9-tetrahydropyrido[3,4-b]indole-2-sulfonamide; 3-[(1R,3R)-1-[2,6-difluoro-4-[1-(3-fluoropropyl)azetidin-3-yl]oxy-phenyl]-3-methyl-1,3,4,9-tetrahydropyrido[3,4-b]indol-2-yl]-2,2-dimethyl-propanenitrile; (1R,3R)-1-[4-[1-(3,3-difluoroallyl)azetidin-3-yl]oxy-2,6-difluoro-phenyl]-2-(2-fluoro-2-methyl-propyl)-3-methyl-1,3,4,9-tetrahydropyrido[3,4-b]indole; (S)-2-(((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)methyl)-3,3,3-trifluoropropan-1-ol; (R)-2-(((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)methyl)-3,3,3-trifluoropropan-1-ol; (1R,3R)-2-ethylsulfonyl-1-[4-[2-[3-(fluoromethyl)azetidin-1-yl]ethoxy]phenyl]-3-methyl-1,3,4,9-tetrahydropyrido[3,4-b]indole; (1R,3R)-1-[4-[2-[3-(fluoromethyl)azetidin-1-yl]ethoxy]phenyl]-N,N,3-trimethyl-1,3,4,9-tetrahydropyrido[3,4-b]indole-2-sulfonamide; (1R,3R)-1-[4-[1-(3-fluoropropyl)azetidin-3-yl]oxyphenyl]-3-methyl-2-methylsulfonyl-1,3,4,9-tetrahydropyrido[3,4-b]indole; 3-[3-[3,5-difluoro-4-[(1R,3R)-2-(2-fluoro-2-methyl-propyl)-3-methyl-1,3,4,9-tetrahydropyrido[3,4-b]indol-1-yl]phenoxy]azetidin-1-yl]cyclobutanol; (1R,3R)-1-(4-(2-(3-(fluoromethyl)azetidin-1-yl)ethoxy)phenyl)-2-((S)-isopropylsulfinyl)-3-methyl-2,3,4,9-tetrahydro-1H-pyrido[3,4-b]indole; (1R,3R)-1-(4-(2-(3-(fluoromethyl)azetidin-1-yl)ethoxy)phenyl)-2-((R)-isopropylsulfinyl)-3-methyl-2,3,4,9-tetrahydro-1H-pyrido[3,4-b]indole; (1S,3 s)-3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)azetidin-1-yl)cyclobutanol; (1R,3R)-1-[2,6-difluoro-4-[1-(5-fluoropentyl)azetidin-3-yl]oxy-phenyl]-2-(2-fluoro-2-methyl-propyl)-3-methyl-1,3,4,9-tetrahydropyrido[3,4-b]indole; (1R,3R)-1-[3,5-difluoro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole; (1R,3R)-1-[2,6-difluoro-4-[1-(4-fluorobutyl)azetidin-3-yl]oxy-phenyl]-2-(2-fluoro-2-methyl-propyl)-3-methyl-1,3,4,9-tetrahydropyrido[3,4-b]indole; (1R,3R)-1-[3,5-difluoro-4-[1-(5-fluoropentyl)azetidin-3-yl]oxy-phenyl]-2-(2-fluoro-2-methyl-propyl)-3-methyl-1,3,4,9-tetrahydropyrido[3,4-b]indole; (1R,3R)-1-[2,5-difluoro-4-[1-(3-fluoropropyl)azetidin-3-yl]oxy-phenyl]-2-(2-fluoro-2-methyl-propyl)-3-methyl-1,3,4,9-tetrahydropyrido[3,4-b]indole; 3-[(1R,3R)-1-[2,6-difluoro-4-[2-[3-(fluoromethyl)azetidin-1-yl]ethylamino]phenyl]-3-methyl-1,3,4,9-tetrahydropyrido[3,4-b]indol-2-yl]-2,2-difluoro-propan-1-ol; (1S,3R)-2-(2-fluoro-2-methylpropyl)-1-(5-((1-(3-fluoropropyl)azetidin-3-yl)oxy)pyrazin-2-yl)-3-methyl-2,3,4,9-tetrahydro-1H-pyrido[3,4-b]indole; (1R,3R)-1-(2,6-difluoro-4-((1-(3-fluoropropyl)-3-methyl azetidin-3-yl)oxy)phenyl)-2-(2-fluoro-2-methylpropyl)-3-methyl-2,3,4,9-tetrahydro-1H-pyrido[3,4-b]indole; 2-[(1R,3R)-2-(2-fluoro-2-methyl-propyl)-3-methyl-1,3,4,9-tetrahydropyrido[3,4-b]indol-1-yl]-5-[1-(3-fluoropropyl)azetidin-3-yl]oxy-benzonitrile; 4-((1R,3R)-2-(2-fluoro-2-methylpropyl)-3-methyl-2,3,4,9-tetrahydro-1H-pyrido[3,4-b]indol-1-yl)-1-(3-(3-(fluoromethyl)azetidin-1-yl)propyl)pyridin-2(1H)-one; [4-[(1R,3R)-2-(2-fluoro-2-methyl-propyl)-3-methyl-1,3,4,9-tetrahydropyrido[3,4-b]indol-1-yl]phenyl]-[1-(3-fluoropropyl)azetidin-3-yl]methanone; (R)-3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2-methylpropanamide; (R)-3-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)-2-methylpropanoic acid; (S)-3-((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)-2-methylpropanoic acid; 3-[1-[2,6-difluoro-4-[1-(3-fluoropropyl)azetidin-3-yl]oxy-phenyl]-3-methyl-1,3,4,9-tetrahydropyrido[3,4-b]indol-2-yl]-2-methyl-propanoic acid; 3-[1-[2,6-difluoro-4-[1-(3-fluoropropyl)azetidin-3-yl]oxy-phenyl]-3-methyl-1,3,4,9-tetrahydropyrido[3,4-b]indol-2-yl]-2-methyl-propanoic acid; (1S,3S)-1-(2,6-difluoro-4-(2-(3-(fluoromethyl)azetidin-1-yl)ethoxy)phenyl)-6-fluoro-3-methyl-2-(2,2,2-trifluoroethyl)-2,3,4,9-tetrahydro-1H-pyrido[3,4-b]indole; (1R,3R)-1-(2,6-difluoro-4-(2-(3-(fluoromethyl)azetidin-1-yl)ethoxy)phenyl)-6-fluoro-3-methyl-2-(2,2,2-trifluoroethyl)-2,3,4,9-tetrahydro-1H-pyrido[3,4-b]indole; (1S,3S)-1-(2,6-difluoro-4-((1-(3-fluoropropyl)azetidin-3-yl)oxy)phenyl)-6-fluoro-3-methyl-2-(2,2,2-trifluoroethyl)-2,3,4,9-tetrahydro-1H-pyrido[3,4-b]indole; (1R,3R)-1-(2,6-difluoro-4-((1-(3-fluoropropyl)azetidin-3-yl)oxy)phenyl)-6-fluoro-3-methyl-2-(2,2,2-trifluoroethyl)-2,3,4,9-tetrahydro-1H-pyrido[3,4-b]indole; 3-((1R,3R)-1-(2,6-difluoro-4-(2-(3-(fluoromethyl)azetidin-1-yl)ethoxy)phenyl)-6-fluoro-3-methyl-1,3,4,9-tetrahydro-2H-pyrido[3,4-b]indol-2-yl)-2,2-difluoropropan-1-ol; 3-((1S,3S)-1-(2,6-difluoro-4-(2-(3-(fluoromethyl)azetidin-1-yl)ethoxy)phenyl)-6-fluoro-3-methyl-1,3,4,9-tetrahydro-2H-pyrido[3,4-b]indol-2-yl)-2,2-difluoropropan-1-ol; (1R,3R)-1-[2,6-difluoro-4-[2-[3-(fluoromethyl)azetidin-1-yl]ethoxy]phenyl]-3-methyl-2-(3,3,3-trifluoropropyl)-1,3,4,9-tetrahydropyrido[3,4-b]indole; (1S,3R)-1-[2,6-difluoro-4-[2-[3-(fluoromethyl)azetidin-1-yl]ethoxy]phenyl]-3-methyl-2-(3,3,3-trifluoropropyl)-1,3,4,9-tetrahydropyrido[3,4-b]indole; 3-((1R,3R)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2,2-difluoropropan-1-ol; 3-((1S,3S)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2,2-difluoropropan-1-ol; 3-((1R,3R)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2-fluoro-2-methylpropan-1-ol; 3-((1S,3S)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2-fluoro-2-methylpropan-1-ol; 3-((1R,3R)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2-fluoro-2-methylpropan-1-ol; 3-((1S,3S)-1-(2,6-difluoro-4-((1-(3-fluoropropyl)azetidin-3-yl)oxy)phenyl)-6-fluoro-3-methyl-1,3,4,9-tetrahydro-2H-pyrido[3,4-b]indol-2-yl)-2-fluoro-2-methylpropan-1-ol; 3-((1R,3R)-1-(2,6-difluoro-4-(2-(3-(fluoromethyl)azetidin-1-yl)ethoxy)phenyl)-3-methyl-1,3,4,9-tetrahydro-2H-pyrido[3,4-b]indol-2-yl)-2,2-dimethylpropanoic acid; (R)-2-(((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)methyl)-3,3,3-trifluoropropan-1-ol; (S)-2-(((1R,3R)-1-(2,6-difluoro-4-((1-(3-fluoropropyl)azetidin-3-yl)oxy)phenyl)-3-methyl-1,3,4,9-tetrahydro-2H-pyrido[3,4-b]indol-2-yl)methyl)-3,3,3-trifluoropropan-1-ol; (1R,3R)-2-(2-fluoro-2-methylpropyl)-1-(2-((1-(3-fluoropropyl)azetidin-3-yl)oxy)pyrimidin-5-yl)-3-methyl-2,3,4,9-tetrahydro-1H-pyrido[3,4-b]indole; 3-[(1S,3R)-1-[2,6-difluoro-4-[2-[3-(fluoromethyl)azetidin-1-yl]ethoxy]phenyl]-3-methyl-1,3,4,9-tetrahydropyrido[3,4-b]indol-2-yl]-2,2-dimethyl-propanoic acid; (1R,3R)-1-(2,6-difluoro-4-(2-(3-(fluoromethyl)azetidin-1-yl)ethoxy)phenyl)-2-(2,2-difluoropropyl)-3-methyl-2,3,4,9- tetrahydro-1H-pyrido[3,4-b]indole; (S)-(4-((1R,3R)-2-(2-fluoro-2-methylpropyl)-3-methyl-2,3,4,9-tetrahydro-1H-pyrido[3,4-b]indol-1-yl)phenyl)(1-(3-fluoropropyl)azetidin-3-yl)methanol; (R)-(4-((1R,3R)-2-(2-fluoro-2-methylpropyl)-3-methyl-2,3,4,9-tetrahydro-1H-pyrido[3,4-b]indol-1-yl)phenyl)(1-(3-fluoropropyl)azetidin-3-yl) methanol; (1R,3R)-1-(2,6-difluoro-4-(2-(3-(fluoromethyl) azetidin-1-yl)ethoxy)phenyl)-2-(2,2-difluoroethyl)-6-fluoro-3-methyl-2,3,4,9-tetrahydro-1H-pyrido[3,4-b]indole; (1S,3S)-1-(2,6-difluoro-4-(2-(3-(fluoromethyl)azetidin-1-yl)ethoxy)phenyl)-2-(2,2-difluoroethyl)-6-fluoro-3-methyl-2,3,4,9-tetrahydro-1H-pyrido[3,4-b]indole; (1R,3R)-1-(2,6-difluoro-4-((1-(3-fluoropropyl)azetidin-3-yl)oxy)phenyl)-2-(2,2-difluoroethyl)-6-fluoro-3-methyl-2,3,4,9-tetrahydro-1H-pyrido[3,4-b]indole; (1S,3S)-1-(2,6-difluoro-4-((1-(3-fluoropropyl)azetidin-3-yl)oxy)phenyl)-2-(2,2-difluoroethyl)-6-fluoro-3-methyl-2,3,4,9-tetrahydro-1H-pyrido[3,4-b]indole; (1R,3R)-1-(2,6-difluoro-4-((1-cis-(3-(fluoromethyl)cyclobutyl)azetidin-3-yl)oxy)phenyl)-2-(2-fluoro-2-methylpropyl)-3-methyl-2,3,4,9-tetrahydro-1H-pyrido[3,4-b]indole; (1R,3R)-1-(2,6-difluoro-4-((1-trans-(3-(fluoromethyl)cyclobutyl)azetidin-3-yl)oxy)phenyl)-2-(2-fluoro-2-methylpropyl)-3-methyl-2,3,4,9-tetrahydro-1H-pyrido[3,4-b]indole; (1R,3R)-1-(2,6-difluoro-4-((1-(3-fluoropropyl)azetidin-3-yl)oxy)phenyl)-2-(1-fluorocyclobutyl)methyl)-3-methyl-2,3,4,9-tetrahydro-1H-pyrido[3,4-b]indole; (S)-3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-fluoropropan-1-ol; (R)-3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2-fluoropropan-1-ol; (R)-3-((1R,3R)-1-(2,6-difluoro-4-(2-(3-(fluoromethyl) azetidin-1-yl)ethoxy)phenyl)-3-methyl-3,4-dihydro-1H-pyrido[3,4-b]indol-2(9H)-yl)-2-(fluoromethyl)propan-1-ol; (S)-3-((1R,3R)-1-(2,6-difluoro-4-(2-(3-(fluoromethyl)azetidin-1-yl)ethoxy)phenyl)-3-methyl-3,4-dihydro-1H-pyrido [3,4-b]indol-2(9H)-yl)-2-(fluoromethyl)propan-1-ol; (1R, 3R)-1-(2,6-difluoro-4-(1-(3-fluoropropyl)azetidin-3-yloxy) phenyl)-2-((3-fluorooxetan-3-yl)methyl)-3-methyl-2,3,4,9-tetrahydro-1H-pyrido[3,4-b]indole; (1R,3R)-1-(2,6-difluoro-4-(1-(3-fluoropropyl)azetidin-3-yloxy)phenyl)-6,8-difluoro-2-(2-fluoro-2-methylpropyl)-3-methyl-2,3,4,9-tetrahydro-1H-pyrido[3,4-b]indole; (1R,3R)-1-(2,6-difluoro-4-((1-((1-(fluoromethyl)cyclopropyl)methyl) azetidin-3-yl)oxy)phenyl)-2-(2-fluoro-2-methylpropyl)-3-methyl-2,3,4,9-tetrahydro-1H-pyrido[3,4-b]indole; (1R, 3R)-1-(2,6-difluoro-4-(1-(3-fluoropropyl)azetidin-3-yloxy) phenyl)-6,7-difluoro-2-(2-fluoro-2-methylpropyl)-3-methyl-2,3,4,9-tetrahydro-1H-pyrido[3,4-b]indole; or (1R, 3R)-2-(2-fluoro-2-methylpropyl)-1-(1-((1-(3-fluoropropyl) azetidin-3-yl)methyl)-1H-pyrazol-4-yl)-3-methyl-2,3,4,9-tetrahydro-1H-pyrido[3,4-b]indole, or a pharmaceutically acceptable salt thereof or combination thereof.

In another aspect, the endocrine therapy comprises a compound having formula:

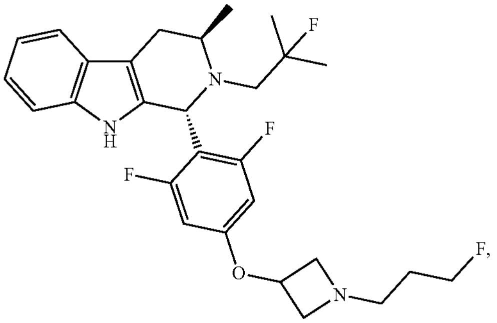

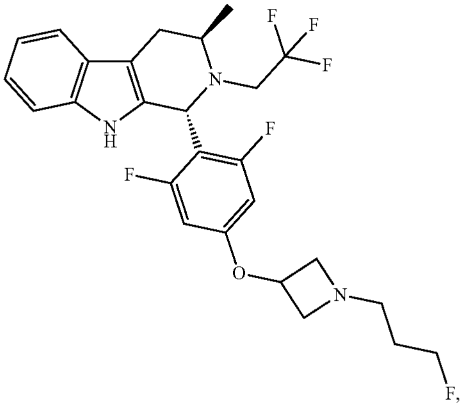

or

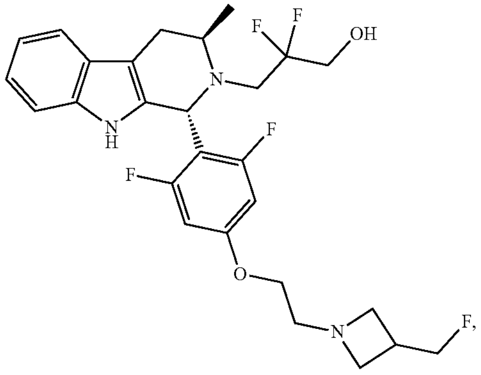

or a pharmaceutically acceptable salt thereof.

In another aspect, the endocrine therapy comprises a compound having formula (4):

(4)

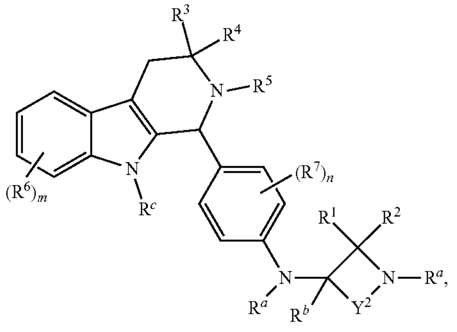

or a stereoisomer, tautomer, or pharmaceutically acceptable salt thereof, wherein:

$Y^2$ is —($CH_2$);

$R^a$ is independently selected from the group consisting of H, $C_1$-$C_6$ alkyl, $C_2$-$C_8$ alkenyl, propargyl, $C_3$-$C_6$ cycloalkyl, and $C_3$-$C_6$ heterocyclyl, each optionally substituted with one or more groups independently selected from the group consisting of F, Cl, Br, I, CN, OH, $OCH_3$, and $SO_2CH_3$;

$R^b$ is independently selected from the group consisting of H, —O($C_1$-$C_3$ alkyl), $C_1$-$C_6$ alkyl, $C_2$-$C_8$ alkenyl, and propargyl, each optionally substituted with one or more groups independently selected from the group consisting of F, Cl, Br, I, CN, —$CH_2F$, —$CHF_2$, —$CF_3$, —$CH_2CF_3$, —$CH_2CHF_2$, —$CH_2CH_2F$, OH, $OCH_3$, and $SO_2CH_3$, $R^c$ is H;

$R^1$, $R^2$, $R^3$ and $R^4$ are independently selected from the group consisting of H, —$CH_3$, —$CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CH_2NH_2$, —$CH_2NHSO_2CH_3$, —$CH_2NHCH_3$, —$CH_2N(CH_3)_2$, —$CF_3$, —$CH_2CF_3$, —$CH_2CHF_2$, —$CH(CH_3)CN$, —$C(CH_3)_2CN$, and —$CH_2CN$;

$R^5$ is selected from the group consisting of $C_1$-$C_9$ alkyl, $C_3$-$C_9$ cycloalkyl, $C_3$-$C_9$ heterocycle, $C_6$-$C_9$ aryl, $C_6$-$C_9$ heteroaryl, alkyldiyl)-($C_3$-$C_9$ cycloalkyl), —($C_1$-$C_6$ alkyldiyl)-($C_3$-$C_9$ heterocycle), C(O)$NR^a$, $SO_2R^a$, and $SO_2NR^a$, each optionally substituted with one or more of halogen, CN, $OR^1$, $N(R^a)_2$, $C_1$-$C_9$ alkyl, $C_3$-$C_9$ cycloalkyl, $C_3$-$C_9$ heterocycle, $C_6$-$C_9$aryl, $C_6$-$C_9$ heteroaryl, C(O)$R^b$, C(O)$NR^a$, $SO_2R^a$, and $SO_2NR^a$;

$R^6$ is independently F or Cl;

m is 0, 1, 2, 3, or 4;

wherein $R^7$ is F, Cl, Br, I, —CN, —$CH_3$, —$CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CH_2NH_2$, —$CH_2NHSO_2CH_3$, —$CH_2NHCH_3$, —$CH_2N(CH_3)_2$, —$CF_3$, —$CH_2CF_3$, —$CH_2CHF_2$, —$CH(CH_3)CN$, —$C(CH_3)_2CN$, —$CH_2CN$, —$CO_2H$, —$COCH_3$, —$CO_2CH_3$, —$CO_2C(CH_3)_3$, —$COCH(OH)CH_3$, —$CONH_2$, —$CONHCH_3$, —$CONHCH_2CH_3$, —$CONHCH(CH_3)_2$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, —$S(O)_3H$, cyclopropyl, cyclopropylamide, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, or morpholino;

n is 0, 1 or 2; and $R^7$ is independently halogen.

Variables $R^1$, $R^2$, $R^3$, $R^4$, $R^5$, IV, $R^b$, m, n, and $Y^2$ are as defined herein for compounds of formula (3).

In one instance, the compound of formula (4) comprises formula (4a):

(4a)

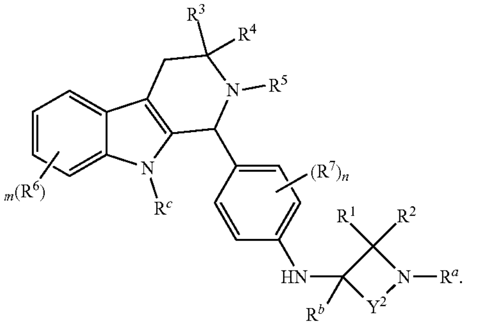

In another instance, the compound of formula (4) comprises formula (4b):

(4b)

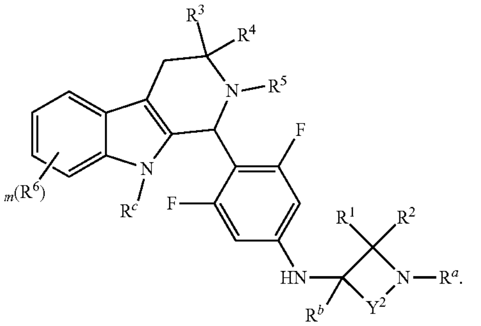

In still another instance, the compound of formula (4) comprises formula (4c):

(4c)

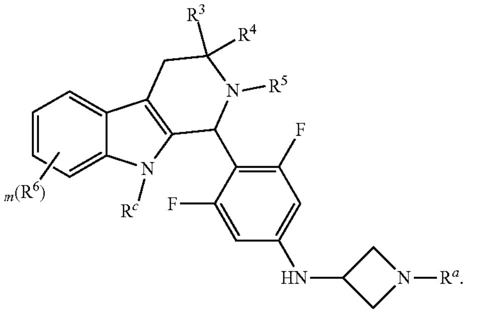

In one instance of the compounds of formula (4a)-(4c), $R^7$ is F. In one instance of the compounds of formula (4a)-(4c), $R^1$ and $R^2$ are H. In one instance of the compounds of formula (4a)-(4c), $R^3$ is H, and $R^4$ is $CH_3$. In one instance of the compounds of formula (4a)-(4c), $R^5$ is $C_1$-$C_6$ fluoroalkyl. In one instance of the compounds of formula (4a)-(4c), m is 0.

In another aspect, the endocrine therapy comprises a compound having formula: N-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1-(3-fluoropropyl)azetidin-3-amine; (R)-3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2-fluoro-2-methylpropan-1-ol; (S)-3-((1R,3R)-1-(2,6-difluoro-4-((1-

(3-fluoropropyl)azetidin-3-yl)amino)phenyl)-3-methyl-1,3,4,9-tetrahydro-2H-pyrido[3,4-b]indol-2-yl)-2-fluoro-2-methylpropan-1-ol; (R)-2-fluoro-3-((1R,3R)-1-(2-fluoro-4-((1-(3-fluoropropyl)azetidin-3-yl)amino)phenyl)-3-methyl-1,3,4,9-tetrahydro-2H-pyrido[3,4-b]indol-2-yl)-2-methylpropan-1-ol; (S)-2-fluoro-3-((1R,3R)-1-(2-fluoro-4-((1-(3-fluoropropyl)azetidin-3-yl)amino)phenyl)-3-methyl-1,3,4,9-tetrahydro-2H-pyrido[3,4-b]indol-2-yl)-2-methylpropan-1-ol; (R)-2-fluoro-3-((1R,3R)-1-(4-((1-(3-fluoropropyl)azetidin-3-yl)amino)phenyl)-3-methyl-1,3,4,9-tetrahydro-2H-pyrido[3,4-b]indol-2-yl)-2-methylpropan-1-ol; (S)-2-fluoro-3-((1R,3R)-1-(4-((1-(3-fluoropropyl)azetidin-3-yl)amino)phenyl)-3-methyl-1,3,4,9-tetrahydro-2H-pyrido[3,4-b]indol-2-yl)-2-methylpropan-1-ol; 3,5-difluoro-N-(2-(3-(fluoromethyl)azetidin-1-yl)ethyl)-4-((1R,3R)-3-methyl-2-(2,2,2-trifluoroethyl)-2,3,4,9-tetrahydro-1H-pyrido[3,4-b]indol-1-yl)aniline; N-(3,5-difluoro-4-((1R,3R)-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; 1-(3-fluoropropyl)-N-[4-[(1R,3R)-3-methyl-2-methylsulfonyl-1,3,4,9-tetrahydropyrido[3,4-b]indol-1-yl]phenyl]azetidin-3-amine; N-[3,5-difluoro-4-[(1R,3R)-3-methyl-2-methyl sulfonyl-1,3,4,9-tetrahydropyrido[3,4-b]indol-1-yl]phenyl]-1-(3-fluoropropyl)azetidin-3-amine; 1-(3-fluoropropyl)-N-[4-[(1S,3R)-3-methyl-2-methyl sulfonyl-1,3,4,9-tetrahydropyrido[3,4-b]indol-1-yl]phenyl]azetidin-3-amine; N-[3,5-difluoro-4-[(1S,3R)-3-methyl-2-methyl sulfonyl-1,3,4,9-tetrahydropyrido[3,4-b]indol-1-yl]phenyl]-1-(3-fluoropropyl)azetidin-3-amine; 3-((1R,3R)-1-(2,6-difluoro-4-((2-(3-(fluoromethyl)azetidin-1-yl)ethyl)amino)phenyl)-3-methyl-1,3,4,9-tetrahydro-2H-pyrido[3,4-b]indol-2-yl)-2-fluoro-2-methylpropan-1-ol; 3,5-difluoro-N-[2-[3-(fluoromethyl)azetidin-1-yl]ethyl]-4-[(R1R,3R)-2-(2-fluoro-2-methyl-propyl)-3-methyl-1,3,4,9-tetrahydropyrido[3,4-b]indol-1-yl]aniline; 3-fluoro-N-[2-[3-(fluoromethyl)azetidin-1-yl]ethyl]-4-[(1R,3R)-2-(2-fluoro-2-methyl-propyl)-3-methyl-1,3,4,9-tetrahydropyrido[3,4-b]indol-1-yl]aniline; N-[2-[3-(fluoromethyl)azetidin-1-yl]ethyl]-4-[(1R,3R)-2-(2-fluoro-2-methyl-propyl)-3-methyl-1,3,4,9-tetrahydropyrido[3,4-b]indol-1-yl]aniline; N-[2-[3-(fluoromethyl)azetidin-1-yl]ethyl]-4-[(1R,3R)-3-methyl-2-methyl sulfonyl-1,3,4,9-tetrahydropyrido[3,4-b]indol-1-yl]aniline; 3,5-difluoro-N-[2-[3-(fluoromethyl)azetidin-1-yl]ethyl]-4-[(R1R, 3R)-3-methyl-2-methylsulfonyl-1,3,4,9-tetrahydropyrido[3,4-b]indol-1-yl]aniline; 2-fluoro-3-((1R,3R)-1-(2-fluoro-4-((2-(3-(fluoromethyl)azetidin-1-yl)ethyl)amino)phenyl)-3-methyl-1,3,4,9-tetrahydro-2H-pyrido[3,4-b]indol-2-yl)-2-methylpropan-1-ol; 2-fluoro-3-((1R,3R)-1-(4-((2-(3-(fluoromethyl)azetidin-1-yl)ethyl)amino)phenyl)-3-methyl-1,3,4,9-tetrahydro-2H-pyrido[3,4-b]indol-2-yl)-2-methylpropan-1-ol; 3-[(1R,3R)-1-[2,6-difluoro-4-[[1-(3-fluoropropyl)azetidin-3-yl]amino]phenyl]-3-methyl-1,3,4,9-tetrahydropyrido[3,4-b]indol-2-yl]-2,2-difluoro-propan-1-ol; (R)-3-((1R,3R)-1-(2,6-difluoro-4-((2-(3-(fluoromethyl)azetidin-1-yl)ethyl)amino)phenyl)-3-methyl-1,3,4,9-tetrahydro-2H-pyrido[3,4-b]indol-2-yl)-2-fluoro-2-methylpropan-1-ol; (S)-3-((1R,3R)-1-(2,6-difluoro-4-((2-(3-(fluoromethyl)azetidin-1-yl)ethyl)amino)phenyl)-3-methyl-1,3,4,9-tetrahydro-2H-pyrido[3,4-b]indol-2-yl)-2-fluoro-2-methylpropan-1-ol; (2R)-3-[(1R,3R)-1-[2,6-difluoro-4-[[1-(3-fluoropropyl)azetidin-3-yl]amino]phenyl]-3-methyl-1,3,4,9-tetrahydropyrido[3,4-b]indol-2-yl]-2-methyl-propanoic acid; 3-((1R,3R)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2,2-difluoropropan-1-ol; 3-((1S,3S)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2,2-difluoropropan-1-ol; (2 S)-3-[(1R,3R)-1-[2,6-difluoro-4-[[1-(3-fluoropropyl)azetidin-3-yl]amino]phenyl]-3-methyl-1,3,4,9-tetrahydropyrido[3,4-b]indol-2-yl]-2-methyl-propanoic acid; N-(3,5-difluoro-4-((1R,3R)-6-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; N-(3,5-difluoro-4-((1S,3S)-6-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; 3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2,2-dimethylpropanoic acid; N-(3,5-difluoro-4-((1R,3R)-6-fluoro-3-methyl-2-(methylsulfonyl)-2,3,4,9-tetrahydro-1H-pyrido[3,4-b]indol-1-yl)phenyl)-1-(3-fluoropropyl)azetidin-3-amine; N-(3,5-difluoro-4-((1S,3S)-6-fluoro-3-methyl-2-(methylsulfonyl)-2,3,4,9-tetrahydro-1H-pyrido[3,4-b]indol-1-yl)phenyl)-1-(3-fluoropropyl)azetidin-3-amine; N-(4-((1R,3R)-2-(2,2-difluoroethyl)-6-fluoro-3-methyl-2,3,4,9-tetrahydro-1H-pyrido[3,4-b]indol-1-yl)-3,5-difluorophenyl)-1-(3-fluoropropyl)azetidin-3-amine; N-(4-((1S,3S)-2-(2,2-difluoroethyl)-6-fluoro-3-methyl-2,3,4,9-tetrahydro-1H-pyrido[3,4-b]indol-1-yl)-3,5-difluorophenyl)-1-(3-fluoropropyl)azetidin-3-amine; N-(3,5-difluoro-4-((1R,3R)-7-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; N-(3,5-difluoro-4-((1S,3S)-7-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; (S)-3-((1R,3R)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2-fluoro-2-methylpropan-1-ol; (R)-3-((1S,3S)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2-fluoro-2-methylpropan-1-ol; (R)-3-((1R,3R)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2-fluoro-2-methylpropan-1-ol; (S)-3-((1S,3S)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2-fluoro-2-methylpropan-1-ol; N-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1-(3-fluoropropyl)-N-methylazetidin-3-amine; (R)—N-(4-(2-(2,2-difluoroethyl)-3,3-dimethyl-2,3,4,9-tetrahydro-1H-pyrido[3,4-b]indol-1-yl)-3,5-difluorophenyl)-1-(3-fluoropropyl)azetidin-3-amine; (S)—N-(4-(2-(2,2-difluoroethyl)-3,3-dimethyl-2,3,4,9-tetrahydro-1H-pyrido[3,4-b]indol-1-yl)-3,5-difluorophenyl)-1-(3-fluoropropyl)azetidin-3-amine; N-(3,5-difluoro-4-((1R,3R)-5-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; N-(3,5-difluoro-44(1S,3S)-5-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; N-(3,5-difluoro-44(1S,3S)-8-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; N-(3,5-difluoro-4-((1R,3R)-8-fluoro-3-methyl-2-(2,2,2-trifluoroethyl)-2,3,4,9-tetrahydro-1H-pyrido[3,4-b]indol-1-yl)phenyl)-1-(3-fluoropropyl)azetidin-3-amine; (S)-3-((1S,3S)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2-fluoro-2-methylpropan-1-ol; (R)-3-((1R, 3R)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2-fluoro-2-methylpropan-1-ol; (S)-3-((1R,3R)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2-fluoro-2-methylpropan-1-ol; (R)-3-((1S,3S)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2-fluoro-2-methylpropan-1-ol; 3-((1R,3R)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2,2-difluoropropan-1-ol; 3-((1S,3S)-1-(2,6-difluoro-4-((1-(3-fluoropropyl)azetidin-3-yl)amino)phenyl)-5-fluoro-3-methyl-3,4-dihydro-1H-pyrido[3,4-b]indol-2(9H)-yl)-2,2-difluoropropan-1-ol; (R)-3-((1R,3R)-1-(2,6-difluoro-4-((1-(3-fluoropropyl)azetidin-3-yl)amino)phenyl)-3-methyl-3,4-dihydro-1H-pyrido[3,4-b]indol-2(9H)-yl)-2-fluoro-2-(hydroxymethyl)propanenitrile; (S)-3-((1R,3R)-1-(2,6-difluoro-4-((1-(3-fluoropropyl)azetidin-3-yl)amino)phenyl)-3-methyl-3,4-dihydro-1H-pyrido[3,4-b]indol-2(9H)-yl)-2-fluoro-2-(hydroxymethyl)propanenitrile; (R)-3-(1-(2,6-difluoro-4-((1-(3-fluoropropyl)azetidin-3-yl)amino)phenyl)-3,3-dimethyl-3,4-dihydro-1H-pyrido[3,4-b]indol-2(9H)-yl)-2,2-difluoropropan-1-ol; (S)-3-(1-(2,6-difluoro-4-((1-(3-fluoropropyl)azetidin-3-yl)amino)phenyl)-3,3-dimethyl-3,4-dihydro-1H-pyrido[3,4-b]indol-2(9H)-yl)-2,2-difluoropropan-1-ol; 3-((1S,3S)-1-(2,6-difluoro-4-((1-(3-fluoropropyl)azetidin-3-yl)amino)phenyl)-8-fluoro-3-methyl-3,4-dihydro-1H-pyrido[3,4-b]indol-2(9H)-yl)-2,2-difluoropropan-1-ol; 3-((1R,3R)-1-(2,6-difluoro-4-((1-(3-fluoropropyl)azetidin-3-yl)amino)phenyl)-8-fluoro-3-methyl-3,4-dihydro-1H-pyrido[3,4-b]indol-2(9H)-yl)-2,2-difluoropropan-1-ol; 3-((1R,3R)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2,2-difluoropropan-1-ol; 3-((1S,3S)-1-(2,6-difluoro-4-((1-(3-fluoropropyl)azetidin-3-yl)amino)phenyl)-7-fluoro-3-methyl-3,4-dihydro-1H-pyrido[3,4-b]indol-2(9H)-yl)-2,2-difluoropropan-1-ol; N-[4-[(1R,3R)-2-(2,2-difluoroethyl)-3-methyl-1,3,4,9-tetrahydropyrido[3,4-b]indol-1-yl]-3,5-difluoro-phenyl]-1-(3-fluoropropyl)azetidin-3-amine; (R)-3-((1R,3R)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2-fluoro-2-methylpropan-1-ol; (S)-3-((1S,3S)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2-fluoro-2-methylpropan-1-ol; (S)-3-((1R,3R)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2-fluoro-2-methylpropan-1-ol; or (R)-3-((1R,3S)-1-(2,6-difluoro-4-((1-(3-fluoropropyl)azetidin-3-yl)amino)phenyl)-6-fluoro-3-methyl-1,3,4,9-tetrahydro-2H-pyrido[3,4-b]indol-2-yl)-2-fluoro-2-methylpropan-1-ol, or a pharmaceutically acceptable salt thereof or a combination thereof.

In another aspect, the endocrine therapy comprises a compound having formula:

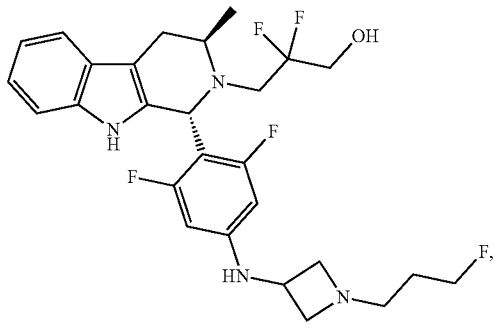 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

In another aspect, the endocrine therapy comprises a compound having formula:

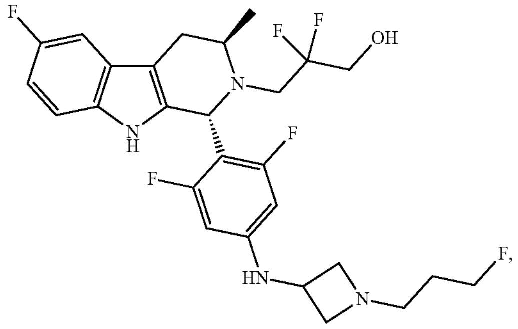 [SMILES: C[C@@H]1Cc2c([nH]c3ccc(F)cc23)[C@@H](c2c(F)cc(NC3CN(CCCF)C3)cc2F)N1CC(F)(F)CO]

or a pharmaceutically acceptable salt thereof.

In another aspect, the endocrine therapy comprises a compound having formula:

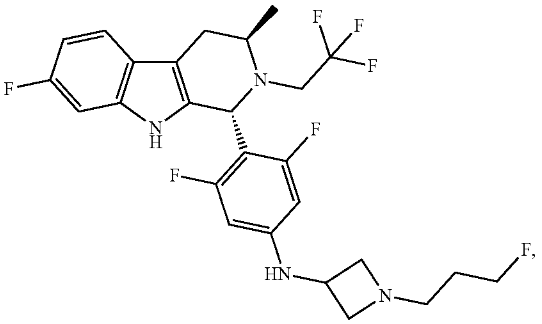 [SMILES: C[C@@H]1Cc2c([nH]c3cc(F)ccc23)[C@@H](c2c(F)cc(NC3CN(CCCF)C3)cc2F)N1CC(F)(F)F]

or a pharmaceutically acceptable salt thereof.

In another aspect, the endocrine therapy comprises a compound having formula:

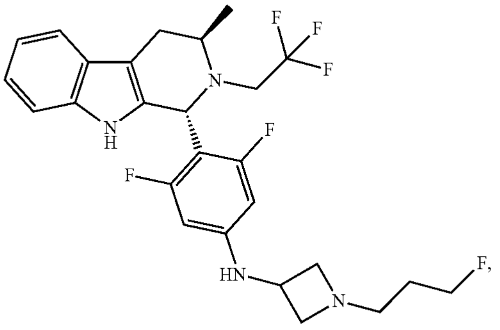 [SMILES: C[C@@H]1Cc2c([nH]c3ccccc23)[C@@H](c2c(F)cc(NC3CN(CCCF)C3)cc2F)N1CC(F)(F)F]

or a pharmaceutically acceptable salt thereof.

In another aspect, the endocrine therapy comprises a compound having formula:

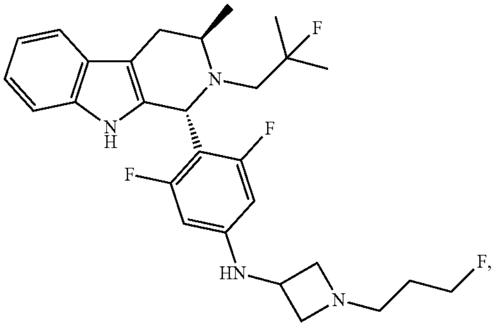 [SMILES: C[C@@H]1Cc2c([nH]c3ccccc23)[C@@H](c2c(F)cc(NC3CN(CCCF)C3)cc2F)N1CC(C)(C)F]

or a pharmaceutically acceptable salt thereof.

In another aspect, the endocrine therapy comprises a compound having formula:

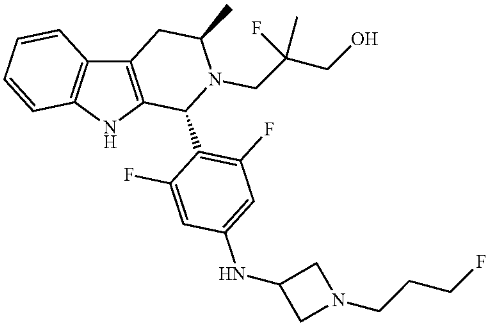

or

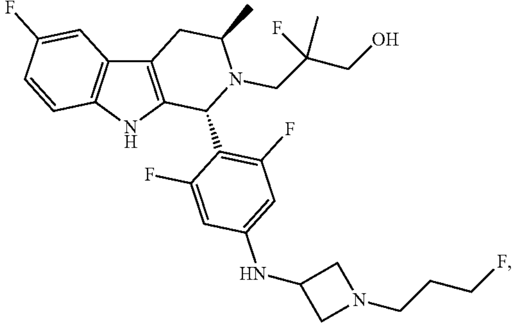

including stereoisomers thereof, or a pharmaceutically acceptable salt thereof.

In another aspect, the endocrine therapy comprises a compound set forth in U.S. Patent Application No. 20170129855, for example in Table 1 therein, which is incorporated herein by reference in its entirety and for all purposes.

In one aspect, the endocrine therapy comprises a compound of formula (5):

(5)

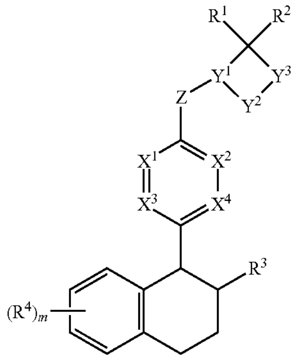

or a stereoisomer, tautomer, or pharmaceutically acceptable salt thereof, wherein:

$Y^1$ is $CR^b$ or N;

$Y^2$ is —($CH_2$)—, —($CH_2CH_2$)—, or $NR^a$;

$Y^3$ is $NR^a$ or $C(R^b)_2$;

where one of $Y^1$, $Y^2$ and $Y^3$ is N or $NR^a$;

$R^a$ and $R^c$ are independently selected from H, $C_1$-$C_6$ alkyl, $C_1$-$C_6$ fluoroalkyl, allyl, propargyl, $C_3$-$C_6$ cycloalkyl, and $C_3$-$C_6$ heterocyclyl, optionally substituted with one or more groups independently selected from F, Cl, Br, I, CN, OH, $OCH_3$, and $SO_2CH_3$;

$R^b$ is independently selected from H, —O($C_1$-$C_3$ alkyl), $C_1$-$C_6$ alkyl, $C_1$-$C_6$ fluoroalkyl, allyl, propargyl, $C_3$-$C_6$ cycloalkyl, and $C_3$-$C_6$ heterocyclyl, optionally substituted with one or more groups independently selected from F, Cl, Br, I, CN, OH, $OCH_3$, and $SO_2CH_3$, where at least one of $R^a$ and $R^b$ is —$CH_2C_1$, —$CH_2F$, —$CHF_2$, —$CF_3$, —$CH_2CH_2F$, —$CH_2CHF_2$, —$CH_2CF_3$, $CH_2CH_2C_1$, $CH_2CH_2CH_2F$, $CH_2CH_2CHF_2$, $CH_2CH_2CF_3$, or $CH_2CH_2CH_2Cl$;

$X^1$, $X^2$, $X^3$, and $X^4$ are independently selected from CH, $CR^5$ and N; where none, one, or two of $X^1$, $X^2$, $X^3$, and $X^4$ is N;

Z is selected from O, S, S(O), $S(O)_2$, C(═O), CH(OH), $C_1$-$C_6$ alkyldiyl, CH(OH)—($C_1$-$C_6$ alkyldiyl), $C_1$-$C_6$ fluoroalkyldiyl, $NR^c$—($C_1$-$C_6$ alkyldiyl), $NR^c$—($C_1$-$C_6$ fluoroalkyldiyl), O—($C_1$-$C_6$ alkyldiyl), and O—($C_1$-$C_6$ fluoroalkyldiyl);

$R^1$ and $R^2$ are independently selected from H, F, Cl, Br, I, —CN, —$CH_3$, —$CH_2CH_3$, —$CH(CH_3)_2$, —$CH_2CH(CH_3)_2$, —CH(OH, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2C_1$, —$CHF_2$, —$CH_2NH_2$, —$CH_2NHSO_2CH_3$, —$CH_2NHCH_3$, —$CH_2N(CH_3)_2$, —$CF_3$, —$CH_2CF_3$, —$CH_2CHF_2$, —$CH(CH_3)CN$, —$C(CH_3)_2CN$, —$CH_2CN$, —$CO_2H$, —$COCH_3$, —$CO_2CH_3$, —$CO_2C(CH_3)_3$, —$COCH(OH)CH_3$, —$CONH_2$, —$CONHCH_3$, —$CONHCH_2CH_3$, —$CONHCH(CH_3)_2$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, ═O, —OH, —$OCH_3$, $—OCH_2CH_3$, $—OCH_2CH_2OCH_3$, $—OCH_2CH_2OH$, $—OCH_2CH_2N(CH_3)_2$, $—OP(O)(OH)_2$, $—S(O)_2N(CH_3)_2$, $—SCH_3$, $—S(O)_2CH_3$, $—S(O)_3H$, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino;

$R^3$ is selected from $C_3$-$C_{20}$ cycloalkyl, $C_2$-$C_{20}$ heterocyclyl, $C_6$-$C_{20}$ aryl, $C_1$-$C_{20}$ heteroaryl, alkyldiyl)-($C_3$-$C_{20}$ cycloalkyl), alkyldiyl)-($C_2$-$C_{20}$ heterocyclyl), alkyldiyl)-($C_6$-$C_{20}$ aryl), and —($C_1$-$C_6$ alkyldiyl)-($C_1$-$C_{20}$ heteroaryl);

or $R^3$ forms a 3-6-membered spiro carbocyclic or heterocyclic group;

$R^4$ and $R^5$ are independently selected from F, Cl, Br, I, —CN, $—CH_3$, $—CH_2CH_3$, $—CH(CH_3)_2$, $—CH_2CH(CH_3)_2$, —CH(OH, $—CH_2OCH_3$, $—CH_2CH_2OH$, $—C(CH_3)_2OH$, $—CH(OH)CH(CH_3)_2$, $—C(CH_3)_2CH_2OH$, $—CH_2CH_2SO_2CH_3$, $—CH_2OP(O)(OH)_2$, $—CHF_2$, $—CH_2NH_2$, $—CH_2NHSO_2CH_3$, $—CH_2NHCH_3$, $—CH_2N(CH_3)_2$, $—CF_3$, $—CH_2CF_3$, $—CH_2CHF_2$, $—CH(CH_3)CN$, $—C(CH_3)_2CN$, $—CH_2CN$, $—CO_2H$, $—COCH_3$, $—CO_2CH_3$, $—CO_2C(CH_3)_3$, $—COCH(OH)CH_3$, $—CONH_2$, $—CONHCH_3$, $—CONHCH_2CH_3$, $—CONHCH(CH_3)_2$, $—CON(CH_3)_2$, $—C(CH_3)_2CONH_2$, $—NH_2$, $—NHCH_3$, $—N(CH_3)_2$, $—NHCOCH_3$, $—N(CH_3)COCH_3$, $—NHS(O)_2CH_3$, $—N(CH_3)C(CH_3)_2CONH_2$, $—N(CH_3)CH_2CH_2S(O)_2CH_3$, $—NO_2$, =O, —OH, $—OCH_3$, $—OCH_2CH_3$, $—OCH_2CH_2OCH_3$, $—OCH_2CH_2OH$, $—OCH_2CH_2N(CH_3)_2$, $—OP(O)(OH)_2$, $—S(O)_2N(CH_3)_2$, $—SCH_3$, $—S(O)_2CH_3$, $—S(O)_3H$, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino; and m is selected from 0, 1, 2, 3, and 4;

where alkyldiyl, fluoroalkyldiyl, aryl, carbocyclyl, heterocyclyl, and heteroaryl are optionally substituted with one or more groups independently selected from F, Cl, Br, I, —CN, $—CH_3$, $—CH_2CH_3$, $—CH(CH_3)_2$, $—CH_2CH(CH_3)_2$, $—CH_2OH$, $—CH_2OCH_3$, $—CH_2CH_2OH$, $—C(CH_3)_2OH$, $—CH(OH)CH(CH_3)_2$, $—C(CH_3)_2CH_2OH$, $—CH_2CH_2SO_2CH_3$, $—CH_2OP(O)(OH)_2$, $—CH_2F$, $—CHF_2$, $—CF_3$, $—CH_2CF_3$, $—CH_2CHF_2$, $—CH(CH_3)CN$, $—C(CH_3)_2CN$, $—CH_2CN$, $—CH_2NH_2$, $—CH_2NHSO_2CH_3$, $—CH_2NHCH_3$, $—CH_2N(CH_3)_2$, $—CO_2H$, $—COCH_3$, $—CO_2CH_3$, $—CO_2C(CH_3)_3$, $—COCH(OH)CH_3$, $—CONH_2$, $—CONHCH_3$, $—CON(CH_3)_2$, $—C(CH_3)_2CONH_2$, $—NH_2$, $—NHCH_3$, $—N(CH_3)_2$, $—NHCOCH_3$, $—N(CH_3)COCH_3$, $—NHS(O)_2CH_3$, $—N(CH_3)C(CH_3)_2CONH_2$, $—N(CH_3)CH_2CH_2S(O)_2CH_3$, $—NO_2$, =O, —OH, $—OCH_3$, $—OCH_2CH_3$, $—OCH_2CH_2OCH_3$, $—OCH_2CH_2OH$, $—OCH_2CH_2N(CH_3)_2$, $—OP(O)(OH)_2$, $—S(O)_2N(CH_3)_2$, $—SCH_3$, $—S(O)_2CH_3$, $—S(O)_3H$, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino.

In one instance of the compounds of formula (5), $Y^1$ is N and $Y^3$ is $C(R^b)_2$. In one instance of the compounds of formula (5), $Y^2$ is $—(CH_2)—$. In one instance of the compounds of formula (5), $Y^2$ is $—(CH_2CH_2)—$. In one instance of the compounds of formula (5), $Y^3$ is $NR^a$ and $R^a$ is $—CH_2C_1$, $—CH_2F$, $—CHF_2$, $—CF_3$, $—CH_2CH_2F$, $—CH_2CHF_2$, or $—CH_2CF_3$. In one instance of the compounds of formula (5), $X^1$, $X^2$, $X^3$, and $X^4$ are independently selected from CH and $CR^5$. In one instance of the compounds of formula (5), one of $X^1$, $X^2$, $X^3$, and $X^4$ is N. In one instance of the compounds of formula (5), Z is O or O—($C_1$-$C_6$ alkyldiyl). In one instance of the compounds of formula (5), $R^1$ and $R^2$ are H. In one instance of the compounds of formula (5), $R^3$ is $C_6$-$C_{20}$ aryl. In one instance of the compounds of formula (5), $C_6$-$C_{20}$ aryl is phenyl. In one instance of the compounds of formula (5), phenyl is substituted with one or more F. In one instance of the compounds of formula (5). In one instance of the compounds of formula (5), $R^4$ is OH, and m is 1. In one instance of the compounds of formula (5), $R^5$ is F and n is 2. In one instance of the compounds of formula (5), $R^5$ is H. In one instance of the compounds of formula (5), n is 0.

In one aspect, the endocrine therapy comprises a compound having formula: (1R,2S)-1-[4-[2-[3-(fluoromethyl)azetidin-1-yl]ethoxy]phenyl]-2-phenyl-tetralin-6-ol; (1S,2R)-1-[4-[2-[3-(fluoromethyl)azetidin-1-yl]ethoxy]phenyl]-2-phenyl-tetralin-6-ol; (1S,2R)-1-[4-[2-[3-(fluoromethyl)azetidin-1-yl]ethoxy]phenyl]-2-(4-fluorophenyl)tetralin-6-ol; (1R,2R)-1-[2,6-difluoro-4-[2-[3-(fluoromethyl)azetidin-1-yl]ethoxy]phenyl]-2-phenyl-tetralin-6-ol; (1S,2S)-1-[2,6-difluoro-4-[2-[3-(fluoromethyl)azetidin-1-yl]ethoxy]phenyl]-2-phenyl-tetralin-6-ol; (1R,2S)-1-[4-[2-[3-(fluo- romethyl)azetidin-1-yl]ethoxy]phenyl]-2-(4-fluorophenyl)tetralin-6-ol; (5R,6R)-5-(4-(2-(3-(fluoromethyl)azetidin-1-yl)ethoxy)phenyl)-6-(tetrahydro-2H-pyran-4-yl)-5,6,7,8-tetrahydronaphthalen-2-ol; (5S,6S)-6-(4,4-difluorocyclohexyl)-5-(4-(2-(3-(fluoromethyl)azetidin-1-yl)ethoxy)phenyl)-5,6,7,8-tetrahydronaphthalen-2-ol; (5S,6S)-5-(4-(2-(3-(fluoromethyl)azetidin-1-yl)ethoxy)phenyl)-6-(tetrahydro-2H-pyran-4-yl)-5,6,7,8-tetrahydronaphthalen-2-ol; (5R,6R)-6-(4,4-difluorocyclohexyl)-5-(4-(2-(3-(fluoromethyl)azetidin-1-yl)ethoxy)phenyl)-5,6,7,8-tetrahydronaphthalen-2-ol; (5R,6S)-5-(4-(2-(3-(fluoromethyl)pyrrolidin-1-yl)ethoxy)phenyl)-6-phenyl-5,6,7,8-tetrahydronaphthalen-2-ol; (5R,6S)-5-(4-(2-(3-(chloromethyl)azetidin-1-yl)ethoxy)phenyl)-6-phenyl-5,6,7,8-tetrahydronaphthalen-2-ol; (5S,6R)-5-(4-(2-(3-(chloromethyl)azetidin-1-yl)ethoxy)phenyl)-6-phenyl-5,6,7,8-tetrahydronaphthalen-2-ol; (5 S,6R)-5-(4-(2-(3-(fluoromethyl)pyrrolidin-1-yl)ethoxy)phenyl)-6-phenyl-5,6,7,8-tetrahydronaphthalen-2-ol; (5S,6R)-5-(4-(2-(3-(fluoromethyl)azetidin-1-yl)ethoxy)phenyl)-6-(4-(methylsulfonyl)phenyl)-5,6,7,8-tetrahydronaphthalen-2-ol; (5S,6R)-5-(4-(2-(3-(difluoromethyl)azetidin-1-yl)ethoxy)phenyl)-6-phenyl-5,6,7,8-tetrahydronaphthalen-2-ol; (5R,6 S)-5-(4-(2-(3-(fluoromethyl)azetidin-1-yl)ethoxy)phenyl)-6-(4-(methylsulfonyl)phenyl)-5,6,7,8-tetrahydronaphthalen-2-ol; (5R,6S)-5-(4-(2-(3-(difluoromethyl)azetidin-1-yl)ethoxy)phenyl)-6-phenyl-5,6,7,8-tetrahydronaphthalen-2-ol; (5R,6R)-5-(2-fluoro-4-(2-(3-(fluoromethyl)azetidin-1-yl)ethoxy)phenyl)-6-phenyl-5,6,7,8-tetrahydronaphthalen-2-ol; (5S,6S)-5-(2-fluoro-4-(2-(3-(fluoromethyl)azetidin-1-yl)ethoxy)phenyl)-6-phenyl-5,6,7,8-tetrahydronaphthalen-2-ol; (S)-1'-(4-(2-(3-(fluoromethyl)azetidin-1-yl)ethoxy)phenyl)-3',4'-dihydro-1'H-spiro[cyclopentane-1,2'-naphthalen]-6'-ol; (R)-1'-(4-(2-(3-(fluoromethyl)azetidin-1-yl)ethoxy)phenyl)-3',4'-dihydro-1'H-spiro[cyclopentane-1,2'-naphthalen]-6'-ol; (5R,6S)-5-(4-((S)-2-((R)-3-(fluoromethyl)pyrrolidin-1-yl)propoxy)phenyl)-6-phenyl-5,6,7,8-tetrahydronaphthalen-2-ol; (5S,6R)-5-(4-((S)-2-((R)-3-(fluoromethyl)pyrrolidin-1-yl)propoxy)phenyl)-6-phenyl-5,6,7,8-tetrahydronaphthalen-2-ol; (5R,6S)-5-(4-(((R)-1-((R)-3-(fluoromethyl)pyrrolidin-1-yl)propan-2-yl)oxy)phenyl)-6-phenyl-5,6,7,8-tetrahydronaphthalen-2-ol; (5S,6R)-5-(4-(((R)-1-((R)-3-(fluoromethyl)pyrrolidin-1-yl)propan-2-yl)oxy)phenyl)-6-phenyl-5,6,7,8-tetrahydronaphthalen-2-ol; (5 S,6S)-5-(6-(2-(3-(fluoromethyl)azetidin-1-yl)ethoxy)pyridin-3-yl)-6-phenyl-5,6,7,8-tetrahydronaphthalen-2-ol; (5R,6R)-5-(6-(2-(3-(fluoromethyl)azetidin-1-yl)ethoxy)pyridin-3-yl)-6-phenyl-5,6,7,8-tetrahydronaphthalen-2-ol; (5S,6R)-5-(4-((1-(3-fluoropropyl)azetidin-3-yl)oxy)phenyl)-6-phenyl-5,6,7,8-tetrahydronaphthalen-2-ol; (5R,6S)-5-(4-((1-(3-fluoropropyl)azetidin-3-yl)oxy)phenyl)-6-phenyl-5,6,7,8-tetrahydronaphthalen-2-ol; (5S,6R)-5-(4-((1-(3-fluoropropyl)azetidin-3-yl)amino)phenyl)-6-phenyl-5,6,7,8-tetrahydronaphthalen-2-ol; or (5R,6S)-5-(44(1-(3-fluoropropyl)azetidin-3-yl)amino)phenyl)-6-phenyl-5,6,7,8-tetrahydronaphthalen-2-ol, or a pharmaceutically acceptable salt thereof or combination.

B. Non-Endocrine Anti-Cancer Therapies

In some instances of any of the preceding methods, an anti-cancer therapy other than an endocrine therapy may be administered to the individual. Exemplary anti-cancer therapies other than endocrine therapies include, but are not limited to, mammalian target of rapamycin (mTOR) inhibitors such as sirolimus (also known as rapamycin), temsirolimus (also known as CCI-779 or TORISEL®), everolimus (also known as RAD001 or AFINITOR®), ridaforolimus (also known as AP-23573, MK-8669, or deforolimus), OSI-027, AZD8055, and INK128; phosphatidylinositol 3-kinase (PI3K) inhibitors such as idelalisib (also known as GS-1101 or CAL-101), BKM120, and perifosine (also known as KRX-0401); dual phosphatidylinositol 3-kinase (PI3K)/mTOR inhibitors such as XL765, GDC-0980, BEZ235 (also known as NVP-BEZ235), BGT226, GSK2126458, PF-04691502, and PF-05212384 (also known as PKI-587); and cyclin-dependent kinase $(CDK)_{4/6}$ inhibitors such as abemaciclib (VERZENIO®), palbociclib (IBRANCE®), ribociclib (KISQALI®), trilaciclib (G1T28); anthracyclines such as daunorubicin, doxorubicin, epirubicin, idarubicin, mitoxantrone, valrubicin; taxanes, including paclitaxel and docetaxel; podophyllotoxin; gemcitabine (GEMZAR®); 5-fluorouracil (5-FU); cyclophosphamide (CYTOXAN®); platinum analogs such as cisplatin and carboplatin; vinorelbine (NAVELBINE®); capecitabine (XELODA®); ixabepilone (IXEMPRA®); eribulin (HALAVEN®); and pharmaceutically acceptable salts acids or derivatives thereof; as well as combinations thereof. In certain instances, an anti-cancer agent described herein can be used in combination with an endocrine therapy as described herein in the methods provided herein. For example, in one embodiment, a CDK4/6 inhibitor such as palbociclib can be administered in combination with an endocrine therapy described herein (e.g. a SERD as set forth herein). For example, in some instances, the anti-cancer therapy other than an endocrine therapy comprises a chemotherapeutic and a PI3K inhibitor.

The non-endocrine therapy can comprise administration of, for example, AKT inhibitors (e.g. Ipatasertib), angiogenic agents (e.g. Avastin), BCL-2 inhibitors (e.g. Venetoclax), HDAC inhibitors, AURK inhibitors, or cancer immunotherapy agents (e.g. anti-PD1/PDL1 agents, including for example, atezoluzimab, pembrolizumab, nivolumab, avelumab, durvalumab, and pidilizumab).

C. Combination Therapies

It is to be understood that the methods described herein can be used with all compounds described herein whether administered as monotherapies or in combination including, for example, double, triple, or quadruple therapy combinations. In one instance, the compounds described herein have been administered before a tested patient has had surgery. In another instance, the compounds described herein have been administered after a tested patient has had surgery. In still another instance, the compounds described herein have been administered as either a 1 L, 2 L, 3 L or more therapy. In particular instance, patients described herein may have received prior treatment with a CDK4/6 inhibitor such as, for example, palbociclib, ribociclib, or abemaciclib before, during, or after treatment with a compound described herein.

In some instances of any of the preceding methods, a combination therapy including an endocrine therapy and one or more additional anti-cancer agents may be administered to the individual. Such combination therapies noted above encompass combined administration (where two or more therapeutic agents are included in the same or separate formulations), and separate administration, in which case, administration of an endocrine therapy as described herein can occur prior to, simultaneously, and/or following, administration of the additional therapeutic agent or agents.

V. Compositions and Pharmaceutical Formulations

Therapeutic formulations of the therapeutic agents, including an anti-cancer agent as provided herein or an endocrine therapy as provided herein, used in accordance with the methods and compositions provided herein are prepared for storage by mixing the therapeutic agent having the desired degree of purity with optional pharmaceutically acceptable carriers, excipients, or stabilizers in the form of lyophilized formulations or aqueous solutions. For general information concerning formulations, see, e.g., Gilman et al. (eds.) *The Pharmacological Bases of Therapeutics,* 8th Ed., Pergamon Press, 1990; A. Gennaro (ed.), *Remington's Pharmaceutical Sciences,* 22nd Edition, Mack Publishing Co., Pennsylvania, 2012; Avis et al. (eds.) *Pharmaceutical Dosage Forms: Parenteral Medications* Dekker, New York, 1993; Lieberman et al. (eds.) *Pharmaceutical Dosage Forms: Tablets* Dekker, New York, 1990; Lieberman et al. (eds.), *Pharmaceutical Dosage Forms: Disperse Systems* Dekker, New York, 1990; and Walters (ed.) *Dermatological and Transdermal Formulations* (Drugs and the Pharmaceutical Sciences), Vol 119, Marcel Dekker, 2002.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

The formulation herein may also contain more than one active compound, preferably those with complementary activities that do not adversely affect each other. The type and effective amounts of such medicaments depend, for example, on the amount and type of therapeutic agent described herein present in the formulation, and clinical parameters of the individuals.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in *Remington's Pharmaceutical Sciences* 16th edition, Osol, A. Ed., 1980.

Sustained-release preparations may be prepared. Suitable examples of sustained-release preparations include semipermeable matrices of solid hydrophobic polymers containing the therapeutic agent, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

VI. Articles of Manufacture and Kits

In another aspect, provided herein is a kit or an article of manufacture containing materials useful for the treatment, diagnosis, and/or monitoring of individuals is provided.

In some instances, such diagnostic kits including one or more reagents for identifying an individual having a breast cancer (e.g., an HR+ breast cancer (e.g., an ER+ breast cancer (e.g., luminal A breast cancer or luminal B breast cancer)), DCIS, and/or a metastatic or a locally advanced breast cancer) who may benefit from a treatment including an endocrine therapy as described herein, by determining an ER pathway activity score or an E2-induced score, as described herein, from a sample (e.g., a tissue sample, e.g., a tumor tissue sample, e.g., a FFPE, a FF, an archival, a fresh, or a frozen tumor tissue sample) from the individual. In some instances, the kit further includes one or more reagents for determining an ER pathway activity score or an E2-induced score from a sample.

Optionally, the kit may further include instructions to use the kit to select a therapy such as an endocrine therapy provided herein for treating a breast cancer if the ER pathway activity score or E2-induced score determined from the sample (e.g., a tissue sample, e.g., a tumor tissue sample, e.g., a FFPE, a FF, an archival, a fresh, or a frozen tumor tissue sample) from the individual is at or above a reference ER pathway activity score or a reference E2-induced score. In another instance, the instructions are to use the kit to select an anti-cancer therapy other than an endocrine therapy, if the ER pathway activity score or E2-induced score determined from the sample (e.g., a tissue sample, e.g., a tumor tissue sample, e.g., a FFPE, a FF, an archival, a fresh, or a frozen tumor tissue sample) from the individual is below a reference ER pathway activity score or a reference E2-induced score.

In other instances, the articles of manufacture or kits may include instructions to use the kit to monitor and/or assess the response of an individual having a breast cancer to treatment with an endocrine therapy as described herein.

In one aspect a kit including a plurality of nucleic acids is provided. The plurality of nucleic acids are at least 5 nucleotides in length and are at least 95, 98, 99, or 100% identical to a 5 nucleotide continuous sequence within at least five genes set forth in Table 1 and at least five genes set forth in Table 4; at least five genes set forth in Table 2 and at least five genes set forth in Table 4; or at least five genes set forth in Table 3 and at least five genes set forth in Table 6, or 95, 98, 99, or 100% identical to a sequence complementary to the 5 nucleotide continuous sequence.

In embodiments, the plurality of nucleic acids are attached to a solid support. In embodiments, the plurality of nucleic acids comprise a detectable label. In embodiments, the plurality of nucleic acids are at least 95, 98, 99, or 100% identical to a 5 nucleotide continuous sequence within at least five genes set forth in Table 1, at least five genes set forth in Table 2 or at least five genes set forth in Table 3 are greater than a standard control. In embodiments, the plurality of nucleic acids are at least 95, 98, 99, or 100% identical to a 5 nucleotide continuous sequence within at least five genes set forth in Table 4, at least five genes set forth in Table 5 or at least five genes set forth in Table 6 are less than a standard control. In embodiments, the plurality of nucleic acids are at least 95, 98, 99, or 100% identical to a 5 nucleotide continuous sequence within all genes set forth in Table 1 and all genes set forth in Table 4. In embodiments, the plurality of nucleic acids are at least 95, 98, 99, or 100% identical to a 5 nucleotide continuous sequence within all genes set forth in Table 2 and all genes set forth in Table 5. In embodiments, the plurality of nucleic acids are at least 95, 98, 99, or 100% identical to a 5 nucleotide continuous sequence within all genes set forth in Table 3 and all genes set forth in Table 6. In embodiments, the plurality of nucleic acids are at least 95, 98, 99, or 100% identical to a 5 nucleotide continuous sequence within all genes set forth in Table 1 and all genes set forth in Table 4 and no other genes. In embodiments, the plurality of nucleic acids are at least 95, 98, 99, or 100% identical to a 5 nucleotide continuous sequence within all genes set forth in Table 2 and all genes set forth in Table 5 and no other genes. In embodiments, the plurality of nucleic acids are at least 95, 98, 99, or 100% identical to a 5 nucleotide continuous sequence within all genes set forth in Table 3 and all genes set forth in Table 6 and no other genes in the subject.

In a further embodiment, the plurality of nucleic acids are at least 95, 98, 99, or 100% identical to a continuous nucleotide sequence comprising at least 10, 20, 25, 50, 75, 100, 150, or 200 nucleotides.

Provided herein are also articles of manufacture including, packaged together an endocrine therapy as described herein in a pharmaceutically acceptable carrier and a package insert indicating that the endocrine therapy is for treating an individual with a breast cancer as described herein based on an ER pathway activity score or an E2-induced score determined from a sample (e.g., a tissue sample, e.g., a tumor tissue sample, e.g., a FFPE, a FF, an archival, a fresh, or a frozen tumor tissue sample) from the individual.

The article of manufacture may include, for example, a container and a label or package insert on or associated with the container. Suitable containers include, for example, bottles, vials, syringes, and the like. The container may be formed from a variety of materials such as glass or plastic. The container holds or contains a composition comprising the cancer medicament as the active agent and may have a sterile access port (e.g., the container may be an intravenous solution bag or a vial having a stopper pierceable by a hypodermic injection needle).

The article of manufacture may further include a second container comprising a pharmaceutically-acceptable diluent buffer, such as bacteriostatic water for injection (BWFI), phosphate-buffered saline, Ringer's solution, and/or dextrose solution. The article of manufacture may further include other materials desirable from a commercial and user standpoint, including other buffers, diluents, filters, needles, and syringes.

The kits or articles of manufacture described herein may have a number of instances. In one instance, the kits or articles of manufacture includes a container, a label on said container, and a composition contained within said container, wherein the composition includes one or more polynucleotides that hybridize to a complement of a gene listed herein (e.g., a set of genes set forth in any one of Tables 1-6) under stringent conditions, and the label on said container indicates that the composition can be used to evaluate the presence a set of genes listed herein (e.g., a set of genes set forth in any one of Tables 1-6) in a sample, and wherein the kit includes instructions for using the polynucleotide(s) for evaluating the presence of the genes' RNA or DNA in a particular sample type.

For oligonucleotide-based articles of manufacture or kits, the article of manufacture or kit can include, for example: (1) an oligonucleotide, e.g., a detectably labeled oligonucleotide, which hybridizes to a nucleic acid sequence encoding a protein or (2) a pair of primers useful for amplifying a nucleic acid molecule. The article of manufacture or kit can also include, e.g., a buffering agent, a preservative, or a protein stabilizing agent. The article of manufacture or kit can further include components necessary for detecting the detectable label (e.g., an enzyme or a substrate). The article of manufacture or kit can also contain a control sample or a series of control samples that can be assayed and compared to the test sample. Each component of the article of manufacture or kit can be enclosed within an individual container and all of the various containers can be within a single package, along with instructions for interpreting the results of the assays performed using the kit.

The article of manufacture provided herein also includes information, for example in the form of a package insert, indicating that the composition is used for treating a breast cancer (e.g., an HR+ breast cancer (e.g., an ER+ breast cancer (e.g., luminal A breast cancer or luminal B breast cancer)), DCIS, and/or a metastatic or a locally advanced breast cancer) based on an ER pathway activity score or an E2-induced score from determined from a sample (e.g., a tissue sample, e.g., a tumor tissue sample, e.g., a FFPE, a FF, an archival, a fresh, or a frozen tumor tissue sample) from an individual as described herein. The insert or label may take any form, such as paper or on electronic media such as a magnetically recorded medium (e.g., floppy disk), a CD-ROM, a Universal Serial Bus (USB) flash drive, and the like. The label or insert may also include other information concerning the pharmaceutical compositions and dosage forms in the kit or article of manufacture.

VII. Examples

The following are examples of the methods and compositions provided herein. It is understood that various other embodiments may be practiced, given the general description provided above.

Example 1. Identification of an ER Pathway Activity Signature

Gene expression levels in breast cancer cell lines and a breast cancer xenograft mouse model were evaluated for their association with estrogen receptor (ER) pathway activity to identify potential biomarkers for predictive purposes.

In Vitro Derived ER Pathway Activity Signature.

To derive a transcriptional signature of ER pathway activity, RNA sequencing was performed on seven breast cancer cell lines following treatment with either DMSO or 1 μM estradiol (E2) for 24 hours. Briefly, RNA libraries for cell lines were made with TRUSEQ® RNA sample preparation kit (ILLUMINA®) according to the manufacturer's protocol. The libraries were sequenced on an ILLUMINA® Hi Seq 2000, using 1-4 lanes per cell line. RNA sequencing (RNA-seq) data were analyzed with HTSeqGenie (R package version 3.14.0) in BioConductor (Huber et al. *Nature Methods.* 112:115-21, 2015) as follows: reads were trimmed to 75 base pairs (bp), filtered for quality and rRNA/adapter contamination, and aligned to the reference genome GRCh38 using GSNAP (Wu et al. *Bioinforma Oxf Engl.* 26:873-81, 2010). Gene expression was quantified as Reads per Kilobase of exon model per Million mapped reads normalized by size factor (nRPKM), defined as number of reads aligning to a gene in a sample/(total number of uniquely mapped reads for that sample x gene length x size factor). Genes without gene symbol and genes of uncertain function (LOC and Corf symbols) were excluded.

Figure 1B:
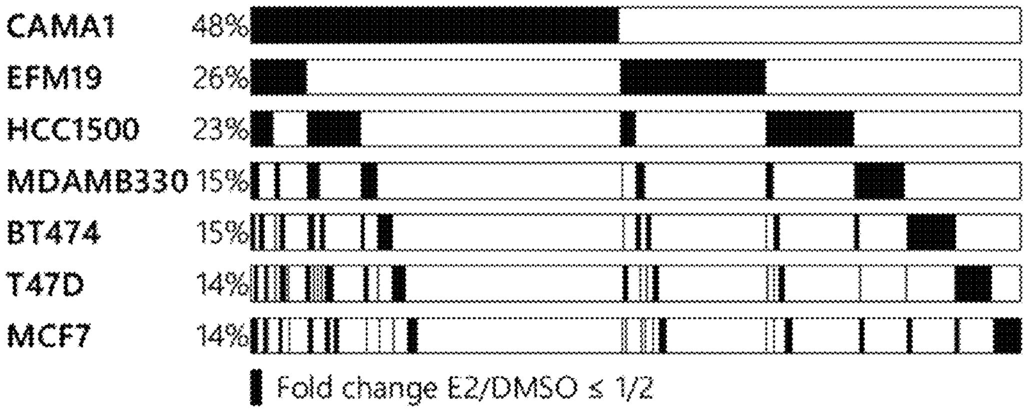
FIG. 1B is an overview of E2-repressed genes shown in blue (columns) in seven breast cancer cell lines (rows). E2 repression is defined as ≤1/2-fold change in expression following E2 treatment compared to treatment with DMSO (p-value ≤0.05).

233 to 1,390 genes were significantly induced by E2 relative to DMSO in individual cell lines (fold change ≥2, and p-value ≤0.05) (FIG. 1A), and 365 to 1,251 genes were significantly suppressed by E2 in individual cell lines (fold change ≤0.5, and p-value ≤0.05) (FIG. 1B). In order to capture a core set of ER-responsive genes that are most reflective of ER pathway activity across heterogeneous tumors, and would thus likely be widely sensitive to ER perturbation, selected genes were those that were significantly and consistently induced or repressed by E2 in at least 6 out of 7 cell lines. E2-induced genes were additionally required to be higher expressed in 12 ER IHC+ breast cell lines compared to 25 ER IHC− breast cell lines (one-sided t-test p<0.05). To compare the genes in a broader panel of ER+ vs. ER− breast cell lines, RNA-sequencing data from 37 breast cell lines was performed as described in Klijn et al, Nat Biotech 2015 and deposited on the European Genome-phenome Archive (http://www.ebi.ac.uk/ega/) under accession number EGAS00001000610. These data were processed in the same way as the RNAseq data for the 7 breast lines (previous paragraph). Together, this resulted in the identification of 28 E2-induced and 19 E2-repressed genes.

In order to generalize this core set of E2-induced and E2-repressed genes to patient data, RNA-seq data from 939 breast tumors from The Cancer Genome Atlas (TCGA), which included 726 ER+ (by IHC) breast tumors and 213 ER− breast tumors were examined. Briefly, RNA-seq data were downloaded from the National Cancer Institute Genomic Data Commons (https://gdc.cancer.gov) and were analyzed with HTSeqGenie in BioConductor as follows: first, reads with low nucleotide qualities (70% of bases with quality <23) or rRNA and adapter contamination were removed. The reads that passed were then aligned to the reference genome GRCh38 using GSNAP. Alignments of the reads that were reported by GSNAP as "uniquely mapping" were used for subsequent analysis. Raw counts were converted to counts per million (cpm), filtered for lowly expressed genes (e.g., cpm <0.25 in over 90% of samples), normalized using TMM normalization in the edgeR package, and finally voom transformed using the limma package in R. ER IHC was available for 84% of tumors, and RNA-seq-derived PAM50 subtype labels were assigned as previously described (Daemen et al. Breast Cancer Research. 20:8, 2018). Genes that were on average low expressed across the 726 ER+(by IHC) breast tumors were discarded (average expression in bottom $15^{th}$ percentile).

Figure 1C:
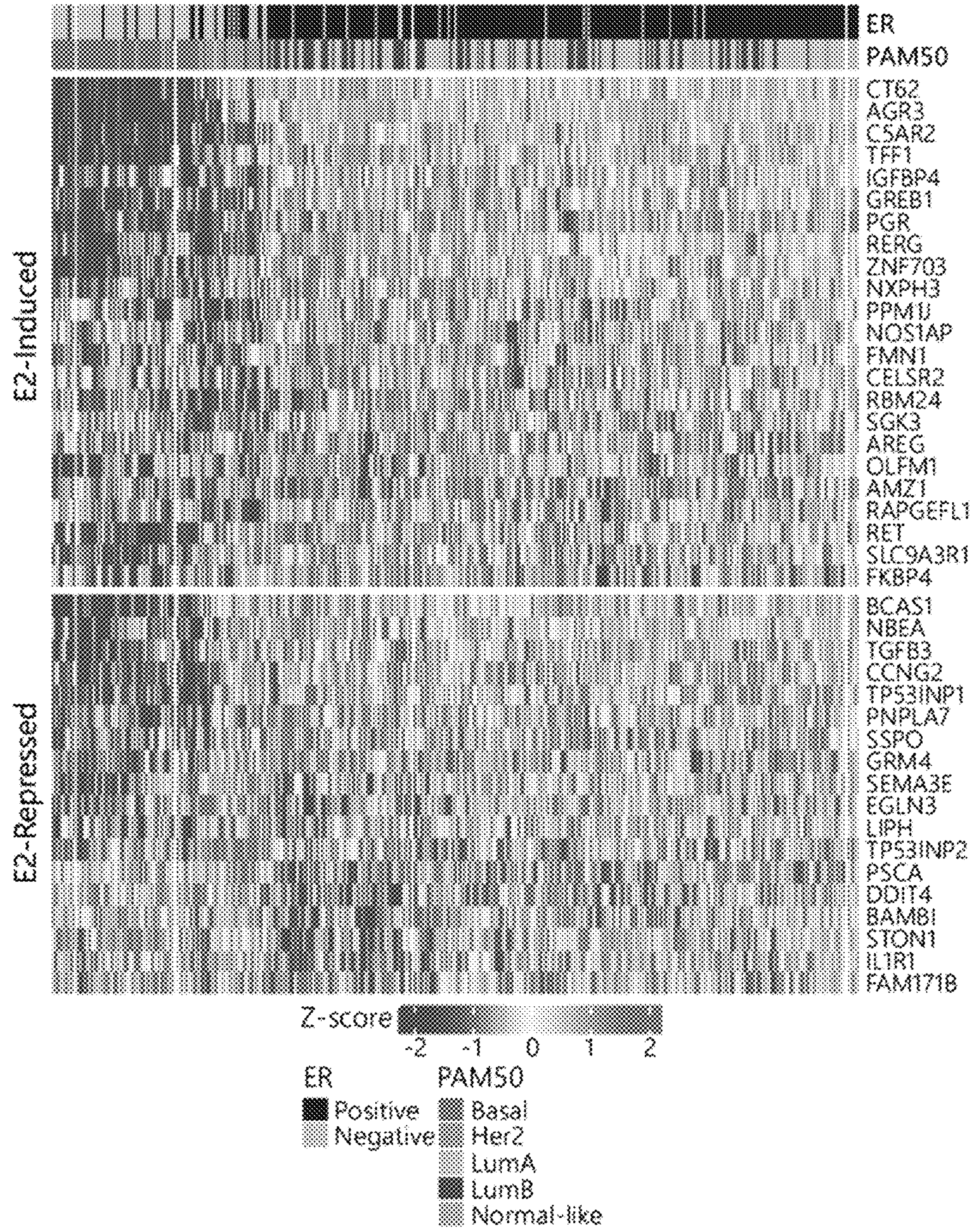
FIG. 1C is a heat map with z-scored expression of 23 E2-induced and 18 E2-repressed genes in 989 breast tumors from The Cancer Genome Atlas (TGCA), annotated by estrogen receptor (ER) immunohistochemistry (IHC) status and PAM50 subtype.

Signature genes were required to be expressed in ER+ TCGA tumors, and E2-induced genes were required to be higher expressed in ER+ compared to ER− tumors (one-sided t-test $p<0.05$). This resulted in a further refinement of the signature to a 41-gene signature composed of 23 E2-induced and 18 E2-repressed genes of which are shown in Table 7 below. (See FIG. 1C).

and two E2-repressed genes, EGLN3 and SEMA3A, that were lowly expressed across the tumors in this study (average housekeeping-normalized expression in bottom $10^{th}$ percentile of expressed genes) (FIG. 2B) were also excluded.

The effect of treatment with Compound A on ER pathway activity in the HCI-013 PDX model was assessed based on 20 E2-induced and 14 E2-repressed genes. The fold change in expression of each gene after Compound A exposure was calculated relative to the average expression of that gene in four vehicle treated animals. The E2-induced score was calculated as the average $\log_{10}$ fold change in expression of 20 E2-induced genes. The E2-repressed score was calculated as the average $\log_{10}$ fold change in expression of 14 E2-repressed genes. A composite score for ER pathway activity was calculated as the difference between the E2-induced score and the E2-repressed score (FIG. 2C). The three scores show a dose-response effect, with increased suppression of the ER pathway with increased dose (0.1 to 1 to 10 mg/kg).

TABLE 7

ER Repressed Genes

| Gene symbol | Entrez gene ID | MDA-MB-330 Log2 FC E2 vs no E2 | HCC1500 Log2 FC E2 vs no E2 | MCF7 Log2 FC E2 vs no E2 | EFM19 Log2 FC E2 vs no E2 | T47D Log2 FC E2 vs no E2 | BT474 Log2 FC E2 vs no E2 | CAMA1 Log2 FC E2 vs no E2 |
|---|---|---|---|---|---|---|---|---|
| BAMBI | 25805 | −1.352 | −1.438 | −0.571 | −1.554 | −1.394 | −1.153 | −1.072 |
| BCAS1 | 8537 | −1.772 | −2.105 | −0.981 | −2.189 | −2.536 | −1.110 | −2.311 |
| CCNG2 | 901 | −1.009 | −1.525 | −1.267 | −1.442 | −1.310 | −0.935 | −2.094 |
| DDEE4 | 54541 | −1.321 | −1.865 | −1.080 | −1.101 | −1.878 | −0.862 | −2.737 |
| EGLN3 | 112399 | −2.785 | −2.504 | −1.090 | −1.008 | −2.052 | −0.118 | −1.533 |
| FAM1718 | 165215 | −2.790 | −0.683 | −1.287 | −1.910 | −1.158 | −1.279 | −2.271 |
| GRM4 | 2914 | −2.281 | −1.071 | −1.106 | −1.141 | −1.340 | −1.883 | −2.021 |
| IL1R1 | 3554 | −0.941 | −1.943 | −2.160 | −2.327 | −2.433 | −1.490 | −1.686 |
| LIPH | 200879 | −1.737 | −1.384 | −1.170 | −1.844 | −1.330 | −0.804 | −1.583 |
| NBEA | 26960 | −1.044 | −1.190 | −1.132 | −1.105 | −1.368 | −0.346 | −1.550 |
| PNPLA7 | 375775 | −1.084 | −1.376 | −1.046 | −0.901 | −1.211 | −1.427 | −2.068 |
| PSCA | 8000 | −2.529 | −1.726 | −2.199 | −1.593 | −1.253 | −1.956 | −3.517 |
| SEMASE | 9723 | −2.427 | −1.058 | −1.034 | −1.100 | −0.741 | −1.101 | −1.374 |
| SSPO | 23145 | −1.383 | −1.304 | −1.338 | −0.605 | −1.181 | −1.739 | −2.298 |
| STON1 | 11037 | −1.081 | −1.279 | −2.067 | −1.500 | −2.304 | −0.650 | −2.609 |
| TGFB3 | 7043 | −1.111 | −1.214 | −1.707 | −1.350 | −1.263 | −0.304 | −1.444 |
| TP53INP1 | 94241 | −1.304 | −1.777 | −1.816 | −1.461 | −1.363 | −1.496 | −3.177 |
| TP53INP2 | 58476 | −1.210 | −1.073 | −1.207 | −1.373 | −0.959 | −2.069 | −2.068 |

Figure 1D:
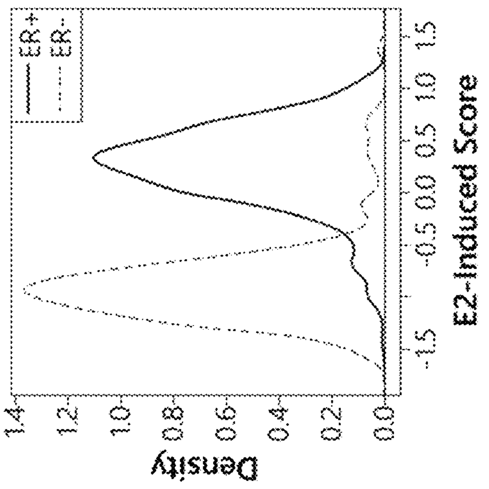
FIG. 1D is a graph showing overlaid reference density curves of the E2-induced score (defined as the average z-scored expression of the 23 E2-induced genes shown in FIG. 1C) for 726 ER IHC+ and 213 ER IHC− breast tumors from the TCGA RNA-seq data.
Figure 1E:
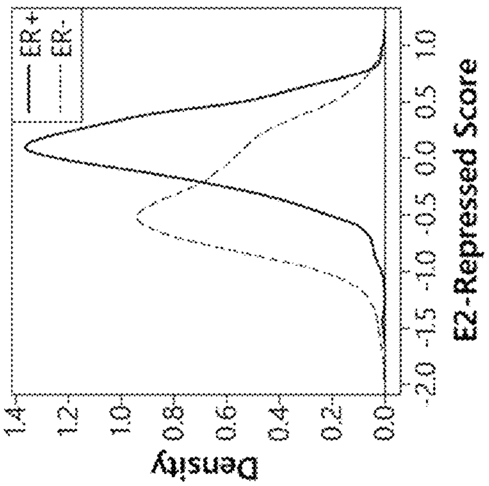
FIG. 1E is a graph showing overlaid reference density curves of the E2-repressed score (defined as average z-scored expression of 18 E2-repressed genes shown in FIG. 1C) in 726 ER IHC+ and 213 ER IHC− breast tumors from the TCGA RNA-seq data.
Figure 1F:
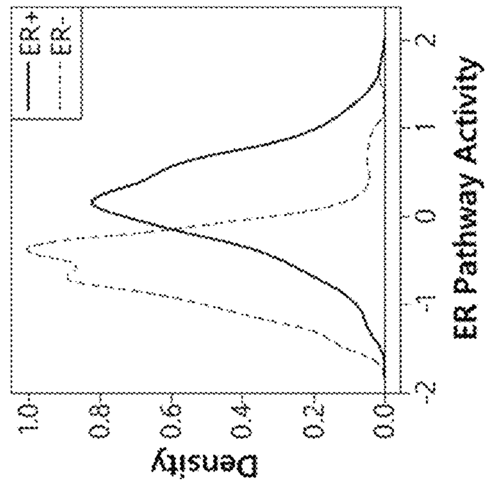
FIG. 1F is a graph showing overlaid reference density curves of the ER pathway activity score (defined as the difference between the E2-induced score and the E2-repressed score) in 726 ER IHC+ and 213 ER IHC− breast tumors from the TCGA RNA-seq data.

To assess the spectrum of ER activity across a large patient population, density curves of three scores were derived using TCGA RNA-seq data from 939 treatment-naïve, primary breast tumors. The E2-induced score was defined as the average z-scored expression of 23 E2-induced genes (FIG. 1D); the E2-repressed score was defined as the average z-scored expression of 18 E2-repressed genes (FIG. 1E); and the ER pathway activity score was defined as the difference between the E2-induced and E2-repressed score (FIG. 1F). Genes identified as being modulated by ER as contained within the signature, irrespective of whether they are induced by, or repressed by E2, were expressed at low levels in ER-/basal tumors; E2 repressed genes are thus not necessarily anticipated to be more highly expressed in ER− tumors versus ER+ tumors.

In Vivo Validation of ER Pathway Activity Signature.

Figure 2A:
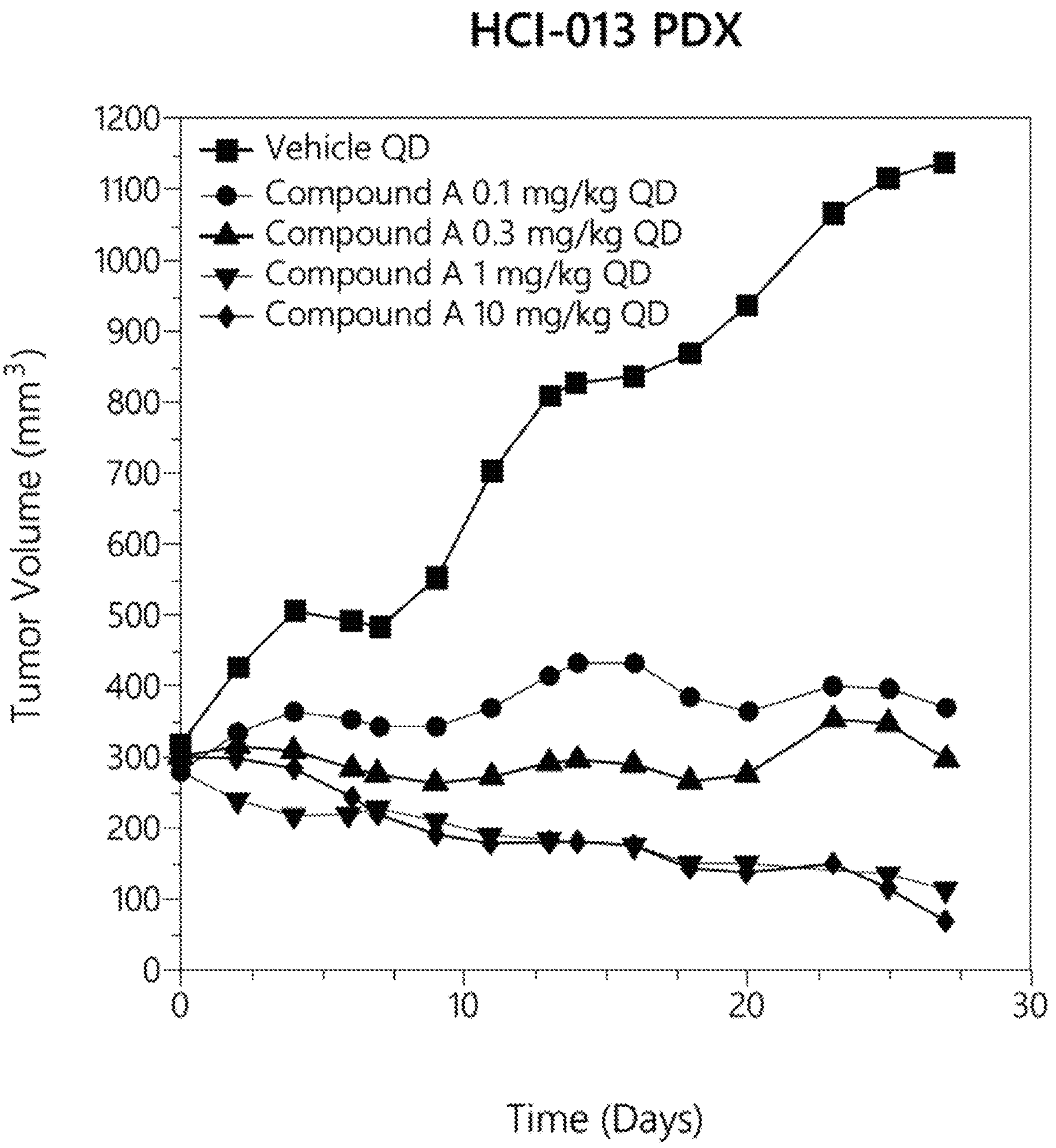
FIG. 2A is a graph showing the in vivo efficacy of treatment with Compound A, a selective estrogen receptor degrader (SERD), in a HCI-013 patient-derived xenograft (PDX) mouse model of hormone receptor (HR)-positive breast cancer, as assessed by tumor volume over time at the indicated Compound A concentrations.
Figure 2B:
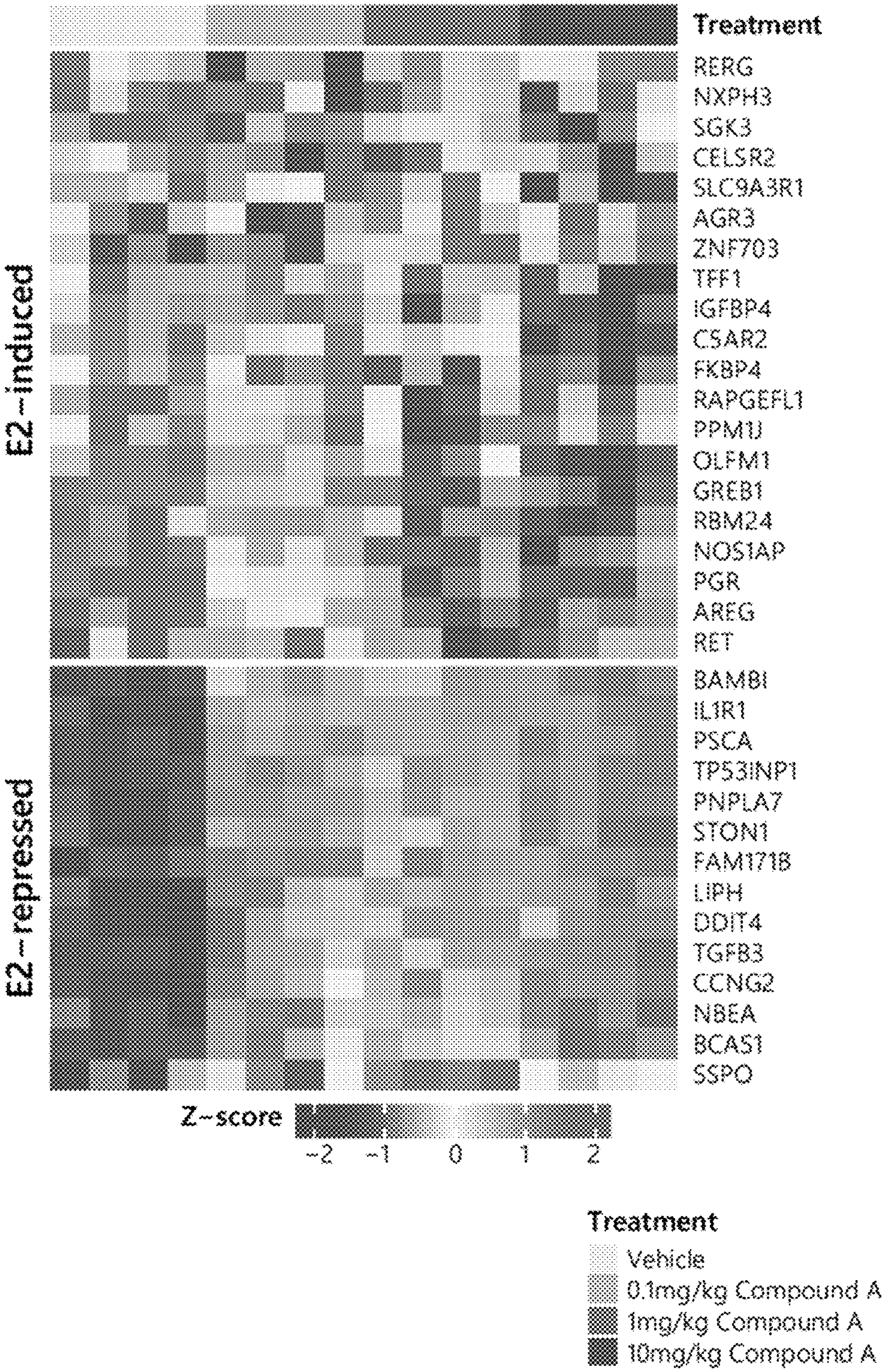
FIG. 2B is a heat map showing the relative change in z-scored expression, for the indicated 20 E2-induced and 14 E2-repressed genes in HCI-013 tumors following treatment with Compound A. Treatment regimens are annotated above.
Figure 2C:
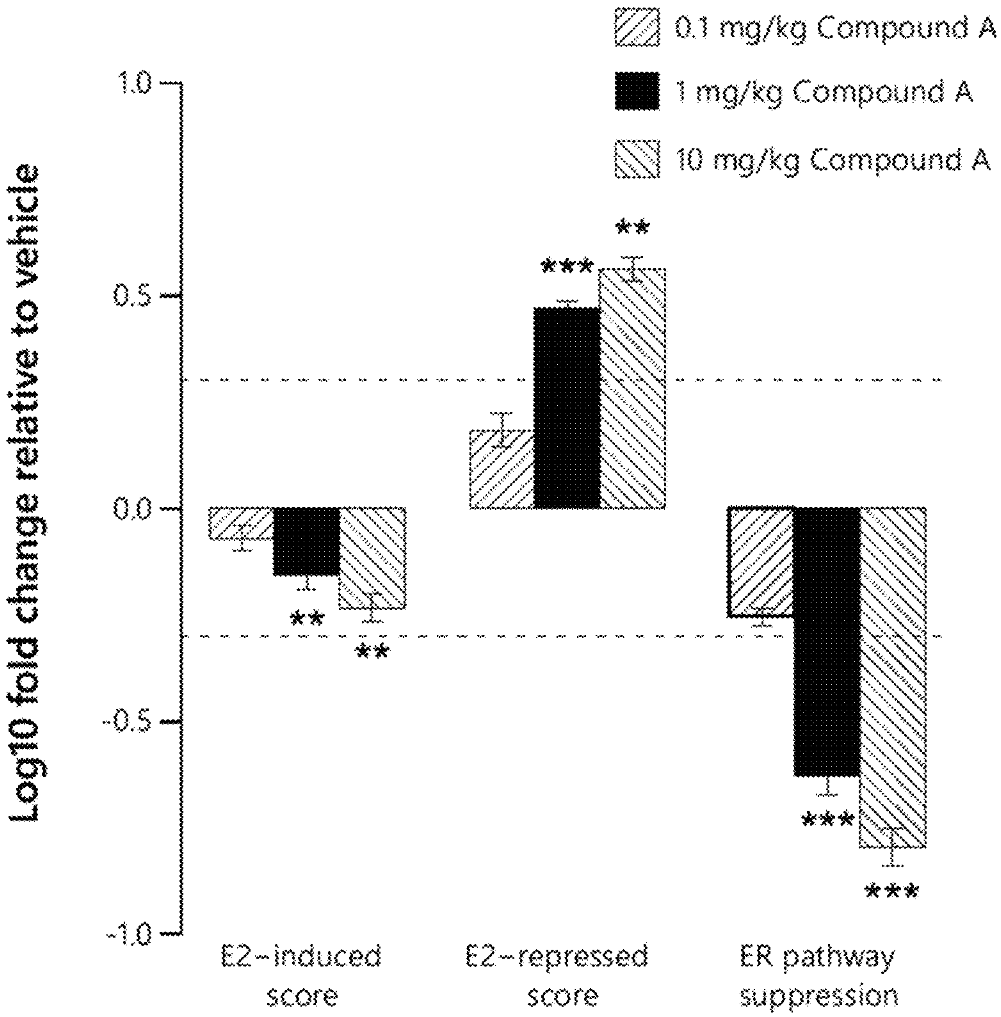
FIG. 2C is a set of bar plots of the E2-induced score, E2-repressed score, and ER pathway activity score expressed as the average $\log_{10}$-fold change, in HCI-013 tumors after Compound A exposure relative to vehicle-treated animals. Bar plots show average relative score and standard error, with n=4. One-sided t-test: *, p<0.05; , p<0.01; *, p<0.001; comparison 1 mg/kg vs. 0.1 mg/kg in black; 10 mg/kg vs. 1 mg/kg in red.
Figure 2D:
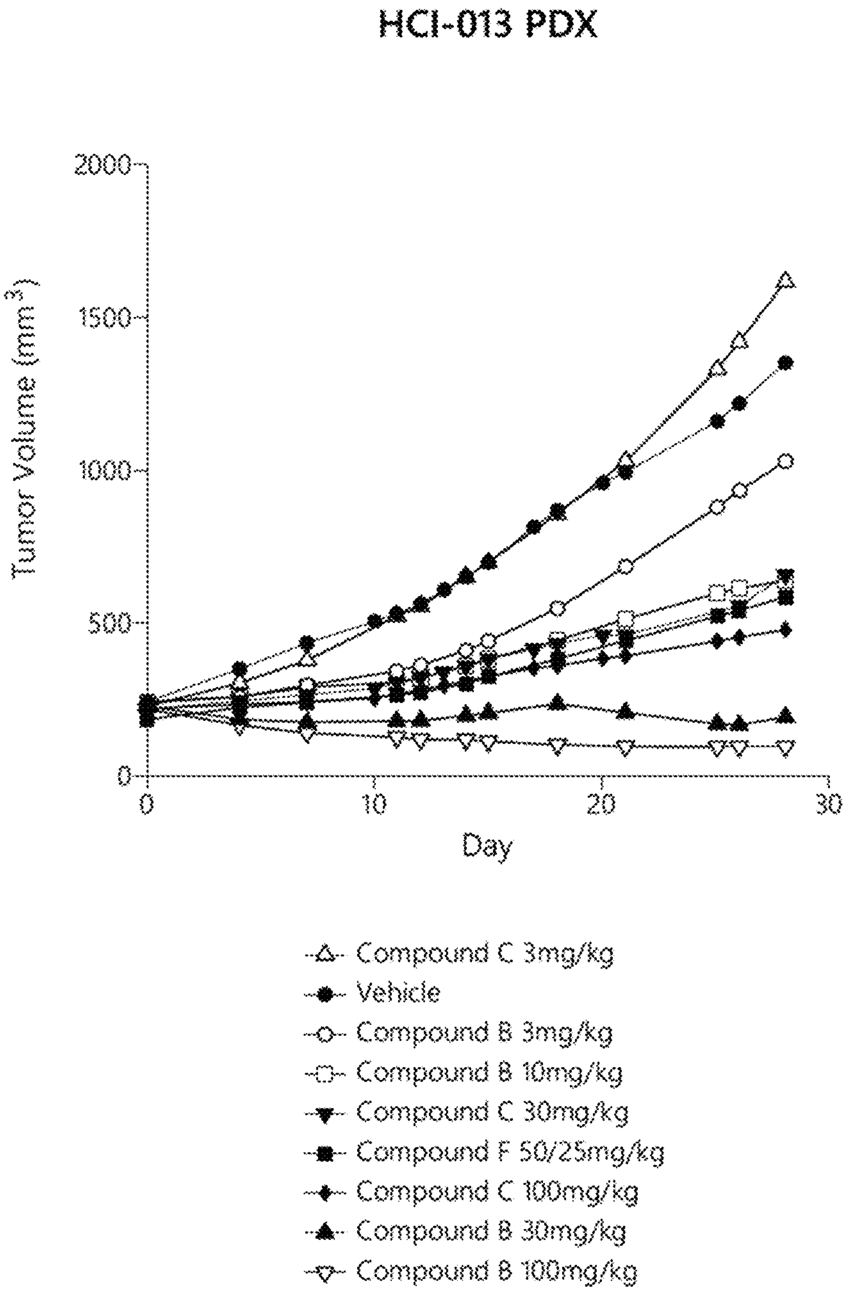
FIG. 2D is a graph showing the in vivo efficacy of treatment with vehicle, or Compound B (a SERD), Compound C (a SERD/SERM hybrid), or Compound F (a SERD) in a HCI-013 PDX mouse model of HR-positive breast cancer, as assessed by tumor volume over time at the indicated concentrations.
Figure 2E:
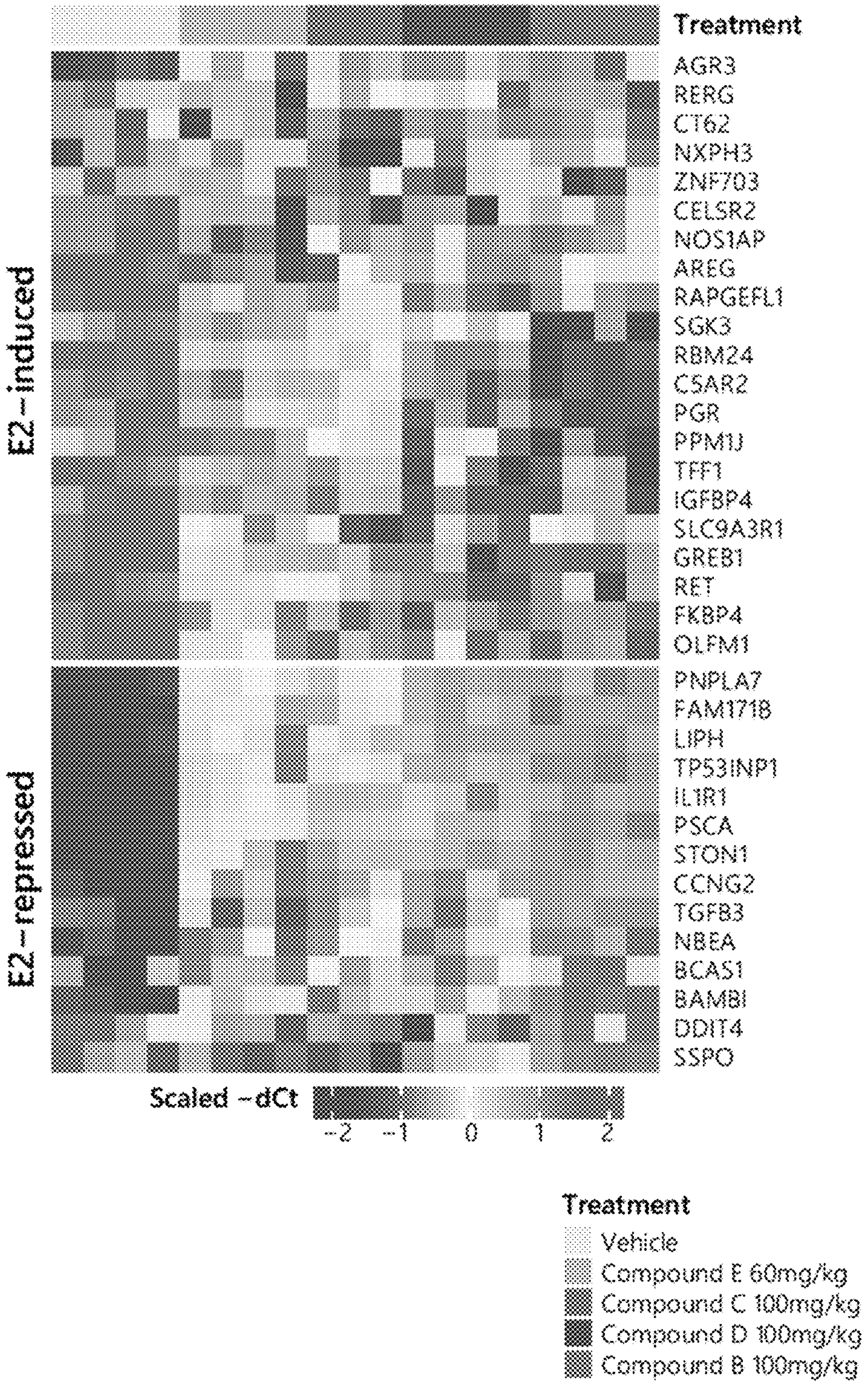
FIG. 2E is a heat map showing the relative change in z-scored expression, for the indicated 20 E2-induced and 14 E2-repressed genes in HCI-013 tumors following treatment with the indicated therapy. Treatment regimens are annotated above.
Figure 2F:
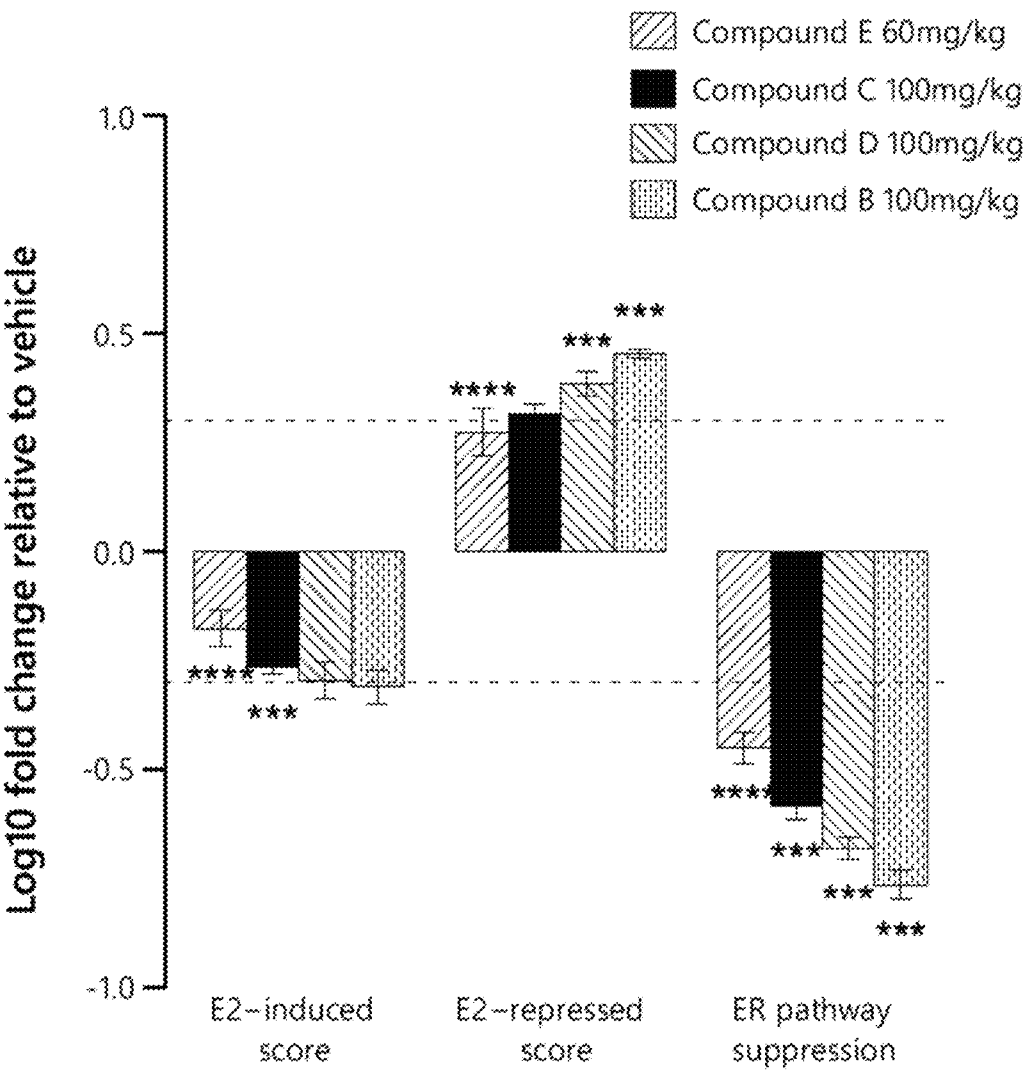
FIG. 2F is a set of bar plots of the E2-induced score, E2-repressed score, and ER pathway activity score expressed as the average $\log_{10}$-fold change, in HCI-013 tumors after exposure to the indicated compounds relative to vehicle-treated animals. Bar plots show average relative score and standard error, with n=4. One-sided t-test: *, p<0.1; , p<0.05; *, p<0.01; ****, p<0.001; comparison Compound E vs. Vehicle, Compound C vs. Compound E, Compound D vs. Compound C, and Compound B vs. Compound D.
Figure 2G:
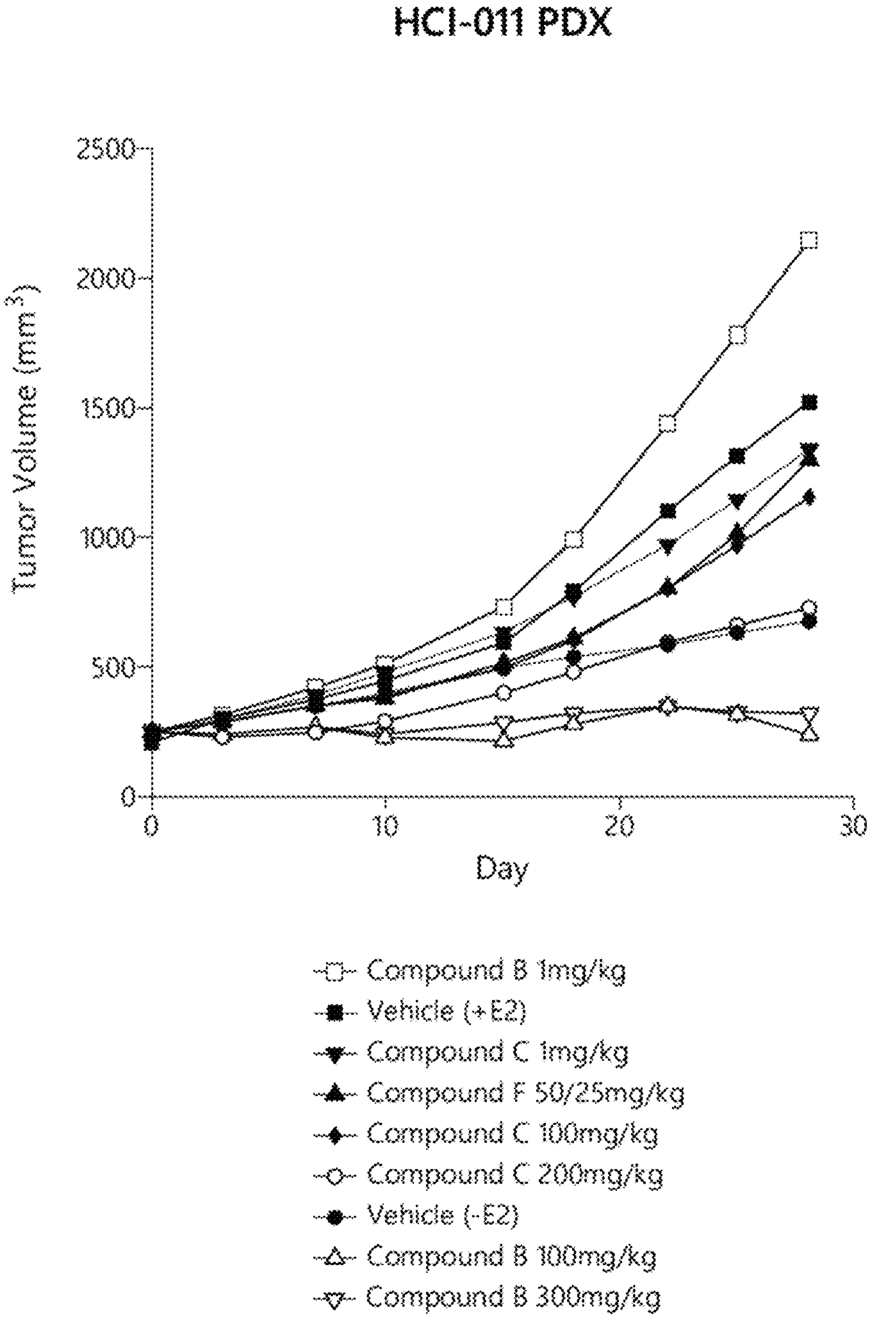
FIG. 2G is a graph showing the in vivo efficacy of treatment with vehicle, Compound B, Compound C, or Compound F in a HCI-011 PDX mouse model of HR-positive breast cancer, as assessed by tumor volume over time at the indicated endocrine therapy concentrations.
Figure 2H:
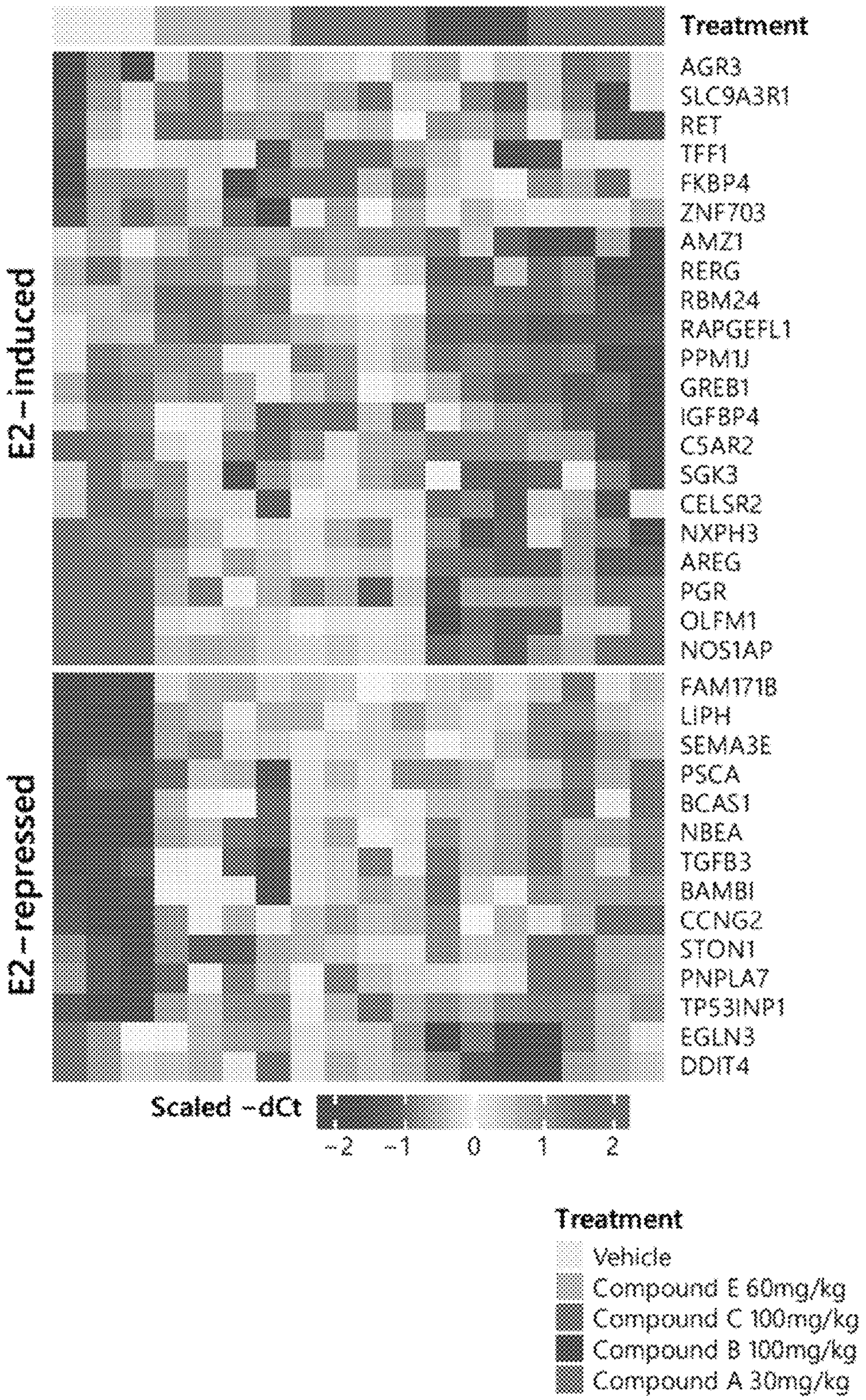
FIG. 2H is a heat map showing the relative change in z-scored expression, for the indicated 20 E2-induced and 14 E2-repressed genes in HCI-011 tumors following treatment with the indicated therapy. Treatment regimens are annotated above.
Figure 2I:
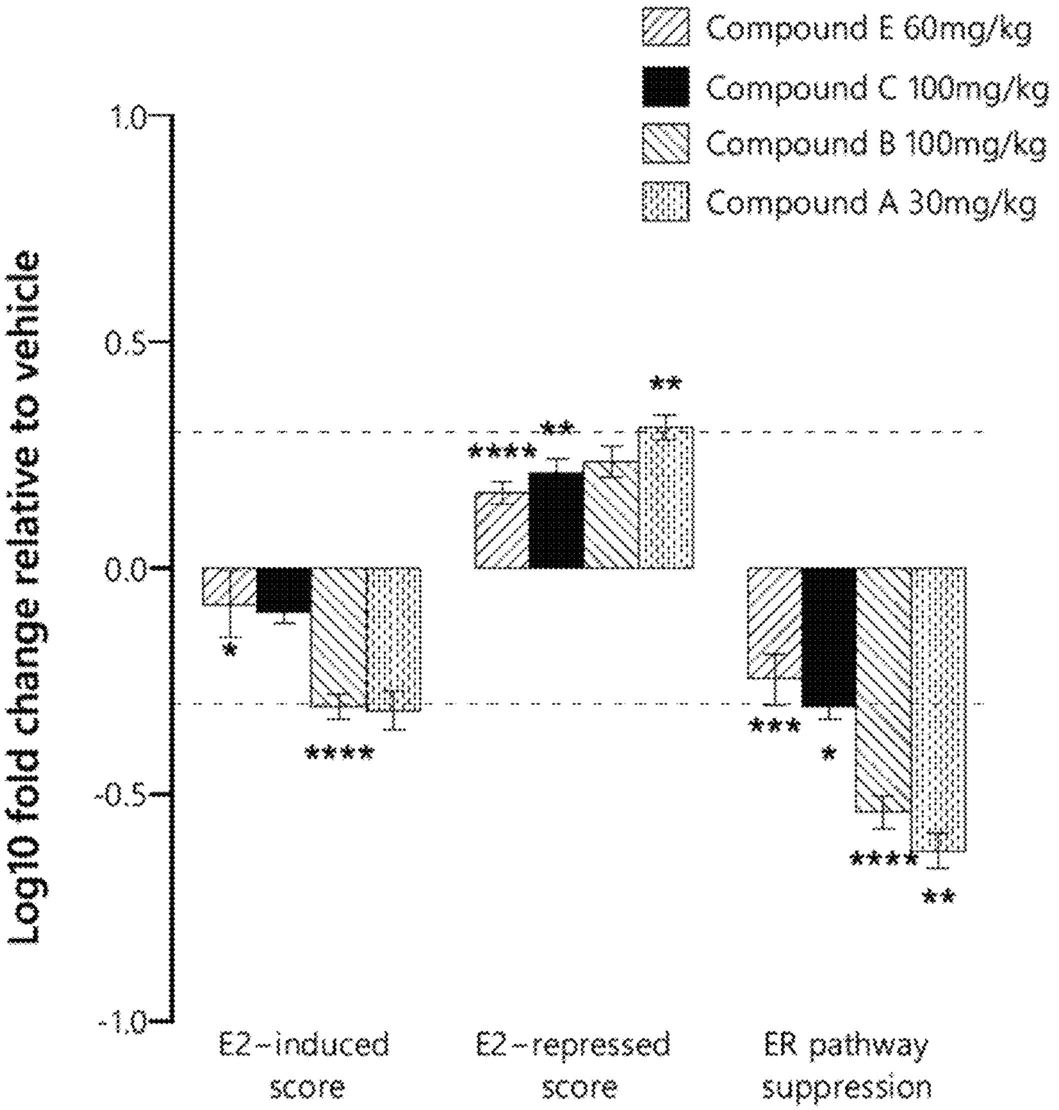
FIG. 2I is a set of bar plots of the E2-induced score, E2-repressed score, and ER pathway activity score expressed as the average $\log_{10}$-fold change, in HCI-011 tumors after exposure to the indicated compounds relative to vehicle-treated animals. Bar plots show average relative score and standard error, with n=4. One-sided t-test: *, p<0.1; , p<0.05; *, p<0.01; ****, p<0.001; comparison Compound E vs. Vehicle, Compound C vs. Compound E, Compound B vs. Compound C, and Compound A vs. Compound B.

The HCI-013 PDX breast model was treated with vehicle or with different doses of Compound A, a selective estrogen receptor degrader (SERD), (0.1 mg/kg, 1 mg/kg, or 10 mg/kg), with four animals per treatment group (FIG. 2A). Samples were collected 8 hrs after the last dose, and expression of the 23 E2-induced genes, 18 E2-repressed genes, and housekeeping genes were measured using FLUIDIGM®, and the data processed using SPOTFIRE® software. Expression data were normalized to housekeeping genes GUSB, PPIA, and UBC. Three genes that did not meet quality control standards were excluded (GRM4, FMN1, and TP52INP2). Two E2-induced genes, AMZ1 and CT62, The HCI-013 and HCI-011 PDX breast models were treated with various endocrine agents including Compound A, Compound B, Compound D, or Compound F at various doses, with four animals per treatment group. Tumor samples were collected 8 hrs after the last dose, and the expression of the 23 E2-induced genes, 18 E2-repressed genes, housekeeping genes were measured using a FLUIDIGM® assay, and genes with low expression or that did not meet quality control standards were removed from the analysis, as described above. For data shown in FIGS. 2D-2F, expression data were normalized to housekeeping genes GUSB, SDHA, and UBC. One gene that did not meet quality control standards was excluded (FMN1). One E2-induced gene, AMZ1, and four E2-repressed genes, EGLN3, GRM4, SEMA3A, and TP53INP2, that were lowly expressed across the tumors in this study (average housekeeping-normalized expression in bottom 10th percentile of expressed genes) (FIG. 2E) were also excluded. For FIGS. 2G-2I, expression data were normalized to housekeeping genes GUSB, PPIA, and UBC. Two genes that did not meet quality control standards were excluded (CXCL12 and TP52INP2). Two E2-induced genes, FMN1 and CT62, and three E2-repressed genes, GRM4, IL1R1 and SSPO, that were lowly expressed across the tumors in this study (average housekeeping-normalized expression in bottom 10th percentile of expressed genes) (FIG. 2B) were also excluded. Gene expression analysis of HCI-013 and HCI-011 tumors revealed that modulation of ER target gene expression: 21 E2-induced genes were robustly decreased by treatment with the compounds, and the 14 E2-repressed genes were significantly up-regulated by the compounds (FIGS. 2E and 2H). The degree of ER pathway suppression, as capture by the signature, associates with anti-tumor activity (FIGS. 2F and 2I).

Example 2. ER Pathway Activity Signature Captures Suppression of ER Pathway Activity in Response to SERD Treatment in Patients In clinical practice, transcriptional profiling is routinely generated from formalin-fixed paraffin-embedded (FFPE) tissue, using the RNA ACCESS® protocol.

In order to use the ER pathway activity signature as PD biomarker for SERD activity or as predictive biomarker of potential ER pathway dependency in patients, a reference distribution of ER activity was derived from RNA ACCESS® data. RNA ACCESS® data were generated from FFPE tissue of a procured collection of 139 HR+/HER2− breast tumors. Raw counts for the 139 breast tumors were converted to counts per million (cpm), filtered for lowly expressed genes (i.e. cpm <0.25 in over 90% of samples), normalized using TMM normalization in the edgeR package, and voom-transformed using the limma package in R. ER pathway signature genes with average voom-normalized expression across all 139 tumors in the bottom 5th percentile of all genes were removed from downstream analyses.

Figure 3A:
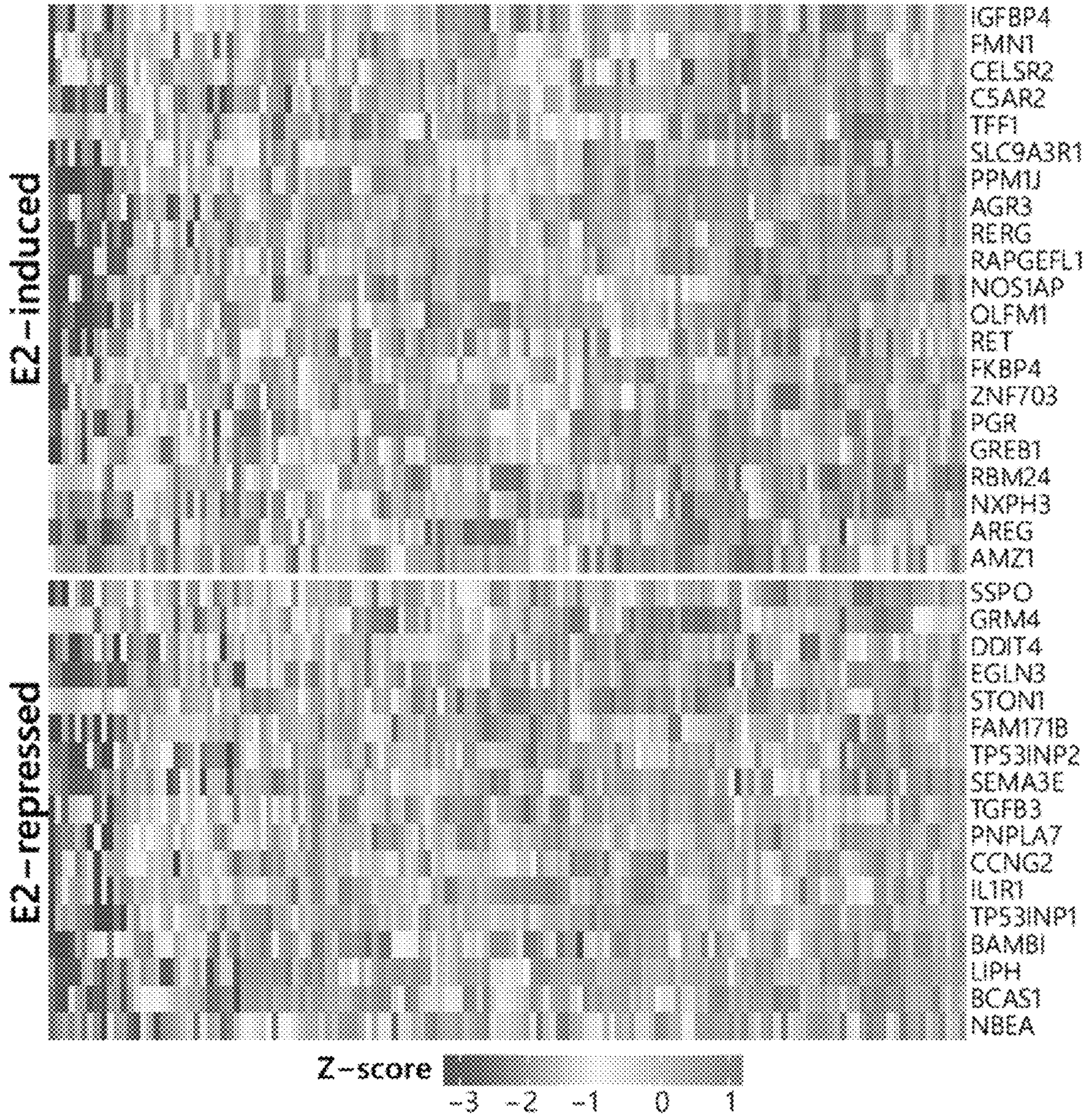
FIG. 3A is a heat map showing the relative change in z-scored expression of the 21 indicated E2-induced and 17 indicated E2-repressed genes from a collection of 139 hormone receptor-positive/human epidermal growth factor receptor 2-negative (HR+/HER2−) breast tumors.
Figure 3B:
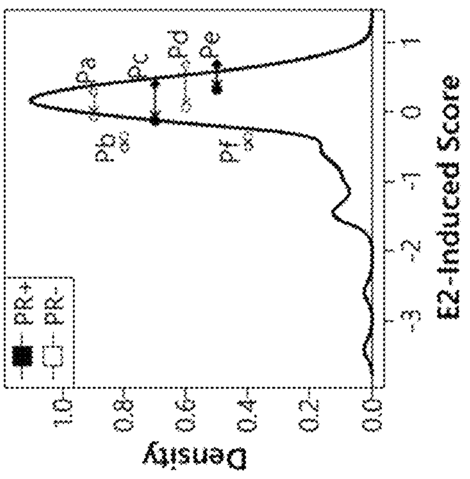
FIGS. 3B-3D are a series of reference density curves for the E2-induced score (FIG. 3B), E2-repressed score (FIG. 3C), and ER pathway activity score (FIG. 3D) in the collection of 139 HR+/HER2− breast tumors. Pre- and post-treatment with Compound B expression data for six patients are overlaid: pre-treatment scores are indicated as a diamond; post-treatment scores as a circle. Arrows show the magnitude and direction of change in ER pathway activity score per patient.
Figure 3C:
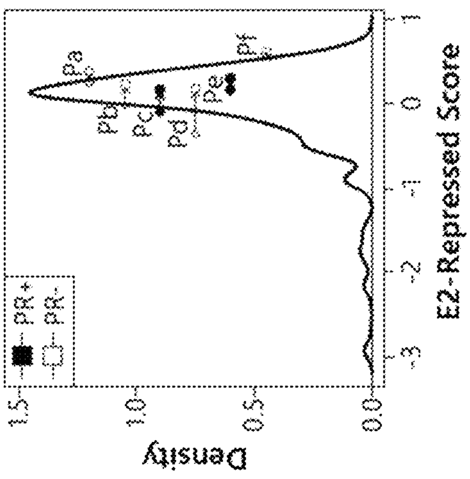
Figure 3D:
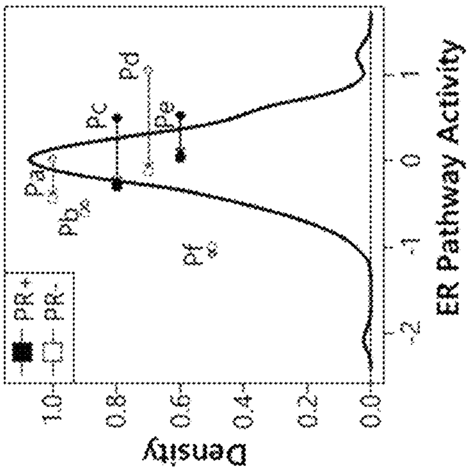

Two E2-induced genes, SGK3 and CT62, were not or low expressed, and E2-repressed gene PSCA was low expressed in this reference collection. The expression of the signature genes, excluding these 3 genes, was next evaluated (FIG. 3A). RNA ACCESS® reference densities were defined for the E2-induced score, E2-repressed score, and ER pathway activity on the basis of 21 E2-induced and 17 E2-repressed genes, for the collection of 139 HR+/HER2− breast tumors (FIGS. 3B-3D, 3H-3J).

Six patients with HR+/HER2− breast cancer were treated with a SERD (Compound B), and seven patients with HR+/HER2− breast cancer were treated with another SERD (Compound A). RNA ACCESS® data were generated (as described above) from FFPE tissue collected at time of screening (pre-treatment), and during the second or third cycle of SERD treatment (post-treatment). Genes were re-centered and re-scaled, using the mean and standard deviation from the reference collection.

Figure 3E:
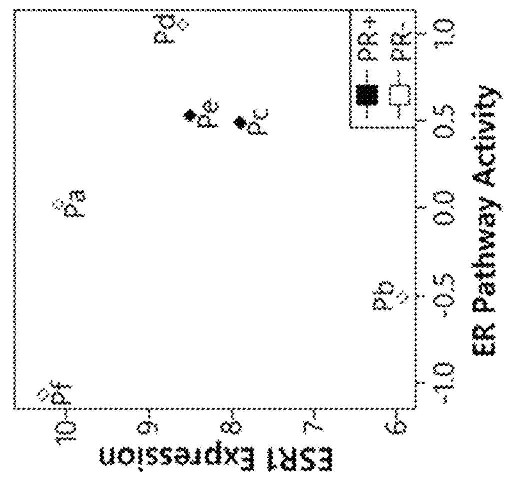
FIG. 3E is a scatter plot of pre-treatment ER pathway activity score versus pre-treatment ESR1 expression levels for six patients treated with Compound B.
Figure 3F:
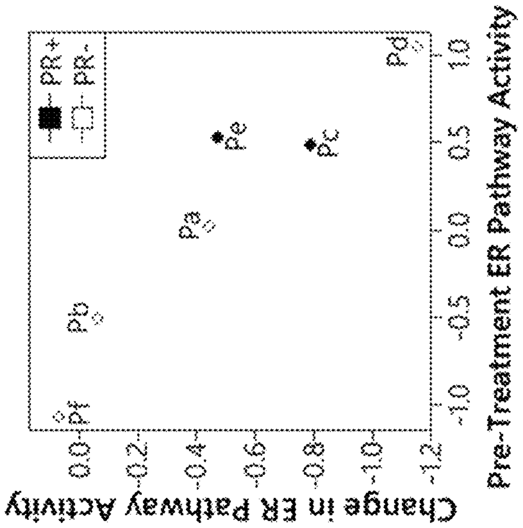
FIG. 3F is a scatter plot of the treatment-induced difference in ER pathway activity pre-treatment to post-treatment versus pre-treatment ER pathway activity levels for six patients treated with Compound B.
Figure 3G:
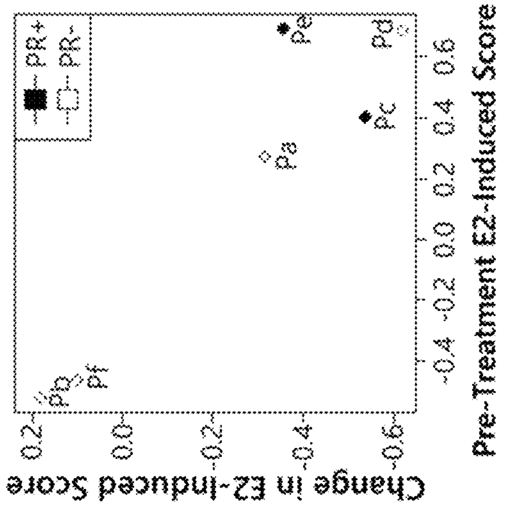
FIG. 3G is a scatter plot of the treatment-induced difference in E2-induced score pre-treatment to post-treatment versus pre-treatment E2-induced scores for six patients treated with Compound B.
Figure 3H:
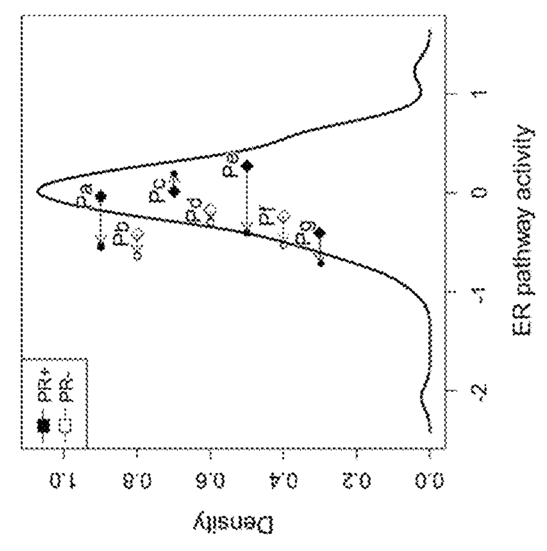
FIGS. 3H-3J are a series of reference density curves for the E2-induced score (FIG. 3H), E2-repressed score (FIG. 3I), and ER pathway activity score (FIG. 3J) in the collection of 139 HR+/HER2− breast tumors. Pre- and post-treatment with Compound A expression data for seven patients are overlaid: pre-treatment scores are indicated as a diamond; post-treatment scores as a circle. Arrows show the magnitude and direction of change in ER pathway activity score per patient.
Figure 3I:
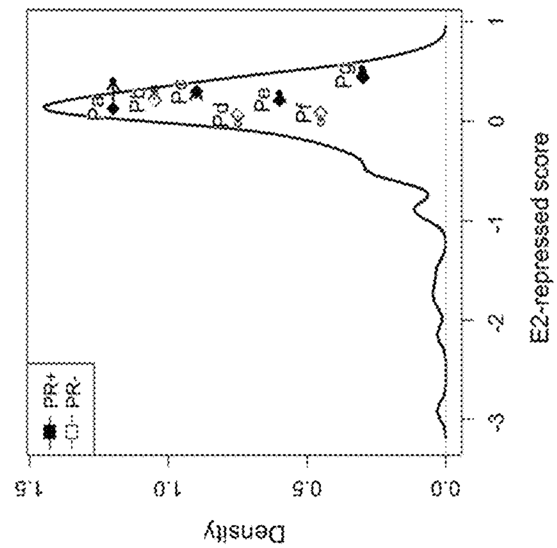
Figure 3J:
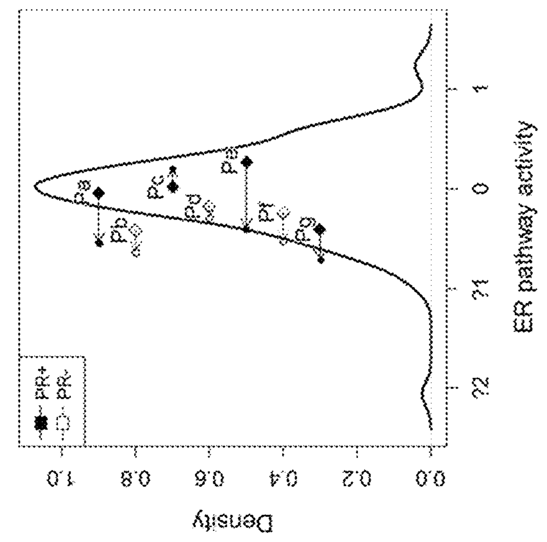
Figure 3M:
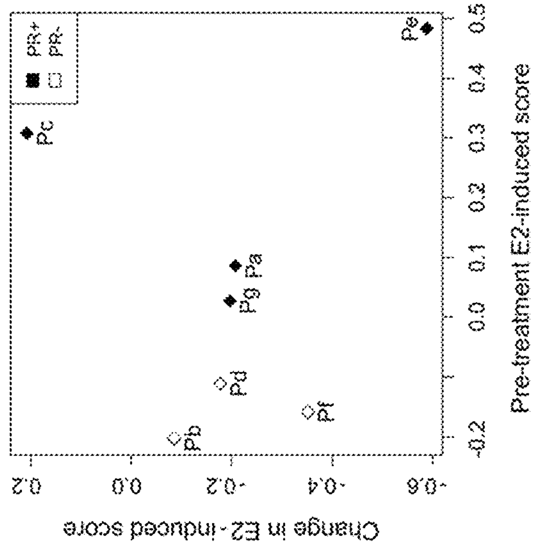
FIG. 3M is a scatter plot of the treatment-induced difference in E2-induced score pre-treatment to post-treatment versus pre-treatment E2-induced scores for seven patients treated with Compound A.
Figure 3L:
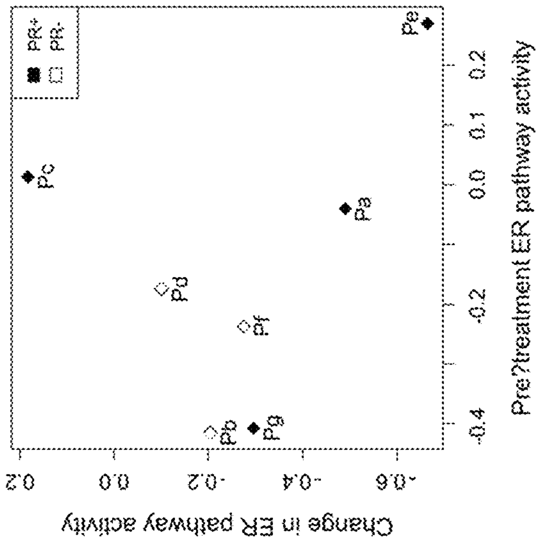
FIG. 3L is a scatter plot of the treatment-induced difference in ER pathway activity pre-treatment to post-treatment versus pre-treatment ER pathway activity levels for seven patients treated with Compound A.
Figure 3K:
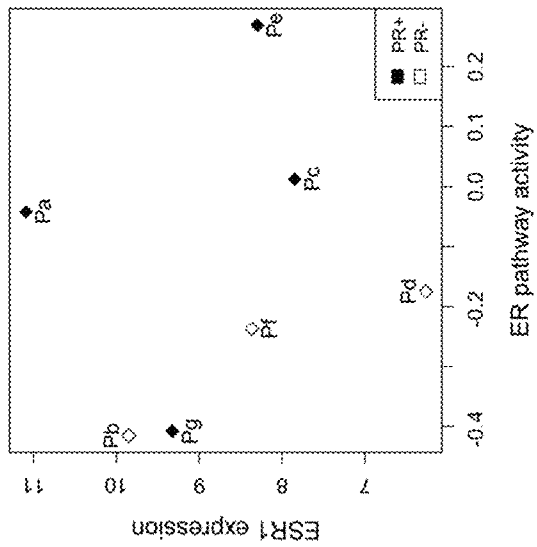
FIG. 3K is a scatter plot of pre-treatment ER pathway activity score versus pre-treatment ESR1 expression levels for seven patients treated with Compound A.

Signature scores for the pre- and post-treated tumors were calculated and displayed on top of the reference densities, for the six patients treated with Compound B (FIGS. 3B-3D) and for the seven patients treated with Compound A (FIGS. 3H-3J). In the first cohort of six patients treated with Compound B, ER pathway activity was suppressed by SERD treatment in 4 out of 6 patients. There was no change in ER pathway activity for the two patients with low pre-treatment ER pathway activity (patients Pb and Pf); ER pathway suppression in response to SERD-treatment is thus captured only in tumors which exhibit evidence of ER pathway activity prior to treatment (FIG. 3F). Two patients were considered PR+(expression >4) and four patients PR−. Pre-treatment ESR1 expression levels are also an insufficient biomarker for ER pathway activity (FIG. 3E). These results were confirmed in the second cohort of seven patients treated with Compound A (FIGS. 3H-M), among which four patients with PR+ and three patients with PR-breast cancer, with an observed suppression of ER pathway activity by SERD treatment in 6 out of 7 patients. Taken together, these results show that the signature can be used as a measure of pre-treatment ER pathway activity and as a PD biomarker in both PR+ and PR− breast tumors.

Example 3: Identification of Core Signature Genes

Figure 4A:
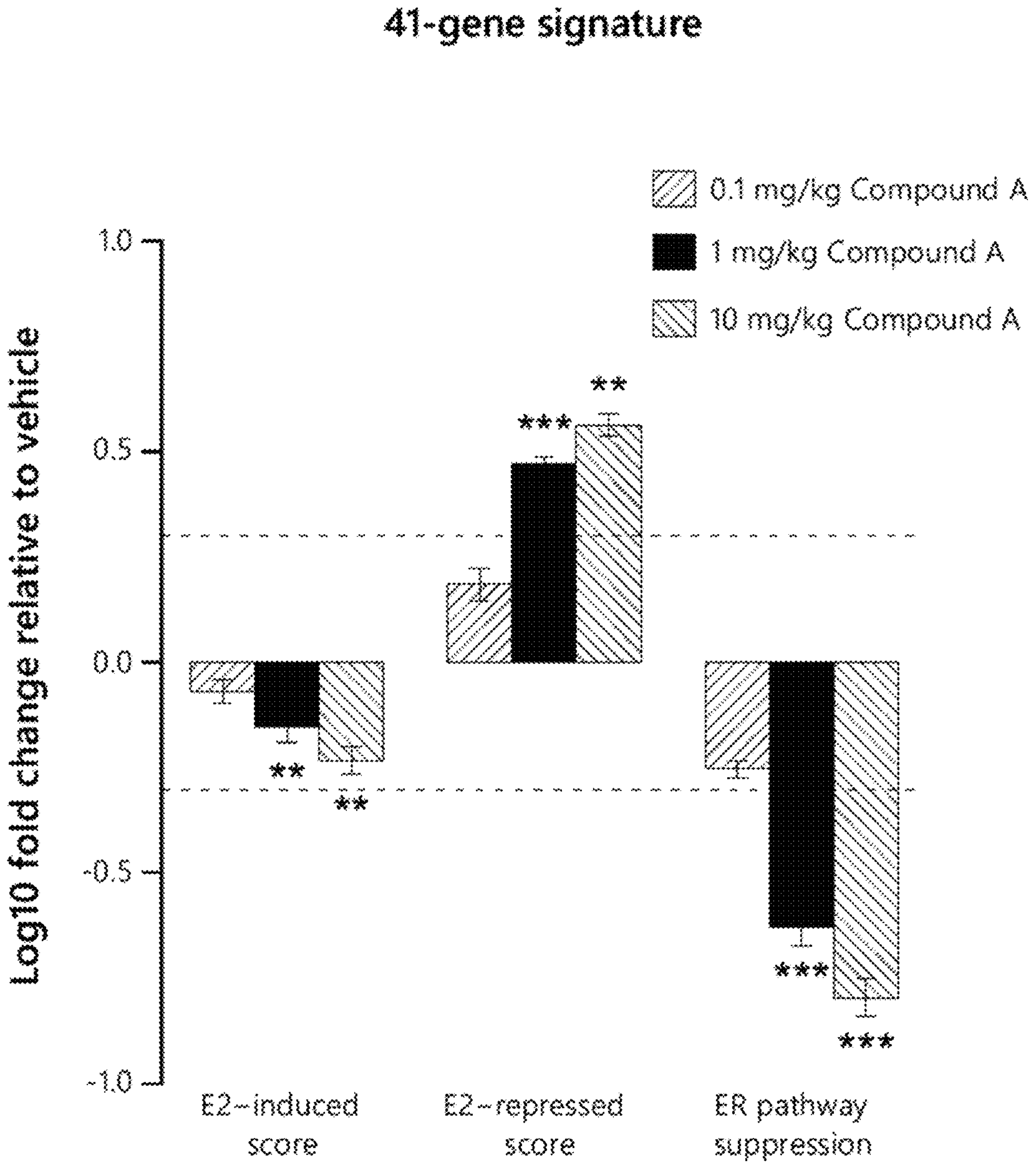
FIGS. 4A-4C are a series of bar plots of the E2-induced score, E2-repressed score, and ER pathway suppression expressed as the average $\log_{10}$-fold change, based on the complete 41-gene signature (FIG. 4A), 19-gene signature (FIG. 4B), or 14-gene signature (FIG. 4C), in HCI-013 PDX breast tumors after exposure to Compound A relative to vehicle-treated animals. Bar plots show average relative score and standard error, with n=4. One-sided t-test: *, p<0.05; , p<0.01; *, p<0.001; comparison 1 mg/kg vs. 0.1 mg/kg in black; 10 mg/kg vs. 1 mg/kg in red.
Figure 4B:
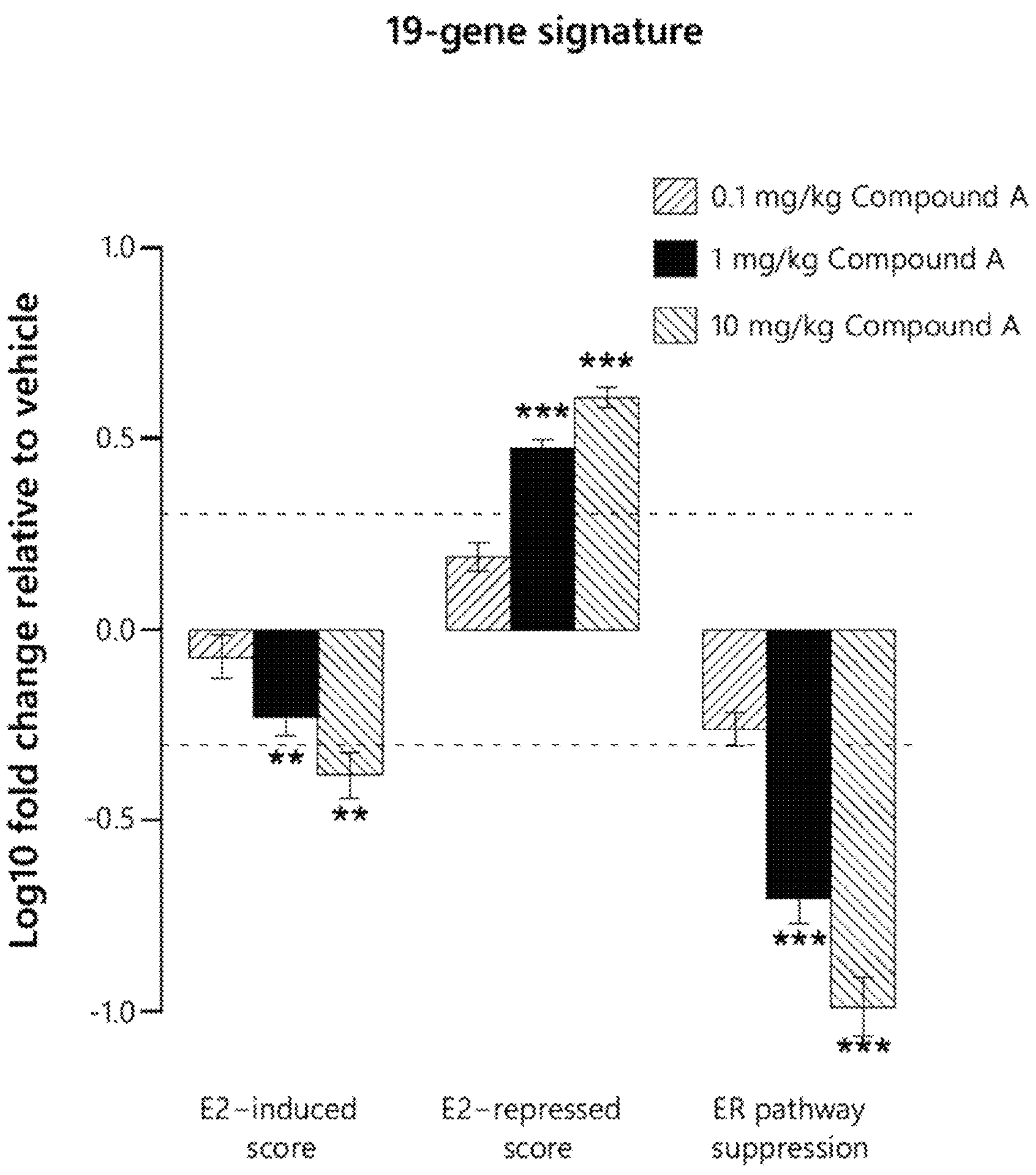
Figure 4C:
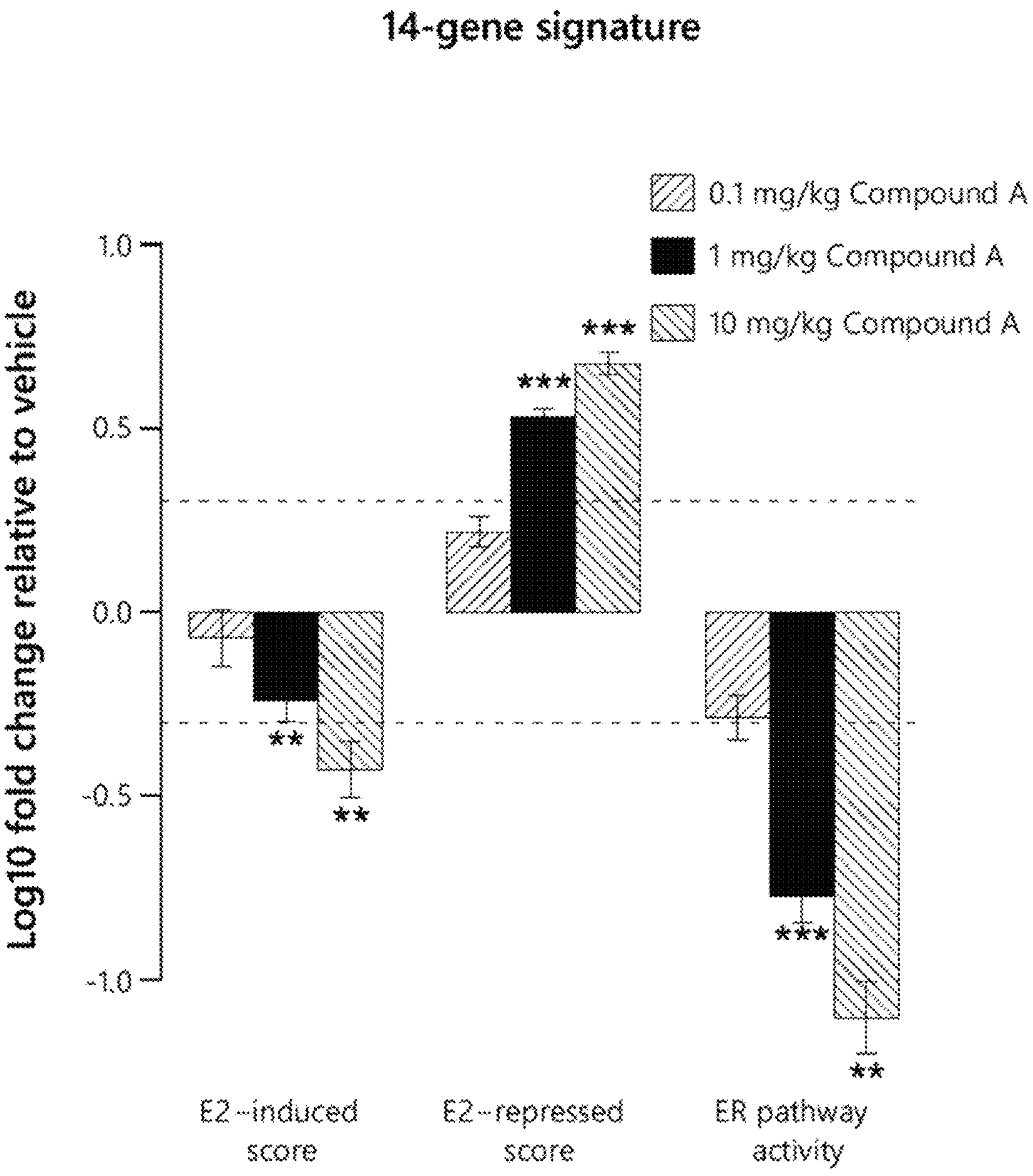
Figure 4D:
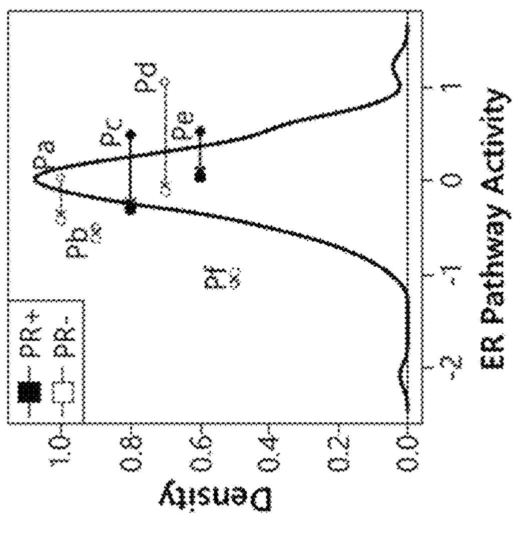
FIGS. 4D-4F are a series of reference density curves for the ER pathway activity score based on the 41-gene signature (FIG. 4D), 19-gene signature (FIG. 4E), or 14-gene signature (FIG. 4F) in the collection of 139 HR+/HER2− breast tumors. Pre- and post-treatment expression data for six patients are overlaid: pre-treatment scores are indicated as a diamond; post-treatment scores as a circle. Arrows show the magnitude and direction of change in ER pathway activity score per patient.
Figure 4E:
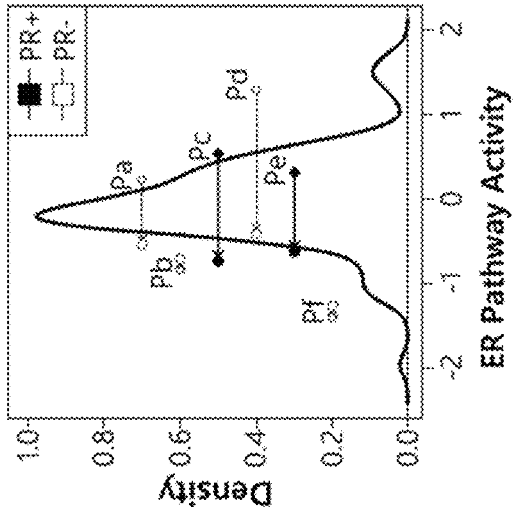
Figure 4F:
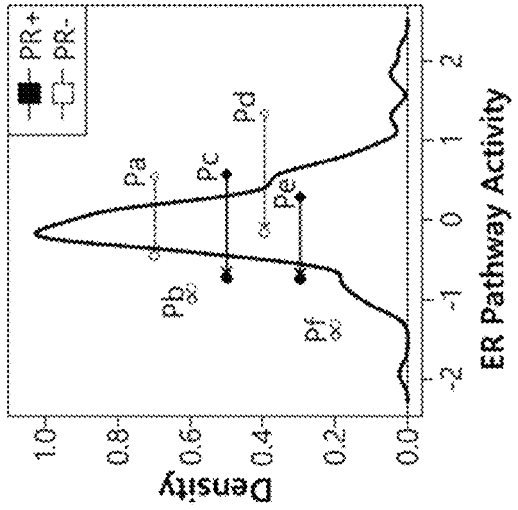
Figure 4I:
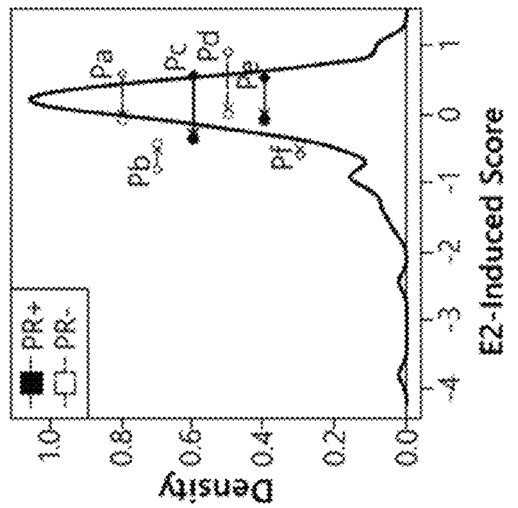
FIGS. 4G-4I are a series of reference density curves for the E2-induced score based on the 41-gene signature (FIG. 4G), 19-gene signature (FIG. 4H), or 14-gene signature (FIG. 4I) in the collection of 139 HR+/HER2− breast tumors. Pre- and post-treatment expression data for six patients are overlaid: pre-treatment scores are indicated as a diamond; post-treatment scores as a circle. Arrows show the magnitude and direction of change in E2-induced score per patient.
Figure 4H:
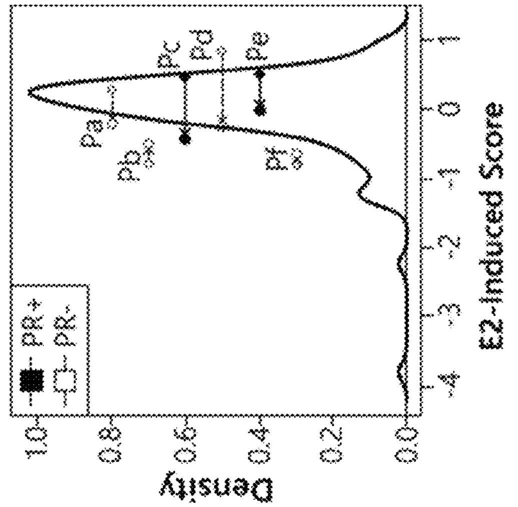
Figure 4G:
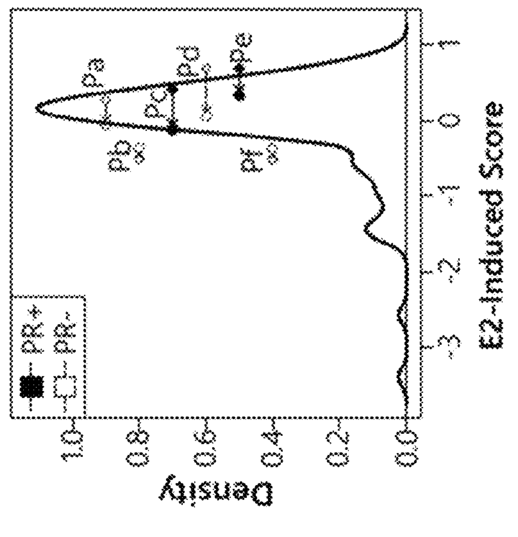

To identify a set of core genes for inclusion in the ER pathway activity score, pre- and post-treatment expression data from the 4 out of 6 patients treated with Compound B for whom Compound B was effective in suppressing the ER pathway (excluding patients Pb and N) were analyzed. A subset of genes among the 41 in vitro derived genes that were impacted most and most consistently by endocrine therapy treatment in those four patients was selected to create a 19-gene signature with 11 E2-induced and 8 E2-repressed genes (one-sided t-test, $p<0.1$) and a 14-gene signature with 8 E2-induced and 6 E2-repressed genes (one-sided t-test, $p<0.05$). Both reduced gene sets performed equally well in the HCI-013 PDX model treated with different doses of compound A compared to the 41-gene signature (FIGS. 4A-4C). Inclusion of both E2-induced and E2-repressed genes provided the largest dynamic range in ER pathway suppression in this in vivo model by dose. The reduced gene sets also resulted in a similar ER pathway suppression by treatment with Compound B in patients Pa through Pf as obtained with the 41-gene signature (FIGS. 4D-4F). Similar results were also observed when assessing changes in ER pathway activity based on only E2-induced genes (FIGS. 4G-4I). Signature genes are provided herein in Tables 1-6.

Figure 5:
FIG. 5 is a scatterplot of ER pathway activity score in 60 tissue samples, with expression data prepared with RIBO-ZERO TRUSEQ® OR RNA ACCESS®. Formalin-fixed and paraffin-embedded (FFPE) samples are shown as triangles; fresh frozen samples are shown as circles. Breast tumors are shown in pink; other tissues are shown in black.

Example 4. ER Pathway Activity Signature Levels are Agnostic to the Sequencing Platform Employed, and to the Tissue Preparation Method The ER pathway activity scores in 30 FFPE samples, including five breast tumor samples, and in 30 FF (fresh frozen) samples, including five breast tumor samples, were determined. All breast samples were primary ER+ breast tissues, stage II or III, ductal carcinoma. RNA-sequencing data were generated for all samples using two different library kits: RNA ACCESS®, and RIBO-ZERO® TRUSEQ®. In the 60 tissue samples, ER pathway activity levels obtained with either sequencing method were highly similar (FIG. 5; Pearson correlation 0.97). Furthermore, ER pathway activity scores in breast FFPE (pink triangles) vs. breast FF samples (pink circles) were in the same range (FIG. 5). These results suggest that the signature can be used in a platform-agnostic way (RNA ACCESS®, TRUSEQ®) and in a tissue preparation-agnostic way (FFPE, FF).

Example 5. ER Inhibition and ER Transcriptional Activity

The relationship between ER pathway activity and the anti-proliferative effect of the ER antagonist fulvestrant was explored in a panel of 14 ER+/HER2− breast cancer cell lines. RNA-sequencing data was leveraged to determine the E2-induced score, determined by expression of a set of E2-induced genes (as described above), of a series of ER+/HER2− breast cancer cell lines grown under standard culture conditions, in the presence of estrogen. The effect of ER inhibition by 300 nM fulvestrant on cellular proliferation was determined in an 8-day in vitro viability assay using the GR (Growth Rate) method described by Hafner et al. (Nat Methods 13:6, 2016). The E2-induced score was then plotted against the effect of fulvestrant on cellular growth rate.

Figure 6:
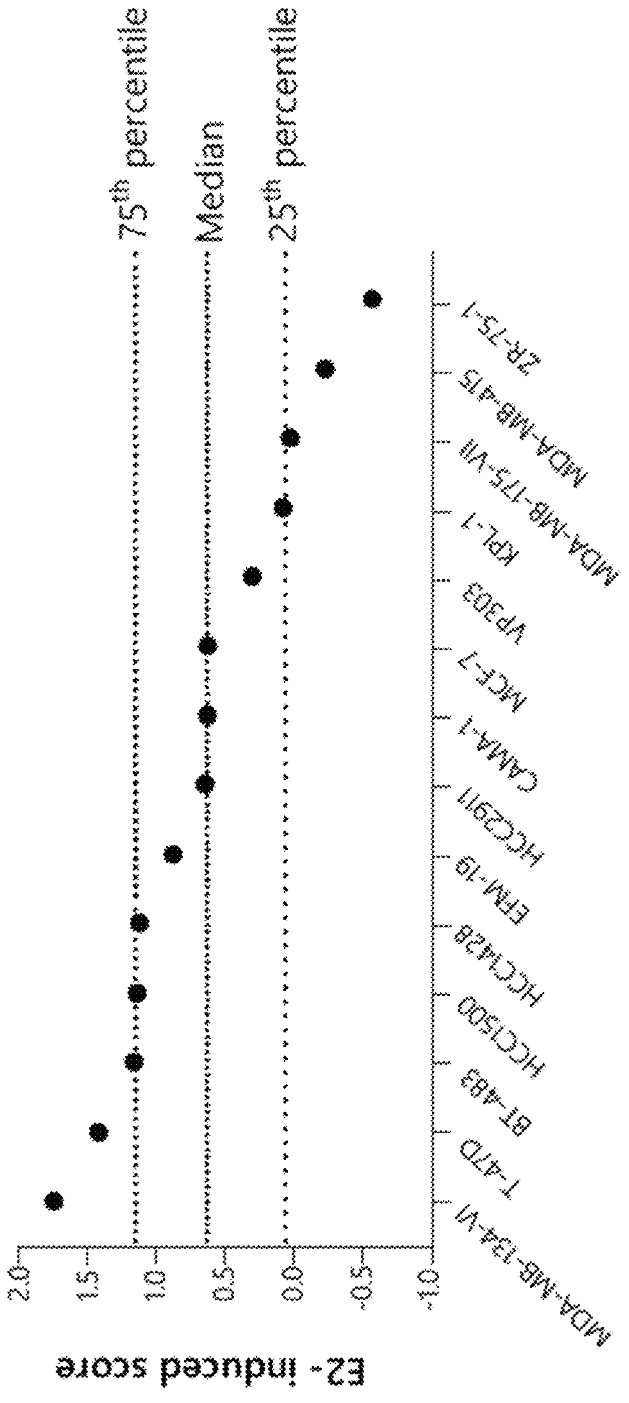
FIG. 6 is a plot of E2-induced scores of ER+/HER2− breast cancer cell lines.
Figure 7:
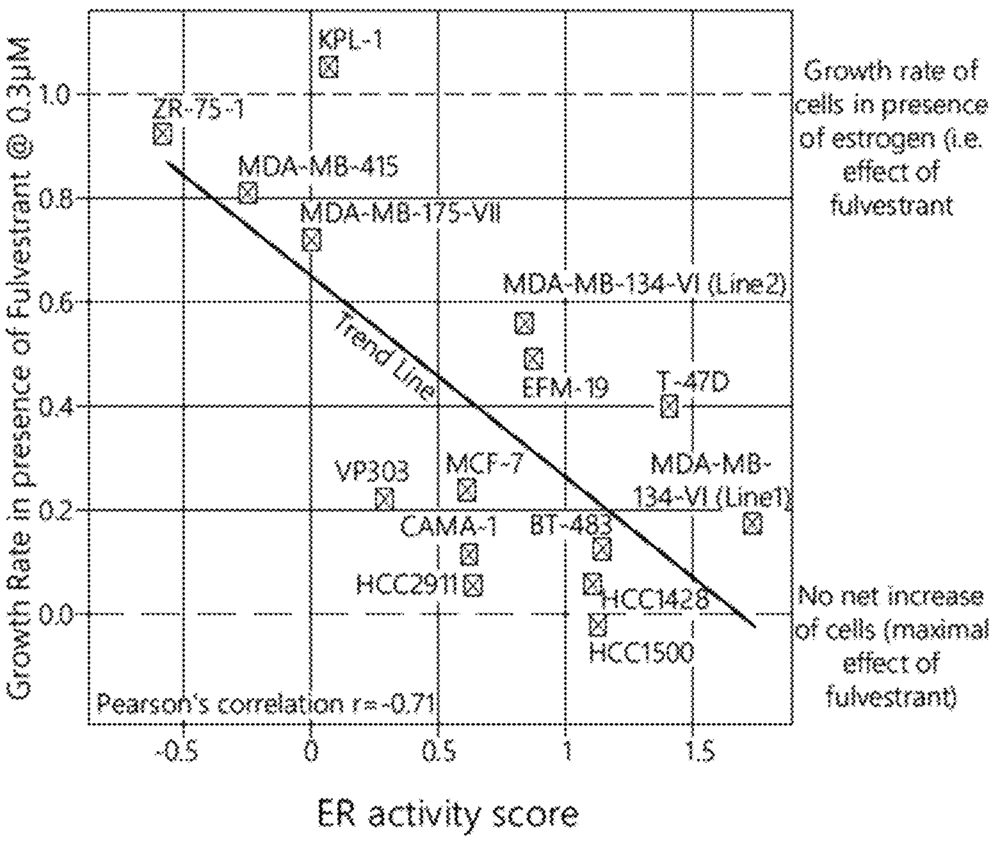
FIG. 7 is a plot of E2-induced score versus impact of fulvestrant on cellular growth rate.

ER+/HER2− breast cancer cell lines displayed E2-induced scores ranging from 1.73 to −0.57, with a median of 0.63 (FIG. 6). Fulvestrant had little impact on the growth rate of cell lines with E2-induced scores in the lowest 25th percentile for the panel of 14 cell lines (ZR-75-1, MDA-MB-415, MDA-MB-175-VII, KPL-1), while having a considerably greater impact on cell lines exhibiting higher E2-induced scores (FIG. 7). These in vitro data support the hypothesis that ER inhibition is likely to be most impactful in contexts in which gene expression profiles reflect ER transcriptional activity.

VIII. Other Embodiments

Although the foregoing methods and compositions have been described in some detail by way of illustration and example for purposes of clarity and understanding, the descriptions and examples should not be construed as limiting the scope of the methods and compositions provided herein. The disclosures of all patent and scientific literature cited herein are expressly incorporated in their entirety by reference.

Embodiments

Embodiment 1

A method of identifying an individual having a breast cancer who may benefit from a treatment comprising an endocrine therapy, the method comprising determining an estrogen receptor (ER) pathway activity score from a sample from the individual, wherein an ER pathway activity score from the sample that is at or above a reference ER pathway activity score identifies the individual as one who may benefit from a treatment comprising an endocrine therapy.

Embodiment 2

A method for selecting a therapy for an individual having a breast cancer, the method comprising determining an ER pathway activity score from a sample from the individual, wherein an ER pathway activity score from the sample that is at or above a reference ER pathway activity score identifies the individual as one who may benefit from a treatment comprising an endocrine therapy.

Embodiment 3

The method of embodiment 1 or 2, wherein the ER pathway activity score determined from the sample is at or above the reference ER pathway activity score, and the method further comprises administering to the individual an effective amount of an endocrine therapy.

Embodiment 4

The method of embodiment 1 or 2, wherein an ER pathway activity score from the sample that is below a reference ER pathway activity score identifies the individual as one who is less likely to benefit from a treatment comprising an endocrine therapy.

Embodiment 5

The method of embodiment 4, wherein the ER pathway activity score determined from the sample is below the reference ER pathway activity score, and the method further comprises administering to the individual an effective amount of an anti-cancer therapy other than an endocrine therapy.

Embodiment 6

A method of treating an individual having a breast cancer, the method comprising administering an effective amount of an endocrine therapy to the individual, wherein the individual has been identified as one who is more likely to benefit from a treatment comprising an endocrine therapy by the method of embodiment 1.

Embodiment 7

A method of treating an individual having a breast cancer, the individual being identified as having an ER pathway activity score that is at or above a reference ER pathway activity score, the method comprising administering to the individual an effective amount of an endocrine therapy.

Embodiment 8

A method of treating an individual having a breast cancer, the method comprising:

(a) determining an ER pathway activity score from a sample from the individual, wherein the ER pathway activity score from the sample is determined to be at or above a reference ER pathway activity score; and (b) administering to the individual an effective amount of an endocrine therapy.

Embodiment 9

The method of any one of embodiments 1-8, wherein the reference ER pathway activity score is an ER pathway activity score in a reference population.

Embodiment 10

The method of any one of embodiments 1-3 and 6-9, wherein the ER pathway activity score in the sample is at or above −1.0.

Embodiment 11

The method of embodiment 10, wherein the ER pathway activity score in the sample is at or above −0.2.

Embodiment 12

The method of embodiment 4 or 5, wherein the ER pathway activity score in the sample is below −0.2.

Embodiment 13

The method of embodiment 4 or 5, wherein the ER pathway activity score in the sample is below −1.0.

Embodiment 14

The method of any one of embodiments 9-13, wherein the reference population is a population of individuals having hormone receptor-positive (HR+) breast cancer.

Embodiment 15

A method for monitoring the response of an individual having a breast cancer to treatment with an endocrine therapy, the method comprising:

(a) determining a first ER pathway activity score from a sample from the individual at a first time point;

(b) following step (a), determining a second ER pathway activity score from a sample from the individual at a second time point following administration of an endocrine therapy; and (c) comparing the first ER pathway activity score with the second ER pathway activity score, wherein a decrease in the second ER pathway activity score relative to the first ER pathway activity score is predictive of an individual who is likely to respond to treatment with an endocrine therapy.

Embodiment 16

The method of embodiment 15, wherein the second ER pathway activity score is decreased relative to the first ER pathway activity score, and the method further comprises administering an additional dose of the endocrine therapy to the individual.

Embodiment 17

The method of embodiment 15 or 16, wherein the decrease in the second ER pathway activity score relative to the first ER pathway activity score is a decrease of at least 0.1.

Embodiment 18

The method of any one of embodiments 15-17, wherein the first ER pathway activity score is:

(a) an ER pathway activity score determined from a sample from the individual obtained prior to administration of a first dose of an endocrine therapy;

(b) an ER pathway activity score determined from a sample from the individual at a previous time point, wherein the previous time point is following administration of a first dose of an endocrine therapy; or (c) a pre-assigned ER pathway activity score.

Embodiment 19

A method of identifying an individual having a breast cancer who may benefit from a treatment comprising an endocrine therapy, the method comprising determining an estradiol (E2)-induced score from a sample from the individual, wherein an E2-induced score from the sample that is at or above a reference E2-induced score identifies the individual as one who may benefit from a treatment comprising an endocrine therapy.

Embodiment 20

A method for selecting a therapy for an individual having a breast cancer, the method comprising determining an E2-induced score from a sample from the individual, wherein an E2-induced score from the sample that is at or above a reference E2-induced score identifies the individual as one who may benefit from a treatment comprising an endocrine therapy.

Embodiment 21

The method of embodiment 19 or 20, wherein the E2-induced score determined from the sample is at or above the reference E2-induced score, and the method further comprises administering to the individual an effective amount of an endocrine therapy.

Embodiment 22

The method of embodiment 19 or 20, wherein an E2-induced score from the sample that is below a reference E2-induced score identifies the individual as one who is less likely to benefit from a treatment comprising an endocrine therapy.

Embodiment 23

The method of embodiment 22, wherein the E2-induced score determined from the sample is below the reference E2-induced score, and the method further comprises administering to the individual an effective amount of an anti-cancer therapy other than an endocrine therapy.

Embodiment 24

A method of treating an individual having a breast cancer, the method comprising administering an effective amount of an endocrine therapy to the individual, wherein the individual has been identified as one who is more likely to benefit from a treatment comprising an endocrine therapy by the method of embodiment 19.

Embodiment 25

A method of treating an individual having a breast cancer, the individual being identified as having an E2-induced score that is at or above a reference E2-induced score, the method comprising administering to the individual an effective amount of an endocrine therapy.

Embodiment 26

A method of treating an individual having a breast cancer, the method comprising:

(a) determining an E2-induced score from a sample from the individual, wherein the E2-induced score from the sample is determined to be at or above a reference E2-induced score; and (b) administering to the individual an effective amount of an endocrine therapy.

Embodiment 27

The method of any one of embodiments 19-26, wherein the reference E2-induced score is an E2-induced score in a reference population.

Embodiment 28

The method of any one of embodiments 19-21 and 24-27, wherein the E2-induced score in the sample is at or above −2.0.

Embodiment 29

The method of embodiment 28, wherein the E2-induced score in the sample is at or above −0.1.

Embodiment 30

The method of embodiment 22 or 23, wherein the E2-induced score in the sample is below −0.1.

Embodiment 31

The method of embodiment 30, wherein the E2-induced score in the sample is below −2.0.

Embodiment 32

The method of any one of embodiments 27-31, wherein the reference population is a population of individuals having HR+ breast tumors.

Embodiment 33

A method for monitoring the response of an individual having a breast cancer to treatment with an endocrine therapy, the method comprising:

(a) determining a first E2-induced score from a sample from the individual at a first time point;

(b) following step (a), determining a second E2-induced score from a sample from the individual at a second time point following administration of an endocrine therapy; and (c) comparing the first E2-induced score with the second E2-induced score, wherein a decrease in the second E2-induced score relative to the first E2-induced score is predictive of an individual who is likely to respond to treatment with an endocrine therapy.

Embodiment 34

The method of embodiment 33, wherein the second E2-induced score is decreased relative to the first E2-induced score, and the method further comprises administering an additional dose of the endocrine therapy to the individual.

Embodiment 35

The method of embodiment 33 or 34, wherein the decrease in the second E2-induced score relative to the first E2-induced score is a decrease of at least 0.1.

Embodiment 36

The method of any one of embodiments 33-35, wherein the first E2-induced score is:

(a) an E2-induced score determined from a sample from the individual obtained prior to administration of a first dose of an endocrine therapy;

(b) an E2-induced score determined from a sample from the individual at a previous time point, wherein the previous time point is following administration of a first dose of an endocrine therapy; or (c) a pre-assigned E2-induced score.

Embodiment 37

The method of any one of embodiments 1-6, 8-24, and 26-36, wherein the sample is a tissue sample.

Embodiment 38

The method of embodiment 37, wherein the tissue sample is a tumor tissue sample.

Embodiment 39

The method of embodiment 38, wherein the tumor tissue sample is a formalin-fixed and paraffin-embedded (FFPE) sample, a fresh frozen (FF) sample, an archival sample, a fresh sample, or a frozen sample.

Embodiment 40

The method of embodiment 39, wherein the tumor tissue sample is a FFPE sample.

Embodiment 41

The method of embodiment 39, wherein the tumor tissue sample is a FF sample.

Embodiment 42

The method of any one of embodiments 1-41, wherein the breast cancer is an ER+ breast cancer.

Embodiment 43

The method of embodiment 42, wherein the ER+ breast cancer is a luminal A breast cancer.

Embodiment 44

The method of embodiment 42, wherein the ER+ breast cancer is a luminal B breast cancer.

Embodiment 45

The method of any one of embodiments 1-44, wherein the breast cancer is an advanced or a metastatic breast cancer.

Embodiment 46

The method of any one of embodiments 3, 5-18, 21, and 23-45, wherein the endocrine therapy is administered orally, intravenously, intratumorally, intramuscularly, subcutaneously, topically, or intranasally.

Embodiment 47

The method of embodiment 46, wherein the endocrine therapy is administered orally.

Embodiment 48

The method of embodiment 46, wherein the endocrine therapy is administered intramuscularly.

Embodiment 49

A method of detecting estrogen receptor (ER) pathway activity in a subject that has breast cancer, the method comprising detecting an expression level of at least five genes set forth in Table 1 and at least five genes set forth in Table 4; at least five genes set forth in Table 2 and at least five genes set forth in Table 5; or at least five genes set forth in Table 3 and at least five genes set forth in Table 6.

Embodiment 50

The method of embodiment 49, wherein the expression level of said at least five genes set forth in Table 1, at least five genes set forth in Table 2 or at least five genes set forth in Table 3 are greater than a standard control.

Embodiment 51

The method of embodiment 49, wherein the expression level of said at least five genes set forth in Table 4, at least five genes set forth in Table 5 or at least five genes set forth in Table 6 are less than a standard control.

Embodiment 52

The method of one of embodiments 49 to 51, wherein the subject has been treated with an endocrine therapy prior to said detecting.

Embodiment 53

The method of one of embodiments 49 to 52, wherein the subject is treated with an endocrine therapy subsequent to said detecting.

Embodiment 54

The method of one of embodiments 49 to 53 comprising detecting an expression level of all genes set forth in Table 1 and all genes set forth in Table 4.

Embodiment 55

The method of one of embodiments 49 to 53 comprising detecting an expression level of all genes set forth in Table 2 and all genes set forth in Table 5.

Embodiment 56

The method of one of embodiments 49 to 53 comprising detecting an expression level of all genes set forth in Table 3 and all genes set forth in Table 6.

Embodiment 57

The method of one of embodiments 49 to 53 comprising detecting an expression level of all genes set forth in Table 1 and all genes set forth in Table 4 and not detecting an expression level of any other genes in said subject.

Embodiment 58

The method of one of embodiments 49 to 53 comprising detecting an expression level of all genes set forth in Table 2 and all genes set forth in Table 5 and not detecting an expression level of any other genes in said subject.

Embodiment 59

The method of one of embodiments 49 to 53 comprising detecting an expression level of all genes set forth in Table 3 and all genes set forth in Table 6 and not detecting an expression level of any other genes in said subject.

Embodiment 60

The method of one of embodiments 49 to 59, wherein the subject is treated with an endocrine therapy comprising a selective estrogen receptor degrader.

Embodiment 61

The method of one of embodiments 49 to 60, further comprising determining an estrogen receptor (ER) pathway activity score from a sample from the subject.

Embodiment 62

The method of embodiment 61, wherein an ER pathway activity score from the sample that is at or above a reference ER pathway activity score identifies the individual as one who may benefit from a treatment comprising an endocrine therapy.

Embodiment 63

The method of embodiment 61, further comprising comparing an ER pathway activity score from the sample that is at or above a reference ER pathway activity score identifies the individual as one who may benefit from a treatment comprising an endocrine therapy.

Embodiment 64

A method, comprising:

detecting, by one or more processors, a first expression level of at least five genes set forth in Table 1, at least five genes set forth in Table 2, or at least five genes set forth in Table 3;

detecting, by the one or more processors, a second expression level of at least five genes set forth in Table 4, at least five genes set forth in Table 5 or at least five genes set forth in Table 6; and detecting, based at least on the first expression level and/or the second expression level, estrogen receptor (ER) pathway activity in a subject that has cancer.

Embodiment 65

The method of embodiment 64, wherein the expression level of said at least five genes set forth in Table 1, at least five genes set forth in Table 2 or at least five genes set forth in Table 3 are greater than a standard control.

Embodiment 66

The method of embodiment 64, wherein the expression level of said at least five genes set forth in Table 4, at least five genes set forth in Table 5 or at least five genes set forth in Table 6 are less than a standard control.

Embodiment 67

The method of one of embodiments 64 to 66, further comprising:

treating the subject with an endocrine therapy prior to said detecting.

Embodiment 68

The method of one of embodiments 64 to 67, further comprising:

treating, based at least on the estrogen receptor (ER) pathway activity detected in the subject, the subject with an endocrine therapy.

Embodiment 69

The method of any one of embodiments 1-68, wherein the endocrine therapy comprises a selective estrogen receptor degrader (SERD), a selective estrogen receptor modulator (SERM), a selective estrogen receptor covalent antagonist (SERCA), a selective human estrogen receptor agonist (ShERPA), an aromatase inhibitor (AI), or a combination thereof.

Embodiment 70

The method of embodiment 69, wherein the SERD comprises brilanestrant (GDC-0810) having the structure:

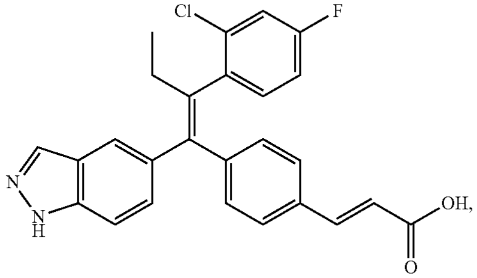 [SMILES: CC/C(=C(/c1ccc(/C=C/C(=O)O)cc1)c1ccc2[nH]ncc2c1)c1ccc(F)cc1Cl]

or a pharmaceutically acceptable salt thereof.

Embodiment 71

The method of embodiment 69, wherein the SERD comprises GDC-0927 (SRN-0927) having the structure:

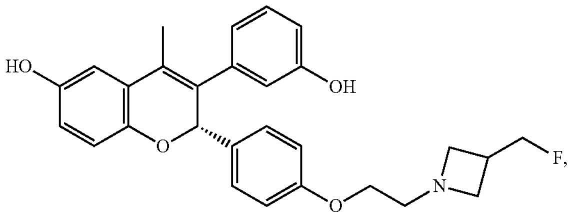 [SMILES: CC1=C(c2cccc(O)c2)[C@H](c2ccc(OCCN3CC(CF)C3)cc2)Oc2ccc(O)cc21]

or a pharmaceutically acceptable salt thereof.

Embodiment 72

The method of any one of embodiments 1-68, wherein the endocrine therapy comprises a compound having formula:

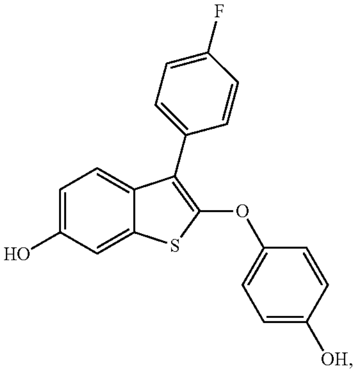

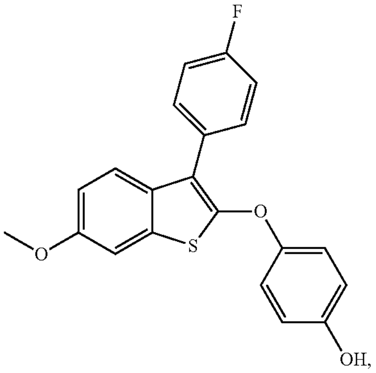

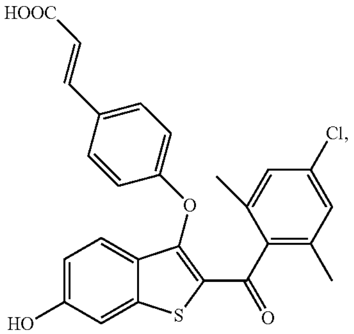

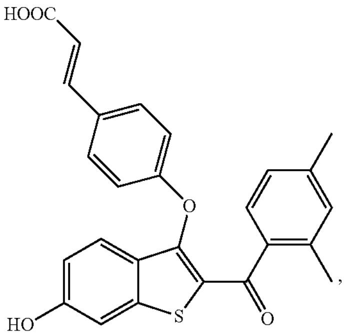

-continued

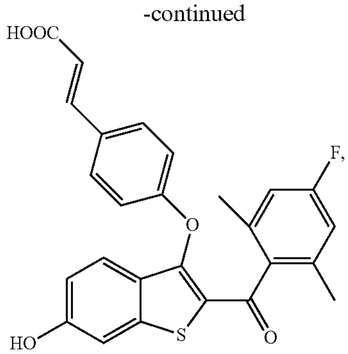

or

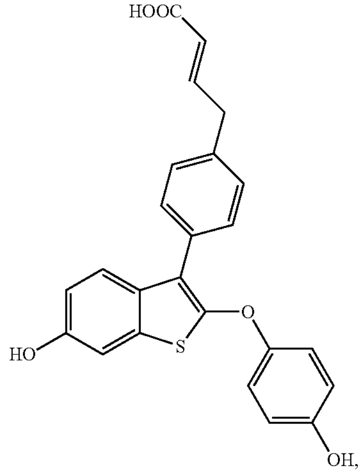 [SMILES: O=C(O)/C=C/Cc1ccc(-c2c(Oc3ccc(O)cc3)sc3cc(O)ccc23)cc1]

or a pharmaceutically acceptable salt thereof.

Embodiment 73

The method of any one of embodiments 1-68, wherein the endocrine therapy comprises a compound having formula:

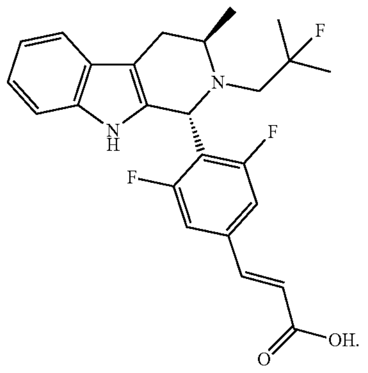 [SMILES: C[C@@H]1Cc2c([nH]c3ccccc23)[C@@H](c2c(F)cc(/C=C/C(=O)O)cc2F)N1CC(C)(C)F]

Embodiment 74

The method of any one of embodiments 1-68, wherein the endocrine therapy comprises a compound having formula:

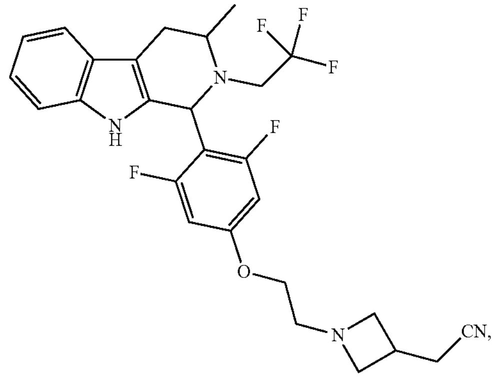 [SMILES: CC1Cc2c([nH]c3ccccc23)C(c2c(F)cc(OCCN3CC(CC#N)C3)cc2F)N1CC(F)(F)F]

or a pharmaceutically acceptable salt thereof.

Embodiment 75

The method of any one of embodiments 1-68, wherein the endocrine therapy comprises a compound having formula:

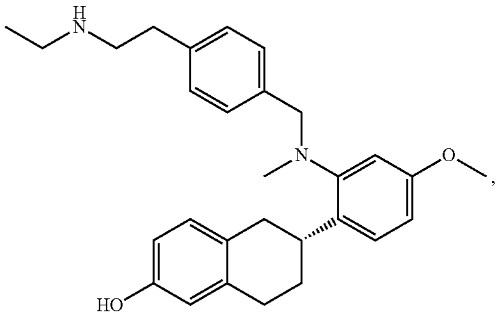 [SMILES: CCNCCc1ccc(CN(C)c2cc(OC)ccc2[C@@H]2CCc3cc(O)ccc3C2)cc1]

or a pharmaceutically acceptable salt thereof.

Embodiment 76

The method of any one of embodiments 1-68, wherein the endocrine therapy comprises a compound having formula:

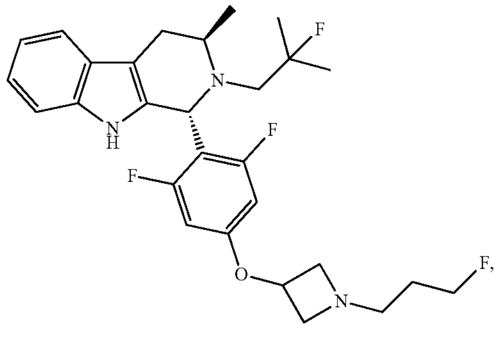

-continued
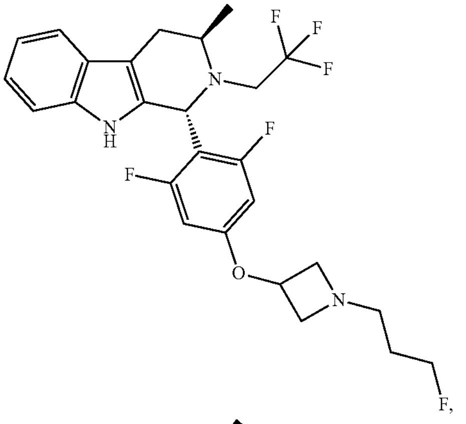
or
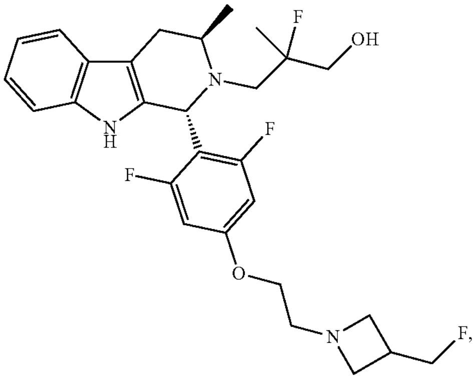
or a pharmaceutically acceptable salt thereof.
Embodiment 77
The method of any one of embodiments 1-68, wherein the endocrine therapy comprises a compound having formula:
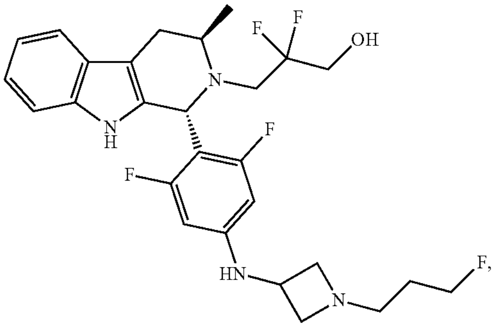 [SMILES: C[C@@H]1Cc2c([nH]c3ccccc23)[C@@H](c2c(F)cc(NC3CN(CCCF)C3)cc2F)N1CC(F)(F)CO]
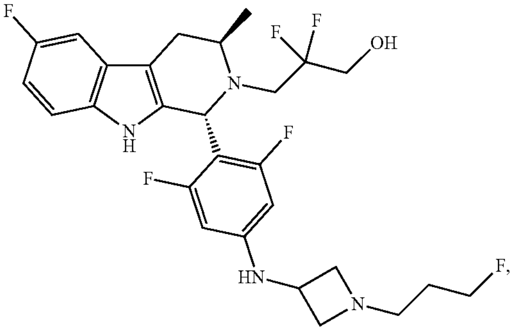
-continued
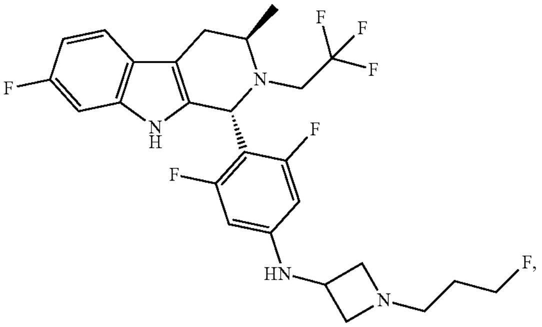
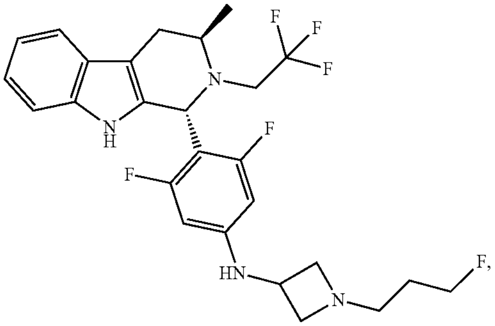
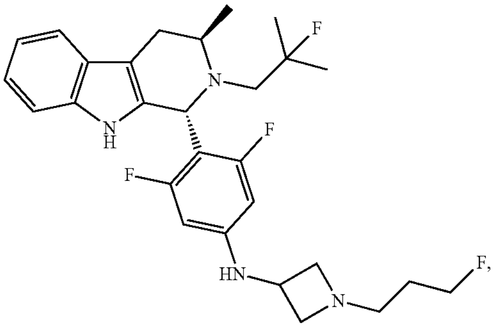
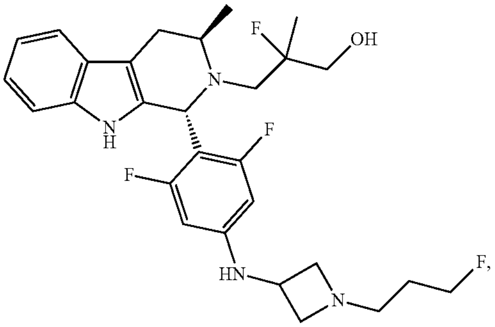 [SMILES: C[C@@H]1Cc2c([nH]c3ccccc23)[C@@H](c2c(F)cc(NC3CN(CCCF)C3)cc2F)N1CC(F)(F)CO]
or
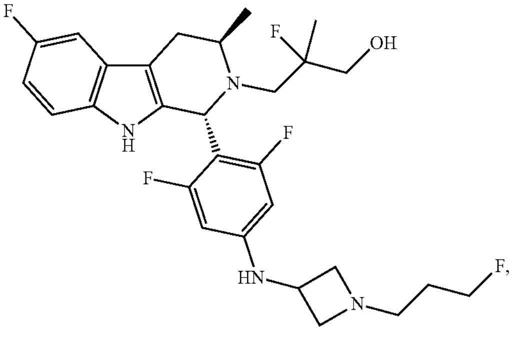
or a pharmaceutically acceptable salt thereof.

Embodiment 78

The method of any one of embodiments 1-68, wherein the endocrine therapy comprises a compound having formula:

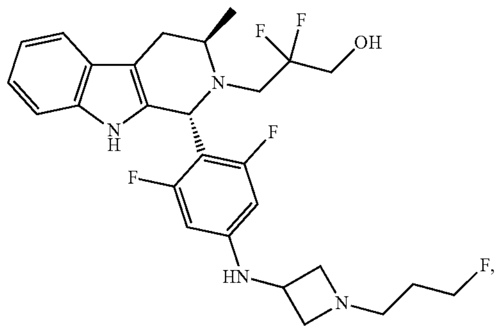 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

Embodiment 79

The method of embodiment 5 or 23, wherein the anti-cancer therapy other than an endocrine therapy comprises a chemotherapy.

Embodiment 80

The method of embodiment 79, wherein the chemotherapy comprises an anthracycline, a taxane, 5-flurouracil, cyclophosphamide, a platinum agent, vinorelbine, capecitabine, gemcitabine, ixabepilone, eribulin, or a combination thereof.

Embodiment 81

The method of embodiment 79, wherein the anti-cancer therapy other than an endocrine therapy comprises a PI3K inhibitor, an mTOR inhibitor, a CDK4/6 inhibitor, or a combination thereof.

Embodiment 82

The method of any one of embodiments 1-81, wherein the individual is a human.

Embodiment 83

A kit comprising a plurality of nucleic acids, wherein said plurality of nucleic acids are at least 5 nucleotides in length and are at least 95% identical to a 5 nucleotide continuous sequence within at least five genes set forth in Table 1 and at least five genes set forth in Table 4; at least five genes set forth in Table 2 and at least five genes set forth in Table 4; or at least five genes set forth in Table 3 and at least five genes set forth in Table 6, or 95% identical to a sequence complementary to said 5 nucleotide continuous sequence.

Embodiment 84

The kit of embodiment 83, wherein said plurality of nucleic acids are attached to a solid support.

Embodiment 85

The kit of embodiment 84, wherein said plurality of nucleic acids comprise a detectable label.

Embodiment 86

The kit of embodiment 83, wherein said plurality of nucleic acids are at least 95% identical to a 5 nucleotide continuous sequence within at least five genes set forth in Table 1, at least five genes set forth in Table 2 or at least five genes set forth in Table 3 are greater than a standard control.

Embodiment 87

The kit of embodiment 83, wherein said plurality of nucleic acids are at least 95% identical to a 5 nucleotide continuous sequence within at least five genes set forth in Table 4, at least five genes set forth in Table 5 or at least five genes set forth in Table 6 are less than a standard control.

Embodiment 88

The kit of one of embodiments 83-87, wherein said plurality of nucleic acids are at least 95% identical to a 5 nucleotide continuous sequence within all genes set forth in Table 1 and all genes set forth in Table 4.

Embodiment 89

The kit of one of embodiments 83-87, wherein said plurality of nucleic acids are at least 95% identical to a 5 nucleotide continuous sequence within all genes set forth in Table 2 and all genes set forth in Table 5.

Embodiment 90

The kit of one of embodiments 83-87, wherein said plurality of nucleic acids are at least 95% identical to a 5 nucleotide continuous sequence within all genes set forth in Table 3 and all genes set forth in Table 6.

Embodiment 91

The kit of one of embodiments 83-87, wherein said plurality of nucleic acids are at least 95% identical to a 5 nucleotide continuous sequence within all genes set forth in Table 1 and all genes set forth in Table 4 and no other genes.

Embodiment 92

The kit of one of embodiments 83-87, wherein said plurality of nucleic acids are at least 95% identical to a 5 nucleotide continuous sequence within all genes set forth in Table 2 and all genes set forth in Table 5 and no other genes.

Embodiment 93

The kit of one of embodiments 83-87, wherein said plurality of nucleic acids are at least 95% identical to a 5 nucleotide continuous sequence within all genes set forth in Table 3 and all genes set forth in Table 6 and no other genes in said subject.

Embodiment 94

The kit of one of embodiments 83-93, wherein the plurality of nucleic acids are identical to a 5 nucleotide continuous sequence within said genes.

Embodiment 95

The kit of one of embodiments 83-94, wherein the plurality of nucleic acids are identical to a continuous nucleotide sequence comprising at least 10, 20, 25, 50, 75, 100, 150, or 200 nucleotides.

What is claimed is:

1. A method of identifying an individual having a breast cancer who may benefit from a treatment comprising an endocrine therapy, the method comprising determining an estrogen receptor (ER) pathway activity score from a sample from the individual, wherein an ER pathway activity score from the sample that is at or above a reference ER pathway activity score identifies the individual as one who may benefit from a treatment comprising an endocrine therapy; wherein the endocrine therapy comprises a selective estrogen receptor degrader, a selective estrogen receptor modulator, a selective estrogen receptor covalent antagonist, a selective human estrogen receptor agonist, an aromatase inhibitor, or a combination of two or more thereof.

2. A method for selecting a therapy for an individual having a breast cancer, the method comprising determining an ER pathway activity score from a sample from the individual, wherein an ER pathway activity score from the sample that is at or above a reference ER pathway activity score identifies the individual as one who may benefit from a treatment comprising an endocrine therapy; wherein the endocrine therapy comprises a selective estrogen receptor degrader, a selective estrogen receptor modulator, a selective estrogen receptor covalent antagonist, a selective human estrogen receptor agonist, an aromatase inhibitor, or a combination of two or more thereof.

3. The method of claim 2, wherein the endocrine therapy comprises a compound having formula:

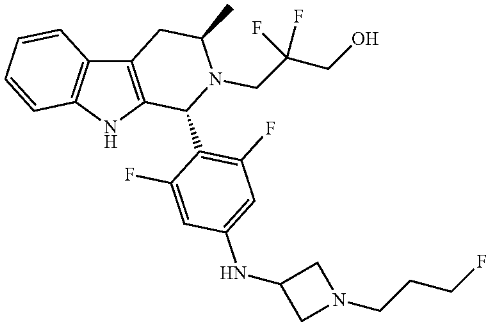 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

4. The method of claim 1, wherein the ER pathway activity score determined from the sample is at or above the reference ER pathway activity score, and the method further comprises administering to the individual an effective amount of the endocrine therapy.

5. The method of claim 1, wherein an ER pathway activity score from the sample that is below a reference ER pathway activity score identifies the individual as one who is less likely to benefit from a treatment comprising the endocrine therapy.

6. A method of treating an individual having a breast cancer, the method comprising administering an effective amount of an endocrine therapy to the individual, wherein the individual has been identified as one who is more likely to benefit from a treatment comprising the endocrine therapy by the method of claim 1.

7. The method of claim 1, wherein the endocrine therapy comprises a compound having formula:

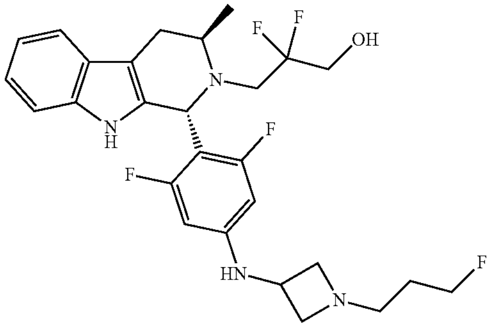 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

8. A method of treating an individual having a breast cancer, the individual being identified as having an ER pathway activity score that is at or above a reference ER pathway activity score, the method comprising administering to the individual an effective amount of an endocrine therapy; wherein the endocrine therapy comprises a selective estrogen receptor degrader, a selective estrogen receptor modulator, a selective estrogen receptor covalent antagonist, a selective human estrogen receptor agonist, an aromatase inhibitor, or a combination of two or more thereof.

9. The method of claim 8, wherein the endocrine therapy comprises a compound having formula:

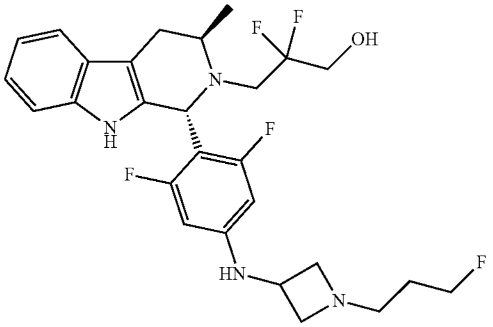 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

10. A method of treating an individual having a breast cancer, the method comprising:

(a) determining an ER pathway activity score from a sample from the individual, wherein the ER pathway activity score from the sample is determined to be at or above a reference ER pathway activity score; and (b) administering to the individual an effective amount of an endocrine therapy; wherein the endocrine therapy comprises a selective estrogen receptor degrader, a selective estrogen receptor modulator, a selective estrogen receptor covalent antagonist, a selective human estrogen receptor agonist, an aromatase inhibitor, or a combination of two or more thereof.

11. The method of claim 10, wherein the endocrine therapy comprises a compound having formula:

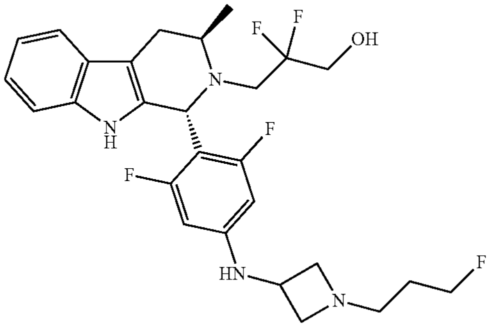 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

12. A method for monitoring the response of an individual having a breast cancer to treatment with an endocrine therapy, the method comprising:

(a) determining a first estrogen receptor pathway activity score from a sample from the individual at a first time point;

(b) following step (a), determining a second estrogen receptor pathway activity score from a sample from the individual at a second time point following administration of an endocrine therapy; and (c) comparing the first estrogen receptor pathway activity score with the second estrogen receptor pathway activity score, wherein a decrease in the second estrogen receptor pathway activity score relative to the first estrogen receptor pathway activity score is predictive of an individual who is likely to respond to treatment with an endocrine therapy.

13. The method of claim 12, wherein the first estrogen receptor pathway activity score is:

(a) an estrogen receptor pathway activity score determined from a sample from the individual obtained prior to administration of a first dose of an endocrine therapy;

(b) an estrogen receptor pathway activity score determined from a sample from the individual at a previous time point, wherein the previous time point is following administration of a first dose of an endocrine therapy; or (c) a pre-assigned estrogen receptor pathway activity score.

14. The method claim 12, wherein the endocrine therapy comprises a selective estrogen receptor degrader (SERD), a selective estrogen receptor modulator (SERM), a selective estrogen receptor covalent antagonist (SERCA), a selective human estrogen receptor agonist (ShERPA), an aromatase inhibitor (AI), or a combination thereof.

15. The method of claim 12, wherein the endocrine therapy comprises a compound having formula:

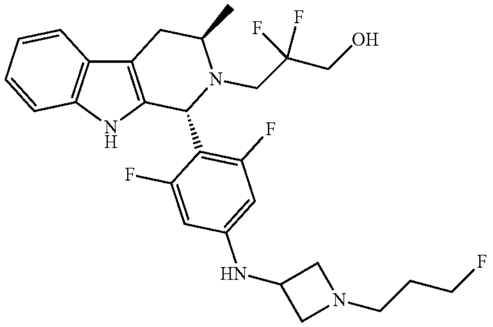 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

16. A method of identifying an individual having a breast cancer who may benefit from a treatment comprising an endocrine therapy, the method comprising determining an estradiol (E2)-induced score from a sample from the individual, wherein an E2-induced score from the sample that is at or above a reference E2-induced score identifies the individual as one who may benefit from a treatment comprising an endocrine therapy; wherein the endocrine therapy comprises a selective estrogen receptor degrader, a selective estrogen receptor modulator, a selective estrogen receptor covalent antagonist, a selective human estrogen receptor agonist, an aromatase inhibitor, or a combination of two or more thereof.

17. The method of claim 16, wherein the endocrine therapy comprises a compound having formula:

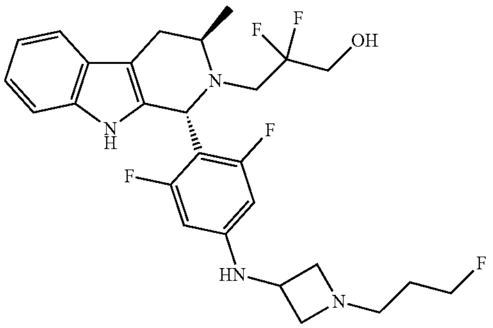 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

18. A method of treating an individual having a breast cancer, the method comprising administering an effective amount of an endocrine therapy to the individual, wherein the individual has been identified as one who is more likely to benefit from a treatment comprising the endocrine therapy by the method of claim 16.

19. A method for selecting a therapy for an individual having a breast cancer, the method comprising determining an E2-induced score from a sample from the individual, wherein an E2-induced score from the sample that is at or above a reference E2-induced score identifies the individual as one who may benefit from a treatment comprising an endocrine therapy; wherein the endocrine therapy comprises a selective estrogen receptor degrader, a selective estrogen receptor modulator, a selective estrogen receptor covalent antagonist, a selective human estrogen receptor agonist, an aromatase inhibitor, or a combination of two or more thereof.

20. The method of claim 19, wherein the endocrine therapy comprises a compound having formula:

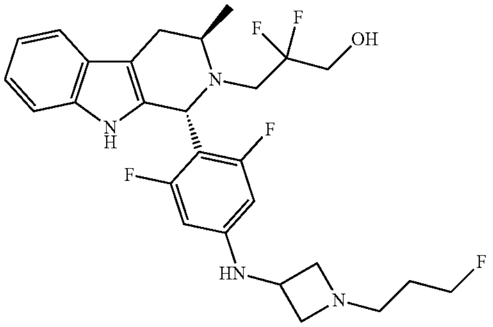 [SMILES: C[C@@H]1Cc2c([nH]c3ccccc23)[C@@H](c2c(F)cc(NC3CN(CCCF)C3)cc2F)N1CC(F)(F)CO]

or a pharmaceutically acceptable salt thereof.

21. A method of treating an individual having a breast cancer, the method comprising:

(a) determining an E2-induced score from a sample from the individual, wherein the E2-induced score from the sample is determined to be at or above a reference E2-induced score; and (b) administering to the individual an effective amount of an endocrine therapy; wherein the endocrine therapy comprises a selective estrogen receptor degrader, a selective estrogen receptor modulator, a selective estrogen receptor covalent antagonist, a selective human estrogen receptor agonist, an aromatase inhibitor, or a combination of two or more thereof.

22. The method of claim 21, wherein the endocrine therapy comprises a compound having formula:

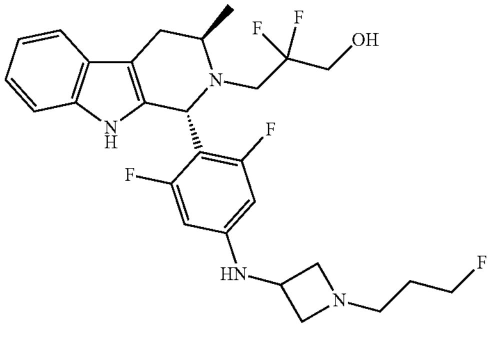

or a pharmaceutically acceptable salt thereof.

23. A method for monitoring the response of an individual having a breast cancer to treatment with an endocrine therapy, the method comprising:

(a) determining a first E2-induced score from a sample from the individual at a first time point;

(b) following step (a), determining a second E2-induced score from a sample from the individual at a second time point following administration of an endocrine therapy, wherein the endocrine therapy comprises a selective estrogen receptor degrader, a selective estrogen receptor modulator, a selective estrogen receptor covalent antagonist, a selective human estrogen receptor agonist, an aromatase inhibitor, or a combination of two or more thereof; and (c) comparing the first E2-induced score with the second E2-induced score, wherein a decrease in the second E2-induced score relative to the first E2-induced score is predictive of an individual who is likely to respond to treatment with an endocrine therapy.

24. The method of claim 23, wherein the first E2-induced score is:

(a) an E2-induced score determined from a sample from the individual obtained prior to administration of a first dose of an endocrine therapy;

(b) an E2-induced score determined from a sample from the individual at a previous time point, wherein the previous time point is following administration of a first dose of an endocrine therapy; or (c) a pre-assigned E2-induced score.

25. The method of claim 23, wherein the endocrine therapy comprises a compound having formula:

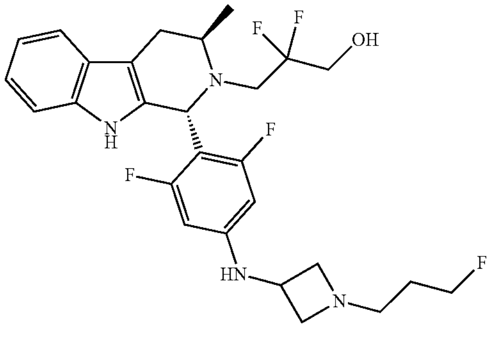

or a pharmaceutically acceptable salt thereof.

26. A method of detecting estrogen receptor pathway activity in a subject that has breast cancer, the method comprising detecting:

(i) an expression level of at least five genes selected from the group consisting of AMZ1, C5AR2, CELSR2, FKBP4, GREB1, OLFM1, SLC9A3R1, and TFF1 and at least five genes selected from the group consisting of BCAS1, CCNG2, IL1R1, PNPLA7, SEMA3E, and STON1;

(ii) an expression level of at least five genes selected from the group consisting of AMZ1, AREG, C5AR2, CELSR2, FKBP4, FMN1, GREB1, OLFM1, RBM24, SLC9A3R1, and TFF1 and at least five genes selected from the group consisting of BCAS1, CCNG2, IL1R1, NBEA, PNPLA7, SEMA3E, STON1, and TP53INP1; or (iii) an expression level of at least five genes selected from the group consisting of AGR3, AMZ1, AREG, C5AR2, CELSR2, CT62, FKBP4, FMN1, GREB1, IGFBP4, NOS1AP, NXPH3, OLFM1, PGR, PPM1J, RAPGEFL1, RBM24, RERG, RET, SGK3, SLC9A3R1, TFF1, and ZNF703 and at least five genes selected from the group consisting of BAMBI, BCAS1, CCNG2, DDIT4, EGLN3, FAM171B, GRM4, IL1R1, LIPH, NBEA, PNPLA7, PSCA, SEMA3E, SSPO, STON1, TGFB3, TP53INP1, and TP53INP2.

27. The method of claim 26, wherein the expression level of said at least five genes selected from the group consisting of AMZ1, C5AR2, CELSR2, FKBP4, GREB1, OLFM1, SLC9A3R1, and TFF1, at least five genes selected from the group consisting of AMZ1, AREG, C5AR2, CELSR2, FKBP4, FMN1, GREB1, OLFM1, RBM24, SLC9A3R1, and TFF1, or at least five genes selected from the group consisting of AGR3, AMZ1, AREG, C5AR2, CELSR2, CT62, FKBP4, FMN1, GREB1, IGFBP4, NOS1AP, NXPH3, OLFM1, PGR, PPM1J, RAPGEFL1, RBM24, RERG, RET, SGK3, SLC9A3R1, TFF1, and ZNF703 are greater than a standard control.

28. The method of claim 26, wherein the expression level of said at least five genes selected from the group consisting of BCAS1, CCNG2, IL1R1, PNPLA7, SEMA3E, and STON1, at least five genes selected from the group consisting of BCAS1, CCNG2, IL1R1, NBEA, PNPLA7, SEMA3E, STON1, and TP53INP1 or at least five genes selected from the group consisting of BAMBI, BCAS1, CCNG2, DDIT4, EGLN3, FAM171B, GRM4, IL1R1, LIPH, NBEA, PNPLA7, PSCA, SEMA3E, SSPO, STON1, TGFB3, TP53INP1, and TP53INP2 are less than a standard control.

29. The method of claim 26, wherein the subject has been treated with an endocrine therapy prior to said detecting.

30. The method of claim 26, wherein the subject is treated with an endocrine therapy subsequent to said detecting.

31. The method claim 26, comprising detecting an expression level of all genes selected from the group consisting of AMZ1, C5AR2, CELSR2, FKBP4, GREB1, OLFM1, SLC9A3R1, and TFF1 and all genes selected from the group consisting of BCAS1, CCNG2, IL1R1, PNPLA7, SEMA3E, and STON1.

32. The method of claim 26, comprising detecting an expression level of all genes selected from the group consisting of AMZ1, AREG, C5AR2, CELSR2, FKBP4, FMN1, GREB1, OLFM1, RBM24, SLC9A3R1, and TFF1 and all genes selected from the group consisting of BCAS1, CCNG2, IL1R1, NBEA, PNPLA7, SEMA3E, STON1, and TP53INP1.

33. The method of claim 26, comprising detecting an expression level of all genes selected from the group consisting of AGR3, AMZ1, AREG, C5AR2, CELSR2, CT62, FKBP4, FMN1, GREB1, IGFBP4, NOS1AP, NXPH3, OLFM1, PGR, PPM1J, RAPGEFL1, RBM24, RERG, RET, SGK3, SLC9A3R1, TFF1, and ZNF703 and all genes selected from the group consisting of BAMBI, BCAS1, CCNG2, DDIT4, EGLN3, FAM171B, GRM4, IL1R1, LIPH, NBEA, PNPLA7, PSCA, SEMA3E, SSPO, STON1, TGFB3, TP53INP1, and TP53INP2.

34. The method of claim 26, comprising detecting an expression level of all genes selected from the group consisting of AMZ1, C5AR2, CELSR2, FKBP4, GREB1, OLFM1, SLC9A3R1, and TFF1 and all genes selected from the group consisting of BCAS1, CCNG2, IL1R1, PNPLA7, SEMA3E, and STON1 and not detecting an expression level of any other genes in said subject.

35. The method of claim 26, comprising detecting an expression level of all genes selected from the group consisting of AMZ1, AREG, C5AR2, CELSR2, FKBP4, FMN1, GREB1, OLFM1, RBM24, SLC9A3R1, and TFF1 and all genes selected from the group consisting of BCAS1, CCNG2, IL1R1, NBEA, PNPLA7, SEMA3E, STON1, and TP53INP1 and not detecting an expression level of any other genes in said subject.

36. The method of claim 26, comprising detecting an expression level of all genes selected from the group consisting of AGR3, AMZ1, AREG, C5AR2, CELSR2, CT62, FKBP4, FMN1, GREB1, IGFBP4, NOS1AP, NXPH3, OLFM1, PGR, PPM1J, RAPGEFL1, RBM24, RERG, RET, SGK3, SLC9A3R1, TFF1, and ZNF703 and all genes selected from the group consisting of BAMBI, BCAS1, CCNG2, DDIT4, EGLN3, FAM171B, GRM4, IL1R1, LIPH, NBEA, PNPLA7, PSCA, SEMA3E, SSPO, STON1, TGFB3, TP53INP1, and TP53INP2 and not detecting an expression level of any other genes in said subject.

37. The method of claim 26, wherein the subject is treated with an endocrine therapy comprising a selective estrogen receptor degrader.

38. The method of claim 26, further comprising determining an estrogen receptor (ER) pathway activity score from a sample from the subject.

39. The method of claim 38, wherein an ER pathway activity score from the sample that is at or above a reference ER pathway activity score identifies the individual as one who may benefit from a treatment comprising an endocrine therapy.

40. The method of claim 38, further comprising comparing an ER pathway activity score from the sample that is at or above a reference ER pathway activity score identifies the individual as one who may benefit from a treatment comprising an endocrine therapy.

41. A method, comprising:

(i) detecting, by one or more processors, a first expression level of at least five genes selected from the group consisting of AMZ1, C5AR2, CELSR2, FKBP4, GREB1, OLFM1, SLC9A3R1, and TFF1, at least five genes selected from the group consisting of AMZ1, AREG, C5AR2, CELSR2, FKBP4, FMN1, GREB1, OLFM1, RBM24, SLC9A3R1, and TFF1, or at least five genes selected from the group consisting of AGR3, AMZ1, AREG, C5AR2, CELSR2, CT62, FKBP4, FMN1, GREB1, IGFBP4, NOS1AP, NXPH3, OLFM1, PGR, PPM1J, RAPGEFL1, RBM24, RERG, RET, SGK3, SLC9A3R1, TFF1, and ZNF703;

(ii) detecting, by the one or more processors, a second expression level of at least five genes selected from the group consisting of BCAS1, CCNG2, IL1R1, PNPLA7, SEMA3E, and STON1, at least five genes selected from the group consisting of BCAS1, CCNG2, IL1R1, NBEA, PNPLA7, SEMA3E, STON1, and TP53INP1, or at least five genes selected from the group consisting of BAMBI, BCAS1, CCNG2, DDIT4, EGLN3, FAM171B, GRM4, IL1R1, LIPH, NBEA, PNPLA7, PSCA, SEMA3E, SSPO, STON1, TGFB3, TP53INP1, and TP53INP2; and (iii) detecting, based at least on the first expression level and/or the second expression level, estrogen receptor (ER) pathway activity in a subject that has cancer.

42. A kit comprising a plurality of nucleic acids, wherein said plurality of nucleic acids are at least 5 nucleotides in length and are at least 95% identical to a 5 nucleotide continuous sequence or are at least 95% identical to a sequence complementary to said 5 nucleotide continuous sequence within:

(i) at least five genes selected from the group consisting of AMZ1, C5AR2, CELSR2, FKBP4, GREB1, OLFM1, SLC9A3R1, and TFF1 and at least five genes selected from the group consisting of BCAS1, CCNG2, IL1R1, PNPLA7, SEMA3E, and STON1;

(ii) at least five genes selected from the group consisting of AMZ1, AREG, C5AR2, CELSR2, FKBP4, FMN1, GREB1, OLFM1, RBM24, SLC9A3R1, and TFF1 and at least five genes selected from the group consisting of BCAS1, CCNG2, IL1R1, NBEA, PNPLA7, SEMA3E, STON1, and TP53INP1; or (iii) at least five genes selected from the group consisting of AGR3, AMZ1, AREG, C5AR2, CELSR2, CT62, FKBP4, FMN1, GREB1, IGFBP4, NOS1AP, NXPH3, OLFM1, PGR, PPM1J, RAPGEFL1, RBM24, RERG, RET, SGK3, SLC9A3R1, TFF1, and ZNF703 and at least five genes selected from the group consisting of BAMBI, BCAS1, CCNG2, DDIT4, EGLN3, FAM171B, GRM4, IL1R1, LIPH, NBEA, PNPLA7, PSCA, SEMA3E, SSPO, STON1, TGFB3, TP53INP1, and TP53INP2.

* * * * *

SEQUENCE LISTING

```
<160> NUMBER OF SEQ ID NOS: 90

<210> SEQ ID NO 1
<211> LENGTH: 767
<212> TYPE: DNA
<213> ORGANISM: Homo sapiens

<400> SEQUENCE: 1

agaaacatcc agaatacatt tccaacaaga gcactggcca agtcagcttc ttctgagaga      60

gtctctagaa gacatgatgc tacactcagc tttgggtctc tgcctcttac tcgtcacagt     120

ttcttccaac cttgccattg caataaaaaa ggaaaagagg cctcctcaga cactctcaag     180

aggatgggga gatgacatca cttgggtaca aacttatgaa gaaggtctct tttatgctca     240

aaaaagtaag aagccattaa tggttattca tcacctggag gattgtcaat actctcaagc     300

actaaagaaa gtatttgccc aaaatgaaga aatacaagaa atggctcaga ataagttcat     360

catgctaaac cttatgcatg aaaccactga taagaattta tcacctgatg ggcaatatgt     420

gcctagaatc atgtttgtag acccttcttt aacagttaga gctgacatag ctggaagata     480

ctctaacaga ttgtacacat atgagcctcg ggatttaccc ctattgatag aaaacatgaa     540

gaaagcatta agacttattc agtcagagct ataagagatg atggaaaaaa gccttcactt     600

caaagaagtc aaatttcatg aagaaaacct ctggcacatt gacaaatact aaatgtgcaa     660

gtatatagat tttgtaatat tactatttag tttttttaat gtgtttgcaa tagtcttatt     720

aaaataaatg ttttttaaat ctgagactga aaaaaaaaaa aaaaaaa                   767


<210> SEQ ID NO 2
<211> LENGTH: 166
<212> TYPE: PRT
<213> ORGANISM: Homo sapiens

<400> SEQUENCE: 2

Met Met Leu His Ser Ala Leu Gly Leu Cys Leu Leu Leu Val Thr Val
1               5                   10                  15

Ser Ser Asn Leu Ala Ile Ala Ile Lys Lys Glu Lys Arg Pro Pro Gln
            20                  25                  30

Thr Leu Ser Arg Gly Trp Gly Asp Asp Ile Thr Trp Val Gln Thr Tyr
        35                  40                  45

Glu Glu Gly Leu Phe Tyr Ala Gln Lys Ser Lys Lys Pro Leu Met Val
    50                  55                  60

Ile His His Leu Glu Asp Cys Gln Tyr Ser Gln Ala Leu Lys Lys Val
65                  70                  75                  80

Phe Ala Gln Asn Glu Glu Ile Gln Glu Met Ala Gln Asn Lys Phe Ile
                85                  90                  95

Met Leu Asn Leu Met His Glu Thr Thr Asp Lys Asn Leu Ser Pro Asp
            100                 105                 110

Gly Gln Tyr Val Pro Arg Ile Met Phe Val Asp Pro Ser Leu Thr Val
        115                 120                 125

Arg Ala Asp Ile Ala Gly Arg Tyr Ser Asn Arg Leu Tyr Thr Tyr Glu
    130                 135                 140
```

```
Pro Arg Asp Leu Pro Leu Leu Ile Glu Asn Met Lys Lys Ala Leu Arg
145                 150                 155                 160

Leu Ile Gln Ser Glu Leu
                165


<210> SEQ ID NO 3
<211> LENGTH: 5531
<212> TYPE: DNA
<213> ORGANISM: Homo sapiens

<400> SEQUENCE: 3

gattggtgct gtgacctgcg gcagcacagc cgcctgcgtt gagcgcccac ggtgggctgg      60

actttgcact aggtgctgac aggaccggca gaggtggcca ctgccctcgt ccccagcctg     120

cactcctggg cgaaggctga cgctgaacag ggtgctgtgg gcccagaagc gcccatgcct     180

gagagcgtcc aggaccaggc agagctgggc cttaagggcc cttggaccag tgtctgtctg     240

cagggagccc ccggtagcca ctcggatcag cccgagggaa gattctggac gagaccgtgg     300

ccgtccccg ggtggcccat ggacagcagc aggggctccc aggagtggcc aggccctgcc     360

cgcccaccat gctgcagtgt agacccgcac aggagttcag cttcgggccc cgggccttga     420

aggacgctct ggtctccact gacgcagccc tgcagcagct gtatgtgtcc gccttctccc     480

ctgccgagcg gctcttcctg gccgaggcct acaacccgca gaggacgctc ttctgcaccc     540

tgctcatccg cacgggcttc gactggctcc tgagccgacc cgaggctccc gaggacttcc     600

agaccttcca cgcctccctg cagcaccgga agccccgcct ggctcggaag cacatctacc     660

tacagccgat agacctgagc gaggagccgg tgggaagctc cctgctgcac cagctgtgca     720

gctgcacaga ggccttcttc ctgggcctgc gcgtcaagtg cctgccgtcg gtggcagccg     780

cgtccatccg ctgctcctcg cggcccagcc gggactctga caggctccag ctccacacag     840

acggcatcct gtccttcttg aagaacaaca agccagggga cgcgctgtgt gtgctgggcc     900

tcacactgtc tgacctgtac ccccatgagg cctggagctt caccttcagc aagttccttc     960

cagggcacga agtgggcgtc tgcagcttcg cccggttctc aggggaattc ccgaagtcgg    1020

ggcccagcgc ccctgatctg gccctggtag aggcagcagc agacggcccc gaggcccccc    1080

tgcaggacag gggctgggcc ctgtgcttca gtgccctggg gatggttcag tgctgcaagg    1140

tcacgtgcca cgagctctgc caccttctgg gcctggggaa ctgccgctgg ctccgctgcc    1200

tcatgcaggg tgcgctcagc ctggacgagg ccctgcggcg gcccctggac ctctgtccca    1260

tctgcctgag gaagctgcag catgtcctgg gtttcaggct catcgagagg taccagagac    1320

tctacacctg gactcaggcg gtggtgggga cgtggcccag ccaggaggcg gggagccgt    1380

cagtgtggga ggacaccccg cctgccagcg ccgactcggg catgtgctgt gagagtgact    1440

cggagcccgg caccagtgtg tcggagcccc tcacccctga tgccgggagt cacaccttcg    1500

cctcggggcc agaggaaggg ctgagctacc tggcagcctc agaggctccg ctgccacctg    1560

ggggccctgc ggaggccatc aaggagcatg aacggtggct ggccatgtgc atccaggccc    1620

tgcagcggga agtggcagag gaggacctgg tgcaggtgga cagagccgtg gacgccctcg    1680

accgctggga gatgttcacg ggccagctcc cggccaccag gcaggaccca cccagcagca    1740

gggacagcgt ggggctgcgc aaggtgctgg gggacaagtt ctcctccctg aggaggaagc    1800

tgagtgcccg aaaactcgcc agagcagagt cggcccccg tccctgggat ggggaagaga    1860

gttagtacag caggggctgc cctacgtctc cttccctaag gatgctggcc agcactgtcc    1920

agtagctgag gccactactg acctgccagg gataaagagg aagggtctgc ctgggtggtg    1980
```

gctcaggcct gtcatcccat cactttgaga ggccaggagt ttgagaccag actgggcaac 2040
atggtgagac tctgcctcta caaaagaaaa attaaaaaat tagctggatg aagtggttca 2100
tgcctgtgtt cccagctatt caggaggctg aggtgggagg attgcttgag cctaggaggt 2160
cgaggctgca gtgggatgtg atcataccac tgtactgcag tctgggccac acagaaagac 2220
tgtctccaga aaaaaaaaag ttctttggag aagccacaga ccacctgtct tcaggcgcct 2280
ccttcaactc ctgagtccca gccagccgct cccaggggcc tgcacacatg gagaggcctc 2340
cctgatcctg ggtgcttctc gtggagtaca agccggactg tgctgaggtt gggacagagc 2400
cccctcccct gcagaggcag aaggaagcag cgtgcgtcct gtctccttcc aggctgtggg 2460
cctgcccttc agttatttat agctggagct ggagaggctg gctcagatga ggagtgaccc 2520
cgggggcaca caggctccac actgccaccc agcttccaag gctgagtctc ctccctaacg 2580
gggaagtgac ggggttttgt ctctatcatc tcaggcgtca accacatgca cacacacact 2640
gtcacgttct gtggcgctaa cagcatcctg atcctgacgg acttcaccgg ggctctccag 2700
gcatctcttc tgacaaacac tgcaggaggt gagggtgtct gacgtgcact gagggcagag 2760
gccccccttat tcctgaggcg gctacagctc accgtgggga agatcaactg tggtgatgtt 2820
tttgggacag tttcttggca aaggtggccg cgctgtcagt accaagtagc tggaggtggt 2880
gatcagatga tctgtctttc cttttttttt cggtctagtt ctgtcagttg ctgagagagg 2940
ggtattattg ccatggctgg gcgtttgatc tgtctccctt tagttttgcc ggattttgct 3000
tcctgcactt tgaagctcct ttacgtccct gcacatttga ttgttgtgtc ttcctgagga 3060
attgaccctt ttattgtcac acgtaccccc tcagcctgtg gtggagggtc tctgggagag 3120
agacttccgg ttctgacagc ggaatccctt cggagtgacg agggcggggt cacagctcgc 3180
gcaccctcat ctggagagag gcaagaacag ggcagcttgg acctttttgtg ggtgggtggc 3240
tcacacggtt atggagggct tctaagaaaa acaaaataca aaactaaaac tagaagggct 3300
atgcaggtga ggtgggctga ggcttccttg tgaatctgac attggtggag gccgactgaa 3360
ggctcccggt cctggtccca ctccgtgttg acttcagaga agcaaagatg cagctcagaa 3420
gtagcattag gatcttcgtc ccgttctctt ttgcgtagct tcaaaaaggc gtaacagtga 3480
cctgggaggg gagatgaaga gctaggcctt tcagaaagtg accaatggaa ggtgccggca 3540
gagcaccctg cagtaacaga aggtgaaagc cggagcctgg tggctgttgc tgcaaacaac 3600
cacccaaaac ttagtggctt aaaatcacca cagtctagct catgaatctg taacttgggc 3660
agagctcggt ggagacggtt tgcccctgtg gctcgactgg agtgttcgtt cacacggctg 3720
ccaagtggaa tttggctggg aatctcaggc cttggttcct gcccacgtga gactctccat 3780
ggaggagggg catcttctta ggaaggcagc tgccataccg tgaggaaacc cgacaaacag 3840
ggcagccaga gccagacagc aggctcctgg tcccagtccc ggaaaatgca aagggacaag 3900
tatgtgttga tttcagagaa gctcagatgt agcattagga ccttcatcca tacccttctc 3960
ttttgcatgg cttctaaagg gcatgacagt gacctgggag gtaactgtgc cagaataaag 4020
aggggagacg aaaaaaagag ggtcactttc agaaagggac ctgggcttcc tcacaatatg 4080
gcggttgccc tcctaaggtg gacatcggga gggtcagatg gaagctctgt ggcctttcct 4140
aactcggcct cacgtcacag agcgtcacct ttcctgcact ccacggcggc agtgacaagg 4200
accccacccc aggttcacgg ggaggggacg tggcagggaa tgtgagacaa cacaatattg 4260
ctgtggccat tcatgaacag tcagtcagcc ccactcggcg ttcactgtgg ggatttggct 4320

-continued

```
ggtgcacctg cgaggtggcc tgacctgttt tccgatttcc ttcatcttct gcaaaaggtt   4380

aaccgctgga gtgatgcgag attaaacaga ggtgataaaa atagaatgcc tggctcatgc   4440

tgagggtggg agcccactgg ggttatgacc aaagcctcgg cgctctctgt acccgtgtcc   4500

tttgaccctc agctgtgatg tgtgtcccaa aaaagcgttt tgaagtggga aggagcaaac   4560

cactaaaaaa aactcctttt atccgcagcg tttaccaact tgcagatgtc agtgaaattt   4620

tttaagacag ctgttagaag gactgttttg aaatgcaact ttgaggaaga gaaattggtt   4680

tccctcctct cccccgtgtt agccccaggt tctgtctgtg ctgtggtgaa gagtgacttg   4740

ggacagtcac caggaaagac gcaaggcaga ggagagagaa tgagggctgc cttctcgagg   4800

aaggtcacag ctcacgaatc tttctaaact taagtgctgc agaagttgaa ctgagattaa   4860

atttagagat gatggtttcc aagacacaca gggccacggt tctttcagtt tttaaacacg   4920

tgcaaagtcc actgaattgc tttctcgtct catctgtcag aagcccctgc attcacaagg   4980

atgggtcttc cagcttgacg atgacctctc ttcggagagc ctcacccatc ttggtaagcc   5040

aagtcagcgg ggcctcatgg agctaaaaat agtttcaggt catgacagat gttatctgta   5100

ttgctgtgtg tgcgatgagt ctggggaagc taacacatgc cttctgaagt ggctagaata   5160

cacactccca cgtcacagcc atgctatgat gaaggggtga gaagcagtgt cccctctgag   5220

gcaaatctct cttcaggcag ccccgcagtc ctcttccgaa atctcattct tttccctctc   5280

ttcctcccca aaaagcccaa actcattgtc agagtgggga gaggggagaa gcagcatcct   5340

gactcctgtc catggtgtga accctgaggg cacgggacag tgagtggagc tctgccacca   5400

cccgtttcca gagcatgggt gaggagggag ggatgccgac ctgttaatat ttgcttcaga   5460

cctttccccg atgaacgaaa tctccaaaag ccttaaacat aaaatggctt agtcaaaaaa   5520

aaaaaaaaaa a                                                        5531
```

<210> SEQ ID NO 4
<211> LENGTH: 498
<212> TYPE: PRT
<213> ORGANISM: Homo sapiens

<400> SEQUENCE: 4

```
Met Leu Gln Cys Arg Pro Ala Gln Glu Phe Ser Phe Gly Pro Arg Ala
1               5                   10                  15

Leu Lys Asp Ala Leu Val Ser Thr Asp Ala Ala Leu Gln Gln Leu Tyr
            20                  25                  30

Val Ser Ala Phe Ser Pro Ala Glu Arg Leu Phe Leu Ala Glu Ala Tyr
        35                  40                  45

Asn Pro Gln Arg Thr Leu Phe Cys Thr Leu Leu Ile Arg Thr Gly Phe
    50                  55                  60

Asp Trp Leu Leu Ser Arg Pro Glu Ala Pro Glu Asp Phe Gln Thr Phe
65                  70                  75                  80

His Ala Ser Leu Gln His Arg Lys Pro Arg Leu Ala Arg Lys His Ile
                85                  90                  95

Tyr Leu Gln Pro Ile Asp Leu Ser Glu Glu Pro Val Gly Ser Ser Leu
            100                 105                 110

Leu His Gln Leu Cys Ser Cys Thr Glu Ala Phe Phe Leu Gly Leu Arg
        115                 120                 125

Val Lys Cys Leu Pro Ser Val Ala Ala Ala Ser Ile Arg Cys Ser Ser
    130                 135                 140

Arg Pro Ser Arg Asp Ser Asp Arg Leu Gln Leu His Thr Asp Gly Ile
145                 150                 155                 160
```

```
Leu Ser Phe Leu Lys Asn Asn Lys Pro Gly Asp Ala Leu Cys Val Leu
                165                 170                 175

Gly Leu Thr Leu Ser Asp Leu Tyr Pro His Glu Ala Trp Ser Phe Thr
            180                 185                 190

Phe Ser Lys Phe Leu Pro Gly His Glu Val Gly Val Cys Ser Phe Ala
        195                 200                 205

Arg Phe Ser Gly Glu Phe Pro Lys Ser Gly Pro Ser Ala Pro Asp Leu
    210                 215                 220

Ala Leu Val Glu Ala Ala Ala Asp Gly Pro Glu Ala Pro Leu Gln Asp
225                 230                 235                 240

Arg Gly Trp Ala Leu Cys Phe Ser Ala Leu Gly Met Val Gln Cys Cys
                245                 250                 255

Lys Val Thr Cys His Glu Leu Cys His Leu Leu Gly Leu Gly Asn Cys
            260                 265                 270

Arg Trp Leu Arg Cys Leu Met Gln Gly Ala Leu Ser Leu Asp Glu Ala
        275                 280                 285

Leu Arg Arg Pro Leu Asp Leu Cys Pro Ile Cys Leu Arg Lys Leu Gln
    290                 295                 300

His Val Leu Gly Phe Arg Leu Ile Glu Arg Tyr Gln Arg Leu Tyr Thr
305                 310                 315                 320

Trp Thr Gln Ala Val Val Gly Thr Trp Pro Ser Gln Glu Ala Gly Glu
                325                 330                 335

Pro Ser Val Trp Glu Asp Thr Pro Pro Ala Ser Ala Asp Ser Gly Met
            340                 345                 350

Cys Cys Glu Ser Asp Ser Glu Pro Gly Thr Ser Val Ser Glu Pro Leu
        355                 360                 365

Thr Pro Asp Ala Gly Ser His Thr Phe Ala Ser Gly Pro Glu Glu Gly
    370                 375                 380

Leu Ser Tyr Leu Ala Ala Ser Glu Ala Pro Leu Pro Pro Gly Gly Pro
385                 390                 395                 400

Ala Glu Ala Ile Lys Glu His Glu Arg Trp Leu Ala Met Cys Ile Gln
                405                 410                 415

Ala Leu Gln Arg Glu Val Ala Glu Glu Asp Leu Val Gln Val Asp Arg
            420                 425                 430

Ala Val Asp Ala Leu Asp Arg Trp Glu Met Phe Thr Gly Gln Leu Pro
        435                 440                 445

Ala Thr Arg Gln Asp Pro Pro Ser Ser Arg Asp Ser Val Gly Leu Arg
    450                 455                 460

Lys Val Leu Gly Asp Lys Phe Ser Ser Leu Arg Arg Lys Leu Ser Ala
465                 470                 475                 480

Arg Lys Leu Ala Arg Ala Glu Ser Ala Pro Arg Pro Trp Asp Gly Glu
                485                 490                 495

Glu Ser
```

<210> SEQ ID NO 5
<211> LENGTH: 1290
<212> TYPE: DNA
<213> ORGANISM: Homo sapiens

<400> SEQUENCE: 5

```
ggctgagcct ataaagcggc aggtgcgcgc cgccctacag acgttcgcac acctgggtgc      60

cagcgcccca gaggtcccgg gacagcccga ggcgccgcgc ccgccgcccc gagctcccca     120

agccttcgag agcggcgcac actcccggtc tccactcgct cttccaacac ccgctcgttt     180
```

```
tggcggcagc tcgtgtccca gagaccgagt tgccccagag accgagacgc cgccgctgcg    240

aaggaccaat gagagccccg ctgctaccgc cggcgccggt ggtgctgtcg ctcttgatac    300

tcggctcagg ccattatgct gctggattgg acctcaatga cacctactct gggaagcgtg    360

aaccattttc tggggaccac agtgctgatg gatttgaggt tacctcaaga agtgagatgt    420

cttcagggag tgagatttcc cctgtgagtg aaatgccttc tagtagtgaa ccgtcctcgg    480

gagccgacta tgactactca gaagagtatg ataacgaacc acaaatacct ggctatattg    540

tcgatgattc agtcagagtt gaacaggtag ttaagccccc ccaaaacaag acggaaagtg    600

aaaatacttc agataaaccc aaaagaaaga aaaagggagg caaaaatgga aaaaatagaa    660

gaaacagaaa gaagaaaaat ccatgtaatg cagaatttca aaatttctgc attcacggag    720

aatgcaaata tatagagcac ctggaagcag taacatgcaa atgtcagcaa gaatatttcg    780

gtgaacggtg tggggaaaag tccatgaaaa ctcacagcat gattgacagt agtttatcaa    840

aaattgcatt agcagccata gctgccttta tgtctgctgt gatcctcaca gctgttgctg    900

ttattacagt ccagcttaga agacaatacg tcaggaaata tgaaggagaa gctgaggaac    960

gaaagaaact tcgacaagag aatggaaatg tacatgctat agcataactg aagataaaat   1020

tacaggatat cacattggag tcactgccaa gtcatagcca taaatgatga gtcggtcctc   1080

tttccagtgg atcataagac aatggaccct tttgttatg atggttttaa actttcaatt   1140

gtcacttttt atgctatttc tgtatataaa ggtgcacgaa ggtaaaaagt atttttcaa    1200

gttgtaaata atttatttaa tatttaatgg aagtgtattt attttacagc tcattaaact   1260

tttttaacca aacagaaaaa aaaaaaaaaa                                    1290
```

<210> SEQ ID NO 6
<211> LENGTH: 252
<212> TYPE: PRT
<213> ORGANISM: Homo sapiens

<400> SEQUENCE: 6

```
Met Arg Ala Pro Leu Leu Pro Pro Ala Pro Val Val Leu Ser Leu Leu
1               5                   10                  15

Ile Leu Gly Ser Gly His Tyr Ala Ala Gly Leu Asp Leu Asn Asp Thr
            20                  25                  30

Tyr Ser Gly Lys Arg Glu Pro Phe Ser Gly Asp His Ser Ala Asp Gly
        35                  40                  45

Phe Glu Val Thr Ser Arg Ser Glu Met Ser Ser Gly Ser Glu Ile Ser
    50                  55                  60

Pro Val Ser Glu Met Pro Ser Ser Ser Glu Pro Ser Ser Gly Ala Asp
65                  70                  75                  80

Tyr Asp Tyr Ser Glu Glu Tyr Asp Asn Glu Pro Gln Ile Pro Gly Tyr
                85                  90                  95

Ile Val Asp Asp Ser Val Arg Val Glu Gln Val Val Lys Pro Pro Gln
            100                 105                 110

Asn Lys Thr Glu Ser Glu Asn Thr Ser Asp Lys Pro Lys Arg Lys Lys
        115                 120                 125

Lys Gly Gly Lys Asn Gly Lys Asn Arg Arg Asn Arg Lys Lys Lys Asn
    130                 135                 140

Pro Cys Asn Ala Glu Phe Gln Asn Phe Cys Ile His Gly Glu Cys Lys
145                 150                 155                 160

Tyr Ile Glu His Leu Glu Ala Val Thr Cys Lys Cys Gln Gln Glu Tyr
                165                 170                 175
```

```
Phe Gly Glu Arg Cys Gly Glu Lys Ser Met Lys Thr His Ser Met Ile
            180                 185                 190

Asp Ser Ser Leu Ser Lys Ile Ala Leu Ala Ala Ile Ala Ala Phe Met
        195                 200                 205

Ser Ala Val Ile Leu Thr Ala Val Ala Val Ile Thr Val Gln Leu Arg
    210                 215                 220

Arg Gln Tyr Val Arg Lys Tyr Glu Gly Glu Ala Glu Glu Arg Lys Lys
225                 230                 235                 240

Leu Arg Gln Glu Asn Gly Asn Val His Ala Ile Ala
                245                 250


<210> SEQ ID NO 7
<211> LENGTH: 1434
<212> TYPE: DNA
<213> ORGANISM: Homo sapiens

<400> SEQUENCE: 7

tataaagatt cactgggact ggtgaggtgg cagtgctcag cagcatccga caggagccct     60

ggcaaacagg acggatttcc aggactctac cagctgccag acacggcagg gagagacccc    120

agacctcctg ggtcctggct gtgggcccgg attgggctcc caagtggcgt ttgactcacg    180

tggggacact cttggaagag acgacaccag gagcctgaat ggggaacgat tctgtcagct    240

acgagtatgg ggattacagc gacctctcgg accgccctgt ggactgcctg gatggcgcct    300

gcctggccat cgacccgctg cgcgtggccc cgctcccact gtatgccgcc atcttcctgg    360

tgggggtgcc gggcaatgcc atggtggcct gggtggctgg gaaggtggcc cgccggaggg    420

tgggtgccac ctggttgctc cacctggccg tggcggattt gctgtgctgt ttgtctctgc    480

ccatcctggc agtgcccatt gcccgtggag gccactggcc gtatggtgca gtgggctgtc    540

gggcgctgcc ctccatcatc ctgctgacca tgtatgccag cgtcctgctc ctggcagctc    600

tcagtgccga cctctgcttc ctggctctcg ggcctgcctg gtggtctacg gttcagcggg    660

cgtgcggggt gcaggtggcc tgtggggcag cctggacact ggccttgctg ctcaccgtgc    720

cctccgccat ctaccgccgg ctgcaccagg agcacttccc agcccggctg cagtgtgtgg    780

tggactacgg cggctcctcc agcaccgaga atgcggtgac tgccatccgg tttctttttg    840

gcttcctggg gcccctggtg gccgtggcca gctgccacag tgccctcctg tgctgggcag    900

cccgacgctg ccggccgctg ggcacagcca ttgtggtggg gtttttttgtc tgctgggcac    960

cctaccacct gctggggctg gtgctcactg tggcggcccc gaactccgca ctcctggcca   1020

gggccctgcg ggctgaaccc ctcatcgtgg gccttgccct cgctcacagc tgcctcaatc   1080

ccatgctctt cctgtatttt gggagggctc aactccgccg gtcactgcca gctgcctgtc   1140

actgggccct gagggagtcc cagggccagg acgaaagtgt ggacagcaag aaatccacca   1200

gccatgacct ggtctcggag atggaggtgt aggctggaga gacattgtgg gtgtgtatct   1260

tcttatctca tttcacaaga ctggcttcag gcatagctgg atccaggagc tcaatgatgt   1320

cttcatttta ttccttcctt cattcaacag atatccatca tgcacttgct atgtgcaagg   1380

ccttttttagg cactagagat atagcagtga ccaaaacaga cacaaatcct gccc         1434


<210> SEQ ID NO 8
<211> LENGTH: 337
<212> TYPE: PRT
<213> ORGANISM: Homo sapiens

<400> SEQUENCE: 8
```

```
Met Gly Asn Asp Ser Val Ser Tyr Glu Tyr Gly Asp Tyr Ser Asp Leu
1               5                   10                  15

Ser Asp Arg Pro Val Asp Cys Leu Asp Gly Ala Cys Leu Ala Ile Asp
            20                  25                  30

Pro Leu Arg Val Ala Pro Leu Pro Leu Tyr Ala Ala Ile Phe Leu Val
        35                  40                  45

Gly Val Pro Gly Asn Ala Met Val Ala Trp Val Ala Gly Lys Val Ala
    50                  55                  60

Arg Arg Arg Val Gly Ala Thr Trp Leu Leu His Leu Ala Val Ala Asp
65                  70                  75                  80

Leu Leu Cys Cys Leu Ser Leu Pro Ile Leu Ala Val Pro Ile Ala Arg
                85                  90                  95

Gly Gly His Trp Pro Tyr Gly Ala Val Gly Cys Arg Ala Leu Pro Ser
            100                 105                 110

Ile Ile Leu Leu Thr Met Tyr Ala Ser Val Leu Leu Leu Ala Ala Leu
        115                 120                 125

Ser Ala Asp Leu Cys Phe Leu Ala Leu Gly Pro Ala Trp Trp Ser Thr
    130                 135                 140

Val Gln Arg Ala Cys Gly Val Gln Val Ala Cys Gly Ala Ala Trp Thr
145                 150                 155                 160

Leu Ala Leu Leu Leu Thr Val Pro Ser Ala Ile Tyr Arg Arg Leu His
                165                 170                 175

Gln Glu His Phe Pro Ala Arg Leu Gln Cys Val Val Asp Tyr Gly Gly
            180                 185                 190

Ser Ser Ser Thr Glu Asn Ala Val Thr Ala Ile Arg Phe Leu Phe Gly
        195                 200                 205

Phe Leu Gly Pro Leu Val Ala Val Ala Ser Cys His Ser Ala Leu Leu
    210                 215                 220

Cys Trp Ala Ala Arg Arg Cys Arg Pro Leu Gly Thr Ala Ile Val Val
225                 230                 235                 240

Gly Phe Phe Val Cys Trp Ala Pro Tyr His Leu Leu Gly Leu Val Leu
                245                 250                 255

Thr Val Ala Ala Pro Asn Ser Ala Leu Leu Ala Arg Ala Leu Arg Ala
            260                 265                 270

Glu Pro Leu Ile Val Gly Leu Ala Leu Ala His Ser Cys Leu Asn Pro
        275                 280                 285

Met Leu Phe Leu Tyr Phe Gly Arg Ala Gln Leu Arg Arg Ser Leu Pro
    290                 295                 300

Ala Ala Cys His Trp Ala Leu Arg Glu Ser Gln Gly Gln Asp Glu Ser
305                 310                 315                 320

Val Asp Ser Lys Lys Ser Thr Ser His Asp Leu Val Ser Glu Met Glu
                325                 330                 335

Val
```

<210> SEQ ID NO 9
<211> LENGTH: 10540
<212> TYPE: DNA
<213> ORGANISM: Homo sapiens

<400> SEQUENCE: 9

```
aggagccgga ggaggagccg ccgccgccgt tgacccggcc gccggccggg agctgggaga     60

gatgcggagc ccggccaccg gcgtccccct cccaacgccg ccgccgccgc tgctgctgct    120

gttgctgctg ctgctgccgc cgccactatt gggagaccaa gtggggccct gtcgttcctt    180
```

-continued

```
ggggtccagg ggacgaggct cttcgggggc ctgcgccccc atgggctggc tctgtccatc    240
ctcagcgtcg aacctctggc tctacaccag ccgctgcagg gatgcgggca ctgagctgac    300
tggccacctg gtaccccacc acgatggcct gagggtttgg tgtccagaat ccgaggccca    360
tattccccta ccaccagctc ctgaaggctg cccctggagc tgtcgcctcc tgggcattgg    420
aggccacctt tccccacagg gcaagctcac actgcccgag gagcacccgt gcttaaaggc    480
tccacggctc agatgccagt cctgcaagct ggcacaggcc cccgggctca gggcagggga    540
aaggtcacca gaagagtccc tgggtgggcg tcggaaaagg aatgtaaata cagcccccca    600
gttccagccc cccagctacc aggccacagt gccggagaac cagccagcag gcacccctgt    660
tgcatccctg agggccatcg acccggacga gggtgaggca ggtcgactgg agtacaccat    720
ggatgccctc tttgatagcc gctccaacca gttcttctcc ctggacccag tcactggtgc    780
agtaaccaca gccgaggagc tggatcgtga gaccaagagc acccacgtct tcagggtcac    840
ggcgcaggac cacggcatgc cccgacgaag tgccctggct acactcacca tcttggttac    900
tgacaccaat gaccatgacc ctgtgttcga gcagcaggag tacaaggaga gcctcaggga    960
gaacctggag gttggctatg aggtgctcac tgtcagggcc acggatggtg atgcccctcc   1020
caatgccaat attctgtacc gcctgctgga ggggtctggg ggcagcccct ctgaagtctt   1080
tgagatcgac cctcgctctg ggtgatccg aacccgtggc cctgtggatc gggaagaggt   1140
ggaatcctac cagctgacgg tagaggcaag tgaccagggt cgggacccgg gtcctcggag   1200
taccacagcc gctgttttcc tttctgtgga ggatgacaat gataatgccc cccagtttag   1260
tgagaagcgc tatgtggtcc aggtgaggga ggatgtgact ccaggggccc cagtactccg   1320
agtcacagcc tcggatcgag acaaggggag caatgccgtg gtgcactata gcatcatgag   1380
tggcaatgct cggggacagt tttatctgga tgcccagact ggagctctgg atgtggtgag   1440
ccctcttgac tatgagacga ccaaggagta caccctacgg gtgcgagcac aggatggtgg   1500
ccgtccccca ctctctaatg tctctggctt ggtgacagta caggtcctgg atatcaacga   1560
caatgccccc atcttcgtca gcaccccttt ccaggctact gtcctggaga gtgtcccctt   1620
aggctacctg gttctccatg tccaggctat cgacgctgat gctggtgaca atgcccgcct   1680
ggaataccgc cttgctgggg tgggacatga cttccccttc accatcaaca atggcacagg   1740
ctggatctct gtggctgctg aactggaccg ggaggaagtt gatttctaca gctttggggt   1800
agaagctcga gaccatggca ctccagcact cactgcctcg gccagtgtca gcgtgactgt   1860
cctggatgtc aacgacaaca atccaacctt tacccaacca gagtacacag tgcggctcaa   1920
tgaggatgca gctgtgggca ccagcgtggt gacggtgtca gctgtggacc gtgatgctca   1980
tagtgtcatc acctaccaga tcaccagtgg caatactcga aaccgcttct ccatcaccag   2040
ccaaagtggt ggtgggctgg tatcccttgc cctgccactg gactacaaac ttgagcggca   2100
gtatgtgttg gctgttaccg cctccgatgg cactcggcag gacacggcac agattgtggt   2160
gaatgtcacc gacgccaaca cccatcgtcc tgtctttcag agctcccact atacagtgaa   2220
tgttaatgag gaccggccgg caggcaccac ggtggtgctg atcagcgcca cggatgagga   2280
cacaggtgag aatgcccgca tcacctactt catggaggac agcatccccc agttccgcat   2340
cgatgcagac acgggggctg tcaccaccca ggctgagctg gactatgaag accaagtgtc   2400
ttacaccctg gccattactg ctcgggacaa tggcattccc cagaagtccg acaccaccta   2460
cctggagatc ctggtgaacg acgtgaatga caatgcccct cagttcctgc gagactccta   2520
```

```
ccagggcagt gtctatgagg atgtgccacc cttcactagc gtcctgcaga tctcagccac   2580
tgatcgtgat tctggactta atggcagggt cttctacacc ttccaaggag gcgacgatgg   2640
agacggtgac tttattgttg agtccacgtc aggcatcgtg cgaacgctac ggaggctgga   2700
tcgagagaac gtggcccagt atgtcttgcg ggcatatgca gtggacaagg ggatgccccc   2760
agcccgcaca cctatggaag tgacagtcac tgtgttggat gtgaatgaca atcccccctgt  2820
ctttgagcag gatgagtttg atgtgtttgt ggaagagaac agccccattg ggctagccgt   2880
ggcccgggtc acagccactg accccgatga aggcaccaat gcccagatta tgtaccagat   2940
tgtggagggc aacatccctg aggtctttca gctggacatc ttctccgggg agctgacagc   3000
cctggtagac ttagactacg aggaccggcc tgagtacgtc ctggtcatcc aggccacgtc   3060
agctcctctg gtgagccggg ctacagtcca cgtccgcctc cttgaccgca atgacaaccc   3120
accagtgctg ggcaactttg agatcctttt caacaactat gtcaccaatc gctcaagcag   3180
cttccctggg ggtgccattg gccgagtacc tgcccatgac cctgatatct cagatagtct   3240
gacttacagc tttgagcggg gaaatgaact cagcctggtc ctgctcaatg cctccacggg   3300
tgagctgaag ctaagccgcg cactggacaa caaccggcct ctggaggcca tcatgagcgt   3360
gctggtgtca gacggcgtac acagcgtgac cgcccagtgc gcgctgcgtg tgaccatcat   3420
caccgatgag atgctcaccc acagcatcac gctgcgcctg gaggacatgt cacccgagcg   3480
cttcctgtca ccactgctag gcctcttcat ccaggcggtg gccgccacgc tggccacgcc   3540
accggaccac gtggtggtct tcaacgtaca gcgggacacc gacgcccccg gggccacat    3600
cctcaacgtg agcctgtcgg tgggccagcc gccagggccc gggggcgggc cgcccttcct   3660
gccctctgag gacctgcagg agcgcctata cctcaaccgc agcctgctga cggccatctc   3720
ggcacagcgc gtgctgccct tcgacgacaa catctgcctg cgggagccct gcgagaacta   3780
catgcgctgc gtgtcggtgc tgcgcttcga ctcctccgcg cccttcatcg cctcctcctc   3840
cgtgctcttc cggcccatcc accccgtcgg agggctgcgc tgccgctgcc cgcccggctt   3900
cacgggtgac tactgcgaga ccgaggtgga cctctgctac tcgcggccct gtggccccca   3960
cgggcgctgc cgcagccgcg agggcggcta cacctgcctc tgtcgtgatg gctacacggg   4020
tgagcactgt gaggtgagtg ctcgctcagg ccgttgcacc ccgggtgtct gcaagaatgg   4080
gggcacctgt gtcaacctgc tggtgggcgg tttcaagtgc gattgcccat ctggagactt   4140
cgagaagccc tactgccagg tgaccacgcg cagcttcccc gcccactcct tcatcacctt   4200
tcgcggcctg cgccagcgtt tccacttcac cctggccctc tcgtttgcca caaaggagcg   4260
cgacgggttg ctgttgtaca atgggcgttt caatgagaag catgactttg tggccctcga   4320
ggtgatccag gagcaggtcc agctcacctt ctctgcaggg gagtcaacca ccacggtgtc   4380
cccattcgtg cccggaggag tcagtgatgg ccagtggcat acggtgcagc tgaaatacta   4440
caataagcca ctgttgggtc agacagggct cccacagggc ccatcagagc agaaggtggc   4500
tgtggtgacc gtggatggct gtgacacagg agtggccttg cgcttcggat ctgtcctggg   4560
caactactcc tgtgctgccc agggcaccca gggtggcagc aagaagtctc tggatctgac   4620
ggggcccctg ctactaggcg gggtgcctga cctgcccgag agcttcccag tccgaatgcg   4680
gcagttcgtg ggctgcatgc ggaacctgca ggtggacagc cggcacatag acatggctga   4740
cttcattgcc aacaatggca ccgtgcctgg ctgccctgcc aagaagaacg tgtgtgacag   4800
caacacttgc cacaatgggg gcacttgcgt gaaccagtgg gacgcgttca gctgcgagtg   4860
ccccctgggc tttgggggca agagctgcgc ccaggaaatg gccaatccac agcacttcct   4920
```

gggcagcagc ctggtggcct ggcatggcct ctcgctgccc atctcccaac cctggtacct 4980
cagcctcatg ttccgcacgc gccaggccga cggtgtcctg ctgcaggcca tcaccagggg 5040
gcgcagcacc atcaccctac agctacgaga gggccacgtg atgctgagcg tggagggcac 5100
agggcttcag gcctcctctc tccgtctgga gccaggccgg gccaatgacg gtgactggca 5160
ccatgcacag ctggcactgg gagccagcgg ggggcccggc catgccattc tgtccttcga 5220
ttatgggcag cagagagcag agggcaacct gggcccccgg ctgcatggtc tgcacctgag 5280
caacataaca gtgggcggaa tacctgggcc agccggcggt gtggcccgtg gctttcgggg 5340
ctgtttgcag ggtgtgcggg tgagcgatac gccggagggg gttaacagcc tggatcccag 5400
ccatggggag agcatcaacg tggagcaagg ctgtagcctg cctgaccctt gtgactcaaa 5460
cccgtgtcct gctaacagct attgcagcaa cgactgggac agctattcct gcagctgtga 5520
tccaggttac tatggtgaca actgtactaa tgtgtgtgac ctgaacccgt gtgagcacca 5580
gtctgtgtgt acccgcaagc ccagtgcccc ccatggctat acctgcgagt gtccccccaaa 5640 ttaccttggg ccatactgtg agaccaggat tgaccagcct tgtccccgtg gctggtgggg 5700
acatcccaca tgtggcccat gcaactgtga tgtcagcaaa ggctttgacc cagactgcaa 5760
caagacaagc ggcgagtgcc actgcaagga gaaccactac cggcccccag gcagccccac 5820
ctgcctcttg tgtgactgct accccacagg ctccttgtcc agagtctgtg accctgagga 5880
tggccagtgt ccatgcaagc caggtgtcat cgggcgtcag tgtgaccgct gtgacaaccc 5940
ttttgctgag gtcaccacca atggctgtga agtgaattat gacagctgcc cacgagcgat 6000
tgaggctggg atctggtggc cccgtacccg cttcgggctg cctgctgctg ctccctgtcc 6060
caaaggctcc tttgggactg ctgtgcgcca ctgtgatgag cacagggggt ggctcccccc 6120
aaacctcttc aactgcacgt ccatcacctt ctcagaactg aagggcttcg ctgagcggct 6180
acagcggaat gagtcaggcc tagactcagg gcgctcccag cagctagccc tgctcctgcg 6240
caacgccacg cagcacacag ctggctactt cggcagcgac gtcaaggtgg cctaccagct 6300
ggccacgcgg ctgctggccc acgagagcac ccagcggggc tttgggctgt ctgccacaca 6360
ggacgtgcac ttcactgaga atctgctgcg ggtgggcagc gccctcctgg acacagccaa 6420
caagcggcac tgggagctga tccagcagac agagggtggc accgcctggc tgctccagca 6480
ctatgaggcc tacgccagtg ccctggccca gaacatgcgg cacacctacc taagcccctt 6540
caccatcgtc acgcccaaca ttgtcatctc cgtagtgcgc ttggacaaag ggaactttgc 6600
tggggccaag ctgccccgct acgaggccct gcgtggggag cagcccccgg accttgagac 6660
aacagtcatt ctgcctgagt ctgtcttcag agagacgccc cccgtggtca ggcccgcagg 6720
ccccggagag gcccaggagc cagaggagct ggcacggcga cagcgacggc acccggagct 6780
gagccagggt gaggctgtgg ccagcgtcat catctaccgc accctggccg ggctactgcc 6840
tcataactat gaccctgaca agcgcagctt gagagtcccc aaacgcccga tcatcaacac 6900
acccgtggtg agcatcagcg tccatgatga tgaggagctt ctgccccggg ccctggacaa 6960
acccgtcacg gtgcagttcc gcctgctgga gacagaggag cggaccaagc ccatctgtgt 7020
cttctggaac cattcaatcc tggtcagtgg cacaggtggc tggtcggcca gaggctgtga 7080
agtcgtcttc cgcaatgaga gccacgtcag ctgccagtgc aaccacatga cgagcttcgc 7140
tgtgctcatg gacgtttctc ggcgggagaa tggggagatc ctgccactga agacactgac 7200
atacgtggct ctaggtgtca ccttggctgc ccttctgctc accttcttct tcctcactct 7260

-continued

```
cttgcgtatc ctgcgctcca accaacacgg catccgacgt aacctgacag ctgccctggg   7320
cctggctcag ctggtcttcc tcctgggaat caaccaggct gacctccctt ttgcctgcac   7380
agtcattgcc atcctgctgc acttcctgta cctctgcacc ttttcctggg ctctgctgga   7440
ggccttgcac ctgtaccggg cactcactga ggtgcgcgat gtcaacaccg gccccatgcg   7500
cttctactac atgctgggct ggggcgtgcc tgccttcatc acagggctag ccgtgggcct   7560
ggaccccgag ggctacggga accctgactt ctgctggctc tccatctatg acacgctcat   7620
ctggagtttt gctggcccgg tggcctttgc cgtctcgatg agtgtcttcc tgtacatcct   7680
ggcggcccgg gcctcctgtg ctgcccagcg gcagggcttt gagaagaaag gtcctgtctc   7740
gggcctgcag ccctccttcg ccgtcctcct gctgctgagc gccacgtggc tgctggcact   7800
gctctctgtc aacagcgaca ccctcctctt ccactacctc tttgctacct gcaattgcat   7860
ccagggcccc ttcatcttcc tctcctatgt ggtgcttagc aaggaggtcc ggaaagcact   7920
caagcttgcc tgcagccgca agcccagccc tgaccctgct ctgaccacca agtccaccct   7980
gacctcgtcc tacaactgcc ccagccccta cgcagatggg cggctgtacc agccctacgg   8040
agactcggcc ggctctctgc acagcaccag tcgctcgggc aagagtcagc ccagctacat   8100
ccccttcttg ctgagggagg agtccgcact gaaccctggc caagggcccc ctggcctggg   8160
ggatccaggc agcctgttcc tggaaggtca agaccagcag catgatcctg acacggactc   8220
cgacagtgac ctgtccttag aagacgacca gagtggctcc tatgcctcta cccactcatc   8280
agacagtgag gaggaagaag aggaggagga agaggaggcc gccttccctg gagagcaggg   8340
ctgggatagc ctgctggggc ctggagcaga gagactgccc ctgcacagta ctcccaagga   8400
tgggggccca gggcctggca aggccccctg gccaggagac tttgggacca cagcaaaaga   8460
gagtagtggc aacggggccc ctgaggagcg gctgcgggag aatggagatg ccctgtctcg   8520
agaggggtcc ctaggccccc ttccaggctc ttctgcccag cctcacaaag gcatccttaa   8580
gaagaagtgt ctgcccacca tcagcgagaa gagcagcctc ctgcggctcc ccctggagca   8640
atgcacaggg tcttcccggg gctcctccgc tagtgagggc agccggggag gcccccctcc   8700
ccgcccaccg ccccggcaga gcctccagga gcagctgaac ggggtcatgc ccatcgccat   8760
gagcatcaag gcaggcacgg tggatgagga ctcgtcaggc tccgaatttc tcttctttaa   8820
cttcctgcat taaccctggg ccgtggttcc tacgcccgag gctcccttcc cttccccagc   8880
cgcactcatg ccctgctcct gtcttgtgct ttatcctgcc ccgctcccca tcgcctgccc   8940
gcagcagcga cgaaacgtcc atctgaggag cctgggcctt gccgggaggg gtactcaccc   9000
cacctaaggc catctagtgc caactccccc cccaccattc ccctcactgc actttggacc   9060
cctggggcca acatctccaa gacaaagttt ttcagaaaag aggaaaaaaa gaatttaaaa   9120
aaggatctcc actcttcatg acttcaggga ttcatttttt ttatacgctg gaaattgact   9180
cccctttccc ttcccaaaga ggataggacc tcccaggatg cttcccagcc tctcctcagt   9240
ttcccatctg ctgtgcctct gggaggagag ggactcctgg ggggcctgcc cctcatacgc   9300
catcaccaaa aggaaaggac aaagccacac gcagccaggg cttcacaccc ttcaggctgc   9360
acccgggcag gcctcagaac ggtgaggggc cagggcaaag ggtgtgcctc gtcctgcccg   9420
cactgcctct cccaggaact ggaaaagccc tgtccggtga gggggcagaa ggactcagcg   9480
cccctggacc cccaaatgct gcatgaacac attttcaggg gagcctgtgc cccccaggcgg   9540
gggtcgggca gccccagccc ctctcctttt cctggactct ggccgtgcgc ggcagcccag   9600
gtgtttgctc agttgctgac ccaaaagtgc ttcatttttc gtgcccgccc cgcgccccgg   9660
```

-continued

```
gcaggccagt catgtgttaa gttgcgcttc tttgctgtga tgtgggtggg ggaggaagag   9720

taaacacagt gctggctcgg ctgccctgag ggtgctcaat caagcacagg tttcaagtct   9780

gggttctggt gtccactcac ccaccccacc ccccaaaatc agacaaatgc tactttgtct   9840

aacctgctgt ggcctctgag acatgttcta tttttaaccc cttcttggaa ttggctctct   9900

tcttcaaagg accaggtcct gttcctcttt ctccccgact ccaccccagc tccctgtgaa   9960

gagagagtta atatatttgt tttatttatt tgctttttgt gttgggatgg gttcgtgtcc  10020

agtcccgggg gtctgatatg gccatcacag gctgggtgtt cccagcagcc ctggcttggg  10080

ggcttgacgc ccttcccctt gccccaggcc atcatctccc cacctctcct cccctctcct  10140

cagttttgcc gactgctttt catctgagtc accatttact ccaagcatgt attccagact  10200

tgtcactgac tttccttctg gagcaggtgg ctagaaaaag aggctgtggg caggaaagaa  10260

aggctcctgt ttctcatttg tgaggccagc ctctggcttt tctgccgtgg attctccccc  10320

gtcttctccc ctcagcaatt cctgcaaagg gttaaaaatt taactggttt ttactactga  10380

tgacttgatt taaaaaaaat acaaagatgc tggatgctaa cttggtacta accatcagat  10440

tgtacagttt ggttgttgct gtaaataggg tagcgttttg ttgttgttgt tttttcatgc  10500

cccatactac tgaataaact agttctgtgc gggtacagca                        10540
```

<210> SEQ ID NO 10
<211> LENGTH: 2923
<212> TYPE: PRT
<213> ORGANISM: Homo sapiens

<400> SEQUENCE: 10

```
Met Arg Ser Pro Ala Thr Gly Val Pro Leu Pro Thr Pro Pro Pro Pro
1               5                   10                  15

Leu Leu Leu Leu Leu Leu Leu Leu Leu Pro Pro Pro Leu Leu Gly Asp
            20                  25                  30

Gln Val Gly Pro Cys Arg Ser Leu Gly Ser Arg Gly Arg Gly Ser Ser
        35                  40                  45

Gly Ala Cys Ala Pro Met Gly Trp Leu Cys Pro Ser Ser Ala Ser Asn
    50                  55                  60

Leu Trp Leu Tyr Thr Ser Arg Cys Arg Asp Ala Gly Thr Glu Leu Thr
65                  70                  75                  80

Gly His Leu Val Pro His His Asp Gly Leu Arg Val Trp Cys Pro Glu
                85                  90                  95

Ser Glu Ala His Ile Pro Leu Pro Pro Ala Pro Glu Gly Cys Pro Trp
            100                 105                 110

Ser Cys Arg Leu Leu Gly Ile Gly Gly His Leu Ser Pro Gln Gly Lys
        115                 120                 125

Leu Thr Leu Pro Glu Glu His Pro Cys Leu Lys Ala Pro Arg Leu Arg
    130                 135                 140

Cys Gln Ser Cys Lys Leu Ala Gln Ala Pro Gly Leu Arg Ala Gly Glu
145                 150                 155                 160

Arg Ser Pro Glu Glu Ser Leu Gly Gly Arg Arg Lys Arg Asn Val Asn
                165                 170                 175

Thr Ala Pro Gln Phe Gln Pro Pro Ser Tyr Gln Ala Thr Val Pro Glu
            180                 185                 190

Asn Gln Pro Ala Gly Thr Pro Val Ala Ser Leu Arg Ala Ile Asp Pro
        195                 200                 205

Asp Glu Gly Glu Ala Gly Arg Leu Glu Tyr Thr Met Asp Ala Leu Phe
```

-continued

```
    210                 215                 220

Asp Ser Arg Ser Asn Gln Phe Phe Ser Leu Asp Pro Val Thr Gly Ala
225                 230                 235                 240

Val Thr Thr Ala Glu Glu Leu Asp Arg Glu Thr Lys Ser Thr His Val
                245                 250                 255

Phe Arg Val Thr Ala Gln Asp His Gly Met Pro Arg Arg Ser Ala Leu
            260                 265                 270

Ala Thr Leu Thr Ile Leu Val Thr Asp Thr Asn Asp His Asp Pro Val
        275                 280                 285

Phe Glu Gln Gln Glu Tyr Lys Glu Ser Leu Arg Glu Asn Leu Glu Val
    290                 295                 300

Gly Tyr Glu Val Leu Thr Val Arg Ala Thr Asp Gly Asp Ala Pro Pro
305                 310                 315                 320

Asn Ala Asn Ile Leu Tyr Arg Leu Leu Glu Gly Ser Gly Gly Ser Pro
                325                 330                 335

Ser Glu Val Phe Glu Ile Asp Pro Arg Ser Gly Val Ile Arg Thr Arg
            340                 345                 350

Gly Pro Val Asp Arg Glu Glu Val Glu Ser Tyr Gln Leu Thr Val Glu
        355                 360                 365

Ala Ser Asp Gln Gly Arg Asp Pro Gly Pro Arg Ser Thr Thr Ala Ala
    370                 375                 380

Val Phe Leu Ser Val Glu Asp Asp Asn Asp Asn Ala Pro Gln Phe Ser
385                 390                 395                 400

Glu Lys Arg Tyr Val Val Gln Val Arg Glu Asp Val Thr Pro Gly Ala
                405                 410                 415

Pro Val Leu Arg Val Thr Ala Ser Asp Arg Asp Lys Gly Ser Asn Ala
            420                 425                 430

Val Val His Tyr Ser Ile Met Ser Gly Asn Ala Arg Gly Gln Phe Tyr
        435                 440                 445

Leu Asp Ala Gln Thr Gly Ala Leu Asp Val Val Ser Pro Leu Asp Tyr
    450                 455                 460

Glu Thr Thr Lys Glu Tyr Thr Leu Arg Val Arg Ala Gln Asp Gly Gly
465                 470                 475                 480

Arg Pro Pro Leu Ser Asn Val Ser Gly Leu Val Thr Val Gln Val Leu
                485                 490                 495

Asp Ile Asn Asp Asn Ala Pro Ile Phe Val Ser Thr Pro Phe Gln Ala
            500                 505                 510

Thr Val Leu Glu Ser Val Pro Leu Gly Tyr Leu Val Leu His Val Gln
        515                 520                 525

Ala Ile Asp Ala Asp Ala Gly Asp Asn Ala Arg Leu Glu Tyr Arg Leu
    530                 535                 540

Ala Gly Val Gly His Asp Phe Pro Phe Thr Ile Asn Asn Gly Thr Gly
545                 550                 555                 560

Trp Ile Ser Val Ala Ala Glu Leu Asp Arg Glu Glu Val Asp Phe Tyr
                565                 570                 575

Ser Phe Gly Val Glu Ala Arg Asp His Gly Thr Pro Ala Leu Thr Ala
            580                 585                 590

Ser Ala Ser Val Ser Val Thr Val Leu Asp Val Asn Asp Asn Asn Pro
        595                 600                 605

Thr Phe Thr Gln Pro Glu Tyr Thr Val Arg Leu Asn Glu Asp Ala Ala
    610                 615                 620

Val Gly Thr Ser Val Val Thr Val Ser Ala Val Asp Arg Asp Ala His
625                 630                 635                 640
```

Ser Val Ile Thr Tyr Gln Ile Thr Ser Gly Asn Thr Arg Asn Arg Phe
645 650 655

Ser Ile Thr Ser Gln Ser Gly Gly Gly Leu Val Ser Leu Ala Leu Pro
660 665 670

Leu Asp Tyr Lys Leu Glu Arg Gln Tyr Val Leu Ala Val Thr Ala Ser
675 680 685

Asp Gly Thr Arg Gln Asp Thr Ala Gln Ile Val Val Asn Val Thr Asp
690 695 700

Ala Asn Thr His Arg Pro Val Phe Gln Ser Ser His Tyr Thr Val Asn
705 710 715 720

Val Asn Glu Asp Arg Pro Ala Gly Thr Thr Val Val Leu Ile Ser Ala
725 730 735

Thr Asp Glu Asp Thr Gly Glu Asn Ala Arg Ile Thr Tyr Phe Met Glu
740 745 750

Asp Ser Ile Pro Gln Phe Arg Ile Asp Ala Asp Thr Gly Ala Val Thr
755 760 765

Thr Gln Ala Glu Leu Asp Tyr Glu Asp Gln Val Ser Tyr Thr Leu Ala
770 775 780

Ile Thr Ala Arg Asp Asn Gly Ile Pro Gln Lys Ser Asp Thr Thr Tyr
785 790 795 800

Leu Glu Ile Leu Val Asn Asp Val Asn Asp Asn Ala Pro Gln Phe Leu
805 810 815

Arg Asp Ser Tyr Gln Gly Ser Val Tyr Glu Asp Val Pro Pro Phe Thr
820 825 830

Ser Val Leu Gln Ile Ser Ala Thr Asp Arg Asp Ser Gly Leu Asn Gly
835 840 845

Arg Val Phe Tyr Thr Phe Gln Gly Gly Asp Asp Gly Asp Gly Asp Phe
850 855 860

Ile Val Glu Ser Thr Ser Gly Ile Val Arg Thr Leu Arg Arg Leu Asp
865 870 875 880

Arg Glu Asn Val Ala Gln Tyr Val Leu Arg Ala Tyr Ala Val Asp Lys
885 890 895

Gly Met Pro Pro Ala Arg Thr Pro Met Glu Val Thr Val Thr Val Leu
900 905 910

Asp Val Asn Asp Asn Pro Pro Val Phe Glu Gln Asp Glu Phe Asp Val
915 920 925

Phe Val Glu Glu Asn Ser Pro Ile Gly Leu Ala Val Ala Arg Val Thr
930 935 940

Ala Thr Asp Pro Asp Glu Gly Thr Asn Ala Gln Ile Met Tyr Gln Ile
945 950 955 960

Val Glu Gly Asn Ile Pro Glu Val Phe Gln Leu Asp Ile Phe Ser Gly
965 970 975

Glu Leu Thr Ala Leu Val Asp Leu Asp Tyr Glu Asp Arg Pro Glu Tyr
980 985 990

Val Leu Val Ile Gln Ala Thr Ser Ala Pro Leu Val Ser Arg Ala Thr
995 1000 1005

Val His Val Arg Leu Leu Asp Arg Asn Asp Asn Pro Pro Val Leu
1010 1015 1020

Gly Asn Phe Glu Ile Leu Phe Asn Asn Tyr Val Thr Asn Arg Ser
1025 1030 1035

Ser Ser Phe Pro Gly Gly Ala Ile Gly Arg Val Pro Ala His Asp
1040 1045 1050

-continued

```
Pro Asp  Ile Ser Asp Ser Leu  Thr Tyr Ser Phe Glu  Arg Gly Asn
    1055                 1060                 1065

Glu Leu  Ser Leu Val Leu Leu  Asn Ala Ser Thr Gly  Glu Leu Lys
    1070                 1075                 1080

Leu Ser  Arg Ala Leu Asp Asn  Asn Arg Pro Leu Glu  Ala Ile Met
    1085                 1090                 1095

Ser Val  Leu Val Ser Asp Gly  Val His Ser Val Thr  Ala Gln Cys
    1100                 1105                 1110

Ala Leu  Arg Val Thr Ile Ile  Thr Asp Glu Met Leu  Thr His Ser
    1115                 1120                 1125

Ile Thr  Leu Arg Leu Glu Asp  Met Ser Pro Glu Arg  Phe Leu Ser
    1130                 1135                 1140

Pro Leu  Leu Gly Leu Phe Ile  Gln Ala Val Ala Ala  Thr Leu Ala
    1145                 1150                 1155

Thr Pro  Pro Asp His Val Val  Val Phe Asn Val Gln  Arg Asp Thr
    1160                 1165                 1170

Asp Ala  Pro Gly Gly His Ile  Leu Asn Val Ser Leu  Ser Val Gly
    1175                 1180                 1185

Gln Pro  Pro Gly Pro Gly Gly  Gly Pro Pro Phe Leu  Pro Ser Glu
    1190                 1195                 1200

Asp Leu  Gln Glu Arg Leu Tyr  Leu Asn Arg Ser Leu  Leu Thr Ala
    1205                 1210                 1215

Ile Ser  Ala Gln Arg Val Leu  Pro Phe Asp Asp Asn  Ile Cys Leu
    1220                 1225                 1230

Arg Glu  Pro Cys Glu Asn Tyr  Met Arg Cys Val Ser  Val Leu Arg
    1235                 1240                 1245

Phe Asp  Ser Ser Ala Pro Phe  Ile Ala Ser Ser Ser  Val Leu Phe
    1250                 1255                 1260

Arg Pro  Ile His Pro Val Gly  Gly Leu Arg Cys Arg  Cys Pro Pro
    1265                 1270                 1275

Gly Phe  Thr Gly Asp Tyr Cys  Glu Thr Glu Val Asp  Leu Cys Tyr
    1280                 1285                 1290

Ser Arg  Pro Cys Gly Pro His  Gly Arg Cys Arg Ser  Arg Glu Gly
    1295                 1300                 1305

Gly Tyr  Thr Cys Leu Cys Arg  Asp Gly Tyr Thr Gly  Glu His Cys
    1310                 1315                 1320

Glu Val  Ser Ala Arg Ser Gly  Arg Cys Thr Pro Gly  Val Cys Lys
    1325                 1330                 1335

Asn Gly  Gly Thr Cys Val Asn  Leu Leu Val Gly Gly  Phe Lys Cys
    1340                 1345                 1350

Asp Cys  Pro Ser Gly Asp Phe  Glu Lys Pro Tyr Cys  Gln Val Thr
    1355                 1360                 1365

Thr Arg  Ser Phe Pro Ala His  Ser Phe Ile Thr Phe  Arg Gly Leu
    1370                 1375                 1380

Arg Gln  Arg Phe His Phe Thr  Leu Ala Leu Ser Phe  Ala Thr Lys
    1385                 1390                 1395

Glu Arg  Asp Gly Leu Leu Leu  Tyr Asn Gly Arg Phe  Asn Glu Lys
    1400                 1405                 1410

His Asp  Phe Val Ala Leu Glu  Val Ile Gln Glu Gln  Val Gln Leu
    1415                 1420                 1425

Thr Phe  Ser Ala Gly Glu Ser  Thr Thr Thr Val Ser  Pro Phe Val
    1430                 1435                 1440

Pro Gly  Gly Val Ser Asp Gly  Gln Trp His Thr Val  Gln Leu Lys
```

```
    1445                1450                1455

Tyr Tyr  Asn Lys Pro Leu Leu  Gly Gln Thr Gly Leu  Pro Gln Gly
    1460                1465                1470

Pro Ser  Glu Gln Lys Val Ala  Val Val Thr Val Asp  Gly Cys Asp
    1475                1480                1485

Thr Gly  Val Ala Leu Arg Phe  Gly Ser Val Leu Gly  Asn Tyr Ser
    1490                1495                1500

Cys Ala  Ala Gln Gly Thr Gln  Gly Gly Ser Lys Lys  Ser Leu Asp
    1505                1510                1515

Leu Thr  Gly Pro Leu Leu Leu  Gly Gly Val Pro Asp  Leu Pro Glu
    1520                1525                1530

Ser Phe  Pro Val Arg Met Arg  Gln Phe Val Gly Cys  Met Arg Asn
    1535                1540                1545

Leu Gln  Val Asp Ser Arg His  Ile Asp Met Ala Asp  Phe Ile Ala
    1550                1555                1560

Asn Asn  Gly Thr Val Pro Gly  Cys Pro Ala Lys Lys  Asn Val Cys
    1565                1570                1575

Asp Ser  Asn Thr Cys His Asn  Gly Gly Thr Cys Val  Asn Gln Trp
    1580                1585                1590

Asp Ala  Phe Ser Cys Glu Cys  Pro Leu Gly Phe Gly  Gly Lys Ser
    1595                1600                1605

Cys Ala  Gln Glu Met Ala Asn  Pro Gln His Phe Leu  Gly Ser Ser
    1610                1615                1620

Leu Val  Ala Trp His Gly Leu  Ser Leu Pro Ile Ser  Gln Pro Trp
    1625                1630                1635

Tyr Leu  Ser Leu Met Phe Arg  Thr Arg Gln Ala Asp  Gly Val Leu
    1640                1645                1650

Leu Gln  Ala Ile Thr Arg Gly  Arg Ser Thr Ile Thr  Leu Gln Leu
    1655                1660                1665

Arg Glu  Gly His Val Met Leu  Ser Val Glu Gly Thr  Gly Leu Gln
    1670                1675                1680

Ala Ser  Ser Leu Arg Leu Glu  Pro Gly Arg Ala Asn  Asp Gly Asp
    1685                1690                1695

Trp His  His Ala Gln Leu Ala  Leu Gly Ala Ser Gly  Gly Pro Gly
    1700                1705                1710

His Ala  Ile Leu Ser Phe Asp  Tyr Gly Gln Gln Arg  Ala Glu Gly
    1715                1720                1725

Asn Leu  Gly Pro Arg Leu His  Gly Leu His Leu Ser  Asn Ile Thr
    1730                1735                1740

Val Gly  Gly Ile Pro Gly Pro  Ala Gly Gly Val Ala  Arg Gly Phe
    1745                1750                1755

Arg Gly  Cys Leu Gln Gly Val  Arg Val Ser Asp Thr  Pro Glu Gly
    1760                1765                1770

Val Asn  Ser Leu Asp Pro Ser  His Gly Glu Ser Ile  Asn Val Glu
    1775                1780                1785

Gln Gly  Cys Ser Leu Pro Asp  Pro Cys Asp Ser Asn  Pro Cys Pro
    1790                1795                1800

Ala Asn  Ser Tyr Cys Ser Asn  Asp Trp Asp Ser Tyr  Ser Cys Ser
    1805                1810                1815

Cys Asp  Pro Gly Tyr Tyr Gly  Asp Asn Cys Thr Asn  Val Cys Asp
    1820                1825                1830

Leu Asn  Pro Cys Glu His Gln  Ser Val Cys Thr Arg  Lys Pro Ser
    1835                1840                1845
```

-continued

```
Ala Pro His Gly Tyr Thr Cys Glu Cys Pro Pro Asn Tyr Leu Gly
    1850                1855                1860

Pro Tyr Cys Glu Thr Arg Ile Asp Gln Pro Cys Pro Arg Gly Trp
    1865                1870                1875

Trp Gly His Pro Thr Cys Gly Pro Cys Asn Cys Asp Val Ser Lys
    1880                1885                1890

Gly Phe Asp Pro Asp Cys Asn Lys Thr Ser Gly Glu Cys His Cys
    1895                1900                1905

Lys Glu Asn His Tyr Arg Pro Pro Gly Ser Pro Thr Cys Leu Leu
    1910                1915                1920

Cys Asp Cys Tyr Pro Thr Gly Ser Leu Ser Arg Val Cys Asp Pro
    1925                1930                1935

Glu Asp Gly Gln Cys Pro Cys Lys Pro Gly Val Ile Gly Arg Gln
    1940                1945                1950

Cys Asp Arg Cys Asp Asn Pro Phe Ala Glu Val Thr Thr Asn Gly
    1955                1960                1965

Cys Glu Val Asn Tyr Asp Ser Cys Pro Arg Ala Ile Glu Ala Gly
    1970                1975                1980

Ile Trp Trp Pro Arg Thr Arg Phe Gly Leu Pro Ala Ala Ala Pro
    1985                1990                1995

Cys Pro Lys Gly Ser Phe Gly Thr Ala Val Arg His Cys Asp Glu
    2000                2005                2010

His Arg Gly Trp Leu Pro Pro Asn Leu Phe Asn Cys Thr Ser Ile
    2015                2020                2025

Thr Phe Ser Glu Leu Lys Gly Phe Ala Glu Arg Leu Gln Arg Asn
    2030                2035                2040

Glu Ser Gly Leu Asp Ser Gly Arg Ser Gln Gln Leu Ala Leu Leu
    2045                2050                2055

Leu Arg Asn Ala Thr Gln His Thr Ala Gly Tyr Phe Gly Ser Asp
    2060                2065                2070

Val Lys Val Ala Tyr Gln Leu Ala Thr Arg Leu Leu Ala His Glu
    2075                2080                2085

Ser Thr Gln Arg Gly Phe Gly Leu Ser Ala Thr Gln Asp Val His
    2090                2095                2100

Phe Thr Glu Asn Leu Leu Arg Val Gly Ser Ala Leu Leu Asp Thr
    2105                2110                2115

Ala Asn Lys Arg His Trp Glu Leu Ile Gln Gln Thr Glu Gly Gly
    2120                2125                2130

Thr Ala Trp Leu Leu Gln His Tyr Glu Ala Tyr Ala Ser Ala Leu
    2135                2140                2145

Ala Gln Asn Met Arg His Thr Tyr Leu Ser Pro Phe Thr Ile Val
    2150                2155                2160

Thr Pro Asn Ile Val Ile Ser Val Val Arg Leu Asp Lys Gly Asn
    2165                2170                2175

Phe Ala Gly Ala Lys Leu Pro Arg Tyr Glu Ala Leu Arg Gly Glu
    2180                2185                2190

Gln Pro Pro Asp Leu Glu Thr Thr Val Ile Leu Pro Glu Ser Val
    2195                2200                2205

Phe Arg Glu Thr Pro Pro Val Val Arg Pro Ala Gly Pro Gly Glu
    2210                2215                2220

Ala Gln Glu Pro Glu Glu Leu Ala Arg Arg Gln Arg Arg His Pro
    2225                2230                2235
```

```
Glu Leu  Ser Gln Gly Glu Ala  Val Ala Ser Val Ile  Ile Tyr Arg
    2240                 2245                 2250

Thr Leu  Ala Gly Leu Leu Pro  His Asn Tyr Asp Pro  Asp Lys Arg
    2255                 2260                 2265

Ser Leu  Arg Val Pro Lys Arg  Pro Ile Ile Asn Thr  Pro Val Val
    2270                 2275                 2280

Ser Ile  Ser Val His Asp Asp  Glu Glu Leu Leu Pro  Arg Ala Leu
    2285                 2290                 2295

Asp Lys  Pro Val Thr Val Gln  Phe Arg Leu Leu Glu  Thr Glu Glu
    2300                 2305                 2310

Arg Thr  Lys Pro Ile Cys Val  Phe Trp Asn His Ser  Ile Leu Val
    2315                 2320                 2325

Ser Gly  Thr Gly Gly Trp Ser  Ala Arg Gly Cys Glu  Val Val Phe
    2330                 2335                 2340

Arg Asn  Glu Ser His Val Ser  Cys Gln Cys Asn His  Met Thr Ser
    2345                 2350                 2355

Phe Ala  Val Leu Met Asp Val  Ser Arg Arg Glu Asn  Gly Glu Ile
    2360                 2365                 2370

Leu Pro  Leu Lys Thr Leu Thr  Tyr Val Ala Leu Gly  Val Thr Leu
    2375                 2380                 2385

Ala Ala  Leu Leu Leu Thr Phe  Phe Phe Leu Thr Leu  Leu Arg Ile
    2390                 2395                 2400

Leu Arg  Ser Asn Gln His Gly  Ile Arg Arg Asn Leu  Thr Ala Ala
    2405                 2410                 2415

Leu Gly  Leu Ala Gln Leu Val  Phe Leu Leu Gly Ile  Asn Gln Ala
    2420                 2425                 2430

Asp Leu  Pro Phe Ala Cys Thr  Val Ile Ala Ile Leu  Leu His Phe
    2435                 2440                 2445

Leu Tyr  Leu Cys Thr Phe Ser  Trp Ala Leu Leu Glu  Ala Leu His
    2450                 2455                 2460

Leu Tyr  Arg Ala Leu Thr Glu  Val Arg Asp Val Asn  Thr Gly Pro
    2465                 2470                 2475

Met Arg  Phe Tyr Tyr Met Leu  Gly Trp Gly Val Pro  Ala Phe Ile
    2480                 2485                 2490

Thr Gly  Leu Ala Val Gly Leu  Asp Pro Glu Gly Tyr  Gly Asn Pro
    2495                 2500                 2505

Asp Phe  Cys Trp Leu Ser Ile  Tyr Asp Thr Leu Ile  Trp Ser Phe
    2510                 2515                 2520

Ala Gly  Pro Val Ala Phe Ala  Val Ser Met Ser Val  Phe Leu Tyr
    2525                 2530                 2535

Ile Leu  Ala Ala Arg Ala Ser  Cys Ala Ala Gln Arg  Gln Gly Phe
    2540                 2545                 2550

Glu Lys  Lys Gly Pro Val Ser  Gly Leu Gln Pro Ser  Phe Ala Val
    2555                 2560                 2565

Leu Leu  Leu Leu Ser Ala Thr  Trp Leu Leu Ala Leu  Leu Ser Val
    2570                 2575                 2580

Asn Ser  Asp Thr Leu Leu Phe  His Tyr Leu Phe Ala  Thr Cys Asn
    2585                 2590                 2595

Cys Ile  Gln Gly Pro Phe Ile  Phe Leu Ser Tyr Val  Val Leu Ser
    2600                 2605                 2610

Lys Glu  Val Arg Lys Ala Leu  Lys Leu Ala Cys Ser  Arg Lys Pro
    2615                 2620                 2625

Ser Pro  Asp Pro Ala Leu Thr  Thr Lys Ser Thr Leu  Thr Ser Ser
```

2630 2635 2640

Tyr Asn Cys Pro Ser Pro Tyr Ala Asp Gly Arg Leu Tyr Gln Pro
2645 2650 2655

Tyr Gly Asp Ser Ala Gly Ser Leu His Ser Thr Ser Arg Ser Gly
2660 2665 2670

Lys Ser Gln Pro Ser Tyr Ile Pro Phe Leu Leu Arg Glu Glu Ser
2675 2680 2685

Ala Leu Asn Pro Gly Gln Gly Pro Pro Gly Leu Gly Asp Pro Gly
2690 2695 2700

Ser Leu Phe Leu Glu Gly Gln Asp Gln Gln His Asp Pro Asp Thr
2705 2710 2715

Asp Ser Asp Ser Asp Leu Ser Leu Glu Asp Asp Gln Ser Gly Ser
2720 2725 2730

Tyr Ala Ser Thr His Ser Ser Asp Ser Glu Glu Glu Glu Glu Glu
2735 2740 2745

Glu Glu Glu Glu Ala Ala Phe Pro Gly Glu Gln Gly Trp Asp Ser
2750 2755 2760

Leu Leu Gly Pro Gly Ala Glu Arg Leu Pro Leu His Ser Thr Pro
2765 2770 2775

Lys Asp Gly Gly Pro Gly Pro Gly Lys Ala Pro Trp Pro Gly Asp
2780 2785 2790

Phe Gly Thr Thr Ala Lys Glu Ser Ser Gly Asn Gly Ala Pro Glu
2795 2800 2805

Glu Arg Leu Arg Glu Asn Gly Asp Ala Leu Ser Arg Glu Gly Ser
2810 2815 2820

Leu Gly Pro Leu Pro Gly Ser Ser Ala Gln Pro His Lys Gly Ile
2825 2830 2835

Leu Lys Lys Lys Cys Leu Pro Thr Ile Ser Glu Lys Ser Ser Leu
2840 2845 2850

Leu Arg Leu Pro Leu Glu Gln Cys Thr Gly Ser Ser Arg Gly Ser
2855 2860 2865

Ser Ala Ser Glu Gly Ser Arg Gly Gly Pro Pro Pro Arg Pro Pro
2870 2875 2880

Pro Arg Gln Ser Leu Gln Glu Gln Leu Asn Gly Val Met Pro Ile
2885 2890 2895

Ala Met Ser Ile Lys Ala Gly Thr Val Asp Glu Asp Ser Ser Gly
2900 2905 2910

Ser Glu Phe Leu Phe Phe Asn Phe Leu His
2915 2920

<210> SEQ ID NO 11
<211> LENGTH: 2091
<212> TYPE: DNA
<213> ORGANISM: Homo sapiens

<400> SEQUENCE: 11
cgctgtgccc cgattccgcg tcgggctgcg cgggcggcca gcggttcagg cgcgcgcgga 60
gagctctggc tcagagtttg cgatccgaga gcgggatccg cgctccctcg gtccttcctc 120
cctcccctct tgcggcctcc cgctgtcatc tggagccgct cctgccgccc cctggcggcg 180
accgcgggaa gggccggccc ccatccgcac ccctgacccc ggaggtcaac aacgggatgg 240
tccctgggtc ccaggggaag agacatcacc cagtaggagg gagtacggtc tagacagagg 300
ccacgagggc gggagggggc gagagtggag agtggcccag ctggccaggg tcgtctaagt 360

-continued

```
gagaggaaaa gggagagggc ggttgagacc aggccctgaa ttccgcgttc atcttatcct    420
gaggtctgtg gggacctgtt gaaggactgg ggcaggggac ggacgcgggc atccttccat    480
ttggaacagc cattccggca gcatcaggat ggggcggagg caaagcgggg agtgggcgag    540
gcaagtggtg ctgtaaacct gtgcgagaag gggggggtga ctctaagggc aggaaggagc    600
cctggtcaca cacacactcc cacgcaaggt attcagtgcc gagtgtggcc ttggtgctag    660
gattcaaaga ggaaaggaag aaaactttcc attctaaaag aaactccacg tgaggcgaag    720
aagatgaaat atagtcagaa aaccatacca gtaggtggta gttaagttga taaatgatgc    780
atacgacatc ctatagaaga ctgtcaccac cccacctcac tgatcagccc tctgcctaca    840
gccacaccca cagaacattc agccatttct cctgtggttc ccagcctgca gcacagcgtc    900
tgcacgtgga actctggaat gctgacctac agtctgagtt cctgtgccct tgcctggggc    960
tgactctcta cttgacctgt aacccacaac tgggcaagag aaaattctgc agccacagct   1020
ctgaggacat gagcaaaatg gtttccagac ggaatgtcaa ggattcccat gaagtgtcag   1080
ggagtcttca ggccacactt caggttatct ccttctcttt cccttttctg cttcacactt   1140
gctctcatcc tctttctcac cccacatctg gtcagaggag ataggaaggt tcttgttacc   1200
tggtacaaga caactttgg aatcccagat attcagatta tttccccttt tcctctttgc    1260
aaatgataat actcacagcc aagaggcatc acccggatcc gaggctgctt ctccttagga   1320
catgcagaca gaaggagaag gcggggctgg cagcctccag tccacagcct ccctttcttc   1380
ttccggcgat gattaactag gcctagacaa tggagatcta cggcatacgc ccagggcctc   1440
ctcttctcaa gcatggctga tcagtcactt tcccgtctat ccttcattta ttgaagccaa   1500
ctatgaacga ctaaaggaag gatgagaaaa gtcacccaaa gtcaaagggg acagcgtggg   1560
agactgttct agacagaagg aaacaccttt gcaaagaccc tgaggaaggc aggggactct   1620
ccaggagcag aagggctgtg tggcttcaga gtccacaaaa gagagcagat acaggacact   1680
ggctagagca ggccctggag cccgctgctg tcctggaggc cttggggagg cccagtgttc   1740
ccagggtgga agaagtaggg gacagcttga cgtagtggct gttgatcagc tgatatggaa   1800
gtatgtcatt ttattaacaa ttgagaaagg agtgctgtgc aattccattc aatgccagtg   1860
atgcttatgg ccgtttttat gagttctgtc attttcaaat gagcaagagg aagcctctaa   1920
gggggtttaa gcagggactg acgtaatcag atctgtgttt ttccaaaggg agagggagaa   1980
aaagaacatt tcttattttt caaaaaaggt aatgcaaaag catcattcca caattctctt   2040
gtaatgaaaa aaataaatgc aaacttaagc aaatccatca ttctgaaaga a            2091
```

<210> SEQ ID NO 12
<211> LENGTH: 136
<212> TYPE: PRT
<213> ORGANISM: Homo sapiens

<400> SEQUENCE: 12

```
Met Met His Thr Thr Ser Tyr Arg Arg Leu Ser Pro Pro His Leu Thr
1               5                   10                  15

Asp Gln Pro Ser Ala Tyr Ser His Thr His Arg Thr Phe Ser His Phe
            20                  25                  30

Ser Cys Gly Ser Gln Pro Ala Ala Gln Arg Leu His Val Glu Leu Trp
        35                  40                  45

Asn Ala Asp Leu Gln Ser Glu Phe Leu Cys Pro Cys Leu Gly Leu Thr
    50                  55                  60

Leu Tyr Leu Thr Cys Asn Pro Gln Leu Gly Lys Arg Lys Phe Cys Ser
```

```
65                  70                  75                  80

His Ser Ser Glu Asp Met Ser Lys Met Val Ser Arg Arg Asn Val Lys
                85                  90                  95

Asp Ser His Glu Val Ser Gly Ser Leu Gln Ala Thr Leu Gln Val Ile
            100                 105                 110

Ser Phe Ser Phe Pro Phe Leu Leu His Thr Cys Ser His Pro Leu Ser
        115                 120                 125

His Pro Thr Ser Gly Gln Arg Arg
    130                 135
```

<210> SEQ ID NO 13
<211> LENGTH: 3715
<212> TYPE: DNA
<213> ORGANISM: Homo sapiens

<400> SEQUENCE: 13

```
cctaccccag ctctcgcgcc gcgtgcagag gtgctcaagc ctcctcgcgg tccgcagtca     60

gtgccgccgc gcccggcctc ccgcacgccc cgcaggtagc gcccccgccc gcggcccaga    120

gtgcgctcgc gccggcacca gctcccggat aaacggcgcg ccgcgcggag atgacagccg    180

aggagatgaa ggcgaccgag agcggggcgc agtcggcgcc gctgcccatg gagggagtgg    240

acatcagccc caaacaggac gaaggcgtgc tgaaggtcat caagagagag ggcacaggta    300

cagagatgcc catgattggg gaccgagtct ttgtccacta cactggctgg ctattagatg    360

gcacaaagtt tgactccagt ctggatcgca aggacaaatt ctcctttgac ctgggaaaag    420

gggaggtcat caaggcttgg gacattgcca tagccaccat gaaggtgggg gaggtgtgcc    480

acatcacctg caaaccagaa tatgcctacg gttcagcagg cagtcctcca aagattcccc    540

ccaatgccac gcttgtattt gaggtggagt tgtttgagtt taagggagaa gatctgacgg    600

aagaggaaga tggcggaatc attcgcagaa tacagactcg cggtgaaggc tatgctaagc    660

ccaatgaggg tgctatcgtg gaggttgcac tggaagggta ctacaaggac aagctctttg    720

accagcggga gctccgcttt gagattggcg agggggagaa cctggatctg ccttatggtc    780

tggagagggc cattcagcgc atggagaaag gagaacattc catcgtgtac ctcaagccca    840

gctatgcttt tggcagtgtt gggaaggaaa agttccaaat cccaccaaat gctgagctga    900

aatatgaatt acacctcaag agttttgaaa aggccaagga gtcttgggag atgaattcag    960

aagagaagct ggaacagagc accatagtga aagagcgggg cactgtgtac ttcaaggaag   1020

gtaaatacaa gcaagcttta ctacagtata agaagatcgt gtcttggctg gaatatgagt   1080

ctagtttttc caatgaggaa gcacagaaag cacaggccct tcgactggcc tctcacctca   1140

acctggccat gtgtcatctg aaactacagg ccttctctgc tgccattgaa agctgtaaca   1200

aggccctaga actggacagc aacaacgaga agggcctctt ccgccgggga gaggcccacc   1260

tggccgtgaa tgactttgaa ctggcacggg ctgatttcca gaaggtcctg cagctctacc   1320

ccaacaacaa agccgccaag acccagctgg ctgtgtgcca gcagcggatc cgaaggcagc   1380

ttgcccggga gaagaagctc tatgccaata tgtttgagag gctggctgag gaggagaaca   1440

aggccaaggc agaggcttcc tcaggagacc atcccactga cacagagatg aaggaggagc   1500

agaagagcaa cacggcaggg agccagtctc aggtggagac agaagcatag cccctctcca   1560

ccagccctac tcctgcggct gcctgccccc cagtctcccc actccaccct gttagttttg   1620

taaaaactga agaattttga gtgaattaga cctttatttt tctatctggt tggatggtgg   1680

ctttagggga agggggaaag gtgtaggctg ggggattgag gtggggaatc attttagctg   1740
```

```
gtgtcagccc ctcttccctt cctccattgc acatgaacat atgtccatcc atatatattc   1800

atcagaatgt taatttattt tgctccctct gttaggtcca ttttctaagg gtagaagagg   1860

caagtggtag ggatgaggtc tgataagaac ccagggtgga gagggagact cctgggcagc   1920

cgttttcctc atcctttccc tctcccagtc catttccaaa tgtggcctcc atgtgggtgc   1980

tagggacatg ggaaaaacca ctgctatgcc atttcttctc tctgttccct tcctcacccc   2040

cgacggtgtg gctgatgatg tcttctggtg tcatggtgac cacccccctgt tccctgttct   2100

ggtatttccc ctgtcagttt cccctctcgg ccaggttgtg tcccaaaatc ccctcagcct   2160

cttctctgca cgttgctgaa ggtccaggct tgcctcaagt tccatgcttg agcaataaag   2220

tggaaacaat aaaacctggg tgtcagacaa ccctttctgt tcagccttgg agtggtgggt   2280

atgggtgggt acataatggg tagtagcaca atcaaggggt cacccactta gttccagttg   2340

agcttaaata agtgagcatc tcatgtagat gccatagttg ggcaggaagc agccccacca   2400

tgcatggctt cctgagcact gcacaggctg ccgctgggat ttgtgtctat ggcttcgccc   2460

aaggttccca gcactccctc cctccagcaa cctggcagtt ttagtgcctc tggttttctt   2520

ccctgacact taggaagacg aaagtataaa gatctagaag actgggacac catgcatgtt   2580

cattttgaag ttggaattgg tcttctgcct acctctgatc tggcagaggt atctgcattt   2640

tggtttgtta acaaggtaaa actcctggtg tcactgacct cctcctgtca gataacttac   2700

atgattaagg ttaagagtaa agcagagtgt tcacgtccag cttccttctc agccttaaca   2760

ggaaaaggct tgtgcttttt ttctaactat gctttgaccc ttaactccta tggcatgatg   2820

gggccctggg agaagccagg cagcacaagc cagtcatgct gagctgcctc cagataatcc   2880

tggctccagg ccagagcccg tgtctgccct catccctctc tcctactgtg agctctccag   2940

tcctttccca acagcgatgt ggttgtctgc ttagccacat gcctgtatag ttccttccag   3000

aagaaatgta taatggtgga agatgtattt ctgtgtgaaa attttcacca agtcatacaa   3060

cacagctgat gctggagcca ggattaaaat tggggtgtac aagtctccca gtgtgagtat   3120

cccttgagcc caagacacca aggatgcaga gaactgtgac tgtgccactg cacgccagcc   3180

tgggcaagag agtgagacca tctctttttt aaaaaagtcc ctgtgtaact gctttcttac   3240

tgggcttacc tcacatcaca gccctgtgtt tgtggtttgt gtctgggtcc tcttggtatt   3300

tcaaaagtag tagattctta cgcctgcagc caacaataat cactaactca agcatttatg   3360

gagtaagcct agcactgtac tgacagcatc acatgagtga aactgaatcc ttgcaaccat   3420

cctacaaaga aggtataact ttaataaccc tatttacaga taagaaaacc aagactcaga   3480

agttaaatgg aaaggtgagg tctctgaact aatccagact ctcccatgag gttcctttgg   3540

caagtcctgg gcttctgtcc tcatctgcaa aatcgaaagc attcctgagg tttcttccag   3600

ctctgcatcc tgtaggattc caagaatgta aaactgcatg taaccgtgga acatctagag   3660

ataagtctta gtttatgtaa cattaaaact gtctagtgag gatgttttgt taaaa        3715
```

<210> SEQ ID NO 14
<211> LENGTH: 459
<212> TYPE: PRT
<213> ORGANISM: Homo sapiens

<400> SEQUENCE: 14

```
Met Thr Ala Glu Glu Met Lys Ala Thr Glu Ser Gly Ala Gln Ser Ala
1               5                   10                  15

Pro Leu Pro Met Glu Gly Val Asp Ile Ser Pro Lys Gln Asp Glu Gly
```

-continued

```
            20                  25                  30

Val Leu Lys Val Ile Lys Arg Glu Gly Thr Gly Thr Glu Met Pro Met
        35                  40                  45

Ile Gly Asp Arg Val Phe Val His Tyr Thr Gly Trp Leu Leu Asp Gly
    50                  55                  60

Thr Lys Phe Asp Ser Ser Leu Asp Arg Lys Asp Lys Phe Ser Phe Asp
65                  70                  75                  80

Leu Gly Lys Gly Glu Val Ile Lys Ala Trp Asp Ile Ala Ile Ala Thr
                85                  90                  95

Met Lys Val Gly Glu Val Cys His Ile Thr Cys Lys Pro Glu Tyr Ala
            100                 105                 110

Tyr Gly Ser Ala Gly Ser Pro Pro Lys Ile Pro Pro Asn Ala Thr Leu
        115                 120                 125

Val Phe Glu Val Glu Leu Phe Glu Phe Lys Gly Glu Asp Leu Thr Glu
    130                 135                 140

Glu Glu Asp Gly Gly Ile Ile Arg Arg Ile Gln Thr Arg Gly Glu Gly
145                 150                 155                 160

Tyr Ala Lys Pro Asn Glu Gly Ala Ile Val Glu Val Ala Leu Glu Gly
                165                 170                 175

Tyr Tyr Lys Asp Lys Leu Phe Asp Gln Arg Glu Leu Arg Phe Glu Ile
            180                 185                 190

Gly Glu Gly Glu Asn Leu Asp Leu Pro Tyr Gly Leu Glu Arg Ala Ile
        195                 200                 205

Gln Arg Met Glu Lys Gly Glu His Ser Ile Val Tyr Leu Lys Pro Ser
    210                 215                 220

Tyr Ala Phe Gly Ser Val Gly Lys Glu Lys Phe Gln Ile Pro Pro Asn
225                 230                 235                 240

Ala Glu Leu Lys Tyr Glu Leu His Leu Lys Ser Phe Glu Lys Ala Lys
                245                 250                 255

Glu Ser Trp Glu Met Asn Ser Glu Glu Lys Leu Glu Gln Ser Thr Ile
            260                 265                 270

Val Lys Glu Arg Gly Thr Val Tyr Phe Lys Glu Gly Lys Tyr Lys Gln
        275                 280                 285

Ala Leu Leu Gln Tyr Lys Lys Ile Val Ser Trp Leu Glu Tyr Glu Ser
    290                 295                 300

Ser Phe Ser Asn Glu Glu Ala Gln Lys Ala Gln Ala Leu Arg Leu Ala
305                 310                 315                 320

Ser His Leu Asn Leu Ala Met Cys His Leu Lys Leu Gln Ala Phe Ser
                325                 330                 335

Ala Ala Ile Glu Ser Cys Asn Lys Ala Leu Glu Leu Asp Ser Asn Asn
            340                 345                 350

Glu Lys Gly Leu Phe Arg Arg Gly Glu Ala His Leu Ala Val Asn Asp
        355                 360                 365

Phe Glu Leu Ala Arg Ala Asp Phe Gln Lys Val Leu Gln Leu Tyr Pro
    370                 375                 380

Asn Asn Lys Ala Ala Lys Thr Gln Leu Ala Val Cys Gln Gln Arg Ile
385                 390                 395                 400

Arg Arg Gln Leu Ala Arg Glu Lys Lys Leu Tyr Ala Asn Met Phe Glu
                405                 410                 415

Arg Leu Ala Glu Glu Glu Asn Lys Ala Lys Ala Glu Ala Ser Ser Gly
            420                 425                 430

Asp His Pro Thr Asp Thr Glu Met Lys Glu Glu Gln Lys Ser Asn Thr
        435                 440                 445
```

Ala Gly Ser Gln Ser Gln Val Glu Thr Glu Ala
450 455

<210> SEQ ID NO 15
<211> LENGTH: 13546
<212> TYPE: DNA
<213> ORGANISM: Homo sapiens

<400> SEQUENCE: 15
ggaggtcggc gcagctgccc ctttgggctt tggctctgga ctggagcgca gcatccttcg 60
aggctgcagc cgccacggct gttgccgtaa gcaatcctcc tgcctcagcc tcccgagtag 120
ctgggactcg ggaccagcct cccgagtatt ggtcagatga catttaccat caccgttttc 180
ttcttctttc atcatcatca tcatcaccat tgccactacc accacctcca aggccactac 240
caccacagca tctctgttcc tccatcagag ctcttcaagt tctgtaaagg cagattctct 300
aaaggcatgc ctggtggcat cacgtttttc acatctccgc atctggaccc tgcccaagcg 360
aaggctgatc taggcagtct cattgctgga gatgactgtc agctgctttc tctgcatagc 420
caccatcaca tgcctcacca ctggagcctg ggaagcctga ccacaaaccg gcatctccaa 480
ggcatgaata attaggtagg cataatggaa ggcactcatt gtaccctcca attgcataag 540
cccattacgg aactctgcta catcagcttc tgtcttccaa agggggaagt cagaggattt 600
tcatacaagg gcactgtaac tctagacaga tccaataaag gttttcataa ctgctaccaa 660
gtcagggagg agtcagacat catcagcctc agccaggagc cggacgaaca tccaggcgac 720
atatttttca agcagactcc cacgaaagac attctaactg agctgtacaa actcacaaca 780
gagagggaga gactgctaac caatctcctg agctcagacc acatcctggg gatcacgatg 840
gggaaccagg aggggaagct gcaagagctg tccgtgagcc tggcccccga ggatgactgt 900
ttccagagtg ctggtgactg gcagggagag ctccccgtgg gccctctcaa taagaggagc 960
acccacggga acaaaaagcc tcggaggtct agtggaagga gagagagctt tggggccctt 1020
ccacagaaga ggaccaaaag aaaagggcgt ggaggccgag aatcagctcc tctgatgggc 1080
aaggacaaga tctgttccag ccactccctt cctctttcta gaacaaggcc taacctttgg 1140
gtactagagg agaaaggaaa tctgctcccg aatggggcac ttgcctgctc cctgcagagg 1200
agagagagct gccccccaga tattcccaag acgccagaca cagaccttgg ctttgggagc 1260
tttgagacgg ctttcaagga cactgggctt ggaagagaag tgctgccccc tgactgcagc 1320
tccacagagg caggaggga tggcattcgg aggccgccga gcgggctgga gcatcagcaa 1380
acaggtttgt ctgaaagtca ccaggaccct gagaagcatc cagaggcaga aaaggatgag 1440
atggagaagc cggctaagcg gacttgcaag cagaaacctg tctccaaagt ggtggccaaa 1500
gttcaggacc tgtcctccca ggtacaaaga gtagttaaaa cgcattctaa gggtaaggag 1560
acgattgcca ttcgcccagc agcccacgct gagtttgtac ccaaagccga cttgctcacc 1620
ctcccgggag ctgaggctgg ggctcatggc tccaggcggc agggcaagga gcggcaaggg 1680
gataggtcat cgcagtcgcc agccggggaa acagcctcca tttctagtgt gtcggccagt 1740
gccgaggggg ccgtgaacaa ggtccccctg aaggtgatag agagtgagaa gttagatgaa 1800
gcccctgagg ggaaaagact gggcttccct gtccacacga gtgtccctca cactcgccca 1860
gaaacgagaa acaagaggag agccgggttg ccccttggtg gccacaagtc cttgtttctg 1920
gatctgcccc acaaagtagg tcctgactcc tcacaaccca gaggtgataa gaagaagcca 1980
tccccaccag caccggcagc tcttggcaag gtgtttaata attcagcctc gcagtccagc 2040
acacacaaac agacgtcacc tgttccctcg cctctgtctc caaggctccc cagccctcag 2100
cagcatcaca ggatcctccg gctccctgca ttgcctggtg agagggaagc tgctcttaat 2160
gactctcctt gtagaaagag ccgtgtcttc tctgggtgcg tctctgctga caccttggag 2220
ccaccatcct ctgcaaaggt cacggagacc aaaggagcca gcccggcctt cctcagagca 2280
ggccaacctc ggttggtgcc tggggaaact ttggaaaaga gcttggggcc agggaagacc 2340
acagctgagc cccagcacca gtcacctcca ggtatctcct ctgagggctt tccctgggac 2400
ggcttcaatg agcagacacc taaagacctt cccaacagag atggaggcgc gtgggttctg 2460
ggctacagag cgggaccagc ctgtccattt ttgcttcatg aggaaaggga gaagtcaaac 2520
aggagcgaat tgtacttgga tctccatcct gaccacagcc tgactgagca ggatgacagg 2580
actcctggca gacttcaagc tgtctggcca cccccaaaga caaaagacac agaagaaaaa 2640
gtgggactga agtacactga agcagaatac caagctgcta ttttacactt gaagagggag 2700
cacaaagaag aaattgaaaa cctgcaggca cagtttgaac ttcgggcatt tcatatccgg 2760
ggcgagcatg caatgataac agcgagacta gaagaaacca ttgaaaatct gaaacacgag 2820
ctagaacaca gatggcgagg gggttgtgaa gagaggaaag atgtgtgcat ttccaccgat 2880
gatgactgcc ctccaaagac cttcagaaat gtgtgcgtcc agacagacag agagaccttc 2940
ctcaagccct gtgaaagtga aagcaagaca accagaagta atcaattagt acccaaaaag 3000
ctgaatatct cctctttaag ccagctctca cccccaaatg accacaaaga catccatgca 3060
gcactccagc caatggaggg catggcatca aatcagcaga aggcattgcc tccgcctccc 3120
gcatccatcc ctcccccctcc gcccctcccc tcaggacttg gatctttgtc tcccgcacct 3180
ccaatgccac ctgtgagtgc tgggccaccg ctaccacctc cgcctcctcc accgccacct 3240
ctacctccac cttcaagtgc tggacctcca ccacccccac ccccaccccc acttcctaac 3300
tcccctgccc cacccaaccc tggagggcct cctcctgctc caccaccccc aggacttgca 3360
cccccacctc cccctggact cttctttgga cttggctctt cttccagtca atgtcctcga 3420
aaaccagcca tcgagcccag ttgtcccatg aagcctttat attggactag gatacaaata 3480
agtgatagga gccaaaatgc tacaccaacc ttatgggact ccttagaaga acctgacatt 3540
cgggaccccca gtgaatttga gtatttattc tccaaagaca caactcaaca gaagaaaaaa 3600
cctctgtcag agacttatga gaagaaaaac aaggtcaaaa agatcatcaa attgttggat 3660
ggaaaacgat ctcaaactgt gggaatcttg atatctagtt tacatttaga aatgaaggat 3720
atccaacagg ccattttcaa tgtggatgac tccgtggttg atctggagac cctggcagcc 3780
ttatatgaaa acagagccca agaggatgag ctggttaaaa taagaaagta ttacgagaca 3840
tccaaagaag aagaactgaa gctgctggat aaacctgagc aatttttaca tgagttagcc 3900
cagattccta attttgctga acgtgcccag tgcataatct tcagatctgt cttttctgag 3960
ggtatcacct ccttgcacag aaaggtagag atcatcacgc gagcttctaa ggacttgctg 4020
cacgtgaaga gcgtgaagga tattttagct ctcatcttgg cttttggaaa ttatatgaat 4080
ggaggaaata ggactcgggg acaagccgat ggatatagct tagaaattct gcccaaactc 4140
aaggatgtca aaagtcggga taatgggatt aatctggtgg actacgttgt taagtattac 4200
ctgcgttact atgatcagga agctggaaca gaaaagagtg ttttcccctt gccggaacca 4260
caggatttct ttctggcctc ccaagtcaag tttgaagacc tcataaaaga tttgagaaaa 4320
ctgaagaggc aactagaagc aagtgagaaa cagatggtgg tggtgtgcaa ggagtcccca 4380

-continued

```
aaggagtatc tccagccttt caaggacaaa ctagaggagt tcttccaaaa agccaaaaaa   4440
gagcataaga tggaagaaag tcacttggag aatgcacaga aaagttttga aacaacagta   4500
cgatattttg ggatgaagcc aaagtctggt gagaaggaga tcacacccag ctacgtgttt   4560
atggtgtggt atgagttctg cagtgacttc aagacaattt ggaaacggga gagtaaaaac   4620
atatctaaag aaagattgaa aatggctcag gaatcagtca gcaagttgac ttcagagaag   4680
aaagtggaga caaagaaaat caatcccact gctagcctga aagaaagact gcgtcagaag   4740
gaagccagtg tgaccactaa ctaagatgaa gacacatgga aatgatggca ctggaggtgg   4800
aggaccttgc acgcatactc tttgtgacca cagggttgca ggacgttctt gaaagatgtg   4860
tcactaaatg tttgtttttg ctcatctctt tctgaggtca tctgcagaga gtgccccatg   4920
ccttctttaa gaagtccctc attaagccgc aggaacaatg gaaaactatt taagggaaca   4980
ttgcagaaat atttgatgac tgtttcttgt ggaagcccaa agtccactct aagagcagaa   5040
gaaataccaa aatgtttcca aaattttttt aaaagctgag atttccagct ttataaccaa   5100
agcttgatat atgtcacatt gtcacagaag agagaaaaga tcattgagga cagttgcctt   5160
gggagagttc aagtctttgt cgttacacac tgctgttttg attattggtc ttagttttga   5220
tcctgttgca gcaaaatcct gcagcatctt tctctccaat aatgttgcaa ctcaccaaaa   5280
ctattcttga agaggtccaa gaacatgtat tatccagact aaaaaaatga tttttttgttg   5340
ttatggttta cgtgatgaaa aggagaaaaa acagaatcat acctgggtgg agagagggag   5400
acaaatagcc ataaacttca tcctggagaa caagttacca tgcaaggagt tgacatcagt   5460
tgttaagtga ggcccattct tgtttttaca tcggtccttt gtggtttttc tgggccagca   5520
gagattctgc accccaactc ccaggagaaa atgtaatacc tgagcaagca cagccttggg   5580
tgtgcttgga caagagaccc agcggcagag caccttttac attttggacc gttcatgaat   5640
gggcaatgtt gtgttgatac gcagccgagt tctacgttat gtgctgtgac tgtgcagctg   5700
gacgaccccc atccccagga ggcagtttcc agacaggaga gcaaatgcaa ctcacagcac   5760
ctgctcatga ccttggctga taggcatgtg aagtaggatg aagcaggact ctttaatgtc   5820
aaaaaaactg aagggcagaa aaaaggttcc ttacatcaaa atgaaagtaa ttacattaat   5880
agaaaacttc caagtggaat attgttcaca ggcagctctt tctgaccctg gctcttgagt   5940
cacataagga aaccaccttt gacctctctg acacttttgt ctttaagcca cgtctctgaa   6000
atcttgtgag gggtgaagaa agaggactgg agatgaatgg acaatatgat caaagactca   6060
tttttaggcc ttgaagaggc cgagctttct ccccccaatt ggtggaggac agtccagaga   6120
tgagcagaaa tcttaaattc cttcctgatc cagcctccac atgtggcctg ccccttgccc   6180
cagcatcttt ccagaacccc tggacttgcc aggtgcctga gcatcttccc aggatatgcc   6240
tgccagccag cagcccctca ggaatgcttc tataatagat ccagtaatga aagcagcacc   6300
atatcctaat ctaatgtcag cttcgagaat gaagactgca gtcaggatca aatcaagtca   6360
cagaagccat attcatgcag gtgctaaccg ccttttctac tggtgcaact gaaaggaata   6420
tggtaacatg gttggatttt taaaattcac aatgaaggaa cgagacaagc aaaacagaaa   6480
agccgagaag gaacatgcat gactaaaaag gcttgaagtt gcttgtgagc aagaagcttt   6540
ttatgctgct ttcttacata gtttctcttc attttcactt aactctgaag acaaccaaaa   6600
gaacggatca attaaaaact gattccactt ataaccattg tatgctcctt ctagtgttat   6660
catgcacaag aaaagtgcca gttttaccca tgccatataa ttcagctctt ttgagttatg   6720
tggggccagc agaagtctca atccttatag gcttgatggt gagagcagcg ggaggtttga   6780
```

```
ggtgtactca ttgcagtcca ctttggtctg taagtaggat gcttacgaga aatcagtgaa   6840
ggtaagcagg gctgccactg tggccacgta acccttcagg aaccagtgct gaagaataat   6900
gagtgagaac acttaatttg agagttagac aaatacagcc cactttggat ttcatcctag   6960
tgaacagact aaaactttgc agtaaaatac ctatttctac aaagcaaggt ttgcctgcct   7020
cggttgggga aacctagtgg ttttgtcaca ctagtcgatg tatgatgtta gtgttgtaag   7080
acaccatggc agaatcttca ttattctcac ctattctgaa ccctgcatca tgtatctggg   7140
atgccccctc ccaagtccac caatgtacca cgttgctgac acagccttca tttttaactc   7200
aaattgatgc tcagtaaagg tcaatgacaa tttgttcaag gaagttcatc taaaataatc   7260
tggaggcctt gaaaatgatc cctctaaaat gctgttgagc ttgtgttcag tgtagcagga   7320
ggatctgaac ttttcctgga gaggaggtga tcgggatgcc atttggcagc ttaagcacat   7380
cctgccagca ggctttaagt ggctgttcta ggcatagccc tccctgaact agaaaggaga   7440
gtaaccagtt tgctatgctg catctaacca gacacacctg acttagtagt aactctaaga   7500
acccttaact tacaaacaac tttgtctcct cttagacaat attcattaaa tctgaggaca   7560
cagtttgaca gtagttcaga ttcttgcatg agcaattgac agcatcagag cacacaatat   7620
cataagttac ataaattaca caaagtacat cataaattac actacagaca cgttaggtaa   7680
aaagcatcag gcccgggccg ggcgtggtgg ctcatgccta taatcccagc actttgggag   7740
gccaagcggg ggcggatcac gaggtcagga gattgagacc atcctggcta acacggtgaa   7800
accccatctc tactaaaaat acaaaaaatt agccgggcgt ggtggtgggc gcctgtagtc   7860
ccagctactc gggaggctga ggcaggagaa tggcgtgaac ccaggaggtg gagcttgcag   7920
ctagccgaga tagcaccact gcactccagc ctgggcgaca gtgagactcc gtttcaaaaa   7980
aaaaagcatc aggcccatga agtatcaaaa accaggttag gaggtgtgct gtatggcttt   8040
tatctcaata agtggcagct tactggggaa aaagaaataa gaaaaagtgt ggccaagcag   8100
aagtggatgt ttatgatgac ggtgggggcc cagaggtcat aggtgatggt cctactgccc   8160
aacagttgcc ttttgaatcc ttatgttgat gatggtgtct ttctacacac tcactgcaac   8220
tactcaggaa ttataaagat tttctgaaat ctgagaagtg gaataaggaa acccagtgga   8280
gctattacac ttttaaatgt tctagccaaa acaaattgcc agtatggttg aggaattgaa   8340
tatcagatgg catgcagtct cccctcccct ccccctatcaa ggacagtaga agctgcaaac   8400
ctcttctcag cctccttcag gcacctcctg ttttcataag caccatgaag aatggtgttt   8460
cctaaatgaa aagttcagat actgctggta aagaaactgg aaaaactgaa ggaaggaata   8520
aaatatgttg gtggtattaa cacctccagt aagataagtc attggtacgg tttttctaag   8580
ggccgcagtg agatgtagca gaagaaatat gtttattttg ggcaaagatt tgcttattgg   8640
cctgggattg cacattttct ctatgatgtt tgcaacagag aaattttcat tttaatgata   8700
ctcttccttt cttgaaagtt acatgtcctc atttctgttt ctgcttctcc cttggccagt   8760
gtcattgatg cagatcattg catacaacag cacagcaaat tgcgccaagt cagtgtgtga   8820
atgggaatta gcaatgcacg cttgcaggct ctttttccag gaaccaggct gtaacattga   8880
ccggggaacc tcttcattcc ctgacatact aaattggtca attttgtagt actcatctcc   8940
atccacaaaa acaacaaaga taaaatcaat ttggagcttt atatgacaaa aaggaagaag   9000
tccaaaaata tatagccttc ccccctccca catatctgat ccaaatatta aatatctgat   9060
tttataaaac agtttaaatt gtctttttaa attgctaaca agcatcagtt atatttgagc   9120
```

-continued

```
ttcatttttc ttttatcctg tctgtcctaa taaaaacaaa aatggccaaa aagtggagag   9180
gaaagaaaaa gcttccactt tttaaaattt gttttgtatt agttatttta cctttaggga   9240
ccctacaact gaagagagtg gagagaataa agaagtgaac tttcattcat gtctgctact   9300
ttgacctcat aaagaaatct gcaacacaga tgaaaccagt ctgtgtggcc aagctgatgg   9360
gatttgaaaa gagtggataa tttttagcct ttccaaaatg caaataactt ggatatattt   9420
ccatttttcca gctatagaga gaaacaatcc agctgcctgg aaactgttat tagtatagaa   9480
gtggcttaaa gaaaagcatc ttcaaatact tgacttagca tatctttctt ctttagactt   9540
acataatgat attcatctct ccattagcaa ttgaatccag gcataaccgg gctcagttac   9600
acagcttgtc tgtgactggg aagcccattt tgtgtcattt ctgcacacct gtccgctgtt   9660
gacaccttat tagaggcact gcattttggt ttcacaattc ttcatctccc ttcccaagga   9720
atgggcaatc tactgaactt ccagatcaat gctttgttgg aaagtgatga atttaagaga   9780
gttttaacat gtcaaatttg aagccaattc agtatcctta tttgttccaa gactcttaac   9840
caatactgtg atataaagtt aggatttggg aaacgtgtag ttaacaactt ggaaacatga   9900
agatattaaa atggcagctg gctaactgtc tcttaagcca ctatgcaatt tctaccaatg   9960
gagagattag ggaagcaaat taagcctcat tcagtaggtc tgctgtctgg tggaacttac  10020
ggaactcatt tcctcctcta tccccagccc ttctcctaac tatggtgata accagggcca  10080
tagaagacct tttctctctt acctttctct gataggatcg tgtccttcag tcaagagctc  10140
atgtgaactc cagactttat attacatctc tgaagttctt gatgtgggga agattgactt  10200
ttattccatt tttatatgaa ggtgttagat atagccatca atttattttt ctacattccc  10260
tctacgctta tgtaattttc tatttttaaa tcttctctta aatatactga gaatctctag  10320
tctccttttc taaaggctga tccaactaca cttgtgggct atttttccaa gctttgtgtg  10380
aaacttgatg acattgggcc agcaaaatgc aaagaagact atagtttcag gcagaaaatc  10440
acgtccaaag aatttggcat ggattaaaca acctctacca cactatagct ctcacatagg  10500
ctgaacattt tcctaaattc tacctgtgca gacactgagg ggctctctac ctttgaaact  10560
atgagaacgt cttaaattaa tatgaatatt tctctccatg tatagtgtga gctgccaatg  10620
cattatctta atacatcaag aaggaaatca gatttcaggc acacattagc aattgtttgt  10680
taatgtcctt ggcaaacgtg tacctgcttt ccttcattgt tctcttcagg ggctttcttc  10740
cactttcctc ttatgaaacg aatgtgtttt tgactgttaa ctgggttcgc tttccagatc  10800
tgtctttccc aaatgaaagg ttagtcccat agaccactgg ctattcaggg aaattactct  10860
ctacctcccc atgacatgga tgataagtgt tgagggatga acactctgga aactcttagc  10920
atggattttg aattccagat ttctttatag gagatgtata aaaaggagtt tatagcatac  10980
aaaaattata ctgctcttcc cagtaaggga ctaaaaggac atttgaaatc tttacatttt  11040
agatgttttt gtgaattata aatatctcct ttttcctcgc ttcatgctaa cttgtctcta  11100
gataaaatct tatttcttca tacattggac cacaaggcat aaagaaggta gctcagcgcc  11160
actgagattg tgttctgcat aatatttgga aggcttccat ttccattgaa aacaaatcca  11220
tgagtgagag ggaaagtcta gtatcaattc ttctgtttgc tcgcaatgac acaaataggt  11280
tttggggatc tacctaaggg ataggtctac tccaaaatta ttaaatttat aattgtgcaa  11340
ttctgtaatt tcccaaggca taagtaatat gaccctactg tcagctagat gtcttatctt  11400
caaagagagt atgcattaat aaaaagaact tccctttaaa gaaccaatct aaaatactaa  11460
aaaggcagaa acttttaaaa ttagaaattg gataattttt aagaatcttt agagaaaaca  11520
```

```
ttggtttatc atagtctttt tctttcattg agttttcatt tagactagca tggcaagcag  11580

ggtggccttg gactttgatt taggggatcg tgctttggcc tggaaaataa gcactggcct  11640

gcatgcctag aacctgagtg aaggcagtca acatcctagt atgaatcaga cctagcagaa  11700

atgtaaatta tttcaagtac ttcagggttt agttttctta gtgacaccct ggaccctgga  11760

tgctgctttc taaagtgcac ctgatccatg cagttttatg tcttcatata actggtatct  11820

tgtgagtttg caagcaatgg gatgagcaag aaaaaaagga cgcatggagg agaaaaattt  11880

gaacgaggct agtgcaatgt tttgctgata gattacattg ttagggagct ggtgattttt  11940

tgccatggtc gtatcgtgga cagcttttcc gtggaaattc aaggcatctg tattaggcaa  12000

atgtgagtgc ccttgatctt gtattgatca gtgccaatgt actgggaaag caggtacccc  12060

agtgaaactg gtctgtgctt ggtttaacag ctccaacaat ttcagatcca tggggctgct  12120

tgaccataga ccctgtttac tccatgcctg ttcaaaagtc attttgactt ctagctttgt  12180

ttcactttct tctttcaata cttctgtttc ctcgtccttt tccttcatat tccatggcta  12240

tttctttcct actttacagt ttcccccaga cccagatttt ttcacacctc tgcatcatag  12300

acaactgagt agctcccttg gcccctcctc catcctctca caccctgtgc tccgttcctc  12360

agccgtttgg acagggagct ccgctgtcac caaggagccc atgtgagaca cactgctgtg  12420

actgcctctt gttaatgtca gcatcacctc atcacttaag caaaaaggaa aatccataaa  12480

agagatggaa aatacgtctc tttttatttt attttaagaa gattgggcgg ggtggggggg  12540

gggttcttat tctaggcctt ctcaatttct catagatttt accttaaact aattaaggcc  12600

attctcttga taaatttgta catcagaccg ggtcaccagc tatgatgcag aacgccagat  12660

ttttgaatct caagtaactt tctgtggtgc tggacaaatt gacttaattc tgtgcaggca  12720

aacactttga atcataagga tttttattgc cgctccattc ttactactat tcatgattca  12780

aacatctacc cctgttctga atcaggatgt tgacacttct tggttatttt cagatgaaca  12840

gtaactgcta cactcttgaa agcacttaaa agtgcaagca tgtcctaaat agccatttaa  12900

cctggtaaaa cataggcttt tctgtttaat taagtattag accagtctgt agatataatc  12960

tgaaaagatt gtaggcagta atgaagacag ttggggaaag gagaaggccc tttaaagaca  13020

tgaaacctta cacgctcttg ggatattttt aagcataata agctcattgg attcaggtat  13080

ttttcccttt gcatttttaa aaatacgtat ttctaatttg tttgcatatt taattttgtc  13140

aaagctgaga aatgctcatg agttgaattt ataaatgtca tttgcaacca aatgaagtat  13200

ttatttttaa aaagagagtg aaggaaccaa cactgatttg tacataataa aaatgtgtgt  13260

attatatata tatatttttt cctccttgac agtacttggt cacaatatca agtgtatttt  13320

tgtacataat atatattgat tagaaaaacg tcaattgtct attcaaaaaa ttctatctct  13380

gtgatagatt atatttatcc taatctgttg atacctctgt taatttgttt taagagaatt  13440

atattttttg gaatttacag agaattgcat tcatggcttt caattgtaaa tatgctaagg  13500

gtattttaat aaatcttggt ttcatgtcca aaaaaaaaaa aaaaaa                13546
```

<210> SEQ ID NO 16
<211> LENGTH: 1419
<212> TYPE: PRT
<213> ORGANISM: Homo sapiens

<400> SEQUENCE: 16

```
Met Glu Gly Thr His Cys Thr Leu Gln Leu His Lys Pro Ile Thr Glu
1               5                   10                  15
```

```
Leu Cys Tyr Ile Ser Phe Cys Leu Pro Lys Gly Glu Val Arg Gly Phe
            20                  25                  30

Ser Tyr Lys Gly Thr Val Thr Leu Asp Arg Ser Asn Lys Gly Phe His
        35                  40                  45

Asn Cys Tyr Gln Val Arg Glu Glu Ser Asp Ile Ile Ser Leu Ser Gln
    50                  55                  60

Glu Pro Asp Glu His Pro Gly Asp Ile Phe Phe Lys Gln Thr Pro Thr
65                  70                  75                  80

Lys Asp Ile Leu Thr Glu Leu Tyr Lys Leu Thr Thr Glu Arg Glu Arg
                85                  90                  95

Leu Leu Thr Asn Leu Leu Ser Ser Asp His Ile Leu Gly Ile Thr Met
            100                 105                 110

Gly Asn Gln Glu Gly Lys Leu Gln Glu Leu Ser Val Ser Leu Ala Pro
        115                 120                 125

Glu Asp Asp Cys Phe Gln Ser Ala Gly Asp Trp Gln Gly Glu Leu Pro
    130                 135                 140

Val Gly Pro Leu Asn Lys Arg Ser Thr His Gly Asn Lys Lys Pro Arg
145                 150                 155                 160

Arg Ser Ser Gly Arg Arg Glu Ser Phe Gly Ala Leu Pro Gln Lys Arg
                165                 170                 175

Thr Lys Arg Lys Gly Arg Gly Gly Arg Glu Ser Ala Pro Leu Met Gly
            180                 185                 190

Lys Asp Lys Ile Cys Ser Ser His Ser Leu Pro Leu Ser Arg Thr Arg
        195                 200                 205

Pro Asn Leu Trp Val Leu Glu Glu Lys Gly Asn Leu Leu Pro Asn Gly
    210                 215                 220

Ala Leu Ala Cys Ser Leu Gln Arg Arg Glu Ser Cys Pro Pro Asp Ile
225                 230                 235                 240

Pro Lys Thr Pro Asp Thr Asp Leu Gly Phe Gly Ser Phe Glu Thr Ala
                245                 250                 255

Phe Lys Asp Thr Gly Leu Gly Arg Glu Val Leu Pro Pro Asp Cys Ser
            260                 265                 270

Ser Thr Glu Ala Gly Gly Asp Gly Ile Arg Arg Pro Pro Ser Gly Leu
        275                 280                 285

Glu His Gln Gln Thr Gly Leu Ser Glu Ser His Gln Asp Pro Glu Lys
    290                 295                 300

His Pro Glu Ala Glu Lys Asp Glu Met Glu Lys Pro Ala Lys Arg Thr
305                 310                 315                 320

Cys Lys Gln Lys Pro Val Ser Lys Val Val Ala Lys Val Gln Asp Leu
                325                 330                 335

Ser Ser Gln Val Gln Arg Val Val Lys Thr His Ser Lys Gly Lys Glu
            340                 345                 350

Thr Ile Ala Ile Arg Pro Ala Ala His Ala Glu Phe Val Pro Lys Ala
        355                 360                 365

Asp Leu Leu Thr Leu Pro Gly Ala Glu Ala Gly Ala His Gly Ser Arg
    370                 375                 380

Arg Gln Gly Lys Glu Arg Gln Gly Asp Arg Ser Ser Gln Ser Pro Ala
385                 390                 395                 400

Gly Glu Thr Ala Ser Ile Ser Ser Val Ser Ala Ser Ala Glu Gly Ala
                405                 410                 415

Val Asn Lys Val Pro Leu Lys Val Ile Glu Ser Glu Lys Leu Asp Glu
            420                 425                 430
```

```
Ala Pro Glu Gly Lys Arg Leu Gly Phe Pro Val His Thr Ser Val Pro
        435                 440                 445

His Thr Arg Pro Glu Thr Arg Asn Lys Arg Arg Ala Gly Leu Pro Leu
    450                 455                 460

Gly Gly His Lys Ser Leu Phe Leu Asp Leu Pro His Lys Val Gly Pro
465                 470                 475                 480

Asp Ser Ser Gln Pro Arg Gly Asp Lys Lys Lys Pro Ser Pro Pro Ala
                485                 490                 495

Pro Ala Ala Leu Gly Lys Val Phe Asn Asn Ser Ala Ser Gln Ser Ser
            500                 505                 510

Thr His Lys Gln Thr Ser Pro Val Pro Ser Pro Leu Ser Pro Arg Leu
        515                 520                 525

Pro Ser Pro Gln Gln His His Arg Ile Leu Arg Leu Pro Ala Leu Pro
    530                 535                 540

Gly Glu Arg Glu Ala Ala Leu Asn Asp Ser Pro Cys Arg Lys Ser Arg
545                 550                 555                 560

Val Phe Ser Gly Cys Val Ser Ala Asp Thr Leu Glu Pro Pro Ser Ser
                565                 570                 575

Ala Lys Val Thr Glu Thr Lys Gly Ala Ser Pro Ala Phe Leu Arg Ala
            580                 585                 590

Gly Gln Pro Arg Leu Val Pro Gly Glu Thr Leu Glu Lys Ser Leu Gly
        595                 600                 605

Pro Gly Lys Thr Thr Ala Glu Pro Gln His Gln Ser Pro Pro Gly Ile
    610                 615                 620

Ser Ser Glu Gly Phe Pro Trp Asp Gly Phe Asn Glu Gln Thr Pro Lys
625                 630                 635                 640

Asp Leu Pro Asn Arg Asp Gly Gly Ala Trp Val Leu Gly Tyr Arg Ala
                645                 650                 655

Gly Pro Ala Cys Pro Phe Leu Leu His Glu Glu Arg Glu Lys Ser Asn
            660                 665                 670

Arg Ser Glu Leu Tyr Leu Asp Leu His Pro Asp His Ser Leu Thr Glu
        675                 680                 685

Gln Asp Asp Arg Thr Pro Gly Arg Leu Gln Ala Val Trp Pro Pro Pro
    690                 695                 700

Lys Thr Lys Asp Thr Glu Glu Lys Val Gly Leu Lys Tyr Thr Glu Ala
705                 710                 715                 720

Glu Tyr Gln Ala Ala Ile Leu His Leu Lys Arg Glu His Lys Glu Glu
                725                 730                 735

Ile Glu Asn Leu Gln Ala Gln Phe Glu Leu Arg Ala Phe His Ile Arg
            740                 745                 750

Gly Glu His Ala Met Ile Thr Ala Arg Leu Glu Glu Thr Ile Glu Asn
        755                 760                 765

Leu Lys His Glu Leu Glu His Arg Trp Arg Gly Gly Cys Glu Glu Arg
    770                 775                 780

Lys Asp Val Cys Ile Ser Thr Asp Asp Asp Cys Pro Pro Lys Thr Phe
785                 790                 795                 800

Arg Asn Val Cys Val Gln Thr Asp Arg Glu Thr Phe Leu Lys Pro Cys
                805                 810                 815

Glu Ser Glu Ser Lys Thr Thr Arg Ser Asn Gln Leu Val Pro Lys Lys
            820                 825                 830

Leu Asn Ile Ser Ser Leu Ser Gln Leu Ser Pro Pro Asn Asp His Lys
        835                 840                 845

Asp Ile His Ala Ala Leu Gln Pro Met Glu Gly Met Ala Ser Asn Gln
```

```
    850                 855                 860

Gln Lys Ala Leu Pro Pro Pro Pro Ala Ser Ile Pro Pro Pro Pro Pro
865                 870                 875                 880

Leu Pro Ser Gly Leu Gly Ser Leu Ser Pro Ala Pro Pro Met Pro Pro
                885                 890                 895

Val Ser Ala Gly Pro Pro Leu Pro Pro Pro Pro Pro Pro Pro Pro Pro
            900                 905                 910

Leu Pro Pro Pro Ser Ser Ala Gly Pro Pro Pro Pro Pro Pro Pro Pro
        915                 920                 925

Pro Leu Pro Asn Ser Pro Ala Pro Pro Asn Pro Gly Gly Pro Pro Pro
    930                 935                 940

Ala Pro Pro Pro Pro Gly Leu Ala Pro Pro Pro Pro Pro Gly Leu Phe
945                 950                 955                 960

Phe Gly Leu Gly Ser Ser Ser Ser Gln Cys Pro Arg Lys Pro Ala Ile
                965                 970                 975

Glu Pro Ser Cys Pro Met Lys Pro Leu Tyr Trp Thr Arg Ile Gln Ile
            980                 985                 990

Ser Asp Arg Ser Gln Asn Ala Thr  Pro Thr Leu Trp Asp  Ser Leu Glu
        995                 1000                1005

Glu Pro  Asp Ile Arg Asp Pro  Ser Glu Phe Glu Tyr  Leu Phe Ser
    1010                1015                1020

Lys Asp  Thr Thr Gln Gln Lys  Lys Lys Pro Leu Ser  Glu Thr Tyr
    1025                1030                1035

Glu Lys  Lys Asn Lys Val Lys  Lys Ile Ile Lys Leu  Leu Asp Gly
    1040                1045                1050

Lys Arg  Ser Gln Thr Val Gly  Ile Leu Ile Ser Ser  Leu His Leu
    1055                1060                1065

Glu Met  Lys Asp Ile Gln Gln  Ala Ile Phe Asn Val  Asp Asp Ser
    1070                1075                1080

Val Val  Asp Leu Glu Thr Leu  Ala Ala Leu Tyr Glu  Asn Arg Ala
    1085                1090                1095

Gln Glu  Asp Glu Leu Val Lys  Ile Arg Lys Tyr Tyr  Glu Thr Ser
    1100                1105                1110

Lys Glu  Glu Glu Leu Lys Leu  Leu Asp Lys Pro Glu  Gln Phe Leu
    1115                1120                1125

His Glu  Leu Ala Gln Ile Pro  Asn Phe Ala Glu Arg  Ala Gln Cys
    1130                1135                1140

Ile Ile  Phe Arg Ser Val Phe  Ser Glu Gly Ile Thr  Ser Leu His
    1145                1150                1155

Arg Lys  Val Glu Ile Ile Thr  Arg Ala Ser Lys Asp  Leu Leu His
    1160                1165                1170

Val Lys  Ser Val Lys Asp Ile  Leu Ala Leu Ile Leu  Ala Phe Gly
    1175                1180                1185

Asn Tyr  Met Asn Gly Gly Asn  Arg Thr Arg Gly Gln  Ala Asp Gly
    1190                1195                1200

Tyr Ser  Leu Glu Ile Leu Pro  Lys Leu Lys Asp Val  Lys Ser Arg
    1205                1210                1215

Asp Asn  Gly Ile Asn Leu Val  Asp Tyr Val Val Lys  Tyr Tyr Leu
    1220                1225                1230

Arg Tyr  Tyr Asp Gln Glu Ala  Gly Thr Glu Lys Ser  Val Phe Pro
    1235                1240                1245

Leu Pro  Glu Pro Gln Asp Phe  Phe Leu Ala Ser Gln  Val Lys Phe
    1250                1255                1260
```

```
Glu Asp  Leu Ile Lys Asp Leu  Arg Lys Leu Lys Arg  Gln Leu Glu
    1265                 1270                 1275

Ala Ser  Glu Lys Gln Met Val  Val Val Cys Lys Glu  Ser Pro Lys
    1280                 1285                 1290

Glu Tyr  Leu Gln Pro Phe Lys  Asp Lys Leu Glu Glu  Phe Phe Gln
    1295                 1300                 1305

Lys Ala  Lys Lys Glu His Lys  Met Glu Glu Ser His  Leu Glu Asn
    1310                 1315                 1320

Ala Gln  Lys Ser Phe Glu Thr  Thr Val Arg Tyr Phe  Gly Met Lys
    1325                 1330                 1335

Pro Lys  Ser Gly Glu Lys Glu  Ile Thr Pro Ser Tyr  Val Phe Met
    1340                 1345                 1350

Val Trp  Tyr Glu Phe Cys Ser  Asp Phe Lys Thr Ile  Trp Lys Arg
    1355                 1360                 1365

Glu Ser  Lys Asn Ile Ser Lys  Glu Arg Leu Lys Met  Ala Gln Glu
    1370                 1375                 1380

Ser Val  Ser Lys Leu Thr Ser  Glu Lys Lys Val Glu  Thr Lys Lys
    1385                 1390                 1395

Ile Asn  Pro Thr Ala Ser Leu  Lys Glu Arg Leu Arg  Gln Lys Glu
    1400                 1405                 1410

Ala Ser  Val Thr Thr Asn
    1415
```

<210> SEQ ID NO 17
<211> LENGTH: 8555
<212> TYPE: DNA
<213> ORGANISM: Homo sapiens

<400> SEQUENCE: 17

```
gctaaatggt taagagatac ataaatactg cagtagagat gggattttac ctcaaagtgc     60

aaaggtaaat gaaataaagt tttttcaatg gaaggcttgc agctcttgag gacctgccaa    120

atggaagaag gacagagacc tggagcccta tggaaagttc tgacaccatg tgtggaagga    180

catggctttt aacacgtgtg gtgactggag tagctgcagc tgaggacagc caccctttct    240

tcgtctctgc tgagcgaagg ctacacggcc cttcctcctt gcagctgttt caccttctac    300

cttgcgtgga gccaggcttt tgcaccgaat ctgagatgcc attttaaaca gaagactcca    360

tcctcttgaa gatgggaaat tcttacgctg gacagctgaa gacgacacgc tttgaagagg    420

tcttgcacaa ttccatcgag gcatccctgc ggtccaacaa cctggtgccc aggcccatct    480

tttcccagct gtacctggaa gctgagcagc agcttgccgc tctagaaggt ggtagccgag    540

tggacaatga ggaagaggaa gaagagggag aaggagggct ggaaacaaat ggccccccaa    600

accctttcca gctgcaccct ctgcctgaag gatgctgtac cacagacggg ttttgccagg    660

ccgggaagga cctgcgcctt gtctccattt ccaacgagcc catggatgtc cctgcgggct    720

ttctcctcgt gggggtcaag tcccccagcc tgccggacca tctcctggtg tgcgccgttg    780

acaagaggtt cttgccagat gacaatggcc acaatgctct tcttggtttc tctgggaatt    840

gtgttggctg tggaaagaaa ggcttctgtt acttcacgga attctccaat catataaatc    900

tgaaactgac cactcaaccc aagaagcaga aacacttgaa gtattacctg gtccgtaatg    960

cacaagggac tctaaccaaa ggacctttaa tctgttggaa aggctcagag tttagaagcc   1020

ggcagatccc cgccagtact tgttccagtt ccctcttccc agccctggag agcacggctg   1080

ccttccccag cgagcccgtt cctgggacga accccagcat cctgatggga gctcagcagg   1140
```

caggaccagc ttctgatcac ccctcactaa acgcagcaat gggtccggct gttttcaacg 1200
gcaaagattc cccgaagtgc caacaactgg caaagaataa cctgttggcc ctgccgcgac 1260
catcggcttt aggtatcttg tcaaactccg ggccccccaa aaaacgccac aaagggtggt 1320
ctccagaatc tccatcagct ccagatggtg gctgccccca aggtggtggg aacagagcta 1380
agtatgagag cgcaggcatg tcctgcgtgc cgcaggttgg cttggtggga ccagcttcag 1440
tcacctttcc agtggtggcc tctggagaac cagtgtctgt tcctgacaac ttgctgaaaa 1500
tatgcaaggc caagccagtg atatttaaag gccatgggaa cttcccttac ctctgtggga 1560
acctgaatga cgtcgtggtc agccccctct tgtacacgtg ctaccagaat tcccagtctg 1620
tctcacgggc atacgagcag tacggcgcct ctgccatcca gcccatctcc gaggagatgc 1680
agctcctgct taccgtctac tacctggtcc agctggccgc ggaccaggtg cccttgatgg 1740
aggacctgga gcagatcttc ctgcgctctt ggcgcgagtc gcacctgacc gagatccggc 1800
agtaccagca ggcgccgccg cagcccttcc cgcccgcgcc cagcgccgcg gcacccgtga 1860
cctccgcgca gctgccctgg ctggccagcc tggccgccag ctcctgcaac gacagcgtgc 1920
acgtcatcga gtgtgcttac tccctggccg agggcctctc cgagatgttc cggctgttgg 1980
tcgagggcaa gcttgccaag accaactacg tggtcatcat ctgcgcctgc cgcagcgcgg 2040
ccatcgactc ctgcatcgcc gtcaccggaa aataccaagc ccggattctt tccgagagcc 2100
ttctcactcc tgcggagtac cagaaggaag tcaattacga gctggttacg ggaaggtag 2160
actcgctggg ggccttcttt agcaccctct gtccagaggg tgacattgac attttgctgg 2220
acaaatttca ccaggaaaat caaggccata tttcttcctc actcgctgcc tcttctgtca 2280
ctaaagcagc atccctggat gtcagtggga caccggtgtg cacaagttac aatctggagc 2340
cacacagcat ccggcccttc cagctggcag tagcgcagaa gctcctctcc catgtgtgtt 2400
ccattgcgga ttccagcacc caaaatctgg acctgggatc ctttgagaag gtggactttc 2460
tcatttgcat tcccccctca gaagtgacct accagcagac tctgctccat gtgtggcatt 2520
caggggtttt gctggagctt ggtctgaaga aagagcacat gacgaagcag agggtggaac 2580
agtatgttct gaagctagac acggaggcac agacaaaatt taaggctttt ctgcaaaact 2640
ccttccagaa cccgcataca ctttttgtcc taatccatga ccatgcgcac tgggatcttg 2700
tgagtagcac tgttcataac ctctattctc aaagtgaccc gtcggtggga ttggtggacc 2760
gattgctcaa ctgcagggag gtgaaggagg cccccaacat tgtgacactt cacgtgacct 2820
ccttcccgta tgcactgcag acacagcaca ccctcatcag cccctacaac gagatccact 2880
ggcctgcctc ctgcagtaat ggagtggact tatatcatga aaataagaag tacttcgggc 2940
tgtcggagtt tattgaatcc accctttcag gacacagcct cccccttgctc agatacgata 3000
gctcctttga ggccatggtc actgcattag gaaaaaggtt cccccgcctg cacagcgcgg 3060
tgatcaggac ctttgttctc gtgcagcact acgcggccgc cctgatggcc gtaagcggcc 3120
tcccgcagat gaagaactac acgtcggtgg agacgctgga gatcacgcag aacctcctca 3180
actccccgaa gcagtgcccc tgcggccacg ggctcatggt cctgctgcgg gtgccctgtt 3240
cgcccctggc ggtggtggcc tatgagcggc tggcccacgt gcgggcccgg ctggcgctgg 3300
aggagcactt tgagatcatc ctgggcagtc ccagctcagg cgtcaccgtg gggaagcact 3360
tcgtaaagca gctcaggatg tggcagaaaa ttgaggatgt ggagtggaga ccccagactt 3420
acttggagct ggagggtctg ccttgcatcc tgatcttcag tgggatggac ccgcatgggg 3480

-continued

```
agtccttgcc gaggtctttg aggtactgtg acctgcgatt gataaactcc tcctgcttgg   3540
tgagaacagc cttggagcag gagctgggcc tggctgccta ctttgtgagc aacgaggttc   3600
ccttggagaa gggggctagg aacgaggcct tggagagtga tgctgagaag ctgagcagca   3660
cagacaacga ggatgaggag ctggggacag aaggctctac ctcggagaag agaagcccca   3720
tgaaaaggga gaggtcccgc tcccacgact cagcatcctc atccctctcc tccaaggctt   3780
ccggttcagc gctcggtggc gagtcctcgg ctcagcccac agcactcccc cagggagagc   3840
atgccaggtc gccccagccc cgtggccccg cagaggaggg cagagcccct ggtgagaaac   3900
agaggccccg ggcaagtcag gggccaccct cggccatcag caggcacagt cccgggccga   3960
cgccccagcc cgactgtagc ctcaggaccg gccagaggag cgtccaggtg tcggtcacct   4020
cgtcgtgctc ccagctgtcc tcctcctcgg gctcatcctc ctcatccgtg gcgcccgctg   4080
ccggcacgtg ggtcctgcag gcctcccagt gctccttgac caaggcctgc cgccagccac   4140
ccattgtctt cttgcccaag ctcgtgtacg acatggttgt gtccactgac agcagtggcc   4200
tgcccaaggc cgcctccctc ctgccctccc cctcggtcat gtgggccagc tctttccgcc   4260
ccctgctcag caagaccatg acatccaccg agcagtccct ctactaccgg cagtggacgg   4320
tgccccggcc cagccacatg gactacggca accgggccga gggccgcgtg gacggcttcc   4380
acccccgcag gctgctgctc agcggccccc ctcagatcgg gaagacaggt gcctacctgc   4440
agttcctcag tgtcctgtcc aggatgcttg ttcggctcac agaagtggat gtctatgacg   4500
aggaggagat caatatcaac ctcagagaag aatctgactg gcattatctc cagcttagcg   4560
acccctggcc agacctggag ctgttcaaga agttgccctt tgactacatc attcacgacc   4620
cgaagtatga agatgccagc ctgatttgtt cgcactatca gggtataaag agtgaagaca   4680
gagggatgtc ccggaagccg gaggaccttt atgtgcggcg tcagacggca cggatgagac   4740
tgtccaagta cgcagcgtac aacacttacc accactgtga gcagtgccac cagtacatgg   4800
gcttccaccc ccgctaccag ctgtatgagt ccaccctgca cgcctttgcc ttctcttact   4860
ccatgctagg agaggagatc cagctgcact tcatcatccc caagtccaag gagcaccact   4920
ttgtcttcag ccaacctgga ggccagctgg agagcatgcg actacccctc gtgacagaca   4980
agagccatga atatataaaa agtccgacat tcactccaac caccggccgt cacgaacatg   5040
ggctctttaa tctgtaccac gcaatggacg gtgccagcca tttgcacgtg ctggttgtca   5100
aggaatacga gatggcaatt tataagaaat attggcccaa ccacatcatg ctggtgctcc   5160
ccagtatctt caacagtgct ggagttggtg ctgctcattt cctcatcaag gagctgtcct   5220
accataacct ggagctcgag cggaaccggc aggaggagct gggaatcaag ccgcaggaca   5280
tctggccttt cattgtgatc tctgatgact cctgcgtgat gtggaacgtg gtggatgtca   5340
actctgctgg ggagagaagc agggagttct cctggtcgga aaggaacgtg tctttgaagc   5400
acatcatgca gcacatcgag gcggcccccg acatcatgca ctacgccctg ctgggcctgc   5460
ggaagtggtc cagcaagacc cgggccagcg aggtgcaaga gcccttctcc cgctgccacg   5520
tgcacaactt catcatcctg aacgtggacc tgacccagaa cgtgcagtac aaccagaacc   5580
ggttcctgtg tgacgatgta gacttcaacc tgcgggtgca cagcgccggc ctcctgctct   5640
gccggttcaa ccgcttcagc gtgatgaaga agcagatcgt ggtgggcggc cacaggtcct   5700
tccacatcac atccaaggtg tctgataact ctgccgcggt cgtgccggcc cagtacatct   5760
gtgccccgga cagcaagcac acgttcctcg cagcgcccgc ccagctcctg ctggagaagt   5820
tcctgcagca ccacagccac ctcttcttcc cgctgtccct gaagaaccat gaccacccag   5880
```

```
tgctgtctgt cgactgttac ctgaacctgg gatctcagat ttctgtttgc tatgtgagct   5940
ccaggcccca ctctttaaac atcagctgct cggacttgct gttcagtggg ctgctgctgt   6000
acctctgtga ctcttttgtg ggagctagct ttttgaaaaa gtttcatttt ctgaaaggtg   6060
cgacgttgtg tgtcatctgt caggaccgga gctcactgcg ccagacggtc gtccgcctgg   6120
agctcgagga cgagtggcag ttccggctgc gcgatgagtt ccagaccgcc aatgccaggg   6180
aagaccggcc gctctttttt ctgacgggac gacacatctg aggaagacag cggcgagttt   6240
tctgaagaga tgagtgctca gagccctcat gctgttgagg ctaaagggag gcctggaacg   6300
gtggggcgtt tgactggaat ggaccccagg gactgtccag gtgcagcccc tcctagtaca   6360
catgggcccc cgaggccgtg gtcctgggag ccaggaagac tccgcagtgg gtgagaatga   6420
aaacttgaga ctcccaagtt ctgggccagc ccattgctct gggctgtttt aaagcccatt   6480
tcacgaggaa caaagattta cttcctgtcc tgccattcgt gtgcttccat ggacaaacct   6540
gatttttttc tcttagttct aaagaatctt gggttatttt gtagcggtgc cagtatttca   6600
gtagatggga tttcagccaa gtaggttccc ctgtaacctc ctacaaagca atattccaaa   6660
ggaacatttt aactgtaaag gctggagaca agaaaaaata agtagatcgt tttaataaca   6720
attatttaat tgcctataag tttgctgttt cagaggctag cccaaaggca tcaaatttaa   6780
taaagttaaa caaattgatt tacttcagag caaatatgat cctattaaaa taatataggg   6840
taaataccct acctcttaga aagggcaaaa atgcaaagaa gctttcttta aaactaaaag   6900
ggtttttttgg gggggagtt ggcggggagg aaataaggct aacagaggtt gacctaaaat   6960
tagccttaca aaggagaaag gaccacattg cttacttgaa acagacaatg aaaacaacca   7020
aagtgatata taaaatagtt gatgagaact agacttatga ctgtagttta ctagagttta   7080
gttttcagtt gctgaagtag ctcattttct cttactaatg tttggttcct cagggaagaa   7140
tctcacttga ctagagagga ggtgggaaca gaagagagaa ggaggcaggg agatgtattt   7200
cttagggctc accccttcac agactgacag aatggttttg ttttgttttg ttttgttttg   7260
ttttgttttt gagatggact ctagctctgt cacccaggct ggagtgcagt ggtgcgatct   7320
cggctcactg caagctccgc ctcccgggtt ctcaccattc tcctgcctca gcctcccgag   7380
tagctgggac tacaggcgcc caccaccacg cccggctaat tttttgtatt ttttagtaga   7440
gacggggttt caccatgtta gccaggatgg tctcgatctc ctgacctcgt gatccgcccg   7500
cctcggcctc ccaaagtgct gggattacag gcgtgagcca ccgtgcctgc cccagaatgg   7560
tttttaaagc cacagttgag aggccaccca ttgcccggcg cctggacagt gatcatcttg   7620
ttcatcttgt tcagtccttt cttgtgtgat tggaattatt catccccttt gaaagatgag   7680
aaggttgaga tgcaaagagt ctacctttcc aagttctcac tgctggaaag agctagaagc   7740
acagttcaaa gttctggctt ctggactctg cagtccaggt ctcccttctc ccacttgcct   7800
accctcaatg ccacactgtt tttgaagtgg cccataactt gaaggaaaag tttaaagaca   7860
gttcaattta atcatcagaa tgcattcttt tttttttcgg agacggagtt tcactcttgc   7920
tgcccaggct ggagtgcaat ggtgcaatga cctcggctca ctgcaacctc tgcctcctgg   7980
gttcaagtga ttctccagcc tcagcctccc gagtagctgg gattatgggc gcccaccacc   8040
atgcccagct aatttttgta tttttttttt ttagtagaga tggggtttcg ccaggttggc   8100
caggctggtc ttgtgaactc ctggcctcag gtgatctgcc cacctcatcc tccaaaagtg   8160
ctgggattac aggcatgagc cactgcgcct ggcctcagaa tgcattctta cacatctatc   8220
```

ctagacattt ataagcactc taatggataa caatccaaga ataaatgatt gtaaaagatg 8280
atgccgaaga gttgatgtca atcttttttt cctaagaaaa aaagtccgcg agtattaaat 8340
atttagatca atgtttataa aatgattact ttgtatatct cattattcct attttggaat 8400
aaaaactgac cttctttaat catatacttg tcttttgtaa atagcagctt ttgtgtcatt 8460
ctccccactt tattagttaa tttaaattgg aaaaaaccct caaactaata ttcttgtctg 8520
ttccagtctt ataaataaaa cttataatgc atgta 8555

<210> SEQ ID NO 18
<211> LENGTH: 1949
<212> TYPE: PRT
<213> ORGANISM: Homo sapiens

<400> SEQUENCE: 18

Met Gly Asn Ser Tyr Ala Gly Gln Leu Lys Thr Thr Arg Phe Glu Glu
1 5 10 15

Val Leu His Asn Ser Ile Glu Ala Ser Leu Arg Ser Asn Asn Leu Val
20 25 30

Pro Arg Pro Ile Phe Ser Gln Leu Tyr Leu Glu Ala Glu Gln Gln Leu
35 40 45

Ala Ala Leu Glu Gly Gly Ser Arg Val Asp Asn Glu Glu Glu Glu Glu
50 55 60

Glu Gly Glu Gly Gly Leu Glu Thr Asn Gly Pro Pro Asn Pro Phe Gln
65 70 75 80

Leu His Pro Leu Pro Glu Gly Cys Cys Thr Thr Asp Gly Phe Cys Gln
85 90 95

Ala Gly Lys Asp Leu Arg Leu Val Ser Ile Ser Asn Glu Pro Met Asp
100 105 110

Val Pro Ala Gly Phe Leu Leu Val Gly Val Lys Ser Pro Ser Leu Pro
115 120 125

Asp His Leu Leu Val Cys Ala Val Asp Lys Arg Phe Leu Pro Asp Asp
130 135 140

Asn Gly His Asn Ala Leu Leu Gly Phe Ser Gly Asn Cys Val Gly Cys
145 150 155 160

Gly Lys Lys Gly Phe Cys Tyr Phe Thr Glu Phe Ser Asn His Ile Asn
165 170 175

Leu Lys Leu Thr Thr Gln Pro Lys Lys Gln Lys His Leu Lys Tyr Tyr
180 185 190

Leu Val Arg Asn Ala Gln Gly Thr Leu Thr Lys Gly Pro Leu Ile Cys
195 200 205

Trp Lys Gly Ser Glu Phe Arg Ser Arg Gln Ile Pro Ala Ser Thr Cys
210 215 220

Ser Ser Ser Leu Phe Pro Ala Leu Glu Ser Thr Ala Ala Phe Pro Ser
225 230 235 240

Glu Pro Val Pro Gly Thr Asn Pro Ser Ile Leu Met Gly Ala Gln Gln
245 250 255

Ala Gly Pro Ala Ser Asp His Pro Ser Leu Asn Ala Ala Met Gly Pro
260 265 270

Ala Val Phe Asn Gly Lys Asp Ser Pro Lys Cys Gln Gln Leu Ala Lys
275 280 285

Asn Asn Leu Leu Ala Leu Pro Arg Pro Ser Ala Leu Gly Ile Leu Ser
290 295 300

Asn Ser Gly Pro Pro Lys Lys Arg His Lys Gly Trp Ser Pro Glu Ser
305 310 315 320

```
Pro Ser Ala Pro Asp Gly Gly Cys Pro Gln Gly Gly Gly Asn Arg Ala
                325                 330                 335

Lys Tyr Glu Ser Ala Gly Met Ser Cys Val Pro Gln Val Gly Leu Val
            340                 345                 350

Gly Pro Ala Ser Val Thr Phe Pro Val Val Ala Ser Gly Glu Pro Val
        355                 360                 365

Ser Val Pro Asp Asn Leu Leu Lys Ile Cys Lys Ala Lys Pro Val Ile
    370                 375                 380

Phe Lys Gly His Gly Asn Phe Pro Tyr Leu Cys Gly Asn Leu Asn Asp
385                 390                 395                 400

Val Val Val Ser Pro Leu Leu Tyr Thr Cys Tyr Gln Asn Ser Gln Ser
                405                 410                 415

Val Ser Arg Ala Tyr Glu Gln Tyr Gly Ala Ser Ala Ile Gln Pro Ile
            420                 425                 430

Ser Glu Glu Met Gln Leu Leu Leu Thr Val Tyr Tyr Leu Val Gln Leu
        435                 440                 445

Ala Ala Asp Gln Val Pro Leu Met Glu Asp Leu Glu Gln Ile Phe Leu
    450                 455                 460

Arg Ser Trp Arg Glu Ser His Leu Thr Glu Ile Arg Gln Tyr Gln Gln
465                 470                 475                 480

Ala Pro Pro Gln Pro Phe Pro Pro Ala Pro Ser Ala Ala Ala Pro Val
                485                 490                 495

Thr Ser Ala Gln Leu Pro Trp Leu Ala Ser Leu Ala Ala Ser Ser Cys
            500                 505                 510

Asn Asp Ser Val His Val Ile Glu Cys Ala Tyr Ser Leu Ala Glu Gly
        515                 520                 525

Leu Ser Glu Met Phe Arg Leu Leu Val Glu Gly Lys Leu Ala Lys Thr
    530                 535                 540

Asn Tyr Val Val Ile Ile Cys Ala Cys Arg Ser Ala Ala Ile Asp Ser
545                 550                 555                 560

Cys Ile Ala Val Thr Gly Lys Tyr Gln Ala Arg Ile Leu Ser Glu Ser
                565                 570                 575

Leu Leu Thr Pro Ala Glu Tyr Gln Lys Glu Val Asn Tyr Glu Leu Val
            580                 585                 590

Thr Gly Lys Val Asp Ser Leu Gly Ala Phe Phe Ser Thr Leu Cys Pro
        595                 600                 605

Glu Gly Asp Ile Asp Ile Leu Leu Asp Lys Phe His Gln Glu Asn Gln
    610                 615                 620

Gly His Ile Ser Ser Ser Leu Ala Ala Ser Ser Val Thr Lys Ala Ala
625                 630                 635                 640

Ser Leu Asp Val Ser Gly Thr Pro Val Cys Thr Ser Tyr Asn Leu Glu
                645                 650                 655

Pro His Ser Ile Arg Pro Phe Gln Leu Ala Val Ala Gln Lys Leu Leu
            660                 665                 670

Ser His Val Cys Ser Ile Ala Asp Ser Ser Thr Gln Asn Leu Asp Leu
        675                 680                 685

Gly Ser Phe Glu Lys Val Asp Phe Leu Ile Cys Ile Pro Pro Ser Glu
    690                 695                 700

Val Thr Tyr Gln Gln Thr Leu Leu His Val Trp His Ser Gly Val Leu
705                 710                 715                 720

Leu Glu Leu Gly Leu Lys Lys Glu His Met Thr Lys Gln Arg Val Glu
                725                 730                 735
```

```
Gln Tyr Val Leu Lys Leu Asp Thr Glu Ala Gln Thr Lys Phe Lys Ala
            740                 745                 750

Phe Leu Gln Asn Ser Phe Gln Asn Pro His Thr Leu Phe Val Leu Ile
        755                 760                 765

His Asp His Ala His Trp Asp Leu Val Ser Ser Thr Val His Asn Leu
    770                 775                 780

Tyr Ser Gln Ser Asp Pro Ser Val Gly Leu Val Asp Arg Leu Leu Asn
785                 790                 795                 800

Cys Arg Glu Val Lys Glu Ala Pro Asn Ile Val Thr Leu His Val Thr
                805                 810                 815

Ser Phe Pro Tyr Ala Leu Gln Thr Gln His Thr Leu Ile Ser Pro Tyr
            820                 825                 830

Asn Glu Ile His Trp Pro Ala Ser Cys Ser Asn Gly Val Asp Leu Tyr
        835                 840                 845

His Glu Asn Lys Lys Tyr Phe Gly Leu Ser Glu Phe Ile Glu Ser Thr
    850                 855                 860

Leu Ser Gly His Ser Leu Pro Leu Leu Arg Tyr Asp Ser Ser Phe Glu
865                 870                 875                 880

Ala Met Val Thr Ala Leu Gly Lys Arg Phe Pro Arg Leu His Ser Ala
                885                 890                 895

Val Ile Arg Thr Phe Val Leu Val Gln His Tyr Ala Ala Ala Leu Met
            900                 905                 910

Ala Val Ser Gly Leu Pro Gln Met Lys Asn Tyr Thr Ser Val Glu Thr
        915                 920                 925

Leu Glu Ile Thr Gln Asn Leu Leu Asn Ser Pro Lys Gln Cys Pro Cys
    930                 935                 940

Gly His Gly Leu Met Val Leu Leu Arg Val Pro Cys Ser Pro Leu Ala
945                 950                 955                 960

Val Val Ala Tyr Glu Arg Leu Ala His Val Arg Ala Arg Leu Ala Leu
                965                 970                 975

Glu Glu His Phe Glu Ile Ile Leu Gly Ser Pro Ser Ser Gly Val Thr
            980                 985                 990

Val Gly Lys His Phe Val Lys Gln  Leu Arg Met Trp Gln  Lys Ile Glu
        995                 1000                1005

Asp Val  Glu Trp Arg Pro Gln  Thr Tyr Leu Glu Leu  Glu Gly Leu
    1010                1015                1020

Pro Cys  Ile Leu Ile Phe Ser  Gly Met Asp Pro His  Gly Glu Ser
    1025                1030                1035

Leu Pro  Arg Ser Leu Arg Tyr  Cys Asp Leu Arg Leu  Ile Asn Ser
    1040                1045                1050

Ser Cys  Leu Val Arg Thr Ala  Leu Glu Gln Glu Leu  Gly Leu Ala
    1055                1060                1065

Ala Tyr  Phe Val Ser Asn Glu  Val Pro Leu Glu Lys  Gly Ala Arg
    1070                1075                1080

Asn Glu  Ala Leu Glu Ser Asp  Ala Glu Lys Leu Ser  Ser Thr Asp
    1085                1090                1095

Asn Glu  Asp Glu Glu Leu Gly  Thr Glu Gly Ser Thr  Ser Glu Lys
    1100                1105                1110

Arg Ser  Pro Met Lys Arg Glu  Arg Ser Arg Ser His  Asp Ser Ala
    1115                1120                1125

Ser Ser  Ser Leu Ser Ser Lys  Ala Ser Gly Ser Ala  Leu Gly Gly
    1130                1135                1140

Glu Ser  Ser Ala Gln Pro Thr  Ala Leu Pro Gln Gly  Glu His Ala
```

1145 1150 1155

Arg Ser Pro Gln Pro Arg Gly Pro Ala Glu Glu Gly Arg Ala Pro
1160 1165 1170

Gly Glu Lys Gln Arg Pro Arg Ala Ser Gln Gly Pro Pro Ser Ala
1175 1180 1185

Ile Ser Arg His Ser Pro Gly Pro Thr Pro Gln Pro Asp Cys Ser
1190 1195 1200

Leu Arg Thr Gly Gln Arg Ser Val Gln Val Ser Val Thr Ser Ser
1205 1210 1215

Cys Ser Gln Leu Ser Ser Ser Ser Gly Ser Ser Ser Ser Ser Val
1220 1225 1230

Ala Pro Ala Ala Gly Thr Trp Val Leu Gln Ala Ser Gln Cys Ser
1235 1240 1245

Leu Thr Lys Ala Cys Arg Gln Pro Pro Ile Val Phe Leu Pro Lys
1250 1255 1260

Leu Val Tyr Asp Met Val Val Ser Thr Asp Ser Ser Gly Leu Pro
1265 1270 1275

Lys Ala Ala Ser Leu Leu Pro Ser Pro Ser Val Met Trp Ala Ser
1280 1285 1290

Ser Phe Arg Pro Leu Leu Ser Lys Thr Met Thr Ser Thr Glu Gln
1295 1300 1305

Ser Leu Tyr Tyr Arg Gln Trp Thr Val Pro Arg Pro Ser His Met
1310 1315 1320

Asp Tyr Gly Asn Arg Ala Glu Gly Arg Val Asp Gly Phe His Pro
1325 1330 1335

Arg Arg Leu Leu Leu Ser Gly Pro Pro Gln Ile Gly Lys Thr Gly
1340 1345 1350

Ala Tyr Leu Gln Phe Leu Ser Val Leu Ser Arg Met Leu Val Arg
1355 1360 1365

Leu Thr Glu Val Asp Val Tyr Asp Glu Glu Glu Ile Asn Ile Asn
1370 1375 1380

Leu Arg Glu Glu Ser Asp Trp His Tyr Leu Gln Leu Ser Asp Pro
1385 1390 1395

Trp Pro Asp Leu Glu Leu Phe Lys Lys Leu Pro Phe Asp Tyr Ile
1400 1405 1410

Ile His Asp Pro Lys Tyr Glu Asp Ala Ser Leu Ile Cys Ser His
1415 1420 1425

Tyr Gln Gly Ile Lys Ser Glu Asp Arg Gly Met Ser Arg Lys Pro
1430 1435 1440

Glu Asp Leu Tyr Val Arg Arg Gln Thr Ala Arg Met Arg Leu Ser
1445 1450 1455

Lys Tyr Ala Ala Tyr Asn Thr Tyr His His Cys Glu Gln Cys His
1460 1465 1470

Gln Tyr Met Gly Phe His Pro Arg Tyr Gln Leu Tyr Glu Ser Thr
1475 1480 1485

Leu His Ala Phe Ala Phe Ser Tyr Ser Met Leu Gly Glu Glu Ile
1490 1495 1500

Gln Leu His Phe Ile Ile Pro Lys Ser Lys Glu His His Phe Val
1505 1510 1515

Phe Ser Gln Pro Gly Gly Gln Leu Glu Ser Met Arg Leu Pro Leu
1520 1525 1530

Val Thr Asp Lys Ser His Glu Tyr Ile Lys Ser Pro Thr Phe Thr
1535 1540 1545

```
Pro Thr  Thr Gly Arg His Glu  His Gly Leu Phe Asn  Leu Tyr His
    1550                 1555                 1560

Ala Met  Asp Gly Ala Ser His  Leu His Val Leu Val  Val Lys Glu
    1565                 1570                 1575

Tyr Glu  Met Ala Ile Tyr Lys  Lys Tyr Trp Pro Asn  His Ile Met
    1580                 1585                 1590

Leu Val  Leu Pro Ser Ile Phe  Asn Ser Ala Gly Val  Gly Ala Ala
    1595                 1600                 1605

His Phe  Leu Ile Lys Glu Leu  Ser Tyr His Asn Leu  Glu Leu Glu
    1610                 1615                 1620

Arg Asn  Arg Gln Glu Glu Leu  Gly Ile Lys Pro Gln  Asp Ile Trp
    1625                 1630                 1635

Pro Phe  Ile Val Ile Ser Asp  Asp Ser Cys Val Met  Trp Asn Val
    1640                 1645                 1650

Val Asp  Val Asn Ser Ala Gly  Glu Arg Ser Arg Glu  Phe Ser Trp
    1655                 1660                 1665

Ser Glu  Arg Asn Val Ser Leu  Lys His Ile Met Gln  His Ile Glu
    1670                 1675                 1680

Ala Ala  Pro Asp Ile Met His  Tyr Ala Leu Leu Gly  Leu Arg Lys
    1685                 1690                 1695

Trp Ser  Ser Lys Thr Arg Ala  Ser Glu Val Gln Glu  Pro Phe Ser
    1700                 1705                 1710

Arg Cys  His Val His Asn Phe  Ile Ile Leu Asn Val  Asp Leu Thr
    1715                 1720                 1725

Gln Asn  Val Gln Tyr Asn Gln  Asn Arg Phe Leu Cys  Asp Asp Val
    1730                 1735                 1740

Asp Phe  Asn Leu Arg Val His  Ser Ala Gly Leu Leu  Leu Cys Arg
    1745                 1750                 1755

Phe Asn  Arg Phe Ser Val Met  Lys Lys Gln Ile Val  Val Gly Gly
    1760                 1765                 1770

His Arg  Ser Phe His Ile Thr  Ser Lys Val Ser Asp  Asn Ser Ala
    1775                 1780                 1785

Ala Val  Val Pro Ala Gln Tyr  Ile Cys Ala Pro Asp  Ser Lys His
    1790                 1795                 1800

Thr Phe  Leu Ala Ala Pro Ala  Gln Leu Leu Leu Glu  Lys Phe Leu
    1805                 1810                 1815

Gln His  His Ser His Leu Phe  Phe Pro Leu Ser Leu  Lys Asn His
    1820                 1825                 1830

Asp His  Pro Val Leu Ser Val  Asp Cys Tyr Leu Asn  Leu Gly Ser
    1835                 1840                 1845

Gln Ile  Ser Val Cys Tyr Val  Ser Ser Arg Pro His  Ser Leu Asn
    1850                 1855                 1860

Ile Ser  Cys Ser Asp Leu Leu  Phe Ser Gly Leu Leu  Leu Tyr Leu
    1865                 1870                 1875

Cys Asp  Ser Phe Val Gly Ala  Ser Phe Leu Lys Lys  Phe His Phe
    1880                 1885                 1890

Leu Lys  Gly Ala Thr Leu Cys  Val Ile Cys Gln Asp  Arg Ser Ser
    1895                 1900                 1905

Leu Arg  Gln Thr Val Val Arg  Leu Glu Leu Glu Asp  Glu Trp Gln
    1910                 1915                 1920

Phe Arg  Leu Arg Asp Glu Phe  Gln Thr Ala Asn Ala  Arg Glu Asp
    1925                 1930                 1935
```

-continued

```
Arg Pro  Leu Phe Phe Leu Thr  Gly Arg His Ile
    1940                 1945
```

<210> SEQ ID NO 19
<211> LENGTH: 2246
<212> TYPE: DNA
<213> ORGANISM: Homo sapiens

<400> SEQUENCE: 19

```
aaagtccggg ggagccggtc ccgggcagcc gctcagcccc ctgcccctcg ccgcccgccg     60
cctgcctggg ccgggccgag gatgcggcgc agcgcctcgg cggccaggct tgctcccctc    120
cggcacgcct gctaacttcc cccgctacgt ccccgttcgc ccgccgggcc gccccgtctc    180
cccgcgccct ccgggtcggg tcctccagga gcgccaggcg ctgccgccgt gtgccctccg    240
ccgctcgccc gcgcgcccgc gctccccgcc tgcgcccagc gccccgcgcc cgcgcccagt    300
cctcgggcgg tcatgctgcc cctctgcctc gtggccgccc tgctgctggc cgccgggccc    360
gggccgagcc tgggcgacga agccatccac tgcccgccct gctccgagga gaagctggcg    420
cgctgccgcc cccccgtggg ctgcgaggag ctggtgcgag agccgggctg cggctgttgc    480
gccacttgcg ccctgggctt ggggatgccc tgcggggtgt acaccccccg ttgcggctcg    540
ggcctgcgct gctacccgcc ccgaggggtg gagaagcccc tgcacacact gatgcacggg    600
caaggcgtgt gcatggagct ggcggagatc gaggccatcc aggaaagcct gcagccctct    660
gacaaggacg agggtgacca ccccaacaac agcttcagcc cctgtagcgc ccatgaccgc    720
aggtgcctgc agaagcactt cgccaaaatt cgagaccgga gcaccagtgg gggcaagatg    780
aaggtcaatg gggcgccccg ggaggatgcc cggcctgtgc cccagggctc ctgccagagc    840
gagctgcacc gggcgctgga gcggctggcc gcttcacaga gccgcaccca cgaggacctc    900
tacatcatcc ccatccccaa ctgcgaccgc aacggcaact tccaccccaa gcagtgtcac    960
ccagctctgg atgggcagcg tggcaagtgc tggtgtgtgg accggaagac gggggtgaag   1020
cttccggggg gcctggagcc aaagggggag ctggactgcc accagctggc tgacagcttt   1080
cgagagtgag gcctgccagc aggccaggga ctcagcgtcc cctgctactc ctgtgctctg   1140
gaggctgcag agctgaccca gagtggagtc tgagtctgag tcctgtctct gcctgcggcc   1200
cagaagtttc cctcaaatgc gcgtgtgcac gtgtgcgtgt gcgtgcgtgt gtgtgtgttt   1260
gtgagcatgg gtgtgccctt ggggtaagcc agagcctggg gtgttctctt tggtgttaca   1320
cagcccaaga ggactgagac tggcacttag cccaagaggt ctgagccctg gtgtgtttcc   1380
agatcgatcc tggattcact cactcactca ttccttcact catccagcca cctaaaaaca   1440
tttactgacc atgtactacg tgccagctct agttttcagc cttgggaggt tttattctga   1500
cttcctctga ttttggcatg tggagacact cctataagga gagttcaagc ctgtgggagt   1560
agaaaaatct cattcccaga gtcagaggag aagagacatg taccttgacc atcgtccttc   1620
ctctcaagct agccagaggg tgggagccta aggaagcgtg gggtagcaga tggagtaatg   1680
gtcacgaggt ccagacccac tcccaaagct cagacttgcc aggctccctt tctcttcttc   1740
cccaggtcct tcctttaggt ctggttgttg caccatctgc ttggttggct ggcagctgag   1800
agccctgctg tgggagagcg aagggggtca aaggaagact tgaagcacag agggctaggg   1860
aggtggggta catttctctg agcagtcagg gtgggaagaa agaatgcaag agtggactga   1920
atgtgcctaa tggagaagac ccacgtgcta ggggatgagg ggcttcctgg gtcctgttcc   1980
ctaccccatt tgtggtcaca gccatgaagt caccgggatg aacctatcct tccagtggct   2040
```

cgctccctgt agctctgcct ccctctccat atctccttcc cctacacctc cctccccaca 2100
cctccctact cccctgggca tcttctggct tgactggatg gaaggagact taggaaccta 2160
ccagttggcc atgatgtctt ttcttctttt tcttttttttt aacaaaacag aacaaaacca 2220
aaaaatgtcc agatgaaaaa aaaaaa 2246

<210> SEQ ID NO 20
<211> LENGTH: 258
<212> TYPE: PRT
<213> ORGANISM: Homo sapiens

<400> SEQUENCE: 20

Met Leu Pro Leu Cys Leu Val Ala Ala Leu Leu Leu Ala Ala Gly Pro
1 5 10 15

Gly Pro Ser Leu Gly Asp Glu Ala Ile His Cys Pro Pro Cys Ser Glu
20 25 30

Glu Lys Leu Ala Arg Cys Arg Pro Pro Val Gly Cys Glu Glu Leu Val
35 40 45

Arg Glu Pro Gly Cys Gly Cys Cys Ala Thr Cys Ala Leu Gly Leu Gly
50 55 60

Met Pro Cys Gly Val Tyr Thr Pro Arg Cys Gly Ser Gly Leu Arg Cys
65 70 75 80

Tyr Pro Pro Arg Gly Val Glu Lys Pro Leu His Thr Leu Met His Gly
85 90 95

Gln Gly Val Cys Met Glu Leu Ala Glu Ile Glu Ala Ile Gln Glu Ser
100 105 110

Leu Gln Pro Ser Asp Lys Asp Glu Gly Asp His Pro Asn Asn Ser Phe
115 120 125

Ser Pro Cys Ser Ala His Asp Arg Arg Cys Leu Gln Lys His Phe Ala
130 135 140

Lys Ile Arg Asp Arg Ser Thr Ser Gly Gly Lys Met Lys Val Asn Gly
145 150 155 160

Ala Pro Arg Glu Asp Ala Arg Pro Val Pro Gln Gly Ser Cys Gln Ser
165 170 175

Glu Leu His Arg Ala Leu Glu Arg Leu Ala Ala Ser Gln Ser Arg Thr
180 185 190

His Glu Asp Leu Tyr Ile Ile Pro Ile Pro Asn Cys Asp Arg Asn Gly
195 200 205

Asn Phe His Pro Lys Gln Cys His Pro Ala Leu Asp Gly Gln Arg Gly
210 215 220

Lys Cys Trp Cys Val Asp Arg Lys Thr Gly Val Lys Leu Pro Gly Gly
225 230 235 240

Leu Glu Pro Lys Gly Glu Leu Asp Cys His Gln Leu Ala Asp Ser Phe
245 250 255

Arg Glu

<210> SEQ ID NO 21
<211> LENGTH: 5016
<212> TYPE: DNA
<213> ORGANISM: Homo sapiens

<400> SEQUENCE: 21
acaggaggag ccgctcgctg gcggctgatc cagcgtctcc gtgacaggca ccctgctccg 60
ccgccaccgc caccgccacc gccaccgtcg ccttttcttc ttcgtcccgg gcggtgcgtt 120
ccactgctct ggggccggcg ccgcgcccag tcccgcttcg ggccgcaagc cccaccgctc 180

```
ccctccccgg gcaggggcgc cgcgcagccc gctcccgccg ccacctcctc ccctgccgcc    240
ctcctagccg gcaggaattg cgcgaccaca gcgccgctcg cgtcgcccgc atcagctcag    300
cccgctgccg ctcggccctc ggcaccgctc cgggtccggc cgccgcgcgg ccagggctcc    360
ccctgcccag cgctcccagg ccccgccacg cgtcgccgcg cccagctcca gtctcccctc    420
cccggggtct cgccagcccc ttcctgcagc cgccgcctcc gaaggagcgg gtccgccgcg    480
ggtaaccatg cctagcaaaa ccaagtacaa ccttgtggac gatgggcacg acctgcggat    540
cccccttgcac aacgaggacg ccttccagca cggcatctgc tttgaggcca agtacgtagg    600
aagcctggac gtgccaaggc ccaacagcag ggtggagatc gtggctgcca tgcgccggat    660
acggtatgag tttaaagcca agaacatcaa gaagaagaaa gtgagcatta tggtttcagt    720
ggatggagtg aaagtgattc tgaagaagaa gaaaaagctt cttttattgc agaaaaagga    780
atggacgtgg gatgagagca agatgctggt gatgcaggac cccatctaca ggatcttcta    840
tgtctctcat gattcccaag acttgaagat cttcagctat atcgctcgag atggtgccag    900
caatatcttc aggtgtaacg tctttaaatc caagaagaag agccaagcta tgagaatcgt    960
tcggacggtg gggcaggcct ttgaggtctg ccacaagctg agcctgcagc acacgcagca   1020
gaatgcagat ggccaggaag atggagagag cgagaggaac agcaacagct caggagaccc   1080
aggccgccag ctcactggag ccgagagggc ctccacggcc actgcagagg agactgacat   1140
cgatgcggtg gaggtcccac ttccagggaa tgatgtcctg gaattcagcc gaggtgtgac   1200
tgatctagat gctgtaggga aggaaggagg ctctcacaca ggctccaagg tttcgcaccc   1260
ccaggagccc atgctgacag cctcacccag gatgctgctc ccttcttctt cctcgaagcc   1320
tccaggcctg ggcacagaga caccgctgtc cactcaccac cagatgcagc tcctccagca   1380
gctcctccag cagcagcagc agcagacaca agtggctgtg gcccaggtac acttgctgaa   1440
ggaccagttg gctgctgagg ctgcggcgcg gctggaggcc caggctcgcg tgcatcagct   1500
tttgctgcag aacaaggaca tgctccagca catctccctg ctggtcaagc aggtgcaaga   1560
gctggaactg aagctgtcag gacagaacgc catgggctcc caggacagct tgctggagat   1620
caccttccgc tccggagccc tgcccgtgct ctgtgacccc acgaccccta agccagagga   1680
cctgcattcg ccgccgctgg gcgcgggctt ggctgacttt gcccaccctg cgggcagccc   1740
cttaggtagg cgcgactgct tggtgaagct ggagtgcttt cgctttcttc cgcccgagga   1800
caccccgccc ccagcgcagg gcgaggcgct cctgggcggt ctggagctca tcaagttccg   1860
agagtcaggc atcgcctcgg agtacgagtc caacacggac gagagcgagg agcgcgactc   1920
gtggtcccag gaggagctgc cgcgcctgct gaatgtcctg cagaggcagg aactgggcga   1980
cggcctggat gatgagatcg ccgtgtaggt gccgagggcg aggagatgga ggcggcggcg   2040
tggctggagg ggccgtgtct ggctgctgcc cgggtagggg atgcccagtg aatgtgcact   2100
gccgaggaga atgccagcca gggcccggga gagtgtgagg tttcaggaaa gtattgagat   2160
tctgctttgg agggtaaagt ggggaagaaa tcggattccc agaggtgaat cagctcctct   2220
cctacttgtg actagagggt ggtggaggta aggccttcca gagcccatgg cttcaggaga   2280
gggtctctct ccaggactgc caggctgctg gaggacctgc ccctacctgc tgcatcgtca   2340
ggctcccacg ctttgtccgt gatgcccccc taccccctca ctctccccgt ctccatggtc   2400
ccgaccagga agggaagcca tcggtacctt ctcaggtact ttgtttctgg atatcacgat   2460
gctgcgagtt gcctaaccct cccccctacct ttatgagagg aattccttct ccaggccctt   2520
```

-continued

```
gctgagattg tagagattga gtgctctgga ccgcaaaagc caggctagtc cttgtagggt   2580
gagcatggaa ttggaatgtg tcacagtgga taagctttta gaggaactga atccaaacat   2640
tttctccagc cggacattga atgttgctac aaagggagcc ttgaagcttt aacatggttc   2700
aggcccttgg tgtgagagcc cagggggagg acagcttgtc tgctgctcca aatcacttag   2760
atctgattcc tgttttgaaa gtcctgccct gccttcctcc tgcctgtagc ccagcccatc   2820
taaatggaag ctgggaattg cccctcacct cccctgtgtc ctgtccagct gaagcttttg   2880
cagcacttta cctctctgaa agccccagag gaccagagcc cccagcctta cctctcaacc   2940
tgtcccctcc actgggcagt ggtggtcagt ttttactgca aaaaaaaaaa aagaaaaaag   3000
agaaagaaaa aaaagaatga atgcaagctg atagctgaga ctgtgagact gtttttgtcc   3060
actcttctga atcactgcca cttgggtcag ggaccacagc cattgccacc cttggcccat   3120
ctctctgcgt gcgtgccttg agcacacata taaaaagtgc catgtgcaat tgtcttatct   3180
tttatgatct aggctttgcc tagggatcac tactccttaa cgggctggct ggggcaatga   3240
ggaaaagctc ctttgctcct gtaaggccat aagtggctgt taacagattt tcaaatgcct   3300
gaagagattg ctgagacctg ctagagtcat atgttcgggg aattaagtct ttatcctaga   3360
caacaaggta cagatgcaaa ctgcagtgtt attggagggt caatcggcaa ggatatgatt   3420
atcccaaaat ggagttcatc gaccctagct ttcctttaga ttatatataa ataaaagtgc   3480
agtcctcttc taatggccac agttggtttt cttgtagccc agaaagtcca aattaaagga   3540
aataaattca gttttatgtt agccttcctt ggtgcatcag ggtgtcagtg gaaataggat   3600
caggtggtgt gtgtgtgtgt gttttgtgtg tgtgtgtaca catgtgttta tatatacatg   3660
tgtgagggaa agtgtgtaca tatatgtagg attgtaacca gacggaaaag aacgaggatc   3720
tccagggtgt ttgaatcagc aacagatttg tgttttctaa catgcattta gttggagagg   3780
catggttctg tttgttttgt tttgatctaa tttgccattg gaaataggta cagttacaca   3840
gagaaggaag aaccaggaaa gtgagatcca tgaaactaaa tgagcagctg tcagaatcca   3900
gtgtggctga gcctacctag cttatgaaat ctaacccagg gttccctgag tccaagacca   3960
cttagattat taagattttg aacgtccaga ggagtgaaaa gtctgttttc tgacgtaagc   4020
cggagctgag gataaagcca gaggccagtg gattaggtgt atggaatgtg gatggagagg   4080
gcttgtgtgg gatgtggcca gggagtgggt gaggaaggcc gcttctaaat ggcctgtaaa   4140
aacttgagat tggatagacg aaaggaaatg gagaaattaa agaattggag aaactagtta   4200
tctgtgttgc tgactttggg acccatccaa gactcctgcc cttggggtgt tccatggtgg   4260
tttcttcctg cctgggcgcc accctttccc cagttcaggc cctccctgga ggactagttt   4320
gtgtattggt atcctcccca gtggacccaa accagcgcat acttggtgtg tggagatggg   4380
agacaaagga cagatctagg agccttgaag gatcaccagc caccgaccct ccatcagggc   4440
caactgggca ggaaagggaa cattgcagac ctgatttccc gacgatgtca ccctgtcctc   4500
cctccttgct tcttgctctg ctaactcaac tctgccttcc tctttttcat tcttctactc   4560
tgccctatat ggaggacaaa tggacaccag gggtgctaac cttattggtg cctgccccag   4620
cctaccccag gtgccagcag actctcgtgc acaggaggct cccacagtta tggagccagg   4680
aaagaatttc tctgcactgg atggactgta tattgagatt aaaaattata ttccttatat   4740
tcctgcttat atcaatgctc tctctgtaaa acctcttcct agcctcattt ctctcaactg   4800
atcttgttta ggcgttgtat tccttttatt tactctttgc ttgactgctt cctcctaacc   4860
ctctacccac tagcactcta cttcctaaag ctgttgtgtc attaactctg ttggatcaac   4920
```

tctctgggaa aagattctgt taatgtaagt gcacttactc cctggatgtt gtcactagtc 4980
tagtggcttt tgctaaataa acctttctta tttcta 5016

<210> SEQ ID NO 22
<211> LENGTH: 506
<212> TYPE: PRT
<213> ORGANISM: Homo sapiens

<400> SEQUENCE: 22

Met Pro Ser Lys Thr Lys Tyr Asn Leu Val Asp Asp Gly His Asp Leu
1 5 10 15

Arg Ile Pro Leu His Asn Glu Asp Ala Phe Gln His Gly Ile Cys Phe
20 25 30

Glu Ala Lys Tyr Val Gly Ser Leu Asp Val Pro Arg Pro Asn Ser Arg
35 40 45

Val Glu Ile Val Ala Ala Met Arg Arg Ile Arg Tyr Glu Phe Lys Ala
50 55 60

Lys Asn Ile Lys Lys Lys Lys Val Ser Ile Met Val Ser Val Asp Gly
65 70 75 80

Val Lys Val Ile Leu Lys Lys Lys Lys Lys Leu Leu Leu Leu Gln Lys
85 90 95

Lys Glu Trp Thr Trp Asp Glu Ser Lys Met Leu Val Met Gln Asp Pro
100 105 110

Ile Tyr Arg Ile Phe Tyr Val Ser His Asp Ser Gln Asp Leu Lys Ile
115 120 125

Phe Ser Tyr Ile Ala Arg Asp Gly Ala Ser Asn Ile Phe Arg Cys Asn
130 135 140

Val Phe Lys Ser Lys Lys Lys Ser Gln Ala Met Arg Ile Val Arg Thr
145 150 155 160

Val Gly Gln Ala Phe Glu Val Cys His Lys Leu Ser Leu Gln His Thr
165 170 175

Gln Gln Asn Ala Asp Gly Gln Glu Asp Gly Glu Ser Glu Arg Asn Ser
180 185 190

Asn Ser Ser Gly Asp Pro Gly Arg Gln Leu Thr Gly Ala Glu Arg Ala
195 200 205

Ser Thr Ala Thr Ala Glu Glu Thr Asp Ile Asp Ala Val Glu Val Pro
210 215 220

Leu Pro Gly Asn Asp Val Leu Glu Phe Ser Arg Gly Val Thr Asp Leu
225 230 235 240

Asp Ala Val Gly Lys Glu Gly Gly Ser His Thr Gly Ser Lys Val Ser
245 250 255

His Pro Gln Glu Pro Met Leu Thr Ala Ser Pro Arg Met Leu Leu Pro
260 265 270

Ser Ser Ser Ser Lys Pro Pro Gly Leu Gly Thr Glu Thr Pro Leu Ser
275 280 285

Thr His His Gln Met Gln Leu Leu Gln Gln Leu Leu Gln Gln Gln Gln
290 295 300

Gln Gln Thr Gln Val Ala Val Ala Gln Val His Leu Leu Lys Asp Gln
305 310 315 320

Leu Ala Ala Glu Ala Ala Ala Arg Leu Glu Ala Gln Ala Arg Val His
325 330 335

Gln Leu Leu Leu Gln Asn Lys Asp Met Leu Gln His Ile Ser Leu Leu
340 345 350

-continued

```
Val Lys Gln Val Gln Glu Leu Glu Leu Lys Leu Ser Gly Gln Asn Ala
        355                 360                 365

Met Gly Ser Gln Asp Ser Leu Leu Glu Ile Thr Phe Arg Ser Gly Ala
    370                 375                 380

Leu Pro Val Leu Cys Asp Pro Thr Thr Pro Lys Pro Glu Asp Leu His
385                 390                 395                 400

Ser Pro Pro Leu Gly Ala Gly Leu Ala Asp Phe Ala His Pro Ala Gly
                405                 410                 415

Ser Pro Leu Gly Arg Arg Asp Cys Leu Val Lys Leu Glu Cys Phe Arg
            420                 425                 430

Phe Leu Pro Pro Glu Asp Thr Pro Pro Pro Ala Gln Gly Glu Ala Leu
        435                 440                 445

Leu Gly Gly Leu Glu Leu Ile Lys Phe Arg Glu Ser Gly Ile Ala Ser
    450                 455                 460

Glu Tyr Glu Ser Asn Thr Asp Glu Ser Glu Glu Arg Asp Ser Trp Ser
465                 470                 475                 480

Gln Glu Glu Leu Pro Arg Leu Leu Asn Val Leu Gln Arg Gln Glu Leu
                485                 490                 495

Gly Asp Gly Leu Asp Asp Glu Ile Ala Val
            500                 505
```

<210> SEQ ID NO 23
<211> LENGTH: 5618
<212> TYPE: DNA
<213> ORGANISM: Homo sapiens

<400> SEQUENCE: 23

```
agcacatctg ggcgagagcg gcgccgctgg agccgagggg ggcgccgagc gcagatctgg     60

agcagcagag ccacggcgca gctggggccc ttcgaggcgc tcggggcgca catctgggac    120

ctcgagcggg ggccgtgccg cgcgcagctg gaccagggga ggggggcggc ggctgcacag    180

ctggaccgaa gggggcgggg tcggccctgg gcgacccgct gaggggaggg ccgcgggccg    240

ccggggactg gagcatggga cggcgcgcct gaaggagcag gaaggggaag gaggcctggg    300

accccgaaaa gagaagggga gagcgagggg acgagagcgg aggaggaaga tgcaactgac    360

tcgctgctgc ttcgtgttcc tggtgcaggg tagcctctat ctggtcatct gtggccagga    420

tgatggtcct cccggctcag aggaccctga gcgtgatgac cacgagggcc agccccggcc    480

ccgggtgcct cggaagcggg gccacatctc acctaagtcc cgccccatgg ccaattccac    540

tctcctaggg ctgctggccc cgcctgggga ggcttggggc attcttgggc agcccccccaa    600

ccgcccgaac cacagccccc caccctcagc caaggtgaag aaaatctttg gctggggcga    660

cttctactcc aacatcaaga cggtggccct gaacctgctc gtcacaggga agattgtgga    720

ccatggcaat gggaccttca gcgtccactt ccaacacaat gccacaggcc agggaaacat    780

ctccatcagc ctcgtgcccc ccagtaaagc tgtagagttc caccaggaac agcagatctt    840

catcgaagcc aaggcctcca aaatcttcaa ctgccggatg gagtgggaga aggtagaacg    900

gggccgccgg acctcgcttt gcacccacga cccagccaag atctgctccc gagaccacgc    960

tcagagctca gccacctgga gctgctccca gcccttcaaa gtcgtctgtg tctacatcgc   1020

cttctacagc acggactatc ggctggtcca gaaggtgtgc ccagattaca actaccatag   1080

tgataccccc tactacccat ctgggtgacc cggggcaggc cacagaggcc aggccagggc   1140

tggaaggaca ggcctgccca tgcaggagac catctggaca ccgggcaggg aaggggttgg   1200

gcctcaggca gggagggggg tggagacgag gagatgccaa gtggggccag ggccaagtct   1260
```

caagtggcag agaaagggtc ccaagtgctg gtcccaacct gaagctgtgg agtgactaga 1320
tcacaggagc actggaggag gagtgggctc tctgtgcagc ctcacagggc tttgccacgg 1380
agccacagag agatgctggg tccccgaggc ctgtgggcag gccgatcagt gtggccccag 1440
atcaagtcat gggaggaagc taagcccttg gttcttgcca tcctgaggaa agatagcaac 1500
agggaggggg agatttcatc agtgtggaca gcctgtcaac ttaggatgga tggctgagag 1560
ggcttcctag gagccagtca gcagggtggg gtggggccag aggagctctc cagccctgcc 1620
tagtgggcgc cctcagcccc ttgtcgtgtg ctgagcatgg catgaggctg aagtggcaac 1680
cctggggtct ttgatgtctt gacagattga ccatctgtct ccagccaggc cacccctttc 1740
caaaattccc tcttctgcca gtactccccc tgtaccaccc attgctgatg gcacacccat 1800
ccttaagcta agacaggacg attgtggtcc tcccacacta aggccacagc ccatccgcgt 1860
gctgtgtgtc cctcttccac cccaacccct gctggctcct ctgggagcat ccatgtcccg 1920
gagaggggtc cctcaacagt cagcctcacc tgtcagaccg gggttctccc ggatctggat 1980
ggcgccgccc tctcagcagc gggcacgggt ggggcggggc cgggccgcag agcatgtgct 2040
ggatctgttc tgtgtgtctg tctgtgggtg gggggagggg agggaagtct tgtgaaaccg 2100
ctgattgctg acttttgtgt gaagaatcgt gttcttggag caggaaataa agcttgcccc 2160
ggggcactgg agtcagagtt gtccaaggaa agggcctcag gcatcccttg gtccaggaag 2220
aatttctctg atggccgcag gacatttgct tgagacccaa gtggcaggga tccaaccgcc 2280
cttggcgctg atgtttgctg agggctcagg gcttccctct ccagccccgg ttccaagctg 2340
tctgatcccc cacgaggaaa cttgagcaaa caccctgggc tcggtgctgg aggagggcgt 2400
agcatcttca agaacagctc agggagggag agctagcagg tagaatgggc caatgagggt 2460
gttccttggt gtcctccctg aactgccatc tgcagaccca gcagggtcct agccccgtca 2520
ttttgctgcg tggccttggc catgtccatt ctcctctctg gctttctttc tttgtttctt 2580
cctctatgac atgaagggct tgcccagacc aggggttctc aaacgcggat cacccagagg 2640
gtttgttaac acacagattt ctgggtccta cccacatttc taattcagca ggcctgggtg 2700
gggcctaaga attagaattt ctaacgagtg cccaggtcta tgctgatgct gctgctccag 2760
ggcccatgct gggagaccca ctcaaaggac cttgaagttc atctctggct atggctccgc 2820
aggaggggga gacacctcgg atgtgatttc ccagctgtaa tttccatctg cttctcctgg 2880
ggaaggggcc tttcagagaa tcggggctat tgtattggat tttcaatctg accacatgcc 2940
agtgaaggaa caggctggag tggggtgtgg acacagggcc tgcgtcagtc actcccctcc 3000
tgcagctagt aagaggcctc agaatggcca gctgccagtg gcaccttgtc tgggagttag 3060
ttgggccctt tgggactctg tgaagggaag acactaccaa ggtcacagtg ccttctggag 3120
gtcattctaa gtcggctctc ttgggagggc agcactcagg gccctttggg ccctcttgag 3180
gagaggagag tcctggcagt aaggtaagat gggcttgcca ccccccacct ttcgcccctg 3240
cccaccagcg ctccgcgcaa actggtcccc tcatactgca gcgcagagtt gggtggggct 3300
gagaagccat ctggttacag cccaccttgt aggaaatgac ccagcttgtt tcccccacat 3360
catgcttcca ggggccgtct ctcctgagtg gagatgtgag acacacaccc ctcctccaga 3420
ccaccctccg ctccccaccc tggaggcttg agactgctgg cactggagca gcccaccaat 3480
ggacacccac cgtgtgccgt tcagcctccc acagtgctgt ggagactgca ggaaggagga 3540
ggaagcaatg ggccagaggc ccctgggcgc cctccccacc tcccctggct gaactctcag 3600

-continued

```
caggcactgg gggcactttg acccccctcc tgctcctctc ctcctgtgga gagccagatg   3660

ctggcgacag ctggagggcc cggccttcct ggcacacagt tctgcctgca ccagggatgg   3720

attcatttta ataacttcat ttcaccctca tgcacactgc cgcctcatcc ctcctttcca   3780

ccttccccag tagcctggct gctctcctca gctaggactt cgctaacaga tttcctccca   3840

aaccttaatt ctttggaata gccctctggt ccctactgtt cttgccagat acttctgtgc   3900

ccgcttggtc ctcacaaggg caaggggtcc atccaacttc ctctggctaa gaagacgtca   3960

cctctgcccc attggcgagc agtgtcccca tggtgatgcc cccccaccat cacgacgaag   4020

tgcgctggcc tcccactctt gccatgcaca cactcacagg agattcctct gaagaaacct   4080

gtccccactc tgcccagacc ccaaagggcc aggtcctact cacactccaa cccgttgacc   4140

ttccccatcc actgcccttc aaggcagtct gaaatgccct cagaccgttt agcggtcccg   4200

tggtcctcca ccctaacccc tcagcccagc tgggggctgc cgggggcctt gtctcctcca   4260

tcagtggagc ctctgggaca agtttaccag gctgggggtt ctttaaggac acagcttgga   4320

tctccccatc aggctgggga acacctaggg ccgggggcca tgcctccctc atcagactga   4380

ggacaccctg atgtcagggg ctggatggcc ccttagactg gggtccctg agggcagaag    4440

ctatgcctcc cctcatcaga ctggagtctc cctgagggca agaactgtgc tatggatggg   4500

agggggacag cttgcctttt cctaggcatc agagcacctg gaggctgcct ctgcccttca   4560

gctttgctca aaggcgctgt ctgggtctca gcattccttt ctcaagtagg gtgaatctcc   4620

tagcactctg tgaagctaat aagggggatt acccgttagg tcaactggta gcaatgcccg   4680

agtctccttc tcgatgaagc ttaaggcaaa agcaaatgaa tatctaggtc ccttcccccc   4740

cttcccccct tccctttcct gggatgagca agcgggaact gagtcaccct gttccccatc   4800

cttggcagga atgctggtga ccttgcattg tggcagattc aggtggcgag gcccattgct   4860

cgagatgcac ctggtgggtg ggtggcaggg atcctggggg agtgtttatg gggacggagg   4920

cagctgaagg gcagggaggg gtgaccaggt gctgggatca tcgagtgagt atgtgcagga   4980

gggattgtag agacacaatg aaacagttgc tctgtgttgg gaagtgatcc agtgtcatcg   5040

ctgggagtgg gagacagaaa tgttacttcc aaagattccg agtcctgtgg tactgccagg   5100

agaaccgggg gctggggtga tgggtaagga gaggcaccat tagccccgcc aggcagaggc   5160

aagatggggt gggggcggca cctgccaatt atgccaaagt cttggagtgg cagctggcac   5220

catcaccaag gcacaaatgc cagcagagac ctggcactca cctgggttgt gattccatag   5280

ggcccctgtc tcctgttggt ctcccaggct caaaggctga cctgataatt caagtgaagg   5340

atgcctagtt caaggcctcc cagttcctca tcccaggcca cctggtcagg tggtcccaag   5400

ggacaagcta ggtcctcctg aactgcagag gctgccaata aactggcaac acaggtgttg   5460

caggaagata tagctgggtc ctcatcctgg gtctgtaatt tattagacgt gtggctttgg   5520

acaaatgaca taatttccca gagcctcctt agataaaaaa ctagggcttt gcttaccttg   5580

gcgtattgtt aggaaaatta aatgagttgc tcaataaa                           5618
```

<210> SEQ ID NO 24
<211> LENGTH: 252
<212> TYPE: PRT
<213> ORGANISM: Homo sapiens

<400> SEQUENCE: 24

```
Met Gln Leu Thr Arg Cys Cys Phe Val Phe Leu Val Gln Gly Ser Leu
1               5                   10                  15
```

```
Tyr Leu Val Ile Cys Gly Gln Asp Asp Gly Pro Pro Gly Ser Glu Asp
            20                  25                  30

Pro Glu Arg Asp Asp His Glu Gly Gln Pro Arg Pro Arg Val Pro Arg
        35                  40                  45

Lys Arg Gly His Ile Ser Pro Lys Ser Arg Pro Met Ala Asn Ser Thr
    50                  55                  60

Leu Leu Gly Leu Leu Ala Pro Pro Gly Glu Ala Trp Gly Ile Leu Gly
65                  70                  75                  80

Gln Pro Pro Asn Arg Pro Asn His Ser Pro Pro Pro Ser Ala Lys Val
                85                  90                  95

Lys Lys Ile Phe Gly Trp Gly Asp Phe Tyr Ser Asn Ile Lys Thr Val
            100                 105                 110

Ala Leu Asn Leu Leu Val Thr Gly Lys Ile Val Asp His Gly Asn Gly
        115                 120                 125

Thr Phe Ser Val His Phe Gln His Asn Ala Thr Gly Gln Gly Asn Ile
    130                 135                 140

Ser Ile Ser Leu Val Pro Pro Ser Lys Ala Val Glu Phe His Gln Glu
145                 150                 155                 160

Gln Gln Ile Phe Ile Glu Ala Lys Ala Ser Lys Ile Phe Asn Cys Arg
                165                 170                 175

Met Glu Trp Glu Lys Val Glu Arg Gly Arg Arg Thr Ser Leu Cys Thr
            180                 185                 190

His Asp Pro Ala Lys Ile Cys Ser Arg Asp His Ala Gln Ser Ser Ala
        195                 200                 205

Thr Trp Ser Cys Ser Gln Pro Phe Lys Val Val Cys Val Tyr Ile Ala
    210                 215                 220

Phe Tyr Ser Thr Asp Tyr Arg Leu Val Gln Lys Val Cys Pro Asp Tyr
225                 230                 235                 240

Asn Tyr His Ser Asp Thr Pro Tyr Tyr Pro Ser Gly
                245                 250


<210> SEQ ID NO 25
<211> LENGTH: 2608
<212> TYPE: DNA
<213> ORGANISM: Homo sapiens

<400> SEQUENCE: 25

agacgcgccg gaaccgggac gcgataaata tgcagagcgg aggcttcgcg cagcagagcc     60

cgcgcgccgc ccgctccggg tgctgaatcc aggcgtgggg acacgagcca ggcgccgccg    120

ccggagccag cggagccggg gccagagccg gagcgcgtcc gcgtccacgc agccgccggc    180

cggccagcac ccagggccct gcatgccagg tcgttggagg tggcagcgag acatgcaccc    240

ggcccggaag ctcctcagcc tcctcttcct catcctgatg ggcactgaac tcactcaagt    300

gctgcccacc aaccctgagg agagctggca ggtgtacagc tctgcccagg acagcgaggg    360

caggtgtatc tgcacagtgg tcgctccaca gcagaccatg tgttcacggg atgcccgcac    420

aaaacagctg aggcagctac tggagaaggt gcagaacatg tctcaatcca tagaggtctt    480

ggacaggcgg acccagagag acttgcagta cgtggagaag atggagaacc aaatgaaagg    540

actggagtcc aagttcaaac aggtggagga gagtcataag caacacctgg ccaggcagtt    600

taaggcgata aaagcgaaaa tggatgaact taggcctttg atacctgtgt tggaagagta    660

caaggccgat gccaaattgg tattgcagtt taaagaggag gtccagaatc tgacgtcagt    720

gcttaacgag ctgcaagagg aaattggcgc ctatgactac gatgaacttc agagcagagt    780
```

gtccaatctt gaagaaaggc tccgtgcatg catgcaaaaa ctagcttgcg ggaagttgac 840
gggcatcagt gaccccgtga ctgtcaagac ctccggctcg aggttcggat cctggatgac 900
agaccctctc gcccctgaag gcgataaccg ggtgtggtac atggacggct atcacaacaa 960
ccgcttcgta cgtgagtaca agtccatggt tgacttcatg aacacggaca atttcacctc 1020
ccaccgtctc ccccacccct ggtcgggcac ggggcaggtg gtctacaacg gttctatcta 1080
cttcaacaag ttccagagcc acatcatcat caggtttgac ctgaagacag agaccatcct 1140
caagacccgc agcctggact atgccggtta caacaacatg taccactacg cctggggtgg 1200
ccactcggac atcgacctca tggtggacga gagcgggctg tgggccgtgt acgccaccaa 1260
ccagaacgct ggcaacatcg tggtcagtag gctggacccc gtgtccctgc agaccctgca 1320
gacctggaac acgagctacc ccaagcgcag cgccggggag gccttcatca tctgcggcac 1380
gctgtacgtc accaacggct actcaggggg taccaaggtc cactatgcat accagaccaa 1440
tgcctccacc tatgaataca tcgacatccc attccagaac aaatactccc acatctccat 1500
gctggactac aaccccaagg accgggccct gtatgcctgg aacaacggcc accagatcct 1560
ctacaacgtg accctcttcc acgtcatccg ctccgacgag ttgtagctcc ctcctcctgg 1620
aagccaaggg cccacgtcct caccacaaag ggactcctgt gaaactgctg ccaaaaagat 1680
accaataaca ctaacaatac cgatcttgaa aaatcatcag cagtgcggat tctgacatcg 1740
agggatggca ttacctccgt gtttctccct ttcgagccgg cgggccacag acgtcggaag 1800
aaactcccgt atttgcagct ggaactgcag cccacggcgc cccggttttc ctccccgccc 1860
tgtccctctc tggtcaaaca acatactaaa gaggcgaggc aatgactgtt ggccagttct 1920
caccggggaa aaacccactg ttaggatggc atgaacattt ccttagatcg tggtcagctc 1980
cgaggaatgt ggcgtccagg ctctttgaga gccatgggct gcacccggcc gtaggctagt 2040
gtaactcgca tcccattgca gtgccgtttc ttgactgtgt tgctgtctct tagattaacc 2100
gtgctgaggc tccacatagc tcctggacct gtgtctagta catactgaag cgatggtcag 2160
agtgtgtaga gtgaagttgc tgtgcccaca ttgtttgaac tcgcgtaccc cgtagataca 2220
ttgtgcaacg ttcttctgtt attcccttga ggtggtaact tcgtatgttc agtttatgcg 2280
atgattgttg taaatgcaat gccgtagttt ggattaataa gtggatggtt tttgtttcta 2340
aaaagaaaaa aaaaatcagt gttcaccctt atagagacat agtcaagttc atgttgataa 2400
taatcaaagg aattactctc ttcttgttaa attagctaaa tcatgtaacc gcagatagga 2460
agggctcgcc tggggaaact ctggtttccg atgggacagg aaagtcatac gggcaacagt 2520
atgcggaaag tacgtttttt aagtaaaaaa caaaggcaaa ctttgtacta tccagttatc 2580
taaggaacaa taaaaacatt aggagatc 2608

<210> SEQ ID NO 26
<211> LENGTH: 485
<212> TYPE: PRT
<213> ORGANISM: Homo sapiens

<400> SEQUENCE: 26

Met Ser Val Pro Leu Leu Lys Ile Gly Val Val Leu Ser Thr Met Ala
1 5 10 15

Met Ile Thr Asn Trp Met Ser Gln Thr Leu Pro Ser Leu Val Gly Leu
20 25 30

Asn Thr Thr Lys Leu Ser Ala Ala Gly Gly Gly Thr Leu Asp Arg Ser
35 40 45

```
Thr Gly Val Leu Pro Thr Asn Pro Glu Glu Ser Trp Gln Val Tyr Ser
    50                  55                  60

Ser Ala Gln Asp Ser Glu Gly Arg Cys Ile Cys Thr Val Val Ala Pro
65                  70                  75                  80

Gln Gln Thr Met Cys Ser Arg Asp Ala Arg Thr Lys Gln Leu Arg Gln
                85                  90                  95

Leu Leu Glu Lys Val Gln Asn Met Ser Gln Ser Ile Glu Val Leu Asp
            100                 105                 110

Arg Arg Thr Gln Arg Asp Leu Gln Tyr Val Glu Lys Met Glu Asn Gln
        115                 120                 125

Met Lys Gly Leu Glu Ser Lys Phe Lys Gln Val Glu Glu Ser His Lys
    130                 135                 140

Gln His Leu Ala Arg Gln Phe Lys Ala Ile Lys Ala Lys Met Asp Glu
145                 150                 155                 160

Leu Arg Pro Leu Ile Pro Val Leu Glu Glu Tyr Lys Ala Asp Ala Lys
                165                 170                 175

Leu Val Leu Gln Phe Lys Glu Glu Val Gln Asn Leu Thr Ser Val Leu
            180                 185                 190

Asn Glu Leu Gln Glu Glu Ile Gly Ala Tyr Asp Tyr Asp Glu Leu Gln
        195                 200                 205

Ser Arg Val Ser Asn Leu Glu Glu Arg Leu Arg Ala Cys Met Gln Lys
    210                 215                 220

Leu Ala Cys Gly Lys Leu Thr Gly Ile Ser Asp Pro Val Thr Val Lys
225                 230                 235                 240

Thr Ser Gly Ser Arg Phe Gly Ser Trp Met Thr Asp Pro Leu Ala Pro
                245                 250                 255

Glu Gly Asp Asn Arg Val Trp Tyr Met Asp Gly Tyr His Asn Asn Arg
            260                 265                 270

Phe Val Arg Glu Tyr Lys Ser Met Val Asp Phe Met Asn Thr Asp Asn
        275                 280                 285

Phe Thr Ser His Arg Leu Pro His Pro Trp Ser Gly Thr Gly Gln Val
    290                 295                 300

Val Tyr Asn Gly Ser Ile Tyr Phe Asn Lys Phe Gln Ser His Ile Ile
305                 310                 315                 320

Ile Arg Phe Asp Leu Lys Thr Glu Thr Ile Leu Lys Thr Arg Ser Leu
                325                 330                 335

Asp Tyr Ala Gly Tyr Asn Asn Met Tyr His Tyr Ala Trp Gly Gly His
            340                 345                 350

Ser Asp Ile Asp Leu Met Val Asp Glu Ser Gly Leu Trp Ala Val Tyr
        355                 360                 365

Ala Thr Asn Gln Asn Ala Gly Asn Ile Val Val Ser Arg Leu Asp Pro
    370                 375                 380

Val Ser Leu Gln Thr Leu Gln Thr Trp Asn Thr Ser Tyr Pro Lys Arg
385                 390                 395                 400

Ser Ala Gly Glu Ala Phe Ile Ile Cys Gly Thr Leu Tyr Val Thr Asn
                405                 410                 415

Gly Tyr Ser Gly Gly Thr Lys Val His Tyr Ala Tyr Gln Thr Asn Ala
            420                 425                 430

Ser Thr Tyr Glu Tyr Ile Asp Ile Pro Phe Gln Asn Lys Tyr Ser His
        435                 440                 445

Ile Ser Met Leu Asp Tyr Asn Pro Lys Asp Arg Ala Leu Tyr Ala Trp
    450                 455                 460

Asn Asn Gly His Gln Ile Leu Tyr Asn Val Thr Leu Phe His Val Ile
```

465 470 475 480

Arg Ser Asp Glu Leu
485

<210> SEQ ID NO 27
<211> LENGTH: 13037
<212> TYPE: DNA
<213> ORGANISM: Homo sapiens

<400> SEQUENCE: 27
agtccacagc tgtcactaat cggggtaagc cttgttgtat ttgtgcgtgt gggtggcatt 60
ctcaatgaga actagcttca cttgtcattt gagtgaaatc tacaacccga ggcggctagt 120
gctcccgcac tactgggatc tgagatcttc ggagatgact gtcgcccgca gtacggagcc 180
agcagaagtc cgacccttcc tgggaatggg ctgtaccgag aggtccgact agccccaggg 240
ttttagtgag gggcagtgg aactcagcga gggactgaga gcttcacagc atgcacgagt 300
ttgatgccag agaaaaagtc gggagataaa ggagccgcgt gtcactaaat tgccgtcgca 360
gccgcagcca ctcaagtgcc ggacttgtga gtactctgcg tctccagtcc tcggacagaa 420
gttggagaac tctcttggag aactccccga gttaggagac gagatctcct aacaattact 480
actttttctt gcgctcccca cttgccgctc gctgggacaa acgacagcca cagttcccct 540
gacgacagga tggaggccaa gggcaggagc tgaccagcgc cgccctcccc cgcccccgac 600
ccaggaggtg gagatccctc cggtccagcc acattcaaca cccactttct cctccctctg 660
cccctatatt cccgaaaccc cctcctcctt cccttttccc tcctcctgga gacgggggag 720
gagaaaaggg gagtccagtc gtcatgactg agctgaaggc aaagggtccc cgggctcccc 780
acgtggcggg cggcccgccc tcccccgagg tcggatcccc actgctgtgt cgcccagccg 840
caggtccgtt cccggggagc cagacctcgg acaccttgcc tgaagtttcg gccataccta 900
tctccctgga cgggctactc ttccctcggc cctgccaggg acaggacccc tccgacgaaa 960
agacgcagga ccagcagtcg ctgtcggacg tggagggcgc atattccaga gctgaagcta 1020
caaggggtgc tggaggcagc agttctagtc ccccagaaaa ggacagcgga ctgctggaca 1080
gtgtcttgga cactctgttg gcgccctcag gtcccgggca gagccaaccc agccctcccg 1140
cctgcgaggt caccagctct tggtgcctgt ttggccccga acttcccgaa gatccaccgg 1200
ctgcccccgc cacccagcgg gtgttgtccc cgctcatgag ccggtccggg tgcaaggttg 1260
gagacagctc cgggacggca gctgcccata aagtgctgcc ccggggcctg tcaccagccc 1320
ggcagctgct gctcccggcc tctgagagcc ctcactggtc cggggcccca gtgaagccgt 1380
ctccgcaggc cgctgcggtg gaggttgagg aggaggatgg ctctgagtcc gaggagtctg 1440
cgggtccgct tctgaagggc aaacctcggg ctctgggtgg cgcggcggct ggaggaggag 1500
ccgcggctgt cccgccgggg gcggcagcag gaggcgtcgc cctggtcccc aaggaagatt 1560
cccgcttctc agcgcccagg gtcgccctgg tggagcagga cgcgccgatg gcgcccgggc 1620
gctccccgct ggccaccacg gtgatggatt tcatccacgt gcctatcctg cctctcaatc 1680
acgccttatt ggcagcccgc actcggcagc tgctggaaga cgaaagttac gacggcgggg 1740
ccggggctgc cagcgccttt gccccgccgc ggagttcacc ctgtgcctcg tccaccccgg 1800
tcgctgtagg cgacttcccc gactgcgcgt acccgcccga cgccgagccc aaggacgacg 1860
cgtaccctct ctatagcgac ttccagccgc ccgctctaaa gataaaggag gaggaggaag 1920
gcgcggaggc ctccgcgcgc tccccgcgtt cctaccttgt ggccggtgcc aaccccgcag 1980
ccttcccgga tttcccgttg gggccaccgc ccccgctgcc gccgcgagcg accccatcca 2040
gacccgggga agcggcggtg acggccgcac ccgccagtgc ctcagtctcg tctgcgtcct 2100
cctcggggtc gaccctggag tgcatcctgt acaaagcgga gggcgcgccg ccccagcagg 2160
gcccgttcgc gccgccgccc tgcaaggcgc cgggcgcgag cggctgcctg ctcccgcggg 2220
acggcctgcc ctccacctcc gcctctgccg ccgccgccgg ggcggccccc gcgctctacc 2280
ctgcactcgg cctcaacggg ctcccgcagc tcggctacca ggccgccgtg ctcaaggagg 2340
gcctgccgca ggtctacccg ccctatctca actacctgag gccggattca gaagccagcc 2400
agagcccaca atacagcttc gagtcattac ctcagaagat ttgtttaatc tgtggggatg 2460
aagcatcagg ctgtcattat ggtgtcctta cctgtgggag ctgtaaggtc ttctttaaga 2520
gggcaatgga agggcagcac aactacttat gtgctggaag aaatgactgc atcgttgata 2580
aaatccgcag aaaaaactgc ccagcatgtc gccttagaaa gtgctgtcag gctggcatgg 2640
tccttggagg tcgaaaattt aaaaagttca ataaagtcag agttgtgaga gcactggatg 2700
ctgttgctct cccacagcca gtgggcgttc caaatgaaag ccaagcccta agccagagat 2760
tcactttttc accaggtcaa gacatacagt tgattccacc actgatcaac ctgttaatga 2820
gcattgaacc agatgtgatc tatgcaggac atgacaacac aaaacctgac acctccagtt 2880
ctttgctgac aagtcttaat caactaggcg agaggcaact tctttcagta gtcaagtggt 2940
ctaaatcatt gccaggtttt cgaaacttac atattgatga ccagataact ctcattcagt 3000
attcttggat gagcttaatg gtgtttggtc taggatggag atcctacaaa cacgtcagtg 3060
ggcagatgct gtattttgca cctgatctaa tactaaatga acagcggatg aaagaatcat 3120
cattctattc attatgcctt accatgtggc agatcccaca ggagtttgtc aagcttcaag 3180
ttagccaaga agagttcctc tgtatgaaag tattgttact tcttaataca attcctttgg 3240
aagggctacg aagtcaaacc cagtttgagg agatgaggtc aagctacatt agagagctca 3300
tcaaggcaat tggtttgagg caaaaaggag ttgtgtcgag ctcacagcgt ttctatcaac 3360
ttacaaaact tcttgataac ttgcatgatc ttgtcaaaca acttcatctg tactgcttga 3420
atacatttat ccagtcccgg gcactgagtg ttgaatttcc agaaatgatg tctgaagtta 3480
ttgctgcaca attacccaag atattggcag ggatggtgaa accccttctc tttcataaaa 3540
agtgaatgtc atcttttttct tttaaagaat taaattttgt ggtatgtctt tttgttttgg 3600
tcaggattat gaggtcttga gtttttataa tgttcttctg aaagccttac atttataaca 3660
tcatagtgtg taaatttaaa agaaaaattg tgaggttcta attattttct tttataaagt 3720
ataattagaa tgtttaactg ttttgtttac ccatattttc ttgaagaatt tacaagattg 3780
aaaaagtact aaaattgtta aagtaaacta tcttatccat attatttcat accatgtagg 3840
tgaggatttt taacttttgc atctaacaaa tcatcgactt aagagaaaaa atcttacatg 3900
taataacaca aagctattat atgttatttc taggtaactc cctttgtgtc aattatattt 3960
ccaaaaatga acctttaaaa tggtatgcaa aattttgtct atatatattt gtgtgaggag 4020
gaaattcata actttcctca gattttcaaa agtattttta atgcaaaaaa tgtagaaaga 4080
gtttaaaacc actaaaatag attgatgttc ttcaaactag gcaaaacaac tcatatgtta 4140
agaccatttt ccagattgga aacacaaatc tcttaggaag ttaataagta gattcatatc 4200
attatgcaaa tagtattgtg ggttttgtag gtttttaaaa taaccttttt tggggagaga 4260
attgtcctct aatgaggtat tgcgagtgga cataagaaat cagaagatta tggcctaact 4320
gtactcctta ccaactgtgg catgctgaaa gttagtcact cttactgatt ctcaattctc 4380

```
tcacctttga aagtagtaaa atatctttcc tgccaattgc tcctttgggt cagagcttat   4440
taacatcttt tcaaatcaaa ggaaagaaga aagggagagg aggaggaggg aggtatcaat   4500
tcacatacct ttctcctctt tatcctccac tatcatgaat tcatattatg tttcagccat   4560
gcaaatcttt ttaccatgaa atttcttcca gaattttccc cctttgacac aaattccatg   4620
catgtttcaa ccttcgagac tcagccaaat gtcatttctg taaaatcttc cctgagtctt   4680
ccaagcagta atttgccttc tcctagagtt tacctgccat tttgtgcaca tttgagttac   4740
agtagcatgt tattttacaa ttgtgactct cctgggagtc tgggagccat ataaagtggt   4800
caatagtgtt tgctgactga gagttgaatg acattttctc tctgtcttgg tattactgta   4860
gatttcgatc attctttggt tacatttctg catatttctg tacccatgac tttatcactt   4920
tcttctccca tgctttatct ccatcaatta tcttcattac ttttaaattt tccacctttg   4980
cttcctactt tgtgagatct ctccctttac tgactataac atagaagaat agaagtgtat   5040
tttatgtgtc ttaaggacaa tactttagat tccttgttct aagtttttaa actgaatgaa   5100
tggaatatta tttctctccc taagcaaaat tccacaaaac aattatttct tatgtttatg   5160
tagccttaaa ttgttttgta ctgtaaacct cagcataaaa actttcttca tttctaattt   5220
cattcaacaa atattgattg aatacctggt attagcacaa gaaaaatgtg ctaataagcc   5280
ttatgagaat ttggagctga agaaagacat ataactcagg aaagttacag tccagtagta   5340
ggtataaatt acagtgcctg ataaataggc attttaatat ttgtacactc aacgtatact   5400
aggtaggtgc aaaacattta catataattt tactgatacc catgcagcac aaaggtacta   5460
actttaaata ttaaataaca cctttatgtg tcagtaattc atttgcatta aatcttattg   5520
aaaaggcttt caatatattt tccccacaaa tgtcatccca agaaaaaagt atttttaaca   5580
tctcccaaat ataatagtta caggaaatct acctctgtga gagtgacacc tctcagaatg   5640
aactgtgtga cacaagaaaa tgaatgtagg tctatccaaa aaaaacccca agaaacaaaa   5700
acaatattat tagcccttta tgcttaagtg atggactcag ggaacagttg atgttgtgat   5760
cattttatta tctgattctt gttactttga attaaaccaa tattttgatg atataaatca   5820
tttccaccag catatattta atttccataa taactttaaa attttctaat ttcactcaac   5880
tatgagggaa tagaatgtgg tggccacagg tttggctttt gttaaaatgt ttgatatctt   5940
cgatgttgat ctctgtctgc aatgtagatg tctaaacact aggatttaat atttaaggct   6000
aagctttaaa aataaagtac ctttttaaaa agaatatggc ttcaccaaat ggaaaatacc   6060
taatttctaa atctttttct ctacaaagtc ctatctacta atgtctccat tactatttag   6120
tcatcataac cattatcttc attttacatg tcgtgttctt tctggtagct ctaaaatgac   6180
actaaatcat aagaagacag gttacatatc aggaaatact tgaaggttac tgaaatagat   6240
tcttgagtta atgaaaatat tttctgtaaa aaggtttgaa aagccatttg agtctaaagc   6300
attataccta cattatcagt agttatgtga caattgtgtg tgtgtttaat gtttaaagat   6360
gtggcacttt ttaataaggc aatgctatgc tattttttcc catttaacat taagataatt   6420
tattgctata cagatgatat ggaaatatga tgaacaatat tttttttgcc aaaactatgc   6480
cttgtaagta gccatggaat gtcaacctgt aacttaaatt atccacagat agtcatgtgt   6540
ttgatgatgg gcactgtgga gataactgac ataggactgt gccccccttc tctgccactt   6600
actagctgga tgagattaag caagtcattt aactgctctg attaaacctg cctttcccaa   6660
gtgctttgta atgaatagaa atggaaacca aaaaaaacgt atacaggcct tcagaaatag   6720
```

-continued

```
taattgctac tattttgttt tcattaagcc atagttctgg ctataatttt atcaaactca   6780
ccagctatat tctacagtga aagcaggatt ctagaaagtc tcactgtttt atttatgtca   6840
ccatgtgcta tgatatattt ggttgaattc atttgaaatt agggctggaa gtattcaagt   6900
aatttcttct gctgaaaaaa tacagtgttt tgagtttagg gcctgtttta tcaaagttct   6960
aaagagccta tcactcttcc attgtagaca ttttaaaata atgacactga ttttaacatt   7020
tttaagtgtc tttttagaac agagagcctg actagaacac agcccctcca aaaacccatg   7080
ctcaaattat ttttactatg gcagcaattc cacaaaaggg aacaatgggt ttagaaatta   7140
caatgaagtc atcaacccaa aaaacatccc tatccctaag aaggttatga tataaaatgc   7200
ccacaagaaa tctatgtctg ctttaatctg tcttttattg ctttggaagg atggctatta   7260
catttttagt ttttgctgtg aatacctgag cagtttctct catccatact tatccttcac   7320
acatcagaag tcaggataga atatgaatca ttttaaaaac ttttacaact ccagagccat   7380
gtgcataaga agcattcaaa acttgccaaa acatacattt tttttcaaat ttaaagatac   7440
tctatttttg tattcaatag ctcaacaact gtggtcccca ctgataaagt gaagtggaca   7500
aggagacaag taatggcata agtttgtttt tcccaaagta tgcctgttca atagccattg   7560
gatgtgggaa atttctacat ctcttaaaat tttacagaaa atacatagcc agatagtcta   7620
gcaaaagttc accaagtcct aaattgctta tccttacttc actaagtcat gaaatcattt   7680
taatgaaaag aacatcacct aggttttgtg gtttcttttt ttcttattca tggctgagtg   7740
aaaacaacaa tctctgtttc tccctagcat ctgtggacta tttaatgtac cattattcca   7800
cactctatgg tccttactaa atacaaaatt gaacaaaaag cagtaaaaca actgactctt   7860
cacccatatt ataaaatata atccaagcca gattagtcaa catccataag atgaatccaa   7920
gctgaactgg gcctagatta ttgagttcag gttggatcac atccctattt attaataaac   7980
ttaggaaaga aggccttaca gaccatcagt tagctggagc taatagaacc tacacttcta   8040
aagttcggcc tagaatcaat gtggccttaa aagctgaaaa gaagcaggaa agaacagttt   8100
tcttcaataa tttgtccacc ctgtcactgg agaaaattta agaatttggg ggtgttggta   8160
gtaagttaaa cacagcagct gttcatggca gaaattattc aatacatacc ttctctgaat   8220
atcctataac caaagcaaag aaaaacacca aggggtttgt tctcctcctt ggagttgacc   8280
tcattccaag gcagagctca ggtcacaggc acaggggctg cgcccaagct tgtccgcagc   8340
cttatgcagc tgtggagtct ggaagactgt tgcaggactg ctggcctagt cccagaatgt   8400
cagcctcatt ttcgatttac tggctcttgt tgctgtatgt catgctgacc ttattgttaa   8460
acacaggttt gtttgctttt tttccactca tggagacatg ggagaggcat tatttttaag   8520
ctggttgaaa gctttaaccg ataaagcatt tttagagaaa tgtgaatcag gcagctaaga   8580
aagcatactc tgtccattac ggtaaagaaa atgcacagat tattaactct gcagtgtggc   8640
attagtgtcc tggtcaatat tcggatagat atgaataaaa tatttaaatg gtattgtaaa   8700
tagttttcag gacatatgct atagcttatt tttattatct tttgaaattg ctcttaatac   8760
atcaaatcct gatgtattca atttatcaga tataaattat tctaaatgaa gcccagttaa   8820
atgtttttgt cttgtcagtt atatgttaag tttctgatct ctttgtctat gacgtttact   8880
aatctgcatt tttactgtta tgaattattt tagacagcag tggtttcaag ctttttgcca   8940
ctaaaaatac cttttatttt ctcctccccc agaaaagtct ataccttgaa gtatctatcc   9000
accaaactgt acttctatta agaaatagtt attgtgtttt cttaatgttt tgttattcaa   9060
agacatatca atgaaagctg ctgagcagca tgaataacaa ttatatccac acagatttga   9120
```

-continued

```
tatattttgt gcagccttaa cttgatagta taaaatgtca ttgcttttta aataatagtt   9180
agtcaatgga cttctatcat agctttccta aactaggtta agatccagag ctttggggtc   9240
ataatatatt acatacaatt aagttatctt tttctaaggg ctttaaaatt catgagaata   9300
accaaaaaag gtatgtggag agttaataca aacataccat attcttgttg aaacagagat   9360
gtggctctgc ttgttctcca taaggtagaa atactttcca gaatttgcct aaactagtaa   9420
gccctgaatt tgctatgatt agggatagga agagattttc acatggcaga ctttagaatt   9480
cttcacttta gccagtaaag tatctccttt tgatcttagt attctgtgta ttttaacttt   9540
tctgagttgt gcatgtttat aagaaaaatc agcacaaagg gtttaagtta aagccttttt   9600
actgaaattt gaaagaaaca gaagaaaata tcaaagttct ttgtattttg agaggattaa   9660
atatgattta caaaagttac atggagggct ctctaaaaca ttaaattaat tatttttttgt   9720
tgaaaagtct tactttaggc atcattttat tcctcagcaa ctagctgtga agcctttact   9780
gtgctgtatg ccagtcactc tgctagattg tggagattac cagtgttccc gtcttctccg   9840
agcttagagt tggatgggga ataaagacag gtaaacagat agctacaata ttgtactgtg   9900
aatgcttatg ctggaggaag tacagggaac tattggagca cctaagagga gcacctacct   9960
tgaatttagg ggttagcaga ggcatcctga aaaaagtcaa agctaagcca caatctataa  10020
gcagtttagg aattagcaga acgtgcgtgg tgaggagatg ccaaaggcaa gaagagaaga  10080
gtattccaaa caggagggat tccaaagaga gaagagtatc ccaaacaaca tttgcacaaa  10140
cctgatgggg agagagaatg tggggtgggg atggatgatg agactgaaga agaaagccag  10200
gtctagataa tcagtggcct tgtacaccat gttaaagagt gtagacttga ttctgttgta  10260
aacaggaaag cagcacaatt catatgaata ttttagaaga ctcccactgg aatatggaga  10320
ataaagttgg agatgactaa tcctggaagc agggagaaca tttttgagga agttgcacta  10380
ttttggtgaa aatgatgatc ataaacatga agaattgtag gtgatcatga cctcctctct  10440
aattttccag aagggttttg gaagatataa cataggaaca ttgacaggac tgacgaaagg  10500
agatgaaata caccatataa attgtcaaac acaaggccag atgtctaatt attttgctta  10560
tgtgttgaaa ttacaaattt ttcatcagga aaccaaaaac tacaaaactt agttttccca  10620
agtcccagaa ttctatctgt ccaaacaatc tgtaccactc cacctatatc cctacctttg  10680
catgtctgtc caacctcaaa gtccaggtct atacacacgg gtaagactag agcagttcaa  10740
gtttcagaaa atgagaaaga ggaactgagt tgtgctgaac ccatacaaaa taaacacatt  10800
ctttgtatag attcttggaa cctcgagagg aattcaccta actcataggt atttgatggt  10860
atgaatccat ggctgggctc ggcttttaaa aagccttatc tgggattcct tctatggaac  10920
caagttccat caaagcccat ttaaaagcct acattaaaaa caaaattctt gctgcattgt  10980
atacaaataa tgatgtcatg atcaaataat cagatgccat tatcaagtgg aattacaaaa  11040
tggtataccc actccaaaaa aaaaaaaaaa gctaaattct cagtagaaca ttgtgacttc  11100
atgagccctc cacagccttg gagctgagga gggagcactg gtgagcagta ggttgaagag  11160
aaaacttggc gcttaataat ctatccatgt tttttcatct aaaagagcct tctttttgga  11220
ttaccttatt caatttccat caaggaaatt gttagttcca ctaaccagac agcagctggg  11280
aaggcagaag cttactgtat gtacatggta gctgtgggaa ggaggtttct ttctccaggt  11340
cctcactggc catacaccag tcccttgtta gttatgcctg gtcatagacc cccgttgcta  11400
tcatctcata tttaagtctt tggcttgtga atttatctat tctttcagct tcagcactgc  11460
```

agagtgctgg gactttgcta acttccattt cttgctggct tagcacattc ctcataggcc 11520
cagctctttt ctcatctggc cctgctgtgg agtcaccttg ccccttcagg agagccatgg 11580
cttaccactg cctgctaagc ctccactcag ctgccaccac actaaatcca agcttctcta 11640
agatgttgca gactttacag gcaagcataa aaggcttgat cttcctggac ttccctttac 11700
ttgtctgaat ctcacctcct tcaactttca gtctcagaat gtaggcattt gtcctctttg 11760
ccctacatct tccttcttct gaatcatgaa agcctctcac ttcctcttgc tatgtgctgg 11820
aggcttctgt caggttttag aatgagttct catctagtcc tagtagcttt tgatgcttaa 11880
gtccaccttt taaggatacc tttgagattt agaccatgtt tttcgcttga gaaagcccta 11940
atctccagac ttgcctttct gtggatttca aagaccaact gaggaagtca aaagctgaat 12000
gttgactttc tttgaacatt tccgctataa caattccaat tctcctcaga gcaatatgcc 12060
tgcctccaac tgaccaggag aaaggtccag tgccaaagag aaaaacacaa agattaatta 12120
tttcagttga gcacatactt tcaaagtggt ttgggtattc atatgaggtt ttctgtcaag 12180
agggtgagac tcttcatcta tccatgtgtg cctgacagtt ctcctggcac tggctggtaa 12240
cagatgcaaa actgtaaaaa ttaagtgatc atgtatttta acgatatcat cacatactta 12300
ttttctatgt aatgttttaa atttccccta acatactttg actgttttgc acatggtaga 12360
tattcacatt tttttgtgtt gaagttgatg caatcttcaa agttatctac cccgttgctt 12420
attagtaaaa ctagtgttaa tacttggcaa gagatgcagg gaatctttct catgactcac 12480
gccctattta gttattaatg ctactaccct attttgagta agtagtaggt ccctaagtac 12540
attgtccaga gttatacttt taaagatatt tagccccata tacttcttga atctaaagtc 12600
atacaccttg ctcctcattt ctgagtggga aagacatttg agagtatgtt gacaattgtt 12660
ctgaaggttt ttgccaagaa ggtgaaactg tcctttcatc tgtgtatgcc tggggctggg 12720
tccctggcag tgatggggtg acaatgcaaa gctgtaaaaa ctaggtgcta gtgggcacct 12780
aatatcatca tcatatactt attttcaagc taatatgcaa aatcccatct ctgtttttaa 12840
actaagtgta gatttcagag aaaatatttt gtggttcaca taagaaaaca gtctactcag 12900
cttgacaagt gttttatgtt aaattggctg gtggtttgaa atgaatcatc ttcacataat 12960
gttttcttta aaaatattgt gaatttaact ctaattcttg ttattctgtg tgataataaa 13020
gaataaacta atttcta 13037

<210> SEQ ID NO 28
<211> LENGTH: 933
<212> TYPE: PRT
<213> ORGANISM: Homo sapiens

<400> SEQUENCE: 28

Met Thr Glu Leu Lys Ala Lys Gly Pro Arg Ala Pro His Val Ala Gly
1 5 10 15

Gly Pro Pro Ser Pro Glu Val Gly Ser Pro Leu Leu Cys Arg Pro Ala
20 25 30

Ala Gly Pro Phe Pro Gly Ser Gln Thr Ser Asp Thr Leu Pro Glu Val
35 40 45

Ser Ala Ile Pro Ile Ser Leu Asp Gly Leu Leu Phe Pro Arg Pro Cys
50 55 60

Gln Gly Gln Asp Pro Ser Asp Glu Lys Thr Gln Asp Gln Gln Ser Leu
65 70 75 80

Ser Asp Val Glu Gly Ala Tyr Ser Arg Ala Glu Ala Thr Arg Gly Ala
85 90 95

```
Gly Gly Ser Ser Ser Ser Pro Pro Glu Lys Asp Ser Gly Leu Leu Asp
            100                 105                 110

Ser Val Leu Asp Thr Leu Leu Ala Pro Ser Gly Pro Gly Gln Ser Gln
        115                 120                 125

Pro Ser Pro Pro Ala Cys Glu Val Thr Ser Ser Trp Cys Leu Phe Gly
    130                 135                 140

Pro Glu Leu Pro Glu Asp Pro Pro Ala Ala Pro Ala Thr Gln Arg Val
145                 150                 155                 160

Leu Ser Pro Leu Met Ser Arg Ser Gly Cys Lys Val Gly Asp Ser Ser
                165                 170                 175

Gly Thr Ala Ala Ala His Lys Val Leu Pro Arg Gly Leu Ser Pro Ala
            180                 185                 190

Arg Gln Leu Leu Leu Pro Ala Ser Glu Ser Pro His Trp Ser Gly Ala
        195                 200                 205

Pro Val Lys Pro Ser Pro Gln Ala Ala Ala Val Glu Val Glu Glu Glu
    210                 215                 220

Asp Gly Ser Glu Ser Glu Glu Ser Ala Gly Pro Leu Leu Lys Gly Lys
225                 230                 235                 240

Pro Arg Ala Leu Gly Gly Ala Ala Ala Gly Gly Gly Ala Ala Ala Val
                245                 250                 255

Pro Pro Gly Ala Ala Ala Gly Gly Val Ala Leu Val Pro Lys Glu Asp
            260                 265                 270

Ser Arg Phe Ser Ala Pro Arg Val Ala Leu Val Glu Gln Asp Ala Pro
        275                 280                 285

Met Ala Pro Gly Arg Ser Pro Leu Ala Thr Thr Val Met Asp Phe Ile
    290                 295                 300

His Val Pro Ile Leu Pro Leu Asn His Ala Leu Leu Ala Ala Arg Thr
305                 310                 315                 320

Arg Gln Leu Leu Glu Asp Glu Ser Tyr Asp Gly Gly Ala Gly Ala Ala
                325                 330                 335

Ser Ala Phe Ala Pro Pro Arg Ser Ser Pro Cys Ala Ser Ser Thr Pro
            340                 345                 350

Val Ala Val Gly Asp Phe Pro Asp Cys Ala Tyr Pro Pro Asp Ala Glu
        355                 360                 365

Pro Lys Asp Asp Ala Tyr Pro Leu Tyr Ser Asp Phe Gln Pro Pro Ala
    370                 375                 380

Leu Lys Ile Lys Glu Glu Glu Glu Gly Ala Glu Ala Ser Ala Arg Ser
385                 390                 395                 400

Pro Arg Ser Tyr Leu Val Ala Gly Ala Asn Pro Ala Ala Phe Pro Asp
                405                 410                 415

Phe Pro Leu Gly Pro Pro Pro Pro Leu Pro Pro Arg Ala Thr Pro Ser
            420                 425                 430

Arg Pro Gly Glu Ala Ala Val Thr Ala Ala Pro Ala Ser Ala Ser Val
        435                 440                 445

Ser Ser Ala Ser Ser Ser Gly Ser Thr Leu Glu Cys Ile Leu Tyr Lys
    450                 455                 460

Ala Glu Gly Ala Pro Pro Gln Gln Gly Pro Phe Ala Pro Pro Pro Cys
465                 470                 475                 480

Lys Ala Pro Gly Ala Ser Gly Cys Leu Leu Pro Arg Asp Gly Leu Pro
                485                 490                 495

Ser Thr Ser Ala Ser Ala Ala Ala Ala Gly Ala Ala Pro Ala Leu Tyr
            500                 505                 510
```

-continued

```
Pro Ala Leu Gly Leu Asn Gly Leu Pro Gln Leu Gly Tyr Gln Ala Ala
        515                 520                 525

Val Leu Lys Glu Gly Leu Pro Gln Val Tyr Pro Pro Tyr Leu Asn Tyr
    530                 535                 540

Leu Arg Pro Asp Ser Glu Ala Ser Gln Ser Pro Gln Tyr Ser Phe Glu
545                 550                 555                 560

Ser Leu Pro Gln Lys Ile Cys Leu Ile Cys Gly Asp Glu Ala Ser Gly
                565                 570                 575

Cys His Tyr Gly Val Leu Thr Cys Gly Ser Cys Lys Val Phe Phe Lys
            580                 585                 590

Arg Ala Met Glu Gly Gln His Asn Tyr Leu Cys Ala Gly Arg Asn Asp
        595                 600                 605

Cys Ile Val Asp Lys Ile Arg Arg Lys Asn Cys Pro Ala Cys Arg Leu
    610                 615                 620

Arg Lys Cys Cys Gln Ala Gly Met Val Leu Gly Gly Arg Lys Phe Lys
625                 630                 635                 640

Lys Phe Asn Lys Val Arg Val Val Arg Ala Leu Asp Ala Val Ala Leu
                645                 650                 655

Pro Gln Pro Val Gly Val Pro Asn Glu Ser Gln Ala Leu Ser Gln Arg
            660                 665                 670

Phe Thr Phe Ser Pro Gly Gln Asp Ile Gln Leu Ile Pro Pro Leu Ile
        675                 680                 685

Asn Leu Leu Met Ser Ile Glu Pro Asp Val Ile Tyr Ala Gly His Asp
    690                 695                 700

Asn Thr Lys Pro Asp Thr Ser Ser Ser Leu Leu Thr Ser Leu Asn Gln
705                 710                 715                 720

Leu Gly Glu Arg Gln Leu Leu Ser Val Val Lys Trp Ser Lys Ser Leu
                725                 730                 735

Pro Gly Phe Arg Asn Leu His Ile Asp Asp Gln Ile Thr Leu Ile Gln
            740                 745                 750

Tyr Ser Trp Met Ser Leu Met Val Phe Gly Leu Gly Trp Arg Ser Tyr
        755                 760                 765

Lys His Val Ser Gly Gln Met Leu Tyr Phe Ala Pro Asp Leu Ile Leu
    770                 775                 780

Asn Glu Gln Arg Met Lys Glu Ser Ser Phe Tyr Ser Leu Cys Leu Thr
785                 790                 795                 800

Met Trp Gln Ile Pro Gln Glu Phe Val Lys Leu Gln Val Ser Gln Glu
                805                 810                 815

Glu Phe Leu Cys Met Lys Val Leu Leu Leu Leu Asn Thr Ile Pro Leu
            820                 825                 830

Glu Gly Leu Arg Ser Gln Thr Gln Phe Glu Glu Met Arg Ser Ser Tyr
        835                 840                 845

Ile Arg Glu Leu Ile Lys Ala Ile Gly Leu Arg Gln Lys Gly Val Val
    850                 855                 860

Ser Ser Ser Gln Arg Phe Tyr Gln Leu Thr Lys Leu Leu Asp Asn Leu
865                 870                 875                 880

His Asp Leu Val Lys Gln Leu His Leu Tyr Cys Leu Asn Thr Phe Ile
                885                 890                 895

Gln Ser Arg Ala Leu Ser Val Glu Phe Pro Glu Met Met Ser Glu Val
            900                 905                 910

Ile Ala Ala Gln Leu Pro Lys Ile Leu Ala Gly Met Val Lys Pro Leu
        915                 920                 925

Leu Phe His Lys Lys
```

930

<210> SEQ ID NO 29
<211> LENGTH: 1762
<212> TYPE: DNA
<213> ORGANISM: Homo sapiens

<400> SEQUENCE: 29
cggccgaggg cggggcaggg aggcagcatg ctaaaccggg tgcgctcggc cgtggcgcac 60
ctggtgagct ccgggggcgc tccgcctccg cgccccaaat ccccggacct gcccaacgcc 120
gcctcggcgc cgcccgccgc cgctccagaa gcgcccagga gccctcccgc gaaggctggg 180
agcgggagcg cgacgcccgc gaaggctgtt gaggctcgag cgagcttctc cagaccgacc 240
tttctgcagc tgagccccgg ggggctgcga cgcgccgatg accacgcggg ccgggctgtg 300
caaagccccc cggacacggg ccgccgcctg ccctggagca caggctacgc cgaggtcatc 360
aatgctggca agagtcggca caatgaggac caggcttgct gtgaagtggt gtatgtggaa 420
ggtcggagga gtgttacagg agtacctagg gagcctagcc gaggccaggg actctgcttc 480
tactactggg gcctatttga tgggcatgca gggggcggag ctgctgaaat ggcctcacgg 540
ctcctgcatc gccatatccg agagcagcta aaggacctgg tagagatact tcaggaccct 600
tcgccaccac ccctctgcct cccaaccact ccggggaccc cagattcctc cgatccctct 660
cacttgcttg gccctcagtc ctgctggtct tcacagaagg aagtgagcca cgagagcctg 720
gtagtggggg ccgttgagaa tgccttccag ctcatggatg agcagatggc ccgggagcgg 780
cgtggccacc aagtggaggg gggctgctgt gcactggttg tgatctacct gctaggcaag 840
gtgtacgtgg ccaatgcagg cgatagcagg gccatcattg tccggaatgg tgaaatcatt 900
ccaatgtccc gggagtttac ccccggagact gagcgccagc gtcttcagct gcttggcttc 960
ctgaaaccag agctgctagg cagtgaattc acccaccttg agttccccccg cagagttctg 1020 cccaaggagc tggggcagag gatgttgtac cgggaccaga acatgaccgg ctgggcctac 1080
aaaaagatcg agctggagga tctcaggttt cctctggtct gtggggaggg caaaaaggct 1140
cgggtgatgg ccaccattgg ggtgacccga ggcttgggag accacagcct taaggtctgc 1200
agttccaccc tgcccatcaa gccctttctc tcctgcttcc ctgaggtacg agtgtatgac 1260
ctgacacaat atgagcactg cccagatgat gtgctagtcc tgggaacaga tggcctgtgg 1320
gatgtcacta ctgactgtga ggtagctgcc actgtggaca gggtgctgtc ggcctatgag 1380
cctaatgacc acagcaggta tacagctctg gcccaagctc tggtcctggg ggcccggggt 1440 acccccccgag accgtggctg gcgtctcccc aacaacaagc tgggttccgg ggatgacatc 1500
tctgtcttcg tcatccccct gggagggcca ggcagttact cctgaggggc tgaacaccat 1560
ccctcccact agcctctcca tacttactcc tctcacagcc caaattctga agttgtctcc 1620
ctgacccttc tttagtggca acttaactga agaagggatg tccgctatat ccaaaattac 1680
agctattggc aaataaacga gatggataaa ggtgaaaaaa aaaaaaaaaa aaaaaaaaaa 1740
aaaaaaaaaa aaaaaaaaaa aa 1762

<210> SEQ ID NO 30
<211> LENGTH: 505
<212> TYPE: PRT
<213> ORGANISM: Homo sapiens

<400> SEQUENCE: 30

Met Leu Asn Arg Val Arg Ser Ala Val Ala His Leu Val Ser Ser Gly

-continued

```
1               5                   10                  15

Gly Ala Pro Pro Pro Arg Pro Lys Ser Pro Asp Leu Pro Asn Ala Ala
            20                  25                  30

Ser Ala Pro Pro Ala Ala Ala Pro Glu Ala Pro Arg Ser Pro Pro Ala
        35                  40                  45

Lys Ala Gly Ser Gly Ser Ala Thr Pro Ala Lys Ala Val Glu Ala Arg
    50                  55                  60

Ala Ser Phe Ser Arg Pro Thr Phe Leu Gln Leu Ser Pro Gly Gly Leu
65                  70                  75                  80

Arg Arg Ala Asp Asp His Ala Gly Arg Ala Val Gln Ser Pro Pro Asp
                85                  90                  95

Thr Gly Arg Arg Leu Pro Trp Ser Thr Gly Tyr Ala Glu Val Ile Asn
            100                 105                 110

Ala Gly Lys Ser Arg His Asn Glu Asp Gln Ala Cys Cys Glu Val Val
        115                 120                 125

Tyr Val Glu Gly Arg Arg Ser Val Thr Gly Val Pro Arg Glu Pro Ser
    130                 135                 140

Arg Gly Gln Gly Leu Cys Phe Tyr Tyr Trp Gly Leu Phe Asp Gly His
145                 150                 155                 160

Ala Gly Gly Gly Ala Ala Glu Met Ala Ser Arg Leu Leu His Arg His
                165                 170                 175

Ile Arg Glu Gln Leu Lys Asp Leu Val Glu Ile Leu Gln Asp Pro Ser
            180                 185                 190

Pro Pro Pro Leu Cys Leu Pro Thr Thr Pro Gly Thr Pro Asp Ser Ser
        195                 200                 205

Asp Pro Ser His Leu Leu Gly Pro Gln Ser Cys Trp Ser Ser Gln Lys
    210                 215                 220

Glu Val Ser His Glu Ser Leu Val Val Gly Ala Val Glu Asn Ala Phe
225                 230                 235                 240

Gln Leu Met Asp Glu Gln Met Ala Arg Glu Arg Arg Gly His Gln Val
                245                 250                 255

Glu Gly Gly Cys Cys Ala Leu Val Val Ile Tyr Leu Leu Gly Lys Val
            260                 265                 270

Tyr Val Ala Asn Ala Gly Asp Ser Arg Ala Ile Ile Val Arg Asn Gly
        275                 280                 285

Glu Ile Ile Pro Met Ser Arg Glu Phe Thr Pro Glu Thr Glu Arg Gln
    290                 295                 300

Arg Leu Gln Leu Leu Gly Phe Leu Lys Pro Glu Leu Leu Gly Ser Glu
305                 310                 315                 320

Phe Thr His Leu Glu Phe Pro Arg Arg Val Leu Pro Lys Glu Leu Gly
                325                 330                 335

Gln Arg Met Leu Tyr Arg Asp Gln Asn Met Thr Gly Trp Ala Tyr Lys
            340                 345                 350

Lys Ile Glu Leu Glu Asp Leu Arg Phe Pro Leu Val Cys Gly Glu Gly
        355                 360                 365

Lys Lys Ala Arg Val Met Ala Thr Ile Gly Val Thr Arg Gly Leu Gly
    370                 375                 380

Asp His Ser Leu Lys Val Cys Ser Ser Thr Leu Pro Ile Lys Pro Phe
385                 390                 395                 400

Leu Ser Cys Phe Pro Glu Val Arg Val Tyr Asp Leu Thr Gln Tyr Glu
                405                 410                 415

His Cys Pro Asp Asp Val Leu Val Leu Gly Thr Asp Gly Leu Trp Asp
            420                 425                 430
```

```
Val Thr Thr Asp Cys Glu Val Ala Ala Thr Val Asp Arg Val Leu Ser
        435                 440                 445

Ala Tyr Glu Pro Asn Asp His Ser Arg Tyr Thr Ala Leu Ala Gln Ala
    450                 455                 460

Leu Val Leu Gly Ala Arg Gly Thr Pro Arg Asp Arg Gly Trp Arg Leu
465                 470                 475                 480

Pro Asn Asn Lys Leu Gly Ser Gly Asp Asp Ile Ser Val Phe Val Ile
                485                 490                 495

Pro Leu Gly Gly Pro Gly Ser Tyr Ser
            500                 505


<210> SEQ ID NO 31
<211> LENGTH: 3468
<212> TYPE: DNA
<213> ORGANISM: Homo sapiens

<400> SEQUENCE: 31

attgtgccct accagagagg acagatgggc accgcctcca gtggcaatgc taattcaccc     60

aagaggcctt cccagctctt ctcacagaag gaagataaac tccacatatt tctatatcct    120

gctggatgac attgtcctta cccattctct cttcctcccg acggagaaat ttctgcagga    180

gctacaccag tactttgttc gggcaggagg catggagggc cctgaagggc tgggccggaa    240

gcaagcctgt ctagccatgc ttctccattt cttggacacc taccaggggc tgcttcaaga    300

ggaagagggg gccggccaca tcatcaagga tctatacctg ctaattatga aggacgagtc    360

cctttaccag ggcctccgag aggacactct gaggctgcac cagctggtgg agacggtgga    420

actaaagatt ccagaggaga accagccacc cagcaagcag gtgaagccac tcttccgcca    480

cttccgccgg atagactcct gtctgcagac ccgggtggcc ttccggggct ctgatgagat    540

cttctgccgt gtatacatgc ctgaccactc ttatgtgacc atacgcagcc gcctttcagc    600

atctgtgcag gacattctgg gctctgtgac ggagaaactt caatattcag aggagcccgc    660

ggggcgtgag gattccctca tcctggtagc tgtgtcctcc tctggagaga aggtccttct    720

ccagcccact gaggactgtg ttttcaccgc actgggcatc aacagccacc tgtttgcctg    780

tactcgggac agctatgagg ctctggtgcc cctccccgag gagatccagg tctcccctgg    840

agacacagag atccaccgag tggagcctga ggacgttgcc aaccacctaa ctgccttcca    900

ctgggagctg ttccgatgtg tgcatgagct ggagttcgtg gactacgtgt tccacgggga    960

gcgcggccgc cgggagacgg ccaacttgga gctgctgctg cagcgctgca gcgaggtcac   1020

gcactgggtg gccaccgaag tgctgctctg cgaggccccg ggcaagcgcg cgcagctgct   1080

caagaagttc atcaagatcg cggccctctg caagcagaac caggacctgc tgtctttcta   1140

cgccgtggtc atggggctgg acaacgccgc tgtcagccgc cttcgactca cctgggagaa   1200

gctgccaggg aaattcaaga acttgtttcg caaatttgag aacctgacgg acccctgcag   1260

gaaccacaaa agctaccgag aagtgatctc caaaatgaag ccccctgtga ttcccttcgt   1320

gcctctgatc ctcaaagacc tgactttcct gcacgaaggg agtaagaccc ttgtagatgg   1380

tttggtgaac atcgagaagc tgcattcagt ggccgaaaaa gtgaggacaa tccgcaaata   1440

ccggagccgg cccctttgcc tggacatgga ggcatccccc aatcacctgc agaccaaggc   1500

ctatgtgcgc cagtttcagg tcatcgacaa ccagaacctc ctcttcgagc tctcctacaa   1560

gctggaggca aacagtcagt gagagtggag gctccagtca gacccgccag atccttgggc   1620

acctggcact caagcacttt gcacgatgtc tcaaccaaca tctgacatct ttcccgtgga   1680
```

```
gcaacttcct gctccacggg aaagaggtcg atggatttac ccctggaccc ataagtctgt   1740
tcatcctgct gaagtcccct ccccattgct ccttcaagcc aaaactacac tttgctggtt   1800
cctgtcccct ctgagaaagg ggatagaaag ctccttcctc tatgtcctcc catcgagatc   1860
tgttctgggg atggagcttc caacttcctc ttgcagcagg aaagaatgct gctcaccctt   1920
ctgtcttgca gagtgggatt gtgggaggga ttggcagcct tcttctccac cacctgtcca   1980
gcttcttcct ggtcagggct gggacccccca ggaatattat gttgccgtgt gtgtgtgtgt   2040
gtgtgtgtgt gtgtgtgtgt gtgtgtgtgt gtgtgtgtgt gtgtcttctt ttagggagca   2100
ggagtgcatc tggtaattga gggtggatgt tgtgtgtgct ggggaggggt ccttctgttt   2160
ggtgctaccc ttgtctactc tgcccctgga tggtgcgggg tgctttctcc acccccacac   2220
tccctgctca gctcctcgtg ctgccctgca tgcccaggct tgtgagccaa gctgcttttt   2280
ggggcaggga gtagcagcag gtgggagggg ttacccatca gcccttgcaa gtcccccact   2340
caggcctctg gaaggtccag ggatgggctc tgatgagagg gtaaaagatg ctcagggaaa   2400
cacaggcctc agctgcctag aggaccctcc ccctgccttg cagtgggctc gggtagagca   2460
gtatcaggag ctagggttgt ctgctgccca cactcctgct ttttgggata tctaactgct   2520
aaggagggag ttgacatccc ccttctggct catgtgtctg acaccaacaa catggtctct   2580
gtccctctct ctttgactct ccctttgtcc tccccataga gctggggtgg ggtggatccc   2640
tatacctggg gcaggcagcc ccaaagtggg ggagggggat ggcagagact gtaaaggcgc   2700
cactggactc tggcaaggcc tttattacct ttactcccct ccctctccca tcaccagcct   2760
caaggcctga ggggtgcagg ggctcctggc agctactggg tgaggtttcc tggcacagac   2820
tcacccttct ttctggcacc acctctttcc cttttgaaga gacagcaaca gccgtagcaa   2880
aagcagctgc tgctcctgct atgagggtgt atatattttt tacccaaagc tctggaattg   2940
tacatttatt ttttaaaact caaagaggga aagagccttg tatcatatgt gaacattgta   3000
tcataggtaa tgttgtacag acccttttat acagtgatct gtcttgttcc tgcagcaaaa   3060
atcctctatg gacataggag gtgctgtgtc ccatgccctc ttgccctgac agtgtcccat   3120
gggccccctt ctgctccctg ccccctccct gctactgctg atgcactctc ctctccctgc   3180
agcccctggc ttcccagcct tcctcctgac cccttccaac agccttggaa ctccagctgc   3240
caccaccctc tgggtcggac actgggaccc actggcccag tcttggctgc tgcttacccc   3300
tagccttgat gcctgcccag ggacccccag ccccctcccg ttgccctgca gctttaacag   3360
agtgaaccat gtgtattgta caggcgcggt tgtcattgca gaaaccgctg ggtggagaag   3420
aagccgataa agtctatgaa tcaacctgcc aaaaaaaaaa aaaaaaaa               3468
```

```
<210> SEQ ID NO 32
<211> LENGTH: 662
<212> TYPE: PRT
<213> ORGANISM: Homo sapiens

<400> SEQUENCE: 32

Met Lys Pro Leu Glu Lys Phe Leu Lys Lys Gln Thr Ser Gln Leu Ala
1               5                   10                  15

Gly Arg Thr Val Ala Gly Gly Pro Gly Gly Gly Leu Gly Ser Cys Gly
            20                  25                  30

Gly Pro Gly Gly Gly Gly Gly Pro Gly Gly Gly Gly Gly Pro Ala Gly
        35                  40                  45

Gly Gln Arg Ser Leu Gln Arg Arg Gln Ser Val Ser Arg Leu Leu Leu
```

```
    50                  55                  60

Pro Ala Phe Leu Arg Glu Pro Pro Ala Glu Pro Gly Leu Glu Pro Pro
65                  70                  75                  80

Val Pro Glu Glu Gly Gly Glu Pro Ala Gly Val Ala Glu Glu Pro Gly
                85                  90                  95

Ser Gly Gly Pro Cys Trp Leu Gln Leu Glu Glu Val Pro Gly Pro Gly
            100                 105                 110

Pro Leu Gly Gly Gly Gly Pro Leu Arg Ser Pro Ser Ser Tyr Ser Ser
        115                 120                 125

Asp Glu Leu Ser Pro Gly Glu Pro Leu Thr Ser Pro Pro Trp Ala Pro
    130                 135                 140

Leu Gly Ala Pro Glu Arg Pro Glu His Leu Leu Asn Arg Val Leu Glu
145                 150                 155                 160

Arg Leu Ala Gly Gly Ala Thr Arg Asp Ser Ala Ala Ser Asp Ile Leu
                165                 170                 175

Leu Asp Asp Ile Val Leu Thr His Ser Leu Phe Leu Pro Thr Glu Lys
            180                 185                 190

Phe Leu Gln Glu Leu His Gln Tyr Phe Val Arg Ala Gly Gly Met Glu
        195                 200                 205

Gly Pro Glu Gly Leu Gly Arg Lys Gln Ala Cys Leu Ala Met Leu Leu
    210                 215                 220

His Phe Leu Asp Thr Tyr Gln Gly Leu Leu Gln Glu Glu Glu Gly Ala
225                 230                 235                 240

Gly His Ile Ile Lys Asp Leu Tyr Leu Leu Ile Met Lys Asp Glu Ser
                245                 250                 255

Leu Tyr Gln Gly Leu Arg Glu Asp Thr Leu Arg Leu His Gln Leu Val
            260                 265                 270

Glu Thr Val Glu Leu Lys Ile Pro Glu Glu Asn Gln Pro Pro Ser Lys
        275                 280                 285

Gln Val Lys Pro Leu Phe Arg His Phe Arg Arg Ile Asp Ser Cys Leu
    290                 295                 300

Gln Thr Arg Val Ala Phe Arg Gly Ser Asp Glu Ile Phe Cys Arg Val
305                 310                 315                 320

Tyr Met Pro Asp His Ser Tyr Val Thr Ile Arg Ser Arg Leu Ser Ala
                325                 330                 335

Ser Val Gln Asp Ile Leu Gly Ser Val Thr Glu Lys Leu Gln Tyr Ser
            340                 345                 350

Glu Glu Pro Ala Gly Arg Glu Asp Ser Leu Ile Leu Val Ala Val Ser
        355                 360                 365

Ser Ser Gly Glu Lys Val Leu Leu Gln Pro Thr Glu Asp Cys Val Phe
    370                 375                 380

Thr Ala Leu Gly Ile Asn Ser His Leu Phe Ala Cys Thr Arg Asp Ser
385                 390                 395                 400

Tyr Glu Ala Leu Val Pro Leu Pro Glu Glu Ile Gln Val Ser Pro Gly
                405                 410                 415

Asp Thr Glu Ile His Arg Val Glu Pro Glu Asp Val Ala Asn His Leu
            420                 425                 430

Thr Ala Phe His Trp Glu Leu Phe Arg Cys Val His Glu Leu Glu Phe
        435                 440                 445

Val Asp Tyr Val Phe His Gly Glu Arg Gly Arg Arg Glu Thr Ala Asn
    450                 455                 460

Leu Glu Leu Leu Leu Gln Arg Cys Ser Glu Val Thr His Trp Val Ala
465                 470                 475                 480
```

Thr Glu Val Leu Leu Cys Glu Ala Pro Gly Lys Arg Ala Gln Leu Leu
485 490 495

Lys Lys Phe Ile Lys Ile Ala Ala Leu Cys Lys Gln Asn Gln Asp Leu
500 505 510

Leu Ser Phe Tyr Ala Val Val Met Gly Leu Asp Asn Ala Ala Val Ser
515 520 525

Arg Leu Arg Leu Thr Trp Glu Lys Leu Pro Gly Lys Phe Lys Asn Leu
530 535 540

Phe Arg Lys Phe Glu Asn Leu Thr Asp Pro Cys Arg Asn His Lys Ser
545 550 555 560

Tyr Arg Glu Val Ile Ser Lys Met Lys Pro Pro Val Ile Pro Phe Val
565 570 575

Pro Leu Ile Leu Lys Asp Leu Thr Phe Leu His Glu Gly Ser Lys Thr
580 585 590

Leu Val Asp Gly Leu Val Asn Ile Glu Lys Leu His Ser Val Ala Glu
595 600 605

Lys Val Arg Thr Ile Arg Lys Tyr Arg Ser Arg Pro Leu Cys Leu Asp
610 615 620

Met Glu Ala Ser Pro Asn His Leu Gln Thr Lys Ala Tyr Val Arg Gln
625 630 635 640

Phe Gln Val Ile Asp Asn Gln Asn Leu Leu Phe Glu Leu Ser Tyr Lys
645 650 655

Leu Glu Ala Asn Ser Gln
660

<210> SEQ ID NO 33
<211> LENGTH: 2467
<212> TYPE: DNA
<213> ORGANISM: Homo sapiens

<400> SEQUENCE: 33
gaagatgcac acgacccaga aggacacgac gtacaccaag atcttcgtcg gggggctgcc 60
ctaccacacc accgacgcca gcctgcgcaa gtacttcgag gtcttcggcg agatcgagga 120
ggcggtggtc atcaccgacc ggcagacggg caagtcccgg ggctatggat ttgtcaccat 180
ggctgaccgg gctgctgccg aaagggcctg caaggatccc aatcccatca ttgatggcag 240
aaaggccaac gtgaacctgg catacttagg agcaaaacca aggatcatgc aaccaggttt 300
tgcctttggt gttcaacaac ttcatccagc ccttatacaa agacctttcg ggatacctgc 360
ccactatgtc tatccgcagg cttttgtgca gccgggagtg gtcattccac acgtccagcc 420
gacagcagct gccgcctcca ccacccctta cattgattac actggagctg catacgcaca 480
atactcagca gctgctgctg ctgccgccgc cgctgctgcc tatgaccagt acccctatgc 540
agcctctcca gctgctgcag gatatgttac tgctgggggc tatggctacg cagtccagca 600
gccaatcacc gcagcggcac ctgggacagc tgccgccgcc gctgcagcag ctgctgccgc 660
tgcagcattt ggccagtacc agcctcagca gctgcagaca gaccgaatgc aatagaccag 720
ccatctgatc aaagttgaat tgttttctct ttccctccca attttccaat ttttagtagc 780
taataagaga gttaacattg acttaacagc tttaaaaaaa aaaacagcca tgctattgtg 840
aagcagagtt attatttttt ttatactcca ggtagtgttc tagatgagaa agaggtaaga 900
atgaggggaa tgggcacaat tttggaaatc aatcccaaag agcctgagta aatgaaaggc 960
cactacgaaa tgacgccagg agtaacaacg gaacttcact tttgtaacgg gatttttatt 1020

-continued

```
tttgctcttt ttatagtatc agggaagcaa actgcctttt acaagttaga aaatgctgtt   1080

tgaatctagt tgaaccaggg aatacagagc gagcaatatg tagcttgaat tacatttaaa   1140

agcagatttt ttacaaacaa aatggcgaaa gcactgattg tcatttttag cagtcactta   1200

aggcctatag aactttttc aagtcggaag gtcctgttct tactatctca aaaatgggca   1260

tcgaacaatc aatctaggag cgtggcagtg ggtaaaatgg tggacaggca ccaaagctat   1320

tttctcatct gtcctgtgga tgagtggaac tgtggaacaa gtgatgtgga attaatgggt   1380

gcaacagctg tacagacaat caataacaca cacagttctg gaaagaacac atcacttgtg   1440

cttgtttgat gagcttgtca cattctaatc cctctcccca tcctgtttca attttgggaa   1500

acttgtatct gctggtgtca gcaattctga ttctgaaata ggatcaggct tttactacaa   1560

cagccttctc tttctattta ttgtgtcgac tcgtggctta tgaataaagg caggcaaagt   1620

ttgcagaact gtcttaagga catttatttt ttttcccttt ttaagtaatt ttacacttta   1680

gtatctattt cagagtcata tttaaaacta tttattagtg actacagtac atgagacaac   1740

aaggttactg agattacaat tcttcaaagg ttaatgataa tgtggtttat actgtgcctt   1800

aatagtaatg ctatttaaga tatttatttt taagttttac tatgctgcac tctaaagaaa   1860

ggaactttag atgtgacact gtaaaattat gtattcatct catggcataa attatttagt   1920

aagtctagat gtagcgtatt aaatattaac ctattcaact aaagatgttg acttggattt   1980

atttaaattc atatgtgcac tgtataagag agtactctta cattaacaca ttttagttta   2040

gtttttagat ttttttttaa acgatatatt gctagtttca tgcttcctcc tctgattttg   2100

cctgtgtaga tttcatttat tggtaattca ttagtttaac actattatgt agtttttaaa   2160

tgctgcttta catttttctt ctgaaactgc aatacttgca atttttattc ttaaactaaa   2220

ttgaatacta ttttacactg tattggattt ttatacttga acaatttcat acaagggaag   2280

acaggttagc atttttatgg actttctcca ttatcactgg atttacttta agtattccca   2340

tactagacag tgttatgtaa tgtagacatg actctcctgt gcaaattatt tattcgttgt   2400

gtatattgct ttataacatt tcagatcttc taatctattc acttgtatta aatataattt   2460

ttaaaaa                                                              2467
```

```
<210> SEQ ID NO 34
<211> LENGTH: 236
<212> TYPE: PRT
<213> ORGANISM: Homo sapiens

<400> SEQUENCE: 34

Met His Thr Thr Gln Lys Asp Thr Thr Tyr Thr Lys Ile Phe Val Gly
1               5                   10                  15

Gly Leu Pro Tyr His Thr Thr Asp Ala Ser Leu Arg Lys Tyr Phe Glu
            20                  25                  30

Val Phe Gly Glu Ile Glu Glu Ala Val Val Ile Thr Asp Arg Gln Thr
        35                  40                  45

Gly Lys Ser Arg Gly Tyr Gly Phe Val Thr Met Ala Asp Arg Ala Ala
    50                  55                  60

Ala Glu Arg Ala Cys Lys Asp Pro Asn Pro Ile Ile Asp Gly Arg Lys
65                  70                  75                  80

Ala Asn Val Asn Leu Ala Tyr Leu Gly Ala Lys Pro Arg Ile Met Gln
                85                  90                  95

Pro Gly Phe Ala Phe Gly Val Gln Gln Leu His Pro Ala Leu Ile Gln
            100                 105                 110
```

-continued

```
Arg Pro Phe Gly Ile Pro Ala His Tyr Val Tyr Pro Gln Ala Phe Val
        115                 120                 125

Gln Pro Gly Val Val Ile Pro His Val Gln Pro Thr Ala Ala Ala Ala
    130                 135                 140

Ser Thr Thr Pro Tyr Ile Asp Tyr Thr Gly Ala Ala Tyr Ala Gln Tyr
145                 150                 155                 160

Ser Ala Ala Ala Ala Ala Ala Ala Ala Ala Ala Ala Tyr Asp Gln Tyr
                165                 170                 175

Pro Tyr Ala Ala Ser Pro Ala Ala Ala Gly Tyr Val Thr Ala Gly Gly
            180                 185                 190

Tyr Gly Tyr Ala Val Gln Gln Pro Ile Thr Ala Ala Ala Pro Gly Thr
        195                 200                 205

Ala Ala Ala Ala Ala Ala Ala Ala Ala Ala Ala Ala Ala Phe Gly Gln
    210                 215                 220

Tyr Gln Pro Gln Gln Leu Gln Thr Asp Arg Met Gln
225                 230                 235
```

<210> SEQ ID NO 35
<211> LENGTH: 2264
<212> TYPE: DNA
<213> ORGANISM: Homo sapiens

<400> SEQUENCE: 35

```
gcagtccctc cgccgctagt cggagcgagc gcgagtgagg agacccccgc cgggccactg     60

gcacttgctt ctgcggcgag tcccacccac gaccgcagcc cagcaactcg caaacgcaac    120

ctgaagcctg ggctgcgcag tgtgggaggg cttcgcgatc ttgggggacc cattccgaac    180

ttgcagagga ccgtagctct cctggcctgg agagtgtgaa caggattgtg gactcttcca    240

agattcacaa tgatatggtg aatccaaaga ctggaaccaa aaagatttac tcagtgcttt    300

agttttaaca acagtaaatt gtctaccaac acccatcatg gctaaaagtg cggaggtcaa    360

actggcaata tttgggagag caggcgtggg caagtcagct cttgtagtga gatttctgac    420

caaacggttc atctgggaat atgatcccac cctcgaatca acctaccgac accaagcaac    480

catcgatgat gaagttgttt ccatggagat actagacact gctggtcagg aagataccat    540

tcagagggag gggcacatgc gatgggggga aggctttgtg ctggtctacg acattactga    600

ccgaggaagt tttgaggaag tgctgccact taagaacatc ctagatgaga tcaaaaagcc    660

caagaatgtg actctcatct tggttggaaa caaagctgac ttggaccact ccaggcaggt    720

tagcacagaa gaaggagaga agctggccac agaattggct tgtgcttttt acgagtgctc    780

tgcctgcact ggagaaggga acatcacaga gatattctat gaattgtgtc gagaggtgcg    840

tcgccggagg atggtgcagg gcaagacgag gcgacgcagc tccaccacgc atgtcaagca    900

agccattaac aagatgctca ccaaaatcag tagttaggca gcccagctga ggtggaccaa    960

ctaattggaa acactcttcc ccttctgttc ccctttcaaa aataaaacaa aatattgcat   1020

tctttgtttg gattctgaga aatgtctggg cttcccattg tttctggcct ctaataggtt   1080

gggaagtttt agcgtgtttt atgcaatttc agtgctaaca atttcttcct ttcctgcttg   1140

aataagatac actctaatgg catttgaaca tgtaatcacc agagattctg aaatgactgg   1200

tttatgttaa gctattttta ggcatcttca ccttgcttta agtaggttga agtttttgca   1260

aaggcattta aaaattcaat ttcttgtcag atactacaaa taattttctt aaaagtctaa   1320

gatagcagaa aatacagtaa aaacacagga gaagaagctg agctattgga acaggaaata   1380

gaaggaactc tagtttctgt ttgaagtgag gattttctga attatctaat atcatctagg   1440
```

```
ttttctttaa aattttattt tgttcttcag ttcaagcatc ttctcactaa tgtttttcac   1500

tataacagag aattcatttc aatttgagtt ggttctctca atgatctatt gatcattaca   1560

ccctaactct ccttccttgg ctcaaacaat attttcccta taacaaaggc aataggacac   1620

aaaattcaca tcctgctggg cctttttca tcaagtcagg gtgatataaa aacattggaa   1680

gtcttttcac caaaccctga ctttattgaa tgctagtaga agatgtagaa ttagagacat   1740

ctgatttgtt tatcacctta gcagaaaaac cacagtccaa aagacaagca aattaagaat   1800

ggagcttaac catgcctcca ttgggaagtc tagactttga gccaggtaca gtaagaaaaa   1860

ttagcctctg attcattaag tttgccacat gacttatttt gatattttgg atacattaac   1920

tcacttagga gaattcagaa aagaatgggt gattaaagtt cattacagct gaataaatgt   1980

gtctaaaaca gactcttgta ttctgaaagt acagtctaca actgataaaa ccttatgatt   2040

cttttctccc ccattatgcc cctatatata tcaagatttg ggtactttat tttagtagaa   2100

aatatatatc ttttacatat gtatgtattt ataaatgcat agatatatgt ataaaaattt   2160

gtaagcgtta gcggcattaa ttcaccaatg catttggaca acttgatgta actgacttta   2220

ttttatgtga ctataataaa aagcataatt ttctcattct gtca                     2264
```

<210> SEQ ID NO 36
<211> LENGTH: 199
<212> TYPE: PRT
<213> ORGANISM: Homo sapiens

<400> SEQUENCE: 36

```
Met Ala Lys Ser Ala Glu Val Lys Leu Ala Ile Phe Gly Arg Ala Gly
1               5                   10                  15

Val Gly Lys Ser Ala Leu Val Val Arg Phe Leu Thr Lys Arg Phe Ile
            20                  25                  30

Trp Glu Tyr Asp Pro Thr Leu Glu Ser Thr Tyr Arg His Gln Ala Thr
        35                  40                  45

Ile Asp Asp Glu Val Val Ser Met Glu Ile Leu Asp Thr Ala Gly Gln
    50                  55                  60

Glu Asp Thr Ile Gln Arg Glu Gly His Met Arg Trp Gly Glu Gly Phe
65                  70                  75                  80

Val Leu Val Tyr Asp Ile Thr Asp Arg Gly Ser Phe Glu Glu Val Leu
                85                  90                  95

Pro Leu Lys Asn Ile Leu Asp Glu Ile Lys Lys Pro Lys Asn Val Thr
            100                 105                 110

Leu Ile Leu Val Gly Asn Lys Ala Asp Leu Asp His Ser Arg Gln Val
        115                 120                 125

Ser Thr Glu Glu Gly Glu Lys Leu Ala Thr Glu Leu Ala Cys Ala Phe
    130                 135                 140

Tyr Glu Cys Ser Ala Cys Thr Gly Glu Gly Asn Ile Thr Glu Ile Phe
145                 150                 155                 160

Tyr Glu Leu Cys Arg Glu Val Arg Arg Arg Arg Met Val Gln Gly Lys
                165                 170                 175

Thr Arg Arg Arg Ser Ser Thr Thr His Val Lys Gln Ala Ile Asn Lys
            180                 185                 190

Met Leu Thr Lys Ile Ser Ser
        195
```

<210> SEQ ID NO 37
<211> LENGTH: 5617

<212> TYPE: DNA
<213> ORGANISM: Homo sapiens

<400> SEQUENCE: 37
agtcccgcga ccgaagcagg gcgcgcagca gcgctgagtg ccccggaacg tgcgtcgcgc 60
ccccagtgtc cgtcgcgtcc gccgcgcccc gggcggggat ggggcggcca gactgagcgc 120
cgcacccgcc atccagaccc gccggcccta gccgcagtcc ctccagccgt ggccccagcg 180
cgcacgggcg atggcgaagg cgacgtccgg tgccgcgggg ctgcgtctgc tgttgctgct 240
gctgctgccg ctgctaggca aagtggcatt gggcctctac ttctcgaggg atgcttactg 300
ggagaagctg tatgtggacc aggcagccgg cacgcccttg ctgtacgtcc atgccctgcg 360
ggacgcccct gaggaggtgc ccagcttccg cctgggccag catctctacg gcacgtaccg 420
cacacggctg catgagaaca actggatctg catccaggag gacaccggcc tcctctacct 480
taaccggagc ctggaccata gctcctggga gaagctcagt gtccgcaacc gcggctttcc 540
cctgctcacc gtctacctca aggtcttcct gtcacccaca tcccttcgtg agggcgagtg 600
ccagtggcca ggctgtgccc gcgtatactt ctccttcttc aacacctcct ttccagcctg 660
cagctccctc aagccccggg agctctgctt cccagagaca aggccctcct tccgcattcg 720
ggagaaccga cccccaggca ccttccacca gttccgcctg ctgcctgtgc agttcttgtg 780
ccccaacatc agcgtggcct acaggctcct ggagggtgag ggtctgccct tccgctgcgc 840
cccggacagc ctggaggtga gcacgcgctg ggccctggac cgcgagcagc gggagaagta 900
cgagctggtg gccgtgtgca ccgtgcacgc cggcgcgcgc gaggaggtgg tgatggtgcc 960
cttcccggtg accgtgtacg acgaggacga ctcggcgccc accttccccg cgggcgtcga 1020
caccgccagc gccgtggtgg agttcaagcg gaaggaggac accgtggtgg ccacgctgcg 1080
tgtcttcgat gcagacgtgg tacctgcatc aggggagctg gtgaggcggt acacaagcac 1140
gctgctcccc ggggacacct gggcccagca gaccttccgg gtggaacact ggcccaacga 1200
gacctcggtc caggccaacg gcagcttcgt gcgggcgacc gtacatgact ataggctggt 1260
tctcaaccgg aacctctcca tctcggagaa ccgcaccatg cagctggcgg tgctggtcaa 1320
tgactcagac ttccagggcc caggagcggg cgtcctcttg ctccacttca acgtgtcggt 1380
gctgccggtc agcctgcacc tgcccagtac ctactccctc tccgtgagca ggagggctcg 1440
ccgatttgcc cagatcggga aagtctgtgt ggaaaactgc caggcattca gtggcatcaa 1500
cgtccagtac aagctgcatt cctctggtgc caactgcagc acgctagggg tggtcacctc 1560
agccgaggac acctcgggga tcctgtttgt gaatgacacc aaggccctgc ggcggcccaa 1620
gtgtgccgaa cttcactaca tggtggtggc caccgaccag cagacctcta ggcaggccca 1680
ggcccagctg cttgtaacag tggaggggtc atatgtggcc gaggaggcgg gctgccccct 1740
gtcctgtgca gtcagcaaga gacggctgga gtgtgaggag tgtggcggcc tgggctcccc 1800
aacaggcagg tgtgagtgga ggcaaggaga tggcaaaggg atcaccagga acttctccac 1860
ctgctctccc agcaccaaga cctgccccga cggccactgc gatgttgtgg agacccaaga 1920
catcaacatt tgccctcagg actgcctccg gggcagcatt gttgggggac acgagcctgg 1980
ggagccccgg gggattaaag ctggctatgg cacctgcaac tgcttccctg aggaggagaa 2040
gtgcttctgc gagcccgaag acatccagga tccactgtgc gacgagctgt gccgcacggt 2100
gatcgcagcc gctgtcctct tctccttcat cgtctcggtg ctgctgtctg ccttctgcat 2160
ccactgctac cacaagtttg cccacaagcc acccatctcc tcagctgaga tgaccttccg 2220
gaggcccgcc caggccttcc cggtcagcta ctcctcttcc ggtgcccgcc ggccctcgct 2280
ggactccatg gagaaccagg tctccgtgga tgccttcaag atcctggagg atccaaagtg 2340
ggaattccct cggaagaact tggttcttgg aaaaactcta ggagaaggcg aatttggaaa 2400
agtggtcaag gcaacggcct tccatctgaa aggcagagca gggtacacca cggtggccgt 2460
gaagatgctg aaagagaacg cctccccgag tgagctgcga gacctgctgt cagagttcaa 2520
cgtcctgaag caggtcaacc acccacatgt catcaaattg tatggggcct gcagccagga 2580
tggcccgctc ctcctcatcg tggagtacgc caaatacggc tccctgcggg gcttcctccg 2640
cgagagccgc aaagtggggc ctggctacct gggcagtgga ggcagccgca actccagctc 2700
cctggaccac ccggatgagc gggccctcac catgggcgac ctcatctcat ttgcctggca 2760
gatctcacag gggatgcagt atctggccga gatgaagctc gttcatcggg acttggcagc 2820
cagaaacatc ctggtagctg aggggcggaa gatgaagatt tcggatttcg gcttgtcccg 2880
agatgtttat gaagaggatt cctacgtgaa gaggagccag ggtcggattc cagttaaatg 2940
gatggcaatt gaatcccttt ttgatcatat ctacaccacg caaagtgatg tatggtcttt 3000
tggtgtcctg ctgtgggaga tcgtgaccct agggggaaac ccctatcctg ggattcctcc 3060
tgagcggctc ttcaaccttc tgaagaccgg ccaccggatg gagaggccag acaactgcag 3120
cgaggagatg taccgcctga tgctgcaatg ctggaagcag gagccggaca aaaggccggt 3180
gtttgcggac atcagcaaag acctggagaa gatgatggtt aagaggagag actacttgga 3240
ccttgcggcg tccactccat ctgactccct gatttatgac gacggcctct cagaggagga 3300
gacaccgctg gtggactgta ataatgcccc cctccctcga gccctccctt ccacatggat 3360
tgaaaacaaa ctctatggca tgtcagaccc gaactggcct ggagagagtc ctgtaccact 3420
cacgagagct gatggcacta acactgggtt tccaagatat ccaaatgata gtgtatatgc 3480
taactggatg ctttcaccct cagcggcaaa attaatggac acgtttgata gttaacattt 3540
ctttgtgaaa ggtaatggac tcacaagggg aagaaacatg ctgagaatgg aaagtctacc 3600
ggccctttct ttgtgaacgt cacattggcc gagccgtgtt cagttcccag gtggcagact 3660
cgtttttggt agtttgtttt aacttccaag gtggttttac ttctgatagc cggtgatttt 3720
ccctcctagc agacatgcca caccgggtaa gagctctgag tcttagtggt taagcattcc 3780
tttctcttca gtgcccagca gcacccagtg ttggtctgtg tccatcagtg accaccaaca 3840
ttctgtgttc acatgtgtgg gtccaacact tactacctgg tgtatgaaat tggacctgaa 3900
ctgttggatt tttctagttg ccgccaaaca aggcaaaaaa atttaaacat gaagcacaca 3960
cacaaaaaag gcagtaggaa aaatgctggc cctgatgacc tgtccttatt cagaatgaga 4020
gactgcgggg ggggcctggg ggtagtgtca atgcccctcc agggctggag ggggaagaggg 4080
gccccgagga tgggcctggg ctcagcattc gagatcttga gaatgatttt ttttaaatca 4140
tgcaaccttt ccttaggaag acatttggtt ttcatcatga ttaagatgat tcctagattt 4200
agcacaatgg agagattcca tgccatcttt actatgtgga tggtggtatc agggaagagg 4260
gctcacaaga cacatttgtc ccccgggccc accacatcat cctcacgtgt tcggtactga 4320
gcagccacta cccctgatga gaacagtatg aagaaagggg gctgttggag tcccagaatt 4380
gctgacagca gaggctttgc tgctgtgaat cccacctgcc accagcctgc agcacacccc 4440
acagccaagt agaggcgaaa gcagtggctc atcctacctg ttaggagcag gtagggcttg 4500
tactcacttt aatttgaatc ttatcaactt actcataaag ggacaggcta gctagctgtg 4560
ttagaagtag caatgacaat gaccaaggac tgctacacct ctgattacaa ttctgatgtg 4620

```
aaaaagatgg tgtttggctc ttatagagcc tgtgtgaaag gcccatggat cagctcttcc   4680

tgtgtttgta atttaatgct gctacaagat gtttctgttt cttagattct gaccatgact   4740

cataagcttc ttgtcattct tcattgcttg tttgtggtca cagatgcaca acactcctcc   4800

agtcttgtgg gggcagcttt tgggaagtct cagcagctct tctggctgtg ttgtcagcac   4860

tgtaacttcg cagaaaagag tcggattacc aaaacactgc ctgctcttca gacttaaagc   4920

actgatagga cttaaaatag tctcattcaa atactgtatt ttatataggc atttcacaaa   4980

aacagcaaaa ttgtggcatt ttgtgaggcc aaggcttgga tgcgtgtgta atagagcctt   5040

gtggtgtgtg cgcacacacc cagagggaga gtttgaaaaa tgcttattgg acacgtaacc   5100

tggctctaat ttgggctgtt tttcagatac actgtgataa gttcttttac aaatatctat   5160

agacatggta aacttttggt tttcagatat gcttaatgat agtcttacta aatgcagaaa   5220

taagaataaa ctttctcaaa ttattaaaaa tgcctacaca gtaagtgtga attgctgcaa   5280

caggtttgtt ctcaggaggg taagaactcc aggtctaaac agctgaccca gtgatgggga   5340

atttatcctt gaccaattta tccttgacca ataacctaat tgtctattcc tgagttataa   5400

aagtccccat ccttattagc tctactggaa ttttcataca cgtaaatgca gaagttacta   5460

agtattaagt attactgagt attaagtagt aatctgtcag ttattaaaat ttgtaaaatc   5520

tatttatgaa aggtcattaa accagatcat gttccttttt ttgtaatcaa ggtgactaag   5580

aaaatcagtt gtgtaaataa aatcatgtat cataaaa                            5617
```

<210> SEQ ID NO 38
<211> LENGTH: 1114
<212> TYPE: PRT
<213> ORGANISM: Homo sapiens

<400> SEQUENCE: 38

```
Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
            20                  25                  30

Arg Asp Ala Tyr Trp Glu Lys Leu Tyr Val Asp Gln Ala Ala Gly Thr
        35                  40                  45

Pro Leu Leu Tyr Val His Ala Leu Arg Asp Ala Pro Glu Glu Val Pro
    50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190
```

-continued

```
Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
            260                 265                 270

Pro Ala Gly Val Asp Thr Ala Ser Ala Val Val Glu Phe Lys Arg Lys
        275                 280                 285

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
        355                 360                 365

Thr Met Gln Leu Ala Val Leu Val Asn Asp Ser Asp Phe Gln Gly Pro
    370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
        435                 440                 445

Cys Ser Thr Leu Gly Val Val Thr Ser Ala Glu Asp Thr Ser Gly Ile
    450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
            500                 505                 510

Ala Gly Cys Pro Leu Ser Cys Ala Val Ser Lys Arg Arg Leu Glu Cys
        515                 520                 525

Glu Glu Cys Gly Gly Leu Gly Ser Pro Thr Gly Arg Cys Glu Trp Arg
    530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
            580                 585                 590

Gly His Glu Pro Gly Glu Pro Arg Gly Ile Lys Ala Gly Tyr Gly Thr
        595                 600                 605

Cys Asn Cys Phe Pro Glu Glu Glu Lys Cys Phe Cys Glu Pro Glu Asp
```

```
    610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Leu Ser Ala Phe Cys
                645                 650                 655

Ile His Cys Tyr His Lys Phe Ala His Lys Pro Pro Ile Ser Ser Ala
            660                 665                 670

Glu Met Thr Phe Arg Arg Pro Ala Gln Ala Phe Pro Val Ser Tyr Ser
        675                 680                 685

Ser Ser Gly Ala Arg Arg Pro Ser Leu Asp Ser Met Glu Asn Gln Val
    690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735

Lys Val Val Lys Ala Thr Ala Phe His Leu Lys Gly Arg Ala Gly Tyr
            740                 745                 750

Thr Thr Val Ala Val Lys Met Leu Lys Glu Asn Ala Ser Pro Ser Glu
        755                 760                 765

Leu Arg Asp Leu Leu Ser Glu Phe Asn Val Leu Lys Gln Val Asn His
    770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
                805                 810                 815

Arg Glu Ser Arg Lys Val Gly Pro Gly Tyr Leu Gly Ser Gly Gly Ser
            820                 825                 830

Arg Asn Ser Ser Ser Leu Asp His Pro Asp Glu Arg Ala Leu Thr Met
        835                 840                 845

Gly Asp Leu Ile Ser Phe Ala Trp Gln Ile Ser Gln Gly Met Gln Tyr
    850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
            900                 905                 910

Ile Pro Val Lys Trp Met Ala Ile Glu Ser Leu Phe Asp His Ile Tyr
        915                 920                 925

Thr Thr Gln Ser Asp Val Trp Ser Phe Gly Val Leu Leu Trp Glu Ile
    930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990

Asp Lys Arg Pro Val Phe Ala Asp  Ile Ser Lys Asp Leu  Glu Lys Met
        995                 1000                1005

Met Val  Lys Arg Arg Asp Tyr  Leu Asp Leu Ala Ala  Ser Thr Pro
    1010                1015                1020

Ser Asp  Ser Leu Ile Tyr Asp  Asp Gly Leu Ser Glu  Glu Glu Thr
    1025                1030                1035
```

```
Pro Leu Val Asp Cys Asn Asn Ala Pro Leu Pro Arg Ala Leu Pro
    1040                1045                1050

Ser Thr Trp Ile Glu Asn Lys Leu Tyr Gly Met Ser Asp Pro Asn
    1055                1060                1065

Trp Pro Gly Glu Ser Pro Val Pro Leu Thr Arg Ala Asp Gly Thr
    1070                1075                1080

Asn Thr Gly Phe Pro Arg Tyr Pro Asn Asp Ser Val Tyr Ala Asn
    1085                1090                1095

Trp Met Leu Ser Pro Ser Ala Ala Lys Leu Met Asp Thr Phe Asp
    1100                1105                1110

Ser


<210> SEQ ID NO 39
<211> LENGTH: 4483
<212> TYPE: DNA
<213> ORGANISM: Homo sapiens

<400> SEQUENCE: 39

actgcgggcg gagcagaggg aaacaccaga gtctgtgact ccagacagga cccactgtgt     60

cctcttgaac tttgcacagc gcgtgacggg ggcagacggt gcaccgtggc ccggcctttc    120

gcgggggtcc tcggggaaga gagaggagcg cgggtttcct cggaggcctg agcgggacgc    180

agcctgcagc ccctccccgc acgggctgcc cccggcccgc cgctcgcgcc gctctgctgg    240

gatccggcgc cttccccggc tgtcctcggc ctcccgcgcg ctccgcggga ggagccgcca    300

gcggccgtga cgcgtcaagg aggaaacgcc ggcgcccggc ggccctgccg ggaaggagga    360

agcgcagtgc gttcggctcc gcgcccgccg cgccgggagc agcaccgcgg ggccaggttg    420

catgatggaa tttgaacatt acttcaagag gttttgtatt ttggattagt taattgggtt    480

tgtcctctgc tgactgtttc ttcggatgca ttttttggtg tgctcttgag ggattaaatg    540

caaagagatc acaccatgga ctacaaggaa agctgcccaa gtgtaagcat tcccagctcc    600

gatgaacaca gagagaaaaa gaagaggttt actgtttata aagttctggt ttcagtggga    660

agaagtgaat ggtttgtctt caggagatat gcagagtttg ataaacttta taacacttta    720

aaaaaacagt ttcctgctat ggccctgaag attcctgcca agagaatatt tggtgataat    780

tttgatccag attttattaa acaaagacga gcaggactaa acgaattcat tcagaaccta    840

gttaggtatc cagaacttta taaccatcca gatgtcagag cattccttca aatggacagt    900

ccaaaacacc agtcagatcc atctgaagat gaggatgaaa gaagttctca gaagctacac    960

tctacctcac agaacatcaa cctgggaccg tctggaaatc ctcatgccaa accaactgac   1020

tttgatttct taaaagttat tggaaaaggc agctttggca aggttcttct tgcaaaacgg   1080

aaactggatg gaaaatttta tgctgtcaaa gtgttacaga aaaaaatagt tctcaacaga   1140

aaagagcaaa aacatattat ggctgaacgt aatgtgctct tgaaaaatgt gaaacatccg   1200

tttttggttg gattgcatta ttccttccaa acaactgaaa agctttattt tgttctggat   1260

tttgttaatg gaggggagct ttttttccac ttacaaagag aacggtcctt tcctgagcac   1320

agagctaggt tttacgctgc tgaaattgct agtgcattgg gttacttaca ttccatcaaa   1380

atagtataca gagacttgaa accagaaaat attcttttgg attcagtagg acatgttgtc   1440

ttaacagatt ttgggctttg taaagaagga attgctattt ctgacaccac taccacattt   1500

tgtgggacac cagagtatct tgcacctgaa gtaattagaa aacagcccta tgacaatact   1560

gtagattggt ggtgccttgg ggctgttctg tatgaaatgc tgtatggatt gcctcctttt   1620
```

```
tattgccgag atgttgctga aatgtatgac aatatccttc acaaacccct aagtttgagg   1680
ccaggagtga gtcttacagc ctggtccatt ctggaagaac tcctagaaaa agacaggcaa   1740
aatcgacttg gtgccaagga agactttctt gaaattcaga atcatccttt ttttgaatca   1800
ctcagctggg ctgaccttgt acaaaagaag attccaccac catttaatcc taatgtggct   1860
ggaccagatg atatcagaaa ctttgacaca gcatttacag aagaaacagt tccatattct   1920
gtgtgtgtat cttctgacta ttctatagtg aatgccagtg tattggaggc agatgatgca   1980
ttcgttggtt tctcttatgc acctccttca gaagacttat ttttgtgagc agtttgccat   2040
tcagaaacca ttgagcaaaa taagtctata gatgggactg aaacttctat ttgtgtgaat   2100
atattcaaat atgtataact agtgcctcat ttttatatgt aatgatgaaa actatgaaaa   2160
aatgtatttt cttctatgtg caagaaaaat agggcatttc aaagagctgt tttgattaaa   2220
atttatattc ttgtttaata agcttatttt taaacaattt aaaagctatt attcttagca   2280
ttaacctatt tttaaagaaa ccttttttgc tattgactgt tttttccctc taagtttaca   2340
ctaacatcta cccaagatag actgtttttt aacagtcaat ttcagttcag ctaacatata   2400
ttaatacctt tgtaactctt tgctatggct tttgttatca caccaaaact atgcaattgg   2460
tacatggttg tttaagaaga aaccgtattt ttccatgata aatcactgtt tgaaatattt   2520
ggttcatggt atgatcgaaa tgtaaaagca taattaacac attggctgct agttaacaat   2580
tggaataact ttattctgca gatcatttaa gaagtaacag gccgggcgcg gtggctcacg   2640
cctgtaatcc cagcactttg ggaggctgag gcgggcagat cacctgaggt caggagttgg   2700
agaccagcct gaccaacatg gacaaacccc gtctctacta aaaatacaaa attggcaggg   2760
tgtggtggca catgcctata atcccagcta cttgggaggc taaggcagga gaatcgcttg   2820
aacccgggag gcggaggttg cagtgagccg agatcgcacc attgcactcc tgcctgggca   2880
acaagagtga aactccatct ccaaaaaaaa aaagaaaaag taacaaaagg aaattatttg   2940
tttttgaaat accagttcaa ctttgtggat tatttttcct ctgaaggaaa agaaaaggct   3000
taatggttag gatttttaag tattcccaaa gatctgaagg gtaataaaat gtactggatt   3060
ttttaaggtg gtaccaaaaa tgaatgtctg tcatatattt atattacaaa tacattatat   3120
ttatgttcta ttcatctttt gaatgtttag tatgctatta agtcattctg aatctttgta   3180
tttgcttttg caaataggta tttcaaagct cttttcctaa ctggttaagt aaaataaaaa   3240
attgagcttt ctagaatatt tgcctaattg ggaattaaaa agtaaaataa taggccaggc   3300
atggtggctc atgcctataa gcaccctggg aggccgaggc aggcagatta tttgagctca   3360
ggagtttgag accatcctgg gcaacatggc gaaaccctat ctctacaaaa aatacaaaaa   3420
ttagccagac atggtggcac atgcctttag tcccagctac tctggaggct gaagttggag   3480
gatggcttga gcccacgaga tggaagttgc agtgaactga aattgtgcca ctgcactttt   3540
cagcctgggt gccacagcga gaccctagtt aagagaaaaa aaaagtaaaa acaaattgtg   3600
ggtcaaagta aatgtataca gttttattac aatgtaacaa aagttgaaaa tcaggcagat   3660
gtgtattcag tatccaattc aatatatctt agaaaaagca caggaaacag accttaaaat   3720
tgtaacctac caactaactt acatgcttat aaaagtaaag gagaataact ggccgggcac   3780
ggtggctcat gcctataaaa ttccagcact ttgggaggcc aaggcaggag gatcacttga   3840
gcctatgagt tcaagaccag cctaggcaat gtagtgacac ctcatttcta tttattttaa   3900
aaaaaagaga gagtaactac agaagaactt taaaaaataa aaaataagct taccttggat   3960
```

```
tcttggctta gagtagaggt ttttttaag ttatggagga aacatttttg taaaagttta   4020

atgacccact ttagatgctc caagaacaag catcccttcc atgtatgtct tgagaaagaa   4080

atcacagaag catttctcac caatactctt tggcttaaaa tgttcagcag aattgggcag   4140

tgggggtgac ttttcttata ttaataatat ttacatccaa tacactgaat cttcctttag   4200

aggtaagact ttaatatcta tactgtaaat atttggttta tttggcacta ctgtaagttt   4260

tgtttttcac aaagctctta ttatgaagca aaataaaaat tctagtttct tgtatgattt   4320

tttgtactca ttcattcctg ttaagctgcc aaaaattaaa gtgcaatatt gtatattttt   4380

aagaacaaat ttaaaataga attttgatgt ttctcagatc acaagaaata caaatctata   4440

tagtataata aaatcagcaa aaagatcaaa aaaaaaaaaa aaa                     4483


<210> SEQ ID NO 40
<211> LENGTH: 496
<212> TYPE: PRT
<213> ORGANISM: Homo sapiens

<400> SEQUENCE: 40

Met Gln Arg Asp His Thr Met Asp Tyr Lys Glu Ser Cys Pro Ser Val
1               5                   10                  15

Ser Ile Pro Ser Ser Asp Glu His Arg Glu Lys Lys Lys Arg Phe Thr
            20                  25                  30

Val Tyr Lys Val Leu Val Ser Val Gly Arg Ser Glu Trp Phe Val Phe
        35                  40                  45

Arg Arg Tyr Ala Glu Phe Asp Lys Leu Tyr Asn Thr Leu Lys Lys Gln
    50                  55                  60

Phe Pro Ala Met Ala Leu Lys Ile Pro Ala Lys Arg Ile Phe Gly Asp
65                  70                  75                  80

Asn Phe Asp Pro Asp Phe Ile Lys Gln Arg Arg Ala Gly Leu Asn Glu
                85                  90                  95

Phe Ile Gln Asn Leu Val Arg Tyr Pro Glu Leu Tyr Asn His Pro Asp
            100                 105                 110

Val Arg Ala Phe Leu Gln Met Asp Ser Pro Lys His Gln Ser Asp Pro
        115                 120                 125

Ser Glu Asp Glu Asp Glu Arg Ser Ser Gln Lys Leu His Ser Thr Ser
    130                 135                 140

Gln Asn Ile Asn Leu Gly Pro Ser Gly Asn Pro His Ala Lys Pro Thr
145                 150                 155                 160

Asp Phe Asp Phe Leu Lys Val Ile Gly Lys Gly Ser Phe Gly Lys Val
                165                 170                 175

Leu Leu Ala Lys Arg Lys Leu Asp Gly Lys Phe Tyr Ala Val Lys Val
            180                 185                 190

Leu Gln Lys Lys Ile Val Leu Asn Arg Lys Glu Gln Lys His Ile Met
        195                 200                 205

Ala Glu Arg Asn Val Leu Leu Lys Asn Val Lys His Pro Phe Leu Val
    210                 215                 220

Gly Leu His Tyr Ser Phe Gln Thr Thr Glu Lys Leu Tyr Phe Val Leu
225                 230                 235                 240

Asp Phe Val Asn Gly Gly Glu Leu Phe Phe His Leu Gln Arg Glu Arg
                245                 250                 255

Ser Phe Pro Glu His Arg Ala Arg Phe Tyr Ala Ala Glu Ile Ala Ser
            260                 265                 270

Ala Leu Gly Tyr Leu His Ser Ile Lys Ile Val Tyr Arg Asp Leu Lys
        275                 280                 285
```

Pro Glu Asn Ile Leu Leu Asp Ser Val Gly His Val Val Leu Thr Asp
    290                 295                 300

Phe Gly Leu Cys Lys Glu Gly Ile Ala Ile Ser Asp Thr Thr Thr Thr
305                 310                 315                 320

Phe Cys Gly Thr Pro Glu Tyr Leu Ala Pro Glu Val Ile Arg Lys Gln
                325                 330                 335

Pro Tyr Asp Asn Thr Val Asp Trp Trp Cys Leu Gly Ala Val Leu Tyr
            340                 345                 350

Glu Met Leu Tyr Gly Leu Pro Pro Phe Tyr Cys Arg Asp Val Ala Glu
        355                 360                 365

Met Tyr Asp Asn Ile Leu His Lys Pro Leu Ser Leu Arg Pro Gly Val
    370                 375                 380

Ser Leu Thr Ala Trp Ser Ile Leu Glu Glu Leu Leu Glu Lys Asp Arg
385                 390                 395                 400

Gln Asn Arg Leu Gly Ala Lys Glu Asp Phe Leu Glu Ile Gln Asn His
                405                 410                 415

Pro Phe Phe Glu Ser Leu Ser Trp Ala Asp Leu Val Gln Lys Lys Ile
            420                 425                 430

Pro Pro Pro Phe Asn Pro Asn Val Ala Gly Pro Asp Asp Ile Arg Asn
        435                 440                 445

Phe Asp Thr Ala Phe Thr Glu Glu Thr Val Pro Tyr Ser Val Cys Val
    450                 455                 460

Ser Ser Asp Tyr Ser Ile Val Asn Ala Ser Val Leu Glu Ala Asp Asp
465                 470                 475                 480

Ala Phe Val Gly Phe Ser Tyr Ala Pro Pro Ser Glu Asp Leu Phe Leu
                485                 490                 495

<210> SEQ ID NO 41
<211> LENGTH: 2032
<212> TYPE: DNA
<213> ORGANISM: Homo sapiens

<400> SEQUENCE: 41
ggactctggg acgctcagac gccgcgcggg gcggggattg gtctgtggtc ctctctcggc 60
tcctcgcggc tcgcggcggc cgacggttcc tgggacacct gcttgcttgg cccgtccggc 120
ggctcagggc ttctctgctg cgctcccggt tcgctggacg ggaagaaggg ctgggccgtc 180
ccgtcccgtc cccatcggaa ccccaagtcg cgccgctgac ccgtcgcagg gcgagatgag 240
cgcggacgca gcggccgggg cgcccctgcc ccggctctgc tgcctggaga agggtccgaa 300
cggctacggc ttccacctgc acggggagaa gggcaagttg ggccagtaca tccggctggt 360
ggagcccggc tcgccggccg agaaggcggg gctgctggcg ggggaccggc tggtggaggt 420
gaacggcgaa aacgtggaga aggagaccca ccagcaggtg gtgagccgca tccgcgccgc 480
actcaacgcc gtgcgcctgc tggtggtcga ccccgagacg gacgagcagc tgcagaagct 540
cggcgtccag gtccgagagg agctgctgcg cgcccaggaa gcgccggggc aggccgagcc 600
gccggccgcc gccgaggtgc agggggctgg caacgaaaat gagcctcgcg aggccgacaa 660
gagccacccg gagcagcgcg agcttcggcc tcggctctgt accatgaaga agggccccag 720
tggctatggc ttcaacctgc acagcgacaa gtccaagcca ggccagttca tccggtcagt 780
ggacccagac tccccggctg aggcttcagg gctccgggcc caggatcgca ttgtggaggt 840
gaacggggtc tgcatggagg ggaagcagca tggggacgtg gtgtccgcca tcagggctgg 900
cggggacgag accaagctgc tggtggtgga cagggaaact gacgagttct tcaagaaatg 960

```
cagagtgatc ccatctcagg agcacctgaa tggtcccctg cctgtgccct tcaccaatgg   1020

ggagatacag aaggagaaca gtcgtgaagc cctggcagag gcagccttgg agagccccag   1080

gccagccctg gtgagatccg cctccagtga caccagcgag gagctgaatt cccaagacag   1140

ccccccaaaa caggactcca cagcgccctc gtctacctcc tcctccgacc ccatcctaga   1200

cttcaacatc tccctggcca tggccaaaga gagggcccac cagaaacgca gcagcaaacg   1260

ggccccgcag atggactgga gcaagaaaaa cgaactcttc agcaacctct gagcgccctg   1320

ctgccaccca gtgactggca gggccgagcc agcattccac cccacctttt tccttctccc   1380

caattactcc cctgaatcaa tgtacaaatc agcacccaca tcccctttct tgacaaatga   1440

tttttctaga gaactatgtt cttccctgac tttagggaag gtgaatgtgt tcccgtcctc   1500

ccgcagtcag aaaggagact ctgcctccct cctcctcact gagtgcctca tcctaccggg   1560

tgtccctttg ccaccctgcc tgggacatcg ctggaacctg caccatgcca ggatcatggg   1620

accaggcgag agggcaccct cccttcctcc cccatgtgat aaatgggtcc agggctgatc   1680

aaagaactct gactgcagaa ctgccgctct cagtggacag ggcatctgtt accctgagac   1740

ctgtggcaga cacgtcttgt tttcatttga tttttgttaa gagtgcagta ttgcagagtc   1800

tagaggaatt tttgtttcct tgattaacat gattttcctg gttgttacat ccagggcatg   1860

gcagtggcct cagccttaaa cttttgttcc tactcccacc ctcagcgaac tgggcagcac   1920

ggggagggtt tggctacccc tgcccatccc tgagccaggt accaccattg taaggaaaca   1980

ctttcagaaa ttcagctggt tcctccaaac ccttcaaaaa aaaaaaaaaa aa           2032
```

<210> SEQ ID NO 42
<211> LENGTH: 358
<212> TYPE: PRT
<213> ORGANISM: Homo sapiens

<400> SEQUENCE: 42

```
Met Ser Ala Asp Ala Ala Ala Gly Ala Pro Leu Pro Arg Leu Cys Cys
1               5                   10                  15

Leu Glu Lys Gly Pro Asn Gly Tyr Gly Phe His Leu His Gly Glu Lys
            20                  25                  30

Gly Lys Leu Gly Gln Tyr Ile Arg Leu Val Glu Pro Gly Ser Pro Ala
        35                  40                  45

Glu Lys Ala Gly Leu Leu Ala Gly Asp Arg Leu Val Glu Val Asn Gly
    50                  55                  60

Glu Asn Val Glu Lys Glu Thr His Gln Gln Val Val Ser Arg Ile Arg
65                  70                  75                  80

Ala Ala Leu Asn Ala Val Arg Leu Leu Val Val Asp Pro Glu Thr Asp
                85                  90                  95

Glu Gln Leu Gln Lys Leu Gly Val Gln Val Arg Glu Glu Leu Leu Arg
            100                 105                 110

Ala Gln Glu Ala Pro Gly Gln Ala Glu Pro Pro Ala Ala Ala Glu Val
        115                 120                 125

Gln Gly Ala Gly Asn Glu Asn Glu Pro Arg Glu Ala Asp Lys Ser His
    130                 135                 140

Pro Glu Gln Arg Glu Leu Arg Pro Arg Leu Cys Thr Met Lys Lys Gly
145                 150                 155                 160

Pro Ser Gly Tyr Gly Phe Asn Leu His Ser Asp Lys Ser Lys Pro Gly
                165                 170                 175

Gln Phe Ile Arg Ser Val Asp Pro Asp Ser Pro Ala Glu Ala Ser Gly
```

```
            180                 185                 190

Leu Arg Ala Gln Asp Arg Ile Val Glu Val Asn Gly Val Cys Met Glu
        195                 200                 205

Gly Lys Gln His Gly Asp Val Val Ser Ala Ile Arg Ala Gly Gly Asp
    210                 215                 220

Glu Thr Lys Leu Leu Val Val Asp Arg Glu Thr Asp Glu Phe Phe Lys
225                 230                 235                 240

Lys Cys Arg Val Ile Pro Ser Gln Glu His Leu Asn Gly Pro Leu Pro
                245                 250                 255

Val Pro Phe Thr Asn Gly Glu Ile Gln Lys Glu Asn Ser Arg Glu Ala
            260                 265                 270

Leu Ala Glu Ala Ala Leu Glu Ser Pro Arg Pro Ala Leu Val Arg Ser
        275                 280                 285

Ala Ser Ser Asp Thr Ser Glu Glu Leu Asn Ser Gln Asp Ser Pro Pro
    290                 295                 300

Lys Gln Asp Ser Thr Ala Pro Ser Ser Thr Ser Ser Ser Asp Pro Ile
305                 310                 315                 320

Leu Asp Phe Asn Ile Ser Leu Ala Met Ala Lys Glu Arg Ala His Gln
                325                 330                 335

Lys Arg Ser Ser Lys Arg Ala Pro Gln Met Asp Trp Ser Lys Lys Asn
            340                 345                 350

Glu Leu Phe Ser Asn Leu
        355


<210> SEQ ID NO 43
<211> LENGTH: 492
<212> TYPE: DNA
<213> ORGANISM: Homo sapiens

<400> SEQUENCE: 43

atccctgact cggggtcgcc tttggagcag agaggaggca atggccacca tggagaacaa     60

ggtgatctgc gccctggtcc tggtgtccat gctggccctc ggcaccctgg ccgaggccca    120

gacagagacg tgtacagtgg ccccccgtga aagacagaat tgtggttttc ctggtgtcac    180

gccctcccag tgtgcaaata agggctgctg tttcgacgac accgttcgtg gggtcccctg    240

gtgcttctat cctaatacca tcgacgtccc tccagaagag gagtgtgaat tttagacact    300

tctgcaggga tctgcctgca tcctgacgcg gtgccgtccc cagcacggtg attagtccca    360

gagctcggct gccacctcca ccggacacct cagacacgct tctgcagctg tgcctcggct    420

cacaacacag attgactgct ctgactttga ctactcaaaa ttggcctaaa aattaaaaga    480

gatcgatatt aa                                                        492


<210> SEQ ID NO 44
<211> LENGTH: 84
<212> TYPE: PRT
<213> ORGANISM: Homo sapiens

<400> SEQUENCE: 44

Met Ala Thr Met Glu Asn Lys Val Ile Cys Ala Leu Val Leu Val Ser
1               5                   10                  15

Met Leu Ala Leu Gly Thr Leu Ala Glu Ala Gln Thr Glu Thr Cys Thr
            20                  25                  30

Val Ala Pro Arg Glu Arg Gln Asn Cys Gly Phe Pro Gly Val Thr Pro
        35                  40                  45

Ser Gln Cys Ala Asn Lys Gly Cys Cys Phe Asp Asp Thr Val Arg Gly
```

```
                50                  55                  60

Val Pro Trp Cys Phe Tyr Pro Asn Thr Ile Asp Val Pro Pro Glu Glu
65                  70                  75                  80

Glu Cys Glu Phe


<210> SEQ ID NO 45
<211> LENGTH: 3316
<212> TYPE: DNA
<213> ORGANISM: Homo sapiens

<400> SEQUENCE: 45

ggtttttgtg ttgctagccg gggccagcgg cggtggcggc ggcggcggag gcgtcggtgg     60

aggaggggag gcggcgagga ggcgcagctc ccgctgcacc gcgatcgacg ctgcggagcg    120

agcccacccg ccccgggagc tcgcctcccc ggtgctcccc cgccctcccc gcccccccag    180

cggcgctgcc tcctccaaat gagcgattcg cccgctggat ctaacccaag gacacccgaa    240

agcagcggca gcggcagcgg cggcggcggg aagaggccgg cggtgccggc agcggtgtcc    300

ctcttgccac cggcggaccc cctgcgccag gcgaaccggc tcccgatcag ggtcctgaag    360

atgctgagcg ctcacaccgg tcacctcctg cacccggagt acctgcagcc gctgtcctcc    420

actcccgtca gccccattga gctggacgcc aagaagagcc ccttggcgct gctggctcag    480

acctgctcgc agatcggcaa gccggacccg ccgccctcct ccaaactcaa ctcggtggcg    540

gcggcggcca acgggctggg agcggagaag gaccccggcc gctcagcccc gggcgccgcc    600

tccgcagccg cggccctgaa gcagctgggg gactcaccgg ccgaggacaa gtccagcttc    660

aagccctact ccaagggctc cggcggcggc gactcccgca aagacagcgg ctcctcctcg    720

gtgtcttcca cctcctcctc gtcctcctcg tccccgggag acaaggcggg cttcagggtc    780

cccagcgccg cctgcccgcc ctttcccccg catggagcgc cggtctccgc atcctcgtcc    840

tcgtcgtcgc ccggcggctc ccgcggcggc tccccgcacc actctgactg caagaacggc    900

ggcggggttg gcggcgggga gctggacaag aaagaccagg agcccaagcc cagcccggag    960

ccggcagccg tgagccgcgg cggcggtggg gagcccgggg cgcacggtgg cgccgagtcc   1020

ggggcctccg ggcgcaagtc cgagccgccc tcggcgctgg tgggggccgg ccacgtggcg   1080

ccggtgtctc cctacaagcc gggccactcg gtgttcccgc tgccgccctc cagcattggc   1140

taccacggct ccatcgtggg cgcctacgcc ggctacccgt ctcagttcgt gcctggcctg   1200

gatcctagca agtccggcct cgtgggaggc cagctgtctg gggcctgggg cctgccgccg   1260

ggcaagcccc ccagctccag cccgctcacc ggggcctccc cgccctcctt cctgcaggga   1320

ttatgccgcg accccctattg cttgggaggt taccacggcg cctcgcacct cggcggctcc   1380

agctgctcca cctgcagcgc gcacgaccct gccgggccca gcctgaaggc gggggggctac   1440

ccgctggtgt accccgggca cccgctgcag cccgccgcgc tctcgtccag cgccgcccag   1500

gccgcgctcc ccggccaccc gctctacacc tacggcttca tgctgcagaa cgaaccgctg   1560

ccgcacagct gcaactgggt ggcagccagt gggccgtgcg acaagcgctt cgccacctcg   1620

gaggagctgc tcagccacct acggacccac acggccctgc cgggagccga gaaacttctg   1680

gccgcctacc ccggggcctc gggcctgggc agcgccgccg ccgccgccgc cgccgccgcc   1740

tcctgccatc tgcacctccc cccgcccgcc gcccccggca gccccgggtc gctgtccttg   1800

cggaatccac acactttggg cctaagccgg taccacccct atggcaagag ccacttatcc   1860

acagcggggg gcctggccgt gccgtccctc cccacagccg gaccctacta ttcgccatac   1920
```

```
gcgctgtatg gacagagact agcttcagcc tcggcgctgg gataccagta actacagctc   1980

ttcctccacc ccagcccccct caccctcctc cctctccctc ctcctccctc cccacctgcc   2040

gtcgccgctg caacctccac tactgcttga ccctgccggg attccccacc cagcccttcc   2100

ccaccggact gtgtatttat ttactataat gttagcttac aagctgggaa tataagtgca   2160

ttaacggccc acatgagtca atggtatgca aaaagtctgt gttctcccaa ataataatat   2220

taatcccaca aataacgaca tgatccccgc ccctgttcct ttctgttatt ttttcttaga   2280

tataagtttt acatttttta ttccttttcc tcttttttttg gttttgattg gtttggtttg   2340

agggagagtt ggggtctttg ggttcttcta gacgttttgt tttcccttcc tggggagttt   2400

cttgcatgag tcttaactta aaactacgtt tccgccttct ctttttccct cttccccctt   2460

cattccctct tgtttccttc catttgcggt tctgtttttg ttttttgttt tgttttgttt   2520

tgttttttcc tttgttgtac aagtaacaga gaggaggttt tttttgtaac tcattttggg   2580

ggtggagggg gccacctggg tggcaggggc cctggagctc tattgacctg gtacactgct   2640

ccgggactcc tcccccgcca ccctccgcgc atagggtcct tggtctggac cctgcccccc   2700

aaaagtaggg ccttgctcct ctaccttgct ctgagcacgg agagccctga ccccaccagt   2760

aggctcgccc ccagaagggc ccaagtggcc gtctaccgtc accttccaga ctcccgcccc   2820

taacacccag tggctacagt gcgcctgtcg gggcacctgg agcgctcacc tggttgaatt   2880

caaagtccca gaaggccccg ctggcgtgaa gccggcccct tacattttgc gaagtgcatt   2940

atagtccttg tttttctctc cctcgtgggg gcaacgaccc ctcccctggc agtaggggtg   3000

gggtaggtga ctctcgctag atccctccaa agcagaccgg tggcgatgtc agcggatgtc   3060

acgagctcgt tagctgcgtt cggggaaggt tggggcgtca gggagctctc ggatcacagc   3120

agcccccgcc ctctcctagg cctggcccgg cagagccccc agagtggacc ccccagcgac   3180

tggggtcttc tccccactcc tccctccttc tggtctgatg cggcagcgcg ggggctgcgg   3240

ggcctgtttg ggacgaacag agctctccct tggtaagact tattttgtta ataaatggaa   3300

tacttggcta tattca                                                   3316
```

<210> SEQ ID NO 46
<211> LENGTH: 590
<212> TYPE: PRT
<213> ORGANISM: Homo sapiens

<400> SEQUENCE: 46

```
Met Ser Asp Ser Pro Ala Gly Ser Asn Pro Arg Thr Pro Glu Ser Ser
1               5                   10                  15

Gly Ser Gly Ser Gly Gly Gly Gly Lys Arg Pro Ala Val Pro Ala Ala
            20                  25                  30

Val Ser Leu Leu Pro Pro Ala Asp Pro Leu Arg Gln Ala Asn Arg Leu
        35                  40                  45

Pro Ile Arg Val Leu Lys Met Leu Ser Ala His Thr Gly His Leu Leu
    50                  55                  60

His Pro Glu Tyr Leu Gln Pro Leu Ser Ser Thr Pro Val Ser Pro Ile
65                  70                  75                  80

Glu Leu Asp Ala Lys Lys Ser Pro Leu Ala Leu Leu Ala Gln Thr Cys
                85                  90                  95

Ser Gln Ile Gly Lys Pro Asp Pro Pro Pro Ser Ser Lys Leu Asn Ser
            100                 105                 110

Val Ala Ala Ala Ala Asn Gly Leu Gly Ala Glu Lys Asp Pro Gly Arg
        115                 120                 125
```

```
Ser Ala Pro Gly Ala Ala Ser Ala Ala Ala Ala Leu Lys Gln Leu Gly
    130                 135                 140

Asp Ser Pro Ala Glu Asp Lys Ser Ser Phe Lys Pro Tyr Ser Lys Gly
145                 150                 155                 160

Ser Gly Gly Gly Asp Ser Arg Lys Asp Ser Gly Ser Ser Ser Val Ser
                165                 170                 175

Ser Thr Ser Ser Ser Ser Ser Ser Ser Pro Gly Asp Lys Ala Gly Phe
            180                 185                 190

Arg Val Pro Ser Ala Ala Cys Pro Pro Phe Pro Pro His Gly Ala Pro
        195                 200                 205

Val Ser Ala Ser Ser Ser Ser Ser Ser Pro Gly Gly Ser Arg Gly Gly
    210                 215                 220

Ser Pro His His Ser Asp Cys Lys Asn Gly Gly Gly Val Gly Gly Gly
225                 230                 235                 240

Glu Leu Asp Lys Lys Asp Gln Glu Pro Lys Pro Ser Pro Glu Pro Ala
                245                 250                 255

Ala Val Ser Arg Gly Gly Gly Gly Glu Pro Gly Ala His Gly Gly Ala
            260                 265                 270

Glu Ser Gly Ala Ser Gly Arg Lys Ser Glu Pro Pro Ser Ala Leu Val
        275                 280                 285

Gly Ala Gly His Val Ala Pro Val Ser Pro Tyr Lys Pro Gly His Ser
    290                 295                 300

Val Phe Pro Leu Pro Pro Ser Ser Ile Gly Tyr His Gly Ser Ile Val
305                 310                 315                 320

Gly Ala Tyr Ala Gly Tyr Pro Ser Gln Phe Val Pro Gly Leu Asp Pro
                325                 330                 335

Ser Lys Ser Gly Leu Val Gly Gly Gln Leu Ser Gly Gly Leu Gly Leu
            340                 345                 350

Pro Pro Gly Lys Pro Pro Ser Ser Ser Pro Leu Thr Gly Ala Ser Pro
        355                 360                 365

Pro Ser Phe Leu Gln Gly Leu Cys Arg Asp Pro Tyr Cys Leu Gly Gly
    370                 375                 380

Tyr His Gly Ala Ser His Leu Gly Gly Ser Ser Cys Ser Thr Cys Ser
385                 390                 395                 400

Ala His Asp Pro Ala Gly Pro Ser Leu Lys Ala Gly Gly Tyr Pro Leu
                405                 410                 415

Val Tyr Pro Gly His Pro Leu Gln Pro Ala Ala Leu Ser Ser Ser Ala
            420                 425                 430

Ala Gln Ala Ala Leu Pro Gly His Pro Leu Tyr Thr Tyr Gly Phe Met
        435                 440                 445

Leu Gln Asn Glu Pro Leu Pro His Ser Cys Asn Trp Val Ala Ala Ser
    450                 455                 460

Gly Pro Cys Asp Lys Arg Phe Ala Thr Ser Glu Glu Leu Leu Ser His
465                 470                 475                 480

Leu Arg Thr His Thr Ala Leu Pro Gly Ala Glu Lys Leu Leu Ala Ala
                485                 490                 495

Tyr Pro Gly Ala Ser Gly Leu Gly Ser Ala Ala Ala Ala Ala Ala Ala
            500                 505                 510

Ala Ala Ser Cys His Leu His Leu Pro Pro Pro Ala Ala Pro Gly Ser
        515                 520                 525

Pro Gly Ser Leu Ser Leu Arg Asn Pro His Thr Leu Gly Leu Ser Arg
    530                 535                 540
```

Tyr His Pro Tyr Gly Lys Ser His Leu Ser Thr Ala Gly Gly Leu Ala
545 550 555 560

Val Pro Ser Leu Pro Thr Ala Gly Pro Tyr Tyr Ser Pro Tyr Ala Leu
565 570 575

Tyr Gly Gln Arg Leu Ala Ser Ala Ser Ala Leu Gly Tyr Gln
580 585 590

<210> SEQ ID NO 47
<211> LENGTH: 1691
<212> TYPE: DNA
<213> ORGANISM: Homo sapiens

<400> SEQUENCE: 47
gggctggcgc gggcgggagc tgcggcggat acccttgcgt gctgtggaga ccctactctc 60
ttcgctgaga acggccgcta gcggggactg aaggccggga gcccactccc gacccggggc 120
tagcgtgcgt ccctagagtc gagcggggca agggagccag tggccgccga cgggggaccg 180
ggaaactttt ctgggctcct gggcgcgccc tgtagccgcg ctccatgctc cggcagcggc 240
ccgaaaccca gccccgccgc tgacggcgcc cgccgctccg ggcagggccc atgccctgcg 300
cgctccgggg gtcgtaggct gccgccgagc cggggctccg gaagccggcg ggggcgccgc 360
ggccgtgcgg ggcgtcaatg gatcgccact ccagctacat cttcatctgg ctgcagctgg 420
agctctgcgc catggccgtg ctgctcacca aaggtgaaat tcgatgctac tgtgatgctg 480
cccactgtgt agccactggt tatatgtgta aatctgagct cagcgcctgc ttctctagac 540
ttcttgatcc tcagaactca aattccccac tcacccatgg ctgcctggac tctcttgcaa 600
gcacgacaga catctgccaa gccaaacagg cccgaaacca ctctggcacc accataccca 660
cattggaatg ctgtcatgaa gacatgtgca attacagagg gctgcacgat gttctctctc 720
ctcccagggg tgaggcctca ggacaaggaa acaggtatca gcatgatggt agcagaaacc 780
ttatcaccaa ggtgcaggag ctgacttctt ccaaagagtt gtggttccgg gcagcggtca 840
ttgccgtgcc cattgctgga gggctgattt tagtgttgct tattatgttg gccctgagga 900
tgcttcgaag tgaaaataag aggctgcagg atcagcggca acagatgctc tcccgtttgc 960
actacagctt tcacggacac cattccaaaa aggggcaggt tgcaaagtta gacttggaat 1020
gcatggtgcc ggtcagtggg cacgagaact gctgtctgac ctgtgataaa atgagacaag 1080
cagacctcag caacgataag atcctctcgc ttgttcactg gggcatgtac agtgggcacg 1140
ggaagctgga attcgtatga cggagtctta tctgaactac acttactgaa cagcttgaag 1200
gccttttgag ttctgctgga caggagcact ttatctgaag acaaactcat ttaatcatct 1260
ttgagagaca aaatgacctc tgcaaacaga atcttggata tttcttctga aggattattt 1320
gcacagactt aaatacagtt aaatgtgtta tttgctttta aaattataaa aagcaaagag 1380
aagactttgt acacactgtc accagggtta tttgcatcca agggagctgg aattgagtac 1440
ctaaataaac aaaaatgtgc cctatgtaag cttctacatc ttgatttatt gtaaagattt 1500
aaaagaaata tatatatttt gtctgaaatt taatagtgtc tttcataaat ttaactggga 1560
aacgtgagac agtacatgtt aattatacaa atggccattt gctgttaata atttgttctc 1620
aactctagga tgtggcttgg tttttttttt tctcttttct tttttaaaca agaccaagat 1680
cttgcttatt c 1691

<210> SEQ ID NO 48
<211> LENGTH: 260
<212> TYPE: PRT

<213> ORGANISM: Homo sapiens

<400> SEQUENCE: 48

```
Met Asp Arg His Ser Ser Tyr Ile Phe Ile Trp Leu Gln Leu Glu Leu
1               5                   10                  15

Cys Ala Met Ala Val Leu Leu Thr Lys Gly Glu Ile Arg Cys Tyr Cys
            20                  25                  30

Asp Ala Ala His Cys Val Ala Thr Gly Tyr Met Cys Lys Ser Glu Leu
        35                  40                  45

Ser Ala Cys Phe Ser Arg Leu Leu Asp Pro Gln Asn Ser Asn Ser Pro
    50                  55                  60

Leu Thr His Gly Cys Leu Asp Ser Leu Ala Ser Thr Thr Asp Ile Cys
65                  70                  75                  80

Gln Ala Lys Gln Ala Arg Asn His Ser Gly Thr Thr Ile Pro Thr Leu
                85                  90                  95

Glu Cys Cys His Glu Asp Met Cys Asn Tyr Arg Gly Leu His Asp Val
            100                 105                 110

Leu Ser Pro Pro Arg Gly Glu Ala Ser Gly Gln Gly Asn Arg Tyr Gln
        115                 120                 125

His Asp Gly Ser Arg Asn Leu Ile Thr Lys Val Gln Glu Leu Thr Ser
    130                 135                 140

Ser Lys Glu Leu Trp Phe Arg Ala Ala Val Ile Ala Val Pro Ile Ala
145                 150                 155                 160

Gly Gly Leu Ile Leu Val Leu Leu Ile Met Leu Ala Leu Arg Met Leu
                165                 170                 175

Arg Ser Glu Asn Lys Arg Leu Gln Asp Gln Arg Gln Gln Met Leu Ser
            180                 185                 190

Arg Leu His Tyr Ser Phe His Gly His His Ser Lys Lys Gly Gln Val
        195                 200                 205

Ala Lys Leu Asp Leu Glu Cys Met Val Pro Val Ser Gly His Glu Asn
    210                 215                 220

Cys Cys Leu Thr Cys Asp Lys Met Arg Gln Ala Asp Leu Ser Asn Asp
225                 230                 235                 240

Lys Ile Leu Ser Leu Val His Trp Gly Met Tyr Ser Gly His Gly Lys
                245                 250                 255

Leu Glu Phe Val
            260
```

<210> SEQ ID NO 49
<211> LENGTH: 3490
<212> TYPE: DNA
<213> ORGANISM: Homo sapiens

<400> SEQUENCE: 49

```
actgggtaga atacttgggg tgccagggag gcattaatgc gagaggagtc aggtgctcag      60

tttttattgg agttgggagg gcagccccac atcaggaaga gaacctgttt ctgcaggatg     120

gtccggggag aagggaggac tccacccagg cttgtgtttg ccctgctctg tgtattcagc     180

cagcaggctc tgcacaagga agcaaagtgc agggagccag gctccaccga cagccaggca     240

ctgggcagca cgcactggag acccaggacc ctgtgcagga gcagctccgg gtgacacgag     300

gggactgaag atactcccac aggggctcag caggagcaat gggtaaccaa atgagtgttc     360

cccaaagagt tgaagaccaa gagaatgaac cagaagcaga gacttaccag gacaacgcgt     420

ctgctctgaa cggggttcca gtggtggtgt cgacccacac agttcagcac ttagaggaag     480
```

-continued

```
tcgacttggg aataagtgtc aagacggata atgtggccac ttcttccccc gagacaacgg    540
agataagtgc tgttgcggat gccaacggaa agaatcttgg gaaagaggcc aaacccgagg    600
caccagctgc taaatctcgt tttttcttga tgctctctcg gcctgtacca ggacgtaccg    660
gagaccaagc cgcagattca tcccttggat cagtgaagct tgatgtcagc tccaataaag    720
ctccagcgaa caaagaccca agtgagagct ggacacttcc ggtggcagct ggaccggggc    780
aggacacaga taaaaccccca gggcacgccc cggcccaaga caaggtcctc tctgccgcca    840
gggatcccac gcttctccca cctgagacag ggggagcagg aggagaagct ccctccaagc    900
ccaaggactc cagcttttt gacaaattct tcaagctgga caagggacag gaaaaggtgc    960
caggtgacag ccaacaggaa gccaagaggg cagagcatca agacaaggtg gatgaggttc   1020
ctggcttatc agggcagtcc gatgatgtcc ctgcagggaa ggacatagtt gacggcaagg   1080
aaaaagaagg acaagaactt ggaactgcgg attgctctgt ccctggggac ccagaaggac   1140
tggagactgc aaaggacgat tcccaggcag cagctatagc agagaataat aattccatca   1200
tgagtttctt taaaactctg gtttcaccta acaaagctga aacaaaaaag gacccagaag   1260
acacgggtgc tgaaaagtca cccaccactt cagctgacct taagtcagac aaagccaact   1320
ttacatccca ggagacccaa ggggctggca agaattccaa aggatgcaac ccatcggggc   1380
acacacagtc cgtgacaacc cctgaacctg cgaaggaagg caccaaggag aaatcaggac   1440
ccacctctct gcctctgggc aaactgtttt ggaaaaagtc agttaaagag gactcagtcc   1500
ccacaggtgc ggaggagaat gtggtgtgtg agtcaccagt agagattata aagtccaagg   1560
aagtagaatc agccttacaa acagtggacc tcaacgaagg agatgctgca cctgaaccca   1620
cagaagcgaa actcaaaaga gaagaaagca aaccaagaac ctctctgatg gcgtttctca   1680
gacaaatgtc agtgaaaggg gatggaggga tcacccactc agaagaaata aatgggaaag   1740
actccagctg ccaaacatca gactccacag aaaagactat cacaccgcca gagcctgaac   1800
caacaggagc accacagaag ggtaaagagg gctcctcgaa ggacaagaag tcagcagccg   1860
agatgaacaa gcagaagagc aacaagcagg aagccaaaga accagcccag tgcacagagc   1920
aggccacggt ggacacgaac tcactgcaga atggggacaa gctccaaaag agacctgaga   1980
agcggcagca gtcccttggg ggcttcttta aaggcctggg accaaagcgg atgttggatg   2040
ctcaagtgca aacagaccca gtatccatcg gaccagttgg caaatccaag taaacaaatc   2100
agcacggttc ccaccaggtt ctcctgccac caagatgtgt tctccttact ccatctcctc   2160
cccaaacacg ctccatgtat atattcttct gatggccagc aaatgaaatt ctgcctagaa   2220
attaagcccg agctgttgta tattgaggtg tattatttac gtctctggtc cagtcttttc   2280
tggcaaataa cagtaaagat ggtttagcag gtcacctagt tgggtcagaa gagtcgatga   2340
tcaccaagca ggaaagggag ggaatagagg aatgtgttcg ggttaagtga tgaaaatggc   2400
agtggtggcc gggcgtggtg gctctcgcct gtaatctcag cactttggga ggccgaggca   2460
ggtggatcac ctgaggtcag gagttcaaga ctagcctggc caacatcatg aaaccccgtc   2520
tctactaaaa atacaaaaat tagccaggca tggtggcaca cacctgtagt cccagctact   2580
cgggagccca acgcacgaga accgcttgta cccaggaggt ggaggttgca gtgagccgaa   2640
gttgcaccat tgcactccac cctgggcgac agagcaagat tctatcaaaa aaaaaaaaag   2700
gcagtggcaa gtaagttata gaagagaaat gctgctagaa ggaattaagc gttgtagtaa   2760
atgcgtgctt atcctctaag cttgaagaag ggagacgaaa atccatttgt ttaaattcac   2820
atctcaagga gggagaaccc gggctgtgtt gggtggttgc caatttccta gaacggaatg   2880
```

```
tgtggggtat agaaaaagga atgaataagc gttgtttttc aaatagggtc cttgtaagtt   2940

attgatgaga gggaaaagat tgactgggga gggcttaaaa tgatttggga aaacaattgc   3000

ttttgaggct cagtgacaac ggcaaagatt acaacttaaa aaaaaaaaat aaataaaaaa   3060

taaaggaagt tgcacggtta ttttgcaaca caagggggcg gcaaggtccc catttttatc   3120

ctgtaatact gtatccctaa caaagatttg gtctctgcta tcttacatta ttaatgtttc   3180

tcagatggct gaggggctcg cttcatctgt tccgtctgac acttatctca agtgtgtctg   3240

tcattcctaa tgttctcagg atgtgctctg ataaaaccct ccccataacc tcagttaata   3300

aaaatttaca gaagacttct caaatacctg agttgttttt aatacctgta caaaggagta   3360

aataggaccc tgagtctatt aaaatgtaat tcaaagtagc atatgattga ctgacagtca   3420

tgtaaactgt atctttcttt ttctgattta ataaaaaata catttacttc taaagtaaaa   3480

aaaaaaaaaa                                                          3490


<210> SEQ ID NO 50
<211> LENGTH: 584
<212> TYPE: PRT
<213> ORGANISM: Homo sapiens

<400> SEQUENCE: 50

Met Gly Asn Gln Met Ser Val Pro Gln Arg Val Glu Asp Gln Glu Asn
1               5                   10                  15

Glu Pro Glu Ala Glu Thr Tyr Gln Asp Asn Ala Ser Ala Leu Asn Gly
            20                  25                  30

Val Pro Val Val Val Ser Thr His Thr Val Gln His Leu Glu Glu Val
        35                  40                  45

Asp Leu Gly Ile Ser Val Lys Thr Asp Asn Val Ala Thr Ser Ser Pro
    50                  55                  60

Glu Thr Thr Glu Ile Ser Ala Val Ala Asp Ala Asn Gly Lys Asn Leu
65                  70                  75                  80

Gly Lys Glu Ala Lys Pro Glu Ala Pro Ala Ala Lys Ser Arg Phe Phe
                85                  90                  95

Leu Met Leu Ser Arg Pro Val Pro Gly Arg Thr Gly Asp Gln Ala Ala
            100                 105                 110

Asp Ser Ser Leu Gly Ser Val Lys Leu Asp Val Ser Ser Asn Lys Ala
        115                 120                 125

Pro Ala Asn Lys Asp Pro Ser Glu Ser Trp Thr Leu Pro Val Ala Ala
    130                 135                 140

Gly Pro Gly Gln Asp Thr Asp Lys Thr Pro Gly His Ala Pro Ala Gln
145                 150                 155                 160

Asp Lys Val Leu Ser Ala Ala Arg Asp Pro Thr Leu Leu Pro Pro Glu
                165                 170                 175

Thr Gly Gly Ala Gly Gly Glu Ala Pro Ser Lys Pro Lys Asp Ser Ser
            180                 185                 190

Phe Phe Asp Lys Phe Phe Lys Leu Asp Lys Gly Gln Glu Lys Val Pro
        195                 200                 205

Gly Asp Ser Gln Gln Glu Ala Lys Arg Ala Glu His Gln Asp Lys Val
    210                 215                 220

Asp Glu Val Pro Gly Leu Ser Gly Gln Ser Asp Asp Val Pro Ala Gly
225                 230                 235                 240

Lys Asp Ile Val Asp Gly Lys Glu Lys Glu Gly Gln Glu Leu Gly Thr
                245                 250                 255
```

```
Ala Asp Cys Ser Val Pro Gly Asp Pro Glu Gly Leu Glu Thr Ala Lys
            260                 265                 270

Asp Asp Ser Gln Ala Ala Ala Ile Ala Glu Asn Asn Asn Ser Ile Met
        275                 280                 285

Ser Phe Phe Lys Thr Leu Val Ser Pro Asn Lys Ala Glu Thr Lys Lys
    290                 295                 300

Asp Pro Glu Asp Thr Gly Ala Glu Lys Ser Pro Thr Thr Ser Ala Asp
305                 310                 315                 320

Leu Lys Ser Asp Lys Ala Asn Phe Thr Ser Gln Glu Thr Gln Gly Ala
                325                 330                 335

Gly Lys Asn Ser Lys Gly Cys Asn Pro Ser Gly His Thr Gln Ser Val
            340                 345                 350

Thr Thr Pro Glu Pro Ala Lys Glu Gly Thr Lys Glu Lys Ser Gly Pro
        355                 360                 365

Thr Ser Leu Pro Leu Gly Lys Leu Phe Trp Lys Lys Ser Val Lys Glu
    370                 375                 380

Asp Ser Val Pro Thr Gly Ala Glu Glu Asn Val Val Cys Glu Ser Pro
385                 390                 395                 400

Val Glu Ile Ile Lys Ser Lys Glu Val Glu Ser Ala Leu Gln Thr Val
                405                 410                 415

Asp Leu Asn Glu Gly Asp Ala Ala Pro Glu Pro Thr Glu Ala Lys Leu
            420                 425                 430

Lys Arg Glu Glu Ser Lys Pro Arg Thr Ser Leu Met Ala Phe Leu Arg
        435                 440                 445

Gln Met Ser Val Lys Gly Asp Gly Gly Ile Thr His Ser Glu Glu Ile
    450                 455                 460

Asn Gly Lys Asp Ser Ser Cys Gln Thr Ser Asp Ser Thr Glu Lys Thr
465                 470                 475                 480

Ile Thr Pro Pro Glu Pro Glu Pro Thr Gly Ala Pro Gln Lys Gly Lys
                485                 490                 495

Glu Gly Ser Ser Lys Asp Lys Lys Ser Ala Ala Glu Met Asn Lys Gln
            500                 505                 510

Lys Ser Asn Lys Gln Glu Ala Lys Glu Pro Ala Gln Cys Thr Glu Gln
        515                 520                 525

Ala Thr Val Asp Thr Asn Ser Leu Gln Asn Gly Asp Lys Leu Gln Lys
    530                 535                 540

Arg Pro Glu Lys Arg Gln Gln Ser Leu Gly Gly Phe Phe Lys Gly Leu
545                 550                 555                 560

Gly Pro Lys Arg Met Leu Asp Ala Gln Val Gln Thr Asp Pro Val Ser
                565                 570                 575

Ile Gly Pro Val Gly Lys Ser Lys
            580
```

<210> SEQ ID NO 51
<211> LENGTH: 2767
<212> TYPE: DNA
<213> ORGANISM: Homo sapiens

<400> SEQUENCE: 51

```
cgccgtgggt ttctttgttc gtggtgggga ctgtgggctt tgaggaggtt ggtaccatgc      60

gagtgcctcg gtgctgcctg ctcctcatcc gctggagcga ccagggtgct gccctcagcc     120

ccagccccgg ggggagctgg cgcccgcgat ggacagatag atgctcgtgg ggtggaagga     180

ggttgcgact aggttaaggg cagtctccgc ctcggtgccc cccgccccg ctcgtgttgt     240
```

```
cacggggact tgctggcgtg gtgcttctcg aattgacagc cccggggctc tgcagagttg    300
tggggccccg gcatcagtgg gtggacgggt gttgtcccta cgggcgcggg gcgggcgggc    360
tggactggac ttctctcccc ggaccgtagc cgggtgtgcc gcgccacccc agggctcctg    420
ggacgggggt atccgcctct cggatgaagg atttgggggc agagcacttg gcaggtcatg    480
aaggggtcca acttctcggg ttgttgaacg tctacctgga acaagaagag agattccaac    540
ctcgagaaaa agggctgagt ttgattgagg ctaccccgga gaatgataac actttgtgtc    600
caggattgag aaatgccaaa gttgaagatt taaggagttt agccaacttt tttggatctt    660
gcactgaaac ttttgtcctg gctgtcaata ttttggacag gttcttggct cttatgaagg    720
tgaaacctaa acatttgtct tgcattggag tctgttcttt tttgctggct gctagaatag    780
ttgaagaaga ctgcaatatt ccatccactc atgatgtgat ccggattagt cagtgtaaat    840
gtactgcttc tgacataaaa cggatggaaa aaataatttc agaaaaattg cactatgaat    900
tggaagctac tactgcctta aactttttgc acttatacca tactattata ctttgtcata    960
cttcagaaag gaaagaaata ctgagccttg ataaactaga agctcagctg aaagcttgca   1020
actgccgact catcttttca aaagcaaaac catctgtatt agccttgtgc cttctcaatt   1080
tggaagtgga aactttgaaa tctgttgaat tactggaaat tctcttgcta gttaaaaaac   1140
attccaagat taatgacact gagttcttct actggagaga gttggtttct aaatgcctag   1200
ccgagtattc ttctcctgaa tgttgcaaac cagatcttaa gaagttggtt tggatcgttt   1260
caaggcgcac agcccagaac ctccacaaca gctactatag tgttcctgag ctgccaacga   1320
tacctgaggg gggttgtttt gatgaaagtg aaagtgagga ctcttgtgaa gatatgagtt   1380
gtggagagga gagtctcagc agctctcctc ccagtgatca agagtgcacc ttcttttca   1440
acttcaaagt ggcacaaaca ctgtgctttc catcttagaa atctgattgt tctgtcagaa   1500
tttatattta caggtttcaa agcaataaat gggggaatag gtagtttcct ggtttagccc   1560
ccatctagtc aggaattaat atactggaat acctaccttc tatttgttat tcagatcaga   1620
tctggcctat tttcatattt atcctaagcc atcaaatggg gtagtgcctc ttaaaccatt   1680
aacagtactt tagacattgg cactttattt ttctcgtaga tctttagcta ctttggggag   1740
gagggaaggt gctgatacct tcaatttgtt acttttcaag atttttaaaa ataactagtg   1800
tagcttatct taaacatttt ataaaacctt cagatgtctt taagcagatt ggaagtatgc   1860
aagtgcttcc ttagcaggga cagtggataa tccttaatgg tttatcatag atttcaccct   1920
ccccccttct cagaagagtg agtatgctct taaatgtcaa acacattttt gttgttttgt   1980
tttttaaatg atcagtgtct atttgatgtg atgcagatct tataaatttg ggaattataa   2040
tattgacatt tctgtgattt ttatatatgt aatgtcttaa ttgagatttc tgttaaggca   2100
gaaataatta ggctagggct cttagttttc attcctattg cccaagtatt gtcaaactat   2160
ggtattattt taatgttact ttaaaaatcc ataatctgct agttttgcat gtacttatat   2220
gaaaacagtg cagtaagttg aaaactcagt atctatggaa ttgataaatg ttgatctggt   2280
gtagtatatt ttatcgcatt ttcttatatt aaaaaatgtc tgcatgatta cattttattt   2340
cctttgtaat ttacatttca gaatagtgta ttgctatatg ggtgccaaga ttgaatatga   2400
agaacccgag tgtttgtagt attatagttt taagcaaatc tgtgtggtga tacagccata   2460
agaatggggc ttatataaac tctgtacatg taagattttg tacagagaat ttttaacttt   2520
ataaattgta tatgaacatg taaatctttt aaaatgtaca taaaatactg tattttttta   2580
ccttgtgtgt gatagtctag tcattgcatg taaatataat ttattatgta ttctgtagta   2640
```

taaatcatac attgatgact tacattttta ctggtaagtc aacatccgtt ggatgttttc 2700
tgaagtggct ctttttgaag tgataataga ttgtaattca aaataaaatt attaatgaat 2760
tctcctt 2767

<210> SEQ ID NO 52
<211> LENGTH: 344
<212> TYPE: PRT
<213> ORGANISM: Homo sapiens

<400> SEQUENCE: 52

Met Lys Asp Leu Gly Ala Glu His Leu Ala Gly His Glu Gly Val Gln
1               5                   10                  15

Leu Leu Gly Leu Leu Asn Val Tyr Leu Glu Gln Glu Glu Arg Phe Gln
            20                  25                  30

Pro Arg Glu Lys Gly Leu Ser Leu Ile Glu Ala Thr Pro Glu Asn Asp
        35                  40                  45

Asn Thr Leu Cys Pro Gly Leu Arg Asn Ala Lys Val Glu Asp Leu Arg
    50                  55                  60

Ser Leu Ala Asn Phe Phe Gly Ser Cys Thr Glu Thr Phe Val Leu Ala
65                  70                  75                  80

Val Asn Ile Leu Asp Arg Phe Leu Ala Leu Met Lys Val Lys Pro Lys
                85                  90                  95

His Leu Ser Cys Ile Gly Val Cys Ser Phe Leu Leu Ala Ala Arg Ile
            100                 105                 110

Val Glu Glu Asp Cys Asn Ile Pro Ser Thr His Asp Val Ile Arg Ile
        115                 120                 125

Ser Gln Cys Lys Cys Thr Ala Ser Asp Ile Lys Arg Met Glu Lys Ile
    130                 135                 140

Ile Ser Glu Lys Leu His Tyr Glu Leu Glu Ala Thr Thr Ala Leu Asn
145                 150                 155                 160

Phe Leu His Leu Tyr His Thr Ile Ile Leu Cys His Thr Ser Glu Arg
                165                 170                 175

Lys Glu Ile Leu Ser Leu Asp Lys Leu Glu Ala Gln Leu Lys Ala Cys
            180                 185                 190

Asn Cys Arg Leu Ile Phe Ser Lys Ala Lys Pro Ser Val Leu Ala Leu
        195                 200                 205

Cys Leu Leu Asn Leu Glu Val Glu Thr Leu Lys Ser Val Glu Leu Leu
    210                 215                 220

Glu Ile Leu Leu Leu Val Lys Lys His Ser Lys Ile Asn Asp Thr Glu
225                 230                 235                 240

Phe Phe Tyr Trp Arg Glu Leu Val Ser Lys Cys Leu Ala Glu Tyr Ser
                245                 250                 255

Ser Pro Glu Cys Cys Lys Pro Asp Leu Lys Lys Leu Val Trp Ile Val
            260                 265                 270

Ser Arg Arg Thr Ala Gln Asn Leu His Asn Ser Tyr Tyr Ser Val Pro
        275                 280                 285

Glu Leu Pro Thr Ile Pro Glu Gly Gly Cys Phe Asp Glu Ser Glu Ser
    290                 295                 300

Glu Asp Ser Cys Glu Asp Met Ser Cys Gly Glu Glu Ser Leu Ser Ser
305                 310                 315                 320

Ser Pro Pro Ser Asp Gln Glu Cys Thr Phe Phe Phe Asn Phe Lys Val
                325                 330                 335

Ala Gln Thr Leu Cys Phe Pro Ser

340

<210> SEQ ID NO 53
<211> LENGTH: 1744
<212> TYPE: DNA
<213> ORGANISM: Homo sapiens

<400> SEQUENCE: 53
gcagcaggcc aagggggagg tgcgagcgtg gacctgggac gggtctgggc ggctctcggt 60
ggttggcacg ggttcgcaca cccattcaag cggcaggacg cacttgtctt agcagttctc 120
gctgaccgcg ctagctgcgg cttctacgct ccggcactct gagttcatca gcaaacgccc 180
tggcgtctgt cctcaccatg cctagccttt gggaccgctt ctcgtcgtcg tccacctcct 240
cttcgccctc gtccttgccc cgaactccca ccccagatcg gccgccgcgc tcagcctggg 300
ggtcggcgac ccgggaggag gggtttgacc gctccacgag cctggagagc tcggactgcg 360
agtccctgga cagcagcaac agtggcttcg ggccggagga agacacggct tacctggatg 420
gggtgtcgtt gcccgacttc gagctgctca gtgaccctga ggatgaacac ttgtgtgcca 480
acctgatgca gctgctgcag gagagcctgg cccaggcgcg gctgggctct cgacgccctg 540
cgcgcctgct gatgcctagc cagttggtaa gccaggtggg caaagaacta ctgcgcctgg 600
cctacagcga gccgtgcggc ctgcgggggg cgctgctgga cgtctgcgtg gagcagggca 660
agagctgcca cagcgtgggc cagctggcac tcgaccccag cctggtgccc accttccagc 720
tgaccctcgt gctgcgcctg gactcacgac tctggcccaa gatccagggg ctgtttagct 780
ccgccaactc tcccttcctc cctggcttca gccagtccct gacgctgagc actggcttcc 840
gagtcatcaa gaagaagctg tacagctcgg aacagctgct cattgaggag tgttgaactt 900
caacctgagg gggccgacag tgccctccaa gacagagacg actgaacttt tggggtggag 960
actagaggca ggagctgagg gactgattcc tgtggttgga aaactgaggc agccacctaa 1020
ggtggaggtg ggggaatagt gtttcccagg aagctcattg agttgtgtgc gggtggctgt 1080
gcattgggga cacatacccc tcagtactgt agcatgaaac aaaggcttag ggccaacaa 1140 ggcttccagc tggatgtgtg tgtagcatgt accttattat ttttgttact gacagttaac 1200
agtggtgtga catccagaga gcagctgggc tgctcccgcc ccagcccggc ccagggtgaa 1260
ggaagaggca cgtgctcctc agagcagccg gagggagggg ggaggtcgga ggtcgtggag 1320
gtggtttgtg tatcttactg gtctgaaggg accaagtgtg tttgttgttt gttttgtatc 1380
ttgtttttct gatcggagca tcactactga cctgttgtag gcagctatct tacagacgca 1440
tgaatgtaag agtaggaagg ggtgggtgtc agggatcact tgggatcttt gacacttgaa 1500
aaattacacc tggcagctgc gtttaagcct tcccccatcg tgtactgcag agttgagctg 1560
gcaggggagg ggctgagagg gtgggggctg gaacccctcc ccgggaggag tgccatctgg 1620
gtcttccatc tagaactgtt tacatgaaga taagatactc actgttcatg aatacacttg 1680
atgttcaagt attaagacct atgcaatatt ttttactttt ctaataaaca tgtttgttaa 1740
aaca 1744

<210> SEQ ID NO 54
<211> LENGTH: 232
<212> TYPE: PRT
<213> ORGANISM: Homo sapiens

<400> SEQUENCE: 54

Met Pro Ser Leu Trp Asp Arg Phe Ser Ser Ser Ser Thr Ser Ser Ser

-continued

```
1               5                   10                  15

Pro Ser Ser Leu Pro Arg Thr Pro Thr Pro Asp Arg Pro Pro Arg Ser
            20                  25                  30

Ala Trp Gly Ser Ala Thr Arg Glu Glu Gly Phe Asp Arg Ser Thr Ser
        35                  40                  45

Leu Glu Ser Ser Asp Cys Glu Ser Leu Asp Ser Ser Asn Ser Gly Phe
    50                  55                  60

Gly Pro Glu Glu Asp Thr Ala Tyr Leu Asp Gly Val Ser Leu Pro Asp
65                  70                  75                  80

Phe Glu Leu Leu Ser Asp Pro Glu Asp Glu His Leu Cys Ala Asn Leu
                85                  90                  95

Met Gln Leu Leu Gln Glu Ser Leu Ala Gln Ala Arg Leu Gly Ser Arg
            100                 105                 110

Arg Pro Ala Arg Leu Leu Met Pro Ser Gln Leu Val Ser Gln Val Gly
        115                 120                 125

Lys Glu Leu Leu Arg Leu Ala Tyr Ser Glu Pro Cys Gly Leu Arg Gly
    130                 135                 140

Ala Leu Leu Asp Val Cys Val Glu Gln Gly Lys Ser Cys His Ser Val
145                 150                 155                 160

Gly Gln Leu Ala Leu Asp Pro Ser Leu Val Pro Thr Phe Gln Leu Thr
                165                 170                 175

Leu Val Leu Arg Leu Asp Ser Arg Leu Trp Pro Lys Ile Gln Gly Leu
            180                 185                 190

Phe Ser Ser Ala Asn Ser Pro Phe Leu Pro Gly Phe Ser Gln Ser Leu
        195                 200                 205

Thr Leu Ser Thr Gly Phe Arg Val Ile Lys Lys Lys Leu Tyr Ser Ser
    210                 215                 220

Glu Gln Leu Leu Ile Glu Glu Cys
225                 230
```

<210> SEQ ID NO 55
<211> LENGTH: 2722
<212> TYPE: DNA
<213> ORGANISM: Homo sapiens

<400> SEQUENCE: 55

```
gagtctggcc gcagtcgcgg cagtggtggc ttcccatccc caaaaggcgc cctccgactc      60

cttgcgccgc actgctcgcc gggccagtcc ggaaacgggt cgtggagctc cgcaccactc     120

ccgctggttc ccgaaggcag atcccttctc ccgagagttg cgagaaactt tcccttgtcc     180

ccgacgctgc agcggctcgg gtaccgtggc agccgcaggt ttctgaaccc cgggccacgc     240

tccccgcgcc tcggcttcgc gctcgtgtag atcgttccct ctctggttgc acgctgggga     300

tcccggacct cgattctgcg ggcgagatgc ccctgggaca catcatgagg ctggacctgg     360

agaaaattgc cctggagtac atcgtgccct gtctgcacga ggtgggcttc tgctacctgg     420

acaacttcct gggcgaggtg gtgggcgact gcgtcctgga gcgcgtcaag cagctgcact     480

gcaccggggc cctgcgggac ggccagctgg cggggccgcg cgccggcgtc tccaagcgac     540

acctgcgggg cgaccagatc acgtggatcg gggcaacga ggagggctgc gaggccatca      600

gcttcctcct gtccctcatc gacaggctgg tcctctactg cgggagccgg ctgggcaaat     660

actacgtcaa ggagaggtct aaggcaatgg tggcttgcta tccgggaaat ggaacaggtt     720

atgttcgcca cgtggacaac cccaacggtg atggtcgctg catcacctgc atctactatc     780

tgaacaagaa ttgggatgcc aagctacatg gtgggatcct gcggatattt ccagagggga     840
```

```
aatcattcat agcagatgtg gagcccattt ttgacagact cctgttcttc tggtcagatc    900

gtaggaaccc acacgaagtg cagccctctt acgcaaccag atatgctatg actgtctggt    960

actttgatgc tgaagaaagg gcagaagcca aaaagaaatt caggaattta actaggaaaa   1020

ctgaatctgc cctcactgaa gactgaccgt gctctgaaat ctgctggcct tgttcatttt   1080

agtaacggtt cctgaattct cttaaattct ttgagatcca aagatggcct cttcagtgac   1140

aacaatctcc ctgctacttc ttgcatcctt cacatccctg tcttgtgtgt ggtacttcat   1200

gttttcttgc caagactgtg ttgatcttca gatactctct ttgccagatg aagttacttg   1260

ctaactccag aaattcctgc agacatccta ctcggccagc ggtttacctg atagattcgg   1320

taatactatc aagagaagag cctaggagca cagcgaggga atgaacctta cttgcacttt   1380

atgtatactt cctgatttga aaggaggagg tttgaaaaga aaaaaatgga ggtggtagat   1440

gccacagaga ggcatcacgg aagccttaac agcaggaaac agagaaattt gtgtcatctg   1500

aacaatttcc agatgttctt aatccagggc tgttggggtt tctggagaat tatcacaacc   1560

taatgacatt aatacctcta gaaagggctg ctgtcatagt gaacaattta taagtgtccc   1620

atggggcaga cactcctttt ttcccagtcc tgcaacctgg attttctgcc tcagccccat   1680

tttgctgaaa ataatgactt tctgaataaa gatggcaaca caatttttttc tccattttca   1740

gttcttacct gggaacctaa ttccccagaa gctaaaaaac tagacattag ttgttttggt   1800

tgctttgttg gaatggaatt taaatttaaa tgaaaggaaa aatatatccc tggtagtttt   1860

gtgttaacca ctgataactg tggaaagagc taggtctact gatatacaat aaacatgtgt   1920

gcatcttgaa caatttgaga ggggaggtgg agttggaaat gtgggtgttc ctgttttttt   1980

tttttttttt tttttagttt tccttttttaa tgagctcacc ctttaacaca aaaaaagcaa   2040

ggtgatgtat tttaaaaaag gaagtggaaa taaaaaaatc tcaaagctat ttgagttctc   2100

gtctgtccct agcagtcttt cttcagctca cttggctctc tagatccact gtggttggca   2160

gtatgaccag aatcatggaa tttgctagaa ctgtggaagc ttctactcct gcagtaagca   2220

cagatcgcac tgcctcaata acttggtatt gagcacgtat tttgcaaaag ctacttttcc   2280

tagttttcag tattactttc atgttttaaa aatcccttta atttcttgct tgaaaatccc   2340

atgaacatta aagagccaga aatattttcc tttgttatgt acggatatat atatatatag   2400

tcttccaaga tagaagttta ctttttcctc ttctggtttt ggaaaatttc cagataagac   2460

atgtcaccat taattctcaa cgactgctct attttgttgt acggtaatag ttatcacctt   2520

ctaaattact atgtaattta ttcacttatt atgtttattg tcttgtatcc tttctctgga   2580

gtgtaagcac aatgaagaca ggaattttgt atatttttaa ccaatgcaac atactctcag   2640

cacctaaaat agtgccggga acatagtaag ggctcagtaa atacttgttg aataaactca   2700

gtctcctaca ttagcattct aa                                            2722
```

<210> SEQ ID NO 56
<211> LENGTH: 239
<212> TYPE: PRT
<213> ORGANISM: Homo sapiens

<400> SEQUENCE: 56

```
Met Pro Leu Gly His Ile Met Arg Leu Asp Leu Glu Lys Ile Ala Leu
1               5                   10                  15

Glu Tyr Ile Val Pro Cys Leu His Glu Val Gly Phe Cys Tyr Leu Asp
            20                  25                  30
```

```
Asn Phe Leu Gly Glu Val Val Gly Asp Cys Val Leu Glu Arg Val Lys
        35                  40                  45

Gln Leu His Cys Thr Gly Ala Leu Arg Asp Gly Gln Leu Ala Gly Pro
    50                  55                  60

Arg Ala Gly Val Ser Lys Arg His Leu Arg Gly Asp Gln Ile Thr Trp
65                  70                  75                  80

Ile Gly Gly Asn Glu Glu Gly Cys Glu Ala Ile Ser Phe Leu Leu Ser
                85                  90                  95

Leu Ile Asp Arg Leu Val Leu Tyr Cys Gly Ser Arg Leu Gly Lys Tyr
            100                 105                 110

Tyr Val Lys Glu Arg Ser Lys Ala Met Val Ala Cys Tyr Pro Gly Asn
        115                 120                 125

Gly Thr Gly Tyr Val Arg His Val Asp Asn Pro Asn Gly Asp Gly Arg
    130                 135                 140

Cys Ile Thr Cys Ile Tyr Tyr Leu Asn Lys Asn Trp Asp Ala Lys Leu
145                 150                 155                 160

His Gly Gly Ile Leu Arg Ile Phe Pro Glu Gly Lys Ser Phe Ile Ala
                165                 170                 175

Asp Val Glu Pro Ile Phe Asp Arg Leu Leu Phe Phe Trp Ser Asp Arg
            180                 185                 190

Arg Asn Pro His Glu Val Gln Pro Ser Tyr Ala Thr Arg Tyr Ala Met
        195                 200                 205

Thr Val Trp Tyr Phe Asp Ala Glu Glu Arg Ala Glu Ala Lys Lys Lys
    210                 215                 220

Phe Arg Asn Leu Thr Arg Lys Thr Glu Ser Ala Leu Thr Glu Asp
225                 230                 235
```

<210> SEQ ID NO 57
<211> LENGTH: 5731
<212> TYPE: DNA
<213> ORGANISM: Homo sapiens

<400> SEQUENCE: 57

```
gcagattgcg cgagggggag cgagcgagcg ggcgctgcca ggagcccgca gccctggcgc      60

ccgccgccgc ccggagcccc gcaatatgcc gccgcggccc tctggctcta ggccatggcg     120

aggctctgcc ggcgtgtccc ctgcaccctg cttctcggcc tggccgtggt gctgctgaaa     180

gcgcggctgg tccccgcggc cgccagagcg gaactcagcc gctccgacct cagcctcatc     240

caacagcagc agcagcagca gcaacaacaa caacaacagc aaaagcagct ggaggaggct     300

gaggaggaga ggacagaggt gcctggggca acctccacct tgacggttcc agtgtctgta     360

tttatgttga aagtccaggt gaatgacatc atcagtcgtc agtacctgag ccaagcagtt     420

gtagaagtgt ttgtaaacta cacgaagaca aattccacag taactaaaag caatggagca     480

gtgctgataa aagtacccta caaattagga cttagtttaa ctattattgc ttacaaagat     540

ggctacgtgt tgacccctct gccttggaaa accagaagaa tgccaatata ttcatcagtt     600

acactttcac tgttcccgca aagccaagca aatatatggc tatttgaaga cactgtttta     660

attactggaa aattagctga tgccaagtct caaccaagtg ttcagttttc aaaagcctta     720

attaaacttc ctgacaacca tcatattagc aacgttactg gctatcttac agttctacaa     780

cagtttttga aagtggacaa ttttctgcat acaactggaa ttactctcaa taaaccaggt     840

tttgaaaaca ttgaattgac tcctcttgct gcaatatgtg tgaaaatata ttctggagga     900

aaagaactaa aggtcaatgg ctctattcaa gtttctcttc ctcttctacg tctgaatgat     960
```

ataagtgcag gggatcgcat acctgcttgg acatttgata tgaacacagg tgcttgggta 1020
aatcatggtc ggggaatggt caaggaacat aacaatcatt taatctggac atatgatgca 1080
ccacatttgg ggtactggat agcagctcca cttccaggaa ctagaggttc aggtataaat 1140
gaagattcca aggacataac tgcctaccac acagtgtttc ttacagccat attaggagga 1200
acaatagtca ttgtcattgg attttttgct gtactacttt gttattgcag ggacaagtgt 1260
ggtactccac agaaaagaga aagaaatatc actaaacttg aggtcctcaa gagagaccag 1320
acaacttcaa caacacacat aaatcatatc agtacagtta aagttgcatt aaaagctgag 1380
gacaagtcgc agttattcaa tgccaaaaac tcctcatata gtcctcagaa aaaggaacca 1440
tcaaaggcag aaacagaaga aagagtttcc atggtaaaaa ctcgggacga ttttaaaatc 1500
tacaatgaag atgtttcatt tctatcagtc aatcaaaata attactcaag aaacccaaca 1560
cagtctttgg agcccaatgt agggtccaaa caacctaaac atattaacaa caatctatct 1620
tcatctctag gtgatgctca agatgaaaag aggtatctca caggtaatga ggaggcgtat 1680
gggcgttccc atattcctga acagcttatg catatttaca gccaacccat tgccatcctt 1740
caaacatctg accttttctc cacaccggaa caattacata ctgctaagtc agctactttg 1800
ccaagaaagg gacagttagt ctatggccaa ttgatggaac cagtaaatcg agagaacttt 1860
acgcagacct tgcccaaaat gccaattcat tctcatgcac agcccccaga tgccagggaa 1920
gaggatatca tacttgaagg tcaacagagc ctgccatccc aggcttcaga ttggagccga 1980
tactcaagca gcttactgga atccgtctct gttcctggaa cactaaatga ggctgttgta 2040
atgactccat tttcatcgga acttcaagga atttcagaac agaccctcct ggagctgtcc 2100
aaaggaaagc cctccccgca tcccagagcc tggtttgtgt ctcttgatgg aaagccagtt 2160
gcacaagtga ggcactcctt tatagacctg aaaaagggca agagaaccca gagcaatgac 2220
accagtctgg actctggggt ggacatgaat gagcttcact caagtagaaa gctcgagagg 2280
gagaaaacat tcatcaaaag catgcatcag cccaagatcc tttacttaga agatttagac 2340
ctaagcagca gtgagagtgg aaccaccgtc tgttcccctg aggacccagc tttaaggcac 2400
atcctagatg gagggagtgg agtgatcatg gagcaccctg gagaagagtc gccaggaagg 2460
aaaagcactg ttgaagattt tgaagctaat acatccccca ctaaaagaag gggcagacca 2520
ccactagcca aaagagatag caagactaac atctggaaga agcgagagga acgcccactg 2580
attcccataa attaactcca atggggattg tgtgtctgct gtctcgtgct gtttattctt 2640
gcttcttgtt gtaaattgca gtacgaactt aagaaaatga gactgagcaa tctcatggtt 2700
cttggacatg tctcaagcag agtaaatggt aattcagtaa tcagagagaa agataccaag 2760
gaatgctttt tctggcctat tcatttattt ttgggtgatg aatttacagt atctaagttt 2820
tcaaaatgta aaatagcttc aagatgttag ttatctgaaa atgttgctca gccagccagt 2880
ttggccttga ctctcttaag aataacagtg aaatatatac tcctcaagtt gcctccaaaa 2940
atgttgcctc taccatggtg actaccccat ggaacattta gaaacaaaac tgacttcagg 3000
catcatatta ttttaaatgt tactattacg tcttcttctg cctatactta aaaataactt 3060
gataaatgac ttggactgat gttactctgg agttatcaca aagaaaatgt tgtttggtct 3120
ttaaagagca tgtgtattgt atcatcccaa acgtaaatcc tacatttata taagatgggc 3180
aagaagctac ttggtcatta gagagggaga caccagctct ttggttgttt ttggatataa 3240
ctttacaaaa taagtaagat gttaatttag aaatttgaga aattaatgct ctaatactga 3300
gtttttattt aaaaattatt ttttcttccc ctcaacaatg aagcaagctt agctgtcaag 3360

```
ggaaactttt tacaaatctg aaaaaaacaa tctatgactt tggtttaagg ctcactgata   3420
cttttaggct aaattggttt taatatattt cttctattct aaaaacctga actcagtcac   3480
ttaaaggcta tgaaatttaa aaaaaaagtc gatgtgaaag tttcttttga acactaaaat   3540
aaaatatgtg cagataaaat atacattgat ttgtttttct taaatgttga tgagaagaaa   3600
aagagatgcc attttcctga ggctcaaaaa taccttcagg atagttgtat atccagttat   3660
tgattttctt aaaagatgtg taaggaaaac agtttcaatt tcaggggaaa agtaaaagtt   3720
tttccctaag tcacttaaag cctttgcaac ttcttttttc agttttgtaa gtaatatatc   3780
tatgttcttt tcattatagc aagcattcaa tgtgaacaac tttttaatta actctgaatt   3840
accattcata catcctaaaa ataaaagctc gttattcatt aaaatcaact gatcccattt   3900
ttcttaaaat ttccctgaag gcaaatgtct gaagcacctt tcccttgtgg gggtaaaaat   3960
cctaaattgc tttattttttc attccctcct attcaacatg ggagcagcat agagacccaa   4020
accatgtaaa caagttcagt gaaccaaaac agccacatta gcttcagtaa aattatagct   4080
agatgtgcaa ttttttcctc caacttctaa cgtgtcaaat aaccttccta ctgttctgtg   4140
ttaactgaaa gaacataaag accctaggca aatatttgct atatattacc ccaatccata   4200
gaagaaataa tgttttgggt aatacctagg cttccttttt tttttttttt tttttttttt   4260
agtgataagg ctcataacaa ttaattagag aaggcttctt attggtctta cacagaaaga   4320
tacatcaaaa gcagcatgac tcaaaatgat ttggaaaagg ttaaagttag tgctctgctg   4380
aagtgccttt gatatagact tgcattatta gaaggatata acatcttttt taagtgtgca   4440
ttttctttca gttaaccaaa ttaaacagat gtgcagtttt attaaaaata tagacctagt   4500
gtttcatgtt ggaacaataa atattgcatg tgagtagtat ttcttgtttt ttgaatacag   4560
tatatattga taaattgttt atgttggaat gaagttagaa actatatagc aaaacattat   4620
attttaagtg tttattttc ccacctttaa ataaaaatgt ttcatctcag cttggtaatg   4680
aaatacacat attggtataa gggtatacca ttcaggtatg ccacttattt tattcatttt   4740
tgtgtaaggg aaatgagatg atgtatccca agggcttttc tagaactact tgtttgcttt   4800
cagaataaaa ccttattatt ttttacactg cacatgctgt tctcaattgg taattatagg   4860
caatttatct tttctaatga tcaaaagagt gtgacttctc atttgtgagt agttcacaaa   4920
tttcctgtta aaaagctgaa accatctact ttttcttaac ccaagtgata ataaacaata   4980
ttcacaactt tcttaaattt ttaaattgaa aaccaaggtt ttttcaaata taaacctaga   5040
tgattttggt cacaaattgt taacatttgt cgatcctttg tatatacttt ggatatatat   5100
taaaggcaaa actatctctt gactaactga tggattcatt tactaaagca cagctgtatg   5160
tatttttgaa tacatattat gatcttgaga ctttataaat caatttttat gactttatgc   5220
agttgtatag ggattatgcc ctttcagttc tatagggatt atgccctttt ataatacata   5280
atataccaca gagattacaa atgttgagga atgaaagcac ttctttgctt tggcaatcat   5340
tttcagacca ctatgtgttt gaatcctctg gtatcaatac gtattatagg gttttagaga   5400
tctgtgggtc aaatgatgtc cctcaaaact tcctaaaaag gtgaagctca aagtcacaca   5460
ttcttataag gcgcatgagt ttctcatttt cccatgtacg agcattgtaa aggaattcag   5520
ctgtattaat ttctatttca gatctagaat tgacattttg ccttcttgtt tccaggtgtt   5580
tctatttttt gtattctttc agagaaatct catatttcgg tgtatttatt gctgttacta   5640
ctatatttac tgctgaaaac tgtaacaacc tgaagatttg taaaatgtta aacatagttc   5700
```

attaaaaata ataaaataaa tctaaaatgt a 5731

<210> SEQ ID NO 58
<211> LENGTH: 826
<212> TYPE: PRT
<213> ORGANISM: Homo sapiens

<400> SEQUENCE: 58

Met Ala Arg Leu Cys Arg Arg Val Pro Cys Thr Leu Leu Leu Gly Leu
1               5                   10                  15

Ala Val Val Leu Leu Lys Ala Arg Leu Val Pro Ala Ala Ala Arg Ala
            20                  25                  30

Glu Leu Ser Arg Ser Asp Leu Ser Leu Ile Gln Gln Gln Gln Gln Gln
        35                  40                  45

Gln Gln Gln Gln Gln Gln Gln Gln Lys Gln Leu Glu Glu Ala Glu Glu
    50                  55                  60

Glu Arg Thr Glu Val Pro Gly Ala Thr Ser Thr Leu Thr Val Pro Val
65                  70                  75                  80

Ser Val Phe Met Leu Lys Val Gln Val Asn Asp Ile Ile Ser Arg Gln
                85                  90                  95

Tyr Leu Ser Gln Ala Val Val Glu Val Phe Val Asn Tyr Thr Lys Thr
            100                 105                 110

Asn Ser Thr Val Thr Lys Ser Asn Gly Ala Val Leu Ile Lys Val Pro
        115                 120                 125

Tyr Lys Leu Gly Leu Ser Leu Thr Ile Ile Ala Tyr Lys Asp Gly Tyr
    130                 135                 140

Val Leu Thr Pro Leu Pro Trp Lys Thr Arg Arg Met Pro Ile Tyr Ser
145                 150                 155                 160

Ser Val Thr Leu Ser Leu Phe Pro Gln Ser Gln Ala Asn Ile Trp Leu
                165                 170                 175

Phe Glu Asp Thr Val Leu Ile Thr Gly Lys Leu Ala Asp Ala Lys Ser
            180                 185                 190

Gln Pro Ser Val Gln Phe Ser Lys Ala Leu Ile Lys Leu Pro Asp Asn
        195                 200                 205

His His Ile Ser Asn Val Thr Gly Tyr Leu Thr Val Leu Gln Gln Phe
    210                 215                 220

Leu Lys Val Asp Asn Phe Leu His Thr Thr Gly Ile Thr Leu Asn Lys
225                 230                 235                 240

Pro Gly Phe Glu Asn Ile Glu Leu Thr Pro Leu Ala Ala Ile Cys Val
                245                 250                 255

Lys Ile Tyr Ser Gly Gly Lys Glu Leu Lys Val Asn Gly Ser Ile Gln
            260                 265                 270

Val Ser Leu Pro Leu Leu Arg Leu Asn Asp Ile Ser Ala Gly Asp Arg
        275                 280                 285

Ile Pro Ala Trp Thr Phe Asp Met Asn Thr Gly Ala Trp Val Asn His
    290                 295                 300

Gly Arg Gly Met Val Lys Glu His Asn Asn His Leu Ile Trp Thr Tyr
305                 310                 315                 320

Asp Ala Pro His Leu Gly Tyr Trp Ile Ala Ala Pro Leu Pro Gly Thr
                325                 330                 335

Arg Gly Ser Gly Ile Asn Glu Asp Ser Lys Asp Ile Thr Ala Tyr His
            340                 345                 350

Thr Val Phe Leu Thr Ala Ile Leu Gly Gly Thr Ile Val Ile Val Ile
        355                 360                 365

```
Gly Phe Phe Ala Val Leu Leu Cys Tyr Cys Arg Asp Lys Cys Gly Thr
    370                 375                 380

Pro Gln Lys Arg Glu Arg Asn Ile Thr Lys Leu Glu Val Leu Lys Arg
385                 390                 395                 400

Asp Gln Thr Thr Ser Thr Thr His Ile Asn His Ile Ser Thr Val Lys
                405                 410                 415

Val Ala Leu Lys Ala Glu Asp Lys Ser Gln Leu Phe Asn Ala Lys Asn
            420                 425                 430

Ser Ser Tyr Ser Pro Gln Lys Lys Glu Pro Ser Lys Ala Glu Thr Glu
        435                 440                 445

Glu Arg Val Ser Met Val Lys Thr Arg Asp Asp Phe Lys Ile Tyr Asn
    450                 455                 460

Glu Asp Val Ser Phe Leu Ser Val Asn Gln Asn Asn Tyr Ser Arg Asn
465                 470                 475                 480

Pro Thr Gln Ser Leu Glu Pro Asn Val Gly Ser Lys Gln Pro Lys His
                485                 490                 495

Ile Asn Asn Asn Leu Ser Ser Ser Leu Gly Asp Ala Gln Asp Glu Lys
            500                 505                 510

Arg Tyr Leu Thr Gly Asn Glu Glu Ala Tyr Gly Arg Ser His Ile Pro
        515                 520                 525

Glu Gln Leu Met His Ile Tyr Ser Gln Pro Ile Ala Ile Leu Gln Thr
    530                 535                 540

Ser Asp Leu Phe Ser Thr Pro Glu Gln Leu His Thr Ala Lys Ser Ala
545                 550                 555                 560

Thr Leu Pro Arg Lys Gly Gln Leu Val Tyr Gly Gln Leu Met Glu Pro
                565                 570                 575

Val Asn Arg Glu Asn Phe Thr Gln Thr Leu Pro Lys Met Pro Ile His
            580                 585                 590

Ser His Ala Gln Pro Pro Asp Ala Arg Glu Glu Asp Ile Ile Leu Glu
        595                 600                 605

Gly Gln Gln Ser Leu Pro Ser Gln Ala Ser Asp Trp Ser Arg Tyr Ser
    610                 615                 620

Ser Ser Leu Leu Glu Ser Val Ser Val Pro Gly Thr Leu Asn Glu Ala
625                 630                 635                 640

Val Val Met Thr Pro Phe Ser Ser Glu Leu Gln Gly Ile Ser Glu Gln
                645                 650                 655

Thr Leu Leu Glu Leu Ser Lys Gly Lys Pro Ser Pro His Pro Arg Ala
            660                 665                 670

Trp Phe Val Ser Leu Asp Gly Lys Pro Val Ala Gln Val Arg His Ser
        675                 680                 685

Phe Ile Asp Leu Lys Lys Gly Lys Arg Thr Gln Ser Asn Asp Thr Ser
    690                 695                 700

Leu Asp Ser Gly Val Asp Met Asn Glu Leu His Ser Ser Arg Lys Leu
705                 710                 715                 720

Glu Arg Glu Lys Thr Phe Ile Lys Ser Met His Gln Pro Lys Ile Leu
                725                 730                 735

Tyr Leu Glu Asp Leu Asp Leu Ser Ser Ser Glu Ser Gly Thr Thr Val
            740                 745                 750

Cys Ser Pro Glu Asp Pro Ala Leu Arg His Ile Leu Asp Gly Gly Ser
        755                 760                 765

Gly Val Ile Met Glu His Pro Gly Glu Glu Ser Pro Gly Arg Lys Ser
    770                 775                 780

Thr Val Glu Asp Phe Glu Ala Asn Thr Ser Pro Thr Lys Arg Arg Gly
```

-continued 785 790 795 800

Arg Pro Pro Leu Ala Lys Arg Asp Ser Lys Thr Asn Ile Trp Lys Lys
805 810 815

Arg Glu Glu Arg Pro Leu Ile Pro Ile Asn
820 825

<210> SEQ ID NO 59
<211> LENGTH: 7368
<212> TYPE: DNA
<213> ORGANISM: Homo sapiens

<400> SEQUENCE: 59
gctgtacttt tctgggtgtg tgttagggag gctatgttcc tgaccctccc cctctggggt 60
gagaaggggt ccccgccatg tcctcggggt tggtaggagg agaggattgg agctgttttc 120
tccttgatgc caagatacgc caagctagga gcattctgcc ctttccacag tcatccaccg 180
agaacaggcc tgcaggacgg gacaaggatc agagccttcc tgcaaccccg gccactgcct 240
gctgtctgtg ggcctggact gtgcgggcaa ctgtgcttgg cccgagtgac aaggaggtgg 300
gagagggtag cagcatgggc tacgcggttg gctgccctca gtccccctgc tgctgaagct 360
gccctgccca tgcccaccca ggccgtgggg ccaggggcct gccagggcta ggagtgggcc 420
tgccgttcat gggtctctag ggatttccga gatgcctggg aagagaggct tgggctggtg 480
gtgggcccgg ctgccccttt gcctgctcct cagcctttac ggcccctgga tgccttcctc 540
cctgggaaag cccaaaggcc accctcacat gaattccatc cgcatagatg gggacatcac 600
actgggaggc ctgttcccgg tgcatggccg gggctcagag ggcaagccct gtggagaact 660
taagaaggaa aagggcatcc accggctgga ggccatgctg ttcgccctgg atcgcatcaa 720
caacgacccg gacctgctgc ctaacatcac gctgggcgcc cgcattctgg acacctgctc 780
cagggacacc catgccctcg agcagtcgct gacctttgtg caggcgctca tcgagaagga 840
tggcacagag gtccgctgtg gcagtggcgg cccacccatc atcaccaagc ctgaacgtgt 900
ggtgggtgtc atcggtgctt cagggagctc ggtctccatc atggtggcca acatccttcg 960
cctcttcaag ataccccaga tcagctacgc ctccacagcg ccagacctga gtgacaacag 1020
ccgctacgac ttcttctccc gcgtggtgcc ctcggacacg taccaggccc aggccatggt 1080
ggacatcgtc cgtgccctca agtggaacta tgtgtccaca gtggcctcgg agggcagcta 1140
tggtgagagc ggtgtggagg ccttcatcca gaagtcccgt gaggacgggg gcgtgtgcat 1200
cgcccagtcg gtgaagatac cacgggagcc caaggcaggc gagttcgaca agatcatccg 1260
ccgcctcctg gagacttcga acgccagggc agtcatcatc tttgccaacg aggatgacat 1320
caggcgtgtg ctggaggcag cacgaagggc caaccagaca ggccatttct tctggatggg 1380
ctctgacagc tggggctcca agattgcacc tgtgctgcac ctggaggagg tggctgaggg 1440
tgctgtcacg atcctcccca agaggatgtc cgtacgaggc ttcgaccgct acttctccag 1500
ccgcacgctg gacaacaacc ggcgcaacat ctggtttgcc gagttctggg aggacaactt 1560
ccactgcaag ctgagccgcc acgccctcaa gaagggcagc cacgtcaaga agtgcaccaa 1620
ccgtgagcga attgggcagg attcagctta tgagcaggag gggaaggtgc agtttgtgat 1680
cgatgccgtg tacgccatgg gccacgcgct gcacgccatg caccgtgacc tgtgtcccgg 1740
ccgcgtgggg ctctgcccgc gcatggaccc tgtagatggc acccagctgc ttaagtacat 1800
ccgaaacgtc aacttctcag gcatcgcagg gaaccctgtg accttcaatg agaatggaga 1860
tgcgcctggg cgctatgaca tctaccaata ccagctgcgc aacgattctg ccgagtacaa 1920
ggtcattggc tcctggactg accacctgca ccttagaata gagcggatgc actggccggg 1980
gagcgggcag cagctgcccc gctccatctg cagcctgccc tgccaaccgg gtgagcggaa 2040
gaagacagtg aagggcatgc cttgctgctg gcactgcgag ccttgcacag ggtaccagta 2100
ccaggtggac cgctacacct gtaagacgtg tccctatgac atgcggccca cagagaaccg 2160
cacgggctgc cggcccatcc ccatcatcaa gcttgagtgg ggctcgccct gggccgtgct 2220
gcccctcttc ctggccgtgg tgggcatcgc tgccacgttg ttcgtggtga tcacctttgt 2280
gcgctacaac gacacgccca tcgtcaaggc ctcgggccgt gaactgagct acgtgctgct 2340
ggcaggcatc ttcctgtgct atgccaccac cttcctcatg atcgctgagc ccgaccttgg 2400
cacctgctcg ctgcgccgaa tcttcctggg actagggatg agcatcagct atgcagccct 2460
gctcaccaag accaaccgca tctaccgcat cttcgagcag ggcaagcgct cggtcagtgc 2520
cccacgcttc atcagccccg cctcacagct ggccatcacc ttcagcctca tctcgctgca 2580
gctgctgggc atctgtgtgt ggtttgtggt ggacccctcc cactcggtgg tggacttcca 2640
ggaccagcgg acactcgacc cccgcttcgc caggggtgtg ctcaagtgtg acatctcgga 2700
cctgtcgctc atctgcctgc tgggctacag catgctgctc atggtcacgt gcaccgtgta 2760
tgccatcaag acacgcggcg tgcccgagac cttcaatgag gccaagccca ttggcttcac 2820
catgtacacc acttgcatcg tctggctggc cttcatcccc atcttctttg gcacctcgca 2880
gtcggccgac aagctgtaca tccagacgac gacgctgacg gtctcggtga gtctgagcgc 2940
ctcggtgtcc ctgggaatgc tctacatgcc caaagtctac atcatcctct tccacccgga 3000
gcagaacgtg cccaagcgca agcgcagcct caaagccgtc gttacggcgg ccaccatgtc 3060
caacaagttc acgcagaagg gcaacttccg gcccaacgga gaggccaagt ctgagctctg 3120
cgagaacctt gaggccccag cgctggccac caaacagact tacgtcactt acaccaacca 3180
tgcaatctag cgagtccatg gagctgagca gcaggaggag gagccgtgac cctgtggaag 3240
gtgcgtcggg ccagggccac acccaagggc ccagctgtct tgcctgcccg tgggcaccca 3300
cggacgtggc ttggtgctga ggatagcaga gcccccagcc atcactgctg gcagcctggg 3360
caaaccgggt gagcaacagg aggacgaggg gccggggcgg tgccaggcta ccacaagaac 3420
ctgcgtcttg gaccattgcc cctcccggcc ccaaaccaca ggggctcagg tcgtgtgggc 3480
cccagtgcta gatctctccc tcccttcgtc tctgtctgtg ctgttggcga cccctctgtc 3540
tgtctccagc cctgtctttc tgttctctta tctctttgtt tcaccttttc cctctctggc 3600
gtccccggct gcttgtactc ttggcctttt ctgtgtctcc tttctggctc ttgcctccgc 3660
ctctctctct catcctcttt gtcctcagct cctcctgctt tcttgggtcc caccagtgtc 3720
acttttctgc cgttttcttt cctgttctcc tctgcttcat tctcgtccag ccattgctcc 3780
cctctccctg ccacccttcc ccagttcacc aaaccttaca tgttgcaaaa gagaaaaaag 3840
gaaaaaaaat caaaacacaa aaaagccaaa acgaaaacaa atctcgagtg tgttgccaag 3900
tgctgcgtcc tcctggtggc ctctgtgtgt gtccctgtgg cccgcagcct gcccgcctgc 3960
cccgcccatc tgccgtgtgt cttgcccgcc tgccccgccc gtctgccgtc tgtcttgccc 4020
gcctgcccgc ctgcccctcc tgccgaccac acggagttca gtgcctgggt gtttggtgat 4080
ggttattgac gacaatgtgt agcgcatgat tgtttttata ccaagaacat ttctaataaa 4140
aataaacaca tggttttgca cccgggctcc acatccactg agggtcctgc catgggacca 4200
caggctcagc ctgcagctgg agggcttaga cctagaggga agcgggaact gggctctgga 4260

-continued

```
gacccagggc ttgggggctg tggagactgc tccctaggct gggatctagt gtggtgtggt   4320
gaggccttgg gcatggaggg gccagattcc caggtaaggg gcagggacat tgcaggaaat   4380
tccaggaatc agcacctagt agtcccctaa ttagggggta tgctctgtcc cctgccctgc   4440
agccctggga gggtaacatt tctgccttgc ctgtcctctg tctcacaccc ctcacacctg   4500
ggactgccct tccacccctg cccccataac ctgtgcctct ctccttccag ccaggaagtc   4560
ctcttcttga gaagttagct tcccgggctg ccagcactca tagccgtccc ctcctgcttg   4620
tgttggctcc aggctcgggt gctaagaaga tgtgtgtctg tcctggagat cagtgtgttg   4680
ttatgtgtcc acgtgggccc acaagtgcac ggcacaggca tggccgtgtg gctgtgttgg   4740
ctgtgttggc tgtgtgtctg tgtgcacgtc cagcgcctcc atgcgcatgc gtgcctgtct   4800
tgtttgcgtg tctgatcatc tgtttgggcc ccggtggctc atgcagatgc ctgtctcagg   4860
cccatggcga gtgttcacct cagctggctt ccctggcagg ttgggaggtg ggaaacagga   4920
gcgcttaggg gctgggctct ggctggggta aattatagag ccagaaacac aatgaggcca   4980
taggcagcag ctggagcctg ggctgcctgt gccgtcccct cctgccctgc ccctgggtcc   5040
tgcacccccct cccacctcca ggctagctga cagcgctatg gagcacagtg gaagggactg   5100
gaggaaccct aggcaggggg ccacgcaggg acagagtatg agagtgtgtg tataactgag   5160
gctgggacat tgaatcatgc caggtatgtc ttctccatca gcccactctt actcctggcc   5220
tgggcatctc acacatctgt gcataggaaa tctcttcttc cctggggtct gtgtgcagca   5280
cctagtagat gctcaataaa tgtttgtgtg agggaaggag acaggaaagg aagtgtctcg   5340
ctgatcatct tgcggaatgg ttcctaagac ctctgcccag gaaagattcc acccagtgct   5400
ccagcccggt caggcagaac taggttgcca gatcaagggt atctcccaaa agcttccagg   5460
gcagttgggg gtgggggggt ggggggtagg gatggggaat gcagaagcgg gtgcagccag   5520
ctctccccca gggtgactct ggcagcaccc ccatcctggg caccctgcct gctctgtggc   5580
tcacgcccct cctgaagtga ctgatgctct gaggcccaag gctaggtcca gggcagggcc   5640
tgcaggggtt tcatgctcag tccaggactt gcctaggtcc ccctacatct gtggggcccc   5700
catctaggtt ctaacaggag aatcacctct ccaaggggga tgctgcccct cggctcccct   5760
tggctctcag gaggggccct cagggactac cagtcccctg ccagtgggaa gaaatagccc   5820
tgccctcagg gagcttccag tgtgatgggg gagatacagc agactgtgtc ccaaagtaaa   5880
atgactgtta gaatgaggtg ggtggaggag ggaagccttg ggtgggtgtg actttgggca   5940
tctgagcctg ggtgcagagg gtgggctctg tgggcctgag gtggacagga gggaaccagg   6000
ccctagcaag acttttgcca gctagacctg ctgcagcagt tgggagggtg ggtgctgctg   6060
gagtcctggg tccatcacct agaaggctca ggccagtgca gccagggctg ggcccacag   6120
ctggcctggg tgggacctgc cctgatgccc atggcaggag ggacgcctgg cccttcacaa   6180
ttggcttggc tgctcacctt tgctctcatc ctcaattatt aatgactgga gaaagctgct   6240
aagtatcttc agaatgttag atttcaacaa gatggggggt tcagggtccc tggcaccctg   6300
gatagggagc cagcggcccc tagagacctt tgctgtgtgc agggggtatg tgctcacccc   6360
cgtggcctca gcctcctcaa tgtctgaatg aaggattggg ctagcagaca tcccacccca   6420
cagcacactt tctaaccagc aggggaactt ctagacaata gagacgctgg gctccctcca   6480
gaacactgga cctgaacttc tggggggagg gctgggcacg ggcatatttt aaaagctccc   6540
cagcagatgg gccgtgcagt caagtgggcc aagagtggca ccagactttg gggcttgtga   6600
agtcaggagg gagcaacagt gcccactcga gcttgcctgg ggctcaagcc caaggctggg   6660
```

```
ctgctgccag cctgagcaga cacccaggag cttccaggcc agctggatgc acagggcacc   6720

tttgtggaac tcctaggacc ctggggagac ccacctcagg agcagagtct caggtccctt   6780

ccggctctga ggggctgttc tgagctctaa tgtcttatgg tctgcccctc ccatccttac   6840

ttctcaggcc ctggaggcag aggcatagag ccaggcagga cagaggtctc agtgggccac   6900

atgccagctg cccccacact gcctcagcct ccaggcctcc aaggggtcct ggggagcccc   6960

tgagaagatg ctgagcctgc ataaggctgg gcgcccctct ttctgacacc ctcactggct   7020

ccacggctcc cccttcccat cccaggtttc catctgccca ctgaacaggg aggggaaact   7080

gaggcactcc cctggcactg agggctcctt ctgtcatcct gcctgccctg gatggtcctg   7140

gctgcccctc agggcttggc cctggcactg tgagcctcac agggctcaga cccccacccc   7200

caacccagca ctaaatggca ctcggcacca gaatctcact tcagttggca aaagcagcaa   7260

ttagcatgta atgaggcttc ttgctttatt tttaggtaac ctccaaggcc ctgcctgtgt   7320

aattcagccc gccattgctc ggtggataat taaagcatgt caccataa                7368


<210> SEQ ID NO 60
<211> LENGTH: 912
<212> TYPE: PRT
<213> ORGANISM: Homo sapiens

<400> SEQUENCE: 60

Met Pro Gly Lys Arg Gly Leu Gly Trp Trp Trp Ala Arg Leu Pro Leu
1               5                   10                  15

Cys Leu Leu Leu Ser Leu Tyr Gly Pro Trp Met Pro Ser Ser Leu Gly
            20                  25                  30

Lys Pro Lys Gly His Pro His Met Asn Ser Ile Arg Ile Asp Gly Asp
        35                  40                  45

Ile Thr Leu Gly Gly Leu Phe Pro Val His Gly Arg Gly Ser Glu Gly
    50                  55                  60

Lys Pro Cys Gly Glu Leu Lys Lys Glu Lys Gly Ile His Arg Leu Glu
65                  70                  75                  80

Ala Met Leu Phe Ala Leu Asp Arg Ile Asn Asn Asp Pro Asp Leu Leu
                85                  90                  95

Pro Asn Ile Thr Leu Gly Ala Arg Ile Leu Asp Thr Cys Ser Arg Asp
            100                 105                 110

Thr His Ala Leu Glu Gln Ser Leu Thr Phe Val Gln Ala Leu Ile Glu
        115                 120                 125

Lys Asp Gly Thr Glu Val Arg Cys Gly Ser Gly Gly Pro Pro Ile Ile
    130                 135                 140

Thr Lys Pro Glu Arg Val Val Gly Val Ile Gly Ala Ser Gly Ser Ser
145                 150                 155                 160

Val Ser Ile Met Val Ala Asn Ile Leu Arg Leu Phe Lys Ile Pro Gln
                165                 170                 175

Ile Ser Tyr Ala Ser Thr Ala Pro Asp Leu Ser Asp Asn Ser Arg Tyr
            180                 185                 190

Asp Phe Phe Ser Arg Val Val Pro Ser Asp Thr Tyr Gln Ala Gln Ala
        195                 200                 205

Met Val Asp Ile Val Arg Ala Leu Lys Trp Asn Tyr Val Ser Thr Val
    210                 215                 220

Ala Ser Glu Gly Ser Tyr Gly Glu Ser Gly Val Glu Ala Phe Ile Gln
225                 230                 235                 240

Lys Ser Arg Glu Asp Gly Gly Val Cys Ile Ala Gln Ser Val Lys Ile
```

-continued

```
                245                 250                 255

Pro Arg Glu Pro Lys Ala Gly Glu Phe Asp Lys Ile Ile Arg Arg Leu
            260                 265                 270

Leu Glu Thr Ser Asn Ala Arg Ala Val Ile Ile Phe Ala Asn Glu Asp
        275                 280                 285

Asp Ile Arg Arg Val Leu Glu Ala Ala Arg Arg Ala Asn Gln Thr Gly
    290                 295                 300

His Phe Phe Trp Met Gly Ser Asp Ser Trp Gly Ser Lys Ile Ala Pro
305                 310                 315                 320

Val Leu His Leu Glu Glu Val Ala Glu Gly Ala Val Thr Ile Leu Pro
                325                 330                 335

Lys Arg Met Ser Val Arg Gly Phe Asp Arg Tyr Phe Ser Ser Arg Thr
            340                 345                 350

Leu Asp Asn Asn Arg Arg Asn Ile Trp Phe Ala Glu Phe Trp Glu Asp
        355                 360                 365

Asn Phe His Cys Lys Leu Ser Arg His Ala Leu Lys Lys Gly Ser His
    370                 375                 380

Val Lys Lys Cys Thr Asn Arg Glu Arg Ile Gly Gln Asp Ser Ala Tyr
385                 390                 395                 400

Glu Gln Glu Gly Lys Val Gln Phe Val Ile Asp Ala Val Tyr Ala Met
                405                 410                 415

Gly His Ala Leu His Ala Met His Arg Asp Leu Cys Pro Gly Arg Val
            420                 425                 430

Gly Leu Cys Pro Arg Met Asp Pro Val Asp Gly Thr Gln Leu Leu Lys
        435                 440                 445

Tyr Ile Arg Asn Val Asn Phe Ser Gly Ile Ala Gly Asn Pro Val Thr
    450                 455                 460

Phe Asn Glu Asn Gly Asp Ala Pro Gly Arg Tyr Asp Ile Tyr Gln Tyr
465                 470                 475                 480

Gln Leu Arg Asn Asp Ser Ala Glu Tyr Lys Val Ile Gly Ser Trp Thr
                485                 490                 495

Asp His Leu His Leu Arg Ile Glu Arg Met His Trp Pro Gly Ser Gly
            500                 505                 510

Gln Gln Leu Pro Arg Ser Ile Cys Ser Leu Pro Cys Gln Pro Gly Glu
        515                 520                 525

Arg Lys Lys Thr Val Lys Gly Met Pro Cys Cys Trp His Cys Glu Pro
    530                 535                 540

Cys Thr Gly Tyr Gln Tyr Gln Val Asp Arg Tyr Thr Cys Lys Thr Cys
545                 550                 555                 560

Pro Tyr Asp Met Arg Pro Thr Glu Asn Arg Thr Gly Cys Arg Pro Ile
                565                 570                 575

Pro Ile Ile Lys Leu Glu Trp Gly Ser Pro Trp Ala Val Leu Pro Leu
            580                 585                 590

Phe Leu Ala Val Val Gly Ile Ala Ala Thr Leu Phe Val Val Ile Thr
        595                 600                 605

Phe Val Arg Tyr Asn Asp Thr Pro Ile Val Lys Ala Ser Gly Arg Glu
    610                 615                 620

Leu Ser Tyr Val Leu Leu Ala Gly Ile Phe Leu Cys Tyr Ala Thr Thr
625                 630                 635                 640

Phe Leu Met Ile Ala Glu Pro Asp Leu Gly Thr Cys Ser Leu Arg Arg
                645                 650                 655

Ile Phe Leu Gly Leu Gly Met Ser Ile Ser Tyr Ala Ala Leu Leu Thr
            660                 665                 670
```

Lys Thr Asn Arg Ile Tyr Arg Ile Phe Glu Gln Gly Lys Arg Ser Val
675 680 685

Ser Ala Pro Arg Phe Ile Ser Pro Ala Ser Gln Leu Ala Ile Thr Phe
690 695 700

Ser Leu Ile Ser Leu Gln Leu Leu Gly Ile Cys Val Trp Phe Val Val
705 710 715 720

Asp Pro Ser His Ser Val Val Asp Phe Gln Asp Gln Arg Thr Leu Asp
725 730 735

Pro Arg Phe Ala Arg Gly Val Leu Lys Cys Asp Ile Ser Asp Leu Ser
740 745 750

Leu Ile Cys Leu Leu Gly Tyr Ser Met Leu Leu Met Val Thr Cys Thr
755 760 765

Val Tyr Ala Ile Lys Thr Arg Gly Val Pro Glu Thr Phe Asn Glu Ala
770 775 780

Lys Pro Ile Gly Phe Thr Met Tyr Thr Thr Cys Ile Val Trp Leu Ala
785 790 795 800

Phe Ile Pro Ile Phe Phe Gly Thr Ser Gln Ser Ala Asp Lys Leu Tyr
805 810 815

Ile Gln Thr Thr Thr Leu Thr Val Ser Val Ser Leu Ser Ala Ser Val
820 825 830

Ser Leu Gly Met Leu Tyr Met Pro Lys Val Tyr Ile Ile Leu Phe His
835 840 845

Pro Glu Gln Asn Val Pro Lys Arg Lys Arg Ser Leu Lys Ala Val Val
850 855 860

Thr Ala Ala Thr Met Ser Asn Lys Phe Thr Gln Lys Gly Asn Phe Arg
865 870 875 880

Pro Asn Gly Glu Ala Lys Ser Glu Leu Cys Glu Asn Leu Glu Ala Pro
885 890 895

Ala Leu Ala Thr Lys Gln Thr Tyr Val Thr Tyr Thr Asn His Ala Ile
900 905 910

<210> SEQ ID NO 61
<211> LENGTH: 4959
<212> TYPE: DNA
<213> ORGANISM: Homo sapiens

<400> SEQUENCE: 61
acttgtatct tttcatatca aaaatgggag gtgacaccca gtttaaggaa aattccaagg 60
catttgtctc gactaatgtg aaagatgatt acagtggcca gaggactgcc aaggctcctt 120
ctcaagctgc ttgagtcaat gagggtagac gcaccctctg aagatggtga ctccctcctg 180
agaagctgga ccccttggta aaagacaagg ccttctccaa gaagaatatg aaagtgttac 240
tcagacttat ttgtttcata gctctactga tttcttctct ggaggctgat aaatgcaagg 300
aacgtgaaga aaaaataatt ttagtgtcat ctgcaaatga aattgatgtt cgtccctgtc 360
ctcttaaccc aaatgaacac aaaggcacta taacttggta taaagatgac agcaagacac 420
ctgtatctac agaacaagcc tccaggattc atcaacacaa agagaaactt tggtttgttc 480
ctgctaaggt ggaggattca ggacattact attgcgtggt aagaaattca tcttactgcc 540
tcagaattaa aataagtgca aaatttgtgg agaatgagcc taacttatgt tataatgcac 600
aagccatatt taagcagaaa ctacccgttg caggagacgg aggacttgtg tgcccttata 660
tggagttttt taaaaatgaa aataatgagt tacctaaatt acagtggtat aaggattgca 720
aacctctact tcttgacaat atacacttta gtggagtcaa agataggctc atcgtgatga 780

```
atgtggctga aaagcataga gggaactata cttgtcatgc atcctacaca tacttgggca    840
agcaatatcc tattacccgg gtaatagaat ttattactct agaggaaaac aaacccacaa    900
ggcctgtgat tgtgagccca gctaatgaga caatggaagt agacttggga tcccagatac    960
aattgatctg taatgtcacc ggccagttga gtgacattgc ttactggaag tggaatgggt   1020
cagtaattga tgaagatgac ccagtgctag ggggaagacta ttacagtgtg gaaaatcctg   1080
caaacaaaag aaggagtacc ctcatcacag tgcttaatat atcggaaatt gaaagtagat   1140
tttataaaca tccatttacc tgttttgcca agaatacaca tggtatagat gcagcatata   1200
tccagttaat atatccagtc actaatttcc agaagcacat gattggtata tgtgtcacgt   1260
tgacagtcat aattgtgtgt tctgttttca tctataaaat cttcaagatt gacattgtgc   1320
tttggtacag ggattcctgc tatgattttc tcccaataaa agtcttgcct gaggtcttgg   1380
aaaaacagtg tggatataag ctgttcattt atggaaggga tgactacgtt ggggaagaca   1440
ttgttgaggt cattaatgaa aacgtaaaga aaagcagaag actgattatc attttagtca   1500
gagaaacatc aggcttcagc tggctgggtg gttcatctga agagcaaata gccatgtata   1560
atgctcttgt tcaggatgga attaaagttg tcctgcttga gctggagaaa atccaagact   1620
atgagaaaat gccagaatcg attaaattca ttaagcagaa acatggggct atccgctggt   1680
caggggactt tacacaggga ccacagtctg caaagacaag gttctggaag aatgtcaggt   1740
accacatgcc agtccagcga cggtcacctt catctaaaca ccagttactg tcaccagcca   1800
ctaaggagaa actgcaaaga gaggctcacg tgcctctcgg gtagcatgga gaagttgcca   1860
agagttcttt aggtgcctcc tgtcttatgg cgttgcaggc caggttatgc ctcatgctga   1920
cttgcagagt tcatggaatg taactatatc atcctttatc cctgaggtca cctggaatca   1980
gattattaag ggaataagcc atgacgtcaa tagcagccca gggcacttca gagtagaggg   2040
cttgggaaga tcttttaaaa aggcagtagg cccggtgtgg tggctcacgc ctataatccc   2100
agcactttgg gaggctgaag tgggtggatc accagaggtc aggagttcga gaccagccca   2160
gccaacatgg caaaacccca tctctactaa aaatacaaaa atgagctagg catggtggca   2220
cacgcctgta atcccagcta cacctgaggc tgaggcagga gaattgcttg aaccggggag   2280
acggaggttg cagtgagccg agtttgggcc actgcactct agcctggcaa cagagcaaga   2340
ctccgtctca aaaaaagggc aataaatgcc ctctctgaat gtttgaactg ccaagaaaag   2400
gcatggagac agcgaactag aagaaagggc aagaaggaaa tagccaccgt ctacagatgg   2460
cttagttaag tcatccacag cccaagggcg gggctatgcc ttgtctgggg accctgtaga   2520
gtcactgacc ctggagcggc tctcctgaga ggtgctgcag gcaaagtgag actgacacct   2580
cactgaggaa gggagacata ttcttggaga actttccatc tgcttgtatt ttccatacac   2640
atccccagcc agaagttagt gtccgaagac cgaattttat tttacagagc ttgaaaactc   2700
acttcaatga acaaagggat tctccaggat tccaaagttt tgaagtcatc ttagctttcc   2760
acaggaggga gagaacttaa aaaagcaaca gtagcaggga attgatccac ttcttaatgc   2820
tttcctccct ggcatgacca tcctgtcctt tgttattatc ctgcatttta cgtctttgga   2880
ggaacagctc cctagtggct tcctccgtct gcaatgtccc ttgcacagcc cacacatgaa   2940
ccatccttcc catgatgccg ctcttctgtc atcccgctcc tgctgaaaca cctcccaggg   3000
gctccacctg ttcaggagct gaagcccatg ctttcccacc agcatgtcac tcccagacca   3060
cctccctgcc ctgtcctcca gcttcccctc gctgtcctgc tgtgtgaatt cccaggttgg   3120
```

-continued cctggtggcc atgtcgcctg cccccagcac tcctctgtct ctgctcttgc ctgcaccctt 3180
cctcctcctt tgcctaggag gccttctcgc attttctcta gctgatcaga attttaccaa 3240
aattcagaac atcctccaat tccacagtct ctgggagact ttccctaaga ggcgacttcc 3300
tctccagcct tctctctctg gtcaggccca ctgcagagat ggtggtgagc acatctggga 3360
ggctggtctc cctccagctg gaattgctgc tctctgaggg agaggctgtg gtggctgtct 3420
ctgtccctca ctgccttcca ggagcaattt gcacatgtaa catagattta tgtaatgctt 3480
tatgtttaaa aacattcccc aattatctta tttaattttt gcaattattc taattttata 3540
tatagagaaa gtgacctatt ttttaaaaaa atcacactct aagttctatt gaacctagga 3600
cttgagcctc catttctggc ttctagtctg gtgttctgag tacttgattt caggtcaata 3660
acggtccccc ctcactccac actggcacgt ttgtgagaag aaatgacatt ttgctaggaa 3720
gtgaccgagt ctaggaatgc ttttattcaa gacaccaaat tccaaacttc taaatgttgg 3780
aattttcaaa aattgtgttt agattttatg aaaaactctt ctactttcat ctattctttc 3840
cctagaggca aacatttctt aaaatgtttc attttcatta aaaatgaaag ccaaatttat 3900
atgccaccga ttgcaggaca caagcacagt tttaagagtt gtatgaacat ggagaggact 3960
tttggttttt atatttctcg tatttaatat gggtgaacac caacttttat ttggaataat 4020
aattttcctc ctaaacaaaa acacattgag tttaagtctc tgactcttgc ctttccacct 4080
gctttctcct gggcccgctt tgcctgcttg aaggaacagt gctgttctgg agctgctgtt 4140
ccaacagaca gggcctagct ttcatttgac acacagacta cagccagaag cccatggagc 4200
agggatgtca cgtcttgaaa agcctattag atgttttaca aatttaattt tgcagattat 4260
tttagtctgt catccagaaa atgtgtcagc atgcatagtg ctaagaaagc aagccaattt 4320
ggaaacttag gttagtgaca aaattggcca gagagtgggg gtgatgatga ccaagaatta 4380
caagtagaat ggcagctgga atttaaggag ggacaagaat caatggataa gcgtgggtgg 4440
aggaagatcc aaacagaaaa gtgcaaagtt attccccatc ttccaagggt tgaattctgg 4500
aggaagaaga cacattccta gttccccgtg aacttccttt gacttattgt ccccactaaa 4560
acaaaacaaa aaacttttaa tgccttccac attaattaga ttttcttgca gttttttttat 4620 ggcatttttt taaagatgcc ctaagtgttg aagaagagtt tgcaaatgca acaaaatatt 4680
taattaccgg ttgttaaaac tggtttagca caatttatat tttccctctc ttgcctttct 4740
tatttgcaat aaaaggtatt gagccatttt ttaaatgaca tttttgataa attatgtttg 4800
tactagttga tgaaggagtt ttttttaacc tgtttatata attttgcagc agaagccaaa 4860
ttttttgtat attaaagcac caaattcatg tacagcatgc atcacggatc aatagactgt 4920
acttattttc caataaaatt ttcaaacttt gtactgtta 4959

<210> SEQ ID NO 62
<211> LENGTH: 569
<212> TYPE: PRT
<213> ORGANISM: Homo sapiens

<400> SEQUENCE: 62

Met Lys Val Leu Leu Arg Leu Ile Cys Phe Ile Ala Leu Leu Ile Ser
1 5 10 15

Ser Leu Glu Ala Asp Lys Cys Lys Glu Arg Glu Glu Lys Ile Ile Leu
20 25 30

Val Ser Ser Ala Asn Glu Ile Asp Val Arg Pro Cys Pro Leu Asn Pro
35 40 45

-continued

```
Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
    290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                325                 330                 335

His Met Ile Gly Ile Cys Val Thr Leu Thr Val Ile Ile Val Cys Ser
            340                 345                 350

Val Phe Ile Tyr Lys Ile Phe Lys Ile Asp Ile Val Leu Trp Tyr Arg
        355                 360                 365

Asp Ser Cys Tyr Asp Phe Leu Pro Ile Lys Ala Ser Asp Gly Lys Thr
    370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
                405                 410                 415

Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
        435                 440                 445

Arg Leu Ile Ile Ile Leu Val Arg Glu Thr Ser Gly Phe Ser Trp Leu
    450                 455                 460

Gly Gly Ser Ser Glu Glu Gln Ile Ala Met Tyr Asn Ala Leu Val Gln
```

465 470 475 480

Asp Gly Ile Lys Val Val Leu Leu Glu Leu Glu Lys Ile Gln Asp Tyr
485 490 495

Glu Lys Met Pro Glu Ser Ile Lys Phe Ile Lys Gln Lys His Gly Ala
500 505 510

Ile Arg Trp Ser Gly Asp Phe Thr Gln Gly Pro Gln Ser Ala Lys Thr
515 520 525

Arg Phe Trp Lys Asn Val Arg Tyr His Met Pro Val Gln Arg Arg Ser
530 535 540

Pro Ser Ser Lys His Gln Leu Leu Ser Pro Ala Thr Lys Glu Lys Leu
545 550 555 560

Gln Arg Glu Ala His Val Pro Leu Gly
565

<210> SEQ ID NO 63
<211> LENGTH: 3142
<212> TYPE: DNA
<213> ORGANISM: Homo sapiens

<400> SEQUENCE: 63
aacttcctgt tgtcaccaca cctctgagtc gtctgagctc actgtgagca aaatcccaca 60
gtggaaactc ttaagcctct gcgaagtaaa tcattcttgt gaatgtgaca cacgatctct 120
ccagtttcca tatgttgaga ttctacttat tcatcagttt gttgtgcttg tcaagatcag 180
acgcagaaga aacatgtcct tcattcacca ggctgagctt tcacagtgca gtggttggta 240
cgggactaaa tgtgaggctg atgctctaca caaggaaaaa cctgacctgc gcacaaacca 300
tcaactcctc agcttttggg aacttgaatg tgaccaagaa aaccaccttc attgtccatg 360
gattcaggcc aacaggctcc cctcctgttt ggatggatga cttagtaaag ggtttgctct 420
ctgttgaaga catgaacgta gttgttgttg attggaatcg aggagctaca actttaatat 480
atacccatgc ctctagtaag accagaaaag tagccatggt cttgaaggaa tttattgacc 540
agatgttggc agaaggagct tctcttgatg acatttacat gatcggagta agtctaggag 600
cccacatatc tgggtttgtt ggagagatgt acgatggatg gctggggaga attacaggcc 660
tcgaccctgc aggccccttta ttcaacggga aacctcacca agacagatta gatcccagtg 720
atgcgcagtt tgttgatgtc atccattccg acactgatgg atttcagtat tttaaatgtg 780
accaccagag gtctgtatac ctgtacctgt cttccctgag agagagctgc accatcactg 840
cgtatccctg tgactcctac caggattata ggaatggcaa gtgtgtcagc tgcggcacgt 900
cacaaaaaga gtcctgtccc cttctgggct attatgctga taattggaaa gaccatctaa 960
gggggaaaga tcctccaatg acgaaggcat tctttgacac agctgaggag agcccattct 1020
gcatgtatca ttactttgtg gatattataa catggaacaa gaatgtaaga agaggggaca 1080
ttaccatcaa attgagagac aaagctggaa acaccacaga atccaaaatc aatcatgaac 1140
ccaccacatt tcagaaatat caccaagtga gtctacttgc aagatttaat caagatctgg 1200
ataaagtggc tgcaatttcc ttgatgttct ctacaggatc tctaataggc ccaaggtaca 1260
agctcaggat tctccgaatg aagttaaggt cccttgccca tccggagagg cctcagctgt 1320
gtcggtatga tcttgtcctg atggaaaacg ttgaaacagt cttccaacct attctttgcc 1380
cagagttgca gttgtaactg ttgccaggac acatggccat aaataataga aagaaagcta 1440
caaccacagg ctgtttgaaa gcttcacctc acctttctgc aaggcagaaa aagtatgaaa 1500
aaaaccaagg cttttttcag tagcgtccta tggatgtcac attgtacatc aaacaacctt 1560

```
gtgattataa aacgatcctg ggaaggagcc cctaactagg gcaagtcaga aatagccagg   1620

ctcgcagcag cgcagcgctg tgtctgctgt gtcctggggc ctcccttgtt ccgacctgtc   1680

aattctgctg cctgtcacgc gggtggttct gcccatcgcg gctgcgggtc aagcatcttc   1740

aagggaagga cggactggag gcctcaccgt ggactcaact ctgcattctc cgtgccacat   1800

tcctccagtt cccacacgta gaagggaacg aaactgacgt ctacctcatg ggctgctgt   1860

gtgggtttgg gaggcaaaaa tctatgaagg gttttttgaa atcccatagg tgccacatct   1920

atgagatgtt tgataaatgt gaatatgctt ttacatttgg gcttatctaa tttgcaataa   1980

gagagcctct ctctatcaac accagcttct ctctcgggct gtttgctcag ggaaggcaag   2040

aaagccacgt gctggccctc tgccttctct aaagtgctgt tggagcatgg aggagctgga   2100

ggagatgggg atggactgac agctaagagg gcggctgctg ggactagata gtggatgaag   2160

aaagaaggac gaggaagccg tggggcagcc tcttcacatg ggacagggg atggagcatg   2220

aggcaaggga aggaaaagca gagcttattt ttcacctaag gtggagaagg atcactttac   2280

aggcaacgct cattttaagc aacccttaag aaatgtttat gtttctttat taccaatgta   2340

atctatgatt attgaaggaa atttagaaaa tgcgtagata caaaattaaa aaaaaatact   2400

gtccacgatc ctattagagg taattaatgt tagccttttg gaacaaggct gtcacctatt   2460

ttgccaacac gtgaattcaa aacatgaacc ggtttgcttt tggagaatct gaagactcca   2520

gtttgaggaa tcctttgctt ccctggaggt agatgctgtc tgcaaatcta gaatgacagc   2580

aggagtccag tcaagaggtc ctgtcaggcc aaggccagaa agaagggagg acaatccctg   2640

gggccagatg cccagtgtga ggggaggcat gatctgtccc atggctgtgg ccactgcagg   2700

aaggtctgtg aaaaggaggt gacaggccca gtcacctcct cttcacccaa gtgattgctc   2760

cttcaactgc tatctgtgaa aatagccttt gttatgaaga aattgactct ctctctcttt   2820

ttttttttt ggagttgcct aggctggagt gcaatggtac gatctcagct cactgcaacc   2880

tccacctccc aggttcaatt gattctcctg cctcagcctc ctgagtagct gggattacag   2940

gcatgtgcca ccacacccgg ctaattttg tatttttatt agagacaggg tttcaccacg   3000

ttagccaggc tcgtctcgaa ctcctgtcct caggtgacta cccgtctcgg cctcccaaag   3060

tgctgggatt acaggcatga gccaccacac ccggccaaaa atggattctc tatgtcataa   3120

attaaagaaa tctataaatg ta                                            3142


<210> SEQ ID NO 64
<211> LENGTH: 451
<212> TYPE: PRT
<213> ORGANISM: Homo sapiens

<400> SEQUENCE: 64

Met Leu Arg Phe Tyr Leu Phe Ile Ser Leu Leu Cys Leu Ser Arg Ser
1               5                   10                  15

Asp Ala Glu Glu Thr Cys Pro Ser Phe Thr Arg Leu Ser Phe His Ser
            20                  25                  30

Ala Val Val Gly Thr Gly Leu Asn Val Arg Leu Met Leu Tyr Thr Arg
        35                  40                  45

Lys Asn Leu Thr Cys Ala Gln Thr Ile Asn Ser Ser Ala Phe Gly Asn
    50                  55                  60

Leu Asn Val Thr Lys Lys Thr Thr Phe Ile Val His Gly Phe Arg Pro
65                  70                  75                  80

Thr Gly Ser Pro Pro Val Trp Met Asp Asp Leu Val Lys Gly Leu Leu
```

```
                85                  90                  95

Ser Val Glu Asp Met Asn Val Val Val Val Asp Trp Asn Arg Gly Ala
            100                 105                 110

Thr Thr Leu Ile Tyr Thr His Ala Ser Ser Lys Thr Arg Lys Val Ala
        115                 120                 125

Met Val Leu Lys Glu Phe Ile Asp Gln Met Leu Ala Glu Gly Ala Ser
    130                 135                 140

Leu Asp Asp Ile Tyr Met Ile Gly Val Ser Leu Gly Ala His Ile Ser
145                 150                 155                 160

Gly Phe Val Gly Glu Met Tyr Asp Gly Trp Leu Gly Arg Ile Thr Gly
                165                 170                 175

Leu Asp Pro Ala Gly Pro Leu Phe Asn Gly Lys Pro His Gln Asp Arg
            180                 185                 190

Leu Asp Pro Ser Asp Ala Gln Phe Val Asp Val Ile His Ser Asp Thr
        195                 200                 205

Asp Ala Leu Gly Tyr Lys Glu Pro Leu Gly Asn Ile Asp Phe Tyr Pro
    210                 215                 220

Asn Gly Gly Leu Asp Gln Pro Gly Cys Pro Lys Thr Ile Leu Gly Gly
225                 230                 235                 240

Phe Gln Tyr Phe Lys Cys Asp His Gln Arg Ser Val Tyr Leu Tyr Leu
                245                 250                 255

Ser Ser Leu Arg Glu Ser Cys Thr Ile Thr Ala Tyr Pro Cys Asp Ser
            260                 265                 270

Tyr Gln Asp Tyr Arg Asn Gly Lys Cys Val Ser Cys Gly Thr Ser Gln
        275                 280                 285

Lys Glu Ser Cys Pro Leu Leu Gly Tyr Tyr Ala Asp Asn Trp Lys Asp
    290                 295                 300

His Leu Arg Gly Lys Asp Pro Pro Met Thr Lys Ala Phe Phe Asp Thr
305                 310                 315                 320

Ala Glu Glu Ser Pro Phe Cys Met Tyr His Tyr Phe Val Asp Ile Ile
                325                 330                 335

Thr Trp Asn Lys Asn Val Arg Arg Gly Asp Ile Thr Ile Lys Leu Arg
            340                 345                 350

Asp Lys Ala Gly Asn Thr Thr Glu Ser Lys Ile Asn His Glu Pro Thr
        355                 360                 365

Thr Phe Gln Lys Tyr His Gln Val Ser Leu Leu Ala Arg Phe Asn Gln
    370                 375                 380

Asp Leu Asp Lys Val Ala Ala Ile Ser Leu Met Phe Ser Thr Gly Ser
385                 390                 395                 400

Leu Ile Gly Pro Arg Tyr Lys Leu Arg Ile Leu Arg Met Lys Leu Arg
                405                 410                 415

Ser Leu Ala His Pro Glu Arg Pro Gln Leu Cys Arg Tyr Asp Leu Val
            420                 425                 430

Leu Met Glu Asn Val Glu Thr Val Phe Gln Pro Ile Leu Cys Pro Glu
        435                 440                 445

Leu Gln Leu
    450


<210> SEQ ID NO 65
<211> LENGTH: 11140
<212> TYPE: DNA
<213> ORGANISM: Homo sapiens

<400> SEQUENCE: 65
```

```
aggcaggggg cggcaacatg gcggagtgag cggcggcgtc ggggcttcac aacaacagtg      60
gtggccgtag cagcggcggc agcagcgtca atagcatcgg ccacagcctg agcttcagca     120
ccggccagcg tcgtggccag ctgctcgcgt cctcgggctt ctcggagcgg ctgcagcatc     180
tccgcggggg gcgggccggg ccggacagac cgggagaggg agagagcaga ggcagcggcg     240
gcggcagcgg cagcggcagc ggcacacctg ctgggcgggc acagccgctt gcccggcagc     300
ggttagcggt accgccaccg ccgagaataa gcctgcggat cccccgccgc ctccgcgggg     360
gagagcgccg gagcgggccg ggctgaggcg caggcgggga gcgggcccgg cgccgcggcg     420
ctggtggatg ctggggctcc gaggcgacgg ccgggggggcg ggggccgagg caggtataac    480
ggtaccggcg gcggcagcgc cgctgctctt cccttctcct caggaggggg gccaatggct     540
agcgagaagc cgggcccggg cccggggctc gagcctcagc ccgtggggct cattgccgtc     600
ggggccgctg gcggaggcgg cgggggcagc ggtggtggcg gcaccggggg cagcgggatg     660
ggggagctaa ggggggcgtc cggctccggc tcggtgatgc tccccgcggg gatgattaac     720
ccttcggtgc cgatccgcaa catccggatg aaattcgcag tgttgattgg actcatacag     780
gtcggagagg tcagcaacag ggacatcgtg gagacggtgc tcaacctgct ggttggtgga     840
gaatttgact tggagatgaa ctttattatc caggatgctg agagtataac atgtatgaca     900
gagcttttgg agcactgtga tgtaacatgt caagcagaaa tatggagcat gtttacagcc     960
attctacgaa aaagtgttcg gaatttacag actagcacag aagttgggct aattgaacaa    1020
gtattgctga aaatgagtgc tgtagatgac atgatagcag atcttctagt tgatatgttg    1080
ggggttcttg ccagctacag catcactgtc aaggagttga agcttttgtt cagcatgctt    1140
cgaggagaaa gtggaatctg gccaagacat gcagtaaaat tattatcagt tcttaatcag    1200
atgccacaga gacacggtcc tgatactttt ttcaatttcc ctggttgtag cgctgcggca    1260
attgccttgc ctcctattgc aaagtggcct tatcagaatg gcttcacctt aaacacttgg    1320
tttcgtatgg atccattaaa taatattaat gttgataagg ataaacctta tctttattgt    1380
tttcgtacta gcaaaggagt tggttactct gctcattttg ttggcaactg tttaatagtc    1440
acatcattga agtccaaagg aaaaggtttt cagcattgtg tgaaatatga ttttcaacca    1500
cgcaagtggt acatgatcag cattgtccac atttacaatc gatggaggaa cagtgaaatt    1560
cggtgttatg ttaatggaca actggtatct tatggtgata tggcttggca tgttaacaca    1620
aatgatagct atgacaagtg ctttcttgga tcatcagaaa ctgctgatgc aaatagggta    1680
ttctgtggtc aacttggtgc cgtgtatgtg ttcagtgaag cactcaaccc agcacagata    1740
tttgcaattc atcagttagg acctggatat aagagtacct tcaagtttaa atctgagagt    1800
gatattcatt tggcagaaca tcataaacag gtgttatatg atgggaaact tgcaagtagc    1860
attgccttta catataatgc taaggccact gatgctcagc tctgcctgga atcatcacca    1920
aaagagaatg catcaatttt tgtgcattcc ccacatgctc taatgcttca ggatgtgaaa    1980
gcgatagtaa cacattcaat tcatagtgca attcattcaa ttggagggat tcaagtgctt    2040
tttccacttt ttgcccaatt ggataatagg cagctcaatg acagtcaagt ggaaacaact    2100
gtctgtgcta ctctgttggc attcctggtt gaactactta aaagttcagt agccatgcaa    2160
gaacagatgc tgggtggaaa aggcttttta gtcattggct acttacttga aaagtcatca    2220
agagttcata taactagagc tgtcctggag caatttttat cttttgcaaa ataccttgat    2280
ggtttatctc atggagcacc tttgctgaag cagctttgtg atcacatttt atttaaccca    2340
gccatctgga tacatacacc tgcaaaggtt cagctttccc tatacacata tttgtctgct    2400
```

```
gaatttattg gaactgctac catctacacc accatacgca gagtaggaac agtattacag   2460
ctaatgcaca ccttaaaata ttactactgg gttattaatc ctgctgacag tagtggcatt   2520
acacctaaag gattagatgg tccccggcca tcacaaaaag aaattatatc actgagggca   2580
tttatgctac tttttctgaa acagctgata ctaaaggatc gaggggtcaa ggaagatgaa   2640
cttcagagta tattaaatta cctacttacg atgcatgagg atgaaaatat tcatgatgtg   2700
ctacagttac tggtggcttt aatgtcggaa cacccagcct caatgatacc agcatttgat   2760
caaagaaatg gaataagggt gatctacaaa ttattggctt ctaaaagtga aagtatttgg   2820
gttcaagctt tgaaggttct gggatacttt ctgaagcatt taggtcacaa gagaaaagtt   2880
gaaattatgc acacccatag tcttttcact cttcttggag aaaggctgat gttgcataca   2940
aacactgtga ctgtcaccac atacaacaca ctttatgaga tcttgacaga acaagtatgt   3000
actcaggtcg tacacaaacc acatccagag ccagattcta cagtgaaaat tcagaatcca   3060
atgattctta aagtggtggc aactttgtta aaaaactcta caccaagtgc agagctgatg   3120
gaagttcgtc gtttattttt atctgatatg ataaaacttt tcagtaacag ccgtgaaaat   3180
agaagatgct tattgcagtg ttcagtgtgg caggattgga tgttttctct tggctatatc   3240
aatcctaaaa attctgagga acagaagatt accgaaatgg tctacaatat cttccggatt   3300
cttttgtatc atgcaataaa atatgaatgg ggaggctgga gagtctgggt ggataccctc   3360
tcaatagccc attccaaggt cacttatgaa gctcataagg aatacctagc caaaatgtat   3420
gaggaatatc aaagacaaga ggaggaaaac attaaaaagg gaaagaaagg gaatgtgagc   3480
accatctctg gtctttcatc acagacaaca ggagcaaaag gtggaatgga aattcgagag   3540
atagaagatc tttcacaaag ccagagccca gaaagtgaga ccgattaccc tgtcagcaca   3600
gatactcgag acttactcat gtcaacaaaa gtgtcagatg atattcttgg aaattcagat   3660
agaccaggaa gtggtgtaca tgtggaagta catgatcttt tagtagatat aaaagcagag   3720
aaagtggaag caacagaagt aaagctcgat gatatggatt tatcaccgga gactttagta   3780
ggtggagaga atggtgccct tgtggaggtt gaatctctgt tggataatgt atatagtgct   3840
gctgttgaga aactccagaa caatgtacat ggaagtgttg gtatcattaa aaaaaatgaa   3900
gaaaaggata atggtccatt gataacatta gcagatgaga aagaagacct tcccaatagt   3960
agtacatcat ttctctttga taaaataccc aaacaggagg aaaaactact tcctgaactt   4020
tctagcaatc acattattcc aaatattcag gacacacaag tacatcttgg tgttagtgat   4080
gatcttggat tgcttgctca catgaccggt agcgtagact taacttgtac atccagtata   4140
atagaagaaa aagaattcaa aatccataca acttcagatg gaatgagcag tatttctgaa   4200
agagacttag cgtcatcaac taaggggctg gagtatgctg aaatgactgc tacaactctg   4260
gaaactgagt cttctagtag caaaattgta ccaaatattg atgcaggaag tataatttca   4320
gatactgaaa ggtctgacga tggcaaagaa tcaggaaaag aaatccgaaa aatccaaaca   4380
actactacga cacaagctgt gcagggtcgg tctatcaccc aacaagaccg agatctccga   4440
gttgatttag gatttcgagg aatgccaatg actgaggaac agcgacgcca gtttagccca   4500
ggtccacgga ctacaatgtt tcgtattcct gagtttaaat ggtctccaat gcaccagcgg   4560
cttctcactg atttactatt tgcattagaa actgatgtac atgtttggag gagccattct   4620
acaaagtctg taatggattt tgtcaatagc aatgaaaata ttatttttgt acataacaca   4680
attcacctca tttcccaaat ggtagacaac atcatcattg cttgtggagg aattttacct   4740
```

ttgctctctg ctgctacatc accaactggt tctaagacgg aattggaaaa tattgaagtg 4800
acacaaggca tgtcagctga gacagcagta actttcctca gccggctgat ggctatggtt 4860
gatgtacttg tgtttgcaag ctctctaaat tttagtgaga ttgaagctga gaaaaacatg 4920
tcttctggag gtttaatgcg acagtgccta agattagttt gttgtgttgc tgtgagaaac 4980
tgtttagaat gtcggcaaag acagagagac aggggaaata aatcttccca tggaagcagt 5040
aaacctcagg aagttcctca aagtgtgact gctacagcag cttcgaagac tccattggaa 5100
aatgttccag gtaacctttc tcctattaag gatccggata gacttcttca ggatgttgat 5160
atcaatcgcc ttcgtgctgt tgtctttcgg gatgtggatg atagcaaaca agcacagttc 5220
ttagctctgg ctgttgttta cttcatttcg gttctgatgg tttccaagta tcgtgacata 5280
ttagaacccc agagagagac tacaagaact ggaagccaac caggtagaaa catcaggcaa 5340
gaaataaatt caccaacaag tacagttgtg gtcataccat ctatccctca tccaagtttg 5400
aaccatggat tccttgccaa gttaattcct gagcagagct ttggccactc attttacaaa 5460
gaaacacctg ctgcatttcc agacaccata aaagaaaaag aaacaccaac tcctggtgaa 5520
gatattcagg tagaaagttc aattccccat acagattcag gaattggaga ggagcaagtg 5580
gctagcatcc tgaatggggc agaattagaa acaagtacag gccctgatgc catgagtgaa 5640
ctcttatcca ctttgtcatc cgaagtgaag aaatcacaag agagcttaac tgaaaatcct 5700
agtgaaacgt tgaagcctgc aacatccata tctagcatta gtcaaaccaa aggcatcaat 5760
gtgaaggaaa tactgaaaag tcttgtggct gctccagttg aaatagcaga atgtggccct 5820
gaacctatcc catacccaga tccagcattg aagagagaaa cacaagctat tcttcctatg 5880
cagtttcatt cctttgacag gagtgttgtg gtgcctgtaa agaaaccacc tccaggtagt 5940
ttagctgtaa ccactgtggg agccactact gctggaagtg ggctgccaac aggcagtacc 6000
tctaatatat ttgctgctac tggagctaca ccaaaaaagta tgattaatac aacaggtgcc 6060
gtggattcag ggtcctcctc ctcttcctcc tcttctagtt ttgtgaatgg tgctactagc 6120
aaaaaacttc cagctgtaca aactgttgct ccaatgccag aagattcagc tgaaaatatg 6180
agcatcactg caaaacttga aagagcgtta gaaaaagttg ctcctcttct tcgtgaaatt 6240
tttgtagact ttgccccatt cctatctcgt acacttcttg gcagtcatgg acaagagcta 6300
ttgatagaag gccttgtttg tatgaagtcc agcacatctg tggttgagct tgttatgctg 6360
ctttgttctc aggaatggca aaactctatt cagaagaatg caggacttgc atttattgag 6420
ctcatcaatg aaggaagatt actgtgccat gctatgaagg accatatagt ccgtgttgca 6480
aatgaagctg agtttatttt gaacagacaa agagccgagg atgtacataa acatgcagag 6540
tttgagtcac agtgtgccca atatgctgct gatagaagag aggaagaaaa gatgtgtgac 6600
catcttatca gtgctgctaa acatcgagat catgtaacag caaatcagct gaaacagaag 6660
attctcaata ttctcacaaa taaacatggt gcttggggag cagtttctca tagccaattg 6720
catgatttct ggcgtttgga ttactgggaa gatgatcttc gtcgaaggag acgatttgtt 6780
cgcaatgcat ttggctccac tcatgctgaa gcattgctga aagctgcaat agaatatggc 6840
acggaagaag atgtagtaaa gtcaaagaaa acattcagaa gtcaagcaat agtgaaccaa 6900
aatgcagaga cagaacttat gctggaagga gacgatgatg cagtcagtct gctacaggag 6960
aaagaaattg acaaccttgc aggcccagtg gttctcagca cccctgccca gctcatcgct 7020
cccgtggtgg tggccaaggg gactctctcc atcaccacga cagaaatcta cttcgaggta 7080
gatgaggatg attctgcctt caagaagatc gacacgaaag ttcttgcata cactgaggga 7140

```
cttcacggaa aatggatgtt cagcgagata cgagctgtat tttcaagacg ttaccttcta   7200
caaaacactg ctttggaagt atttatggca aaccgaacct cagttatgtt taatttccct   7260
gatcaagcaa cagtaaaaaa agttgtctat agcttgcctc gggttggagt agggaccagc   7320
tatggtctgc cacaagccag gaggatatca ttggccactc ctcgacagct ttataaatct   7380
tccaatatga ctcagcgctg gcaaagaagg gaaatttcaa acttcgaata tttgatgttc   7440
cttaatacta ttgcaggacg gacatataat gatctgaacc aatatccagt gtttccgtgg   7500
gtgttaacca actatgaatc agaagagttg gacctgactc ttccaggaaa cttcagggat   7560
ctatcaaagc caattggtgc tttgaacccc aagagagctg tgttttatgc agagcgttat   7620
gagacatggg aagatgatca aagcccaccc taccattata atacccatta ttcaacagca   7680
acatctactt tatcctggct tgttcgaatt gaacctttca caaccttctt cctcaatgca   7740
aatgatggaa aatttgatca tccagatcga accttctcat ccgttgcaag gtcttggaga   7800
actagtcaga gagatacttc tgatgtaaag gaactaattc cagagttcta ctacctacca   7860
gagatgtttg tcaacagtaa tggatataat cttggagtca gagaagatga agtagtggta   7920
aatgatgttg atcttccccc ttgggcaaaa aaacctgaag actttgtgcg gatcaacagg   7980
atggccctag aaagtgaatt tgtttcttgc caacttcatc agtggatcga ccttatattt   8040
ggctataagc agcgaggacc agaagcagtt cgtgctctga atgtttttca ctacttgact   8100
tatgaaggct ctgtgaacct ggatagtatc actgatcctg tgctcaggga ggccatggag   8160
gcacagatac agaactttgg acagacgcca tctcagttgc ttattgagcc acatccgcct   8220
cggagctctg ccatgcacct gtgtttcctt ccacagagtc cgctcatgtt taaagatcag   8280
atgcaacagg atgtgataat ggtgctgaag tttccttcaa attctccagt aacccatgtg   8340
gcagccaaca ctctgcccca cttgaccatc cccgcagtgg tgacagtgac ttgcagccga   8400
ctctttgcag tgaatagatg gcacaacaca gtaggcctca gaggagctcc aggatactcc   8460
ttggatcaag cccaccatct tcccattgaa atggatccat taatagccaa taattcaggt   8520
gtaaacaaac ggcagatcac agacctcgtt gaccagagta tacaaatcaa tgcacattgt   8580
tttgtggtaa cagcagataa tcgctatatt cttatctgtg gattctggga taagagcttc   8640
agagtttatt ctacagaaac agggaaattg actcagattg tatttggcca ttgggatgtg   8700
gtcacttgct tggccaggtc cgagtcatac attggtgggg actgctacat cgtgtccgga   8760
tctcgagatg ccaccctgct gctctggtac tggagtgggc ggcaccatat cataggagac   8820
aaccctaaca gcagtgacta tccggcacca agagccgtcc tcacaggcca tgaccatgaa   8880
gttgtctgtg tttctgtctg tgcagaactt gggcttgtta tcagtggtgc taaagagggc   8940
ccttgccttg tccacaccat cactggagat ttgctgagag cccttgaagg accagaaaac   9000
tgcttattcc cacgcttgat atctgtctcc agcgaaggcc actgtatcat atactatgaa   9060
cgagggcgat tcagtaattt cagcattaat gggaaacttt tggctcaaat ggagatcaat   9120
gattcaacac gggccattct cctgagcagt gacggccaga acctggtcac cggaggggac   9180
aatggggtag tagaggtctg gcaggcctgt gacttcaagc aactgtacat ttaccctgga   9240
tgtgatgctg gcattagagc aatggacttg tcccatgacc agaggactct gatcactggc   9300
atggcttctg gtagcattgt agcttttaat atagatttta atcggtggca ttatgagcat   9360
cagaacagat actgaagata aaggaagaac caaaagccaa gttaaagctg agagcacaag   9420
tgctgcatgg aaaggcaata tctctggtgg aaaaaactcg tctacatcga cctccgtttg   9480
```

-continued

```
tacattccat cacacccagc aatagctgta cattgtagtc agcaaccatt ttactttgtg   9540

tgtttttca cgactgaaca ccagctgcta tcaagcaagc ttatatcatg taaattatat   9600

gaattaggag atgttttggt aattatttca tatattgttg tttattgaga aaaggttgta   9660

ggatgtgtca caagagactt ttgacaattc tgaggaacct tgtgtccagt tgttacaaag   9720

tttaagcttt gaacctaacc tgcatcccat ttccagcctc ttttcaagct gagaaaaaaa   9780

aaaaaaaaca cgtttgatac tttgtacatc agatgcatct tatttaaaag ggatactttt   9840

gtaaaagtaa aaccttgtat aaagaacaaa atgtttctta attttattgt ggagttacaa   9900

cttgcatgtt ccttactcct gttggcttga tggaacaggt gcattcacac tatgaaacag   9960

aaagatctgt ccaaggacac agcttgtatg aaagggttga atttgggctc catcagtaat  10020

ttttgacatt ttcaccaaaa tatagtttgc actttttaat ctaaagtcat cccttctgag  10080

tgaaatttgc tcataaagca tttggatact aagccattat ttgccatttt gggtacttta  10140

tacaaagaaa attcagccct accctgcata atttgaagac acagcagaaa gggggcttag  10200

ggatgaggtc ctggtttttc ttgtataaat aggagtcatg ggcgttagtt ctgtagtaat  10260

aacttcccag cacctggaca tctcttccag agttatccca ctggcttggt gtgtatacat  10320

taggggagga taatctgatg ctaacttttt ttttctcttt ggttcttgaa tagcttagtt  10380

tctttaataa caagtcaaac tttattacaa caataactga agttattctt ttaggttctc  10440

gtgaaattct cactgaaagc cacattctta gcctaaggca tttcatcttt tatgatataa  10500

aatgatggct atcaaatgat tttccataca ttgtactgat caagttatac acccaggggt  10560

atatacactt tcttcatgtt tcttctttgt atatttggtg actgtatcgt catagatgta  10620

catattgtgt cggtagggct atgaggcatg ttacaggaat gtaattttct cagaatttac  10680

actcactcgc agtcatttat ttaaaaagat aaaacaagat aatgggttct ttgtattggc  10740

actttgcacc agaaacatat cattatttat tgatgtgatt acttatttgt tatccacctt  10800

gtactagtaa gttttagcac tgaattcctt cttcactgtt gtttgtattt atgaaattct  10860

gaaattatgg ggaatcagcg taatgattaa gttattcatc accaggctgt aagcaatatc  10920

ttgagtttgt agcttagaat tgggaggata cttaacatct ggaagacaag ttcatttcat  10980

cttgagatca tggtgaaata ttttggatat ataaattcct taagctattg taaccatgtt  11040

ttattgcaaa gatgtaaaat atgccagatg tgtgtgagtt ggaaatcaaa aaaagaaaaa  11100

taaaatatgc aaagaattca aaaaaaaaaa aaaaaaaaaa                        11140
```

<210> SEQ ID NO 66
<211> LENGTH: 2946
<212> TYPE: PRT
<213> ORGANISM: Homo sapiens

<400> SEQUENCE: 66

```
Met Ala Ser Glu Lys Pro Gly Pro Gly Pro Gly Leu Glu Pro Gln Pro
1               5                   10                  15

Val Gly Leu Ile Ala Val Gly Ala Ala Gly Gly Gly Gly Gly Gly Ser
            20                  25                  30

Gly Gly Gly Gly Thr Gly Gly Ser Gly Met Gly Glu Leu Arg Gly Ala
        35                  40                  45

Ser Gly Ser Gly Ser Val Met Leu Pro Ala Gly Met Ile Asn Pro Ser
    50                  55                  60

Val Pro Ile Arg Asn Ile Arg Met Lys Phe Ala Val Leu Ile Gly Leu
65                  70                  75                  80
```

```
Ile Gln Val Gly Glu Val Ser Asn Arg Asp Ile Val Glu Thr Val Leu
                85                  90                  95

Asn Leu Leu Val Gly Gly Glu Phe Asp Leu Glu Met Asn Phe Ile Ile
            100                 105                 110

Gln Asp Ala Glu Ser Ile Thr Cys Met Thr Glu Leu Leu Glu His Cys
        115                 120                 125

Asp Val Thr Cys Gln Ala Glu Ile Trp Ser Met Phe Thr Ala Ile Leu
    130                 135                 140

Arg Lys Ser Val Arg Asn Leu Gln Thr Ser Thr Glu Val Gly Leu Ile
145                 150                 155                 160

Glu Gln Val Leu Leu Lys Met Ser Ala Val Asp Asp Met Ile Ala Asp
                165                 170                 175

Leu Leu Val Asp Met Leu Gly Val Leu Ala Ser Tyr Ser Ile Thr Val
            180                 185                 190

Lys Glu Leu Lys Leu Leu Phe Ser Met Leu Arg Gly Glu Ser Gly Ile
        195                 200                 205

Trp Pro Arg His Ala Val Lys Leu Leu Ser Val Leu Asn Gln Met Pro
    210                 215                 220

Gln Arg His Gly Pro Asp Thr Phe Phe Asn Phe Pro Gly Cys Ser Ala
225                 230                 235                 240

Ala Ala Ile Ala Leu Pro Pro Ile Ala Lys Trp Pro Tyr Gln Asn Gly
                245                 250                 255

Phe Thr Leu Asn Thr Trp Phe Arg Met Asp Pro Leu Asn Asn Ile Asn
            260                 265                 270

Val Asp Lys Asp Lys Pro Tyr Leu Tyr Cys Phe Arg Thr Ser Lys Gly
        275                 280                 285

Val Gly Tyr Ser Ala His Phe Val Gly Asn Cys Leu Ile Val Thr Ser
    290                 295                 300

Leu Lys Ser Lys Gly Lys Gly Phe Gln His Cys Val Lys Tyr Asp Phe
305                 310                 315                 320

Gln Pro Arg Lys Trp Tyr Met Ile Ser Ile Val His Ile Tyr Asn Arg
                325                 330                 335

Trp Arg Asn Ser Glu Ile Arg Cys Tyr Val Asn Gly Gln Leu Val Ser
            340                 345                 350

Tyr Gly Asp Met Ala Trp His Val Asn Thr Asn Asp Ser Tyr Asp Lys
        355                 360                 365

Cys Phe Leu Gly Ser Ser Glu Thr Ala Asp Ala Asn Arg Val Phe Cys
    370                 375                 380

Gly Gln Leu Gly Ala Val Tyr Val Phe Ser Glu Ala Leu Asn Pro Ala
385                 390                 395                 400

Gln Ile Phe Ala Ile His Gln Leu Gly Pro Gly Tyr Lys Ser Thr Phe
                405                 410                 415

Lys Phe Lys Ser Glu Ser Asp Ile His Leu Ala Glu His His Lys Gln
            420                 425                 430

Val Leu Tyr Asp Gly Lys Leu Ala Ser Ser Ile Ala Phe Thr Tyr Asn
        435                 440                 445

Ala Lys Ala Thr Asp Ala Gln Leu Cys Leu Glu Ser Ser Pro Lys Glu
    450                 455                 460

Asn Ala Ser Ile Phe Val His Ser Pro His Ala Leu Met Leu Gln Asp
465                 470                 475                 480

Val Lys Ala Ile Val Thr His Ser Ile His Ser Ala Ile His Ser Ile
                485                 490                 495

Gly Gly Ile Gln Val Leu Phe Pro Leu Phe Ala Gln Leu Asp Asn Arg
```

```
            500                 505                 510

Gln Leu Asn Asp Ser Gln Val Glu Thr Thr Val Cys Ala Thr Leu Leu
        515                 520                 525

Ala Phe Leu Val Glu Leu Leu Lys Ser Ser Val Ala Met Gln Glu Gln
    530                 535                 540

Met Leu Gly Gly Lys Gly Phe Leu Val Ile Gly Tyr Leu Leu Glu Lys
545                 550                 555                 560

Ser Ser Arg Val His Ile Thr Arg Ala Val Leu Glu Gln Phe Leu Ser
                565                 570                 575

Phe Ala Lys Tyr Leu Asp Gly Leu Ser His Gly Ala Pro Leu Leu Lys
            580                 585                 590

Gln Leu Cys Asp His Ile Leu Phe Asn Pro Ala Ile Trp Ile His Thr
        595                 600                 605

Pro Ala Lys Val Gln Leu Ser Leu Tyr Thr Tyr Leu Ser Ala Glu Phe
    610                 615                 620

Ile Gly Thr Ala Thr Ile Tyr Thr Thr Ile Arg Arg Val Gly Thr Val
625                 630                 635                 640

Leu Gln Leu Met His Thr Leu Lys Tyr Tyr Tyr Trp Val Ile Asn Pro
                645                 650                 655

Ala Asp Ser Ser Gly Ile Thr Pro Lys Gly Leu Asp Gly Pro Arg Pro
            660                 665                 670

Ser Gln Lys Glu Ile Ile Ser Leu Arg Ala Phe Met Leu Leu Phe Leu
        675                 680                 685

Lys Gln Leu Ile Leu Lys Asp Arg Gly Val Lys Glu Asp Glu Leu Gln
    690                 695                 700

Ser Ile Leu Asn Tyr Leu Leu Thr Met His Glu Asp Glu Asn Ile His
705                 710                 715                 720

Asp Val Leu Gln Leu Leu Val Ala Leu Met Ser Glu His Pro Ala Ser
                725                 730                 735

Met Ile Pro Ala Phe Asp Gln Arg Asn Gly Ile Arg Val Ile Tyr Lys
            740                 745                 750

Leu Leu Ala Ser Lys Ser Glu Ser Ile Trp Val Gln Ala Leu Lys Val
        755                 760                 765

Leu Gly Tyr Phe Leu Lys His Leu Gly His Lys Arg Lys Val Glu Ile
    770                 775                 780

Met His Thr His Ser Leu Phe Thr Leu Leu Gly Glu Arg Leu Met Leu
785                 790                 795                 800

His Thr Asn Thr Val Thr Val Thr Thr Tyr Asn Thr Leu Tyr Glu Ile
                805                 810                 815

Leu Thr Glu Gln Val Cys Thr Gln Val Val His Lys Pro His Pro Glu
            820                 825                 830

Pro Asp Ser Thr Val Lys Ile Gln Asn Pro Met Ile Leu Lys Val Val
        835                 840                 845

Ala Thr Leu Leu Lys Asn Ser Thr Pro Ser Ala Glu Leu Met Glu Val
    850                 855                 860

Arg Arg Leu Phe Leu Ser Asp Met Ile Lys Leu Phe Ser Asn Ser Arg
865                 870                 875                 880

Glu Asn Arg Arg Cys Leu Leu Gln Cys Ser Val Trp Gln Asp Trp Met
                885                 890                 895

Phe Ser Leu Gly Tyr Ile Asn Pro Lys Asn Ser Glu Glu Gln Lys Ile
            900                 905                 910

Thr Glu Met Val Tyr Asn Ile Phe Arg Ile Leu Leu Tyr His Ala Ile
        915                 920                 925
```

```
Lys Tyr Glu Trp Gly Gly Trp Arg Val Trp Val Asp Thr Leu Ser Ile
    930                 935                 940

Ala His Ser Lys Val Thr Tyr Glu Ala His Lys Glu Tyr Leu Ala Lys
945                 950                 955                 960

Met Tyr Glu Glu Tyr Gln Arg Gln Glu Glu Glu Asn Ile Lys Lys Gly
                965                 970                 975

Lys Lys Gly Asn Val Ser Thr Ile Ser Gly Leu Ser Ser Gln Thr Thr
            980                 985                 990

Gly Ala Lys Gly Gly Met Glu Ile  Arg Glu Ile Glu Asp  Leu Ser Gln
        995                 1000                1005

Ser Gln  Ser Pro Glu Ser Glu  Thr Asp Tyr Pro Val  Ser Thr Asp
    1010                 1015                 1020

Thr Arg  Asp Leu Leu Met Ser  Thr Lys Val Ser Asp  Asp Ile Leu
    1025                 1030                 1035

Gly Asn  Ser Asp Arg Pro Gly  Ser Gly Val His Val  Glu Val His
    1040                 1045                 1050

Asp Leu  Leu Val Asp Ile Lys  Ala Glu Lys Val Glu  Ala Thr Glu
    1055                 1060                 1065

Val Lys  Leu Asp Asp Met Asp  Leu Ser Pro Glu Thr  Leu Val Gly
    1070                 1075                 1080

Gly Glu  Asn Gly Ala Leu Val  Glu Val Glu Ser Leu  Leu Asp Asn
    1085                 1090                 1095

Val Tyr  Ser Ala Ala Val Glu  Lys Leu Gln Asn Asn  Val His Gly
    1100                 1105                 1110

Ser Val  Gly Ile Ile Lys Lys  Asn Glu Glu Lys Asp  Asn Gly Pro
    1115                 1120                 1125

Leu Ile  Thr Leu Ala Asp Glu  Lys Glu Asp Leu Pro  Asn Ser Ser
    1130                 1135                 1140

Thr Ser  Phe Leu Phe Asp Lys  Ile Pro Lys Gln Glu  Glu Lys Leu
    1145                 1150                 1155

Leu Pro  Glu Leu Ser Ser Asn  His Ile Ile Pro Asn  Ile Gln Asp
    1160                 1165                 1170

Thr Gln  Val His Leu Gly Val  Ser Asp Asp Leu Gly  Leu Leu Ala
    1175                 1180                 1185

His Met  Thr Gly Ser Val Asp  Leu Thr Cys Thr Ser  Ser Ile Ile
    1190                 1195                 1200

Glu Glu  Lys Glu Phe Lys Ile  His Thr Thr Ser Asp  Gly Met Ser
    1205                 1210                 1215

Ser Ile  Ser Glu Arg Asp Leu  Ala Ser Ser Thr Lys  Gly Leu Glu
    1220                 1225                 1230

Tyr Ala  Glu Met Thr Ala Thr  Thr Leu Glu Thr Glu  Ser Ser Ser
    1235                 1240                 1245

Ser Lys  Ile Val Pro Asn Ile  Asp Ala Gly Ser Ile  Ile Ser Asp
    1250                 1255                 1260

Thr Glu  Arg Ser Asp Asp Gly  Lys Glu Ser Gly Lys  Glu Ile Arg
    1265                 1270                 1275

Lys Ile  Gln Thr Thr Thr Thr  Thr Gln Ala Val Gln  Gly Arg Ser
    1280                 1285                 1290

Ile Thr  Gln Gln Asp Arg Asp  Leu Arg Val Asp Leu  Gly Phe Arg
    1295                 1300                 1305

Gly Met  Pro Met Thr Glu Glu  Gln Arg Arg Gln Phe  Ser Pro Gly
    1310                 1315                 1320
```

```
Pro Arg  Thr Thr Met Phe Arg  Ile Pro Glu Phe Lys  Trp Ser Pro
    1325                 1330                 1335

Met His  Gln Arg Leu Leu Thr  Asp Leu Leu Phe Ala  Leu Glu Thr
    1340                 1345                 1350

Asp Val  His Val Trp Arg Ser  His Ser Thr Lys Ser  Val Met Asp
    1355                 1360                 1365

Phe Val  Asn Ser Asn Glu Asn  Ile Ile Phe Val His  Asn Thr Ile
    1370                 1375                 1380

His Leu  Ile Ser Gln Met Val  Asp Asn Ile Ile Ile  Ala Cys Gly
    1385                 1390                 1395

Gly Ile  Leu Pro Leu Leu Ser  Ala Ala Thr Ser Pro  Thr Gly Ser
    1400                 1405                 1410

Lys Thr  Glu Leu Glu Asn Ile  Glu Val Thr Gln Gly  Met Ser Ala
    1415                 1420                 1425

Glu Thr  Ala Val Thr Phe Leu  Ser Arg Leu Met Ala  Met Val Asp
    1430                 1435                 1440

Val Leu  Val Phe Ala Ser Ser  Leu Asn Phe Ser Glu  Ile Glu Ala
    1445                 1450                 1455

Glu Lys  Asn Met Ser Ser Gly  Gly Leu Met Arg Gln  Cys Leu Arg
    1460                 1465                 1470

Leu Val  Cys Cys Val Ala Val  Arg Asn Cys Leu Glu  Cys Arg Gln
    1475                 1480                 1485

Arg Gln  Arg Asp Arg Gly Asn  Lys Ser Ser His Gly  Ser Ser Lys
    1490                 1495                 1500

Pro Gln  Glu Val Pro Gln Ser  Val Thr Ala Thr Ala  Ala Ser Lys
    1505                 1510                 1515

Thr Pro  Leu Glu Asn Val Pro  Gly Asn Leu Ser Pro  Ile Lys Asp
    1520                 1525                 1530

Pro Asp  Arg Leu Leu Gln Asp  Val Asp Ile Asn Arg  Leu Arg Ala
    1535                 1540                 1545

Val Val  Phe Arg Asp Val Asp  Asp Ser Lys Gln Ala  Gln Phe Leu
    1550                 1555                 1560

Ala Leu  Ala Val Val Tyr Phe  Ile Ser Val Leu Met  Val Ser Lys
    1565                 1570                 1575

Tyr Arg  Asp Ile Leu Glu Pro  Gln Arg Glu Thr Thr  Arg Thr Gly
    1580                 1585                 1590

Ser Gln  Pro Gly Arg Asn Ile  Arg Gln Glu Ile Asn  Ser Pro Thr
    1595                 1600                 1605

Ser Thr  Val Val Val Ile Pro  Ser Ile Pro His Pro  Ser Leu Asn
    1610                 1615                 1620

His Gly  Phe Leu Ala Lys Leu  Ile Pro Glu Gln Ser  Phe Gly His
    1625                 1630                 1635

Ser Phe  Tyr Lys Glu Thr Pro  Ala Ala Phe Pro Asp  Thr Ile Lys
    1640                 1645                 1650

Glu Lys  Glu Thr Pro Thr Pro  Gly Glu Asp Ile Gln  Val Glu Ser
    1655                 1660                 1665

Ser Ile  Pro His Thr Asp Ser  Gly Ile Gly Glu Glu  Gln Val Ala
    1670                 1675                 1680

Ser Ile  Leu Asn Gly Ala Glu  Leu Glu Thr Ser Thr  Gly Pro Asp
    1685                 1690                 1695

Ala Met  Ser Glu Leu Leu Ser  Thr Leu Ser Ser Glu  Val Lys Lys
    1700                 1705                 1710

Ser Gln  Glu Ser Leu Thr Glu  Asn Pro Ser Glu Thr  Leu Lys Pro
```

```
    1715                1720                1725

Ala Thr  Ser Ile Ser Ser Ile  Ser Gln Thr Lys Gly  Ile Asn Val
    1730                1735                1740

Lys Glu  Ile Leu Lys Ser Leu  Val Ala Ala Pro Val  Glu Ile Ala
    1745                1750                1755

Glu Cys  Gly Pro Glu Pro Ile  Pro Tyr Pro Asp Pro  Ala Leu Lys
    1760                1765                1770

Arg Glu  Thr Gln Ala Ile Leu  Pro Met Gln Phe His  Ser Phe Asp
    1775                1780                1785

Arg Ser  Val Val Val Pro Val  Lys Lys Pro Pro Pro  Gly Ser Leu
    1790                1795                1800

Ala Val  Thr Thr Val Gly Ala  Thr Thr Ala Gly Ser  Gly Leu Pro
    1805                1810                1815

Thr Gly  Ser Thr Ser Asn Ile  Phe Ala Ala Thr Gly  Ala Thr Pro
    1820                1825                1830

Lys Ser  Met Ile Asn Thr Thr  Gly Ala Val Asp Ser  Gly Ser Ser
    1835                1840                1845

Ser Ser  Ser Ser Ser Ser Ser  Phe Val Asn Gly Ala  Thr Ser Lys
    1850                1855                1860

Asn Leu  Pro Ala Val Gln Thr  Val Ala Pro Met Pro  Glu Asp Ser
    1865                1870                1875

Ala Glu  Asn Met Ser Ile Thr  Ala Lys Leu Glu Arg  Ala Leu Glu
    1880                1885                1890

Lys Val  Ala Pro Leu Leu Arg  Glu Ile Phe Val Asp  Phe Ala Pro
    1895                1900                1905

Phe Leu  Ser Arg Thr Leu Leu  Gly Ser His Gly Gln  Glu Leu Leu
    1910                1915                1920

Ile Glu  Gly Leu Val Cys Met  Lys Ser Ser Thr Ser  Val Val Glu
    1925                1930                1935

Leu Val  Met Leu Leu Cys Ser  Gln Glu Trp Gln Asn  Ser Ile Gln
    1940                1945                1950

Lys Asn  Ala Gly Leu Ala Phe  Ile Glu Leu Ile Asn  Glu Gly Arg
    1955                1960                1965

Leu Leu  Cys His Ala Met Lys  Asp His Ile Val Arg  Val Ala Asn
    1970                1975                1980

Glu Ala  Glu Phe Ile Leu Asn  Arg Gln Arg Ala Glu  Asp Val His
    1985                1990                1995

Lys His  Ala Glu Phe Glu Ser  Gln Cys Ala Gln Tyr  Ala Ala Asp
    2000                2005                2010

Arg Arg  Glu Glu Glu Lys Met  Cys Asp His Leu Ile  Ser Ala Ala
    2015                2020                2025

Lys His  Arg Asp His Val Thr  Ala Asn Gln Leu Lys  Gln Lys Ile
    2030                2035                2040

Leu Asn  Ile Leu Thr Asn Lys  His Gly Ala Trp Gly  Ala Val Ser
    2045                2050                2055

His Ser  Gln Leu His Asp Phe  Trp Arg Leu Asp Tyr  Trp Glu Asp
    2060                2065                2070

Asp Leu  Arg Arg Arg Arg Arg  Phe Val Arg Asn Ala  Phe Gly Ser
    2075                2080                2085

Thr His  Ala Glu Ala Leu Leu  Lys Ala Ala Ile Glu  Tyr Gly Thr
    2090                2095                2100

Glu Glu  Asp Val Val Lys Ser  Lys Lys Thr Phe Arg  Ser Gln Ala
    2105                2110                2115
```

Ile Val Asn Gln Asn Ala Glu Thr Glu Leu Met Leu Glu Gly Asp
2120 2125 2130

Asp Asp Ala Val Ser Leu Leu Gln Glu Lys Glu Ile Asp Asn Leu
2135 2140 2145

Ala Gly Pro Val Val Leu Ser Thr Pro Ala Gln Leu Ile Ala Pro
2150 2155 2160

Val Val Val Ala Lys Gly Thr Leu Ser Ile Thr Thr Thr Glu Ile
2165 2170 2175

Tyr Phe Glu Val Asp Glu Asp Asp Ser Ala Phe Lys Lys Ile Asp
2180 2185 2190

Thr Lys Val Leu Ala Tyr Thr Glu Gly Leu His Gly Lys Trp Met
2195 2200 2205

Phe Ser Glu Ile Arg Ala Val Phe Ser Arg Arg Tyr Leu Leu Gln
2210 2215 2220

Asn Thr Ala Leu Glu Val Phe Met Ala Asn Arg Thr Ser Val Met
2225 2230 2235

Phe Asn Phe Pro Asp Gln Ala Thr Val Lys Lys Val Val Tyr Ser
2240 2245 2250

Leu Pro Arg Val Gly Val Gly Thr Ser Tyr Gly Leu Pro Gln Ala
2255 2260 2265

Arg Arg Ile Ser Leu Ala Thr Pro Arg Gln Leu Tyr Lys Ser Ser
2270 2275 2280

Asn Met Thr Gln Arg Trp Gln Arg Arg Glu Ile Ser Asn Phe Glu
2285 2290 2295

Tyr Leu Met Phe Leu Asn Thr Ile Ala Gly Arg Thr Tyr Asn Asp
2300 2305 2310

Leu Asn Gln Tyr Pro Val Phe Pro Trp Val Leu Thr Asn Tyr Glu
2315 2320 2325

Ser Glu Glu Leu Asp Leu Thr Leu Pro Gly Asn Phe Arg Asp Leu
2330 2335 2340

Ser Lys Pro Ile Gly Ala Leu Asn Pro Lys Arg Ala Val Phe Tyr
2345 2350 2355

Ala Glu Arg Tyr Glu Thr Trp Glu Asp Asp Gln Ser Pro Pro Tyr
2360 2365 2370

His Tyr Asn Thr His Tyr Ser Thr Ala Thr Ser Thr Leu Ser Trp
2375 2380 2385

Leu Val Arg Ile Glu Pro Phe Thr Thr Phe Phe Leu Asn Ala Asn
2390 2395 2400

Asp Gly Lys Phe Asp His Pro Asp Arg Thr Phe Ser Ser Val Ala
2405 2410 2415

Arg Ser Trp Arg Thr Ser Gln Arg Asp Thr Ser Asp Val Lys Glu
2420 2425 2430

Leu Ile Pro Glu Phe Tyr Tyr Leu Pro Glu Met Phe Val Asn Ser
2435 2440 2445

Asn Gly Tyr Asn Leu Gly Val Arg Glu Asp Glu Val Val Val Asn
2450 2455 2460

Asp Val Asp Leu Pro Pro Trp Ala Lys Lys Pro Glu Asp Phe Val
2465 2470 2475

Arg Ile Asn Arg Met Ala Leu Glu Ser Glu Phe Val Ser Cys Gln
2480 2485 2490

Leu His Gln Trp Ile Asp Leu Ile Phe Gly Tyr Lys Gln Arg Gly
2495 2500 2505

Pro Glu Ala Val Arg Ala Leu Asn Val Phe His Tyr Leu Thr Tyr
2510 2515 2520

Glu Gly Ser Val Asn Leu Asp Ser Ile Thr Asp Pro Val Leu Arg
2525 2530 2535

Glu Ala Met Glu Ala Gln Ile Gln Asn Phe Gly Gln Thr Pro Ser
2540 2545 2550

Gln Leu Leu Ile Glu Pro His Pro Pro Arg Ser Ser Ala Met His
2555 2560 2565

Leu Cys Phe Leu Pro Gln Ser Pro Leu Met Phe Lys Asp Gln Met
2570 2575 2580

Gln Gln Asp Val Ile Met Val Leu Lys Phe Pro Ser Asn Ser Pro
2585 2590 2595

Val Thr His Val Ala Ala Asn Thr Leu Pro His Leu Thr Ile Pro
2600 2605 2610

Ala Val Val Thr Val Thr Cys Ser Arg Leu Phe Ala Val Asn Arg
2615 2620 2625

Trp His Asn Thr Val Gly Leu Arg Gly Ala Pro Gly Tyr Ser Leu
2630 2635 2640

Asp Gln Ala His His Leu Pro Ile Glu Met Asp Pro Leu Ile Ala
2645 2650 2655

Asn Asn Ser Gly Val Asn Lys Arg Gln Ile Thr Asp Leu Val Asp
2660 2665 2670

Gln Ser Ile Gln Ile Asn Ala His Cys Phe Val Val Thr Ala Asp
2675 2680 2685

Asn Arg Tyr Ile Leu Ile Cys Gly Phe Trp Asp Lys Ser Phe Arg
2690 2695 2700

Val Tyr Ser Thr Glu Thr Gly Lys Leu Thr Gln Ile Val Phe Gly
2705 2710 2715

His Trp Asp Val Val Thr Cys Leu Ala Arg Ser Glu Ser Tyr Ile
2720 2725 2730

Gly Gly Asp Cys Tyr Ile Val Ser Gly Ser Arg Asp Ala Thr Leu
2735 2740 2745

Leu Leu Trp Tyr Trp Ser Gly Arg His His Ile Ile Gly Asp Asn
2750 2755 2760

Pro Asn Ser Ser Asp Tyr Pro Ala Pro Arg Ala Val Leu Thr Gly
2765 2770 2775

His Asp His Glu Val Val Cys Val Ser Val Cys Ala Glu Leu Gly
2780 2785 2790

Leu Val Ile Ser Gly Ala Lys Glu Gly Pro Cys Leu Val His Thr
2795 2800 2805

Ile Thr Gly Asp Leu Leu Arg Ala Leu Glu Gly Pro Glu Asn Cys
2810 2815 2820

Leu Phe Pro Arg Leu Ile Ser Val Ser Ser Glu Gly His Cys Ile
2825 2830 2835

Ile Tyr Tyr Glu Arg Gly Arg Phe Ser Asn Phe Ser Ile Asn Gly
2840 2845 2850

Lys Leu Leu Ala Gln Met Glu Ile Asn Asp Ser Thr Arg Ala Ile
2855 2860 2865

Leu Leu Ser Ser Asp Gly Gln Asn Leu Val Thr Gly Gly Asp Asn
2870 2875 2880

Gly Val Val Glu Val Trp Gln Ala Cys Asp Phe Lys Gln Leu Tyr
2885 2890 2895

Ile Tyr Pro Gly Cys Asp Ala Gly Ile Arg Ala Met Asp Leu Ser

```
    2900                2905                2910

His Asp  Gln Arg Thr Leu Ile  Thr Gly Met Ala Ser  Gly Ser Ile
    2915                2920                2925

Val Ala  Phe Asn Ile Asp Phe  Asn Arg Trp His Tyr  Glu His Gln
    2930                2935                2940

Asn Arg  Tyr
    2945


<210> SEQ ID NO 67
<211> LENGTH: 4675
<212> TYPE: DNA
<213> ORGANISM: Homo sapiens

<400> SEQUENCE: 67

agatgacaga cacttctcaa aagacagctt ttcttcctgg agaacagact ttttcagcag     60

gattttcctt tcagtgaaac ataatttgac ttgaaaggaa cccagggaaa agtgtccagg    120

tgtgagcatg agcgggtaga ggtgtgccct tgtttgcttc aggctgtctg cttttcgccc    180

ctgactgttt tttctgtttc tggccatgga ggaagagaaa gatgacagcc cacaggctga    240

cttctgcctg ggcaccgccc tgcactcttg gggactgtgg ttcacggagg aaggttcacc    300

gtccaccatg ctgacgggga ttgcagttgg agccctcctg gccctggcct tggttggtgt    360

cctcatcctt ttcatgttca gaaggcttag acaatttcga caagcacagc ccactcctca    420

gtaccggttc cggaagagag acaaagtgat gttttacggc cggaagatca tgaggaaggt    480

gaccacactc cccaacaccc ttgtggagaa cactgccctg ccccggcagc gggccaggaa    540

gaggaccaag gtgctgtctt tggccaagag gattctgcgt ttcaagaagg aatacccggc    600

cctgcagccc aaggagcccc cgccctccct gctggaggcc gacctcacgg agtttgacgt    660

gaagaattct cacctgccat cggaagttct gtacatgctg aaaaacgttc gggtcctggg    720

ccactttgag aagccgctgt tcctggagct ttgcaaacac atcgtctttg tgcagctgca    780

ggaaggggag cacgtcttcc agcccaggga gccggacccc agcatctgtg tggtgcagga    840

cgggcggctg gaggtctgca tccaggacac tgacggcacc gaggtggtgg tgaaagaggt    900

tctggcggga gacagcgtcc acagcctgct cagcatcctg gacatcatca ccggccatgc    960

tgcaccttac aaaacggtct ccgtccgcgc ggccatcccg tccaccatcc tccggcttcc   1020

agctgcggct tttcatggag tttttgagaa atatccggaa actctggtga gggtggtgca   1080

gatcatcatg gtgcggctgc agagggtgac ctttctggct ctgcacaact acctcggcct   1140

gaccacagag ctcttcaacg ctgagagcca ggccatccct ctcgtgtctg tagccagtgt   1200

ggctgccggg aaggccaaga agcaggtgtt ctatggcgaa gaagagcggc ttaaaaagcc   1260

accgcggctc caggagtcct gtgactcaga tcacgggggc ggccgcccgg cagctgctgg   1320

gcccctgctg aagaggagcc actccgtccc cgcgccttcc attcgcaaac agatcttgga   1380

ggagctggag aagcccgggg caggtgaccc tgacccttcg gccccacaag gggcccaggg   1440

cagtgccact tctgatctgg ggatggcatg tgaccgtgcc agggtcttcc tgcactcgga   1500

cgagcacccc gggagctccg tggccagcaa gtccaggaaa agcgtgatgg ttgcagagat   1560

accctccacg gtctcccagc actcagagag tcacacggat gagaccctgg ccagcaggaa   1620

gtcggatgcc atcttcagag ctgccaagaa ggacctgctc accctgatga agctggaaga   1680

ctcatctctg ttggatggcc gggtggcgct tctgcacgtt cctgcaggca cggtggtgtc   1740

aaggcaggga gaccaggacg ccagcatcct gttcgtggtc tcggggctgc tgcacgtgta   1800
```

```
ccagcggaag atcggcagcc aggaggacac ctgcttgttc ctcacgcgcc ccggggagat   1860
ggtgggccag ctggccgtgc tcaccgggga gcctctcatc ttcaccgtca aggccaacag   1920
ggactgcagc ttcctgtcca tctccaaggc ccacttctat gaaatcatgc ggaagcagcc   1980
gaccgtcgtc ctgggtgtgg cgcacactgt ggtgaagagg atgtcgtcct tcgtgcggca   2040
aatcgacttt gccctggact gggtggaggt ggaggccggg cgagcaatat acaggcaggg   2100
ggacaagtcc gactgcacgt acatcatgct cagcggccgg ctgcgctctg tgatccggaa   2160
ggatgatggg aagaagcgcc tggccgggga gtacggccga ggagacctcg tcggcgtggt   2220
ggagacactg acccaccagg cccgggcgac cacggtgcat gccgttcggg actcagaatt   2280
ggccaagctg ccggcaggag ccctcacgtc catcaagcgc aggtacccac aggtggtgac   2340
tcggctgatt catctcttgg gtgagaagat cctgggcagc ctccagcagg gacctgtgac   2400
aggccaccag cttgggctcc ccacggaggg cagcaagtgg gacttgggga acccggctgt   2460
caacctgtcc acggtggcag tgatgcccgt gtcagaggaa gtgcccctca ccgccttcgc   2520
cctggagctg gagcatgccc tcagcgccat cggcccgacc ctgctgctga ctagtgacaa   2580
cataaaacgg cgccttggct ccgctgccct ggacagtgtt cacgagtacc ggctgtccag   2640
ctggctgggg cagcaggagg acacccacag gatcgtgctc taccaggcag atggcacgct   2700
cacaccctgg acccagcgct gcgtgcgcca ggccgactgc atcctcatcg tgggcctggg   2760
tgaccaggag cccacagtgg gcgagctgga gcggatgctg gagagcacag ctgtgcgtgc   2820
ccagaagcag ctgatcctgc tgcacaggga ggagggcccg gcgccagcgc gcaccgtgga   2880
gtggctcaac atgcggagct ggtgctccgg ccacctgcac ctctgctgcc cgcgccgcgt   2940
cttctccagg aggagcctgc ccaagctggt ggagatgtac aagcatgtct tccagcggcc   3000
cccggaccga cactcagact tctcccgcct ggcgagggtg ctgacgggca acgccattgc   3060
cctggtgctt gggggagggg gagcaagagg ctgtgcccag gtgggcgttc tcaaggcctt   3120
ggcggagtgc ggcatccctg tggacatggt gggaggcacg tccatcgggg ccttcgtggg   3180
tgccctgtac tctgaggagc ggaactacag ccagatgcgg atccgggcca agcagtgggc   3240
cgagggcatg acgtccttga tgaaggccgc gctggacctc acctacccca tcacgtccat   3300
gttctccgga gccggcttca acagcagcat cttcagcgtc ttcaaggacc agcagatcga   3360
ggacctgtgg attccttatt tcgccatcac caccgacatc acagcctcgg ccatgcgggt   3420
ccacaccgac ggctccctgt ggtggtacgt gcgtgccagc atgtccctgt ccggttacat   3480
gcccccctctc tgtgacccga aggacggaca cctgctgatg gacgggggct acatcaacaa   3540
cctcccagcg gatgtggccc ggtccatggg ggcaaaagtg gtgatcgcca ttgacgtggg   3600
cagccgagat gagacggacc tcaccaacta tggggatgcg ctgtctgggt ggtggctgct   3660
gtggaaacgc tggaacccct tggccacgaa agtcaaggtg ttgaacatgg cagagattca   3720
gacgcgcctg gcctacgtgt gttgcgtgcg gcagctggag gtggtgaaga gcagtgacta   3780
ctgcgagtac ctgcgccccc ccatcgacag ctacagcacc ctggacttcg gcaagttcaa   3840
cgagatctgc gaagtgggct accagcacgg gcgcacggtg tttgacatct ggggccgcag   3900
cggcgtgctg gagaagatgc tccgcgacca gcaggggccg agcaagaagc ccgcgagtgc   3960
ggtcctcacc tgtcccaacg cctccttcac ggaccttgcc gaaattgtgt ctcgcattga   4020
gcccgccaag cccgccatgg tggatgacga atctgactac cagacggagt acgaggagga   4080
gctgctggac gtccccaggg atgcatacgc agacttccag agcacctcag cccagcaggg   4140
ctcagacttg gaggacgagt cctcactgcg gcatcgacac cccagtctgg ctttcccaaa   4200
```

```
actgtctgag ggctcctctg accaggacgg gtagaggcct ctgctaaaga gcccggatgc   4260

agcgtcttcc gtgggactgt ccccaaggct gaggctcctg ccaagtccta ggggcctctg   4320

tacctgccct gctggaagcc ctgacttccc cggggcccca ggctgtgtta gggttctctg   4380

ggcctcttct ttgtaccagc agccctgcat acagggccct gtgagccccc ctgcagtcct   4440

gtgaggcccc tgaagctctg tgaggcccct gaagctctgt gaaccccctg cagccctgtg   4500

aggccccccg aagccctgtg aggccccccg aagccctgtg aaccacctgc tgccctgtga   4560

ggcccccaaa gccctgtgaa ctgcctgctg tcctgtgaac tgcctgctgc cctgtgaggt   4620

gtgggagccc tgatgctgcc gtgtgatgtt tcaataaagg tggatctcac tgttg        4675


<210> SEQ ID NO 68
<211> LENGTH: 1317
<212> TYPE: PRT
<213> ORGANISM: Homo sapiens

<400> SEQUENCE: 68

Met Glu Glu Glu Lys Asp Asp Ser Pro Gln Leu Thr Gly Ile Ala Val
1               5                   10                  15

Gly Ala Leu Leu Ala Leu Ala Leu Val Gly Val Leu Ile Leu Phe Met
            20                  25                  30

Phe Arg Arg Leu Arg Gln Phe Arg Gln Ala Gln Pro Thr Pro Gln Tyr
        35                  40                  45

Arg Phe Arg Lys Arg Asp Lys Val Met Phe Tyr Gly Arg Lys Ile Met
    50                  55                  60

Arg Lys Val Thr Thr Leu Pro Asn Thr Leu Val Glu Asn Thr Ala Leu
65                  70                  75                  80

Pro Arg Gln Arg Ala Arg Lys Arg Thr Lys Val Leu Ser Leu Ala Lys
                85                  90                  95

Arg Ile Leu Arg Phe Lys Lys Glu Tyr Pro Ala Leu Gln Pro Lys Glu
            100                 105                 110

Pro Pro Pro Ser Leu Leu Glu Ala Asp Leu Thr Glu Phe Asp Val Lys
        115                 120                 125

Asn Ser His Leu Pro Ser Glu Val Leu Tyr Met Leu Lys Asn Val Arg
    130                 135                 140

Val Leu Gly His Phe Glu Lys Pro Leu Phe Leu Glu Leu Cys Lys His
145                 150                 155                 160

Ile Val Phe Val Gln Leu Gln Glu Gly Glu His Val Phe Gln Pro Arg
                165                 170                 175

Glu Pro Asp Pro Ser Ile Cys Val Val Gln Asp Gly Arg Leu Glu Val
            180                 185                 190

Cys Ile Gln Asp Thr Asp Gly Thr Glu Val Val Val Lys Glu Val Leu
        195                 200                 205

Ala Gly Asp Ser Val His Ser Leu Leu Ser Ile Leu Asp Ile Ile Thr
    210                 215                 220

Gly His Ala Ala Pro Tyr Lys Thr Val Ser Val Arg Ala Ala Ile Pro
225                 230                 235                 240

Ser Thr Ile Leu Arg Leu Pro Ala Ala Ala Phe His Gly Val Phe Glu
                245                 250                 255

Lys Tyr Pro Glu Thr Leu Val Arg Val Val Gln Ile Ile Met Val Arg
            260                 265                 270

Leu Gln Arg Val Thr Phe Leu Ala Leu His Asn Tyr Leu Gly Leu Thr
        275                 280                 285
```

```
Thr Glu Leu Phe Asn Ala Glu Ser Gln Ala Ile Pro Leu Val Ser Val
    290                 295                 300

Ala Ser Val Ala Ala Gly Lys Ala Lys Lys Gln Val Phe Tyr Gly Glu
305                 310                 315                 320

Glu Glu Arg Leu Lys Lys Pro Pro Arg Leu Gln Glu Ser Cys Asp Ser
                325                 330                 335

Asp His Gly Gly Gly Arg Pro Ala Ala Ala Gly Pro Leu Leu Lys Arg
            340                 345                 350

Ser His Ser Val Pro Ala Pro Ser Ile Arg Lys Gln Ile Leu Glu Glu
        355                 360                 365

Leu Glu Lys Pro Gly Ala Gly Asp Pro Asp Pro Ser Ala Pro Gln Gly
    370                 375                 380

Gly Pro Gly Ser Ala Thr Ser Asp Leu Gly Met Ala Cys Asp Arg Ala
385                 390                 395                 400

Arg Val Phe Leu His Ser Asp Glu His Pro Gly Ser Ser Val Ala Ser
                405                 410                 415

Lys Ser Arg Lys Ser Val Met Val Ala Glu Ile Pro Ser Thr Val Ser
            420                 425                 430

Gln His Ser Glu Ser His Thr Asp Glu Thr Leu Ala Ser Arg Lys Ser
        435                 440                 445

Asp Ala Ile Phe Arg Ala Ala Lys Lys Asp Leu Leu Thr Leu Met Lys
    450                 455                 460

Leu Glu Asp Ser Ser Leu Leu Asp Gly Arg Val Ala Leu Leu His Val
465                 470                 475                 480

Pro Ala Gly Thr Val Val Ser Arg Gln Gly Asp Gln Asp Ala Ser Ile
                485                 490                 495

Leu Phe Val Val Ser Gly Leu Leu His Val Tyr Gln Arg Lys Ile Gly
            500                 505                 510

Ser Gln Glu Asp Thr Cys Leu Phe Leu Thr Arg Pro Gly Glu Met Val
        515                 520                 525

Gly Gln Leu Ala Val Leu Thr Gly Glu Pro Leu Ile Phe Thr Val Lys
    530                 535                 540

Ala Asn Arg Asp Cys Ser Phe Leu Ser Ile Ser Lys Ala His Phe Tyr
545                 550                 555                 560

Glu Ile Met Arg Lys Gln Pro Thr Val Val Leu Gly Val Ala His Thr
                565                 570                 575

Val Val Lys Arg Met Ser Ser Phe Val Arg Gln Ile Asp Phe Ala Leu
            580                 585                 590

Asp Trp Val Glu Val Glu Ala Gly Arg Ala Ile Tyr Arg Gln Gly Asp
        595                 600                 605

Lys Ser Asp Cys Thr Tyr Ile Met Leu Ser Gly Arg Leu Arg Ser Val
    610                 615                 620

Ile Arg Lys Asp Asp Gly Lys Lys Arg Leu Ala Gly Glu Tyr Gly Arg
625                 630                 635                 640

Gly Asp Leu Val Gly Val Val Glu Thr Leu Thr His Gln Ala Arg Ala
                645                 650                 655

Thr Thr Val His Ala Val Arg Asp Ser Glu Leu Ala Lys Leu Pro Ala
            660                 665                 670

Gly Ala Leu Thr Ser Ile Lys Arg Arg Tyr Pro Gln Val Val Thr Arg
        675                 680                 685

Leu Ile His Leu Leu Gly Glu Lys Ile Leu Gly Ser Leu Gln Gln Gly
    690                 695                 700

Pro Val Thr Gly His Gln Leu Gly Leu Pro Thr Glu Gly Ser Lys Trp
```

-continued

```
705                 710                 715                 720

Asp Leu Gly Asn Pro Ala Val Asn Leu Ser Thr Val Ala Val Met Pro
                725                 730                 735

Val Ser Glu Glu Val Pro Leu Thr Ala Phe Ala Leu Glu Leu Glu His
            740                 745                 750

Ala Leu Ser Ala Ile Gly Pro Thr Leu Leu Leu Thr Ser Asp Asn Ile
        755                 760                 765

Lys Arg Arg Leu Gly Ser Ala Ala Leu Asp Ser Val His Glu Tyr Arg
    770                 775                 780

Leu Ser Ser Trp Leu Gly Gln Gln Glu Asp Thr His Arg Ile Val Leu
785                 790                 795                 800

Tyr Gln Ala Asp Gly Thr Leu Thr Pro Trp Thr Gln Arg Cys Val Arg
                805                 810                 815

Gln Ala Asp Cys Ile Leu Ile Val Gly Leu Gly Asp Gln Glu Pro Thr
            820                 825                 830

Val Gly Glu Leu Glu Arg Met Leu Glu Ser Thr Ala Val Arg Ala Gln
        835                 840                 845

Lys Gln Leu Ile Leu Leu His Arg Glu Glu Gly Pro Ala Pro Ala Arg
    850                 855                 860

Thr Val Glu Trp Leu Asn Met Arg Ser Trp Cys Ser Gly His Leu His
865                 870                 875                 880

Leu Cys Cys Pro Arg Arg Val Phe Ser Arg Arg Ser Leu Pro Lys Leu
                885                 890                 895

Val Glu Met Tyr Lys His Val Phe Gln Arg Pro Pro Asp Arg His Ser
            900                 905                 910

Asp Phe Ser Arg Leu Ala Arg Val Leu Thr Gly Asn Ala Ile Ala Leu
        915                 920                 925

Val Leu Gly Gly Gly Gly Ala Arg Gly Cys Ala Gln Val Gly Val Leu
    930                 935                 940

Lys Ala Leu Ala Glu Cys Gly Ile Pro Val Asp Met Val Gly Gly Thr
945                 950                 955                 960

Ser Ile Gly Ala Phe Val Gly Ala Leu Tyr Ser Glu Glu Arg Asn Tyr
                965                 970                 975

Ser Gln Met Arg Ile Arg Ala Lys Gln Trp Ala Glu Gly Met Thr Ser
            980                 985                 990

Leu Met Lys Ala Ala Leu Asp Leu  Thr Tyr Pro Ile Thr  Ser Met Phe
        995                 1000                1005

Ser Gly  Ala Gly Phe Asn Ser  Ser Ile Phe Ser Val  Phe Lys Asp
    1010                1015                1020

Gln Gln  Ile Glu Asp Leu Trp  Ile Pro Tyr Phe Ala  Ile Thr Thr
    1025                1030                1035

Asp Ile  Thr Ala Ser Ala Met  Arg Val His Thr Asp  Gly Ser Leu
    1040                1045                1050

Trp Trp  Tyr Val Arg Ala Ser  Met Ser Leu Ser Gly  Tyr Met Pro
    1055                1060                1065

Pro Leu  Cys Asp Pro Lys Asp  Gly His Leu Leu Met  Asp Gly Gly
    1070                1075                1080

Tyr Ile  Asn Asn Leu Pro Ala  Asp Val Ala Arg Ser  Met Gly Ala
    1085                1090                1095

Lys Val  Val Ile Ala Ile Asp  Val Gly Ser Arg Asp  Glu Thr Asp
    1100                1105                1110

Leu Thr  Asn Tyr Gly Asp Ala  Leu Ser Gly Trp Trp  Leu Leu Trp
    1115                1120                1125
```

```
Lys Arg  Trp Asn Pro Leu Ala  Thr Lys Val Lys Val  Leu Asn Met
    1130                 1135                 1140

Ala Glu  Ile Gln Thr Arg Leu  Ala Tyr Val Cys Cys  Val Arg Gln
    1145                 1150                 1155

Leu Glu  Val Val Lys Ser Ser  Asp Tyr Cys Glu Tyr  Leu Arg Pro
    1160                 1165                 1170

Pro Ile  Asp Ser Tyr Ser Thr  Leu Asp Phe Gly Lys  Phe Asn Glu
    1175                 1180                 1185

Ile Cys  Glu Val Gly Tyr Gln  His Gly Arg Thr Val  Phe Asp Ile
    1190                 1195                 1200

Trp Gly  Arg Ser Gly Val Leu  Glu Lys Met Leu Arg  Asp Gln Gln
    1205                 1210                 1215

Gly Pro  Ser Lys Lys Pro Ala  Ser Ala Val Leu Thr  Cys Pro Asn
    1220                 1225                 1230

Ala Ser  Phe Thr Asp Leu Ala  Glu Ile Val Ser Arg  Ile Glu Pro
    1235                 1240                 1245

Ala Lys  Pro Ala Met Val Asp  Asp Glu Ser Asp Tyr  Gln Thr Glu
    1250                 1255                 1260

Tyr Glu  Glu Glu Leu Leu Asp  Val Pro Arg Asp Ala  Tyr Ala Asp
    1265                 1270                 1275

Phe Gln  Ser Thr Ser Ala Gln  Gln Gly Ser Asp Leu  Glu Asp Glu
    1280                 1285                 1290

Ser Ser  Leu Arg His Arg His  Pro Ser Leu Ala Phe  Pro Lys Leu
    1295                 1300                 1305

Ser Glu  Gly Ser Ser Asp Gln  Asp Gly
    1310                 1315
```

<210> SEQ ID NO 69
<211> LENGTH: 982
<212> TYPE: DNA
<213> ORGANISM: Homo sapiens

<400> SEQUENCE: 69

```
acagcccacc agtgaccacg aaggctgtgc tgcttgccct gttgatggca ggcttggccc     60

tgcagccagg cactgccctg ctgtgctact cctgcaaagc ccaggtgagc aacgaggact    120

gcctgcaggt ggagaactgc acccagctgg gggagcagtg ctggaccgcg cgcatccgcg    180

cagttggcct cctgaccgtc atcagcaaag gctgcagctt gaactgcgtg gatgactcac    240

aggactacta cgtgggcaag aagaacatca cgtgctgtga caccgacttg tgcaacgcca    300

gcggggccca tgccctgcag ccggctgctg ccatccttgc gctgctccct gcactcggcc    360

tgctgctctg gggacccggc cagctctagg ctctgggggg ccccgctgca gcccacactg    420

ggtgtggtgc cccaggcctc tgtgccactc ctcacacacc cggcccagtg ggagcctgtc    480

ctggttcctg aggcacatcc taacgcaagt ctgaccatgt atgtctgcgc ccctgtcccc    540

caccctgacc ctcccatggc cctctccagg actcccaccc ggcagatcgg ctctattgac    600

acagatccgc ctgcagatgg cccctccaac cctctctgct gctgtttcca tggcccagca    660

ttctccaccc ttaaccctgt gctcaggcac ctcttccccc aggaagcctt ccctgcccac    720

cccatctatg acttgagcca ggtctggtcc gtggtgtccc ccgcacccag caggggacag    780

gcactcagga gggcccggta aaggctgaga tgaagtggac tgagtagaac tggaggacag    840

gagtcgacgt gagttcctgg gagtctccag agatggggcc tggaggcctg gaggaagggg    900

ccaggcctca cattcgtggg gctccctgaa tggcagcctc agcacagcgt aggcccttaa    960
```

taaacacctg ttggataagc ca 982

<210> SEQ ID NO 70
<211> LENGTH: 114
<212> TYPE: PRT
<213> ORGANISM: Homo sapiens

<400> SEQUENCE: 70

Met Ala Gly Leu Ala Leu Gln Pro Gly Thr Ala Leu Leu Cys Tyr Ser
1               5                   10                  15

Cys Lys Ala Gln Val Ser Asn Glu Asp Cys Leu Gln Val Glu Asn Cys
            20                  25                  30

Thr Gln Leu Gly Glu Gln Cys Trp Thr Ala Arg Ile Arg Ala Val Gly
        35                  40                  45

Leu Leu Thr Val Ile Ser Lys Gly Cys Ser Leu Asn Cys Val Asp Asp
    50                  55                  60

Ser Gln Asp Tyr Tyr Val Gly Lys Lys Asn Ile Thr Cys Cys Asp Thr
65                  70                  75                  80

Asp Leu Cys Asn Ala Ser Gly Ala His Ala Leu Gln Pro Ala Ala Ala
                85                  90                  95

Ile Leu Ala Leu Leu Pro Ala Leu Gly Leu Leu Leu Trp Gly Pro Gly
            100                 105                 110

Gln Leu

<210> SEQ ID NO 71
<211> LENGTH: 7273
<212> TYPE: DNA
<213> ORGANISM: Homo sapiens

<400> SEQUENCE: 71
aaccctgcct gaactttcct gtaaacagcc actgacagac tgcatccctg ctgggtggat 60
cctgcgactc ctagagggaa tggcacttct tgtttttaat tagcaaggtg aaaggtgaat 120
taaaactagc agtttggcaa gtcagtgcaa gaggctgact tctgagaggc ttccaggagc 180
ccgaagagag gacctccacg ggagaaggga gtgcgtgtgc tcggttttgt ttttttctct 240
cttttttttt tttttttctg aatgaacagc tttgcccaag tgactgaaaa atacagcttc 300
ttcctgaatc taccggcgta gttgctgaag agcgctctag acaggacatg gctctgaaga 360
ctcactcttt ggaatgtcct cttgctcccg gcttataaac aactgtcccg aggaaagaaa 420
ggttttacat agccaaatac agcctgacaa atggcacttc ggaactgtgc tttctgatga 480
caacgcgttc gatttctgac aaagcctctc gcacgctgcc cctggaggga agtcctaagt 540
aaaactcaga ccctccttaa agtgaggagc gagggcttgg acggtgaaca cggcagcatg 600
gcatccgcgg ggcacattat caccttgctc ctgtggggtt acttactgga gctttggaca 660
ggaggtcata cagctgatac tacccacccc cggttacgcc tgtcacataa agagctcttg 720
aatctgaaca gaacatcaat atttcatagc ccttttggat ttcttgatct ccatacaatg 780
ctgctggatg aatatcaaga gaggctcttc gtgggaggca gggaccttgt atattccctc 840
agcttggaga gaatcagtga cggctataaa gagatacact ggccgagtac agctctaaaa 900
atggaagaat gcataatgaa gggaaaagat gcgggtgaat gtgcaaatta tgttcgggtt 960
ttgcatcact ataacaggac acaccttctg acctgtggta ctggagcttt tgatccagtt 1020
tgtgccttca tcagagttgg atatcatttg gaggatcctc tgtttcacct ggaatcaccc 1080
agatctgaga gaggaagggg cagatgtcct tttgacccca gctcctcctt catctccact 1140

```
ttaattggta gtgaattgtt tgctggactc tacagtgact actggagcag agacgctgcg   1200
atcttccgca gcatggggcg actggcccat atccgcactg agcatgacga tgagcgtctg   1260
ttgaaagaac caaaatttgt aggttcatac atgattcctg acaatgaaga cagagatgac   1320
aacaaagtat atttcttttt tactgagaag gcactggagg cagaaaacaa tgctcacgca   1380
atttacacca gggtcgggcg actctgtgtg aatgatgtag gagggcagag aatactggtg   1440
aataagtgga gcactttcct aaaagcgaga ctcgtttgct cagtaccagg aatgaatgga   1500
attgacacat attttgatga attagaggac gttttttgc tacctaccag agatcataag    1560
aatccagtga tatttggact ctttaacact accagtaata tttttcgagg gcatgctata   1620
tgtgtctatc acatgtctag cattcgggca gccttcaacg gaccatatgc acataaggaa   1680
ggacctgaat accactggtc agtctatgaa ggaaaagtcc cttatccaag gcctggttct   1740
tgtgccagca aagtaaatgg agggagatac ggaaccacca aggactatcc tgatgatgcc   1800
atccgatttg caagaagtca tccactaatg taccaggcca taaaacctgc ccataaaaaa   1860
ccaatattgg taaaaacaga tggaaaatat aacctgaaac aaatagcagt agatcgagtg   1920
gaagctgagg atggccaata tgacgtcttg tttattggga cagataatgg aattgtgctg   1980
aaagtaatca caatttacaa ccaagaaatg gaatcaatgg aagaagtaat tctagaagaa   2040
cttcagatat tcaaggatcc agttcctatt atttctatgg agatttcttc aaagcggcaa   2100
cagctgtata ttggatctgc ttctgctgtg gctcaagtca gattccatca ctgtgacatg   2160
tatggaagtg cttgtgctga ctgctgcctg gctcgagacc cttactgtgc ctgggatggc   2220
atatcctgct cccggtatta cccaacaggc acacatgcaa aaaggcgttt ccggagacaa   2280
gatgttcgac atggaaatgc agctcagcag tgctttggac aacagtttgt tggggatgct   2340
ttggataaga ctgaagaaca tctggcttat ggcatagaga acaacagtac tttgctggaa   2400
tgtaccccac gatctttaca agcgaaagtt atctggtttg tacagaaagg acgtgagaca   2460
agaaaagagg aggtgaagac agatgacaga gtggttaaga tggaccttgg tttactcttc   2520
ctaaggttac acaaatcaga tgctgggacc tatttttgcc agacagtaga gcatagcttt   2580
gtccatacgg tccgtaaaat caccttggag gtagtggaag aggagaaagt cgaggatatg   2640
tttaacaagg acgatgagga ggacaggcat cacaggatgc cttgtcctgc tcagagtagc   2700
atctcgcagg gagcaaaacc atggtacaag gaattcttgc agctgatcgg ttatagcaac   2760
ttccagagag tggaagaata ctgcgagaaa gtatggtgca cagatagaaa gaggaaaaag   2820
cttaaaatgt caccctccaa gtggaagtat gccaaccctc aggaaaagaa gctccgttcc   2880
aaacctgagc attaccgcct gcccaggcac acgctggact cctgatgggg tgagactatc   2940
tactgtcttt tgaagaattt atatttggaa agtaaaaaag taaaaaaata aatcatccaa   3000
cttctttgca ttacttaaaa gagatttctg taatacagga atgactatga aggtgttata   3060
ataaattatt ctacatactc atttgactgg ataaacttta cataaaatta actaattttt   3120
taaataaatg cattgcttaa tggtttctca ttatgtttat caaaaaacaa ctgtagctgt   3180
tattttcagt acttggctgc ttttctgtga aaattattat tttacttttg gaagacaaga   3240
ttattagaat attgaagaaa aattggagac ttataatcat ggtaaatata aaactaaata   3300
tgttttaata tttctgaatt tttcttttcc atcacaatgt aagatatgca gaatacaaga   3360
tactttggca ttctcatgtg aactttctgt actctttaag gattatttta ttagtgttgt   3420
ttaagccatg agtgttaagt agcaggtgtg ttgtgagtgc tgtaacccat gaaaggaaaa   3480
```

```
atgtcattct gaggcttgtg cccttcgtaa aatattcatt aaagtacatt cacactattt   3540
ttgctttata acacagtctt taattttcac tcactgtgga aataaaaact aaggtaactt   3600
ctcagaaaga tatcaaatct cagaaagaat gtcaaatcag atgaagttat agttaggatt   3660
ctaactactg taaaagattt ttgcttccct cttgtggtaa aaaaaattat attctcacac   3720
atttcttttt tctctacaga cggatatctg tttaggaaag atttgaaagc agattatcag   3780
taggtacatg gatacatcaa gttcatttgc agaaacaaat aactgaaata aaaaacatgt   3840
taatccttgt atcatacttt aatatgaaag tattgtttat agataattta tctcacaagt   3900
caaaaatgaa gattttgcag cactgaaaat ctattaaagc tccaaatttt aagtttctaa   3960
ataatcttcg ctgaaatcta aaatatacta taacaaccgt gttttatttg tgaaaaaaat   4020
attaaagtga tttgctctca aatatcaaat tttcttctct cttttatatt aagagacaga   4080
aaattgtttc atgagttcac ttaactactg agatattcag agcattttta cctctctctt   4140
aaatgttata aaaaacaatt gtatttttaa gaatgtttat ttatcaaagt ctttccttct   4200
tctattaaat atttagcaat tacctttcta aaatatgaaa ttttgtaaga tgttttcacc   4260
taaataaaaa ttgaaagcaa gtggattaca caggagaacc attatgaaca tttatttaga   4320
tattaatctt aaacagtgtt tatttcagtt ttcaaagtta gcttataggt tatacattta   4380
agttaaagtg ctcataatca cttgcaattt cattgtaaaa tgaacaaata cataaatatt   4440
ttaagaaaaa tttaagttta ttcagataag tcaccatgct tcaaaagatc taagaaatgc   4500
aaatatactg aaaattgaca tcctctgaaa attccacttg ctatttaccc aagaatccac   4560
tggaggtcat tactgccatt aaataataac tgaaaagact atgtagtgaa atgtattttt   4620
aaaaactata ttcagtaaaa gcctgctcaa tttggagaaa tagaaccaca aacacagatc   4680
acaggggcct tacaaagttt atgtctgaac aaataagtca attaagtaca ctttattgaa   4740
aattgccttc cattaacaca caagaaagaa agcaggattt tctcctgtat ctgaatttta   4800
aaattaaaaa ggcagataag acataaatag ttatcatttt aattgcaata acacagacaa   4860
gtagttaatg atgataacaa tggtgtaact tgtaaactaa atatttggta actgaagcaa   4920
taggcagagg aaaatagctt ttctatgaca caagtcataa gaagtccata tactgaagag   4980
cgtttgatta aaataaagtg actattaacc agaaaagaaa cattttacat aaaatgctaa   5040
aatttattat aggaaaataa atcaaaccca aagaaagttt attcaatgct aatttgaaag   5100
aaaattgata agaaaacttt gagggcccaa gtccacaatt tggtgagacc actaaatttt   5160
acatataatt atacacacac atatgtacat atatatgtat ataatcttgc ttcccgcctg   5220
tttatggcag tactgaagag aaatgggaaa gaagagggag ggagagagaa agacgaaggg   5280
agagagaaag cagtttccaa ggatatgttt catgtcccac cattttctca gtttctccct   5340
ctctctccca acacacacac acacacaccc ctcacatact ataaaataaa tcttcactgc   5400
cctatcaaaa tacaaataaa tcaatctatg ctgttctgtc cttcttgaga atctaaaaca   5460
taccacaaaa atacatcccc agtcttttgt tctgtctgag gttagaatta attcaaattc   5520
agaatctgtt gtgagaaatg cccaggcttt aaaaattaaa aatggatgga tcttctctga   5580
actcagggag ggcacatact tagataccta caagacttgg aggaattaag agttcaccct   5640
tcatctcacc aaattttccc catttttctc tttcttgtag aaggagagaa accatgctct   5700
ctagcaacat tgagcaaaaa tcataaccac tcatctaatt tctaagaggc acctccatcg   5760
agggccggtc tcctgcttct ttagacctct tctatctttg ttacaggaga ggacctgtgg   5820
atagacttag ttttgacata aaacaatgcc cattcacctc ctccttcagc acaacgtcac   5880
```

```
ccattgggca agagatccag atttgttaac aaaaaagatt ttacttcgtg attccacgtc   5940

tataattcta tattgctaat tttttctttt gtgtgaatta ctgaatattt cagagcaaag   6000

ctatcaactt ggagaaacag ggattaaaaa taaggataaa cactaataag agctctagaa   6060

aaaagggaac agaaagtctg cctgtttagt aagtggcaat tccatacata ttttagagtt   6120

ttttctatct aaaattagtt aaatacttag aatgtttgta atgagtgttc gatatttgct   6180

ataggtttta gggttttgta aatcttcata gtaattataa acatttgtaa aatttgtaaa   6240

atactataag tcattttgag tgttggtgtt aagcatgaaa caaacagcag ctgttgtcct   6300

taaaaatgaa ttgacctggc cgggcgcggt ggctcacgcc tgtaatccca gcactttggg   6360

aggccgaggc gggtggatca tgaggtcagg agatcgagac catcctggct aacaaggtga   6420

aaccccgtct ctactaaaaa tacaaaaaat tagccgggcg cggtggcggg cgcctgtagt   6480

cccagctact tgggaggctg aggcaggaga atggcgtgaa cccgggaagc ggagcttgca   6540

gtgagccgag attgcgccac tgcagtccgc agtccggcct gggcgacaga gcgagactcc   6600

gtctcaaaaa aaaaaaaaaa aaaaaaaaaa aaaaaaaaaa aaaaaaaaaa tgaattgacc   6660

tgtgacacct gtagcctaat aaacatatta agaaaagtac ttagtattgt atagatattt   6720

ggattccaag agaaaatgca acatttataa taagaagtcc atactctttt tcttacagca   6780

gagcgtcaca ctgagttcca ttttaaaaaa ggactcattt ttcaggccaa caactgttgc   6840

atttgaatca gatataaata atagattttc cacaaacact cagctgattg tagcagtgtt   6900

atttaagctg gtatgtttat tttttttttc ttggaaggat agctttatat tttggctttc   6960

attataaatt gtgttctgct tgtgtttaaa tggcttactt ataagctaga gcactatatg   7020

ggagtgttct tctctgtatg gtatcctttt atttgcttgg ctgggttcat aacagtgtgt   7080

gccatattct ttcttttcac tgattctaag ccatgagact tattagcatc tggtggcaag   7140

ctgcagggac cattaacagt gtgtctcttt gactacaacg tggatctgcc actacgcgct   7200

atgtaccatt atgtacaatc tctatttggc tcaacttcga tgaaaaagaa ataaatattt   7260

gctaaactct caa                                                      7273
```

<210> SEQ ID NO 72
<211> LENGTH: 775
<212> TYPE: PRT
<213> ORGANISM: Homo sapiens

<400> SEQUENCE: 72

```
Met Ala Ser Ala Gly His Ile Ile Thr Leu Leu Leu Trp Gly Tyr Leu
1               5                   10                  15

Leu Glu Leu Trp Thr Gly Gly His Thr Ala Asp Thr Thr His Pro Arg
            20                  25                  30

Leu Arg Leu Ser His Lys Glu Leu Leu Asn Leu Asn Arg Thr Ser Ile
        35                  40                  45

Phe His Ser Pro Phe Gly Phe Leu Asp Leu His Thr Met Leu Leu Asp
    50                  55                  60

Glu Tyr Gln Glu Arg Leu Phe Val Gly Gly Arg Asp Leu Val Tyr Ser
65                  70                  75                  80

Leu Ser Leu Glu Arg Ile Ser Asp Gly Tyr Lys Glu Ile His Trp Pro
                85                  90                  95

Ser Thr Ala Leu Lys Met Glu Glu Cys Ile Met Lys Gly Lys Asp Ala
            100                 105                 110

Gly Glu Cys Ala Asn Tyr Val Arg Val Leu His His Tyr Asn Arg Thr
```

-continued

```
        115                 120                 125

His Leu Leu Thr Cys Gly Thr Gly Ala Phe Asp Pro Val Cys Ala Phe
    130                 135                 140

Ile Arg Val Gly Tyr His Leu Glu Asp Pro Leu Phe His Leu Glu Ser
145                 150                 155                 160

Pro Arg Ser Glu Arg Gly Arg Gly Arg Cys Pro Phe Asp Pro Ser Ser
                165                 170                 175

Ser Phe Ile Ser Thr Leu Ile Gly Ser Glu Leu Phe Ala Gly Leu Tyr
            180                 185                 190

Ser Asp Tyr Trp Ser Arg Asp Ala Ala Ile Phe Arg Ser Met Gly Arg
        195                 200                 205

Leu Ala His Ile Arg Thr Glu His Asp Asp Glu Arg Leu Leu Lys Glu
    210                 215                 220

Pro Lys Phe Val Gly Ser Tyr Met Ile Pro Asp Asn Glu Asp Arg Asp
225                 230                 235                 240

Asp Asn Lys Val Tyr Phe Phe Phe Thr Glu Lys Ala Leu Glu Ala Glu
                245                 250                 255

Asn Asn Ala His Ala Ile Tyr Thr Arg Val Gly Arg Leu Cys Val Asn
            260                 265                 270

Asp Val Gly Gly Gln Arg Ile Leu Val Asn Lys Trp Ser Thr Phe Leu
        275                 280                 285

Lys Ala Arg Leu Val Cys Ser Val Pro Gly Met Asn Gly Ile Asp Thr
    290                 295                 300

Tyr Phe Asp Glu Leu Glu Asp Val Phe Leu Leu Pro Thr Arg Asp His
305                 310                 315                 320

Lys Asn Pro Val Ile Phe Gly Leu Phe Asn Thr Thr Ser Asn Ile Phe
                325                 330                 335

Arg Gly His Ala Ile Cys Val Tyr His Met Ser Ser Ile Arg Ala Ala
            340                 345                 350

Phe Asn Gly Pro Tyr Ala His Lys Glu Gly Pro Glu Tyr His Trp Ser
        355                 360                 365

Val Tyr Glu Gly Lys Val Pro Tyr Pro Arg Pro Gly Ser Cys Ala Ser
    370                 375                 380

Lys Val Asn Gly Gly Arg Tyr Gly Thr Thr Lys Asp Tyr Pro Asp Asp
385                 390                 395                 400

Ala Ile Arg Phe Ala Arg Ser His Pro Leu Met Tyr Gln Ala Ile Lys
                405                 410                 415

Pro Ala His Lys Lys Pro Ile Leu Val Lys Thr Asp Gly Lys Tyr Asn
            420                 425                 430

Leu Lys Gln Ile Ala Val Asp Arg Val Glu Ala Glu Asp Gly Gln Tyr
        435                 440                 445

Asp Val Leu Phe Ile Gly Thr Asp Asn Gly Ile Val Leu Lys Val Ile
    450                 455                 460

Thr Ile Tyr Asn Gln Glu Met Glu Ser Met Glu Glu Val Ile Leu Glu
465                 470                 475                 480

Glu Leu Gln Ile Phe Lys Asp Pro Val Pro Ile Ile Ser Met Glu Ile
                485                 490                 495

Ser Ser Lys Arg Gln Gln Leu Tyr Ile Gly Ser Ala Ser Ala Val Ala
            500                 505                 510

Gln Val Arg Phe His His Cys Asp Met Tyr Gly Ser Ala Cys Ala Asp
        515                 520                 525

Cys Cys Leu Ala Arg Asp Pro Tyr Cys Ala Trp Asp Gly Ile Ser Cys
    530                 535                 540
```

```
Ser Arg Tyr Tyr Pro Thr Gly Thr His Ala Lys Arg Arg Phe Arg Arg
545                 550                 555                 560

Gln Asp Val Arg His Gly Asn Ala Ala Gln Gln Cys Phe Gly Gln Gln
                565                 570                 575

Phe Val Gly Asp Ala Leu Asp Lys Thr Glu Glu His Leu Ala Tyr Gly
            580                 585                 590

Ile Glu Asn Asn Ser Thr Leu Leu Glu Cys Thr Pro Arg Ser Leu Gln
        595                 600                 605

Ala Lys Val Ile Trp Phe Val Gln Lys Gly Arg Glu Thr Arg Lys Glu
    610                 615                 620

Glu Val Lys Thr Asp Asp Arg Val Val Lys Met Asp Leu Gly Leu Leu
625                 630                 635                 640

Phe Leu Arg Leu His Lys Ser Asp Ala Gly Thr Tyr Phe Cys Gln Thr
                645                 650                 655

Val Glu His Ser Phe Val His Thr Val Arg Lys Ile Thr Leu Glu Val
            660                 665                 670

Val Glu Glu Glu Lys Val Glu Asp Met Phe Asn Lys Asp Asp Glu Glu
        675                 680                 685

Asp Arg His His Arg Met Pro Cys Pro Ala Gln Ser Ser Ile Ser Gln
    690                 695                 700

Gly Ala Lys Pro Trp Tyr Lys Glu Phe Leu Gln Leu Ile Gly Tyr Ser
705                 710                 715                 720

Asn Phe Gln Arg Val Glu Glu Tyr Cys Glu Lys Val Trp Cys Thr Asp
                725                 730                 735

Arg Lys Arg Lys Lys Leu Lys Met Ser Pro Ser Lys Trp Lys Tyr Ala
            740                 745                 750

Asn Pro Gln Glu Lys Lys Leu Arg Ser Lys Pro Glu His Tyr Arg Leu
        755                 760                 765

Pro Arg His Thr Leu Asp Ser
    770                 775
```

<210> SEQ ID NO 73
<211> LENGTH: 15580
<212> TYPE: DNA
<213> ORGANISM: Homo sapiens

<400> SEQUENCE: 73

```
atgctactcc ctgccctcct ctttgggatg gcgtgggccc tggctgacgg gcggtggtgt      60

gagtggacag agaccatccg tgtggaggag gaagtggcac cccgtcagga ggacctggta     120

ccctgtgcca gcctcgacca ttacagccgc ctgggctggc ggctggacct gccctggagt     180

ggccgctcgg ggcttacccg gtccccagcg cctgggctct gtcctatcta caaacctcca     240

gaaacccggc ctgccaagtg gaaccggaca gtgaggactt gttgcccagg ctgggggggc     300

gcccactgca ctgaggccct tgccaaagcc agtcctgaag gccactgctt tgccatgtgg     360

cagtgccagc tacaggcagg ctcagctaat gcctcagcag gaagcctgga ggagtgctgc     420

gcccggccct ggggacaaag ctggtgggat ggcagctccc aggcctgccg cagctgctcc     480

agccgacacc tgccaggcag tgcctcttct ccagccctcc tgcagcccct ggcaggggct     540

gtgggccagc tctggagcca gcaccagcgt ccctcggcca cctgtgcctc ctggtcgggc     600

ttccactacc gcacctttga tggccgccac tatcacttcc tgggccgctg cacctacctg     660

ctggcgggtg ctgcggactc cacctgggct gtccacctaa cacccgggga ccgctgcccc     720

cagcctggac actgtcagcg ggtgactatg ggacccgagg aggtgctgat ccaggctgga     780
```

-continued

```
aatgtgtctg tgaaggggca gctggtacct gaagggcagt cttggctgct ccacgggctg    840
agcctgcaat ggctggggga ctggctggtg ctgtcaggag gcctgggggt cgtggtgcgg    900
ctggacagga ctggctccat ctccatctct gtggaccacg agctctgggg acagacacaa    960
ggcctctgtg ggctctacaa tggctggcca gaggatgact tcatggagcc aggcggaggg   1020
ctggccatgt tagcagccac ctttggaaat tcctggaggc tccctggctc ggagtctggg   1080
tgtctggatg cagtggaggt ggcccagggc tgtgaccccc tggggctcat agacgcagat   1140
gtagaacctg gccacctgcg ggctgaagcc caggacgtgt gccatcagct gctggaaggt   1200
ccattcgggc agtgccatgc ccaggtttcc cctgctgagt accacgaggc ctgtctcttt   1260
gcctactgcg caggggccat ggcaggcagt gggcaagagg ggcggcagca ggctgtttgt   1320
gccacctttg ccagctatgt ccaggcctgt gccaggcggc acatccacat tcgctggagg   1380
aagcctggct tctgcgagcg cctgtgcccc gggggccagc tctactccga ctgcgtctcc   1440
ctctgcccac ccagctgcga ggcggtgggt cagggagagg aggagtcctg cagggaagag   1500
tgtgtgagtg gctgtgagtg cccgcgaggc ctcttctgga atggcaccct ctgtgtgcct   1560
gctgcccact gcccctgcta ctactgccgc cagcgctatg tacccggtga caccgtgcgc   1620
cagctgtgta acccctgcgt gtgcagggat ggccgctggc actgtgccca ggcactgtgc   1680
cccgccgagt gtgcagtggg tggggacggg cactacctca ccttcgatgg gcggagctac   1740
tccttctggg gtggtcaagg ttgccgctac agcctggtgc aggactatgt gaagggacag   1800
ctactgatcc tactggagca tggggcctgc gacgctggga gctgcctgca cgccatctcc   1860
gtctccctgg aggacaccca catccagctc agggactcag gagctgtgct ggtcaatggg   1920
caggatgtgg gcttgccctg gattggcgct gagggcctca gtgtgcgccg agcttcctct   1980
gcctttctgc tgctgcgctg gcctggggcc caggtgctct ggggactgtc tgaccctgta   2040
gcctacatca ccctggaccc ccgccatgcc caccaggtgc agggtctgtg tggcaccttc   2100
acccagaacc agcaggacga cttcctgaca ccagccggag atgtggaaac tagcattgct   2160
gcctttgcta gcaagttcca ggtggccggc aagggaagat gcccctctga ggacagtgcc   2220
ctgctgtctc cctgcaccac ccactcccag cgccacgcct tcgcagaggc ggcctgtgcc   2280
atcctgcaca gctctgtctt ccaggaatgc cacaggctgg tggacaaaga gccattctat   2340
ctgcgctgcc tggcagccgt gtgtggctgt gatcccggca gtgactgcct gtgcccggtg   2400
ctgtctgcct atgcgcgtcg ctgtgcccag gaaggtgcct cacctccctg gaggaaccag   2460
accctctgcc ctgttatgtg tcctggtggc caggagtacc gagagtgtgc cccagcatgc   2520
ggtcaacact gcgggaaacc agaggactgt ggagagctgg gcagctgtgt ggctggttgt   2580
aactgtcctc tggggctgct gtgggaccct gagggccagt gtgtgccccc cagcttgtgc   2640
ccctgccagc tcggagcccg tcgctatgcc cctggcagtg ccaccatgaa ggagtgcaac   2700
cgctgcatct gccaggaaag gggcctctgg aattgcacgg ctcgccactg cccttcacag   2760
gcattctgcc ccagggagct tgtctatgcc cctggtgcct gtctcctcac ctgtgacagc   2820
cccagcgcca atcactcctg ccctgcaggc agtactgatg gctgtgtctg tccaccaggc   2880
acggtgctgc tggacgagcg ctgtgtgcct cctgacctct gtccctgccg tcacagtggg   2940
cagtggtacc tgcccaacgc caccatccag gaagactgca acgtttgcgt gtgccggggc   3000
cggcagtggc actgcacagg ccagcggcgc agtgggcggt gccaggcatc aggcgccccc   3060
cactatgtga catttgacgg actggccttc acctatcctg ggcctgcga gtatctgctg    3120
```

```
gtgcgagagg ccagtggcct attcacagtc tctgcccaga acctgccctg tggggccagc   3180
ggtctcacct gcaccaaagc gctggccgtg cgtctggagg gcactgttgt gcacatgctc   3240
agaggccggg cagtgacggt gaatggggtg agcgtgacgc cccccaaggt ctacacaggc   3300
cctgggctga gcctgcgtcg tgctggcctc ttcctgctgc tctcgaccca cctgggcctc   3360
accctgctct gggatggagg gactcgggtc ctggtgcaac tgtcccctca gttccgtggt   3420
cgcgtggctg ggctgtgtgg tgactttgat ggagatgcca gtaatgatct gcggagccgc   3480
cagggcgtcc tggagcccac agctgaactg gctgcccact cctggcgcct cagcccccctc  3540
tgccctgagc caggagacct gccacacccc tgcacgatga acacacaccg ggctggttgg   3600
gctcgggccc gctgtggggc gctgctgcag ccgctcttca cattatgcca cgcggaggtc   3660
cccccgcagc agcactatga gtggtgcctg tatgacgcct gcggctgcga ctcgggggt   3720
gactgtgagt gcctctgctc ggccattgcc acctatgcag atgagtgtgc ccggcatggg   3780
caccacgtgc gctggcgtag ccaggagctc tgctccctgc agtgtgaagg gggacaggta   3840
tatgaggcct gtggccccac gtgtcccccc acctgccatg agcagcatcc tgagcccggg   3900
tggcactgcc aggtggtggc ctgtgtggag ggctgcttct gccccgaggg gactctgctg   3960
cacggaggag cctgcttgga gccagcttcc tgcccctgtg agtggggccg caactccttc   4020
ccgccggggt ctgtgctgca aaaggactgc gggaactgca cgtgccagga aggtcaatgg   4080
cattgtgggg gtgacggtgg ccactgtgag gagcttgtgc ctgcctgtgc agagggagag   4140
gccctgtgcc aagagaatgg gcactgtgtg ccccatgggt ggctttgtga caaccaggac   4200
gactgtggcg atggctctga tgaggagggt tgtgccgccc caggctgtgg ggaggggcag   4260
atgacttgca gctccggcca ctgcctgccc ctggccctgc tctgtgaccg ccaggatgac   4320
tgtggagatg gcacggatga gccgagctat ccgtgccccc agggcttgct ggcctgtgcc   4380
gatggacgct gcctgccgcc ggccctgctc tgcgatgggc atcctgactg tctggatgcc   4440
gccgacgagg agtcctgtct ggggcaggtg acctgcgtcc ccggggaggt gtcctgtgtt   4500
gatggcacct gcctgggggc catccagctg tgtgacggag tctgggactg cccagatgga   4560
gccgatgagg ggccgggaca ctgcccccta ccttctctgc ccacacctcc tgccagcacc   4620
ttgcctggcc cctccccagg ctccctggac actgcgtcaa gtcccctggc cagcgccagc   4680
cctgcgccac cctgcggccc cttcgagttt cggtgcggca gcggcgagtg cacccccgcgg  4740
ggctggcgct gcgaccagga ggaagactgc gccgacggca gcgacgagcg cggctgcgga   4800
gggccctgcg cgccgcacca cgcgccctgc gcccgcggcc ctcactgcgt gtcccccgag   4860
cagctgtgcg acggcgtgcg gcagtgtccc gacggctcgg acgagggccc cgacgcctgc   4920
ggggggctgc cagccctggg aggccccaac aggacagggc ttccctgccc agaatacacc   4980
tgccccaatg gcacctgcat aggcttccag ctggtgtgtg atgggcagcc tgactgtgga   5040
aggccagggc aggtgggccc ctccccagaa gagcagggtt gtggggcctg gggcccctgg   5100
agcccatggg ggccctgcag ccggacgtgt gggccctggg gccagggccg gagccgccgc   5160
tgctccccac tcggcctcct ggtgctacag aactgcccag ggcctgagca ccagtctcag   5220
gcctgcttca cggcagcctg cccagtggac ggtgaatgga gcacctggtc cccctggtct   5280
gtgtgctctg agccgtgcag ggcaccatg acgcggcaac ggcagtgcca ctcaccccag   5340
aatgggggcc gcacctgtgc tgcactgccc ggaggcctgc acagcacccg ccagaccaag   5400
ccttgccctc aggacggctg ccccaatgcc acttgctctg ggagctgat gttccagccc   5460
tgtgcccccct gcccactgac ctgtgatgac atctctggcc aggtcacgtg cccacctgat  5520
```

```
tggccctgcg gcagcccggg ctgctggtgc ccagaagggc aggtgctggg cagcgagggg   5580
tggtgtgtgt ggccccggca gtgcccctgc ctggtggacg gtgcccgcta ctggcctggg   5640
caacgcatca aggccgactg ccagctctgc atctgccaag acggacggcc ccgacgctgc   5700
cgactcaacc cggactgcgc tgtggactgt ggctggtcct cctggtcacc ctgggccaag   5760
tgcctgggcc cctgtggaag ccagagcatc cagtggtcct tccggagctc caacaacccc   5820
cgcccctccg gccgaggtcg ccagtgccgt ggcatccacc gcaaggcacg caggtgccag   5880
acggagccct gtgaggggtg tgagcatcag ggccaggtcc accgtgtcgg ggaacgctgg   5940
catgggggcc cctgcagggt gtgccagtgt ctgcacaacc tcaccgcaca ctgctcaccc   6000
tactgcccgc tcggcagctg cccccagggc tgggtcttgg tggaggggac gggagaatca   6060
tgctgccact gtgccctacc tggagagaac cagacggtcc agcccatggc cactcctgcc   6120
gcagctccgg ctcccagtcc ccagatcaga ttccctttgg ccacttacat tctgcctccg   6180
tcaggagacc cctgctattc tcccctgggg ctggccggac tggctgaggg gagtctgcat   6240
gcatcgtccc agcagctgga acaccccacc caggctgccc tcctgggggc tcccacccag   6300
gggcccagcc ctcagggatg gcacgctgga ggggatgctt atgccaagtg gcacactcgg   6360
ccccattacc tgcagctgga cctgcttcag cctcggaacc tcactggcat cctagtgccg   6420
gagactggct cctccaacgc atatgccagc agcttctcac tccagttcag cagcaatggt   6480
ctacactggc atgactatcg tgacctcctg cctggcatct tgcccctgcc caagcttttc   6540
cccagaaact gggatgacct ggaccctgcc gtatggactt tcggccgcat ggtgcaggcg   6600
aggtttgtca gggtgtggcc ccacgatgtc caccacagcg atgtcccccct gcaggtggag   6660
ctgctgggct gcgagccagg gtccccaccg gcacctctgt gcccaggggt tggactccgc   6720
tgtgccagtg gtgagtgtgt cctgagaggg ggcccttgtg acggtgttct ggactgcgag   6780
gatggctcgg atgaggaggg ctgtgtgttg ctgcctgagg gcactggcag attccattcc   6840
acagccaaga ccctggccct ctcctctgcc cagccggggc agctgctgca ctggcccagg   6900
gagggcctgg cagagactga gcactggccc cctgggcagg aatcccccac gtccccgaca   6960
gagacaaggc ccgtgagtcc tggcccagcc tccggggtgc ctcaccatgg ggaatctgtg   7020
cagatggtga ccaccacccc catacccag atggaggcca ggaccctgcc accaggtatg   7080
gcagctgtga cggtggtgcc cccacaccct gtgactccag cgacccctgc tggccagagc   7140
gtcgccccag gacccttccc acctgtgcag tgtggccccg gccagacgcc ctgtgaggtg   7200
ctgggctgcg tggaacaggc gcaggtgtgt gatggcaggg aggattgcct cgacggctcc   7260
gacgagaggc actgcgccag gaatctactt atgtggctcc cttctctccc tgccttgtgg   7320
gcagcgagca ctgtgccctt catgatgcct accatggccc tgcctgggct tccagcctca   7380
agggccctct gttccccgag ccagctgagc tgtggcagcg gggagtgtct gtctgctgag   7440
cggcgctgtg acctgcggcc tgactgccag gatggctcgg acgaggatgg ctgtgtggac   7500
tgcgtgctgg ccccctggtc tgtctggagc agctgcagcc gcagctgtgg cctgggcctc   7560
accttccagc gccaggagct gctgcggcct cctctgccag ggggcagctg cccgcgtgac   7620
cggttccgaa gccagtcctg ctttgtgcag gcctgcccag tggctggggc atgggccatg   7680
tgggaggcct ggggaccctg cagcgtctcc tgcgggggtg gccatcagag tcgccagaga   7740
agctgtgtgg accccccacc caagaatggc ggtgccccct gccccggggc ctcccaagag   7800
agggcaccct gcggcttgca gccctgctca ggtggcacag actgcgagct gggccgtgtg   7860
```

tatgtgagtg ccgatctgtg ccagaagggg ctggtgcccc catgcccacc ctcctgcctg 7920
gatcccaagg ccaacagaag ctgcagtggg cattgtgtgg aaggatgccg ctgtcccccg 7980
gggctccttc tgcatgacac tcgctgcctg cccctctctg agtgcccctg cctggtgggc 8040
gaagagctga agtggccagg ggtgtccttc ctcctgggca actgcagcca atgcgtgtgt 8100
gagaaggggg agttgctgtg ccaaccaggg ggctgccccc tgccctgcgg ctggtcagcc 8160
tggtcctcct gggctccctg cgaccgctcc tgtggctctg gagtgagggc caggttcagg 8220
tctccctcca accctccggc agcctggggg ggtgccccgt gtgaaggtga ccggcaggaa 8280
ctgcagggct gccacacagt gtgtgggaca gaggtgttcg gctggacgcc ctggacttcc 8340
tggtcctcct gctcccaaag ctgccttgcc ccgggagggg gccctggctg gcgcagtcgt 8400
tcccgactct gccccagccc tggggattca tcctgcccag gagatgccac ccaggaggag 8460
ccctgcagcc cccctgtatg cccagtgcca agcatctggg gtctgtgggc tccctggtcc 8520
acttgctcag ccccctgtga tggaggcatc cagacacgtg ggcgcagctg ctccagcttg 8580
gctccagggg acaccacgtg cccaggaccc cacagtcaga ccagggactg caacacgcag 8640
ccctgcacag cccagtgccc agagaacatg ttgttccgct cagcagagca gtgtcaccag 8700 gagggggggtc cttgccctcg gctatgcctg acgcagggcc ccgggataga gtgtacgggc 8760
ttctgcgccc ccggctgcac ctgccccccct ggtcttttcc tgcacaatgc tagctgcctg 8820
ccccgcagcc agtgcccctg ccagctgcac gggcagctct atgcatcagg agcaatggct 8880
cgcctggact cctgcaacaa ctgcacctgt gtctctggta agatggcatg cacctcggag 8940
cgctgcccag tggcctgtgg ctggagtccc tggaccctgt ggagtctctg tagctgcagc 9000
tgcaacgtgg gcattcggcg ccgcttccgg gcaggcactg cacccccagc tgcctttggg 9060
ggtgctgagt gccaaggccc caccatggag gctgaattct gcagcctgcg gccatgtcca 9120
ggtcctggtg gggagtgggg cccttggtct ccgtgctccg tgccctgtgg tggtggctac 9180
aggaaccgca cccgaggcag cagccgcagc ctcatggagt tttccacctg tggcctgcag 9240
ccctgcgcag ggccagtgcc tggcatgtgt cccagggaca agcagtggct ggactgtgcc 9300
cagggccctg cctcttgtgc agagctcagc gccccaagag ggactaacca gacctgccac 9360
cctggctgcc actgcccctc tgggatgctt ctgctgaaca acgtgtgtgt gcccacccag 9420
gactgcccct gtgcccacga ggggcacctc taccccccgg gcagcactgt ggttcgtcca 9480
tgtgaaaact gctcctgtgt ctccgggctc atcgccaact gcagctcctg gccttgtgcg 9540
gagggtgagc ccacgtggtc accctggacc ccttggagcc agtgttcagc ctcctgtggc 9600
cctgcccggt gccatcggca ccggttctgt gccaggtccc ccagtgcagt gccatccacc 9660
gtggctccgc tgcccctgcc agccaccccc acacctctct gctcaggccc cgaggctgaa 9720
gaggagccat gtctcctgca ggggtgtgat cgagctgggg gatggggtcc atgggggccc 9780
tggtcccact gtagccggag ctgtggggga ggcctgcgga gccggacccg ggcctgtgac 9840
cagcccccac cccagggcct gggggattac tgcgaggggc cacgggcaca gggggaggtc 9900
tgccaggctc tgccctgccc agtgaccaac tgcactgcca ttgaaggggc cgagtatagc 9960
ccctgtggcc ctccgtgccc tcgctcctgt gatgacctag tgcactgcgt gtggcgctgc 10020
cagcctggct gctactgccc accaggccag gtactgagtt ccaacggggc catctgcgtg 10080
cagccgggtc actgcagctg cctggacctg ctgaccgggc agcggcacca tccgggtgct 10140
cggctggcaa ggcctgacgg ctgcaaccac tgcacctgcc tggaggggag gctgaactgc 10200
acagacctgc cctgcccagt gcccggaggc tggtgcccgt ggtcggagtg gacaatgtgc 10260
tcccagccct gcaggggcca gaccaggagc cgctccaggg cctgtgcctg ccccactcct 10320
cagcacggtg gtgccccgtg cactggagag gctggggagg caggggccca gcatcagagg 10380
gaggcctgcc ccagctacgc cacgtgccca gtggacggag cctggggccc atgggggcca 10440
tggtctccct gcgacatgtg cttggggcag tcccaccgga gccgggcgtg cagccggccc 10500 cccaccccctg agggagggag gccctgccct gggaaccaca cgcagagtcg cccttgccag 10560
gaaaattcca cccagtgcac agactgcggg ggtggccaga gtctgcatcc ctgtgggcag 10620
ccctgccccc gctcctgcca ggacctgtcc cctgggagtg tgtgccagcc aggctctgtg 10680
ggctgccagc ccacttgtgg gtgcccccctg ggccagctct cccaggacgg gctgtgcgtg 10740
cccccagccc actgccgctg ccagtaccag cctggagcca tggggatccc tgagaaccag 10800
agccgctcag cagggtctag gtttagctcc tgggagagcc tggaacccgg agaggtggtc 10860
actgggccat gtgacaactg cacctgtgtg gcaggcattc tgcaatgcca ggaggtgcct 10920
gactgcccgg accctggggt gtggagctct tggggccctt gggaagactg cagtgtttcg 10980
tgtgggggcg gggagcagct gcgctcccgg cgctgtgctc gtcctccctg cccagggcct 11040
gcccgccaga gccgcacatg cagcacacag gtctgcagag aggcaggctg cccggctggc 11100
cgcctgtacc gtgaatgcca gcccggcgag ggatgcccct tctcctgcgc ccacgtcacg 11160
cagcaggtgg gctgcttctc tgagggctgc gaggagggct gccactgccc cgagggcacc 11220
ttccagcacc gcctggcctg tgtgcaggag tgcccttgtg tgctgacagc ctggctgctg 11280
caggagctgg gagccaccat aggtgaccct ggtcagcccc tcgggcctgg agatgagctg 11340
gactcaggcc agacacttcg tacaagctgt ggcaactgct cgtgtgcaca cgggaagctg 11400
tcttgctccc tggacgactg cttcgaggcc gatggtggtt tcggtccctg gagcccgtgg 11460
ggcccgtgct cccgctcctg tggagggctg ggcacccgta cccgcagccg ccagtgtgtg 11520
ctcaccatgc ccaccctcag tggtcagggc tgccgtgggc cccgccagga cctcgagtgc 11580
cccagcccag actgccctgg ggctgaaggg tccacggtgg agccagtaac aggccttcca 11640
ggtggctggg gcccatggtc ctcctggtcc ccctgctcca gaagctgcac ggaccccgct 11700
cgccctgcat ggcgcagccg cacccgcctc tgcctggcta actgcaccat gggggaccca 11760
ttacaggagc gcccctgcaa cctgccctca tgcacagagc tgcccgtgtg ccctggccct 11820
ggctgtgggg ctgggaactg ttcctggacc tcctgggccc cgtgggaacc ttgctcccgc 11880
agctgcggag tgggccagca gcgccgcctg cgggcatacc gtccccctgg gcccggcggg 11940
cactggtgcc ccaacatcct tactgcctac caagagcgcc gcttctgcaa cctgcgagcc 12000
tgcccagtgc ccgggggctg gtcacgctgg agtccctggt cctggtgtga ccgcagctgt 12060
gggggaggcc aatccctgag aagccgcagc tgctcaagcc ccccatccaa gaacgggggga 12120 gcccccctgtg ctggggagcg gcaccaggcc cgcctctgca atcccatgcc ttgtgaggcc 12180
ggctgcccag caggcatgga ggtggtcacc tgtgccaacc gctgcccccg ccgctgctca 12240
gacctccagg agggaattgt gtgtcaggac gaccaggtct gccagaaggg ctgccgctgc 12300
ccaaaggggt ccctggagca ggatggtggc tgcgtgccaa ttgggcactg tgactgcacc 12360
gatgcccagg gccacagctg ggccccgggg agccagcacc aggatgcctg caacaactgc 12420
tcatgccaag ctgggcagct ctcctgcacg gctcagccct gcccgcctcc cacccactgt 12480
gcctggagcc actggtcggc ctggagtccc tgcagccact catgcgggcc cagagggcag 12540
cagagccgct tccggtcctc cacgtcgggc tcgtgggccc cagagtgtcg ggaggagcag 12600

```
tcccagagcc agccctgccc tcagccctcg tgcccacccc tgtgcctgca gggcactcgc  12660
tcccgcaccc tgggggacag ctggctgcag ggggagtgcc agcggtgctc ctgcaccccg  12720
gagggtgtga tctgcgaaga tacggagtgt gcagtgcctg aggcttggac gctgtggtcc  12780
tcctggtccg actgccctgt ctcctgtgga ggtggaaacc aggtccgaac ccgggcctgc  12840
agggccgcag cccctcacca caggagccca ccctgcctgg gccctgacac ccagaccagg  12900
cagcagcctt gcccagggct gctggaggcc tgctcctggg gcccgtgggg gccctgttcc  12960
cgcagctgcg gcccgggcct ggcctctcgc tctgggtcct gcccctgcct gatggccaag  13020
gccgacccca cctgcaacag caccttcctc cacctggaca cccagggctg ctactcaggg  13080
ccctgcccag aggagtgtgt gtggagcagc tggagcagct ggacgcgctg ctcttgccgg  13140
gtgctggtgc agcagcgcta ccgacaccag ggcccggcgt cccgaggggc cagggcaggc  13200
gccccctgca cgcggctgga tggccacttc cggccttgcc ttatcagcaa ctgctctgag  13260
gacagctgca cgcctccctt tgagttccat gcctgcggct cccccctgtgc tgggctctgt  13320
gccacacacc tgagccatca gctctgccag gacctgccac cctgccagcc gggctgctac  13380
tgccccaagg ggctgctgga gcaggctggg ggctgcattc ccccagagga gtgtaactgc  13440
tggcatacct cagcagcagg agccgggatg accctggccc ctggggaccg cctgcagctg  13500
ggctgtaagg agtgtgaatg ccggcgtggg gagctgcact gcaccagcca gggctgtcaa  13560
ggtcttctgc ctctgagtga gtggtccgag tggtcgccct gtgggccctg cctgccgccc  13620
agcgccctgg cccctgcctc caggactgcc ctagaggagc actggctccg agacccaact  13680
ggcctctccc ccaccttggc cccgctgctg gcttcagagc agcaccgcca ccggctctgt  13740
ctggatcctg cgacagggag gccctggact ggagcccctc acctctgcac cgcacccctc  13800
agccagcagc gcctctgccc tgaccctgga gcctgccctg actcatgcca gtggagtctg  13860
tgggggccat ggagcccctg ccaggtgccc tgcagtgggg ggttcaggct acgctggaga  13920
gaggcagagg ccctctgtgg aggaggctgc cgggagccat gggctcaaga aagctgcaac  13980
ggagggccct gcccagagtg cgaggcccaa gacactgtat tcaccctgga ctgtgccaac  14040
cagtgcccac acagctgtgc cgacctctgg gaccgcgttc agtgtctgca gggaccctgc  14100
cgcccaggct gccgctgtcc ccctggccag ctggtccagg atgggcgctg tgtgccgatc  14160
tcctcttgcc gctgtggcct ccccagtgcc aatgcctctt gggagctggc cccggcccag  14220
gcggtgcagc tggactgcca aaactgcacc tgtgtcaacg agtccctggt gtgcccacac  14280
caggagtgtc cagtccttgg gccttggtca gcctggagca gttgctcggc cccctgtggt  14340
gggggcacta tggagcgaca tcggacttgt gaggggggtc ctggggtggc accatgccag  14400
gcccaggaca cagagcaacg gcaggagtgt aacctgcagc cctgccctga gtgcccccct  14460
ggccaggtgc ttagtgcctg tgccacctca tgcccgtgcc tctgctggca tctgcagcct  14520
ggtgccatct gtgtgcagga gccctgccag cctggctgtg gctgccctgg agggcagctg  14580
ctgcacaatg gcacgtgtgt gcctcccact gcctgcccct gcacccagca ttctctgccc  14640
tggggcctca ccctgaccct ggaagagcag gcccaggagc tgcccccagg gactgtgctc  14700
acccggaact gcacccgctg tgtctgccac ggtggagcct tcagctgctc cctcgttgac  14760
tgtcaggtgc cccctgggga aacgtggcag caggtggccc cgggggagct ggggctctgc  14820
gagcagacgt gcctggagat gaacgccaca aagacccaga gtaactgcag ttcagctcga  14880
gcctcgggct gcgtgtgcca gcccgggcac ttccgcagcc aggcaggccc ctgcgtcccc  14940
gaagaccact gcgagtgctg gcaccttggg cgtccccacc tgcctggatc tgaatggcag  15000
```

```
gaggcctgtg agagctgcct ctgcctcagt gggaggcctg tctgcaccca gcactgctcc  15060

ccactcacct gtgctcaggg cgaggagatg gtgctggagc cagggagctg ctgtccctct  15120

tgccgcaggg aggctccgga ggagcagtcg ccctcctgcc agctcctcac ggagcttcga  15180

aacttcacca aagggacctg ttacctggac caggtagaag tgagctactg cagtgggtac  15240

tgcccatcca gcacccatgt catgccagag gagccatacc tgcagagcca gtgtgactgc  15300

tgcagctacc gtctagaccc ggagagccct gtgcggatcc tgaacctgcg ctgtctgggt  15360

ggccacacag agcccgtggt gctgccggtc atccacagct gccagtgcag ctcctgccag  15420

ggtggggact tctcaaagcg ctaacaggct ccgctgggtg agtccacagc tgtccctctt  15480

gtgatcatgg gactcagcag cactgaccac gtccttccac gctctctcac ctgcccccaa  15540

ctgggggccc atgacttggc attagcatgt tccaaataaa                        15580
```

<210> SEQ ID NO 74
<211> LENGTH: 5150
<212> TYPE: PRT
<213> ORGANISM: Homo sapiens

<400> SEQUENCE: 74

```
Met Leu Leu Pro Ala Leu Leu Phe Gly Met Ala Trp Ala Leu Ala Asp
1               5                   10                  15

Gly Arg Trp Cys Glu Trp Thr Glu Thr Ile Arg Val Glu Glu Glu Val
            20                  25                  30

Ala Pro Arg Gln Glu Asp Leu Val Pro Cys Ala Ser Leu Asp His Tyr
        35                  40                  45

Ser Arg Leu Gly Trp Arg Leu Asp Leu Pro Trp Ser Gly Arg Ser Gly
    50                  55                  60

Leu Thr Arg Ser Pro Ala Pro Gly Leu Cys Pro Ile Tyr Lys Pro Pro
65                  70                  75                  80

Glu Thr Arg Pro Ala Lys Trp Asn Arg Thr Val Arg Thr Cys Cys Pro
                85                  90                  95

Gly Trp Gly Gly Ala His Cys Thr Glu Ala Leu Ala Lys Ala Ser Pro
            100                 105                 110

Glu Gly His Cys Phe Ala Met Trp Gln Cys Gln Leu Gln Ala Gly Ser
        115                 120                 125

Ala Asn Ala Ser Ala Gly Ser Leu Glu Glu Cys Cys Ala Arg Pro Trp
    130                 135                 140

Gly Gln Ser Trp Trp Asp Gly Ser Ser Gln Ala Cys Arg Ser Cys Ser
145                 150                 155                 160

Ser Arg His Leu Pro Gly Ser Ala Ser Ser Pro Ala Leu Leu Gln Pro
                165                 170                 175

Leu Ala Gly Ala Val Gly Gln Leu Trp Ser Gln His Gln Arg Pro Ser
            180                 185                 190

Ala Thr Cys Ala Ser Trp Ser Gly Phe His Tyr Arg Thr Phe Asp Gly
        195                 200                 205

Arg His Tyr His Phe Leu Gly Arg Cys Thr Tyr Leu Leu Ala Gly Ala
    210                 215                 220

Ala Asp Ser Thr Trp Ala Val His Leu Thr Pro Gly Asp Arg Cys Pro
225                 230                 235                 240

Gln Pro Gly His Cys Gln Arg Val Thr Met Gly Pro Glu Glu Val Leu
                245                 250                 255

Ile Gln Ala Gly Asn Val Ser Val Lys Gly Gln Leu Val Pro Glu Gly
            260                 265                 270
```

```
Gln Ser Trp Leu Leu His Gly Leu Ser Leu Gln Trp Leu Gly Asp Trp
        275                 280                 285

Leu Val Leu Ser Gly Gly Leu Gly Val Val Val Arg Leu Asp Arg Thr
    290                 295                 300

Gly Ser Ile Ser Ile Ser Val Asp His Glu Leu Trp Gly Gln Thr Gln
305                 310                 315                 320

Gly Leu Cys Gly Leu Tyr Asn Gly Trp Pro Glu Asp Asp Phe Met Glu
                325                 330                 335

Pro Gly Gly Gly Leu Ala Met Leu Ala Ala Thr Phe Gly Asn Ser Trp
            340                 345                 350

Arg Leu Pro Gly Ser Glu Ser Gly Cys Leu Asp Ala Val Glu Val Ala
        355                 360                 365

Gln Gly Cys Asp Ser Pro Leu Gly Leu Ile Asp Ala Asp Val Glu Pro
    370                 375                 380

Gly His Leu Arg Ala Glu Ala Gln Asp Val Cys His Gln Leu Leu Glu
385                 390                 395                 400

Gly Pro Phe Gly Gln Cys His Ala Gln Val Ser Pro Ala Glu Tyr His
                405                 410                 415

Glu Ala Cys Leu Phe Ala Tyr Cys Ala Gly Ala Met Ala Gly Ser Gly
            420                 425                 430

Gln Glu Gly Arg Gln Gln Ala Val Cys Ala Thr Phe Ala Ser Tyr Val
        435                 440                 445

Gln Ala Cys Ala Arg Arg His Ile His Ile Arg Trp Arg Lys Pro Gly
    450                 455                 460

Phe Cys Glu Arg Leu Cys Pro Gly Gly Gln Leu Tyr Ser Asp Cys Val
465                 470                 475                 480

Ser Leu Cys Pro Pro Ser Cys Glu Ala Val Gly Gln Gly Glu Glu Glu
                485                 490                 495

Ser Cys Arg Glu Glu Cys Val Ser Gly Cys Glu Cys Pro Arg Gly Leu
            500                 505                 510

Phe Trp Asn Gly Thr Leu Cys Val Pro Ala Ala His Cys Pro Cys Tyr
        515                 520                 525

Tyr Cys Arg Gln Arg Tyr Val Pro Gly Asp Thr Val Arg Gln Leu Cys
    530                 535                 540

Asn Pro Cys Val Cys Arg Asp Gly Arg Trp His Cys Ala Gln Ala Leu
545                 550                 555                 560

Cys Pro Ala Glu Cys Ala Val Gly Gly Asp Gly His Tyr Leu Thr Phe
                565                 570                 575

Asp Gly Arg Ser Tyr Ser Phe Trp Gly Gly Gln Gly Cys Arg Tyr Ser
            580                 585                 590

Leu Val Gln Asp Tyr Val Lys Gly Gln Leu Leu Ile Leu Leu Glu His
        595                 600                 605

Gly Ala Cys Asp Ala Gly Ser Cys Leu His Ala Ile Ser Val Ser Leu
    610                 615                 620

Glu Asp Thr His Ile Gln Leu Arg Asp Ser Gly Ala Val Leu Val Asn
625                 630                 635                 640

Gly Gln Asp Val Gly Leu Pro Trp Ile Gly Ala Glu Gly Leu Ser Val
                645                 650                 655

Arg Arg Ala Ser Ser Ala Phe Leu Leu Leu Arg Trp Pro Gly Ala Gln
            660                 665                 670

Val Leu Trp Gly Leu Ser Asp Pro Val Ala Tyr Ile Thr Leu Asp Pro
        675                 680                 685
```

```
Arg His Ala His Gln Val Gln Gly Leu Cys Gly Thr Phe Thr Gln Asn
    690                 695                 700

Gln Gln Asp Asp Phe Leu Thr Pro Ala Gly Asp Val Glu Thr Ser Ile
705                 710                 715                 720

Ala Ala Phe Ala Ser Lys Phe Gln Val Ala Gly Lys Gly Arg Cys Pro
                725                 730                 735

Ser Glu Asp Ser Ala Leu Leu Ser Pro Cys Thr Thr His Ser Gln Arg
            740                 745                 750

His Ala Phe Ala Glu Ala Ala Cys Ala Ile Leu His Ser Ser Val Phe
        755                 760                 765

Gln Glu Cys His Arg Leu Val Asp Lys Glu Pro Phe Tyr Leu Arg Cys
    770                 775                 780

Leu Ala Ala Val Cys Gly Cys Asp Pro Gly Ser Asp Cys Leu Cys Pro
785                 790                 795                 800

Val Leu Ser Ala Tyr Ala Arg Arg Cys Ala Gln Glu Gly Ala Ser Pro
                805                 810                 815

Pro Trp Arg Asn Gln Thr Leu Cys Pro Val Met Cys Pro Gly Gly Gln
            820                 825                 830

Glu Tyr Arg Glu Cys Ala Pro Ala Cys Gly Gln His Cys Gly Lys Pro
        835                 840                 845

Glu Asp Cys Gly Glu Leu Gly Ser Cys Val Ala Gly Cys Asn Cys Pro
    850                 855                 860

Leu Gly Leu Leu Trp Asp Pro Glu Gly Gln Cys Val Pro Pro Ser Leu
865                 870                 875                 880

Cys Pro Cys Gln Leu Gly Ala Arg Arg Tyr Ala Pro Gly Ser Ala Thr
                885                 890                 895

Met Lys Glu Cys Asn Arg Cys Ile Cys Gln Glu Arg Gly Leu Trp Asn
            900                 905                 910

Cys Thr Ala Arg His Cys Pro Ser Gln Ala Phe Cys Pro Arg Glu Leu
        915                 920                 925

Val Tyr Ala Pro Gly Ala Cys Leu Leu Thr Cys Asp Ser Pro Ser Ala
    930                 935                 940

Asn His Ser Cys Pro Ala Gly Ser Thr Asp Gly Cys Val Cys Pro Pro
945                 950                 955                 960

Gly Thr Val Leu Leu Asp Glu Arg Cys Val Pro Pro Asp Leu Cys Pro
                965                 970                 975

Cys Arg His Ser Gly Gln Trp Tyr Leu Pro Asn Ala Thr Ile Gln Glu
            980                 985                 990

Asp Cys Asn Val Cys Val Cys Arg  Gly Arg Gln Trp His  Cys Thr Gly
        995                 1000                1005

Gln Arg  Arg Ser Gly Arg Cys  Gln Ala Ser Gly Ala  Pro His Tyr
    1010                 1015                 1020

Val Thr  Phe Asp Gly Leu Ala  Phe Thr Tyr Pro Gly  Ala Cys Glu
    1025                 1030                 1035

Tyr Leu  Leu Val Arg Glu Ala  Ser Gly Leu Phe Thr  Val Ser Ala
    1040                 1045                 1050

Gln Asn  Leu Pro Cys Gly Ala  Ser Gly Leu Thr Cys  Thr Lys Ala
    1055                 1060                 1065

Leu Ala  Val Arg Leu Glu Gly  Thr Val Val His Met  Leu Arg Gly
    1070                 1075                 1080

Arg Ala  Val Thr Val Asn Gly  Val Ser Val Thr Pro  Pro Lys Val
    1085                 1090                 1095

Tyr Thr  Gly Pro Gly Leu Ser  Leu Arg Arg Ala Gly  Leu Phe Leu
```

```
    1100                1105                1110

Leu Leu  Ser Thr His Leu Gly  Leu Thr Leu Leu Trp  Asp Gly Gly
    1115                1120                1125

Thr Arg  Val Leu Val Gln Leu  Ser Pro Gln Phe Arg  Gly Arg Val
    1130                1135                1140

Ala Gly  Leu Cys Gly Asp Phe  Asp Gly Asp Ala Ser  Asn Asp Leu
    1145                1150                1155

Arg Ser  Arg Gln Gly Val Leu  Glu Pro Thr Ala Glu  Leu Ala Ala
    1160                1165                1170

His Ser  Trp Arg Leu Ser Pro  Leu Cys Pro Glu Pro  Gly Asp Leu
    1175                1180                1185

Pro His  Pro Cys Thr Met Asn  Thr His Arg Ala Gly  Trp Ala Arg
    1190                1195                1200

Ala Arg  Cys Gly Ala Leu Leu  Gln Pro Leu Phe Thr  Leu Cys His
    1205                1210                1215

Ala Glu  Val Pro Pro Gln Gln  His Tyr Glu Trp Cys  Leu Tyr Asp
    1220                1225                1230

Ala Cys  Gly Cys Asp Ser Gly  Gly Asp Cys Glu Cys  Leu Cys Ser
    1235                1240                1245

Ala Ile  Ala Thr Tyr Ala Asp  Glu Cys Ala Arg His  Gly His His
    1250                1255                1260

Val Arg  Trp Arg Ser Gln Glu  Leu Cys Ser Leu Gln  Cys Glu Gly
    1265                1270                1275

Gly Gln  Val Tyr Glu Ala Cys  Gly Pro Thr Cys Pro  Pro Thr Cys
    1280                1285                1290

His Glu  Gln His Pro Glu Pro  Gly Trp His Cys Gln  Val Val Ala
    1295                1300                1305

Cys Val  Glu Gly Cys Phe Cys  Pro Glu Gly Thr Leu  Leu His Gly
    1310                1315                1320

Gly Ala  Cys Leu Glu Pro Ala  Ser Cys Pro Cys Glu  Trp Gly Arg
    1325                1330                1335

Asn Ser  Phe Pro Pro Gly Ser  Val Leu Gln Lys Asp  Cys Gly Asn
    1340                1345                1350

Cys Thr  Cys Gln Glu Gly Gln  Trp His Cys Gly Gly  Asp Gly Gly
    1355                1360                1365

His Cys  Glu Glu Leu Val Pro  Ala Cys Ala Glu Gly  Glu Ala Leu
    1370                1375                1380

Cys Gln  Glu Asn Gly His Cys  Val Pro His Gly Trp  Leu Cys Asp
    1385                1390                1395

Asn Gln  Asp Asp Cys Gly Asp  Gly Ser Asp Glu Glu  Gly Cys Ala
    1400                1405                1410

Ala Pro  Gly Cys Gly Glu Gly  Gln Met Thr Cys Ser  Ser Gly His
    1415                1420                1425

Cys Leu  Pro Leu Ala Leu Leu  Cys Asp Arg Gln Asp  Asp Cys Gly
    1430                1435                1440

Asp Gly  Thr Asp Glu Pro Ser  Tyr Pro Cys Pro Gln  Gly Leu Leu
    1445                1450                1455

Ala Cys  Ala Asp Gly Arg Cys  Leu Pro Pro Ala Leu  Leu Cys Asp
    1460                1465                1470

Gly His  Pro Asp Cys Leu Asp  Ala Ala Asp Glu Glu  Ser Cys Leu
    1475                1480                1485

Gly Gln  Val Thr Cys Val Pro  Gly Glu Val Ser Cys  Val Asp Gly
    1490                1495                1500
```

```
Thr Cys  Leu Gly Ala Ile Gln  Leu Cys Asp Gly Val  Trp Asp Cys
    1505                 1510                 1515

Pro Asp  Gly Ala Asp Glu Gly  Pro Gly His Cys Pro  Leu Pro Ser
    1520                 1525                 1530

Leu Pro  Thr Pro Pro Ala Ser  Thr Leu Pro Gly Pro  Ser Pro Gly
    1535                 1540                 1545

Ser Leu  Asp Thr Ala Ser Ser  Pro Leu Ala Ser Ala  Ser Pro Ala
    1550                 1555                 1560

Pro Pro  Cys Gly Pro Phe Glu  Phe Arg Cys Gly Ser  Gly Glu Cys
    1565                 1570                 1575

Thr Pro  Arg Gly Trp Arg Cys  Asp Gln Glu Glu Asp  Cys Ala Asp
    1580                 1585                 1590

Gly Ser  Asp Glu Arg Gly Cys  Gly Gly Pro Cys Ala  Pro His His
    1595                 1600                 1605

Ala Pro  Cys Ala Arg Gly Pro  His Cys Val Ser Pro  Glu Gln Leu
    1610                 1615                 1620

Cys Asp  Gly Val Arg Gln Cys  Pro Asp Gly Ser Asp  Glu Gly Pro
    1625                 1630                 1635

Asp Ala  Cys Gly Gly Leu Pro  Ala Leu Gly Gly Pro  Asn Arg Thr
    1640                 1645                 1650

Gly Leu  Pro Cys Pro Glu Tyr  Thr Cys Pro Asn Gly  Thr Cys Ile
    1655                 1660                 1665

Gly Phe  Gln Leu Val Cys Asp  Gly Gln Pro Asp Cys  Gly Arg Pro
    1670                 1675                 1680

Gly Gln  Val Gly Pro Ser Pro  Glu Glu Gln Gly Cys  Gly Ala Trp
    1685                 1690                 1695

Gly Pro  Trp Ser Pro Trp Gly  Pro Cys Ser Arg Thr  Cys Gly Pro
    1700                 1705                 1710

Trp Gly  Gln Gly Arg Ser Arg  Arg Cys Ser Pro Leu  Gly Leu Leu
    1715                 1720                 1725

Val Leu  Gln Asn Cys Pro Gly  Pro Glu His Gln Ser  Gln Ala Cys
    1730                 1735                 1740

Phe Thr  Ala Ala Cys Pro Val  Asp Gly Glu Trp Ser  Thr Trp Ser
    1745                 1750                 1755

Pro Trp  Ser Val Cys Ser Glu  Pro Cys Arg Gly Thr  Met Thr Arg
    1760                 1765                 1770

Gln Arg  Gln Cys His Ser Pro  Gln Asn Gly Gly Arg  Thr Cys Ala
    1775                 1780                 1785

Ala Leu  Pro Gly Gly Leu His  Ser Thr Arg Gln Thr  Lys Pro Cys
    1790                 1795                 1800

Pro Gln  Asp Gly Cys Pro Asn  Ala Thr Cys Ser Gly  Glu Leu Met
    1805                 1810                 1815

Phe Gln  Pro Cys Ala Pro Cys  Pro Leu Thr Cys Asp  Asp Ile Ser
    1820                 1825                 1830

Gly Gln  Val Thr Cys Pro Pro  Asp Trp Pro Cys Gly  Ser Pro Gly
    1835                 1840                 1845

Cys Trp  Cys Pro Glu Gly Gln  Val Leu Gly Ser Glu  Gly Trp Cys
    1850                 1855                 1860

Val Trp  Pro Arg Gln Cys Pro  Cys Leu Val Asp Gly  Ala Arg Tyr
    1865                 1870                 1875

Trp Pro  Gly Gln Arg Ile Lys  Ala Asp Cys Gln Leu  Cys Ile Cys
    1880                 1885                 1890
```

```
Gln Asp Gly Arg Pro Arg Arg Cys Arg Leu Asn Pro Asp Cys Ala
    1895                1900                1905

Val Asp Cys Gly Trp Ser Ser Trp Ser Pro Trp Ala Lys Cys Leu
    1910                1915                1920

Gly Pro Cys Gly Ser Gln Ser Ile Gln Trp Ser Phe Arg Ser Ser
    1925                1930                1935

Asn Asn Pro Arg Pro Ser Gly Arg Gly Arg Gln Cys Arg Gly Ile
    1940                1945                1950

His Arg Lys Ala Arg Arg Cys Gln Thr Glu Pro Cys Glu Gly Cys
    1955                1960                1965

Glu His Gln Gly Gln Val His Arg Val Gly Glu Arg Trp His Gly
    1970                1975                1980

Gly Pro Cys Arg Val Cys Gln Cys Leu His Asn Leu Thr Ala His
    1985                1990                1995

Cys Ser Pro Tyr Cys Pro Leu Gly Ser Cys Pro Gln Gly Trp Val
    2000                2005                2010

Leu Val Glu Gly Thr Gly Glu Ser Cys Cys His Cys Ala Leu Pro
    2015                2020                2025

Gly Glu Asn Gln Thr Val Gln Pro Met Ala Thr Pro Ala Ala Ala
    2030                2035                2040

Pro Ala Pro Ser Pro Gln Ile Arg Phe Pro Leu Ala Thr Tyr Ile
    2045                2050                2055

Leu Pro Pro Ser Gly Asp Pro Cys Tyr Ser Pro Leu Gly Leu Ala
    2060                2065                2070

Gly Leu Ala Glu Gly Ser Leu His Ala Ser Ser Gln Gln Leu Glu
    2075                2080                2085

His Pro Thr Gln Ala Ala Leu Leu Gly Ala Pro Thr Gln Gly Pro
    2090                2095                2100

Ser Pro Gln Gly Trp His Ala Gly Gly Asp Ala Tyr Ala Lys Trp
    2105                2110                2115

His Thr Arg Pro His Tyr Leu Gln Leu Asp Leu Leu Gln Pro Arg
    2120                2125                2130

Asn Leu Thr Gly Ile Leu Val Pro Glu Thr Gly Ser Ser Asn Ala
    2135                2140                2145

Tyr Ala Ser Ser Phe Ser Leu Gln Phe Ser Ser Asn Gly Leu His
    2150                2155                2160

Trp His Asp Tyr Arg Asp Leu Leu Pro Gly Ile Leu Pro Leu Pro
    2165                2170                2175

Lys Leu Phe Pro Arg Asn Trp Asp Asp Leu Asp Pro Ala Val Trp
    2180                2185                2190

Thr Phe Gly Arg Met Val Gln Ala Arg Phe Val Arg Val Trp Pro
    2195                2200                2205

His Asp Val His His Ser Asp Val Pro Leu Gln Val Glu Leu Leu
    2210                2215                2220

Gly Cys Glu Pro Gly Ser Pro Pro Ala Pro Leu Cys Pro Gly Val
    2225                2230                2235

Gly Leu Arg Cys Ala Ser Gly Glu Cys Val Leu Arg Gly Gly Pro
    2240                2245                2250

Cys Asp Gly Val Leu Asp Cys Glu Asp Gly Ser Asp Glu Glu Gly
    2255                2260                2265

Cys Val Leu Leu Pro Glu Gly Thr Gly Arg Phe His Ser Thr Ala
    2270                2275                2280

Lys Thr Leu Ala Leu Ser Ser Ala Gln Pro Gly Gln Leu Leu His
```

-continued

```
    2285                2290                2295

Trp Pro  Arg Glu Gly Leu Ala  Glu Thr Glu His Trp  Pro Pro Gly
    2300                2305                2310

Gln Glu  Ser Pro Thr Ser Pro  Thr Glu Thr Arg Pro  Val Ser Pro
    2315                2320                2325

Gly Pro  Ala Ser Gly Val Pro  His His Gly Glu Ser  Val Gln Met
    2330                2335                2340

Val Thr  Thr Thr Pro Ile Pro  Gln Met Glu Ala Arg  Thr Leu Pro
    2345                2350                2355

Pro Gly  Met Ala Ala Val Thr  Val Val Pro Pro His  Pro Val Thr
    2360                2365                2370

Pro Ala  Thr Pro Ala Gly Gln  Ser Val Ala Pro Gly  Pro Phe Pro
    2375                2380                2385

Pro Val  Gln Cys Gly Pro Gly  Gln Thr Pro Cys Glu  Val Leu Gly
    2390                2395                2400

Cys Val  Glu Gln Ala Gln Val  Cys Asp Gly Arg Glu  Asp Cys Leu
    2405                2410                2415

Asp Gly  Ser Asp Glu Arg His  Cys Ala Arg Asn Leu  Leu Met Trp
    2420                2425                2430

Leu Pro  Ser Leu Pro Ala Leu  Trp Ala Ala Ser Thr  Val Pro Phe
    2435                2440                2445

Met Met  Pro Thr Met Ala Leu  Pro Gly Leu Pro Ala  Ser Arg Ala
    2450                2455                2460

Leu Cys  Ser Pro Ser Gln Leu  Ser Cys Gly Ser Gly  Glu Cys Leu
    2465                2470                2475

Ser Ala  Glu Arg Arg Cys Asp  Leu Arg Pro Asp Cys  Gln Asp Gly
    2480                2485                2490

Ser Asp  Glu Asp Gly Cys Val  Asp Cys Val Leu Ala  Pro Trp Ser
    2495                2500                2505

Val Trp  Ser Ser Cys Ser Arg  Ser Cys Gly Leu Gly  Leu Thr Phe
    2510                2515                2520

Gln Arg  Gln Glu Leu Leu Arg  Pro Pro Leu Pro Gly  Gly Ser Cys
    2525                2530                2535

Pro Arg  Asp Arg Phe Arg Ser  Gln Ser Cys Phe Val  Gln Ala Cys
    2540                2545                2550

Pro Val  Ala Gly Ala Trp Ala  Met Trp Glu Ala Trp  Gly Pro Cys
    2555                2560                2565

Ser Val  Ser Cys Gly Gly Gly  His Gln Ser Arg Gln  Arg Ser Cys
    2570                2575                2580

Val Asp  Pro Pro Pro Lys Asn  Gly Gly Ala Pro Cys  Pro Gly Ala
    2585                2590                2595

Ser Gln  Glu Arg Ala Pro Cys  Gly Leu Gln Pro Cys  Ser Gly Gly
    2600                2605                2610

Thr Asp  Cys Glu Leu Gly Arg  Val Tyr Val Ser Ala  Asp Leu Cys
    2615                2620                2625

Gln Lys  Gly Leu Val Pro Pro  Cys Pro Pro Ser Cys  Leu Asp Pro
    2630                2635                2640

Lys Ala  Asn Arg Ser Cys Ser  Gly His Cys Val Glu  Gly Cys Arg
    2645                2650                2655

Cys Pro  Pro Gly Leu Leu Leu  His Asp Thr Arg Cys  Leu Pro Leu
    2660                2665                2670

Ser Glu  Cys Pro Cys Leu Val  Gly Glu Glu Leu Lys  Trp Pro Gly
    2675                2680                2685
```

Val Ser Phe Leu Leu Gly Asn Cys Ser Gln Cys Val Cys Glu Lys
2690 2695 2700

Gly Glu Leu Leu Cys Gln Pro Gly Gly Cys Pro Leu Pro Cys Gly
2705 2710 2715

Trp Ser Ala Trp Ser Ser Trp Ala Pro Cys Asp Arg Ser Cys Gly
2720 2725 2730

Ser Gly Val Arg Ala Arg Phe Arg Ser Pro Ser Asn Pro Pro Ala
2735 2740 2745

Ala Trp Gly Gly Ala Pro Cys Glu Gly Asp Arg Gln Glu Leu Gln
2750 2755 2760

Gly Cys His Thr Val Cys Gly Thr Glu Val Phe Gly Trp Thr Pro
2765 2770 2775

Trp Thr Ser Trp Ser Ser Cys Ser Gln Ser Cys Leu Ala Pro Gly
2780 2785 2790

Gly Gly Pro Gly Trp Arg Ser Arg Ser Arg Leu Cys Pro Ser Pro
2795 2800 2805

Gly Asp Ser Ser Cys Pro Gly Asp Ala Thr Gln Glu Glu Pro Cys
2810 2815 2820

Ser Pro Pro Val Cys Pro Val Pro Ser Ile Trp Gly Leu Trp Ala
2825 2830 2835

Pro Trp Ser Thr Cys Ser Ala Pro Cys Asp Gly Gly Ile Gln Thr
2840 2845 2850

Arg Gly Arg Ser Cys Ser Ser Leu Ala Pro Gly Asp Thr Thr Cys
2855 2860 2865

Pro Gly Pro His Ser Gln Thr Arg Asp Cys Asn Thr Gln Pro Cys
2870 2875 2880

Thr Ala Gln Cys Pro Glu Asn Met Leu Phe Arg Ser Ala Glu Gln
2885 2890 2895

Cys His Gln Glu Gly Gly Pro Cys Pro Arg Leu Cys Leu Thr Gln
2900 2905 2910

Gly Pro Gly Ile Glu Cys Thr Gly Phe Cys Ala Pro Gly Cys Thr
2915 2920 2925

Cys Pro Pro Gly Leu Phe Leu His Asn Ala Ser Cys Leu Pro Arg
2930 2935 2940

Ser Gln Cys Pro Cys Gln Leu His Gly Gln Leu Tyr Ala Ser Gly
2945 2950 2955

Ala Met Ala Arg Leu Asp Ser Cys Asn Asn Cys Thr Cys Val Ser
2960 2965 2970

Gly Lys Met Ala Cys Thr Ser Glu Arg Cys Pro Val Ala Cys Gly
2975 2980 2985

Trp Ser Pro Trp Thr Leu Trp Ser Leu Cys Ser Cys Ser Cys Asn
2990 2995 3000

Val Gly Ile Arg Arg Arg Phe Arg Ala Gly Thr Ala Pro Pro Ala
3005 3010 3015

Ala Phe Gly Gly Ala Glu Cys Gln Gly Pro Thr Met Glu Ala Glu
3020 3025 3030

Phe Cys Ser Leu Arg Pro Cys Pro Gly Pro Gly Gly Glu Trp Gly
3035 3040 3045

Pro Trp Ser Pro Cys Ser Val Pro Cys Gly Gly Gly Tyr Arg Asn
3050 3055 3060

Arg Thr Arg Gly Ser Ser Arg Ser Leu Met Glu Phe Ser Thr Cys
3065 3070 3075

-continued

```
Gly Leu  Gln Pro Cys Ala Gly  Pro Val Pro Gly Met  Cys Pro Arg
    3080                 3085                 3090

Asp Lys  Gln Trp Leu Asp Cys  Ala Gln Gly Pro Ala  Ser Cys Ala
    3095                 3100                 3105

Glu Leu  Ser Ala Pro Arg Gly  Thr Asn Gln Thr Cys  His Pro Gly
    3110                 3115                 3120

Cys His  Cys Pro Ser Gly Met  Leu Leu Leu Asn Asn  Val Cys Val
    3125                 3130                 3135

Pro Thr  Gln Asp Cys Pro Cys  Ala His Glu Gly His  Leu Tyr Pro
    3140                 3145                 3150

Pro Gly  Ser Thr Val Val Arg  Pro Cys Glu Asn Cys  Ser Cys Val
    3155                 3160                 3165

Ser Gly  Leu Ile Ala Asn Cys  Ser Ser Trp Pro Cys  Ala Glu Gly
    3170                 3175                 3180

Glu Pro  Thr Trp Ser Pro Trp  Thr Pro Trp Ser Gln  Cys Ser Ala
    3185                 3190                 3195

Ser Cys  Gly Pro Ala Arg Cys  His Arg His Arg Phe  Cys Ala Arg
    3200                 3205                 3210

Ser Pro  Ser Ala Val Pro Ser  Thr Val Ala Pro Leu  Pro Leu Pro
    3215                 3220                 3225

Ala Thr  Pro Thr Pro Leu Cys  Ser Gly Pro Glu Ala  Glu Glu Glu
    3230                 3235                 3240

Pro Cys  Leu Leu Gln Gly Cys  Asp Arg Ala Gly Gly  Trp Gly Pro
    3245                 3250                 3255

Trp Gly  Pro Trp Ser His Cys  Ser Arg Ser Cys Gly  Gly Gly Leu
    3260                 3265                 3270

Arg Ser  Arg Thr Arg Ala Cys  Asp Gln Pro Pro Pro  Gln Gly Leu
    3275                 3280                 3285

Gly Asp  Tyr Cys Glu Gly Pro  Arg Ala Gln Gly Glu  Val Cys Gln
    3290                 3295                 3300

Ala Leu  Pro Cys Pro Val Thr  Asn Cys Thr Ala Ile  Glu Gly Ala
    3305                 3310                 3315

Glu Tyr  Ser Pro Cys Gly Pro  Pro Cys Pro Arg Ser  Cys Asp Asp
    3320                 3325                 3330

Leu Val  His Cys Val Trp Arg  Cys Gln Pro Gly Cys  Tyr Cys Pro
    3335                 3340                 3345

Pro Gly  Gln Val Leu Ser Ser  Asn Gly Ala Ile Cys  Val Gln Pro
    3350                 3355                 3360

Gly His  Cys Ser Cys Leu Asp  Leu Leu Thr Gly Gln  Arg His His
    3365                 3370                 3375

Pro Gly  Ala Arg Leu Ala Arg  Pro Asp Gly Cys Asn  His Cys Thr
    3380                 3385                 3390

Cys Leu  Glu Gly Arg Leu Asn  Cys Thr Asp Leu Pro  Cys Pro Val
    3395                 3400                 3405

Pro Gly  Gly Trp Cys Pro Trp  Ser Glu Trp Thr Met  Cys Ser Gln
    3410                 3415                 3420

Pro Cys  Arg Gly Gln Thr Arg  Ser Arg Ser Arg Ala  Cys Ala Cys
    3425                 3430                 3435

Pro Thr  Pro Gln His Gly Gly  Ala Pro Cys Thr Gly  Glu Ala Gly
    3440                 3445                 3450

Glu Ala  Gly Ala Gln His Gln  Arg Glu Ala Cys Pro  Ser Tyr Ala
    3455                 3460                 3465

Thr Cys  Pro Val Asp Gly Ala  Trp Gly Pro Trp Gly  Pro Trp Ser
```

3470 3475 3480

Pro Cys Asp Met Cys Leu Gly Gln Ser His Arg Ser Arg Ala Cys
3485 3490 3495

Ser Arg Pro Pro Thr Pro Glu Gly Gly Arg Pro Cys Pro Gly Asn
3500 3505 3510

His Thr Gln Ser Arg Pro Cys Gln Glu Asn Ser Thr Gln Cys Thr
3515 3520 3525

Asp Cys Gly Gly Gly Gln Ser Leu His Pro Cys Gly Gln Pro Cys
3530 3535 3540

Pro Arg Ser Cys Gln Asp Leu Ser Pro Gly Ser Val Cys Gln Pro
3545 3550 3555

Gly Ser Val Gly Cys Gln Pro Thr Cys Gly Cys Pro Leu Gly Gln
3560 3565 3570

Leu Ser Gln Asp Gly Leu Cys Val Pro Pro Ala His Cys Arg Cys
3575 3580 3585

Gln Tyr Gln Pro Gly Ala Met Gly Ile Pro Glu Asn Gln Ser Arg
3590 3595 3600

Ser Ala Gly Ser Arg Phe Ser Ser Trp Glu Ser Leu Glu Pro Gly
3605 3610 3615

Glu Val Val Thr Gly Pro Cys Asp Asn Cys Thr Cys Val Ala Gly
3620 3625 3630

Ile Leu Gln Cys Gln Glu Val Pro Asp Cys Pro Asp Pro Gly Val
3635 3640 3645

Trp Ser Ser Trp Gly Pro Trp Glu Asp Cys Ser Val Ser Cys Gly
3650 3655 3660

Gly Gly Glu Gln Leu Arg Ser Arg Arg Cys Ala Arg Pro Pro Cys
3665 3670 3675

Pro Gly Pro Ala Arg Gln Ser Arg Thr Cys Ser Thr Gln Val Cys
3680 3685 3690

Arg Glu Ala Gly Cys Pro Ala Gly Arg Leu Tyr Arg Glu Cys Gln
3695 3700 3705

Pro Gly Glu Gly Cys Pro Phe Ser Cys Ala His Val Thr Gln Gln
3710 3715 3720

Val Gly Cys Phe Ser Glu Gly Cys Glu Glu Gly Cys His Cys Pro
3725 3730 3735

Glu Gly Thr Phe Gln His Arg Leu Ala Cys Val Gln Glu Cys Pro
3740 3745 3750

Cys Val Leu Thr Ala Trp Leu Leu Gln Glu Leu Gly Ala Thr Ile
3755 3760 3765

Gly Asp Pro Gly Gln Pro Leu Gly Pro Gly Asp Glu Leu Asp Ser
3770 3775 3780

Gly Gln Thr Leu Arg Thr Ser Cys Gly Asn Cys Ser Cys Ala His
3785 3790 3795

Gly Lys Leu Ser Cys Ser Leu Asp Asp Cys Phe Glu Ala Asp Gly
3800 3805 3810

Gly Phe Gly Pro Trp Ser Pro Trp Gly Pro Cys Ser Arg Ser Cys
3815 3820 3825

Gly Gly Leu Gly Thr Arg Thr Arg Ser Arg Gln Cys Val Leu Thr
3830 3835 3840

Met Pro Thr Leu Ser Gly Gln Gly Cys Arg Gly Pro Arg Gln Asp
3845 3850 3855

Leu Glu Tyr Cys Pro Ser Pro Asp Cys Pro Gly Ala Glu Gly Ser
3860 3865 3870

-continued

```
Thr Val  Glu Pro Val Thr Gly  Leu Pro Gly Gly Trp  Gly Pro Trp
    3875                 3880                 3885

Ser Ser  Trp Ser Pro Cys Ser  Arg Ser Cys Thr Asp  Pro Ala Arg
    3890                 3895                 3900

Pro Ala  Trp Arg Ser Arg Thr  Arg Leu Cys Leu Ala  Asn Cys Thr
    3905                 3910                 3915

Met Gly  Asp Pro Leu Gln Glu  Arg Pro Cys Asn Leu  Pro Ser Cys
    3920                 3925                 3930

Thr Glu  Leu Pro Val Cys Pro  Gly Pro Gly Cys Gly  Ala Gly Asn
    3935                 3940                 3945

Cys Ser  Trp Thr Ser Trp Ala  Pro Trp Glu Pro Cys  Ser Arg Ser
    3950                 3955                 3960

Cys Gly  Val Gly Gln Gln Arg  Arg Leu Arg Ala Tyr  Arg Pro Pro
    3965                 3970                 3975

Gly Pro  Gly Gly His Trp Cys  Pro Asn Ile Leu Thr  Ala Tyr Gln
    3980                 3985                 3990

Glu Arg  Arg Phe Cys Asn Leu  Arg Ala Cys Pro Val  Pro Gly Gly
    3995                 4000                 4005

Trp Ser  Arg Trp Ser Pro Trp  Ser Trp Cys Asp Arg  Ser Cys Gly
    4010                 4015                 4020

Gly Gly  Gln Ser Leu Arg Ser  Arg Ser Cys Ser Ser  Pro Pro Ser
    4025                 4030                 4035

Lys Asn  Gly Gly Ala Pro Cys  Ala Gly Glu Arg His  Gln Ala Arg
    4040                 4045                 4050

Leu Cys  Asn Pro Met Pro Cys  Glu Ala Gly Cys Pro  Ala Gly Met
    4055                 4060                 4065

Glu Val  Val Thr Cys Ala Asn  Arg Cys Pro Arg Arg  Cys Ser Asp
    4070                 4075                 4080

Leu Gln  Glu Gly Ile Val Cys  Gln Asp Asp Gln Val  Cys Gln Lys
    4085                 4090                 4095

Gly Cys  Arg Cys Pro Lys Gly  Ser Leu Glu Gln Asp  Gly Gly Cys
    4100                 4105                 4110

Val Pro  Ile Gly His Cys Asp  Cys Thr Asp Ala Gln  Gly His Ser
    4115                 4120                 4125

Trp Ala  Pro Gly Ser Gln His  Gln Asp Ala Cys Asn  Asn Cys Ser
    4130                 4135                 4140

Cys Gln  Ala Gly Gln Leu Ser  Cys Thr Ala Gln Pro  Cys Pro Pro
    4145                 4150                 4155

Pro Thr  His Cys Ala Trp Ser  His Trp Ser Ala Trp  Ser Pro Cys
    4160                 4165                 4170

Ser His  Ser Cys Gly Pro Arg  Gly Gln Gln Ser Arg  Phe Arg Ser
    4175                 4180                 4185

Ser Thr  Ser Gly Ser Trp Ala  Pro Glu Cys Arg Glu  Glu Gln Ser
    4190                 4195                 4200

Gln Ser  Gln Pro Cys Pro Gln  Pro Ser Cys Pro Pro  Leu Cys Leu
    4205                 4210                 4215

Gln Gly  Thr Arg Ser Arg Thr  Leu Gly Asp Ser Trp  Leu Gln Gly
    4220                 4225                 4230

Glu Cys  Gln Arg Cys Ser Cys  Thr Pro Glu Gly Val  Ile Cys Glu
    4235                 4240                 4245

Asp Thr  Glu Cys Ala Val Pro  Glu Ala Trp Thr Leu  Trp Ser Ser
    4250                 4255                 4260
```

```
Trp Ser Asp Cys Pro Val Ser Cys Gly Gly Gly Asn Gln Val Arg
    4265                4270                4275

Thr Arg Ala Cys Arg Ala Ala Ala Pro His His Arg Ser Pro Pro
    4280                4285                4290

Cys Leu Gly Pro Asp Thr Gln Thr Arg Gln Gln Pro Cys Pro Gly
    4295                4300                4305

Leu Leu Glu Ala Cys Ser Trp Gly Pro Trp Gly Pro Cys Ser Arg
    4310                4315                4320

Ser Cys Gly Pro Gly Leu Ala Ser Arg Ser Gly Ser Cys Pro Cys
    4325                4330                4335

Leu Met Ala Lys Ala Asp Pro Thr Cys Asn Ser Thr Phe Leu His
    4340                4345                4350

Leu Asp Thr Gln Gly Cys Tyr Ser Gly Pro Cys Pro Glu Glu Cys
    4355                4360                4365

Val Trp Ser Ser Trp Ser Ser Trp Thr Arg Cys Ser Cys Arg Val
    4370                4375                4380

Leu Val Gln Gln Arg Tyr Arg His Gln Gly Pro Ala Ser Arg Gly
    4385                4390                4395

Ala Arg Ala Gly Ala Pro Cys Thr Arg Leu Asp Gly His Phe Arg
    4400                4405                4410

Pro Cys Leu Ile Ser Asn Cys Ser Glu Asp Ser Cys Thr Pro Pro
    4415                4420                4425

Phe Glu Phe His Ala Cys Gly Ser Pro Cys Ala Gly Leu Cys Ala
    4430                4435                4440

Thr His Leu Ser His Gln Leu Cys Gln Asp Leu Pro Pro Cys Gln
    4445                4450                4455

Pro Gly Cys Tyr Cys Pro Lys Gly Leu Leu Glu Gln Ala Gly Gly
    4460                4465                4470

Cys Ile Pro Pro Glu Glu Cys Asn Cys Trp His Thr Ser Ala Ala
    4475                4480                4485

Gly Ala Gly Met Thr Leu Ala Pro Gly Asp Arg Leu Gln Leu Gly
    4490                4495                4500

Cys Lys Glu Cys Glu Cys Arg Arg Gly Glu Leu His Cys Thr Ser
    4505                4510                4515

Gln Gly Cys Gln Gly Leu Leu Pro Leu Ser Glu Trp Ser Glu Trp
    4520                4525                4530

Ser Pro Cys Gly Pro Cys Leu Pro Pro Ser Ala Leu Ala Pro Ala
    4535                4540                4545

Ser Arg Thr Ala Leu Glu Glu His Trp Leu Arg Asp Pro Thr Gly
    4550                4555                4560

Leu Ser Pro Thr Leu Ala Pro Leu Leu Ala Ser Glu Gln His Arg
    4565                4570                4575

His Arg Leu Cys Leu Asp Pro Ala Thr Gly Arg Pro Trp Thr Gly
    4580                4585                4590

Ala Pro His Leu Cys Thr Ala Pro Leu Ser Gln Gln Arg Leu Cys
    4595                4600                4605

Pro Asp Pro Gly Ala Cys Pro Asp Ser Cys Gln Trp Ser Leu Trp
    4610                4615                4620

Gly Pro Trp Ser Pro Cys Gln Val Pro Cys Ser Gly Gly Phe Arg
    4625                4630                4635

Leu Arg Trp Arg Glu Ala Glu Ala Leu Cys Gly Gly Gly Cys Arg
    4640                4645                4650

Glu Pro Trp Ala Gln Glu Ser Cys Asn Gly Gly Pro Cys Pro Glu
```

```
    4655                4660                4665

Ser Cys  Glu Ala Gln Asp Thr  Val Phe Thr Leu Asp  Cys Ala Asn
    4670                4675                4680

Gln Cys  Pro His Ser Cys Ala  Asp Leu Trp Asp Arg  Val Gln Cys
    4685                4690                4695

Leu Gln  Gly Pro Cys Arg Pro  Gly Cys Arg Cys Pro  Pro Gly Gln
    4700                4705                4710

Leu Val  Gln Asp Gly Arg Cys  Val Pro Ile Ser Ser  Cys Arg Cys
    4715                4720                4725

Gly Leu  Pro Ser Ala Asn Ala  Ser Trp Glu Leu Ala  Pro Ala Gln
    4730                4735                4740

Ala Val  Gln Leu Asp Cys Gln  Asn Cys Thr Cys Val  Asn Glu Ser
    4745                4750                4755

Leu Val  Cys Pro His Gln Glu  Cys Pro Val Leu Gly  Pro Trp Ser
    4760                4765                4770

Ala Trp  Ser Ser Cys Ser Ala  Pro Cys Gly Gly Gly  Thr Met Glu
    4775                4780                4785

Arg His  Arg Thr Cys Glu Gly  Gly Pro Gly Val Ala  Pro Cys Gln
    4790                4795                4800

Ala Gln  Asp Thr Glu Gln Arg  Gln Glu Cys Asn Leu  Gln Pro Cys
    4805                4810                4815

Pro Glu  Cys Pro Pro Gly Gln  Val Leu Ser Ala Cys  Ala Thr Ser
    4820                4825                4830

Cys Pro  Cys Leu Cys Trp His  Leu Gln Pro Gly Ala  Ile Cys Val
    4835                4840                4845

Gln Glu  Pro Cys Gln Pro Gly  Cys Gly Cys Pro Gly  Gly Gln Leu
    4850                4855                4860

Leu His  Asn Gly Thr Cys Val  Pro Pro Thr Ala Cys  Pro Cys Thr
    4865                4870                4875

Gln His  Ser Leu Pro Trp Gly  Leu Thr Leu Thr Leu  Glu Glu Gln
    4880                4885                4890

Ala Gln  Glu Leu Pro Pro Gly  Thr Val Leu Thr Arg  Asn Cys Thr
    4895                4900                4905

Arg Cys  Val Cys His Gly Gly  Ala Phe Ser Cys Ser  Leu Val Asp
    4910                4915                4920

Cys Gln  Val Pro Pro Gly Glu  Thr Trp Gln Gln Val  Ala Pro Gly
    4925                4930                4935

Glu Leu  Gly Leu Cys Glu Gln  Thr Cys Leu Glu Met  Asn Ala Thr
    4940                4945                4950

Lys Thr  Gln Ser Asn Cys Ser  Ser Ala Arg Ala Ser  Gly Cys Val
    4955                4960                4965

Cys Gln  Pro Gly His Phe Arg  Ser Gln Ala Gly Pro  Cys Val Pro
    4970                4975                4980

Glu Asp  His Cys Glu Cys Trp  His Leu Gly Arg Pro  His Leu Pro
    4985                4990                4995

Gly Ser  Glu Trp Gln Glu Ala  Cys Glu Ser Cys Leu  Cys Leu Ser
    5000                5005                5010

Gly Arg  Pro Val Cys Thr Gln  His Cys Ser Pro Leu  Thr Cys Ala
    5015                5020                5025

Gln Gly  Glu Glu Met Val Leu  Glu Pro Gly Ser Cys  Cys Pro Ser
    5030                5035                5040

Cys Arg  Arg Glu Ala Pro Glu  Glu Gln Ser Pro Ser  Cys Gln Leu
    5045                5050                5055
```

Leu Thr Glu Leu Arg Asn Phe Thr Lys Gly Thr Cys Tyr Leu Asp
    5060                5065                5070

Gln Val Glu Val Ser Tyr Cys Ser Gly Tyr Cys Pro Ser Ser Thr
    5075                5080                5085

His Val Met Pro Glu Glu Pro Tyr Leu Gln Ser Gln Cys Asp Cys
    5090                5095                5100

Cys Ser Tyr Arg Leu Asp Pro Glu Ser Pro Val Arg Ile Leu Asn
    5105                5110                5115

Leu Arg Cys Leu Gly Gly His Thr Glu Pro Val Val Leu Pro Val
    5120                5125                5130

Ile His Ser Cys Gln Cys Ser Ser Cys Gln Gly Gly Asp Phe Ser
    5135                5140                5145

Lys Arg
    5150

<210> SEQ ID NO 75
<211> LENGTH: 5651
<212> TYPE: DNA
<213> ORGANISM: Homo sapiens

<400> SEQUENCE: 75
ctggtgtggc tggctgcggc cagaatcgga gccccaaccg cgctgccgct cggaccttag 60
cctgtgcctg cagcccggag tcccctcctg ccctggaagg caaggagcca ggccacgggg 120
ccacagccgc gggggccacc acactggccc aaatatttcc tgcagagtca acctatttga 180
tttcttgaca agaccacaat ctgatcccaa agatgtgctc cacaaatcca ggcaaatggg 240
tcacctttga tgatgatcct gctgttcaat cttctcaaaa gtcaaagaat tttcctctgg 300
agaatcaagg tgtctgtaga ccaaatggac tgaagctgaa ccttcctggc ctcagggaat 360
ttcccagtgg atcttcctcc accagcagca ctcctctctc ctcccccatt gtagattttt 420
atttcagtcc aggacctcca agtaactctc ctctttctac acctaccaaa gacttcccag 480
gttttcctgg catccccaaa gcagggactc atgtgcttta tcctattcca gaatcatctt 540
cagacagccc actcgcaata tcaggaggag aatcttcctt actgcctacc agaccaacat 600
gtttatccca tgccttgtta cccagtgacc actcatgtac acatccaact cccaaagtag 660
gtcttccaga tgaagttaat cctcaacagg ctgaaagcct aggattccaa agtgatgatc 720
tcccccagtt tcagtatttt cgagaggact gtgctttttc aagtccattt tggaaagatg 780
aaggcagtga ttcccatttc acccttgacc caccaggaag caaaaagatg ttctcatcaa 840
gaaacaagga gatgcctatt gaccaaaaaa gcctaaataa gtgttcactc aactatatct 900
gtgagaagct tgaacatctc cagtcagctg agaaccaaga ctcacttaga agtttgtcta 960
tgcactgtct atgtgctgaa gaaaatgcct cttcctttgt cccccacaca ctcttcagga 1020
gtcagccaaa atccggatgg tctttcatgc tgagaattcc tgagaagaag aatatgatgt 1080
cttcccggca atggggacca atttttctga aagttttgcc tggaggaatt ttgcagatgt 1140
attatgaaca gggattagaa aaaccattta aagagataca gcttgatcca tattgtaggc 1200
tttctgaacc caaggttgag aacttcagtg tagcaggaaa aatccacact gtgaagattg 1260
aacatgtgtc ttacacagaa aaaaggaaat accattctaa gacagaagta gttcatgaac 1320
ctgacataga gcagatgctg aagttggggt ccacatcgta ccatgacttc cttgactttc 1380
tgactactgt ggaggaggag ctgatgaagt tgccagctgt ttcaaaacca aaaaagaact 1440
acgaggagca agaaatttcc ttggaaattg tggacaactt ttggggtaaa gtcacaaaag 1500
aaggaaaatt tgttgaaagt gctgtgataa ctcaaattta ttgcctctgc tttgtgaatg 1560
ggaacctgga atgcttttta accttgaatg accttgagtt gccgaagcga gatgaatcct 1620
attatgagaa ggactcagaa aaaaagggga ttgatattct tgactaccat tttcataagt 1680
gtgtgaatgt acaagaattt gagcaatcaa gaatcattaa gtttgtacct ctggatgcct 1740
gccggtttga gctgatgcgt ttcaagactt tgtataatgg ggataatctt cccttttcct 1800
tgaagtctgt agtggttgtc cagggagcat acgtggaact tcaggctttt gtcaacatgg 1860
cctcattggc gcagaggtca tcctatgctg gttccttaag gtcctgtgac aatataagga 1920
tacactttcc tgtcccatcg cagtggatca aggccctttg gaccatgaac ctccagaggc 1980
agaagtctct gaaagctaaa atgaaccgcc gagcatgtct ggggagttta caggaacttg 2040
aatctgaacc tgtcattcaa gtcactgtgg ggtcagcaaa atatgagagt gcctaccagg 2100
cagtggtatg gaagatagat cggcttccag acaaaaattc aagtctagat catccccatt 2160
gtctgtcata caaattagag cttggatcag accaagaaat tccctctgat tggtatccat 2220
ttgctactgt tcagttttcc gtgcctgaca cctgtgcctc aaggacagag gtcaggtctc 2280
tgggagtgga gagtgatgtc cagccacaga aacatgttca gcagcgagct tgctacaaca 2340
tccaggttga aatagaaaag aagtggatta aaatcgatgg agaagaccca gataaaattg 2400
gtgactgcat aactcagtag gagtagcaag agtttatgat gacagcccac ttgtcaaata 2460
tgtaattcac cgaaaccaca ccaagtcctg ctactgtaga gtggaaatga cttctgaata 2520
gcggttttag gacaggtctg atggctgtgt ttagagaagt ttagacctaa aaccgaacaa 2580
tctgtatttt ttgcttttca tgtgtttttg tcctaggggt tcgatctaaa atgtttctat 2640
aattcgtgtg atgttttgct tcctattgaa actcaaaggc actgttactc gttgtgtgac 2700
cccgcagcca gtatgatttt tgattactca gtggctgact gttttgctct ctggattact 2760
gaggtgccgt cttcatttct tcccatctct tcttgctgct tagtgtctgt actagagggt 2820
aagggaatca aaggagacat aaaccaaaat agttaatttt ccctctttct tgcctctgaa 2880
atgtggctag gtgtagaatg atgttgaaac cacaggctaa aatgtagatc tggaagtatc 2940
tgtgcttttg aattacttat ttacctgtcc tcttaccgtt ggtaaataat aattggctat 3000
atttggtacc tgtctctctc ctactgtatt gtcattttca aaatgtgttt gttttctggc 3060
gcgtgctgca aagaagctat ttctgttgtc ctacatattt tagtataaat cactaagaca 3120
tatttccttt cacttggcag gattcctttc aaaatggaat ctgagtatta gacactagtt 3180
aacatatttg tgtatattaa atatgaattt ttaaaattta taaatactat tttccaaaag 3240
tacagactct aaggacatat tttgataaag tattatttgt aatgaacaca agcctctctt 3300
gagtagaagt ctaaatcaca ttatgattat tttatactag ttctgctatc atgctgtttt 3360
atgctaattc tgcttatttt agagtatttt tcattaaaag gtgagcaaag tgaaagatac 3420
ttggtatttt acccagattt ctaagtggca acatttttat tcttcagagt caggtaaatg 3480
actataatag tttggtttct aatgaaaagt caatagcatt agcagttata attctgttta 3540
taatttcctt tcagcattta cagtgaaaag tgagaatttt aaaatttatg aaatctatat 3600
tccaggtatt gtttttagtc tgaaaaacaa actcccccat gtggtattaa tataccttca 3660
atttatgttg agtcttaaac ataattagga gatatttttc tctatttgct agatttgttt 3720
tgagtcaaaa ctgatttagt gttcttccaa acaacattta tgtgttggcc tacagagttt 3780
atttcatgtg tttttttttaa tatttaatat tatattacat tcattgaaat ctgttcaaaa 3840
acagattaag acaaacattt atgatggtct gtatcaatca gcagatttta ttgcttttca 3900
ttattttact gtaaaggcaa agaatgcaat aggtgatggt tggttgaaag gaattgttat 3960
tgctgttttt attttttact ttttttgaga cagagtctca ctctgttgcc cagcctggag 4020
tgcagtgtgt catcttggct cactgcaacc tccgcctcct gggttcaagg gattctcctg 4080
cctcagcctc caactagctg ggattacagg cacaagccac catgcctggc taaaattctt 4140
ttgtattttt actacagacg gagtttcccc atgttggccg ggctagtctc gaactcctga 4200
cctcaggtga tccaccagcc tcggcctccc aaagttctgg gattaaatgc gtgagccacc 4260
atgcccggcc gctattgctc tttttaactt catttgatgc cttgcttata atatcatatg 4320
cttgaggctc actgttgatg tagagtaggg caaatctgtg tgtgtatgtc attaaaaaaa 4380
ttctaccatc tttctttatc atctggtgtg ggcgcactct acagtgactt cagtctgctc 4440
agaacgaatg tggaggccgg ccgaaactga tgctgcccac agtcccagtg aagttaggtg 4500
ggttaattac tgccattcct ttctaagtgt gttttatggc atcctgccca caaagaactc 4560
acagtctgat taggatgaac ttaatgacta tttacacctc aaaatatatt cagcaaaggg 4620
ttcacttagt tgcccctcat gcttcacagg ttgactagta tctgtgggta cctccctgcc 4680
caggttattc actcacaagc caccgggcct tcaggacatc tcaagattca gtcttgacaa 4740
tataatagca aaagctggac taaagcccaa atggattgtc tgtggcaatg cagaagctga 4800
tagcattaac agcagggtgt tacagcataa ttgttaattc gcacatctat taggatcctt 4860
aaatattcat tacttaatgt taaattaaca ttctgtgtag ggaggggagg cttattcaat 4920
tcttctgacc tcagaactgg cagaaggtca gatgtgacta cagaactcta ggtgaaaaat 4980
caggtagggt tcaaattaag tagaactgcc cttgccggaa tagtgatctt caaaaaaccc 5040
ttgcttttag gggagggaag cggggaagga aaggaatgag ggaggaaata ttcctttcta 5100
gcattcattt tgcttagatc actccattgt gagtttgacc attttggagt caaatgagca 5160
gacttccaag gagttgacca gtttgtgact agtctggtca cctttccagt tacaggatca 5220
tattaactgt gtaaatgaat tcatgggtag atgatttgtg cagatctgaa tttaagaaca 5280
tttccttttt ctgtgggaat cacaagagtt tatccactaa aaaaagatat gtaaaaaaga 5340
tactttccag cacataaata aaggctggaa ttttacaacc tgatgtatat attagacagt 5400
tctaggatgt tagttccctt cattccagag ctatgcttgt gatacagccc cttttcttat 5460
aaagtcagtt agaaggactt ccttaacaat gactattata atgtcttact taaaatacag 5520
ttttgtattc tgtcaatgca aatataagac aggttgagcc ttaatcatgt aacaaaatat 5580
tttgtagatt acatattgat ttttcaaaaa ttaaaaatgt atttcaaact attaaaaaaa 5640
aaaaaaaaaa a 5651

<210> SEQ ID NO 76
<211> LENGTH: 735
<212> TYPE: PRT
<213> ORGANISM: Homo sapiens

<400> SEQUENCE: 76

Met Cys Ser Thr Asn Pro Gly Lys Trp Val Thr Phe Asp Asp Asp Pro
1               5                   10                  15

Ala Val Gln Ser Ser Gln Lys Ser Lys Asn Phe Pro Leu Glu Asn Gln
            20                  25                  30

Gly Val Cys Arg Pro Asn Gly Leu Lys Leu Asn Leu Pro Gly Leu Arg
        35                  40                  45

```
Glu Phe Pro Ser Gly Ser Ser Ser Thr Ser Ser Thr Pro Leu Ser Ser
    50                  55                  60

Pro Ile Val Asp Phe Tyr Phe Ser Pro Gly Pro Pro Ser Asn Ser Pro
65                  70                  75                  80

Leu Ser Thr Pro Thr Lys Asp Phe Pro Gly Phe Pro Gly Ile Pro Lys
                85                  90                  95

Ala Gly Thr His Val Leu Tyr Pro Ile Pro Glu Ser Ser Ser Asp Ser
            100                 105                 110

Pro Leu Ala Ile Ser Gly Gly Glu Ser Ser Leu Leu Pro Thr Arg Pro
        115                 120                 125

Thr Cys Leu Ser His Ala Leu Leu Pro Ser Asp His Ser Cys Thr His
    130                 135                 140

Pro Thr Pro Lys Val Gly Leu Pro Asp Glu Val Asn Pro Gln Gln Ala
145                 150                 155                 160

Glu Ser Leu Gly Phe Gln Ser Asp Asp Leu Pro Gln Phe Gln Tyr Phe
                165                 170                 175

Arg Glu Asp Cys Ala Phe Ser Ser Pro Phe Trp Lys Asp Glu Gly Ser
            180                 185                 190

Asp Ser His Phe Thr Leu Asp Pro Pro Gly Ser Lys Lys Met Phe Ser
        195                 200                 205

Ser Arg Asn Lys Glu Met Pro Ile Asp Gln Lys Ser Leu Asn Lys Cys
    210                 215                 220

Ser Leu Asn Tyr Ile Cys Glu Lys Leu Glu His Leu Gln Ser Ala Glu
225                 230                 235                 240

Asn Gln Asp Ser Leu Arg Ser Leu Ser Met His Cys Leu Cys Ala Glu
                245                 250                 255

Glu Asn Ala Ser Ser Phe Val Pro His Thr Leu Phe Arg Ser Gln Pro
            260                 265                 270

Lys Ser Gly Trp Ser Phe Met Leu Arg Ile Pro Glu Lys Lys Asn Met
        275                 280                 285

Met Ser Ser Arg Gln Trp Gly Pro Ile Phe Leu Lys Val Leu Pro Gly
    290                 295                 300

Gly Ile Leu Gln Met Tyr Tyr Glu Gln Gly Leu Glu Lys Pro Phe Lys
305                 310                 315                 320

Glu Ile Gln Leu Asp Pro Tyr Cys Arg Leu Ser Glu Pro Lys Val Glu
                325                 330                 335

Asn Phe Ser Val Ala Gly Lys Ile His Thr Val Lys Ile Glu His Val
            340                 345                 350

Ser Tyr Thr Glu Lys Arg Lys Tyr His Ser Lys Thr Glu Val Val His
        355                 360                 365

Glu Pro Asp Ile Glu Gln Met Leu Lys Leu Gly Ser Thr Ser Tyr His
    370                 375                 380

Asp Phe Leu Asp Phe Leu Thr Thr Val Glu Glu Glu Leu Met Lys Leu
385                 390                 395                 400

Pro Ala Val Ser Lys Pro Lys Lys Asn Tyr Glu Glu Gln Glu Ile Ser
                405                 410                 415

Leu Glu Ile Val Asp Asn Phe Trp Gly Lys Val Thr Lys Glu Gly Lys
            420                 425                 430

Phe Val Glu Ser Ala Val Ile Thr Gln Ile Tyr Cys Leu Cys Phe Val
        435                 440                 445

Asn Gly Asn Leu Glu Cys Phe Leu Thr Leu Asn Asp Leu Glu Leu Pro
    450                 455                 460

Lys Arg Asp Glu Ser Tyr Tyr Glu Lys Asp Ser Glu Lys Lys Gly Ile
```

465 470 475 480

Asp Ile Leu Asp Tyr His Phe His Lys Cys Val Asn Val Gln Glu Phe
485 490 495

Glu Gln Ser Arg Ile Ile Lys Phe Val Pro Leu Asp Ala Cys Arg Phe
500 505 510

Glu Leu Met Arg Phe Lys Thr Leu Tyr Asn Gly Asp Asn Leu Pro Phe
515 520 525

Ser Leu Lys Ser Val Val Val Val Gln Gly Ala Tyr Val Glu Leu Gln
530 535 540

Ala Phe Val Asn Met Ala Ser Leu Ala Gln Arg Ser Ser Tyr Ala Gly
545 550 555 560

Ser Leu Arg Ser Cys Asp Asn Ile Arg Ile His Phe Pro Val Pro Ser
565 570 575

Gln Trp Ile Lys Ala Leu Trp Thr Met Asn Leu Gln Arg Gln Lys Ser
580 585 590

Leu Lys Ala Lys Met Asn Arg Arg Ala Cys Leu Gly Ser Leu Gln Glu
595 600 605

Leu Glu Ser Glu Pro Val Ile Gln Val Thr Val Gly Ser Ala Lys Tyr
610 615 620

Glu Ser Ala Tyr Gln Ala Val Val Trp Lys Ile Asp Arg Leu Pro Asp
625 630 635 640

Lys Asn Ser Ser Leu Asp His Pro His Cys Leu Ser Tyr Lys Leu Glu
645 650 655

Leu Gly Ser Asp Gln Glu Ile Pro Ser Asp Trp Tyr Pro Phe Ala Thr
660 665 670

Val Gln Phe Ser Val Pro Asp Thr Cys Ala Ser Arg Thr Glu Val Arg
675 680 685

Ser Leu Gly Val Glu Ser Asp Val Gln Pro Gln Lys His Val Gln Gln
690 695 700

Arg Ala Cys Tyr Asn Ile Gln Val Glu Ile Glu Lys Lys Trp Ile Lys
705 710 715 720

Ile Asp Gly Glu Asp Pro Asp Lys Ile Gly Asp Cys Ile Thr Gln
725 730 735

<210> SEQ ID NO 77
<211> LENGTH: 3510
<212> TYPE: DNA
<213> ORGANISM: Homo sapiens

<400> SEQUENCE: 77
aaaatttcag cagagagaaa tagagaaagc agtgtgtgtg catgtgtgtg tgtgtgagag 60
agagagggag aggagcgaga gggagaggga gagggagaga gagaaaggga gggaagcaga 120
gagtcaagtc caagggaatg agcgagagag gcagagacag gggaagaggc gtgcgagaga 180
aggaataaca gctttccgga gcaggcgtgc cgtgaactgg cttctatttt attttatttt 240
tttctccttt ttatttttta aagagaagca ggggacagaa gcaatggccg aggcagaaga 300
caagccgagg tgctggtgac cctgggcgtc tgagtggatg attggggctg ctgcgctcag 360
aggcctgcct ccctgccttc caatgcatat aaccccacac cccagccaat gaagacgaga 420
ggcagcgtga acaaagtcat ttagaaagcc cccgaggaag tgtaaacaaa agagaaagca 480
tgaatggagt gcctgagaga caagtgtgtc ctgtactgcc cccaccttta gctgggccag 540
caactgcccg gccctgcttc tccccaccta ctcactggtg atcttttttt ttttactttt 600
ttttcccttt tcttttccat tctcttttct tattttcttt caaggcaagg caaggatttt 660

```
gattttggga cccagccatg gtccttctgc ttcttcttta aaatacccac tttctcccca    720
tcgccaagcg gcgtttggca atatcagata tccactctat ttatttttac ctaaggaaaa    780
actccagctc ccttcccact cccagctgcc ttgccacccc tcccagccct ctgcttgccc    840
tccacctggc ctgctgggag tcagagccca gcaaaacctg tttagacaca tggacaagaa    900
tcccagcgct acaaggcaca cagtccgctt cttcgtcctc agggttgcca gcgcttcctg    960
gaagtcctga agctctcgca gtgcagtgag ttcatgcacc ttcttgccaa gcctcagtct   1020
ttgggatctg gggaggccgc ctggttttcc tccctccttc tgcacgtctg ctggggtctc   1080
ttcctctcca ggccttgccg tccccctggc ctctcttccc agctcacaca tgaagatgca   1140
cttgcaaagg gctctggtgg tcctggccct gctgaacttt gccacggtca gcctctctct   1200
gtccacttgc accaccttgg acttcggcca catcaagaag aagagggtgg aagccattag   1260
gggacagatc ttgagcaagc tcaggctcac cagccccccct gagccaacgg tgatgaccca   1320
cgtcccctat caggtcctgg ccctttacaa cagcacccgg gagctgctgg aggagatgca   1380
tggggagagg gaggaaggct gcacccagga aaacaccgag tcggaatact atgccaaaga   1440
aatccataaa ttcgacatga tccaggggct ggcggagcac aacgaactgg ctgtctgccc   1500
taaaggaatt acctccaagg ttttccgctt caatgtgtcc tcagtggaga aaaatagaac   1560
caacctattc cgagcagaat tccgggtctt gcgggtgccc aaccccagct ctaagcggaa   1620
tgagcagagg atcgagctct tccagatcct tcggccagat gagcacattg ccaaacagcg   1680
ctatatcggt ggcaagaatc tgcccacacg gggcactgcc gagtggctgt cctttgatgt   1740
cactgacact gtgcgtgagt ggctgttgag aagagagtcc aacttaggtc tagaaatcag   1800
cattcactgt ccatgtcaca cctttcagcc caatggagat atcctggaaa acattcacga   1860
ggtgatggaa atcaaattca aaggcgtgga caatgaggat gaccatggcc gtggagatct   1920
ggggcgcctc aagaagcaga aggatcacca caaccctcat ctaatcctca tgatgattcc   1980
cccacaccgg ctcgacaacc cgggccaggg gggtcagagg aagaagcggg ctttggacac   2040
caattactgc ttccgcaact tggaggagaa ctgctgtgtg cgcccccctct acattgactt   2100
ccgacaggat ctgggctgga agtgggtcca tgaacctaag ggctactatg ccaacttctg   2160
ctcaggccct tgcccatacc tccgcagtgc agacacaacc cacagcacgg tgctgggact   2220
gtacaacact ctgaaccctg aagcatctgc ctcgccttgc tgcgtgcccc aggacctgga   2280
gcccctgacc atcctgtact atgttgggag gacccccaaa gtggagcagc tctccaacat   2340
ggtggtgaag tcttgtaaat gtagctgaga ccccacgtgc gacagagaga ggggagagag   2400
aaccaccact gcctgactgc ccgctcctcg ggaaacacac aagcaacaaa cctcactgag   2460
aggcctggag cccacaacct tcggctccgg gcaaatggct gagatggagg tttccttttg   2520
gaacatttct ttcttgctgg ctctgagaat cacggtggta aagaaagtgt gggtttggtt   2580
agaggaaggc tgaactcttc agaacacaca gactttctgt gacgcagaca gaggggatgg   2640
ggatagagga aagggatggt aagttgagat gttgtgtggc aatgggattt gggctaccct   2700
aaagggagaa ggaagggcag agaatggctg ggtcagggcc agactggaag acacttcaga   2760
tctgaggttg gatttgctca ttgctgtacc acatctgctc tagggaatct ggattatgtt   2820
atacaaggca agcatttttt tttttttttt aaagacaggt tacgaagaca aagtcccaga   2880
attgtatctc atactgtctg ggattaaggg caaatctatt acttttgcaa actgtcctct   2940
acatcaatta acatcgtggg tcactacagg gagaaaatcc aggtcatgca gttcctggcc   3000
```

```
catcaactgt attgggcctt ttggatatgc tgaacgcaga agaaagggtg gaaatcaacc   3060

ctctcctgtc tgccctctgg gtccctcctc tcacctctcc ctcgatcata tttccccttg   3120

gacacttggt tagacgcctt ccaggtcagg atgcacattt ctggattgtg gttccatgca   3180

gccttggggc attatgggtt cttcccccac ttcccctcca agaccctgtg ttcatttggt   3240

gttcctggaa gcaggtgcta caacatgtga ggcattcggg gaagctgcac atgtgccaca   3300

cagtgacttg gccccagacg catagactga ggtataaaga caagtatgaa tattactctc   3360

aaaatctttg tataaataaa tatttttggg gcatcctgga tgatttcatc ttctggaata   3420

ttgtttctag aacagtaaaa gccttattct aaggtgtatg tctgactcga taaatatcct   3480

tcaattaccc ttaaaaaaaa aaaaaaaaaa                                    3510
```

<210> SEQ ID NO 78
<211> LENGTH: 412
<212> TYPE: PRT
<213> ORGANISM: Homo sapiens

<400> SEQUENCE: 78

```
Met Lys Met His Leu Gln Arg Ala Leu Val Val Leu Ala Leu Leu Asn
1               5                   10                  15

Phe Ala Thr Val Ser Leu Ser Leu Ser Thr Cys Thr Thr Leu Asp Phe
            20                  25                  30

Gly His Ile Lys Lys Lys Arg Val Glu Ala Ile Arg Gly Gln Ile Leu
        35                  40                  45

Ser Lys Leu Arg Leu Thr Ser Pro Pro Glu Pro Thr Val Met Thr His
    50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Glu Gly Cys Thr Gln Glu Asn Thr
                85                  90                  95

Glu Ser Glu Tyr Tyr Ala Lys Glu Ile His Lys Phe Asp Met Ile Gln
            100                 105                 110

Gly Leu Ala Glu His Asn Glu Leu Ala Val Cys Pro Lys Gly Ile Thr
        115                 120                 125

Ser Lys Val Phe Arg Phe Asn Val Ser Ser Val Glu Lys Asn Arg Thr
    130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
            180                 185                 190

Thr Arg Gly Thr Ala Glu Trp Leu Ser Phe Asp Val Thr Asp Thr Val
        195                 200                 205

Arg Glu Trp Leu Leu Arg Arg Glu Ser Asn Leu Gly Leu Glu Ile Ser
    210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
            260                 265                 270

His His Asn Pro His Leu Ile Leu Met Met Ile Pro Pro His Arg Leu
        275                 280                 285
```

```
Asp Asn Pro Gly Gln Gly Gly Gln Arg Lys Lys Arg Ala Leu Asp Thr
    290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
            340                 345                 350

Ser Ala Asp Thr Thr His Ser Thr Val Leu Gly Leu Tyr Asn Thr Leu
        355                 360                 365

Asn Pro Glu Ala Ser Ala Ser Pro Cys Cys Val Pro Gln Asp Leu Glu
    370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410


<210> SEQ ID NO 79
<211> LENGTH: 5605
<212> TYPE: DNA
<213> ORGANISM: Homo sapiens

<400> SEQUENCE: 79

gttgcgagcg ctgcacaaca acaaaaggac ttggactggc cggcctgggc gcagcgaccc      60

gagggctgga gccggccccg cgcctgccgt ctgggtacct gaacgaggtg cagcgcagcc     120

cggccccacc gcagctacct cagcagtccc gccccgcccg cgtccttccc cgccgagccg     180

gcggccgctc ccttccccgc gcagccccgc acggcccggg cccacgtaca atgactcttc     240

ttgcttttca cctaagttga ataagcaccc tgtgcacttt aatctcctgt cggtaccatt     300

gggccaacta aagacaaggt tttgaaatct cagctataaa agacatccag ccaaactctc     360

agtcttgcct taacaatgtt ccagaggctg aataaaatgt ttgtgggtga agtcagttct     420

tcctccaacc aagaaccaga attcaatgag aaagaagatg atgaatggat tcttgttgac     480

ttcatagata cttgcactgg tttctcagca gaagaagaag aagaagagga ggacatcagt     540

gaagagtcac ctactgagca cccttcagtc ttttcctgtt taccggcatc tcttgagtgc     600

ttggctgata caagtgattc ctgctttctc cagtttgagt catgtccaat ggaggagagc     660

tggtttatca ccccaccccc atgttttact gcaggtggat taaccactat caaggtggaa     720

acaagtccta tggaaaacct tctcattgaa catcccagca tgtctgtcta tgctgtgcat     780

aactcctgcc ctggtctcag tgaggccacc cgtgggactg atgaattaca tagcccaagt     840

agtcccagag tggaagctca aaatgaaatg ggcagcata ttcattgtta tgttgcagct     900

cttgctgctc atacaacttt tctggaacaa cccaagagct ttcgcccttc ccagtggata     960

aaagaacaca gtgaaagaca gcctcttaac agaaatagcc ttcgtcgcca aaatcttacc    1020

agggattgcc accctcggca agtcaagcac aatggctggg ttgttcatca gccctgcccg    1080

cgtcagtaca attactaata gtttcaagtt ttgttggttg gtttctcttg gtttgtgctt    1140

acatgtatgg atgtgtgtat atgtacagtg aaaatgttgt ctctttacaa ccaattgata    1200

accaatcaca tagttttatc agtgtattta gacactatct tgaaaatcag atttatatgc    1260

tgtgtatcac ataatgcctt gcctttaaca tttactttt ttgtacactt tttcagatta    1320

tttctggaaa catatcaata taattacagt gtttgggggt gtctttaaat atattaggtt    1380
```

```
atacattagt cagcatttta aagacatttc ttcccaagta cgagaatagg catctttcat   1440
tttcatttta ttttgtatta cttaatcttt taagcaagca aaaatttatt ctcagggtca   1500
gctgtacact ttattgacca gtacttgata atctctctgt atatgatgaa tacattttta   1560
cacactaaca ttagcattaa caggtgatag ttgccatgga tataatggaa ttatggctgg   1620
actttctttt gaaagaaaac ttgatgtatt ctgtgtgtat ggtttttccc cagattagtc   1680
atacagttca tttggaattc aggtacatta agctttagtg aagagtgcat gcagtaattc   1740
caatgtgact gcatgacgtg gtacagacat tacaggtgtt gtagacagag gcacttgtct   1800
cgtgcagagg gattaaatta gacctgtgag attatatttg gaaaaattca tgtctgtaac   1860
taacccatta gtgcagtatt taatttgtta ctattccttc ccgccaattc tgtccactcc   1920
tcacctcgca tcagctataa atttggaagt acttgtccag gcactcaagt gacttcatat   1980
ttctctctgc ccatgggaaa agagataggc tttatatttc cacagagtga aaaatcctct   2040
gtcatggagc ctgtcctgcc aagtggcaag agtgtgggga ctgtctggtg atgatgtctt   2100
tcatggcatc tgagtgaaga gtgacaggtt ggctcaactt ttttcttttt tttttttaa   2160
ttgccttgta ttgtaagtat tcttccctgc agtccaagtg acttttcatt ttttgtttta   2220
acttcaggca aaatctttaa ccactctggc ctctgtttcc cccaccaacg gggagcagtg   2280
acatttacct ccctcacaga gtcactgtga ggattctata ctgatttgaa gtggagctgt   2340
tcagaactga accttgtagg aaattccaag ggcctttcta ctgaatctgg tgatggggtg   2400
gggccgtggc actttctctg ccacagctgt tcttcacagt gttggtgcta atgaggccag   2460
ggtgcagggt tcgattcaca cgtaggccag ttaacttaga gaaaatctat ttccttacct   2520
ctagccagtc acttcctttt tccgcagttg tgatgggttt tgctgagcca tccactctga   2580
ctgatttcct ctgaagtaaa catatttaca atccaaagca attctactga cagaagtgtt   2640
gccttcataa tcaaacagct tgtttttcca tctcctctgc aaccctaatt aaatgagtac   2700
aggtctacaa aatgttttca aggagaaaag cagcatatcc ttaagtgaag tattatattt   2760
ttcaataacc ctgtagtggc ttgatgcagg gaaccctggg ggactttcag cgaagagctg   2820
tgctcttttc tgactagatt agagcgtttg gagtggaaga cgtcaaatgt gtagtgagat   2880
ggaggtttta cattgttctt ctactggctg tgatgaagtg ccagaatgtc tctttagaac   2940
aagagttaga ttccccccttt ctccttattg ccccttccgt tttgacttcc cctttattta   3000
tttgttgtct aattaggggc caagtctgta aagttttgtc aaagtgagtt agaagttgtt   3060
ttctcttact atttgtgttt accagagttg ggagataaga tagtttccat gaaggtgtgt   3120
atgttttata cgatgtttgt tatagggcca tgcattggta acttgaaaat agaccagctt   3180
aatgtcttca ggatgtaaaa ctctgaatac acggcgtctc tttttcatac attgcatgta   3240
agttgttagt acctcacaag ctacagaagt tcagccatga gattttgttt ggcaacatga   3300
acagatttgt gtataactgc aatggccttt ttttccagat ttccttattg actttttgtt   3360
tgccttacct ggggctagtt ttttatgctt tgtacctaga aaacaaaaaa ttacattcgt   3420
tgggcttttt ttcaaggttg ggattaccac accacctgga atatcatact gtggtttctg   3480
cctaaaattg gcacatgtaa gtattgaaga aaatggttat ataattcagt tgaaactctt   3540
ggttattaga tgttaggcat ctcctgtatg taagacacaa ggccaaccac aacacagaac   3600
gatgttgacc tgttaagtat tctctgaaac atggccaaaa tgcattttat gagctttttt   3660
ttttgctatt gtaaatatta gtggtttaca atgcgcttta gacatatttc tttaaaatgc   3720
aagcagtgag aaataagacc tctctgaatt agtagctcta aactgttaac atagaatgtt   3780
```

```
acttggaaaa agtctggaat atgtggtgta cacaagcagt gcttcgtgaa tgagtttctt   3840

agcttttata gtgcgccatg tttctcaaag tttgtttttg ttgacaaaac attttataat   3900

atatatctta tgtttatttt ttttctcaac taattgtgta ctgcactgta aggtgaaaat   3960

tagccatcca ttatttatct tctgtggcaa tgcatttata tggttgattg ggtggggaat   4020

tttttgcaga aagatgcaaa gtgattgggt tttcgacttc ctatcgcagg gagcttttaa   4080

gaaatattaa tttcctatac atttttccaa tccccatgca aactgttcct gtttacatac   4140

cttctctgtt gtatcagtac tttgagtgag aagacagttt atttaaaact tgagcaggct   4200

gttcagcatt gtttctgctt ctgaaatctg tatagtacac tggtttgtaa tcattatgtc   4260

ttcattgaaa tccttgctac ttctcttcct cctcaatgaa atacattata tattatcttt   4320

atgtactctt aagaaaaacg agcaaggaag agtatcttca ttattctcat tttctctgag   4380

ttggaaacaa aaacatgaag gactccaact agaagacaga tatttacatt taaatagatt   4440

agtgggaaaa ctttaagagt ttccacatat tagttttcat tttttgagtc aagagactgc   4500

tccttgtact gggagacact agtagtatat gtttgtaatg ttactttaaa attatctttt   4560

tattttataa ggcccataaa tactggttaa actctgttaa aagtgggcct tctatcttgg   4620

atggtttcac tgccatcagc catgctgata tattagaaat ggcatcccta tctacttact   4680

ttaatgctta aaattataca taaaatgctt tatttagaaa acctacatga tacagtggtg   4740

tcagccttgc catgtatcag tttcacttga aatttgagac caattaaatt tcaactgttt   4800

agggtggaga aagaggtact ggaaaacatg cagatgagga tatcttttat gtgcaacagt   4860

atcctttgca tgggaggaga gttactcttg aaaggcaggc agcttaagtg gacaatgttt   4920

tgtatatagt tgagaatttt acgacacttt taaaaattgt gtaattgtta aatgtccagt   4980

tttgctctgt tttgcctgaa gttttagtat ttgttttcta ggtggacctc tgaaaaccaa   5040

accagtacct ggggaggtta gatgtgtgtt tcaggcttgg agtgtatgag tggttttgct   5100

tgtattttcc tccagagatt ttgaacttta ataattgcgt gtgttttttt tttttttaag   5160

tggctttgtt tttttttctc aagtaaaatt gtgaacatat ttcctttata ggggcagggc   5220

atgagttagg gagactgaag agtattgtag actgtacatg tgccttctta atgtgtttct   5280

cgacacattt tttttcagta acttgaaaat tcaaaaggga catttggtta ggttactgta   5340

catcaatcta tgcataaatg gcagcttgtt ttcttgagcc acggtctaaa ttttgttttt   5400

atagaaattt tttatactga ttggttcata gatggtcagt tttgtacaca gactgaacaa   5460

tacagcactt tgccaaaaat gagtgtagca ttgtttaaac attgtgtgtt aacacctgtt   5520

ctttgtaatt gggttgtggt gcattttgca ctacctggag ttacagtttt caatctgtca   5580

gtaaataaag tgtcctttaa cttca                                         5605
```

<210> SEQ ID NO 80
<211> LENGTH: 240
<212> TYPE: PRT
<213> ORGANISM: Homo sapiens

<400> SEQUENCE: 80

```
Met Phe Gln Arg Leu Asn Lys Met Phe Val Gly Glu Val Ser Ser Ser
1               5                   10                  15

Ser Asn Gln Glu Pro Glu Phe Asn Glu Lys Glu Asp Asp Glu Trp Ile
            20                  25                  30

Leu Val Asp Phe Ile Asp Thr Cys Thr Gly Phe Ser Ala Glu Glu Glu
        35                  40                  45
```

```
Glu Glu Glu Glu Asp Ile Ser Glu Glu Ser Pro Thr Glu His Pro Ser
    50                  55                  60

Val Phe Ser Cys Leu Pro Ala Ser Leu Glu Cys Leu Ala Asp Thr Ser
65                  70                  75                  80

Asp Ser Cys Phe Leu Gln Phe Glu Ser Cys Pro Met Glu Glu Ser Trp
                85                  90                  95

Phe Ile Thr Pro Pro Pro Cys Phe Thr Ala Gly Gly Leu Thr Thr Ile
            100                 105                 110

Lys Val Glu Thr Ser Pro Met Glu Asn Leu Leu Ile Glu His Pro Ser
        115                 120                 125

Met Ser Val Tyr Ala Val His Asn Ser Cys Pro Gly Leu Ser Glu Ala
    130                 135                 140

Thr Arg Gly Thr Asp Glu Leu His Ser Pro Ser Ser Pro Arg Val Glu
145                 150                 155                 160

Ala Gln Asn Glu Met Gly Gln His Ile His Cys Tyr Val Ala Ala Leu
                165                 170                 175

Ala Ala His Thr Thr Phe Leu Glu Gln Pro Lys Ser Phe Arg Pro Ser
            180                 185                 190

Gln Trp Ile Lys Glu His Ser Glu Arg Gln Pro Leu Asn Arg Asn Ser
        195                 200                 205

Leu Arg Arg Gln Asn Leu Thr Arg Asp Cys His Pro Arg Gln Val Lys
    210                 215                 220

His Asn Gly Trp Val Val His Gln Pro Cys Pro Arg Gln Tyr Asn Tyr
225                 230                 235                 240
```

<210> SEQ ID NO 81
<211> LENGTH: 4127
<212> TYPE: DNA
<213> ORGANISM: Homo sapiens

<400> SEQUENCE: 81

```
gcacagactc aaagccccgc gggcgagctc agcagcccgg agcgaccgcg gccccgccgc     60

ctcccccgcg agtcccggcg atgcggcccg gcctgtgagc ggccggcgac cctgggacgc    120

cccgccgcac aactacctca acgccgtgcc gccccccctcc cgcccccagg gaatctctgg    180

agattggttc accttttgtg gtcctgaccc cttctgtcct cactgtacct tgaagtccta    240

gagtccaata aaatcgctgc ctcccagctg tttggatcac agagaggttt ttgcactgcc    300

atagggcgcc cccgtgaggc gcttcgcccc ccaccatgtt ccagcgcctc tccagcctct    360

tcttcagcac cccctcgccc cccgaagacc ccgactgccc ccgcgccttc gtgtcggagg    420

aggatgaagt ggacggctgg ctcatcattg acctgccgga cagctacgcg gctccaccca    480

gccccggggc cgcccctgcc cccgcgggcc gccctccgcc cgcgccctcc ttgatggacg    540

agagctggtt tgttacccct cccgcctgtt ttacggcaga ggggcctgga ctcggtcccg    600

cccgcctcca gagcagtccc ctggaggacc tcctcatcga gcaccccagc atgtccgttt    660

acgtcaccgg cagcaccata gtgctagagc ccgggtcccc ttccccgctc ccggacgcgg    720

ccctgcctga cggcgacctc agcgaagggg aattgacgcc cgcccgccgc gagccgcggg    780

ccgcgcgcca cgccgctcct ctcccagcgc gggcggcgct gctggagaag gcgggccagg    840

tgcggcggct gcagcgggcc cggcagcggg cagagcgcca cgcgctgagc gccaaggcgg    900

tgcagcggca gaaccgagcc cgcgagagcc gtccgcgccg gtccaagaac cagagcagct    960

tcatctacca gccgtgccag cgccagttca actactgagc gtccaccggc cgcgccacga   1020
```

-continued accccttgcc gatcccgatc cctgtcgggc tcctccgact cctcgggctg gacaccgaaa 1080
cctcccttct taaagcgtgt gaggttgggt gatagccgtt ccttccccga caccctcaat 1140
ttccccatct ctgatcctct aatctgcctc tgaacccatt cacccttcac cctcactcct 1200
ggtccccata cccagcatct aatcatccat gccccctact cctggcccct ccatcctttc 1260
ttctctggtc cccatccctg tctctccctt tcacccttgc cctccagtcc tctacctctg 1320
gcctgcccct atttctgaaa gcttcttcca gtccctgatc tggctcattc cccaccttca 1380
actcccacct tacatgtctc acactatccc atggttggca ttacactcac tcctgttccc 1440
ttattcttca ttcccagtaa ttccctacca aatggtgggg accctgagcc cagctctgac 1500
caggtagagc ctgtgcagcc tgggctgctg tcattgccct ccagtaaggg ctcagggttt 1560
tgcttttagt ctccccttcc ttctgccttg ggggcggtac tctgtggagc tgcttaggcc 1620
tggaaaggta cagtatgtag aagaggactg tgagacgtga gttagaggga gaagatggag 1680
ggaatctagg gaacgaggca gcctattgga gatgcggaca ggacagacac gttgagaagc 1740
tgcagggagc agggcaccaa gggagtgtgc actgtgcttg ctcagagagg ccaaaccctg 1800
ctcccaggct gaagcctgga gtctgccccc acttcccttt tctataatcc acccttctgc 1860
aggccctgaa atctgaaggg cttagttagt accttgccac tctaccccca acacgtcacc 1920
cgagtagaag ctgggcaagg ccctaccatc ctggccgtct gttcacaagc ccaaggtgct 1980
agaactagct taggagacat gcaggccaca gggcttctag gcagggaaag ggcacacacc 2040
ctaggtcagc gtgcagagca gtgatgctgg aggacacacc atggggtgaa gccatcccaa 2100
ggctgacagc tcagtcttca ccttgcctct ggccttgtat ttcacaccct gctcagtatg 2160
gctagccagc agtcctgagt aggagtccag gactcccact gtctcaatct gcaaattgtt 2220
cctatccagg ttcagggcct tcagggggcc tcttttcatt ttctcccaca ggcctctctt 2280
tctttctagg ttgctgggga gaaatgggta ccctatgatc cccctcccct tctcctccag 2340
taaatacctg gaagagggaa cctgaatccc tgggggagac agaaggggca ggggccacca 2400
gcctcccctt cttgtggtga gactgaattt tgggctcaga caccagcaac agcctcttgg 2460
gatgccctga gttgcttccc atttcctctt tctagccgtc cttttctagt gtgtgctcac 2520
tcttcctagg aacttttaag acttcttggt acctatgaac ataggtcctc ccctcacccc 2580
aactctaggt ttccaggcct cacagccaag ctgaagcttg gagaaaactc tgcattccca 2640
tgagggcaaa ggcagctgcc ctccctgacc ctatagcccc aggcctcatg gggggtatgt 2700
ggggaaggga tggggtatcc ccatggatgc tgggatgagg acagaggaag acctgatggg 2760
gtctcctatt ccagggaata agccaaatta acactaaaaa cggatcaaag ctcccacgcc 2820
agtccactag ggccccagta gttgacagcc ttgctcctct cccaagttct ccttcagaac 2880
ctagttgctt ttattcttcc agctaccact tgggcacttc acagccagcc tagggtcttc 2940
ggcacctcca agagctgaat ctccctccaa cccttcttgc ctactcctca ctgccagctg 3000
ggacctaggc tcagtcctgt gtggtgccca tgatccttct ggtgggggaa gagtttaagt 3060
tatagggcat ttggctcaaa ttttaaaagg ccttttgttt acctatattt ctggaggctc 3120
ctgtattcta gaacccaatc tctcacctgc ttggttgcaa ggctcatatt tttttgtacc 3180
tttcctatag attctgtagc atttgagtgt ggcaatattt taattgtgta tagatttcta 3240
agaaccaaca ctactcagtc tcctgctagt ctgactcctg aagcatcagc ccttgtcata 3300
ctgtattgac tgtgtacgtg cctttcacct tgagcatgct tcaggatttt tttttaaacc 3360
acagaacttg aatacatgag ggaaccagag ttcaaagtcc tatgcaacct taggaggggg 3420
ttagagagtc tgttttgatt gatgttttct gaggccctag aggagtttgt atcaatttgt 3480
gagtattaat gtcagtacta ccagcacttt gccaaaactg tcagagggac ccgtttctag 3540
agtgagtccc agttacatca aacagtgact tccagttatt ccccagtaag tctgagtggt 3600
tccttcaagc tgggtgtctt tccagccttt gccagtctag ccccagcagg gcaccgtgta 3660
tgaatgcagt ttggtgctgt tttagagtat gcctgctccc cagccccctg cctggaaccc 3720
tctgagcaac ttgctctgac ctataatgtc ttaggtgcaa cacggacccc accagagctc 3780
ttggataccc ccctagatcc atgtggcttt atgtgagggg actgaatgca gacacaccat 3840 agccccccttc tactactttc cctctcgccc tgccacctag ttccacatgg aaccaacaag 3900
ttgagtgcat ccctgttggg tgttttgtgt tgagactggc tgaaatgagg agactttgac 3960
catgtgacgt gtcaacagac tcaaggagac aaccacctca actgggtcat gtggcatgcc 4020
tgtgtatgtg tgtaacagaa ttctgattgt tagactgtaa tgctattcct ctatgggaga 4080
aaaaaattaa tataaagaaa aacaaataaa aatatattta aagcaca 4127

<210> SEQ ID NO 82
<211> LENGTH: 220
<212> TYPE: PRT
<213> ORGANISM: Homo sapiens

<400> SEQUENCE: 82

Met Phe Gln Arg Leu Ser Ser Leu Phe Phe Ser Thr Pro Ser Pro Pro
1               5                   10                  15

Glu Asp Pro Asp Cys Pro Arg Ala Phe Val Ser Glu Glu Asp Glu Val
            20                  25                  30

Asp Gly Trp Leu Ile Ile Asp Leu Pro Asp Ser Tyr Ala Ala Pro Pro
        35                  40                  45

Ser Pro Gly Ala Ala Pro Ala Pro Ala Gly Arg Pro Pro Pro Ala Pro
    50                  55                  60

Ser Leu Met Asp Glu Ser Trp Phe Val Thr Pro Pro Ala Cys Phe Thr
65                  70                  75                  80

Ala Glu Gly Pro Gly Leu Gly Pro Ala Arg Leu Gln Ser Ser Pro Leu
                85                  90                  95

Glu Asp Leu Leu Ile Glu His Pro Ser Met Ser Val Tyr Val Thr Gly
            100                 105                 110

Ser Thr Ile Val Leu Glu Pro Gly Ser Pro Ser Pro Leu Pro Asp Ala
        115                 120                 125

Ala Leu Pro Asp Gly Asp Leu Ser Glu Gly Glu Leu Thr Pro Ala Arg
    130                 135                 140

Arg Glu Pro Arg Ala Ala Arg His Ala Ala Pro Leu Pro Ala Arg Ala
145                 150                 155                 160

Ala Leu Leu Glu Lys Ala Gly Gln Val Arg Arg Leu Gln Arg Ala Arg
                165                 170                 175

Gln Arg Ala Glu Arg His Ala Leu Ser Ala Lys Ala Val Gln Arg Gln
            180                 185                 190

Asn Arg Ala Arg Glu Ser Arg Pro Arg Arg Ser Lys Asn Gln Ser Ser
        195                 200                 205

Phe Ile Tyr Gln Pro Cys Gln Arg Gln Phe Asn Tyr
    210                 215                 220

<210> SEQ ID NO 83
<211> LENGTH: 2199
<212> TYPE: DNA

<213> ORGANISM: Homo sapiens

<400> SEQUENCE: 83
agacggtggc cgagcggggg accgggaagc atggcccggg ggtcggcggt tgcctgggcg 60
gcgctcgggc cgttgttgtg gggctgcgcg ctggggctgc agggcgggat gctgtacccc 120
caggagagcc cgtcgcggga gtgcaaggag ctggacggcc tctggagctt ccgcgccgac 180
ttctctgaca accgacgccg ggcttcgag gagcagtggt accggcggcc gctgtgggag 240
tcaggcccca ccgtggacat gccagttccc tccagcttca atgacatcag ccaggactgg 300
cgtctgcggc attttgtcgg ctgggtgtgg tacgaacggg aggtgatcct gccggagcga 360
tggacccagg acctgcgcac aagagtggtg ctgaggattg gcagtgccca ttcctatgcc 420
atcgtgtggg tgaatggggt cgacacgcta gagcatgagg ggggctacct ccccttcgag 480
gccgacatca gcaacctggt ccaggtgggg cccctgccct cccggctccg aatcactatc 540
gccatcaaca acacactcac ccccaccacc ctgccaccag ggaccatcca atacctgact 600
gacacctcca agtatcccaa gggttacttt gtccagaaca catattttga ctttttcaac 660
tacgctggac tgcagcggtc tgtacttctg tacacgacac ccaccaccta catcgatgac 720
atcaccgtca ccaccagcgt ggagcaagac agtgggctgg tgaattacca gatctctgtc 780
aagggcagta acctgttcaa gttggaagtg cgtcttttgg atgcagaaaa caaagtcgtg 840
gcgaatggga ctgggaccca gggccaactt aaggtgccag gtgtcagcct ctggtggccg 900
tacctgatgc acgaacgccc tgcctatctg tattcattgg aggtgcagct gactgcacag 960
acgtcactgg ggcctgtgtc tgacttctac acactccctg tggggatccg cactgtggct 1020
gtcaccaaga gccagttcct catcaatggg aaacctttct atttccacgg tgtcaacaag 1080
catgaggatg cggacatccg agggaagggc ttcgactggc cgctgctggt gaaggacttc 1140
aacctgcttc gctggcttgg tgccaacgct ttccgtacca gccactaccc ctatgcagag 1200
gaagtgatgc agatgtgtga ccgctatggg attgtggtca tcgatgagtg tcccggcgtg 1260
ggcctggcgc tgccgcagtt cttcaacaac gtttctctgc atcaccacat gcaggtgatg 1320
gaagaagtgg tgcgtaggga caagaaccac cccgcggtcg tgatgtggtc tgtggccaac 1380
gagcctgcgt cccacctaga atctgctggc tactacttga agatggtgat cgctcacacc 1440
aaatccttgg acccctcccg gcctgtgacc tttgtgagca actctaacta tgcagcagac 1500
aagggggctc cgtatgtgga tgtgatctgt ttgaacagct actactcttg gtatcacgac 1560
tacgggcacc tggagttgat tcagctgcag ctggccaccc agtttgagaa ctggtataag 1620
aagtatcaga agcccattat tcagagcgag tatggagcag aaacgattgc agggtttcac 1680
caggatccac ctctgatgtt cactgaagag taccagaaaa gtctgctaga gcagtaccat 1740
ctgggtctgg atcaaaaacg cagaaaatac gtggttggag agctcatttg gaattttgcc 1800
gatttcatga ctgaacagtc accgacgaga gtgctgggga ataaaaaggg gatcttcact 1860
cggcagagac aaccaaaaag tgcagcgttc cttttgcgag agagatactg gaagattgcc 1920
aatgaaacca ggtatcccca ctcagtagcc aagtcacaat gtttggaaaa cagcctgttt 1980
acttgagcaa gactgatacc acctgcgtgt cccttcctcc ccgagtcagg gcgacttcca 2040
cagcagcaga acaagtgcct cctggactgt tcacggcaga ccagaacgtt tctggcctgg 2100
gttttgtggt catctattct agcagggaac actaaaggtg gaaataaaag attttctatt 2160
atggaaataa agagttggca tgaaagtggc tactgaaaa 2199

<210> SEQ ID NO 84
<211> LENGTH: 651
<212> TYPE: PRT
<213> ORGANISM: Homo sapiens

<400> SEQUENCE: 84

```
Met Ala Arg Gly Ser Ala Val Ala Trp Ala Ala Leu Gly Pro Leu Leu
1               5                   10                  15

Trp Gly Cys Ala Leu Gly Leu Gln Gly Gly Met Leu Tyr Pro Gln Glu
            20                  25                  30

Ser Pro Ser Arg Glu Cys Lys Glu Leu Asp Gly Leu Trp Ser Phe Arg
        35                  40                  45

Ala Asp Phe Ser Asp Asn Arg Arg Arg Gly Phe Glu Glu Gln Trp Tyr
    50                  55                  60

Arg Arg Pro Leu Trp Glu Ser Gly Pro Thr Val Asp Met Pro Val Pro
65                  70                  75                  80

Ser Ser Phe Asn Asp Ile Ser Gln Asp Trp Arg Leu Arg His Phe Val
                85                  90                  95

Gly Trp Val Trp Tyr Glu Arg Glu Val Ile Leu Pro Glu Arg Trp Thr
            100                 105                 110

Gln Asp Leu Arg Thr Arg Val Val Leu Arg Ile Gly Ser Ala His Ser
        115                 120                 125

Tyr Ala Ile Val Trp Val Asn Gly Val Asp Thr Leu Glu His Glu Gly
    130                 135                 140

Gly Tyr Leu Pro Phe Glu Ala Asp Ile Ser Asn Leu Val Gln Val Gly
145                 150                 155                 160

Pro Leu Pro Ser Arg Leu Arg Ile Thr Ile Ala Ile Asn Asn Thr Leu
                165                 170                 175

Thr Pro Thr Thr Leu Pro Pro Gly Thr Ile Gln Tyr Leu Thr Asp Thr
            180                 185                 190

Ser Lys Tyr Pro Lys Gly Tyr Phe Val Gln Asn Thr Tyr Phe Asp Phe
        195                 200                 205

Phe Asn Tyr Ala Gly Leu Gln Arg Ser Val Leu Leu Tyr Thr Thr Pro
    210                 215                 220

Thr Thr Tyr Ile Asp Asp Ile Thr Val Thr Thr Ser Val Glu Gln Asp
225                 230                 235                 240

Ser Gly Leu Val Asn Tyr Gln Ile Ser Val Lys Gly Ser Asn Leu Phe
                245                 250                 255

Lys Leu Glu Val Arg Leu Leu Asp Ala Glu Asn Lys Val Val Ala Asn
            260                 265                 270

Gly Thr Gly Thr Gln Gly Gln Leu Lys Val Pro Gly Val Ser Leu Trp
        275                 280                 285

Trp Pro Tyr Leu Met His Glu Arg Pro Ala Tyr Leu Tyr Ser Leu Glu
    290                 295                 300

Val Gln Leu Thr Ala Gln Thr Ser Leu Gly Pro Val Ser Asp Phe Tyr
305                 310                 315                 320

Thr Leu Pro Val Gly Ile Arg Thr Val Ala Val Thr Lys Ser Gln Phe
                325                 330                 335

Leu Ile Asn Gly Lys Pro Phe Tyr Phe His Gly Val Asn Lys His Glu
            340                 345                 350

Asp Ala Asp Ile Arg Gly Lys Gly Phe Asp Trp Pro Leu Leu Val Lys
        355                 360                 365

Asp Phe Asn Leu Leu Arg Trp Leu Gly Ala Asn Ala Phe Arg Thr Ser
    370                 375                 380
```

-continued

```
His Tyr Pro Tyr Ala Glu Glu Val Met Gln Met Cys Asp Arg Tyr Gly
385                 390                 395                 400

Ile Val Val Ile Asp Glu Cys Pro Gly Val Gly Leu Ala Leu Pro Gln
                405                 410                 415

Phe Phe Asn Asn Val Ser Leu His His His Met Gln Val Met Glu Glu
            420                 425                 430

Val Val Arg Arg Asp Lys Asn His Pro Ala Val Val Met Trp Ser Val
        435                 440                 445

Ala Asn Glu Pro Ala Ser His Leu Glu Ser Ala Gly Tyr Tyr Leu Lys
    450                 455                 460

Met Val Ile Ala His Thr Lys Ser Leu Asp Pro Ser Arg Pro Val Thr
465                 470                 475                 480

Phe Val Ser Asn Ser Asn Tyr Ala Ala Asp Lys Gly Ala Pro Tyr Val
                485                 490                 495

Asp Val Ile Cys Leu Asn Ser Tyr Tyr Ser Trp Tyr His Asp Tyr Gly
            500                 505                 510

His Leu Glu Leu Ile Gln Leu Gln Leu Ala Thr Gln Phe Glu Asn Trp
        515                 520                 525

Tyr Lys Lys Tyr Gln Lys Pro Ile Ile Gln Ser Glu Tyr Gly Ala Glu
    530                 535                 540

Thr Ile Ala Gly Phe His Gln Asp Pro Pro Leu Met Phe Thr Glu Glu
545                 550                 555                 560

Tyr Gln Lys Ser Leu Leu Glu Gln Tyr His Leu Gly Leu Asp Gln Lys
                565                 570                 575

Arg Arg Lys Tyr Val Val Gly Glu Leu Ile Trp Asn Phe Ala Asp Phe
            580                 585                 590

Met Thr Glu Gln Ser Pro Thr Arg Val Leu Gly Asn Lys Lys Gly Ile
        595                 600                 605

Phe Thr Arg Gln Arg Gln Pro Lys Ser Ala Ala Phe Leu Leu Arg Glu
    610                 615                 620

Arg Tyr Trp Lys Ile Ala Asn Glu Thr Arg Tyr Pro His Ser Val Ala
625                 630                 635                 640

Lys Ser Gln Cys Leu Glu Asn Ser Leu Phe Thr
                645                 650
```

<210> SEQ ID NO 85
<211> LENGTH: 2237
<212> TYPE: DNA
<213> ORGANISM: Homo sapiens

<400> SEQUENCE: 85

```
gttttgcaga cgccaccgcc gaggaaaacc gtgtactatt agccatggtc aaccccaccg     60

tgttcttcga cattgccgtc gacggcgagc ccttgggccg cgtctccttt gagctgtttg    120

cagacaaggt cccaaagaca gcagaaaatt ttcgtgctct gagcactgga gagaaaggat    180

ttggttataa gggttcctgc tttcacagaa ttattccagg gtttatgtgt cagggtggtg    240

acttcacacg ccataatggc actggtggca agtccatcta tggggagaaa tttgaagatg    300

agaacttcat cctaaagcat acgggtcctg gcatcttgtc catggcaaat gctggaccca    360

acacaaatgg ttcccagttt ttcatctgca ctgccaagac tgagtggttg gatggcaagc    420

atgtggtgtt tggcaaagtg aaagaaggca tgaatattgt ggaggccatg gagcgctttg    480

ggtccaggaa tggcaagacc agcaagaaga tcaccattgc tgactgtgga caactcgaat    540

aagtttgact tgtgttttat cttaaccacc agatcattcc ttctgtagct caggagagca    600
```

```
ccccctccacc ccatttgctc gcagtatcct agaatctttg tgctctcgct gcagttccct    660

ttgggttcca tgttttcctt gttccctccc atgcctagct ggattgcaga gttaagttta    720

tgattatgaa ataaaaacta aataacaatt gtcctcgttt gagttaagag tgttgatgta    780

ggctttattt taagcagtaa tgggttactt ctgaaacatc acttgtttgc ttaattctac    840

acagtactta gattttttt actttccagt cccaggaagt gtcaatgttt gttgagtgga    900

atattgaaaa tgtaggcagc aactgggcat ggtggctcac tgtctgtaat gtattacctg    960

aggcagaaga ccacctgagg gtaggagtca agatcagcct gggcaacata gtgagacgct   1020

gtctctacaa aaaataatta gcctggcctg gtggtgcatg cctagtccta gctgatctgg   1080

aggctgacgt gggaggattg cttgagccta gagtgagcta ttatcatgcc actgtacagc   1140

ctgggtgttc acagatcttg tgtctcaaag gtaggcagag gcaggaaaag caaggagcca   1200

gaattaagag gttgggtcag tctgcagtga gttcatgcat ttagaggtgt tcttcaagat   1260

gactaatgtc aaaaattgag acatctgttg cggttttttt ttttttttt tcccctggaa   1320

tgcagtggcg tgatctcagc tcactgcagc ctccgcctcc tgggttcaag tgattctagt   1380

gcctcagcct cctgagtagc tgggataatg ggcgtgtgcc accatgccca gctaattttt   1440

gtatttttag tatagatggg gtttcatcat tttgaccagg ctggtctcaa actcttgacc   1500

tcagctgatg cgcctgcctt ggcctcccaa actgctgaga ttacagatgt gagccaccgc   1560

accctacctc attttctgta acaaagctaa gcttgaacac tgttgatgtt cttgagggaa   1620

gcatattggg ctttaggctg taggtcaagt ttatacatct taattatggt ggaattccta   1680

tgtagagtct aaaaagccag gtacttggtg ctacagtcag tctccctgca gagggttaag   1740

gcgcagacta cctgcagtga ggaggtactg cttgtagcat atagagcctc tccctagctt   1800

tggttatgga ggctttgagg ttttgcaaac ctgaccaatt taagccataa gatctggtca   1860

aagggatacc cttcccacta aggacttggt ttctcaggaa attatatgta cagtgcttgc   1920

tggcagttag atgtcaggac aatctaagct gagaaaaccc cttctctgcc caccttaaca   1980

gacctctagg gttcttaacc cagcaatcaa gtttgcctat cctagaggtg gcggatttga   2040

tcatttggtg tgttgggcaa tttttgtttt actgtctggt tccttctgcg tgaattacca   2100

ccaccaccac ttgtgcatct cagtcttgtg tgttgtctgg ttacgtattc cctgggtgat   2160

accattcaat gtcttaatgt acttgtggct cagacctgag tgcaaggtgg aaataaacat   2220

caaacatctt ttcatta                                                  2237
```

```
<210> SEQ ID NO 86
<211> LENGTH: 165
<212> TYPE: PRT
<213> ORGANISM: Homo sapiens

<400> SEQUENCE: 86

Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Leu Ser Thr Gly Glu Lys Gly Phe Gly Tyr
        35                  40                  45

Lys Gly Ser Cys Phe His Arg Ile Ile Pro Gly Phe Met Cys Gln Gly
    50                  55                  60

Gly Asp Phe Thr Arg His Asn Gly Thr Gly Gly Lys Ser Ile Tyr Gly
65                  70                  75                  80
```

-continued

```
Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
    130                 135                 140

Phe Gly Ser Arg Asn Gly Lys Thr Ser Lys Lys Ile Thr Ile Ala Asp
145                 150                 155                 160

Cys Gly Gln Leu Glu
                165
```

<210> SEQ ID NO 87
<211> LENGTH: 2193
<212> TYPE: DNA
<213> ORGANISM: Homo sapiens

<400> SEQUENCE: 87

```
agttccgtcg cagccgggat ttgggtcgca gttcttgttt gtggatcgct gtgatcgtca      60

cttgacaatg cagatcttcg tgaagactct gactggtaag accatcaccc tcgaggttga     120

gcccagtgac accatcgaga atgtcaaggc aaagatccaa gataaggaag gcatccctcc     180

tgaccagcag aggctgatct ttgctggaaa acagctggaa gatgggcgca ccctgtctga     240

ctacaacatc cagaaagagt ccaccctgca cctggtgctc cgtctcagag gtgggatgca     300

aatcttcgtg aagacactca ctggcaagac catcaccctt gaggtcgagc ccagtgacac     360

catcgagaac gtcaaagcaa agatccagga caaggaaggc attcctcctg accagcagag     420

gttgatcttt gccggaaagc agctggaaga tgggcgcacc ctgtctgact acaacatcca     480

gaaagagtct accctgcacc tggtgctccg tctcagaggt gggatgcaga tcttcgtgaa     540

gaccctgact ggtaagacca tcaccctcga ggtggagccc agtgacacca tcgagaatgt     600

caaggcaaag atccaagata aggaaggcat tcctcctgat cagcagaggt tgatctttgc     660

cggaaaacag ctggaagatg gtcgtaccct gtctgactac aacatccaga aagagtccac     720

cttgcacctg gtactccgtc tcagaggtgg gatgcaaatc ttcgtgaaga cactcactgg     780

caagaccatc acccttgagg tcgagcccag tgacactatc gagaacgtca aagcaaagat     840

ccaagacaag gaaggcattc ctcctgacca gcagaggttg atctttgccg gaaagcagct     900

ggaagatggg cgcaccctgt ctgactacaa catccagaaa gagtctaccc tgcacctggt     960

gctccgtctc agaggtggga tgcagatctt cgtgaagacc ctgactggta agaccatcac    1020

tctcgaagtg gagccgagtg acaccattga gaatgtcaag gcaaagatcc aagacaagga    1080

aggcatccct cctgaccagc agaggttgat ctttgccgga aaacagctgg aagatggtcg    1140

taccctgtct gactacaaca tccagaaaga gtccaccttg cacctggtgc tccgtctcag    1200

aggtgggatg cagatcttcg tgaagaccct gactggtaag accatcactc tcgaggtgga    1260

gccgagtgac accattgaga atgtcaaggc aaagatccaa gacaaggaag gcatccctcc    1320

tgaccagcag aggttgatct ttgctgggaa acagctggaa gatggacgca ccctgtctga    1380

ctacaacatc cagaaagagt ccaccctgca cctggtgctc cgtcttagag gtgggatgca    1440

gatcttcgtg aagaccctga ctggtaagac catcactctc gaagtggagc cgagtgacac    1500

cattgagaat gtcaaggcaa agatccaaga caaggaaggc atccctcctg accagcagag    1560

gttgatcttt gctgggaaac agctggaaga tggacgcacc ctgtctgact acaacatcca    1620
```

```
gaaagagtcc accctgcacc tggtgctccg tcttagaggt gggatgcaga tcttcgtgaa   1680

gaccctgact ggtaagacca tcactctcga agtggagccg agtgacacca ttgagaatgt   1740

caaggcaaag atccaagaca aggaaggcat ccctcctgac cagcagaggt tgatctttgc   1800

tgggaaacag ctggaagatg gacgcaccct gtctgactac aacatccaga aagagtccac   1860

cctgcacctg gtgctccgtc tcagaggtgg gatgcaaatc ttcgtgaaga ccctgactgg   1920

taagaccatc accctcgagg tggagcccag tgacaccatc gagaatgtca aggcaaagat   1980

ccaagataag gaaggcatcc ctcctgatca gcagaggttg atctttgctg ggaaacagct   2040

ggaagatgga cgcaccctgt ctgactacaa catccagaaa gagtccactc tgcacttggt   2100

cctgcgcttg aggggggtg tctaagtttc cccttttaag gtttcaacaa atttcattgc   2160

actttccttt caataaagtt gttgcattcc caa                                2193
```

<210> SEQ ID NO 88
<211> LENGTH: 685
<212> TYPE: PRT
<213> ORGANISM: Homo sapiens

<400> SEQUENCE: 88

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ser Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Pro Ser Asp Thr Ile Glu
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ser Asp Tyr Asn Ile Gln Lys Glu Ser Thr Leu His Leu Val Leu Arg
    210                 215                 220

Leu Arg Gly Gly Met Gln Ile Phe Val Lys Thr Leu Thr Gly Lys Thr
225                 230                 235                 240

Ile Thr Leu Glu Val Glu Pro Ser Asp Thr Ile Glu Asn Val Lys Ala
                245                 250                 255

Lys Ile Gln Asp Lys Glu Gly Ile Pro Pro Asp Gln Gln Arg Leu Ile
            260                 265                 270
```

```
Phe Ala Gly Lys Gln Leu Glu Asp Gly Arg Thr Leu Ser Asp Tyr Asn
        275                 280                 285

Ile Gln Lys Glu Ser Thr Leu His Leu Val Leu Arg Leu Arg Gly Gly
    290                 295                 300

Met Gln Ile Phe Val Lys Thr Leu Thr Gly Lys Thr Ile Thr Leu Glu
305                 310                 315                 320

Val Glu Pro Ser Asp Thr Ile Glu Asn Val Lys Ala Lys Ile Gln Asp
                325                 330                 335

Lys Glu Gly Ile Pro Pro Asp Gln Gln Arg Leu Ile Phe Ala Gly Lys
            340                 345                 350

Gln Leu Glu Asp Gly Arg Thr Leu Ser Asp Tyr Asn Ile Gln Lys Glu
        355                 360                 365

Ser Thr Leu His Leu Val Leu Arg Leu Arg Gly Gly Met Gln Ile Phe
    370                 375                 380

Val Lys Thr Leu Thr Gly Lys Thr Ile Thr Leu Glu Val Glu Pro Ser
385                 390                 395                 400

Asp Thr Ile Glu Asn Val Lys Ala Lys Ile Gln Asp Lys Glu Gly Ile
                405                 410                 415

Pro Pro Asp Gln Gln Arg Leu Ile Phe Ala Gly Lys Gln Leu Glu Asp
            420                 425                 430

Gly Arg Thr Leu Ser Asp Tyr Asn Ile Gln Lys Glu Ser Thr Leu His
        435                 440                 445

Leu Val Leu Arg Leu Arg Gly Gly Met Gln Ile Phe Val Lys Thr Leu
    450                 455                 460

Thr Gly Lys Thr Ile Thr Leu Glu Val Glu Pro Ser Asp Thr Ile Glu
465                 470                 475                 480

Asn Val Lys Ala Lys Ile Gln Asp Lys Glu Gly Ile Pro Pro Asp Gln
                485                 490                 495

Gln Arg Leu Ile Phe Ala Gly Lys Gln Leu Glu Asp Gly Arg Thr Leu
            500                 505                 510

Ser Asp Tyr Asn Ile Gln Lys Glu Ser Thr Leu His Leu Val Leu Arg
        515                 520                 525

Leu Arg Gly Gly Met Gln Ile Phe Val Lys Thr Leu Thr Gly Lys Thr
    530                 535                 540

Ile Thr Leu Glu Val Glu Pro Ser Asp Thr Ile Glu Asn Val Lys Ala
545                 550                 555                 560

Lys Ile Gln Asp Lys Glu Gly Ile Pro Pro Asp Gln Gln Arg Leu Ile
                565                 570                 575

Phe Ala Gly Lys Gln Leu Glu Asp Gly Arg Thr Leu Ser Asp Tyr Asn
            580                 585                 590

Ile Gln Lys Glu Ser Thr Leu His Leu Val Leu Arg Leu Arg Gly Gly
        595                 600                 605

Met Gln Ile Phe Val Lys Thr Leu Thr Gly Lys Thr Ile Thr Leu Glu
    610                 615                 620

Val Glu Pro Ser Asp Thr Ile Glu Asn Val Lys Ala Lys Ile Gln Asp
625                 630                 635                 640

Lys Glu Gly Ile Pro Pro Asp Gln Gln Arg Leu Ile Phe Ala Gly Lys
                645                 650                 655

Gln Leu Glu Asp Gly Arg Thr Leu Ser Asp Tyr Asn Ile Gln Lys Glu
            660                 665                 670

Ser Thr Leu His Leu Val Leu Arg Leu Arg Gly Gly Val
        675                 680                 685
```

<210> SEQ ID NO 89
<211> LENGTH: 2547
<212> TYPE: DNA
<213> ORGANISM: Homo sapiens

<400> SEQUENCE: 89
actgcagccc cgctcgactc cggcgtggtg cgcaggcgcg gtatcccccc tcccccgcca 60
gctcgacccc ggtgtggtgc gcaggcgcag tctgcgcagg gactggcggg actgcgcggc 120
ggcaacagca gacatgtcgg gggtccgggg cctgtcgcgg ctgctgagcg ctcggcgcct 180
ggcgctggcc aaggcgtggc caacagtgtt gcaaacagga acccgaggtt ttcacttcac 240
tgttgatggg aacaagaggg catctgctaa agtttcagat tccatttctg ctcagtatcc 300
agtagtggat catgaatttg atgcagtggt ggtaggcgct ggaggggcag gcttgcgagc 360
tgcatttggc ctttctgagg cagggtttaa tacagcatgt gttaccaagc tgtttcctac 420
caggtcacac actgttgcag cacagggagg aatcaatgct gctctgggga acatggagga 480
ggacaactgg aggtggcatt tctacgacac cgtgaagggc tccgactggc tgggggacca 540
ggatgccatc cactacatga cggagcaggc ccccgccgcc gtggtcgagc tagaaaatta 600
tggcatgccg tttagcagaa ctgaagatgg gaagatttat cagcgtgcat ttggtggaca 660
gagcctcaag tttggaaagg gcgggcaggc ccatcggtgc tgctgtgtgg ctgatcggac 720
tggccactcg ctattgcaca ccttatatgg aaggtctctg cgatatgata ccagctattt 780
tgtggagtat tttgccttgg atctcctgat ggagaatggg gagtgccgtg gtgtcatcgc 840
actgtgcata gaggacgggt ccatccatcg cataagagca aagaacactg ttgttgccac 900
aggaggctac gggcgcacct acttcagctg cacgtctgcc cacaccagca ctggcgacgg 960
cacggccatg atcaccaggg caggccttcc ttgccaggac ctagagtttg ttcagttcca 1020
ccctacaggc atatatggtg ctggttgtct cattacggaa ggatgtcgtg gagagggagg 1080
cattctcatt aacagtcaag gcgaaaggtt tatggagcga tacgcccctg tcgcgaagga 1140
cctggcgtct agagatgtgg tgtctcggtc catgactctg gagatccgag aaggaagagg 1200
ctgtggccct gagaaagatc acgtctacct gcagctgcac cacctacctc cagagcagct 1260
ggccacgcgc ctgcctggca tttcagagac agccatgatc ttcgctggcg tggacgtcac 1320
gaaggagccg atccctgtcc tccccaccgt gcattataac atgggcggca ttcccaccaa 1380
ctacaagggg caggtcctga ggcacgtgaa tggccaggat cagattgtgc ccggcctgta 1440
cgcctgtggg gaggccgcct gtgcctcggt acatggtgcc aaccgcctcg gggcaaactc 1500
gctcttggac ctggttgtct ttggtcgggc atgtgccctg agcatcgaag agtcatgcag 1560
gcctggagat aaagtccctc caattaaacc aaacgctggg gaagaatctg tcatgaatct 1620
tgacaaattg agatttgctg atggaagcat aagaacatcg gaactgcgac tcagcatgca 1680
gaaggtgcgg attgatgagt acgattactc caagcccatc caggggcaac agaagaagcc 1740
ctttgaggag cactggagga agcacaccct gtcctatgtg gacgttggca ctgggaaggt 1800
cactctggaa tatagacccg tgatcgacaa aactttgaac gaggctgact gtgccaccgt 1860
cccgccagcc attcgctcct actgatgaga caagatgtgg tgatgacaga atcagctttt 1920
gtaattatgt ataatagctc atgcatgtgt ccatgtcata actgtcttca tacgcttctg 1980
cactctgggg aagaaggagt acattgaagg gagattggca cctagtggct gggagcttgc 2040
caggaaccca gtggccaggg agcgtggcac ttacctttgt cccttgcttc attcttgtga 2100
gatgataaaa ctgggcacag ctcttaaata aaatataaat gaacaaactt tcttttattt 2160

```
ccaaatccat ttgaaatatt ttactgttgt gactttagtc atatttgttg acctaaaaat   2220

caaatgtaat ctttgtattg tgttacatca aaatccagat attttgtata gtttcttttt   2280

tctttttctt ttcttttttt tttttgagac aggatcggtg cagtagtaca atcacagctc   2340

actgcagcct caaactcctg ggcagctcag gtgatcttcc tgactcagcc ttctgagtag   2400

ttggggctac aggtgtgcac caccatgccc agctcattta ttttgtaatt gtagggacag   2460

ggtctcactg tgttgcctag gctggtctca agtgatcctc cctccttggc ctcccaaggt   2520

gctggaatta taggtgtgaa caaacca                                        2547
```

```
<210> SEQ ID NO 90
<211> LENGTH: 664
<212> TYPE: PRT
<213> ORGANISM: Homo sapiens

<400> SEQUENCE: 90

Met Ser Gly Val Arg Gly Leu Ser Arg Leu Leu Ser Ala Arg Arg Leu
1               5                   10                  15

Ala Leu Ala Lys Ala Trp Pro Thr Val Leu Gln Thr Gly Thr Arg Gly
            20                  25                  30

Phe His Phe Thr Val Asp Gly Asn Lys Arg Ala Ser Ala Lys Val Ser
        35                  40                  45

Asp Ser Ile Ser Ala Gln Tyr Pro Val Val Asp His Glu Phe Asp Ala
    50                  55                  60

Val Val Val Gly Ala Gly Gly Ala Gly Leu Arg Ala Ala Phe Gly Leu
65                  70                  75                  80

Ser Glu Ala Gly Phe Asn Thr Ala Cys Val Thr Lys Leu Phe Pro Thr
                85                  90                  95

Arg Ser His Thr Val Ala Ala Gln Gly Gly Ile Asn Ala Ala Leu Gly
            100                 105                 110

Asn Met Glu Glu Asp Asn Trp Arg Trp His Phe Tyr Asp Thr Val Lys
        115                 120                 125

Gly Ser Asp Trp Leu Gly Asp Gln Asp Ala Ile His Tyr Met Thr Glu
    130                 135                 140

Gln Ala Pro Ala Ala Val Val Glu Leu Glu Asn Tyr Gly Met Pro Phe
145                 150                 155                 160

Ser Arg Thr Glu Asp Gly Lys Ile Tyr Gln Arg Ala Phe Gly Gly Gln
                165                 170                 175

Ser Leu Lys Phe Gly Lys Gly Gly Gln Ala His Arg Cys Cys Cys Val
            180                 185                 190

Ala Asp Arg Thr Gly His Ser Leu Leu His Thr Leu Tyr Gly Arg Ser
        195                 200                 205

Leu Arg Tyr Asp Thr Ser Tyr Phe Val Glu Tyr Phe Ala Leu Asp Leu
    210                 215                 220

Leu Met Glu Asn Gly Glu Cys Arg Gly Val Ile Ala Leu Cys Ile Glu
225                 230                 235                 240

Asp Gly Ser Ile His Arg Ile Arg Ala Lys Asn Thr Val Val Ala Thr
                245                 250                 255

Gly Gly Tyr Gly Arg Thr Tyr Phe Ser Cys Thr Ser Ala His Thr Ser
            260                 265                 270

Thr Gly Asp Gly Thr Ala Met Ile Thr Arg Ala Gly Leu Pro Cys Gln
        275                 280                 285

Asp Leu Glu Phe Val Gln Phe His Pro Thr Gly Ile Tyr Gly Ala Gly
    290                 295                 300
```

-continued

```
Cys Leu Ile Thr Glu Gly Cys Arg Gly Glu Gly Gly Ile Leu Ile Asn
305                 310                 315                 320

Ser Gln Gly Glu Arg Phe Met Glu Arg Tyr Ala Pro Val Ala Lys Asp
                325                 330                 335

Leu Ala Ser Arg Asp Val Val Ser Arg Ser Met Thr Leu Glu Ile Arg
            340                 345                 350

Glu Gly Arg Gly Cys Gly Pro Glu Lys Asp His Val Tyr Leu Gln Leu
        355                 360                 365

His His Leu Pro Pro Glu Gln Leu Ala Thr Arg Leu Pro Gly Ile Ser
    370                 375                 380

Glu Thr Ala Met Ile Phe Ala Gly Val Asp Val Thr Lys Glu Pro Ile
385                 390                 395                 400

Pro Val Leu Pro Thr Val His Tyr Asn Met Gly Gly Ile Pro Thr Asn
                405                 410                 415

Tyr Lys Gly Gln Val Leu Arg His Val Asn Gly Gln Asp Gln Ile Val
            420                 425                 430

Pro Gly Leu Tyr Ala Cys Gly Glu Ala Ala Cys Ala Ser Val His Gly
        435                 440                 445

Ala Asn Arg Leu Gly Ala Asn Ser Leu Leu Asp Leu Val Val Phe Gly
    450                 455                 460

Arg Ala Cys Ala Leu Ser Ile Glu Glu Ser Cys Arg Pro Gly Asp Lys
465                 470                 475                 480

Val Pro Pro Ile Lys Pro Asn Ala Gly Glu Glu Ser Val Met Asn Leu
                485                 490                 495

Asp Lys Leu Arg Phe Ala Asp Gly Ser Ile Arg Thr Ser Glu Leu Arg
            500                 505                 510

Leu Ser Met Gln Lys Ser Met Gln Asn His Ala Ala Val Phe Arg Val
        515                 520                 525

Gly Ser Val Leu Gln Glu Gly Cys Gly Lys Ile Ser Lys Leu Tyr Gly
    530                 535                 540

Asp Leu Lys His Leu Lys Thr Phe Asp Arg Gly Met Val Trp Asn Thr
545                 550                 555                 560

Asp Leu Val Glu Thr Leu Glu Leu Gln Asn Leu Met Leu Cys Ala Leu
                565                 570                 575

Gln Thr Ile Tyr Gly Ala Glu Ala Arg Lys Glu Ser Arg Gly Ala His
            580                 585                 590

Ala Arg Glu Asp Tyr Lys Val Arg Ile Asp Glu Tyr Asp Tyr Ser Lys
        595                 600                 605

Pro Ile Gln Gly Gln Gln Lys Lys Pro Phe Glu Glu His Trp Arg Lys
    610                 615                 620

His Thr Leu Ser Tyr Val Asp Val Gly Thr Gly Lys Val Thr Leu Glu
625                 630                 635                 640

Tyr Arg Pro Val Ile Asp Lys Thr Leu Asn Glu Ala Asp Cys Ala Thr
                645                 650                 655

Val Pro Pro Ala Ile Arg Ser Tyr
            660
```